(12) United States Patent
Motomura et al.

(10) Patent No.: US 8,871,934 B2
(45) Date of Patent: Oct. 28, 2014

(54) FLUORENE COMPOUND AND PHARMACEUTICAL USE THEREOF

(71) Applicant: Japan Tobacco Inc., Tokyo (JP)

(72) Inventors: Takahisa Motomura, Takatsuki (JP); Hironobu Nagamori, Takatsuki (JP); Koichi Suzawa, Takatsuki (JP); Hirotsugu Ito, Takatsuki (JP); Toru Morita, Takatsuki (JP); Satoru Kobayashi, Takatsuki (JP); Hisashi Shinkai, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 13/668,919

(22) Filed: Nov. 5, 2012

(65) Prior Publication Data

US 2013/0274240 A1 Oct. 17, 2013

Related U.S. Application Data

(63) Continuation of application No. 12/576,605, filed on Oct. 9, 2009, now Pat. No. 8,343,994.

(60) Provisional application No. 61/196,290, filed on Oct. 16, 2008, provisional application No. 61/276,772, filed on Sep. 16, 2009.

(30) Foreign Application Priority Data

Oct. 10, 2008 (JP) .................................. 2008-264681
Sep. 10, 2009 (JP) .................................. 2009-209855

(51) Int. Cl.
    *C07D 221/16* (2006.01)
(52) U.S. Cl.
    USPC .......................................... 546/111; 546/329
(58) Field of Classification Search
    USPC ............................ 514/290, 344; 546/111, 329
    See application file for complete search history.

(56) References Cited

U.S. PATENT DOCUMENTS

| | | | |
|---|---|---|---|
| 7,098,241 B2 | 8/2006 | Grossmann et al. | |
| 7,485,634 B2 | 2/2009 | Martin et al. | 514/215 |
| 7,585,837 B2 | 9/2009 | Shechter et al. | |
| 7,799,782 B2 * | 9/2010 | Munson et al. | 514/234.5 |
| 8,133,992 B2 | 3/2012 | Martin et al. | 540/543 |
| 8,343,910 B2 | 1/2013 | Shechter et al. | 514/1.3 |
| 2004/0023947 A1 | 2/2004 | Martin et al. | |
| 2006/0171920 A1 | 8/2006 | Shechter et al. | |
| 2008/0153837 A1 | 6/2008 | Mailliet et al. | |
| 2008/0200551 A1 | 8/2008 | Yamada et al. | |
| 2009/0326218 A1 | 12/2009 | Martin et al. | |
| 2013/0116175 A1 | 5/2013 | Shechter et al. | 514/5.9 |
| 2014/0121352 A1 | 5/2014 | Shechter et al. | 530/303 |

FOREIGN PATENT DOCUMENTS

| | | | |
|---|---|---|---|
| WO | 03/011844 A2 | 2/2003 | |
| WO | 03/099821 A1 | 12/2003 | .......... C07D 487/04 |
| WO | 2004/089280 A2 | 10/2004 | |
| WO | 2005/080322 A1 | 9/2005 | |
| WO | 2006/123061 A2 | 11/2006 | |

OTHER PUBLICATIONS

Langlois et al. CAS: 138: 187207, 2003.*
Karpov et al. CAS: 134: 280583, 2001.*
Selnick et al. CAS: 137: 63475, 2002.*
Heintzelman et al. CAS: 137: 337793, 2002.*
Provstakov et al. 106: 176128, 1987.*
Goldfarb et al. CAS: 151:92845, 2009.*
Rodgers et al. CAS: 143: 460175, 2005.*
Extended European Search Report issued in European Application No. 09819281.8 (4 pages) (May 14, 2012).
Karpov, et al., "Skeletal Transformations of Perfluoro-1-phenylindan under the Action of Antimony Pentafluoride", Journal of Fluorine Chemistry, 107, pp. 53-57 (2001).
Alcher, et al. "(R)-3,3,3-Trifluoro-2-hydroxy-2-methyl-propionamides Are Orally Active Inhibitors of Pyruvate Dehydrogenase Kinase", Journal of Medicinal Chemistry, 42(15), pp. 2741-2746 (1999).
International Search Report issued in PCT/JP2009/067668 issued Dec. 8, 2009 (4 pages).
Bebernitz, et al., "The Effect of 1,3-Diaryl-[1H]-pyrazole-4-acetamides on Glucose Utilization in ob/ob Mice", Journal of Medicinal Chemistry, 44(16), pp. 2601-2611 (2001).
Communication issued in EP Application No. 09 819 281.8, dated Apr. 16, 2014 (6 pages).

* cited by examiner

*Primary Examiner* — Rei-tsang Shiao
(74) *Attorney, Agent, or Firm* — Fitzpatrick, Cella, Harper & Scinto

(57) ABSTRACT

The present invention provides an agent for the prophylactic or treatment of diabetes, diabetic complications, insulin resistance syndrome, metabolic syndrome, hyperglycemia, dyslipidemia, atherosclerosis, cardiac failure, cardiomyopathy, myocardial ischemia, brain ischemia, cerebral apoplexy, pulmonary hypertension, hyperlactacidemia, mitochondrial disease, mitochondrial encephalomyopathy or cancer, namely, a PDHK inhibitor and the like. A compound represented by the following formula [I] or a pharmaceutically acceptable salt thereof, or a solvate thereof:

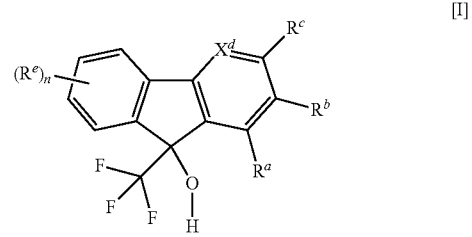

wherein each symbol is as defined in the specification.

1 Claim, No Drawings

FLUORENE COMPOUND AND PHARMACEUTICAL USE THEREOF

CROSS-REFERENCE TO RELATED APPLICATIONS

This application is a continuation of U.S. patent application Ser. No. 12/576,605, filed Oct. 9, 2009, which in-turn claims the benefit of U.S. Provisional Application No. 61/196,290, filed Oct. 16, 2008 and U.S. Provisional Application No. 61/276,772, filed Sep. 16, 2009, which claims the benefit of Japanese Patent Application No. 2008-264681, filed Oct. 10, 2008 and Japanese Patent Application No. 2009-209855, filed Sep. 10, 2009. The contents of the aforementioned applications are incorporated herein by reference in their entirety.

TECHNICAL FIELD OF THE INVENTION

The present invention relates to a fluorene compound and a pharmaceutical use thereof. More particularly, the present invention relates to a compound for the prophylaxis or treatment of diabetes, cardiovascular diseases, hyperlactacidemia and cancer based on activation of pyruvate dehydrogenase (PDH) by inhibition of pyruvate dehydrogenase kinase (PDHK), and use thereof. Furthermore, the present invention relates to a compound for the prophylaxis or treatment of diabetic complications (e.g., neuropathy, retinopathy, nephropathy, cataract etc.), brain ischemia, cerebral apoplexy or pulmonary hypertension, and use thereof.

BACKGROUND OF THE INVENTION

In tissue, for reaction using energy, for example, biosynthesis, active biological transport, muscle contraction etc., the energy is supplied by hydrolysis of adenosine triphosphate (ATP). ATP is produced by oxidation of metabolic fuel which yields much energy, such as glucose and free fatty acids. In oxidative tissues such as muscle, ATP is mostly produced from acetyl-CoA that enters citric acid cycle. Acetyl-CoA is produced by oxidation of glucose via glycolytic pathway or β oxidation of free fatty acid. An enzyme that plays a pivotal role in controlling acetyl-CoA production from glucose is PDH. PDH catalyses the oxidation of pyruvate to acetyl-CoA and carbon dioxide with concomitant reduction of nicotinamide adenine dinucleotide (NAD) to NADH.

PDH is a multienzyme complex consisting of three enzyme components (E1, E2 and E3) and some subunits localized in mitochondria matrix. E1, E2 and E3 are responsible for decarboxylation from pyruvate, production of acetyl-CoA and reduction of NAD to NADH, respectively. Two classes of enzyme having regulatory function are associated with the complex. One is PDHK, which are protein kinases having specificity to PDH. The role thereof is to inactivate E1α subunit of the complex by phosphorylation. The other is PDH phosphatases, which are specific protein phosphatases which activate PDH via dephosphorylation of E1α subunit. The proportion of PDH in its active (dephosphorylated) state is determined by the balance of kinase activity and phosphatase activity. The kinase activity is regulated by relative concentrations of metabolic substrates. For example, the kinase activity is activated by an increase in the NADH/NAD, acetyl-CoA/CoA or ATP/adenosine diphosphate (ADP) ratios, and inhibited by pyruvate.

Four PDHK isoenzymes have been identified in mammalian tissues. Particularly, PDHK2 is expressed in a wide range of tissues including the liver, skeletal muscles and adipose tissues involved in glucose metabolism. Since it shows comparatively high sensitivity to activation by increased NADH/NAD or acetyl-CoA/CoA and inhibition by pyruvate, involvement in a short-term regulation of glucose metabolism is suggested.

In diseases such as insulin-dependent (type 1) diabetes and non-insulin-dependent (type 2) diabetes and the like, oxidation of lipids is increased with a concomitant reduction in utilization of glucose. This is one of the factors causing hyperglycemia. When the oxidative glucose metabolism is reduced in type 1 and type 2 diabetes and obesity, PDH activity is also reduced. It suggests involvement of reduced PDH activity in the reduced utilization of glucose in type 1 and type 2 diabetes. On the contrary, hepatic gluconeogenesis is enhanced in type 1 and type 2 diabetes, which also forms one factor causing hyperglycemia. The reduced PDH activity increases pyruvate concentration, which in turn increases availability of lactate as a substrate for hepatic gluconeogenesis. It suggests possible involvement of reduced PDH activity in the enhanced gluconeogenesis in type 1 and type 2 diabetes. When PDH is activated by inhibition of PDHK, the rate of glucose oxidation is considered to rise. As a result, glucose utilization in the body is promoted and hepatic gluconeogenesis is suppressed, whereby hyperglycemia in type 1 and type 2 diabetes is expected to be improved. Another factor contributing to diabetes is impaired insulin secretion, which is known to be associated with reduced PDH activity in pancreatic β cells. It is also known that sustained hyperglycemia due to diabetes causes complications such as neuropathy, retinopathy, nephropathy, cataract and the like. Thiamine and α-lipoic acid contribute to activation of PDH as coenzymes, and also, they or derivatives thereof have been shown to have a promising effect in the treatment of diabetic complications. Thus, activation of PDH is expected to improve diabetic complications.

Under ischemic conditions, limited oxygen supply reduces oxidation of both glucose and fatty acid oxidation and reduces the amount of ATP produced by oxidative phosphorylation in the tissues. In the absence of sufficient oxygen, ATP level is maintained by promoted anaerobic glycolysis. As a result, lactic acid increases and intracellular pH decreases. Even though the body tries to maintain homeostasis of ion by energy consumption, abnormally low ATP level and disrupted cellular osmolarity lead to cell death. In addition, adenosine monophosphate-activating kinase, activated during ischemia, phosphorylates and thus inactivates acetyl-CoA carboxylase. The levels of total malonyl-CoA in the tissue drop, carnitine palmitoyltransferase-I activity is therefore increased and fatty acid oxidation is favored over glucose oxidation by allowing the transport of acyl-CoA into mitochondria. Oxidation of glucose is capable yielding more ATP per mole of oxygen than is oxidation of fatty acids. Under ischemic conditions, therefore, when energy metabolism becomes glucose oxidation dominant by activation of PDH, the ability to maintain ATP level is considered to be enhanced. In addition, since activation of PDH causes oxidation of pyruvate produced by glycolysis, and reducing production of loactate, the net proton burden is considered to be reduced in ischemic tissues. Accordingly, PDH activation by inhibition of PDHK is expected to protectively act in ischemic diseases such as cardiac muscle ischemia.

A drug that activates PDH by inhibition of PDHK is considered to decrease lactate production since it promotes pyruvate metabolism. Hence, such drug is expected to be useful for the treatment of hyperlactacidemia such as mitochondrial disease, mitochondrial encephalomyopathy and sepsis.

In cancer cells, ATP production by oxidative phosphorylation in mitochondria decreases, and ATP production via the anaerobic glycolysis in cytoplasm increases. PDH activation by inhibition of PDHK is expected to promote oxidative phosphorylation in mitochondria, which will induce apoptosis of cancer cells. Therefore, the mechanism is useful for the treatment of cancer diseases. Pulmonary hypertension is characterized by high blood pressure caused by partial narrowing of the pulmonary artery due to promoted cell proliferation therein. In pulmonary hypertension, therefore, activation of PDH in the pulmonary artery cell is expected to promote oxidative phosphorylation in mitochondria, and induce apoptosis of the pulmonary artery cells. Therefore, the mechanism is useful for the treatment of pulmonary hypertension.

It has been shown that dichloroacetic acid, which is a drug having a PDH activating action, provides promising effects for amelioration of hyperglycemia, treatment of myocardial ischemia, treatment of hyperlactacidemia and treatment of cancer diseases. Moreover, usefulness of dichloroacetic acid for the treatment of cerebral ischemia, cerebral apoplexy or pulmonary hypertension has been shown.

From the foregoing findings, a PDHK inhibitor is considered to be useful for the treatment or prophylaxis of diseases relating to glucose utilization disorder, for example, diabetes (e.g., type 1 diabetes, type 2 diabetes etc.), insulin resistance syndrome, metabolic syndrome, hyperglycemia and hyperlactacidemia. In addition, a PDHK inhibitor is considered to be useful for the treatment or prophylaxis of diabetic complications (e.g., neuropathy, retinopathy, nephropathy, cataract etc.). Furthermore, a PDHK inhibitor is considered to be useful for the treatment or prophylaxis of diseases caused by limited energy substrate supply to the tissues, for example, cardiac failure, cardiomyopathy, myocardial ischemia, dyslipidemia and atherosclerosis. Additionally, a PDHK inhibitor is considered to be useful for the treatment or prophylaxis of cerebral ischemia or cerebral apoplexy. Moreover, a PDHK inhibitor is considered to be useful for the treatment or prophylaxis of mitochondrial disease, mitochondrial encephalomyopathy, cancer and the like. Also, it is considered to be useful for the treatment or prophylaxis of pulmonary hypertension.

SUMMARY OF THE INVENTION

Problems to be Solved by the Invention

The present invention aims to provide an agent for the prophylactic or treatment of diabetes (e.g., type 1 diabetes, type 2 diabetes etc.), insulin resistance syndrome, metabolic syndrome, hyperglycemia, dyslipidemia, atherosclerosis, cardiac failure, cardiomyopathy, myocardial ischemia, hyperlactacidemia, mitochondrial disease, mitochondrial encephalomyopathy or cancer, namely, a PDHK inhibitor and the like. Moreover, the present invention aims to provide a PDHK inhibitor also useful as an agent for the prophylactic or treatment of diabetic complications (e.g., neuropathy, retinopathy, nephropathy, cataract etc.), brain ischemia, cerebral apoplexy or pulmonary hypertension, and the like.

Means of Solving the Problems

The present inventors have conducted intensive studies in an attempt to develop an agent for the prophylactic or treatment of diabetes (e.g., type 1 diabetes, type 2 diabetes etc.), insulin resistance syndrome, metabolic syndrome, hyperglycemia, dyslipidemia, atherosclerosis, cardiac failure, cardiomyopathy, myocardial ischemia, hyperlactacidemia, mitochondrial disease, mitochondrial encephalomyopathy, cancer, diabetic complications (e.g., neuropathy, retinopathy, nephropathy, cataract etc.), brain ischemia, cerebral apoplexy or pulmonary hypertension, which is based on a PDHK inhibitory action and found a fluorene compound having a PDHK inhibitory action, and completed the present invention.

Accordingly, the present invention provides the following.

[1] A compound represented by the following formula [I] or a pharmaceutically acceptable salt thereof, or a solvate thereof.

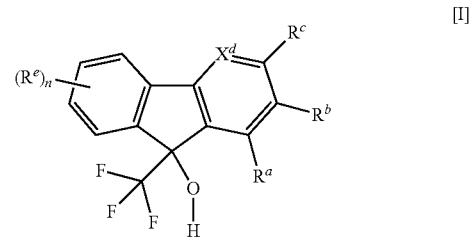

wherein, $R^a$ is
(1) a hydrogen atom, or
(2) a halogen atom;

$R^b$ is
(1) a hydrogen atom,
(2) a halogen atom,
(3) a $C_{1-6}$ alkyl group optionally substituted by the same or different 1 to 5 substituents selected from the following group A,
(4) a $C_{2-6}$ alkenyl group optionally substituted by the same or different 1 to 5 substituents selected from the following group C,
(5) a $C_{2-6}$ alkynyl group optionally substituted by the same or different 1 to 5 substituents selected from the following group C,
(6) a cyano group,
(7) —C(=O)—$R^{b1}$ wherein $R^{b1}$ is a hydrogen atom or a $C_{1-6}$ alkyl group optionally substituted by the same or different 1 to 5 substituents selected from the following group B,
(8) —C(=O)—$OR^{b2}$ wherein $R^{b2}$ is a hydrogen atom or a $C_{1-6}$ alkyl group optionally substituted by the same or different 1 to 5 substituents selected from the following group B,
(9) —C(=O)—$NR^{b3}R^{b4}$ wherein $R^{b3}$ and $R^{b4}$ are the same or different and each is a hydrogen atom or a $C_{1-6}$ alkyl group optionally substituted by the same or different 1 to 5 substituents selected from the following group B,
(10) —C(=O)—$NR^{b5}$—$OR^{b6}$ wherein $R^{b5}$ and $R^{b6}$ are the same or different and each is a hydrogen atom or a $C_{1-6}$ alkyl group optionally substituted by the same or different 1 to 5 substituents selected from the following group B,
(11) —$OR^{b7}$ wherein $R^{b7}$ is a hydrogen atom or a $C_{1-6}$ alkyl group optionally substituted by the same or different 1 to 5 substituents selected from the following group B,
(12) —$NR^{b8}R^{b9}$ wherein $R^{b8}$ and $R^{b9}$ are the same or different and each is a hydrogen atom or a $C_{1-6}$ alkyl group optionally substituted by the same or different 1 to 5 substituents selected from the following group B,
(13) —$NR^{b10}$—C(=O)—$R^{b11}$ wherein $R^{b10}$ and $R^{b11}$ are the same or different and each is a hydrogen atom or a $C_{1-6}$ alkyl group optionally substituted by the same or different 1 to 5 substituents selected from the following group B,

(14) —NR$^{b12}$—C(=O)—OR$^{b13}$ wherein R$^{b12}$ is a hydrogen atom or a C$_{1-6}$ alkyl group optionally substituted by the same or different 1 to 5 substituents selected from the following group B, and R$^{b13}$ is a C$_{1-6}$ alkyl group optionally substituted by the same or different 1 to 5 substituents selected from the following group B,

(15) —O—C(=O)—NR$^{b14}$R$^{b15}$ wherein R$^{b14}$ and R$^{b15}$ are the same or different and each is a hydrogen atom or a C$_{1-6}$ alkyl group optionally substituted by the same or different 1 to 5 substituents selected from the following group B, or

(16) a group represented by the following formula:

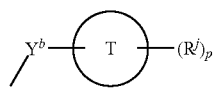

wherein
Y$^b$ is
(i) a single bond,
(ii) a C$_{1-6}$ alkylene,
(iii) a C$_{2-6}$ alkenylene,
(iv) —O—(CH$_2$)$_{n1}$— wherein n1 is an integer of 0, or 1 to 4,
(v) —O—(CH$_2$)$_{n2}$—C(=O)— wherein n2 is an integer of 0, or 1 to 4,
(vi) —C(=O)—, or
(vii) —NR$^{b16}$— wherein R$^{b16}$ is a hydrogen atom or a C$_{1-6}$ alkyl group optionally substituted by the same or different 1 to 5 substituents selected from the following group B;
ring T is
(i) a C$_{6-10}$ aryl group,
(ii) a C$_{3-10}$ cycloalkyl group,
(iii) a C$_{5-10}$ bridged cycloalkyl group,
(iv) a monocyclic aromatic heterocyclic group which contains, besides carbon atom, 1 to 4 hetero atoms selected from a nitrogen atom, an oxygen atom and a sulfur atom, and has 3 to 7 ring-constituting atoms, or
(v) a monocyclic non-aromatic heterocyclic group which contains, besides carbon atom, 1 to 4 hetero atoms selected from a nitrogen atom, an oxygen atom and a sulfur atom, and has 3 to 7 ring-constituting atoms,
R$^j$ are the same or different and each is a substituent selected from the following group D, and p is an integer of 0, or 1 to 4;
R$^c$ is
(1) a hydrogen atom,
(2) a halogen atom,
(3) a C$_{1-6}$ alkyl group,
(4) —C(=O)—OR$^{c1}$ wherein R$^{c1}$ is a hydrogen atom or a C$_{1-6}$ alkyl group,
(5) —OR$^{c2}$ wherein R$^{c2}$ is a hydrogen atom or a C$_{1-6}$ alkyl group,
(6) —NR$^{c3}$R$^{c4}$ wherein R$^{c3}$ and R$^{c4}$ are the same or different and each is a hydrogen atom or a C$_{1-6}$ alkyl group, or
(7) —NR$^{c5}$—C(=O)—R$^{c6}$ wherein R$^{c5}$ and R$^{c6}$ are the same or different and each is a hydrogen atom or a C$_{1-6}$ alkyl group;
X$^d$ is
(1) a nitrogen atom, or
(2) C—R$^d$
wherein R$^d$ is
(i) a hydrogen atom,
(ii) a halogen atom,
(iii) a C$_{1-6}$ alkyl group optionally substituted by the same or different 1 to 5 substituents selected from the following group A,
(iv) a C$_{2-6}$ alkenyl group optionally substituted by the same or different 1 to 5 substituents selected from the following group C,
(v) a C$_{2-6}$ alkynyl group optionally substituted by the same or different 1 to 5 substituents selected from the following group C,
(vi) a cyano group,
(vii) —C(=O)—R$^{d1}$ wherein R$^{d1}$ is a hydrogen atom or a C$_{1-6}$ alkyl group optionally substituted by the same or different 1 to 5 substituents selected from the following group B,
(viii) —C(=O)—OR$^{d2}$ wherein R$^{d2}$ is a hydrogen atom or a C$_{1-6}$ alkyl group optionally substituted by the same or different 1 to 5 substituents selected from the following group B,
(ix) —C(=O)—NR$^{d3}$R$^{d4}$ wherein R$^{d3}$ and R$^{d4}$ are the same or different and each is a hydrogen atom or a C$_{1-6}$ alkyl group optionally substituted by the same or different 1 to 5 substituents selected from the following group B,
(x) —C(=O)—NR$^{d5}$—OR$^{d6}$ wherein R$^{d5}$ and R$^{d6}$ are the same or different and each is a hydrogen atom or a C$_{1-6}$ alkyl group optionally substituted by the same or different 1 to 5 substituents selected from the following group B,
(xi) —OR$^{d7}$ wherein R$^{d7}$ is a hydrogen atom or a C$_{1-6}$ alkyl group optionally substituted by the same or different 1 to 5 substituents selected from the following group B,
(xii) —NR$^{d8}$R$^{d9}$ wherein R$^{d8}$ and R$^{d9}$ are the same or different and each is a hydrogen atom or a C$_{1-6}$ alkyl group optionally substituted by the same or different 1 to 5 substituents selected from the following group B,
(xiii) —NR$^{d10}$—C(=O)—R$^{d11}$ wherein R$^{d10}$ and R$^{d11}$ are the same or different and each is a hydrogen atom or a C$_{1-6}$ alkyl group optionally substituted by the same or different 1 to 5 substituents selected from the following group B,
(xiv) —NR$^{d12}$—C(=O)—OR$^{d13}$ wherein R$^{d12}$ is a hydrogen atom or a C$_{1-6}$ alkyl group optionally substituted by the same or different 1 to 5 substituents selected from the following group B, and R$^{d13}$ is a C$_{1-6}$ alkyl group optionally substituted by the same or different 1 to 5 substituents selected from the following group B, or
(xv) a group represented by the following formula:

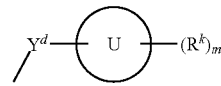

wherein
Y$^d$ is
(I) a single bond, or
(II) —C(=O)—,
ring U is
(I) a C$_{6-10}$ aryl group,
(II) a C$_{3-10}$ cycloalkyl group,
(III) a C$_{5-10}$ bridged cycloalkyl group,
(IV) a monocyclic aromatic heterocyclic group which contains, besides carbon atom, 1 to 4 hetero atoms selected from a nitrogen atom, an oxygen atom and a sulfur atom, and has 3 to 7 ring-constituting atoms, or
(V) a monocyclic non-aromatic heterocyclic group which contains, besides carbon atom, 1 to 4 hetero atoms selected from a nitrogen atom, an oxygen atom and a sulfur atom, and has 3 to 7 ring-constituting atoms, $R^k$ are the same or different and each is a substituent selected from the following group D, and m is an integer of 0, or 1 to 4;

$R^e$ are the same or different and each is,
(1) a halogen atom, or
(2) a $C_{1-6}$ alkyl group optionally substituted by the same or different 1 to 5 substituents selected from the following group C; and n is an integer of 0, or 1 to 3, provided when $X^d$ is C—$R^d$, and $R^d$ is a hydrogen atom, at least one of $R^a$, $R^b$ and $R^c$ is not a hydrogen atom.

Group A is selected from the group consisting of
(a) a halogen atom,
(b) a cyano group,
(c) —C(=O)—$R^{A1}$ wherein $R^{A1}$ is a hydrogen atom or a $C_{1-6}$ alkyl group optionally substituted by the same or different 1 to 5 substituents selected from the following group B,
(d) —C(=O)—$OR^{A2}$ wherein $R^{A2}$ is a hydrogen atom or a $C_{1-6}$ alkyl group optionally substituted by the same or different 1 to 5 substituents selected from the following group B,
(e) —C(=O)—$NR^{A3}R^{A4}$ wherein e and $R^{A4}$ are the same or different and each is a hydrogen atom or a $C_{1-6}$ alkyl group optionally substituted by the same or different 1 to 5 substituents selected from the following group B,
(f) —C(=O)—$NR^{A5}$—$OR^{A6}$ wherein $R^{A5}$ and $R^{A6}$ are the same or different and each is a hydrogen atom or a $C_{1-6}$ alkyl group optionally substituted by the same or different 1 to 5 substituents selected from the following group B,
(g) —$OR^{A7}$ wherein $R^{A7}$ is a hydrogen atom or a $C_{1-6}$ alkyl group optionally substituted by the same or different 1 to 5 substituents selected from the following group B,
(h) —$NR^{A8}R^{A9}$ wherein $R^{A8}$ and $R^{A9}$ are the same or different and each is a hydrogen atom or a $C_{1-6}$ alkyl group optionally substituted by the same or different 1 to 5 substituents selected from the following group B,
(i) —$NR^{A10}$—C(=O)—$R^{A11}$ wherein $R^{A10}$ and $R^{A11}$ are the same or different and each is a hydrogen atom or a $C_{1-6}$ alkyl group optionally substituted by the same or different 1 to 5 substituents selected from the following group B,
(j) —$NR^{A12}$—C(=O)—$OR^{A13}$ wherein $R^{A12}$ is a hydrogen atom or a $C_{1-6}$ alkyl group optionally substituted by the same or different 1 to 5 substituents selected from the following group B, and $R^{A13}$ is a $C_{1-6}$ alkyl group optionally substituted by the same or different 1 to 5 substituents selected from the following group B,
(k) —S(=O)$_2$—$R^{A14}$ wherein $R^{A14}$ is a hydrogen atom or a $C_{1-6}$ alkyl group optionally substituted by the same or different 1 to 5 substituents selected from the following group B,
(l) —S(=O)$_2$—$OR^{A15}$ wherein $R^{A15}$ is a hydrogen atom or a $C_{1-6}$ alkyl group optionally substituted by the same or different 1 to 5 substituents selected from the following group B, and
(m) —Si—(CH$_2$—CH$_3$)$_3$.

Group B is selected from the group consisting of
(a) a halogen atom,
(b) a cyano group,
(c) —C(=O)—$R^{B1}$ wherein $R^{B1}$ is a hydrogen atom or a $C_{1-6}$ alkyl group optionally substituted by the same or different 1 to 5 substituents selected from the following group C,
(d) —C(=O)—$OR^{B2}$ wherein $R^{B2}$ is a hydrogen atom or a $C_{1-6}$ alkyl group optionally substituted by the same or different 1 to 5 substituents selected from the following group C,
(e) —C(=O)—$NR^{B3}R^{B4}$ wherein $R^{B3}$ and $R^{B4}$ are the same or different and each is a hydrogen atom or a $C_{1-6}$ alkyl group optionally substituted by the same or different 1 to 5 substituents selected from the following group C,
(f) —C(=O)—$NR^{B5}$—$OR^{B6}$ wherein $R^{B5}$ and $R^{B6}$ are the same or different and each is a hydrogen atom or a $C_{1-6}$ alkyl group optionally substituted by the same or different 1 to 5 substituents selected from the following group C,
(g) —$OR^{B7}$ wherein $R^{B7}$ is a hydrogen atom or a $C_{1-6}$ alkyl group optionally substituted by the same or different 1 to 5 substituents selected from the following group C,
(h) —$NR^{B8}R^{B9}$ wherein $R^{B8}$ and $R^{B9}$ are the same or different and each is a hydrogen atom or a $C_{1-6}$ alkyl group optionally substituted by the same or different 1 to 5 substituents selected from the following group C,
(i) —$NR^{B10}$—C(=O)—$R^{B11}$ wherein $R^{B10}$ and $R^{B11}$ are the same or different and each is a hydrogen atom or a $C_{1-6}$ alkyl group optionally substituted by the same or different 1 to 5 substituents selected from the following group C,
(j) —$NR^{B12}$—S(=O)$_2$—$R^{B13}$ wherein $R^{B12}$ and $R^{B13}$ are the same or different and each is a hydrogen atom or a $C_{1-6}$ alkyl group optionally substituted by the same or different 1 to 5 substituents selected from the following group C,
(k) —$NR^{B14}$—C(=O)—$OR^{B15}$ wherein $R^{B14}$ is a hydrogen atom or a $C_{1-6}$ alkyl group optionally substituted by the same or different 1 to 5 substituents selected from the following group C, and $R^{B15}$ is a $C_{1-6}$ alkyl group optionally substituted by the same or different 1 to 5 substituents selected from the following group C,
(l) —S(=O)$_2$—$R^{B16}$ wherein $R^{B16}$ is a hydrogen atom or a $C_{1-6}$ alkyl group optionally substituted by the same or different 1 to 5 substituents selected from the following group C, and
(m) —S(=O)$_2$—$R^{B17}$ wherein $R^{B17}$ is a hydrogen atom or a $C_{1-6}$ alkyl group optionally substituted by the same or different 1 to 5 substituents selected from the following group C.

Group C is selected from the group consisting of
(a) a halogen atom,
(b) —C(=O)—$R^{C1}$ wherein $R^{C1}$ is a hydrogen atom or a $C_{1-6}$ alkyl group optionally substituted by the same or different 1 to 5 halogen atoms,
(c) —C(=O)—$OR^{C2}$ wherein $R^{C2}$ is a hydrogen atom or a $C_{1-6}$ alkyl group, and
(d) —$OR^{C3}$ wherein $R^{C3}$ is a hydrogen atom or a $C_{1-6}$ alkyl group.

Group D is selected from the group consisting of
(a) a halogen atom,
(b) a $C_{1-6}$ alkyl group optionally substituted by the same or different 1 to 5 substituents selected from the following group E,
(c) a $C_{1-6}$ alkyl group substituted by a $C_{6-10}$ aryl group optionally substituted by the same or different 1 to 5 substituents selected from the following group F,
(d) a $C_{1-6}$ alkyl group substituted by a $C_{3-10}$ cycloalkyl optionally substituted by the same or different 1 to 5 substituents selected from the following group F,
(e) a $C_{1-6}$ alkyl group substituted by a $C_{5-10}$ bridged cycloalkyl optionally substituted by the same or different 1 to 5 substituents selected from the following group F,
(f) a $C_{1-6}$ alkyl group substituted by a monocyclic aromatic heterocyclic group optionally substituted by the same or different 1 to 5 $C_{1-6}$ alkyl groups (the monocyclic aromatic heterocyclic group contains, besides carbon atom, 1 to 4 hetero atoms selected from a nitrogen atom, an oxygen atom and a sulfur atom, and has 3 to 7 ring-constituting atoms), (g) a $C_{3-10}$ cycloalkyl group optionally substituted by the same or different 1 to 5 substituents selected from the following group F,
(h) a $C_{5-10}$ bridged cycloalkyl group optionally substituted by the same or different 1 to 5 substituents selected from the following group F,
(i) a cyano group,
(j) —C(=O)—$R^{D1}$ wherein $R^{D1}$ is a hydrogen atom, a $C_{1-6}$ alkyl group optionally substituted by the same or different 1 to 5 substituents selected from the following group E, or a monocyclic non-aromatic heterocyclic group optionally substituted by the same or different 1 to 5 substituents selected from the following group F (the monocyclic non-aromatic heterocyclic group contains, besides carbon atom, 1 to 4 hetero atoms selected from a nitrogen atom, an oxygen atom and a sulfur atom, and has 3 to 7 ring-constituting atoms),
(k) —C(=O)—$OR^{D2}$ wherein $R^{D2}$ is a hydrogen atom, or a $C_{1-6}$ alkyl group optionally substituted by the same or different 1 to 5 substituents selected from the following group E,
(l) —C(=O)—$NR^{D3}R^{D4}$ wherein $R^{D3}$ and $R^{D4}$ are the same or different and each is a hydrogen atom, or a $C_{1-6}$ alkyl group optionally substituted by the same or different 1 to 5 substituents selected from the following group E,
(m) —C(=O)—$NR^{D5}$—$OR^{D6}$ wherein $R^{D5}$ and $R^{D6}$ are the same or different and each is a hydrogen atom, or a $C_{1-6}$ alkyl group optionally substituted by the same or different 1 to 5 substituents selected from the following group E,
(n) —$OR^{D7}$ wherein $R^{D7}$ is a hydrogen atom, or a $C_{1-6}$ alkyl group optionally substituted by the same or different 1 to 5 substituents selected from the following group E,
(o) —$NR^{D8}R^{D9}$ wherein $R^{D8}$ and $R^{D9}$ are the same or different and each is a hydrogen atom, or a $C_{1-6}$ alkyl group optionally substituted by the same or different 1 to 5 substituents selected from the following group E,
(p) $NR^{D10}$—C(=O)—$R^{D11}$ wherein $R^{D10}$ and $R^{D11}$ are the same or different and each is a hydrogen atom, or a $C_{1-6}$ alkyl group optionally substituted by the same or different 1 to 5 substituents selected from the following group E,
(q) —$NR^{D12}$—C(=O)—$OR^{D13}$ wherein $R^{D12}$ is a hydrogen atom, or a $C_{1-6}$ alkyl group optionally substituted by the same or different 1 to 5 substituents selected from the following group E, and $R^{D13}$ is a $C_{1-6}$ alkyl group optionally substituted by the same or different 1 to 5 substituents selected from the following group E,
(r) —S(=O)$_2$—$R^{D14}$ wherein $R^{D14}$ is a hydrogen atom, or a $C_{1-6}$ alkyl group optionally substituted by the same or different 1 to 5 substituents selected from the following group E, and
(s) —S(=O)$_2$—$OR^{D15}$ wherein $R^{D15}$ is a hydrogen atom, or a $C_{1-6}$ alkyl group optionally substituted by the same or different 1 to 5 substituents selected from the following group E.

Group E is selected from the group consisting of
(a) a halogen atom,
(b) a cyano group,
(c) —C(=O)—$R^{E1}$ wherein $R^{E1}$ is a hydrogen atom or a $C_{1-6}$ alkyl group optionally substituted by the same or different 1 to 5 substituents selected from the following group F,
(d) —C(=O)—$OR^{E2}$ wherein $R^{E2}$ is a hydrogen atom or a $C_{1-6}$ alkyl group optionally substituted by the same or different 1 to 5 substituents selected from the following group F,
(e) —C(=O)—$NR^{E3}R^{E4}$ wherein $R^{E3}$ and $R^{E4}$ are the same or different and each is a hydrogen atom or a $C_{1-6}$ alkyl group optionally substituted by the same or different 1 to 5 substituents selected from the following group F,
(f) —C(=O)—$NR^{E5}$—$OR^{E6}$ wherein $R^{E5}$ and $R^{E6}$ are the same or different and each is a hydrogen atom or a $C_{1-6}$ alkyl group optionally substituted by the same or different 1 to 5 substituents selected from the following group F,
(g) —$OR^{E7}$ wherein $R^{E7}$ is a hydrogen atom or a $C_{1-6}$ alkyl group optionally substituted by the same or different 1 to 5 substituents selected from the following group F,
(h) —$NR^{E8}R^{E9}$ wherein $R^{E8}$ and $R^{E9}$ are the same or different and each is a hydrogen atom or a $C_{1-6}$ alkyl group optionally substituted by the same or different 1 to 5 substituents selected from the following group F,
(i) —$NR^{E10}$—C(=O)—$R^{E11}$ wherein $R^{E10}$ and $R^{E11}$ are the same or different and each is a hydrogen atom or a $C_{1-6}$ alkyl group optionally substituted by the same or different 1 to 5 substituents selected from the following group F,
(j) —$NR^{E12}$—C(=O)—$OR^{E13}$ wherein $R^{E12}$ is a hydrogen atom or a $C_{1-6}$ alkyl group optionally substituted by the same or different 1 to 5 substituents selected from the following group F, and $R^{E13}$ is a $C_{1-6}$ alkyl group optionally substituted by the same or different 1 to 5 substituents selected from the following group F,
(k) —S(=O)$_2$—$R^{E14}$ wherein $R^{E14}$ is a hydrogen atom or a $C_{1-6}$ alkyl group optionally substituted by the same or different 1 to 5 substituents selected from the following group F,
(l) —S(=O)$_2$—$OR^{E15}$ wherein $R^{E15}$ is a hydrogen atom or a $C_{1-6}$ alkyl group optionally substituted by the same or different 1 to 5 substituents selected from the following group F, and
(m) —$NR^{E16}$—S(=O)$_2$—$R^{E17}$ wherein $R^{E16}$ and $R^{E17}$ are the same or different and each is a hydrogen atom or a $C_{1-6}$ alkyl group.

Group F is selected from the group consisting of
(a) —(CH$_2$)$_{nF1}$—C(=O)—$OR^{F1}$ wherein $R^{F1}$ is a hydrogen atom or a $C_{1-6}$ alkyl group, and nF1 is an integer of 0, or 1 to 4, and
(b) —(CH$_2$)$_{nF2}$—$OR^{F2}$ wherein $R^{F2}$ is a hydrogen atom or a $C_{1-6}$ alkyl group, and nF2 is an integer of 0, or 1 to 4.

[2] The compound of the above-mentioned [1], wherein $X^d$ is C—$R^d$ wherein $R^d$ is as defined in the above-mentioned [1], or a pharmaceutically acceptable salt thereof, or a solvate thereof.

[3] The compound of the above-mentioned [1] or [2], which is represented by the following formula [II], or a pharmaceutically acceptable salt thereof, or a solvate thereof.

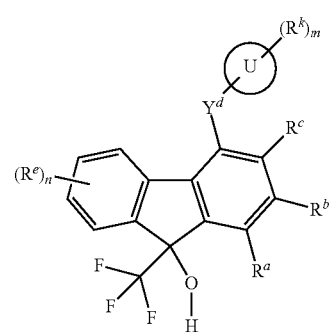

wherein each symbol is as defined in the above-mentioned [1].

[4] The compound of the above-mentioned [3], wherein ring U is a monocyclic aromatic heterocyclic group, or a pharmaceutically acceptable salt thereof, or a solvate thereof.

[5] The compound of the above-mentioned [3], wherein $Y^d$ is a single bond, or a pharmaceutically acceptable salt thereof, or a solvate thereof.

[6] The compound of the above-mentioned [4], which is represented by the following formula [III], or a pharmaceutically acceptable salt thereof, or a solvate thereof.

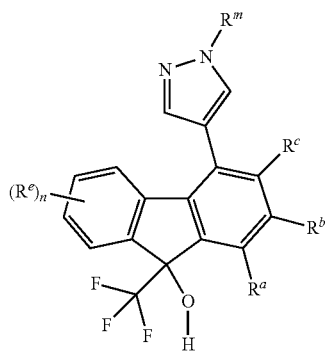

[III]

wherein
$R^m$ is
(1) a $C_{1-6}$ alkyl group optionally substituted by the same or different 1 to 5 substituents selected from group E,
(2) a $C_{1-6}$ alkyl group substituted by a $C_{6-10}$ aryl group optionally substituted by the same or different 1 to 5 substituents selected from group F,
(3) a $C_{1-6}$ alkyl group substituted by a $C_{3-10}$ cycloalkyl optionally substituted by the same or different 1 to 5 substituents selected from group F,
(4) a $C_{1-6}$ alkyl group substituted by a $C_{5-10}$ bridged cycloalkyl optionally substituted by the same or different 1 to 5 substituents selected from group F,
(5) a $C_{1-6}$ alkyl group substituted by a monocyclic aromatic heterocyclic group optionally substituted by the same or different 1 to 5 $C_{1-6}$ alkyl groups (the monocyclic aromatic heterocyclic group contains, besides carbon atom, 1 to 4 hetero atoms selected from a nitrogen atom, an oxygen atom and a sulfur atom, and has 3 to 7 ring-constituting atoms),
(6) a $C_{3-10}$ cycloalkyl optionally substituted by the same or different 1 to 5 substituents selected from group F, or
(7) a $C_{5-10}$ bridged cycloalkyl optionally substituted by the same or different 1 to 5 substituents selected from group F, and other symbols are as defined in the above-mentioned [1].

[7] The compound of the above-mentioned [6], wherein $R^m$ is
(1) a $C_{1-6}$ alkyl group optionally substituted by the same or different 1 to 5 substituents selected from group E',
(2) a $C_{1-6}$ alkyl group substituted by a $C_{3-10}$ cycloalkyl optionally substituted by the same or different 1 to 5 substituents selected from group F,
(3) a $C_{1-6}$ alkyl group substituted by a $C_{5-10}$ bridged cycloalkyl optionally substituted by the same or different 1 to 5 substituents selected from group F,
(4) a $C_{3-10}$ cycloalkyl optionally substituted by the same or different 1 to 5 substituents selected from group F, or
(5) a $C_{5-10}$ bridged cycloalkyl optionally substituted by the same or different 1 to 5 substituents selected from group F, and group E' is selected from the group consisting of (a) a halogen atom,
(b) a cyano group,
(c) $-C(=O)-R^{E1}$ wherein $R^{E1}$ is a hydrogen atom or a $C_{1-6}$ alkyl group optionally substituted by the same or different 1 to 5 substituents selected from the following group F,
(d) $-C(=O)-OR^{E2}$ wherein $R^{E2}$ is a hydrogen atom or a $C_{1-6}$ alkyl group optionally substituted by the same or different 1 to 5 substituents selected from the following group F,
(e) $-C(=O)-NR^{E3}R^{E4}$ wherein $R^{E3}$ and $R^{E4}$ are the same or different and each is a hydrogen atom or a $C_{1-6}$ alkyl group optionally substituted by the same or different 1 to 5 substituents selected from the following group F,
(f) $-C(=O)-NR^{E5}-OR^{E6}$ wherein $R^{E5}$ and $R^{E6}$ are the same or different and each is a hydrogen atom or a $C_{1-6}$ alkyl group optionally substituted by the same or different 1 to 5 substituents selected from the following group F,
(g) $-OR^{E7}$ wherein $R^{E7}$ is a hydrogen atom or a $C_{1-6}$ alkyl group optionally substituted by the same or different 1 to 5 substituents selected from the following group F,
(h) $-NR^{E8}R^{E9}$ wherein $R^{E8}$ and $R^{E9}$ are the same or different and each is a hydrogen atom or a $C_{1-6}$ alkyl group optionally substituted by the same or different 1 to 5 substituents selected from the following group F,
(i) $-NR^{E10}-C(=O)-R^{E11}$ wherein $R^{E10}$ and $R^{E11}$ are the same or different and each is a hydrogen atom or a $C_{1-6}$ alkyl group optionally substituted by the same or different 1 to 5 substituents selected from the following group F,
(j) $-NR^{E12}-C(=O)-OR^{E13}$ wherein $R^{E12}$ is a hydrogen atom or a $C_{1-6}$ alkyl group optionally substituted by the same or different 1 to 5 substituents selected from the following group F, and $R^{E13}$ is a $C_{1-6}$ alkyl group optionally substituted by the same or different 1 to 5 substituents selected from the following group F,
(k) $-S(=O)_2-R^{E14}$ wherein $R^{E14}$ is a hydrogen atom or a alkyl group optionally substituted by the same or different 1 to 5 substituents selected from the following group F, and
(l) $-S(=O)_2-OR^{E15}$ wherein $R^{E25}$ is a hydrogen atom or a $C_{1-6}$ alkyl group optionally substituted by the same or different 1 to 5 substituents selected from the following group F,
or a pharmaceutically acceptable salt thereof, or a solvate thereof.

[8] The compound of the above-mentioned [7], which is represented by the following formula [III-A], or a pharmaceutically acceptable salt thereof, or a solvate thereof.

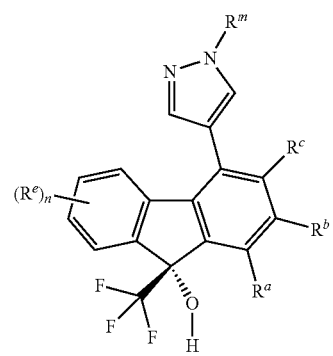

[III-A]

wherein each symbol is as defined in the above-mentioned [7].

[9] The compound of the above-mentioned [7], wherein $R^c$ is a hydrogen atom, or a pharmaceutically acceptable salt thereof, or a solvate thereof.

[10] The compound of the above-mentioned [7], wherein $R^b$ is
(1) a hydrogen atom,
(2) a halogen atom,
(3) a $C_{1-6}$ alkyl group optionally substituted by the same or different 1 to 5 substituents selected from group A,
(4) a $C_{2-6}$ alkenyl group optionally substituted by the same or different 1 to 5 substituents selected from group C,
(5) a $C_{2-6}$ alkynyl group optionally substituted by the same or different 1 to 5 substituents selected from group C,
(6) a cyano group,
(7) —C(=O)—$R^{b1}$ wherein $R^{b1}$ is a hydrogen atom or a $C_{1-6}$ alkyl group optionally substituted by the same or different 1 to 5 substituents selected from group B,
(8) —C(=O)—$OR^{b2}$ wherein $R^{b2}$ is a hydrogen atom or a $C_{1-6}$ alkyl group optionally substituted by the same or different 1 to 5 substituents selected from group B,
(9) —C(=O)—$NR^{b3}R^{b4}$ wherein $R^{b3}$ and $R^{b4}$ are the same or different and each is a hydrogen atom or a $C_{1-6}$ alkyl group optionally substituted by the same or different 1 to 5 substituents selected from group B,
(10) —C(=O)—$NR^{b5}$—$OR^{b6}$ wherein $R^{b5}$ and $R^{b6}$ are the same or different and each is a hydrogen atom or a $C_{1-6}$ alkyl group optionally substituted by the same or different 1 to 5 substituents selected from group B,
(11) —$OR^{b7}$ wherein $R^{b7}$ is a hydrogen atom or a $C_{1-6}$ alkyl group optionally substituted by the same or different 1 to 5 substituents selected from group B,
(12) —$NR^{b8}R^{b9}$ wherein $R^{b8}$ and $R^{b9}$ are the same or different and each is a hydrogen atom or a $C_{1-6}$ alkyl group optionally substituted by the same or different 1 to 5 substituents selected from group B,
(13) —$NR^{b10}$—C(=O)—$R^{b11}$ wherein $R^{b10}$ and $R^{b11}$ are the same or different and each is a hydrogen atom or a $C_{1-6}$ alkyl group optionally substituted by the same or different 1 to 5 substituents selected from group B,
(14) —$NR^{b12}$—C(=O)—$OR^{b13}$ wherein $R^{b12}$ is a hydrogen atom or a $C_{1-6}$ alkyl group optionally substituted by the same or different 1 to 5 substituents selected from group B, and $R^{b13}$ is a $C_{1-6}$ alkyl group optionally substituted by the same or different 1 to 5 substituents selected from group B, or
(15) —O—C(=O)—$NR^{b14}R^{b15}$ wherein $R^{b14}$ and $R^{b15}$ are the same or different and each is a hydrogen atom or a $C_{1-6}$ alkyl group optionally substituted by the same or different 1 to 5 substituents selected from group B,
or a pharmaceutically acceptable salt thereof, or a solvate thereof.

[11] The compound of the above-mentioned [7], wherein $R^a$ is a hydrogen atom, or a pharmaceutically acceptable salt thereof, or a solvate thereof.

[12] The compound of the above-mentioned [7], wherein n is 0, or a pharmaceutically acceptable salt thereof, or a solvate thereof.

[13] The compound of the above-mentioned [7], wherein $R^m$ is (1) a $C_{1-6}$ alkyl group optionally substituted by the same or different 1 to 5 substituents selected from
(i) —C(=O)—$OR^{E2}$ wherein $R^{E2}$ is a hydrogen atom or a $C_{1-6}$ alkyl group optionally substituted by the same or different 1 to 5 substituents selected from group F,
(ii) —C(=O)—$NR^{E3}R^{E4}$ wherein $R^{E3}$ and $R^{E4}$ are the same or different and each is a hydrogen atom or a $C_{1-6}$ alkyl group optionally substituted by the same or different 1 to 5 substituents selected from group F,
(iii) —$OR^{E7}$ wherein $R^{E7}$ is a hydrogen atom or a $C_{1-6}$ alkyl group optionally substituted by the same or different 1 to 5 substituents selected from group F, and
(iv) —$NR^{E12}$—C(=O)—$R^{E13}$ wherein $R^{E12}$ and $R^{E13}$ are the same or different and each is a hydrogen atom or a $C_{1-6}$ alkyl group optionally substituted by the same or different 1 to 5 substituents selected from group F,
(2) a $C_{3-10}$ cycloalkyl group optionally substituted by the same or different 1 to 5 substituents selected from group F, or
(3) a $C_{5-10}$ bridged cycloalkyl group optionally substituted by the same or different 1 to 5 substituents selected from group F,
or a pharmaceutically acceptable salt thereof, or a solvate thereof.

[14] The compound of the above-mentioned [7], wherein $R^m$ is
(1) a $C_{1-6}$ alkyl group optionally substituted by the same or different 1 to 5 substituents selected from
(i) —C(=O)—$OR^{E2}$ wherein $R^{E2}$ is a hydrogen atom or a $C_{1-6}$ alkyl group optionally substituted by the same or different 1 to 5 substituents selected from group F, and
(ii) —$OR^{E7}$ wherein $R^{E7}$ is a hydrogen atom or a $C_{1-6}$ alkyl group optionally substituted by the same or different 1 to 5 substituents selected from group F,
(2) a $C_{3-10}$ cycloalkyl group optionally substituted by the same or different 1 to 5 substituents selected from group F, or
(3) a $C_{5-10}$ bridged cycloalkyl group optionally substituted by the same or different 1 to 5 substituents selected from group F,
or a pharmaceutically acceptable salt thereof, or a solvate thereof.

[15] The compound of the above-mentioned [4], which is represented by the following formula [VI], or a pharmaceutically acceptable salt thereof, or a solvate thereof.

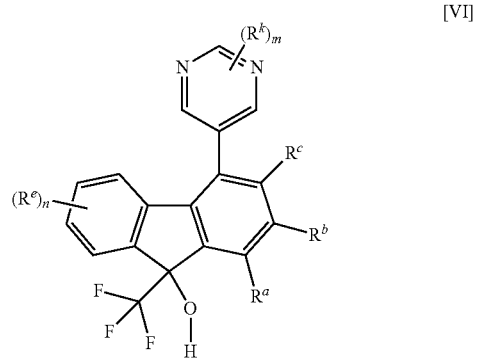

[VI]

wherein each symbol is as defined in the above-mentioned [4].

[16] The compound of the above-mentioned [1], which is represented by the following formula, or a pharmaceutically acceptable salt thereof, or a solvate thereof.

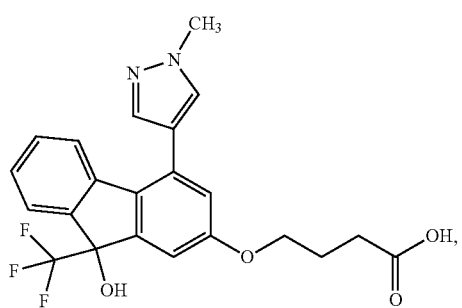
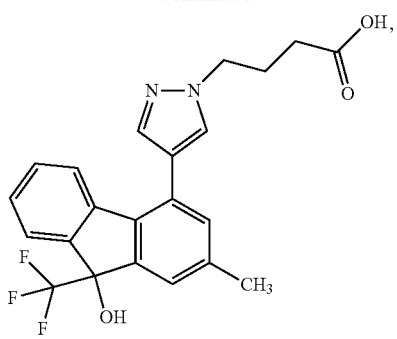
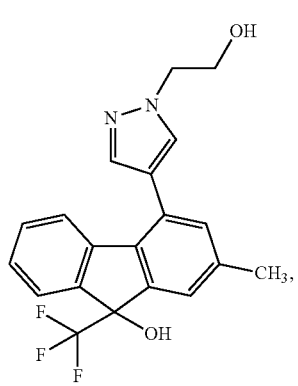
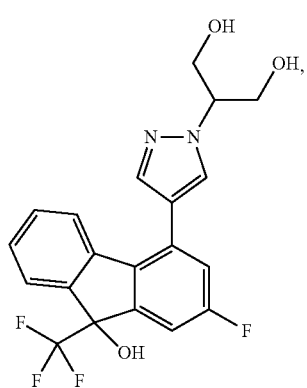
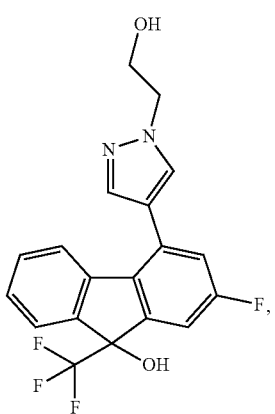
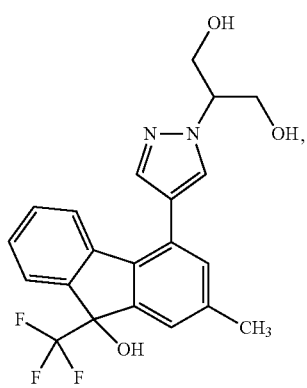
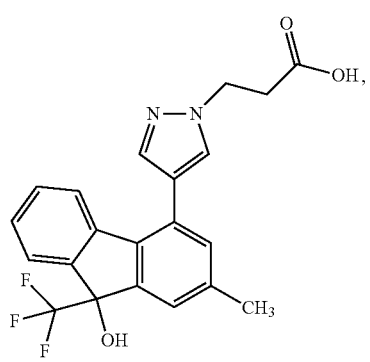
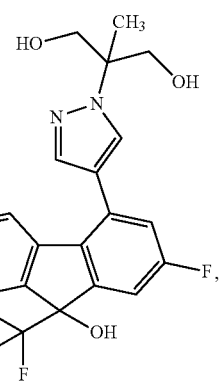

-continued
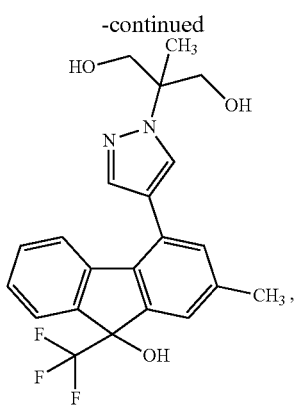
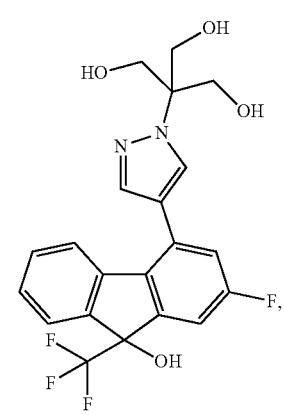
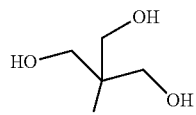
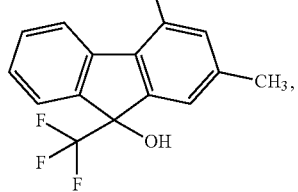
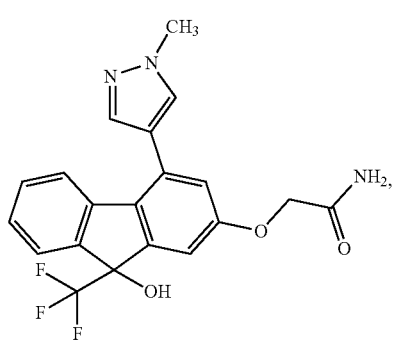
-continued
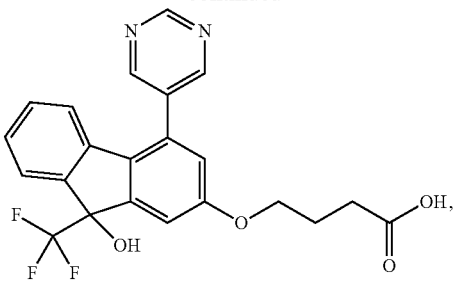
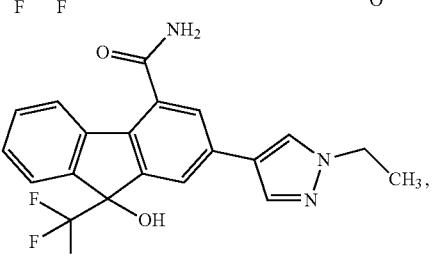
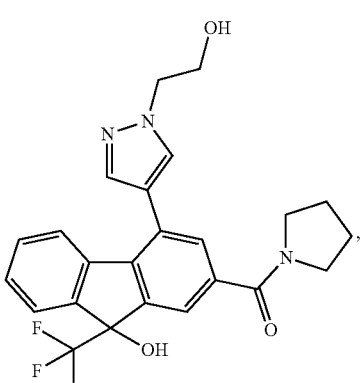
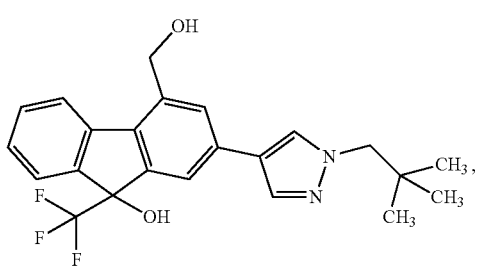
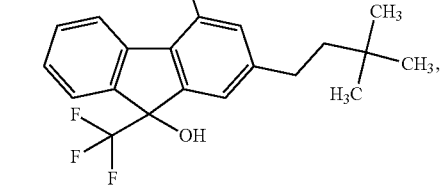

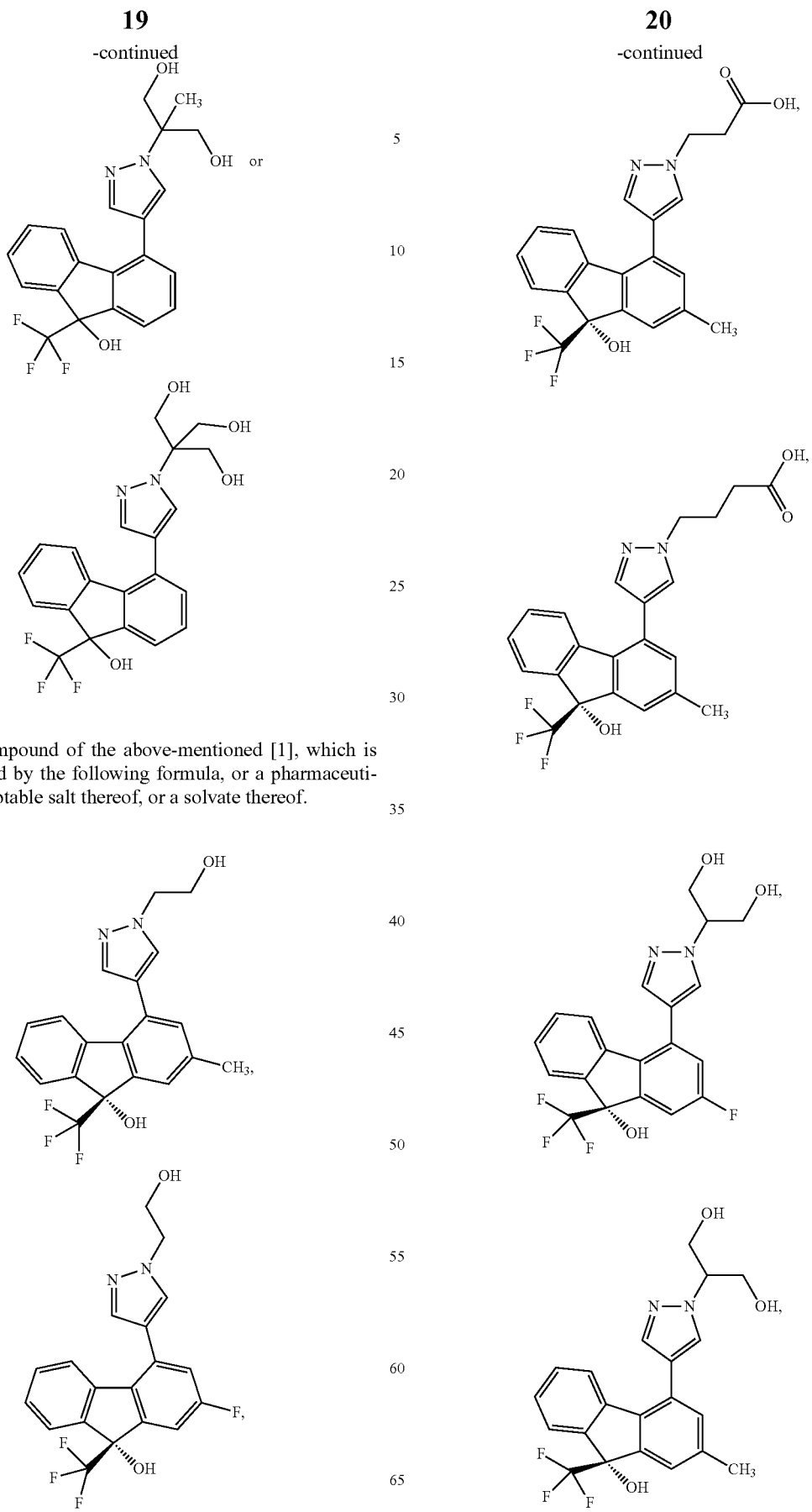
[17] The compound of the above-mentioned [1], which is represented by the following formula, or a pharmaceutically acceptable salt thereof, or a solvate thereof.

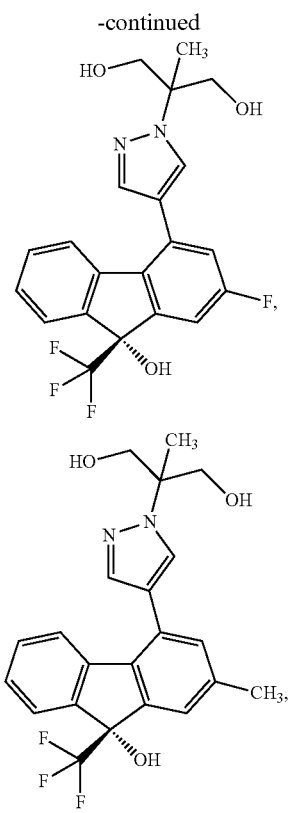
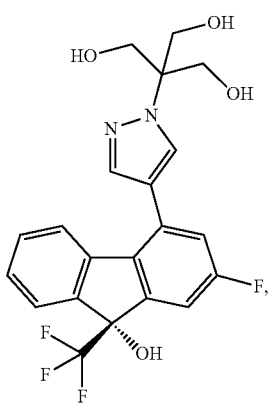
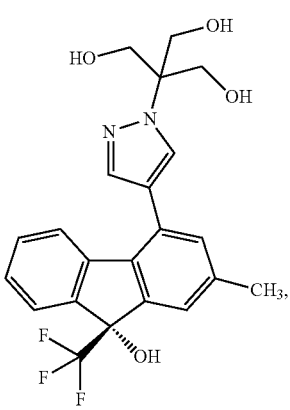
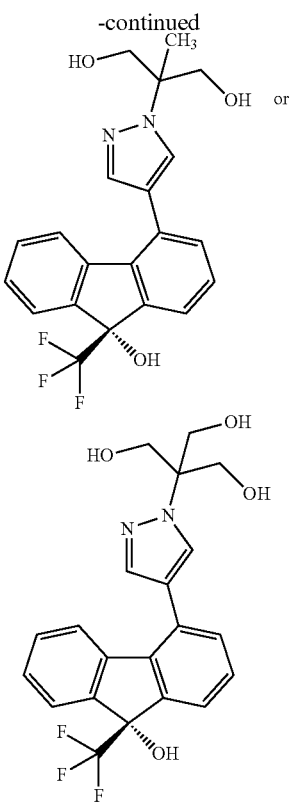

[18] A pharmaceutical composition comprising the compound of any one of the above-mentioned [1] to [17], or a pharmaceutically acceptable salt thereof, or a solvate thereof, and a pharmaceutically acceptable carrier.

[19] A PDHK inhibitor comprising the compound of any one of the above-mentioned [1] to [17], or a pharmaceutically acceptable salt thereof, or a solvate thereof.

[20] A PDH activator comprising the compound of any one of the above-mentioned [1] to [17], or a pharmaceutically acceptable salt thereof, or a solvate thereof.

[21] A PDHK2 inhibitor comprising the compound of any one of the above-mentioned [1] to [17], or a pharmaceutically acceptable salt thereof, or a solvate thereof.

[22] A blood glucose level-lowering agent comprising the compound of any one of the above-mentioned [1] to [17], or a pharmaceutically acceptable salt thereof, or a solvate thereof.

[23] A lactate level-lowering agent comprising the compound of any one of the above-mentioned [1] to [17], or a pharmaceutically acceptable salt thereof, or a solvate thereof.

[24] An agent for the treatment or prophylaxis of diabetes (e.g., type 1 diabetes, type 2 diabetes etc.), insulin resistance syndrome, metabolic syndrome, hyperglycemia, dyslipidemia, atherosclerosis, cardiac failure, cardiomyopathy, myocardial ischemia, hyperlactacidemia, mitochondrial disease, mitochondrial encephalomyopathy or cancer, comprising the compound of any one of the above-mentioned [1] to [17], or a pharmaceutically acceptable salt thereof, or a solvate thereof.

[25] An agent for the treatment or prophylaxis of diabetes (e.g., type 1 diabetes, type 2 diabetes etc.), diabetic complications (e.g., neuropathy, retinopathy, nephropathy, cataract etc.), insulin resistance syndrome, metabolic syndrome, hyperglycemia, dyslipidemia, atherosclerosis, cardiac failure, cardiomyopathy, myocardial ischemia, brain ischemia, cerebral apoplexy, pulmonary hypertension, hyperlactacidemia, mitochondrial disease, mitochondrial encephalomyopathy or cancer, comprising the compound of any one of the above-mentioned [1] to [17], or a pharmaceutically acceptable salt thereof, or a solvate thereof.

[26] A method of inhibiting PDHK in a mammal, comprising administering a pharmaceutically effective amount of the compound of any one of the above-mentioned [1] to [17], or a pharmaceutically acceptable salt thereof, or a solvate thereof to the mammal.

[27] A method of activating PDH in a mammal, comprising administering a pharmaceutically effective amount of the compound of any one of the above-mentioned [1] to [17], or a pharmaceutically acceptable salt thereof, or a solvate thereof to the mammal.

[28] A method of inhibiting PDHK2 in a mammal, comprising administering a pharmaceutically effective amount of the compound of any one of the above-mentioned [1] to [17], or a pharmaceutically acceptable salt thereof, or a solvate thereof to the mammal.

[29] A method of decreasing the blood glucose level in a mammal, comprising administering a pharmaceutically effective amount of the compound of any one of the above-mentioned [1] to [17], or a pharmaceutically acceptable salt thereof, or a solvate thereof to the mammal.

[30] A method of decreasing lactate level in a mammal, comprising administering a pharmaceutically effective amount of the compound of any one of the above-mentioned [1] to [17], or a pharmaceutically acceptable salt thereof, or a solvate thereof to the mammal.

[31] A method for the treatment or prophylaxis of diabetes (e.g., type 1 diabetes, type 2 diabetes etc.), insulin resistance syndrome, metabolic syndrome, hyperglycemia, dyslipidemia, atherosclerosis, cardiac failure, cardiomyopathy, myocardial ischemia, hyperlactacidemia, mitochondrial disease, mitochondrial encephalomyopathy or cancer in mammal, comprising administering a pharmaceutically effective amount of the compound of any one of the above-mentioned [1] to [17], or a pharmaceutically acceptable salt thereof, or a solvate thereof to the mammal.

[32] A method for the treatment or prophylaxis of diabetes (e.g., type 1 diabetes, type 2 diabetes etc.), diabetic complications (e.g., neuropathy, retinopathy, nephropathy, cataract etc.), insulin resistance syndrome, metabolic syndrome, hyperglycemia, dyslipidemia, atherosclerosis, cardiac failure, cardiomyopathy, myocardial ischemia, brain ischemia, cerebral apoplexy, pulmonary hypertension, hyperlactacidemia, mitochondrial disease, mitochondrial encephalomyopathy or cancer in mammal, comprising administering a pharmaceutically effective amount of the compound of any one of the above-mentioned [1] to [17], or a pharmaceutically acceptable salt thereof, or a solvate thereof to the mammal.

[33] Use of the compound of any one of the above-mentioned [1] to [17], or a pharmaceutically acceptable salt thereof, or a solvate thereof for the production of a PDHK inhibitor.

[34] Use of the compound of any one of the above-mentioned [1] to [17], or a pharmaceutically acceptable salt thereof, or a solvate thereof for the production of a PDH activator.

[35] Use of the compound of any one of the above-mentioned [1] to [17], or a pharmaceutically acceptable salt thereof, or a solvate thereof for the production of a PDHK2 inhibitor.

[36] Use of the compound of any one of the above-mentioned [1] to [17], or a pharmaceutically acceptable salt thereof, or a solvate thereof for the production of a blood glucose level-lowering agent.

[37] Use of the compound of any one of the above-mentioned [1] to [17], or a pharmaceutically acceptable salt thereof, or a solvate thereof for the production of a lactate level-lowering agent.

[38] Use of the compound of any one of the above-mentioned [1] to [17], or a pharmaceutically acceptable salt thereof, or a solvate thereof for the production of an agent for the treatment or prophylaxis of diabetes (e.g., type 1 diabetes, type 2 diabetes etc.), insulin resistance syndrome, metabolic syndrome, hyperglycemia, dyslipidemia, atherosclerosis, cardiac failure, cardiomyopathy, myocardial ischemia, hyperlactacidemia, mitochondrial disease, mitochondrial encephalomyopathy or cancer.

[39] Use of the compound of any one of the above-mentioned [1] to [17], or a pharmaceutically acceptable salt thereof, or a solvate thereof for the production of an agent for the treatment or prophylaxis of diabetes (e.g., type 1 diabetes, type 2 diabetes etc.), diabetic complications (e.g., neuropathy, retinopathy, nephropathy, cataract etc.), insulin resistance syndrome, metabolic syndrome, hyperglycemia, dyslipidemia, atherosclerosis, cardiac failure, cardiomyopathy, myocardial ischemia, brain ischemia, cerebral apoplexy, pulmonary hypertension, hyperlactacidemia, mitochondrial disease, mitochondrial encephalomyopathy or cancer.

[40] A commercial kit comprising (a) a pharmaceutical composition comprising the compound of any one of the above-mentioned [1] to [17], or a pharmaceutically acceptable salt thereof, or a solvate thereof as active ingredient, and (b) a written matter stating that the pharmaceutical composition can or should be used for the treatment or prophylaxis of diabetes (e.g., type 1 diabetes, type 2 diabetes etc.), diabetic complications (e.g., neuropathy, retinopathy, nephropathy, cataract etc.), insulin resistance syndrome, metabolic syndrome, hyperglycemia, dyslipidemia, atherosclerosis, cardiac failure, cardiomyopathy, myocardial ischemia, brain ischemia, cerebral apoplexy, pulmonary hypertension, hyperlactacidemia, mitochondrial disease, mitochondrial encephalomyopathy or cancer.

[41] A commercial package comprising (a) a pharmaceutical composition comprising the compound of any one of the above-mentioned [1] to [17], or a pharmaceutically acceptable salt thereof, or a solvate thereof as active ingredient, and (b) a written matter stating that the pharmaceutical composition can or should be used for the treatment or prophylaxis of diabetes (e.g., type 1 diabetes, type 2 diabetes etc.), diabetic complications (e.g., neuropathy, retinopathy, nephropathy, cataract etc.), insulin resistance syndrome, metabolic syndrome, hyperglycemia, dyslipidemia, atherosclerosis, cardiac failure, cardiomyopathy, myocardial ischemia, brain ischemia, cerebral apoplexy, pulmonary hypertension, hyperlactacidemia, mitochondrial disease, mitochondrial encephalomyopathy or cancer.

Effect of the Invention

Since the fluorene compound of the present invention effectively inhibits the PDHK activity, and further, has preferable properties as a drug such as chemical stability and the like, it is effective as an agent for the prophylaxis or treatment of diabetes (e.g., type 1 diabetes, type 2 diabetes etc.), insulin resistance syndrome, metabolic syndrome, hyperglycemia, dyslipidemia, atherosclerosis, cardiac failure, cardiomyopathy, myocardial ischemia, hyperlactacidemia, mitochondrial disease, mitochondrial encephalomyopathy or cancer, and the like. Furthermore, the fluorene compound of the present invention is also effective as an agent for the prophylaxis or treatment of diabetic complications (e.g., neuropathy, retinopathy, nephropathy, cataract etc.), brain ischemia, cerebral apoplexy or pulmonary hypertension.

EMBODIMENT OF THE INVENTION

The present invention is explained in detail in the following.

The definitions of the terms used in the present specification are as follows.

The "optionally substituted" includes both being substituted at substitutable position(s) of an object group and being unsubstituted. Here, the "unsubstituted" means that all substitutable positions of an object group are occupied by hydrogen atoms.

For example, a "$C_{1-6}$ alkyl group optionally substituted by the same or different 1 to 5 substituents selected from group A" means both when the substitutable position(s) of a $C_{1-6}$ alkyl group is(are) substituted by the same or different 1 to 5 substituents selected from group A, and is(are) not substituted (unsubstituted).

Examples of the "halogen atom" include a fluorine atom, a chlorine atom, a bromine atom, an iodine atom and the like.

The "$C_{1-6}$ alkyl group" means a straight chain or branched chain saturated hydrocarbon group having 1 to 6 carbon atoms. Examples thereof include a methyl group, an ethyl group, a propyl group, an isopropyl group, a butyl group, an isobutyl group, a sec-butyl group, a tert-butyl group, a pentyl group, an isopentyl group, a neopentyl group, a 1-ethylpropyl group, a hexyl group, an isohexyl group, a 1,1-dimethylbutyl group, a 2,2-dimethylbutyl group, a 3,3-dimethylbutyl group, a 2-ethylbutyl group and the like. Preferred are a methyl group, an ethyl group, a propyl group, an isopropyl group, a butyl group, an isobutyl group, a sec-butyl group, a tert-butyl group, a pentyl group, an isopentyl group, a neopentyl group, a hexyl group, an isohexyl group, a 3,3-dimethylbutyl group and the like.

The "$C_{2-6}$ alkenyl group" means a linear or branched chain unsaturated hydrocarbon group having 2 to 6 a carbon atoms and containing one or more double bonds. Examples thereof include a vinyl group, a 1-methylvinyl group, a 1-propenyl group, an allyl group, a methylpropenyl group (1-methyl-1-propenyl group, 2-methyl-1-propenyl group etc.), a 1-butenyl group, a 2-butenyl group, a 3-butenyl group, a methylbutenyl group (1-methyl-1-butenyl group, a 2-methyl-1-butenyl group, a 3-methyl-1-butenyl group etc.), a pentenyl group, a methylpentenyl group, a hexenyl group and the like. Preferred are a vinyl group, a 1-methylvinyl group, a 1-propenyl group, a methylpropenyl group and the like.

The "$C_{2-6}$ alkynyl group" means a linear or branched chain unsaturated hydrocarbon group having 2 to 6 a carbon atoms and containing one or more triple bonds. Examples thereof include an ethynyl group, a propynyl group (1-propynyl group, 2-propynyl group), a butynyl group, a pentynyl group, a hexynyl group and the like. Preferred are an ethynyl group, a 1-propynyl group and the like.

The "$C_{1-6}$ alkylene" means a divalent group derived from the above-mentioned "$C_{1-6}$ alkyl group". Examples thereof include methylene, ethylene, trimethylene, tetramethylene, pentamethylene, hexamethylene and the like. Preferred are methylene, ethylene, trimethylene and the like.

The "$C_{2-6}$ alkenylene" means a divalent group derived from the above-mentioned "$C_{2-6}$ alkenyl group". Examples thereof include vinylene, propenylene, butenylene, pentenylene, hexenylene and the like. Preferred are vinylene and the like.

The "$C_{6-10}$ aryl group" means an aromatic hydrocarbon group having 6 to 10 carbon atoms. Examples thereof include a phenyl group, a 1-naphthyl group, a 2-naphthyl group and the like. Preferred is a phenyl group.

The "$C_{3-10}$ cycloalkyl group" means a monocycle saturated hydrocarbon group having 3 to 10 carbon atoms. Examples thereof include a cyclopropyl group, a cyclobutyl group, a cyclopentyl group, a cyclohexyl group, a cycloheptyl group, a cyclooctyl group and the like. Particularly, a $C_{3-6}$ cycloalkyl group (e.g., a cyclopropyl group, a cyclobutyl group, a cyclopentyl group, a cyclohexyl group etc.) is preferable.

The "$C_{6-13}$ bridged cycloalkyl group" means a bridged cyclic saturated hydrocarbon group having 5 to 10 carbon atoms. Examples thereof include a bicyclopentanyl group, a bicyclohexyl group, a bicycloheptyl group, a tricycloheptyl group, a bicyclooctyl group, an adamantyl group and the like. Particularly, an adamantyl group is preferable.

The "monocyclic aromatic heterocyclic group" means a monocyclic aromatic heterocyclic group, containing, besides carbon atom, 1 to 4 hetero atoms selected from a nitrogen atom, an oxygen atom and a sulfur atom, and having 3 to 7 ring-constituting atoms. Examples thereof include a furyl group, a thienyl group, a pyrrolyl group, an oxazolyl group, an isoxazolyl group, a thiazolyl group, an isothiazolyl group, an imidazolyl group, a pyrazolyl group, an oxadiazolyl group (1,2,5-oxadiazolyl group, 1,3,4-oxadiazolyl group, 1,2,4-oxadiazolyl group), a thiadiazolyl group (1,2,5-thiadiazolyl group, 1,3,4-thiadiazolyl group, 1,2,4-thiadiazolyl group), a triazolyl group (1,2,3-triazolyl group, 1,2,4-triazolyl group), a tetrazolyl group, a pyridyl group, a pyrimidinyl group, a pyridazinyl group, a pyrazinyl group, a triazinyl group and the like. Preferred are a thienyl group, an oxazolyl group, a thiazolyl group, an imidazolyl group, a pyrazolyl group, an oxadiazolyl group (1,3,4-oxadiazolyl group, 1,2,4-oxadiazolyl group), a triazolyl group (1,2,4-triazolyl group), a tetrazolyl group, a pyridyl group, a pyrimidinyl group and the like.

The "monocyclic non-aromatic heterocyclic group" means a monocyclic saturated or partially unsaturated heterocyclic group, which contains, besides carbon atom, 1 to 4 hetero atoms selected from a nitrogen atom, an oxygen atom and a sulfur atom, and has 3 to 7 ring-constituting atoms. Examples thereof include an oxiranyl group, a thioranyl group, an aziridinyl group, an azetidinyl group, an oxetanyl group, a pyrrolidinyl group, a pyrrolidino group (1-pyrrolidinyl group), a tetrahydrofuranyl group, a tetrahydrothienyl group, an oxazolinyl group, an oxazolidinyl group, an isoxazolinyl group, an isoxazolidinyl group, a thiazolinyl group, a thiazolidinyl group, an isothiazolinyl group, an isothiazolidinyl group, an imidazolinyl group, an imidazolidinyl group, a pyrazolinyl group, a pyrazolidinyl group, a piperidinyl group, a piperidino group (1-piperidinyl group), a morpholinyl group, a morpholino group (4-morpholinyl group), a thiomorpholinyl group, a thiomorpholino group (4-thiomorpholinyl group), a piperazinyl group, a piperazino group (1-piperazinyl group), a hexahydro-1,3-oxazinyl group and the like. The group may have 1 or 2 oxo groups. In addition, when the group contains a sulfur atom as a hetero atom, the sulfur atom may be mono- or dioxide.

Particularly, an aziridinyl group, an azetidinyl group, a pyrrolidinyl group, a 2-oxopyrrolidinyl group, a 2-oxopyrrolidino group, an oxazolidinyl group, a 2-oxooxazolidinyl group, an isothiazolidinyl group, a 1,1-dioxoisothiazolidinyl group, an imidazolidinyl group, a 2-oxoimidazolidinyl group, a 2-oxopiperidinyl group, a 2-oxopiperidino group, a morpholinyl group, a morpholino group, a 2-oxomorpholino group, a piperazinyl group, a piperazino group, a 2-oxopiperazino group, a hexahydro-2-oxo-1,3-oxazinyl group and the like are preferable.

The "—C(=O)—NR$^{b3}$R$^{b4}$ wherein R$^{b3}$ and R$^{b4}$ are the same or different and each is a hydrogen atom or a C$_{1-6}$ alkyl group optionally substituted by the same or different 1 to 5 substituents selected from group B" in the specification is represented by the following formula

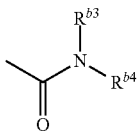

wherein R$^{b3}$ and R$^{b4}$ are the same or different and each is a hydrogen atom or a C$_{1-6}$ alkyl group optionally substituted by the same or different 1 to 5 substituents selected from group B.

Specific examples thereof include

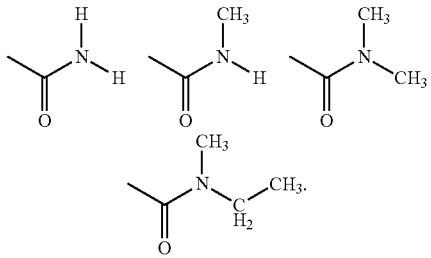

Furthermore, the "—C(=O)—NR$^{b5}$—OR$^{b6}$ wherein R$^{b5}$ and R$^{b6}$ are the same or different and each is a hydrogen atom or a C$_{1-6}$ alkyl group optionally substituted by the same or different 1 to 5 substituents selected from group B" is represented by the following formula

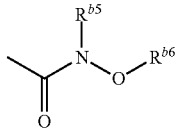

wherein R$^{b5}$ and R$^{b6}$ are the same or different and each is a hydrogen atom or a C$_{1-6}$ alkyl group optionally substituted by the same or different 1 to 5 substituents selected from group B.

Specific examples thereof include

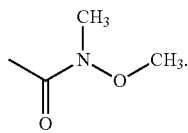

Preferable embodiment of each group of the compound represented by the formula [I] (hereinafter to be sometimes abbreviated as compound [I]) is explained in the following.

R$^a$

R$^a$ is (1) a hydrogen atom, or (2) a halogen atom, preferably, a hydrogen atom, a fluorine atom or a chlorine atom, more preferably, a hydrogen atom.

R$^b$

Preferable embodiments of R$^b$ are classified into the following type A and type B.

[Type A]

A type wherein R$^b$ is a group represented by the following formula:

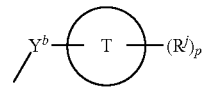

wherein each symbol is as defined above. When X$^d$ is C—R$^d$, compound [I] is represented by the formula [IV]

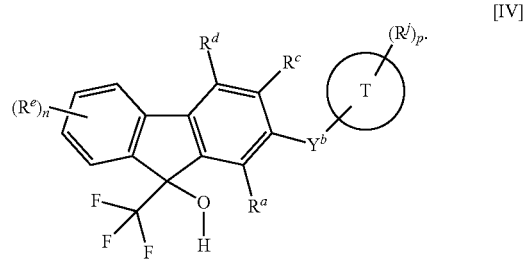

[Type B]

A type wherein R$^b$ is (1) a hydrogen atom,
(2) a halogen atom,
(3) a C$_{1-6}$ alkyl group optionally substituted by the same or different 1 to 5 substituents selected from group A,
(4) a C$_{2-6}$ alkenyl group optionally substituted by the same or different 1 to 5 substituents selected from group C,
(5) a C$_{2-6}$ alkynyl group optionally substituted by the same or different 1 to 5 substituents selected from group C,
(6) a cyano group,
(7) —C(=O)—R$^{b1}$ wherein R$^{b1}$ is a hydrogen atom or a C$_{1-6}$ alkyl group optionally substituted by the same or different 1 to 5 substituents selected from group B,
(8) —C(=O)—OR$^{b2}$ wherein R$^{b2}$ is a hydrogen atom or a C$_{1-6}$ alkyl group optionally substituted by the same or different 1 to 5 substituents selected from group B,
(9) —C(=O)—NR$^{b3}$R$^{b4}$ wherein R$^{b3}$ and R$^{b4}$ are the same or different and each is a hydrogen atom or a C$_{1-6}$ alkyl group optionally substituted by the same or different 1 to 5 substituents selected from group B,
(10) —C(=O)—NR$^{b5}$—OR$^{b6}$ wherein R$^{b5}$ and R$^{b6}$ are the same or different and each is a hydrogen atom or a C$_{1-6}$ alkyl group optionally substituted by the same or different 1 to 5 substituents selected from group B,
(11) —OR$^{b7}$ wherein R$^{b7}$ is a hydrogen atom or a C$_{1-6}$ alkyl group optionally substituted by the same or different 1 to 5 substituents selected from group B,
(12) —NR$^{b8}$R$^{b9}$ wherein R$^{b8}$ and R$^{b9}$ are the same or different and each is a hydrogen atom or a C$_{1-6}$ alkyl group optionally substituted by the same or different 1 to 5 substituents selected from group B,
(13) —NR$^{b10}$—C(=O)—R$^{b11}$ wherein R$^{b10}$ and R$^{b11}$ are the same or different and each is a hydrogen atom or a C$_{1-6}$ alkyl group optionally substituted by the same or different 1 to 5 substituents selected from group B,
(14) —NR$^{b12}$—C(=O)—OR$^{b13}$ wherein R$^{b12}$ is a hydrogen atom or a C$_{1-6}$ alkyl group optionally substituted by the same or different 1 to 5 substituents selected from group B, and $R^{b13}$ is a $C_{1-6}$ alkyl group optionally substituted by the same or different 1 to 5 substituents selected from group B, or

(15) —O—C(=O)—NR$^{b14}$R$^{b15}$ wherein R$^{14}$ and R$^{b15}$ are the same or different and each is a hydrogen atom or a $C_{1-6}$ alkyl group optionally substituted by the same or different 1 to 5 substituents selected from group B.

Preferable embodiments of type A and type B are explained in the following.

[Type A1]

As $Y^b$, preferred is
(i) a single bond,
(ii) a alkylene (particularly, methylene, trimethylene),
(iii) a $C_{2-3}$ alkenylene (particularly, vinylene),
(iv) —O—(CH$_2$)$_{n1}$— wherein n1 is an integer of 0, or 1 to 4 (particularly, 0, or 1 to 3),
(v) —O—(CH$_2$)$_{n2}$—C(=O)— wherein n2 is an integer of 0, or 1 to 4 (particularly, 1),
(vi) —C(=O)—, or
(vii) —NR$^{b16}$— wherein R$^{b16}$ is a hydrogen atom or a $C_{1-6}$ alkyl group (particularly, a methyl group);
more preferably, a single bond, —O—CH$_2$—, —O—(CH$_2$)$_2$—, —O—CH$_2$—C(=O)—, or —C(=O)—.

As ring T, preferred is
(i) a $C_{6-10}$ aryl group,
(ii) a $C_{3-6}$ cycloalkyl group,
(iii) a $C_{5-10}$ bridged cycloalkyl group,
(iv) a monocyclic aromatic heterocyclic group which contains, besides carbon atom, 1 to 4 hetero atoms selected from a nitrogen atom, an oxygen atom and a sulfur atom, and 5 or 6 ring-constituting atoms, or
(v) a monocyclic non-aromatic heterocyclic group which contains, besides carbon atom, 1 or 2 hetero atoms selected from a nitrogen atom, an oxygen atom and a sulfur atom, and 3 or 6 ring-constituting atoms;
more preferred is
(i) a phenyl group,
(ii) a $C_{3-6}$ cycloalkyl group (particularly, a cyclopropyl group, a cyclobutyl group, a cyclopentyl group, a cyclohexyl group),
(iii) an adamantyl group,
(iv) a monocyclic aromatic heterocyclic group selected from a thiazolyl group, a pyridyl group, a thienyl group, an oxazolyl group, a 1,2,4-oxadiazolyl group, a pyrazolyl group, a tetrazolyl group, and a pyrimidinyl group, or
(v) a monocyclic non-aromatic heterocyclic group selected from a piperidino group, a pyrrolidino group, an azetidinyl group, an aziridinyl group, a morpholino group, a piperazino group, a 2-oxopyrrolidino group, a 2-oxopiperidino group, a 2-oxopyrrolidin-5-yl group, a 2-oxo-1,3-oxazolidin-3-yl group, a 3-oxomorpholino group, a 1,1-dioxoisothiazolidinyl group, a 2-oxoimidazolidinyl group and a hexahydro-2-oxo-1,3-oxazinyl group.

$R^j$ is preferably,
(1) a halogen atom,
(2) a $C_{1-6}$ alkyl group optionally substituted by the same or different 1 to 5 substituents selected from group E,
(3) a $C_{1-6}$ alkyl group substituted by a $C_{3-10}$ cycloalkyl optionally substituted by the same or different 1 to 5 substituents selected from group F,
(4) a cyano group,
(5) —C(=O)—R$^{D1}$ wherein R$^{D1}$ is a hydrogen atom, a $C_{1-6}$ alkyl group optionally substituted by the same or different 1 to 5 substituents selected from group E, or a monocyclic non-aromatic heterocyclic group optionally substituted by the same or different 1 to 5 substituents selected from group F (the monocyclic non-aromatic heterocyclic group contains, besides carbon atom, 1 to 4 hetero atoms selected from a nitrogen atom, an oxygen atom and a sulfur atom, and has 3 to 7 ring-constituting atoms),
(6) —C(=O)—OR$^{D2}$ wherein R$^{D2}$ is a hydrogen atom, or a $C_{1-6}$ alkyl group optionally substituted by the same or different 1 to 5 substituents selected from group E,
(7) —C(=O)—NR$^{D3}$R$^{D4}$ wherein R$^{D3}$ and R$^{D4}$ are the same or different and each is a hydrogen atom, or a $C_{1-6}$ alkyl group optionally substituted by the same or different 1 to 5 substituents selected from group E,
(8) —OR$^{D7}$ wherein R$^{D7}$ is a hydrogen atom, or a $C_{1-6}$ alkyl group optionally substituted by the same or different 1 to 5 substituents selected from group E,
(9) —NR$^{D8}$R$^{D9}$ wherein R$^{D8}$ and R$^{D9}$ are the same or different and each is a hydrogen atom, or a $C_{1-6}$ alkyl group optionally substituted by the same or different 1 to 5 substituents selected from group E, or
(10) —NR$^{D10}$—C(=O)—R$^{D11}$ wherein R$^{D10}$ and R$^{D11}$ are the same or different and each is a hydrogen atom, or a $C_{1-6}$ alkyl group optionally substituted by the same or different 1 to 5 substituents selected from group E, more preferably,
(1) a halogen atom (particularly, a fluorine atom, a chlorine atom),
(2) a $C_{1-6}$ alkyl group (particularly, a methyl group, an ethyl group, a propyl group, an isopropyl group, an isobutyl group, a tert-butyl group, a neopentyl group) optionally substituted by the same or different 1 to 5 substituents selected from group E (particularly, a hydroxy group, a methoxymethoxy group, a carboxyl group, a carbamoyl group),
(3) a $C_{1-6}$ alkyl group substituted by a $C_{3-10}$ cycloalkyl (particularly, a cyclohexylmethyl group),
(4) a cyano group,
(5) —C(=O)—R$^{D1}$ wherein R$^{D1}$ is a hydrogen atom, a $C_{1-6}$ alkyl group (particularly, a methyl group, an ethyl group, an isopropyl group, a tert-butyl group), or a monocyclic non-aromatic heterocyclic group which contains besides carbon atom, 1 to 4 hetero atoms selected from a nitrogen atom, an oxygen atom and a sulfur atom, and has 3 to 7 ring-constituting atoms (particularly, a pyrrolidino group, a piperidino group, a 4-hydroxypiperidino group, a 3-hydroxypyrrolidino group),
(6) —C(=O)—OR$^{D2}$ wherein R$^{D2}$ is a hydrogen atom, or a $C_{1-6}$ alkyl group (particularly, a methyl group, an ethyl group, an isopropyl group, a tert-butyl group),
(7) —C(=O)—NR$^{D3}$R$^{D4}$ wherein R$^{D3}$ and R$^{D4}$ are the same or different and each is a hydrogen atom, or a $C_{1-6}$ alkyl group (particularly, a methyl group, an ethyl group),
(8) —OR$^{D7}$ wherein R$^{D7}$ is a hydrogen atom, or a $C_{1-6}$ alkyl group (particularly, a methyl group, an ethyl group, a propyl group) optionally substituted by the same or different 1 to 5 substituents selected from group E (particularly, a methoxy group, a carboxy group, a hydroxy group, a methoxycarbonyl group, a carbamoyl group, a methylcarbamoyl group, a dimethylcarbamoyl group),
(9) —NR$^{D8}$R$^{D9}$ wherein R$^{D8}$ and R$^{D9}$ are the same or different and each is a hydrogen atom, or a $C_{1-6}$ alkyl group (particularly, a methyl group), or
(10) —NR$^{D10}$—C(=O)—R$^{D11}$ wherein R$^{D10}$ and R$^{D11}$ are the same or different and each is a hydrogen atom, or a $C_{1-6}$ alkyl group (particularly, a methyl group).

Specifically preferable examples of R$^j$ include a fluorine atom, a chlorine atom, a methyl group, an ethyl group, an isopropyl group, an isobutyl group, a tert-butyl group, a neopentyl group, a hydroxy group, a hydroxymethyl group, a 2-hydroxyethyl group, a 3-hydroxypropyl group, a 2-hydroxy-2-methylpropyl group, a carboxymethyl group, a carbamoylmethyl group, a 2-carboxyethyl group, a 2-carbamoylethyl group, a cyclohexylmethyl group, a cyano group, an acetyl group, a propionyl group, an isobutyryl group, a 2,2-dimethylpropionyl group, a pyrrolidinocarbonyl group, a piperidinocarbonyl group, a 4-hydroxypiperidinocarbonyl group, a 3-hydroxypyrrolidinocarbonyl group, a carboxyl group, a methoxycarbonyl group, an ethoxycarbonyl group, an isopropoxycarbonyl group, a tert-butoxycarbonyl group, a carbamoyl group, a methylcarbamoyl group, a dimethylcarbamoyl group, a diethylcarbamoyl group, a methoxy group, an ethoxy group, a propoxy group, a 2-methoxyethoxy group, a 2-hydroxyethoxy group, a carboxymethoxy group, a methoxycarbonylmethoxy group, a carbamoylmethoxy group, a methylcarbamoylmethoxy group, a dimethylcarbamoylmethoxy group, an amino group, a methylamino group, a dimethylamino group, an acetylamino group, an N-methyl-N-acetylamino group, a 2-(methoxymethoxy)ethyl group and the like.

p is an integer of 0, or 1 to 4, preferably, an integer of 0, or 1 to 3.

In type A, specifically preferable examples of $R^b$ include a phenyl group, a 2-fluorophenyl group, a 3-fluorophenyl group, a 4-fluorophenyl group, a 2-chlorophenyl group, a 3-chlorophenyl group, a 4-chlorophenyl group, a 3,5-dichlorophenyl group, a 2-methylphenyl group, a 3-methylphenyl group, a 4-methylphenyl group, a 2-(hydroxymethyl)phenyl group, a 4-(hydroxymethyl)phenyl group, a 4-hydroxyphenyl group, a 2-methoxyphenyl group, a 3-methoxycarbonylphenyl group, a 4-methoxyphenyl group, a 3-chloro-4-methoxyphenyl group, a 3-chloro-4-methoxycarbonylphenyl group, a 2-carboxyphenyl group, a 3-carboxyphenyl group, a 4-carboxyphenyl group, a 2-ethoxycarbonylphenyl group, a 4-ethoxycarbonylphenyl group, a 4-(tert-butoxycarbonyl)phenyl group, a 3-carbamoylphenyl group, a 3-(methylcarbamoyl)phenyl group, a 3-(dimethylcarbamoyl)phenyl group, a 2-carbamoylphenyl group, a 2-(methylcarbamoyl)phenyl group, a 2-(dimethylcarbamoyl)phenyl group, a 4-carbamoylphenyl group, a 4-(methylcarbamoyl)phenyl group, a 4-(dimethylcarbamoyl)phenyl group, a 3-chloro-4-carboxyphenyl group, a 3-chloro-4-carbamoylphenyl group, a 3-chloro-4-(methylcarbamoyl)phenyl group, a 3-chloro-4-(dimethylcarbamoyl)phenyl group, a 4-aminophenyl group, a 2-(acetylamino)phenyl group, a 4-(acetylamino)phenyl group, a 3-cyanophenyl group, a 4-cyanophenyl group, a benzyl group, a 2-phenylethenyl group, a benzoyl group, a phenoxy group, a phenylamino group, an N-phenyl-N-methylamino group, a benzyloxy group, a cyclopropyl group, a cyclohexyl group, a cyclobutoxy group, a cyclopentyloxy group, a cyclohexyloxy group, a cyclobutanecarbonyl group, a cyclopentanecarbonyl group, a cyclopropylmethyloxy group, a cyclobutylmethyloxy group, a cyclopentylmethyloxy group, a cyclohexylmethyloxy group, a 2-(adamantan-1-yl)ethoxy group, a 2-(3-hydroxyadamantan-1-yl)ethoxy group, a 2-pyridyl group, a 3-pyridyl group, a 4-pyridyl group, a 2-thienyl group, a 3-thienyl group, a 2-methyl-4-pyridyl group, a 5-pyrimidinyl group, a 5-oxazolyl group, a 3-methyl-1,2,4-oxadiazol-5-yl group, a 1-methyl-pyrazol-4-yl group, a 1,3,5-trimethyl-pyrazol-4-yl group, a 1-ethyl-pyrazol-4-yl group, a 1-isopropyl-pyrazol-4-yl group, a 1-isobutyl-pyrazol-4-yl group, a 1-tert-butyl-pyrazol-4-yl group, a 1-neopentyl-pyrazol-4-yl group, a 1-carboxymethyl-pyrazol-4-yl group, a 1-(2-hydroxyethyl)-pyrazol-4-yl group, a 1-carbamoylmethyl-pyrazol-4-yl group, a 1-(2-carboxyethyl)-pyrazol-4-yl group, a 1-(2-carbamoylethyl)-pyrazol-4-yl group, a 1-(2-hydroxy-2-methylpropyl)-pyrazol-4-yl group, a 1-cyclohexylmethyl-pyrazol-4-yl group, a pyrazol-1-yl group, a 2-thienylcarbonyl group, a 2-thienylmethyloxy group, a pyrazol-1-ylmethyl group, a 3-(2-oxopyrrolidino)propyl group, a 3-(tetrazol-5-yl)propoxy group, a 2-oxopyrrolidino group, a pyrrolidino group, a piperidino group, a morpholino group, a piperazino group, a 2-methylpyrrolidino group, a 3-methylpyrrolidino group, a 4-carboxypiperidino group, a 4-methylpiperazino group, a 4-acetylpiperazino group, a 4-propionylpiperazino group, a 4-isobutyrylpiperazino group, a 4-(2,2-dimethylpropionyl)piperazino group, a 4-(tert-butoxycarbonyl)piperazino group, a 4-(methoxycarbonyl)piperazino group, a 4-(ethoxycarbonyl)piperazino group, a 4-(isopropoxycarbonyl)piperazino group, an aziridinocarbonyl group, an azetidinocarbonyl group, a piperidinocarbonyl group, a pyrrolidinocarbonyl group, a morpholinocarbonyl group, a 2-methylazetidinocarbonyl group, a 3-methylazetidinocarbonyl group, a 3-hydroxyazetidinocarbonyl group, a 3-hydroxymethylazetidinocarbonyl group, a 3-methoxyazetidinocarbonyl group, a 3-ethoxyazetidinocarbonyl group, a 3-propoxyazetidinocarbonyl group, a 3-(2-methoxyethoxy)azetidinocarbonyl group, a 3-(2-hydroxyethoxy)azetidinocarbonyl group, a 3-(carboxymethoxy)azetidinocarbonyl group, a 3-(methoxycarbonylmethoxy)azetidinocarbonyl group, a 3-(carbamoylmethoxy)azetidinocarbonyl group, a 3-(methylcarbamoylmethoxy)azetidinocarbonyl group, a 3-(dimethylcarbamoylmethoxy)azetidinocarbonyl group, a 2-methoxycarbonylazetidinocarbonyl group, a 2-carboxyazetidinocarbonyl group, a 2-(ethylcarbamoyl)azetidinocarbonyl group, a 2-(propylcarbamoyl)azetidinocarbonyl group, a 3-methoxycarbonylazetidinocarbonyl group, a 3-carboxyazetidinocarbonyl group, a 3-carbamoylazetidinocarbonyl group, a 3-(methylcarbamoyl)azetidinocarbonyl group, a 3-(dimethylcarbamoyl)azetidinocarbonyl group, a 3-dimethylaminoazetidinocarbonyl group, a 3-(diethylcarbamoyl)azetidinocarbonyl group, a 3-(pyrrolidinocarbonyl)azetidinocarbonyl group, a 3-(3-hydroxypyrrolidinocarbonyl)azetidinocarbonyl group, a 3-(piperidinocarbonyl)azetidinocarbonyl group, a 3-(4-hydroxypiperidinocarbonyl)azetidinocarbonyl group, a 2-methylpyrrolidinocarbonyl group, a 3-hydroxypyrrolidinocarbonyl group, a 2-methoxycarbonylpyrrolidinocarbonyl group, a 3-methoxycarbonylpyrrolidinocarbonyl group, a 2-carboxypyrrolidinocarbonyl group, a 3-carboxypyrrolidinocarbonyl group, a 2-carbamoylpyrrolidinocarbonyl group, a 2-(methylcarbamoyl)pyrrolidinocarbonyl group, a 2-(dimethylcarbamoyl)pyrrolidinocarbonyl group, a 3-carbamoylpyrrolidinocarbonyl group, a 3-(methylcarbamoyl)pyrrolidinocarbonyl group, a 3-(dimethylcarbamoyl)pyrrolidinocarbonyl group, a 2-(hydroxymethyl)pyrrolidinocarbonyl group, a 3-(hydroxymethyl)pyrrolidinocarbonyl group, a 3-methylaminopyrrolidinocarbonyl group, a 3-dimethylaminopyrrolidinocarbonyl group, a 3-(N-acetyl-N-methylamino)pyrrolidinocarbonyl group, a 4-hydroxypiperidinocarbonyl group, a 4-methoxycarbonylpiperidinocarbonyl group, a 4-methoxycarbonylpiperidino group, a 4-ethoxycarbonylpiperidinocarbonyl group, a 4-ethoxycarbonylpiperidino group, a 4-carboxypiperidinocarbonyl group, a 4-carbamoylpiperidinocarbonyl group, a 4-carbamoylpiperidino group, a 4-(methylcarbamoyl)piperidinocarbonyl group, a 4-(methylcarbamoyl)piperidino group, a 4-(dimethylcarbamoyl)piperidinocarbonyl group, a 4-(dimethylcarbamoyl)piperidino group, a 4-(hydroxymethyl)piperidinocarbonyl group, a 2-(2-oxopyrrolidino)ethoxy group, a 2-(5-hydroxymethyl-2-oxopyrrolidino)ethoxy group, a 3-(2-oxopyrrolidino)propoxy group, a 2-(2-oxopiperidino)ethoxy group, a 3-(2-oxopiperidino)propoxy group, a 2-(2-oxo-1,3-oxazolidin-3-yl)ethoxy group, a 2-(1,1-dioxoisothiazolidin-2-yl)ethoxy group, a 2-(2-oxo-imidazolidin-1-yl)ethoxy group, a 2-(hexahydro-2-oxo-1,3-ox-azin-3-yl)ethoxy group, a 2-(3-oxomorpholino)ethoxy group, a (2-oxopyrrolidin-5-yl)methoxy group, an (1-methyl-2-oxopyrrolidin-5-yl)methoxy group, an (1-(3-hydroxypropyl)-2-oxopyrrolidin-5-yl)methoxy group, an (1-(2-(methoxymethoxy)ethyl)-2-oxopyrrolidin-5-yl)methoxy group, an (1-(2-hydroxyethyl)-2-oxopyrrolidin-5-yl)methoxy group, an azetidinocarbonylmethoxy group, a pyrrolidinocarbonylmethoxy group, a piperidinocarbonylmethoxy group, a morpholinocarbonylmethoxy group, a (3-hydroxyazetidino)carbonylmethoxy group, a (3-hydroxymethylazetidino)carbonylmethoxy group, a (2-hydroxymethylpyrrolidino)carbonylmethoxy group, a (3-hydroxypyrrolidino)carbonylmethoxy group, a (4-hydroxypiperidino)carbonylmethoxy group, a (4-hydroxymethylpiperidino)carbonylmethoxy group and the like.

Specific structural formulas of $R^b$ in type A are as follows.

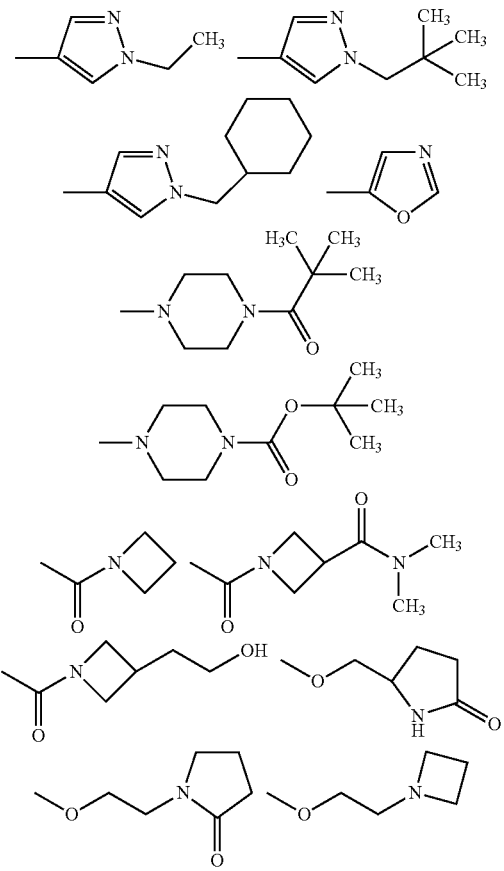

[Type B]
In type B, preferable examples of $R^b$ include
(1) a hydrogen atom,
(2) a halogen atom (particularly, a fluorine atom, a chlorine atom, a bromine atom),
(3) a $C_{1-6}$ alkyl group (particularly, a methyl group, an ethyl group, a propyl group, an isopropyl group, an isobutyl group, an isopentyl group, a neopentyl group, a 3,3-dimethylbutyl group) optionally substituted by the same or different 1 to 5 substituents selected from group A [particularly,
(i) —C(=O)—OR$^{A2}$ wherein R$^{A2}$ is a hydrogen atom or a $C_{1-6}$ alkyl group (particularly, a methyl group),
(ii) —C(=O)—NR$^{A3}$R$^{A4}$ wherein R$^{A3}$ and R$^{A4}$ are the same or different and each is a hydrogen atom or a $C_{1-6}$ alkyl group,
(iii) —OR$^{A7}$ wherein R$^{A7}$ is a hydrogen atom or a $C_{1-6}$ alkyl group (particularly, a methyl group),
(iv) —NR$^{A8}$R$^{A9}$ wherein R$^{A8}$ and R$^{A9}$ are the same or different and each is a hydrogen atom or a $C_{1-6}$ alkyl group (particularly, a methyl group),
(v) —NR$^{A10}$—C(=O)—R$^{A11}$ wherein R$^{A10}$ and R$^{A11}$ are the same or different and each is a hydrogen atom or a $C_{1-6}$ alkyl group (particularly, a methyl group), and
(vi) —Si—(CH$_2$—CH$_3$)$_3$]
(particularly, a hydroxy group, a methoxy group, a carboxy group, a methoxycarbonyl group, a carbamoyl group, an acetylamino group, a methylamino group, an N-acetyl-N-methylamino group, a triethylsilyl group),
(4) a $C_{2-6}$ alkenyl group (particularly, a 1-propenyl group, a 2-methyl-1-propenyl group),
(5) a $C_{2-6}$ alkynyl group (particularly, an ethynyl group),
(6) a cyano group,
(7) —C(=O)—R$^{b1}$ wherein R$^{b1}$ is a hydrogen atom or a $C_{1-6}$ alkyl group (particularly, a methyl group),
(8) —C(=O)—OR$^{b2}$ wherein R$^{b2}$ is a hydrogen atom or a $C_{1-6}$ alkyl group (particularly, a methyl group),
(9) —C(=O)—NR$^{b3}$R$^{b4}$ wherein R$^{b3}$ and R$^{b4}$ are the same or different and each is a hydrogen atom or a $C_{1-6}$ alkyl group (particularly, a methyl group, an ethyl group, a propyl group, a butyl group) optionally substituted by the same or different 1 to 5 substituents selected from group B (particularly, a hydroxy group),
(10) —OR$^{b7}$ wherein R$^{b7}$ is a hydrogen atom or a $C_{1-6}$ alkyl group (particularly, a methyl group, an ethyl group, a propyl group, an isopropyl group, a butyl group, an isobutyl group, a tert-butyl group, a pentyl group, an isopentyl group, a neopentyl group, a hexyl group) optionally substituted by the same or different 1 to 5 substituents selected from group B [particularly,
(i) —C(=O)—OR$^{B2}$ wherein R$^{B2}$ is a hydrogen atom or a $C_{1-6}$ alkyl group (particularly, a methyl group, an ethyl group),
(ii) —C(=O)—NR$^{B3}$R$^{B4}$ wherein R$^{B3}$ and R$^{B4}$ are the same or different and each is a hydrogen atom or a $C_{1-6}$ alkyl group (particularly, a methyl group, an ethyl group) optionally substituted by the same or different 1 to 5 substituents selected from group C (particularly, a hydroxy group, a carboxyl group),
(iii) —OR$^{B7}$ wherein R$^{B7}$ is a hydrogen atom or a $C_{1-6}$ alkyl group,
(iv) —NR$^{B8}$R$^{B9}$ wherein R$^{B8}$ and R$^{B9}$ are the same or different and each is a hydrogen atom or a $C_{1-6}$ alkyl group (particularly, a methyl group) optionally substituted by the same or different 1 to 5 substituents selected from group C (particularly, a carboxyl group),
(v) —NR$^{B10}$—C(=O)—R$^{B11}$ wherein R$^{10}$ and R$^{B11}$ are the same or different and each is a hydrogen atom or a $C_{1-6}$ alkyl group (particularly, a methyl group, an ethyl group, an isopropyl group, a tert-butyl group) optionally substituted by the same or different 1 to 5 substituents selected from group C (particularly, a hydroxy group, a carboxyl group, a trifluoroacetyl group),
(vi) —NR$^{B12}$—S(=O)$_2$—R$^{B13}$ wherein R$^{B12}$ and R$^{B13}$ are the same or different and each is a hydrogen atom or a $C_{1-6}$ alkyl group (particularly, a methyl group), and
(vii) —NR$^{B14}$—C(=O)—OR$^{B15}$ wherein R$^{B14}$ is a hydrogen atom or a $C_{1-6}$ alkyl group (particularly, a methyl group, a tert-butyl group), and R$^{B15}$ is a $C_{1-6}$ alkyl group (particularly, a methyl group, a tert-butyl group)]

(particularly, a carboxyl group, a methoxycarbonyl group, an ethoxycarbonyl group, a hydroxy group, a carbamoyl group, a methylcarbamoyl group, a dimethylcarbamoyl group, an amino group, a methylamino group, a dimethylamino group, a tert-butoxycarbonylamino group, an acetylamino group, an N-tert-butoxycarbonyl-N-methylamino group, an N-acetyl-N-methylamino group, an N-hydroxyacetyl-N-methylamino group, an N-acetyl-N-(2-hydroxyethyl)amino group, an N-(2-hydroxyethyl)carbamoyl group, an N-(2-hydroxyethyl)-N-methylcarbamoyl group, an N,N-bis(2-hydroxyethyl)carbamoyl group, an N-methyl-N-methanesulfonylamino group, an N-acetyl-N-(2-carboxyethyl)amino group, an N-carboxymethyl-N-methylamino group, an N-carboxymethyl-N-methylcarbamoyl group, an N-(2-carboxyethyl)-N-methylcarbamoyl group, a 3-(trifluoroacetyl)propionylamino group, an N-(2,2-dimethylpropionyl)-N-methylamino group, an N-(2,2-dimethyl-3-hydroxypropionyl)-N-methylamino group, an N-(2-hydroxy-2-methylpropionyl)-N-methylamino group),

(11) —$NR^{b8}R^{b9}$ wherein $R^{b8}$ and $R^{b9}$ are the same or different and each is a hydrogen atom or a $C_{1-6}$ alkyl group (particularly, a methyl group),

(12) —$NR^{b10}$—$C(=O)$—$R^{b11}$ wherein $R^{b10}$ and $Rb^{11}$ are the same or different and each is a hydrogen atom or a $C_{1-6}$ alkyl group (particularly, a methyl group), or

(13) —O—$C(=O)$—$NR^{b14}R^{b15}$ wherein $R^{b14}$ and $R^{b15}$ are the same or different and each is a hydrogen atom or a $C_{1-6}$ alkyl group (particularly, a methyl group).

In type B, specifically preferable examples of $R^b$ include, a hydrogen atom, a fluorine atom, a chlorine atom, a bromine atom, a cyano group, a methyl group, an ethyl group, a propyl group, an isopropyl group, an isobutyl group, a neopentyl group, a 3,3-dimethylbutyl group, a hydroxymethyl group, a methoxymethyl group, a 2-hydroxyethyl group, a 2-hydroxy-2-methylpropyl group, a 3-hydroxy-3-methylbutyl group, a 4-hydroxy-3,3-dimethylbutyl group, a methoxycarbonylmethyl group, a carboxymethyl group, a carbamoylmethyl group, an acetylaminomethyl group, a methylaminomethyl group, an N-acetyl-N-methylaminomethyl group, a (triethylsilyl)ethyl group, a 1-propenyl group, a 2-methyl-1-propenyl group, an ethynyl group, an acetyl group, a carboxyl group, a methoxycarbonyl group, a carbamoyl group, a methylcarbamoyl group, an ethylcarbamoyl group, a propylcarbamoyl group, a dimethylcarbamoyl group, a diethylcarbamoyl group, an N-methyl-N-ethylcarbamoyl group, an N-(2-hydroxyethyl)carbamoyl group, an N-(2-hydroxyethyl)-N-methylcarbamoyl group, an N-methyl-N-propylcarbamoyl group, an N-(3-hydroxypropyl)carbamoyl group, an N-(3-hydroxypropyl)-N-methylcarbamoyl group, an N-butyl-N-methylcarbamoyl group, an N-(4-hydroxybutyl) carbamoyl group, an N-(4-hydroxybutyl)-N-methylcarbamoyl group, a hydroxy group, a methoxy group, an ethoxy group, a propoxy group, an isopropoxy group, a butoxy group, an isobutoxy group, a pentoxy group, an isopentoxy group, a neopentoxy group, a hexyloxy group, a carboxymethoxy group, a methoxycarbonylmethoxy group, a carbamoylmethoxy group, a methylcarbamoylmethoxy group, a dimethylcarbamoylmethoxy group, a (2-hydroxyethyl)carbamoylmethoxy group, a bis(2-hydroxyethyl)carbamoylmethoxy group, an N-(2-hydroxyethyl)-N-methylcarbamoylmethoxy group, an N-carboxymethyl-N-methylcarbamoylmethoxy group, a 2-hydroxyethoxy group, a 2-carboxyethoxy group, a 2-hydroxy-1,1-dimethylethoxy group, a 2-carbamoylethoxy group, a 1-carbamoylethoxy group, a 2-(methylcarbamoyl)ethoxy group, a 2-(dimethylcarbamoyl)ethoxy group, a 2-aminoethoxy group, a 2-(methylamino)ethoxy group, a 2-(dimethylamino)ethoxy group, a 2-(tert-butoxycarbonylamino)ethoxy group, a 2-(N-tert-butoxycarbonyl-N-methylamino)ethoxy group, a 2-(acetylamino)ethoxy group, a 2-(N-acetyl-N-methylamino) ethoxy group, a 2-(N-hydroxyacetyl-N-methylamino)ethoxy group, a 2-(N-acetyl-N-(2-hydroxyethyl)amino)ethoxy group, a 2-(N-acetyl-N-methylamino)-1-methylethoxy group, a 2-(N-acetyl-N-methylamino)-2-methylethoxy group, a 2-(N-methanesulfonyl-N-methylamino)-2-methylethoxy group, a 2-(N-methanesulfonyl-N-methylamino)ethoxy group, a 2-(N-acetyl-N-(2-carboxyethyl)amino)ethoxy group, a 2-(N-carboxymethyl-N-methylamino)ethoxy group, a 2-(4-oxo-5,5,5-trifluoropentanoylamino)ethoxy group, a 2-(N-(2,2-dimethylpropionyl)-N-methylamino)ethoxy group, a 2-(N-(2,2-dimethyl-3-hydroxypropionyl)-N-methylamino)ethoxy group, a 2-(N-(2-methyl-2-hydroxypropionyl)-N-methylamino)ethoxy group, a 2-hydroxy-1-(hydroxymethyl)ethoxy group, a 3-hydroxypropoxy group, a 3-ethoxycarbonylpropoxy group, a 3-carboxypropoxy group, a 3-carbamoylpropoxy group, a 3-(methylcarbamoyl)propoxy group, a 3-(dimethylcarbamoyl)propoxy group, a 3-aminopropoxy group, a 3-(methylamino)propoxy group, a 3-(dimethylamino)propoxy group, a 3-(acetylamino)propoxy group, a 3-(N-acetyl-N-methylamino)propoxy group, a 3-(N-acetyl-N-methylamino)-2-hydroxypropoxy group, a 2-(N-acetyl-N-methylamino)propoxy group, a 2,3-dihydroxypropoxy group, a 2-(hydroxymethyl)-3-hydroxypropoxy group, a 2-hydroxy-2-methylpropoxy group, a 3-hydroxy-2,2-dimethylpropoxy group, a 4-hydroxybutoxy group, a 4-ethoxycarbonylbutoxy group, a 3-carboxybutoxy group, a 4-carboxybutoxy group, a 4-carbamoylbutoxy group, a 4-(methylcarbamoyl)butoxy group, a 4-(dimethylcarbamoyl) butoxy group, a 5-hydroxypentoxy group, a 5-carboxypentoxy group, a 6-hydroxyhexyloxy group, an amino group, a dimethylamino group, a methylamino group, an acetylamino group, an N-acetyl-N-methylamino group, a dimethylaminocarbonyloxy group and the like.

$R^c$ $R^c$ is (1) a hydrogen atom, (2) a halogen atom, (3) a $C_{1-6}$ alkyl group, (4) —$C(=O)$—$OR^{c1}$ wherein $R^{c1}$ is a hydrogen atom or a $C_{1-6}$ alkyl group, (5) —$OR^{c2}$ wherein $R^{c2}$ is a hydrogen atom or a $C_{1-6}$ alkyl group, (6) —$NR^{c3}R^{c4}$ wherein $R^{c3}$ and $R^{c4}$ are the same or different and each is a hydrogen atom or a $C_{1-6}$ alkyl group, or (7) —$NR^{c5}$—$C(=O)$—$R^{c6}$ wherein $R^{c5}$ and $R^{c6}$ are the same or different and each is a hydrogen atom or a $C_{1-6}$ alkyl group.

As $R^c$, preferred is (1) a hydrogen atom, (2) a halogen atom (particularly, a fluorine atom, a chlorine atom), (3) a methyl group, (4) —$C(=O)$—$OR^{c1}$ wherein $R^{c1}$ is a hydrogen atom or a methyl group, (5) —$OR^{c2}$ wherein $R^{c2}$ is a hydrogen atom, a methyl group or an ethyl group, (6) —$NH_2$, or (7) —$NR^{c5}$—$C(=O)$—$R^{c6}$ wherein $R^{c5}$ and $R^{c6}$ are the same or different and each is a hydrogen atom or a $C_{1-6}$ alkyl group (particularly, a methyl group, an ethyl group, an isopropyl group), particularly preferably, a hydrogen atom.

Specifically preferable examples of $R^c$ include a hydrogen atom, a fluorine atom, a chlorine atom, a methyl group, a hydroxy group, a methoxy group, an ethoxy group, an amino group, an acetylamino group, a propionylamino group, an isobutyrylamino group, a carboxyl group, a methoxycarbonyl group and the like.

$X^d$

Preferable embodiments of $X^d$ are classified into the following type C to type E.

[Type C]

A type wherein $X^d$ is C—$R^d$, and $R^d$ is a group represented by the following formula:

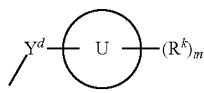

wherein each symbol is as defined above. In this case, compound [I] is represented by the formula [II]

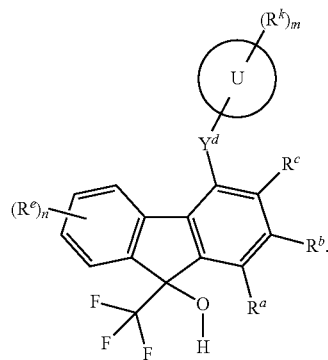

[II]

[Type D]

A type wherein $X^d$ is C—$R^d$, and $R^d$ is
(i) a hydrogen atom,
(ii) a halogen atom,
(iii) a $C_{1-6}$ alkyl group optionally substituted by the same or different 1 to 5 substituents selected from group A,
(iv) a $C_{2-6}$ alkenyl group optionally substituted by the same or different 1 to 5 substituents selected from group C,
(v) a $C_{2-6}$ alkynyl group optionally substituted by the same or different 1 to 5 substituents selected from group C,
(vi) a cyano group,
(vii) —C(=O)—$R^{d1}$ wherein $R^{d1}$ is a hydrogen atom or a $C_{1-6}$ alkyl group optionally substituted by the same or different 1 to 5 substituents selected from group B,
(viii) —C(=O)—O$R^{d2}$ wherein $R^{d2}$ is a hydrogen atom or a $C_{1-6}$ alkyl group optionally substituted by the same or different 1 to 5 substituents selected from group B,
(ix) —C(=O)—NR$^{d3}$R$^{d4}$ wherein $R^{d3}$ and 10 are the same or different and each is a hydrogen atom or a $C_{1-6}$ alkyl group optionally substituted by the same or different 1 to 5 substituents selected from group B,
(x) —C(=O)—NR$^{d5}$—OR$^{d6}$ wherein $R^{d5}$ and $R^{d6}$ are the same or different and each is a hydrogen atom or a $C_{1-6}$ alkyl group optionally substituted by the same or different 1 to 5 substituents selected from group B,
(xi) —OR$^{d7}$ wherein $R^{d7}$ is a hydrogen atom or a $C_{1-6}$ alkyl group optionally substituted by the same or different 1 to 5 substituents selected from group B,
(xii) —NR$^{d8}$R$^{d9}$ wherein $R^{d8}$ and $R^{d9}$ are the same or different and each is a hydrogen atom or a $C_{1-6}$ alkyl group optionally substituted by the same or different 1 to 5 substituents selected from group B,
(xiii) —NR$^{d10}$—C(=O)—$R^{d11}$ wherein $R^{d10}$ and $R^{d11}$ are the same or different and each is a hydrogen atom or a $C_{1-6}$ alkyl group optionally substituted by the same or different 1 to 5 substituents selected from group B, or
(xiv) —NR$^{d12}$—C(=O)—OR$^{d13}$ wherein $R^{d12}$ is a hydrogen atom or a $C_{1-6}$ alkyl group optionally substituted by the same or different 1 to 5 substituents selected from group B, and $R^{d13}$ is a $C_{1-6}$ alkyl group optionally substituted by the same or different 1 to 5 substituents selected from group B.

[Type E]

In this type, $X^d$ is a nitrogen atom.

In this case, compound [I] is represented by the formula [V]

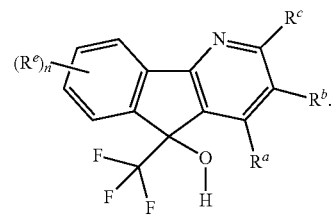

[V]

Preferable embodiment of type C is explained in the following.

[Type C]

As $Y^d$, preferred is
(I) a single bond, or
(II) —C(=O)—,
more preferred is a single bond.

As ring U, preferred is
(I) a $C_{6-10}$ aryl group,
(II) a $C_{3-10}$ cycloalkyl group,
(III) a monocyclic aromatic heterocyclic group which contains, besides carbon atom, 1 to 4 hetero atoms selected from a nitrogen atom, an oxygen atom and a sulfur atom, and has 3 to 7 ring-constituting atoms, or
(IV) a monocyclic non-aromatic heterocyclic group which contains, besides carbon atom, 1 to 4 hetero atoms selected from a nitrogen atom, an oxygen atom and a sulfur atom, and has 3 to 7 ring-constituting atoms,
more preferred is
(I) a phenyl group,
(II) a cyclopropyl group,
(III) a monocyclic aromatic heterocyclic group selected from an oxazolyl group, a pyridyl group, a 1,3,4-oxadiazolyl group, a 1,2,4-oxadiazolyl group, a tetrazolyl group, a pyrazolyl group, a pyrimidinyl group, a thienyl group, a 1,2,4-triazolyl group, or
(IV) an aziridinyl group.

$R^k$ is preferably
(1) a $C_{1-6}$ alkyl group optionally substituted by the same or different 1 to 5 substituents selected from group E,
(2) a $C_{1-6}$ alkyl group substituted by a $C_{6-10}$ aryl group optionally substituted by the same or different 1 to 5 substituents selected from group F,
(3) a $C_{1-6}$ alkyl group substituted by a $C_{3-10}$ cycloalkyl optionally substituted by the same or different 1 to 5 substituents selected from group F,
(4) a $C_{1-6}$ alkyl group substituted by a $C_{5-10}$ bridged cycloalkyl optionally substituted by the same or different 1 to 5 substituents selected from group F, (5) a $C_{1-6}$ alkyl group substituted by a monocyclic aromatic heterocyclic group optionally substituted by the same or different 1 to 5 $C_{1-6}$ alkyl groups (the monocyclic aromatic heterocyclic group contains, besides carbon atom, 1 to 4 hetero atoms selected from a nitrogen atom, an oxygen atom and a sulfur atom, and has 3 to 7 ring-constituting atoms), (6) a $C_{3-10}$ cycloalkyl group optionally substituted by the same or different 1 to 5 substituents selected from group F, or (7) a $C_{5-10}$ bridged cycloalkyl group optionally substituted by the same or different 1 to 5 substituents selected from group F, more preferably, (1) a —$C_{1-6}$ alkyl group (particularly, a methyl group, an ethyl group, a propyl group, an isopropyl group, a butyl group, an isobutyl group, a tert-butyl group, a neopentyl group, a 1,1-dimethylpropyl group, a 1-ethylpropyl group, a 1,1,2-trimethylpropyl group) optionally substituted by the same or different 1 to 5 substituents selected from group E (particularly, a halogen atom (particularly, a fluorine atom), a hydroxy group, a carboxyl group, a carbamoyl group, a methylcarbamoyl group, an ethylcarbamoyl group, an isopropylcarbamoyl group, a dimethylcarbamoyl group, an acetylamino group, an N-acetyl-N-methylamino group, a methanesulfonylamino group, a cyano group), (2) a $C_{1-6}$ alkyl group substituted by a $C_{6-10}$ aryl group (particularly, a benzyl group), (3) a $C_{1-6}$ alkyl group substituted by a $C_{3-10}$ cycloalkyl (particularly, a cyclohexylmethyl group) optionally substituted by the same or different 1 to 5 substituents selected from group F (particularly, a hydroxy group), (4) a $C_{1-6}$ alkyl group substituted by a $C_{5-10}$ bridged cycloalkyl (particularly, an adamantan-1-ylmethyl group) optionally substituted by the same or different 1 to 5 substituents selected from group F (particularly, a hydroxy group), (5) a $C_{1-6}$ alkyl group (particularly, a propyl group) substituted by a monocyclic aromatic heterocyclic group which contains, besides carbon atom, 1 to 4 hetero atoms selected from a nitrogen atom, an oxygen atom and a sulfur atom, and has 3 to 7 ring-constituting atoms (particularly, tetrazolyl) (particularly, a 3-(5-tetrazolyl)propyl group) optionally substituted by the same or different 1 to 5 $C_{1-6}$ alkyl groups (particularly, a methyl group), (6) a $C_{3-10}$ cycloalkyl group, (particularly, a cyclohexyl group, a cyclopentyl group) optionally substituted by the same or different 1 to 5 substituents selected from group F (particularly, a hydroxymethyl group, a carboxyl group), (7) a $C_{5-10}$ bridged cycloalkyl group (particularly, a 1-adamantyl group).

Specifically preferable examples of $R^k$ include a methyl group, an ethyl group, an isopropyl group, an isobutyl group, a tert-butyl group, a neopentyl group, a 2-hydroxyethyl group, a 3-hydroxypropyl group, a 2,3-dihydroxypropyl group, a 2-hydroxy-1-(hydroxymethyl)ethyl group, a carboxymethyl group, a carbamoylmethyl group, a methylcarbamoylmethyl group, an ethylcarbamoylmethyl group, an isopropylcarbamoylmethyl group, a dimethylcarbamoylmethyl group, a 2-carboxyethyl group, a 2-carbamoylethyl group, a 2-(methylcarbamoyl)ethyl group, a 2-(dimethylcarbamoyl)ethyl group, a 2-(acetylamino)ethyl group, a 2-(N-acetyl-N-methylamino)ethyl group, a 2-hydroxy-1,1-dimethylethyl group, a 2-hydroxy-1-(hydroxymethyl)-1-methylethyl group, a 1-carbamoyl-1-methylethyl group, a 1-methylcarbamoyl-1-methylethyl group, a 1-dimethylcarbamoyl-1-methylethyl group, a 2-hydroxy-1,1-bis(hydroxymethyl)ethyl group, a 3-hydroxy-2-(hydroxymethyl)propyl group, a 2-hydroxy-2-methylpropyl group, a 2-hydroxy-1,1,2-trimethylpropyl group, a 2-hydroxy-3,3,3-trifluoropropyl group, a 3-methanesulfonylaminopropyl group, a 3-(5-tetrazolyl)propyl group, a 3-(1-methyl-5-tetrazolyl)propyl group, a 3-(2-methyl-5-tetrazolyl)propyl group, a 1,1-bis(hydroxymethyl)propyl group, a 3-hydroxy-1-(2-hydroxyethyl)propyl group, a 3-carboxypropyl group, a 4-carboxybutyl group, a 1-carboxy-1-methylethyl group, a 2-carboxy-2-methylpropyl group, a 2-carboxy-1,1-dimethylethyl group, a cyanomethyl group, a benzyl group, an (1-hydroxycyclohexyl)methyl group, a 3-hydroxyadamantan-1-ylmethyl group, a 1-hydroxymethylcyclohexyl group, a 1-hydroxymethylcyclopentyl group, a 1-carboxycyclopentyl group, a 1-adamantyl group and the like.

m is an integer of 0, or 1 to 4, preferably, an integer of 0, or 1 to 3.

Specifically preferable examples of $R^d$ include a phenyl group, a cyclopropyl group, a cyclopropanecarbonyl group, an oxazol-5-yl group, a 2-methyl-oxazol-5-yl group, an oxazol-2-yl group, a 2-(2-hydroxy-1-(hydroxymethyl)ethyl)-oxazol-5-yl group, a 2-pyridyl group, a 3-pyridyl group, a 4-methyl-3-pyridyl group, a 6-methyl-3-pyridyl group, a 4-pyridyl group, a 1,3,4-oxadiazol-2-yl group, a 5-methyl-1,3,4-oxadiazol-2-yl group, a 3-methyl-1,2,4-oxadiazol-5-yl group, a 5-methyl-1,2,4-oxadiazol-3-yl group, a 3-(2-hydroxy-1-(hydroxymethyl)ethyl)-1,2,4-oxadiazol-5-yl group, a 2-methyl-5-tetrazolyl group, a 1-methyl-5-tetrazolyl group, a pyrazol-4-yl group, a 1-methyl-pyrazol-4-yl group, a 1,3,5-trimethyl-pyrazol-4-yl group, a 1-ethyl-pyrazol-4-yl group, a 1-isopropyl-pyrazol-4-yl group, a 1-isobutyl-pyrazol-4-yl group, a 1-tert-butyl-pyrazol-4-yl group, a 1-neopentyl-pyrazol-4-yl group, a 1-benzyl-pyrazol-4-yl group, a 1-(adamantan-1-yl)-pyrazol-4-yl group, a 1-(2-hydroxyethyl)-pyrazol-4-yl group, a 1-(3-hydroxypropyl)-pyrazol-4-yl group, a 1-(2-(acetylamino)ethyl)-pyrazol-4-yl group, a 1-(2-(N-acetyl-N-methylamino)ethyl)-pyrazol-4-yl group, a 1-carboxymethyl-pyrazol-4-yl group, a 1-carbamoylmethyl-pyrazol-4-yl group, a 1-methylcarbamoylmethyl-pyrazol-4-yl group, a 1-dimethylcarbamoylmethyl-pyrazol-4-yl group, a 1-ethylcarbamoylmethyl-pyrazol-4-yl group, a 1-isopropylcarbamoylmethyl-pyrazol-4-yl group, a 1-(2-carboxyethyl)-pyrazol-4-yl group, a 1-(2-carbamoylethyl)-pyrazol-4-yl group, a 1-(2-(methylcarbamoyl)ethyl)-pyrazol-4-yl group, a 1-(2-(dimethylcarbamoyl)ethyl)-pyrazol-4-yl group, a 1-(3-carboxypropyl)-pyrazol-4-yl group, a 1-(4-carboxybutyl)-pyrazol-4-yl group, a 5-pyrimidinyl group, a 3-thienyl group, a 3-methyl-1,2,4-triazol-5-yltriazolyl group, a 3-methyl-1,2,4-triazol-5-yl group, a 1-(1-hydroxycyclohexylmethyl)-pyrazol-4-yl group, a 1-(1-(hydroxymethyl)cyclohexyl)-pyrazol-4-yl group, a 1-(1-(hydroxymethyl)cyclopentyl)-pyrazol-4-yl group, a 1-(1-(3-hydroxyadamantan-1-ylmethyl)-pyrazol-4-yl group, a 1-(1-carboxycyclohexyl)-pyrazol-4-yl group, a 1-(1-carboxycyclopentyl)-pyrazol-4-yl group, a 1-(2,3-dihydroxypropyl)-pyrazol-4-yl group, a 1-(1-carboxy-1-methylethyl)-pyrazol-4-yl group, a 1-(2-carboxy-2-methylpropyl)-pyrazol-4-yl group, a 1-(2-carboxy-1,1-dimethylethyl)-pyrazol-4-yl group, a 1-(2-hydroxy-1,1-dimethylethyl)-pyrazol-4-yl group, a 1-(2-hydroxy-1-(hydroxymethyl)ethyl)-pyrazol-4-yl group, a 1-(2-hydroxy-1-(hydroxymethyl)-1-methylethyl)-pyrazol-4-yl group, a 1-(1-carbamoyl-1-methylethyl)-pyrazol-4-yl group, a 1-(1-methylcarbamoyl-1-methylethyl)-pyrazol-4-yl group, a 1-(1-dimethylcarbamoyl-1-methylethyl)-pyrazol-4-yl group, a 1-(2-hydroxy-1,1-bis(hydroxymethyl)ethyl)-pyrazol-4-yl group, a 1-(3-hydroxy-2-(hydroxymethyl)propyl)-pyrazol-4-yl group, a 1-(2-hydroxy-2-methylpropyl)-pyrazol-4-yl group, a 1-(2-hydroxy-1,1,2-trimethylpropyl)-pyrazol-4-yl group, a 1-(2-hydroxy-3,3,3-trifluoropropyl)-pyrazol-4-yl group, a 1-(3-methanesulfonylaminopropyl)-pyrazol-4-yl group, a 1-(3-(5-tetrazolyl)propyl)-pyrazol-4-yl group, a 1-(3-(1-methyl-5-tetrazolyl)propyl)-pyrazol-4-yl group, a 1-(3-(2-methyl-5-tetrazolyl)propyl)-pyrazol-4-yl group, a 1-(1,1-bis(hydroxymethyl)propyl)-pyrazol-4-yl group, a 1-(3-hydroxy-1-(2-hydroxyethyl)propyl)-pyrazol-4-yl group, an aziridinocarbonyl group and the like.

Ring U is preferably a monocyclic aromatic heterocyclic group.

Furthermore, a compound wherein $Y^d$ is a single bond is preferable, and more preferred is a pyrazolyl group (particularly, a pyrazol-4-yl group) or a pyrimidinyl group (particularly, a pyrimidin-5-yl group) for ring U.

Still more preferred is a compound represented by the following formula, which is a compound wherein ring U is a pyrazol-4-yl group:

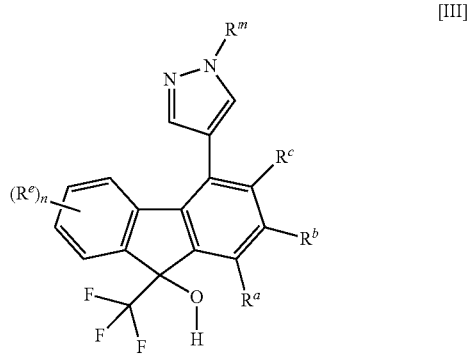

[III]

wherein
$R^m$ is
(1) a $C_{1-6}$ alkyl group optionally substituted by the same or different 1 to 5 substituents selected from group E,
(2) a $C_{1-6}$ alkyl group substituted by a $C_{6-10}$ aryl group optionally substituted by the same or different 1 to 5 substituents selected from group F,
(3) a $C_{1-6}$ alkyl group substituted by a $C_{3-10}$ cycloalkyl optionally substituted by the same or different 1 to 5 substituents selected from group F,
(4) a $C_{1-6}$ alkyl group substituted by a $C_{5-10}$ bridged cycloalkyl optionally substituted by the same or different 1 to 5 substituents selected from group F,
(5) a $C_{1-6}$ alkyl group substituted by a monocyclic aromatic heterocyclic group optionally substituted by the same or different 1 to 5 $C_{1-6}$ alkyl groups (the monocyclic aromatic heterocyclic group contains, besides carbon atom, 1 to 4 hetero atoms selected from a nitrogen atom, an oxygen atom and a sulfur atom, and has 3 to 7 ring-constituting atoms),
(6) a $C_{3-10}$ cycloalkyl optionally substituted by the same or different 1 to 5 substituents selected from group F, or
(7) a $C_{5-10}$ bridged cycloalkyl optionally substituted by the same or different 1 to 5 substituents selected from group F, and other symbols are as defined above.

Here, as $R^m$, preferred is
(1) a $C_{1-6}$ alkyl group (particularly, a methyl group, an ethyl group, a propyl group, an isopropyl group, a butyl group, an isobutyl group, a tert-butyl group, a neopentyl group, a 1,1-dimethylpropyl group, a 1-ethylpropyl group, a 1,1,2-trimethylpropyl group) optionally substituted by the same or different 1 to 5 substituents selected from
  (i) a halogen atom (particularly, a fluorine atom),
  (ii) —C(=O)—OR$^{E2}$ wherein R$^{E2}$ is a hydrogen atom or a $C_{1-6}$ alkyl group (particularly, a methyl group) optionally substituted by the same or different 1 to 5 substituents selected from group F,
  (iii) —C(=O)—NR$^{E3}$R$^{E4}$ wherein R$^{E3}$ and R$^{E4}$ are the same or different and each is a hydrogen atom or a $C_{1-6}$ alkyl group (particularly, a methyl group, an ethyl group, an isopropyl group) optionally substituted by the same or different 1 to 5 substituents selected from group F,
  (iv) —OR$^{E7}$ wherein R$^{E7}$ is a hydrogen atom or a $C_{1-6}$ alkyl group (particularly, a methyl group) optionally substituted by the same or different 1 to 5 substituents selected from group F,
  (v) —NR$^{E12}$—C(=O)—R$^{E13}$ wherein R$^{E12}$ and R$^{E13}$ are the same or different and each is a hydrogen atom or a $C_{1-6}$ alkyl group (particularly, a methyl group) optionally substituted by the same or different 1 to 5 substituents selected from group F, and
  (vi) —NR$^{E16}$—S(=O)$_2$—R$^{E17}$ wherein R$^{E16}$ and R$^{E17}$ are the same or different and each is a hydrogen atom or a $C_{1-6}$ alkyl group (particularly, a methyl group),
(2) a $C_{1-6}$ alkyl group substituted by a $C_{6-10}$ aryl group (particularly, a benzyl group),
(3) a $C_{1-6}$ alkyl group substituted by a $C_{3-10}$ cycloalkyl (particularly, a cyclohexylmethyl group) optionally substituted by the same or different 1 to 5 substituents selected from group F (particularly, a hydroxy group),
(4) a $C_{1-6}$ alkyl group substituted by a $C_{5-10}$ bridged cycloalkyl (particularly, an adamantan-1-ylmethyl group) optionally substituted by the same or different 1 to 5 substituents selected from group F (particularly, a hydroxy group),
(5) a $C_{1-6}$ alkyl group (particularly, a propyl group) substituted by a monocyclic aromatic heterocyclic group which contains, besides carbon atom, 1 to 4 hetero atoms selected from a nitrogen atom, an oxygen atom and a sulfur atom, and has 3 to 7 ring-constituting atoms (particularly, tetrazolyl) (particularly, a 3-(5-tetrazolyl)propyl group) optionally substituted by the same or different 1 to 5 $C_{1-6}$ alkyl groups (particularly, a methyl group),
(6) a $C_{3-10}$ cycloalkyl group (particularly, a cyclohexyl group, a cyclopentyl group) optionally substituted by the same or different 1 to 5 substituents selected from group F (particularly, a hydroxy group, a hydroxymethyl group, a carboxyl group), and
(7) a $C_{5-10}$ bridged cycloalkyl group (particularly, an adamantyl group) optionally substituted by the same or different 1 to 5 substituents selected from group F.

Specifically preferable examples of $R^m$ include a methyl group, an ethyl group, an isopropyl group, an isobutyl group, a tert-butyl group, a neopentyl group, a 1-benzyl group, an adamantan-1-yl group, a 2-hydroxyethyl group, a 3-hydroxypropyl group, a 2-(acetylamino)ethyl group, a 2-(N-acetyl-N-methylamino)ethyl group, a carboxymethyl group, a carbamoylmethyl group, a methylcarbamoylmethyl group, a dimethylcarbamoylmethyl group, an ethylcarbamoylmethyl group, an isopropylcarbamoylmethyl group, a 2-carboxyethyl group, a 2-carbamoylethyl group, a 2-(methylcarbamoyl)ethyl group, a 2-(dimethylcarbamoyl)ethyl group, a 3-carboxypropyl group, a 4-carboxybutyl group, a 1-hydroxycyclohexylmethyl group, a 1-(hydroxymethyl)cyclohexyl group, a 1-(hydroxymethyl)cyclopentyl group, a (3-hydroxyadamantan-1-yl)methyl group, a 1-carboxycyclohexyl group, a 1-carboxycyclopentyl group, a 2,3-dihydroxypropyl group, a 1-carboxy-1-methylethyl group, a 2-carboxy-2-methylpropyl group, a 2-carboxy-1,1-dimethylethyl group, a 2-hydroxy-1-(hydroxymethyl)ethyl group, a 3-hydroxy-2-(hydroxymethyl)propyl group, a 2-hydroxy-1,1-dimethylethyl group, a 2-hydroxy-1-(hydroxymethyl)-1-methylethyl group, a 1-carbamoyl-1-methylethyl group, a 1-methylcarbamoyl-1-methylethyl group, a 1-dimethylcarbamoyl-1-methylethyl group, a 2-hydroxy-1,1-bis(hydroxymethyl)ethyl group, a 2-hydroxy-2-methylpropyl group, a 2-hydroxy-1,1,2-trimethylpropyl group, a 2-hydroxy-3,3,3-trifluoropropyl group, a 3-methanesulfonylaminopropyl group, a 3-(5-tetrazolyl)propyl group, a 3-(1-methyl-5-tetrazolyl)propyl group, a 3-(2-methyl-5-tetrazolyl)propyl group, a 1,1-bis(hydroxymethyl)propyl group, a 3-hydroxy-1-(2-hydroxyethyl)propyl group and the like.

In other embodiments, as $R^m$, preferred is
(1) a $C_{1-6}$ alkyl group optionally substituted by the same or different 1 to 5 substituents selected from group E',
(2) a $C_{1-6}$ alkyl group substituted by a $C_{3-10}$ cycloalkyl optionally substituted by the same or different 1 to 5 substituents selected from group F,
(3) a $C_{1-6}$ alkyl group substituted by a $C_{5-10}$ bridged cycloalkyl optionally substituted by the same or different 1 to 5 substituents selected from group F,
(4) a $C_{3-10}$ cycloalkyl optionally substituted by the same or different 1 to 5 substituents selected from group F, or
(5) a $C_{5-10}$ bridged cycloalkyl optionally substituted by the same or different 1 to 5 substituents selected from group F,
more preferred is,
(1) a $C_{1-6}$ alkyl group (particularly, a methyl group, an ethyl group, a propyl group, an isopropyl group, a butyl group, an isobutyl group, a tert-butyl group, a neopentyl group) optionally substituted by the same or different 1 to 5 substituents selected from
(i) —C(=O)—OR$^{E2}$ wherein R$^{E2}$ is a hydrogen atom or a $C_{1-6}$ alkyl group (particularly, a methyl group) optionally substituted by the same or different 1 to 5 substituents selected from group F,
(ii) —C(=O)—NR$^{E3}$R$^{E4}$ wherein R$^{E3}$ and R$^{E4}$ are the same or different and each is a hydrogen atom or a $C_{1-6}$ alkyl group (particularly, a methyl group, an ethyl group, an isopropyl group) optionally substituted by the same or different 1 to 5 substituents selected from group F,
(iii) —OR$^{E7}$ wherein R$^{E7}$ is a hydrogen atom or a $C_{1-6}$ alkyl group (particularly, a methyl group) optionally substituted by the same or different 1 to 5 substituents selected from group F, and
(iv) —NR$^{E12}$—C(=O)—R$^{E13}$ wherein R$^{E12}$ and R$^{E13}$ are the same or different and each is a hydrogen atom or a $C_{1-6}$ alkyl group (particularly, a methyl group) optionally substituted by the same or different 1 to 5 substituents selected from group F,
(2) a $C_{3-10}$ cycloalkyl group (particularly, a cyclohexyl group, a cyclopentyl group) optionally substituted by the same or different 1 to 5 substituents selected from group F (particularly, a hydroxy group, a hydroxymethyl group, a carboxyl group), or
(3) a $C_{5-10}$ bridged cycloalkyl group (particularly, an adamantyl group) optionally substituted by the same or different 1 to 5 substituents selected from group F,
and further preferably,
(1) a $C_{1-6}$ alkyl group (particularly, a methyl group, an ethyl group, a propyl group, an isopropyl group, a butyl group, an isobutyl group, a tert-butyl group, a neopentyl group) optionally substituted by the same or different 1 to 5 substituents selected from
(i) —C(=O)—OR$^{E2}$ wherein R$^{E2}$ is a hydrogen atom or a $C_{1-6}$ alkyl group (particularly, a methyl group) optionally substituted by the same or different 1 to 5 substituents selected from group F, and
(ii) —OR$^{E7}$ wherein R$^{E7}$ is a hydrogen atom or a $C_{1-6}$ alkyl group (particularly, a methyl group) optionally substituted by the same or different 1 to 5 substituents selected from group F,
(2) a $C_{3-10}$ cycloalkyl group (particularly, a cyclohexyl group, a cyclopentyl group) optionally substituted by the same or different 1 to 5 substituents selected from group F (particularly, a hydroxy group, a hydroxymethyl group, a carboxyl group), or
(3) a $C_{5-10}$ bridged cycloalkyl group (particularly, a 1-adamantyl group) optionally substituted by the same or different 1 to 5 substituents selected from group F.

In the above-mentioned formula [III],
$R^c$ is preferably a hydrogen atom;
$R^b$ is preferably
(1) a hydrogen atom,
(2) a halogen atom,
(3) a $C_{1-6}$ alkyl group optionally substituted by the same or different 1 to 5 substituents selected from group A,
(4) a $C_{2-6}$ alkenyl group optionally substituted by the same or different 1 to 5 substituents selected from group C,
(5) a $C_{2-6}$ alkynyl group optionally substituted by the same or different 1 to 5 substituents selected from group C,
(6) a cyano group,
(7) —C(=O)—R$^{b1}$ wherein R$^{b1}$ is a hydrogen atom or a $C_{1-6}$ alkyl group optionally substituted by the same or different 1 to 5 substituents selected from group B,
(8) —C(=O)—OR$^{b2}$ wherein R$^{b2}$ is a hydrogen atom or a $C_{1-6}$ alkyl group optionally substituted by the same or different 1 to 5 substituents selected from group B,
(9) —C(=O)—NR$^{b3}$R$^{b4}$ wherein R$^{b3}$ and R$^{b4}$ are the same or different and each is a hydrogen atom or a $C_{1-6}$ alkyl group optionally substituted by the same or different 1 to 5 substituents selected from group B,
(10) —C(=O)—NR$^{b5}$—OR$^{b6}$ wherein R$^{b5}$ and R$^{b6}$ are the same or different and each is a hydrogen atom or a $C_{1-6}$ alkyl group optionally substituted by the same or different 1 to 5 substituents selected from group B,
(11) —OR$^{b7}$ wherein R$^{b7}$ is a hydrogen atom or a $C_{1-6}$ alkyl group optionally substituted by the same or different 1 to 5 substituents selected from group B,
(12) —NR$^{b8}$R$^{b9}$ wherein R$^{b8}$ and R$^{b9}$ are the same or different and each is a hydrogen atom or a $C_{1-6}$ alkyl group optionally substituted by the same or different 1 to 5 substituents selected from group B,
(13) —NR$^{b10}$—C(=O)—R$^{b11}$ wherein R$^{b10}$ and R$^{b11}$ are the same or different and each is a hydrogen atom or a $C_{1-6}$ alkyl group optionally substituted by the same or different 1 to 5 substituents selected from group B,
(14) —NR$^{b12}$—C(=O)—OR$^{b13}$ wherein R$^{b12}$ is a hydrogen atom or a $C_{1-6}$ alkyl group optionally substituted by the same or different 1 to substituents selected from group B, and R$^{b13}$ is a $C_{1-6}$ alkyl group optionally substituted by the same or different 1 to 5 substituents selected from group B, or
(15) —O—C(=O)—NR$^{b14}$R$^{b15}$ wherein R$^{b14}$ and R$^{b15}$ are the same or different and each is a hydrogen atom or a $C_{1-6}$ alkyl group optionally substituted by the same or different 1 to 5 substituents selected from group B;
$R^a$ is preferably a hydrogen atom; and
n is preferably 0.

In addition, a compound wherein $Y^d$ is a single bond and ring U is a pyrimidin-5-yl group, which is represented by the following formula:

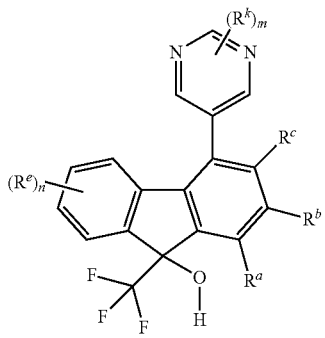

[VI]

wherein each symbol is as defined above,
is preferable.

Here, m is preferably 0;
$R^a$ is preferably a hydrogen atom; and
n is preferably 0.

In the following, a preferable embodiment of type D is explained.

[Type D]
$R^d$ is preferably
(i) a hydrogen atom,
(ii) a halogen atom (particularly, a fluorine atom, a chlorine atom, a bromine atom),
(iii) a alkyl group optionally substituted by the same or different 1 to 5 substituents selected from group A [particularly,
(1) a halogen atom (particularly, a fluorine atom),
(2) a cyano group,
(3) —C(=O)—NR$^{43}$R$^{44}$ wherein R$^{43}$ and R$^{44}$ are the same or different and each is a hydrogen atom or a C$_{1-6}$ alkyl group,
(4) —OR$^{47}$ wherein R$^{47}$ is a hydrogen atom or a C$_{1-6}$ alkyl group (particularly, a methyl group), and
(5) —NR$^{48}$R$^{49}$ wherein R$^{48}$ and R$^{49}$ are the same or different and each is a hydrogen atom or a C$_{1-6}$ alkyl group (particularly, a methyl group)] (particularly, a fluorine atom, a hydroxy group, a methoxy group, an amino group, a cyano group, a carbamoyl group) (particularly, a methyl group, an ethyl group, an isopropyl group, a trifluoromethyl group, an aminomethyl group),
(iv) a C$_{2-6}$ alkenyl group (particularly, a 1-methylvinyl group),
(v) a C$_{2-6}$ alkynyl group (particularly, an ethynyl group, a 3-hydroxy-1-propynyl group) optionally substituted by the same or different 1 to 5 substituents selected from group C (particularly, a hydroxy group),
(vi) a cyano group,
(vii) —C(=O)—R$^{d1}$ wherein R$^{d1}$ is a hydrogen atom or a C$_{1-6}$ alkyl group (particularly, a methyl group, an ethyl group, an isopropyl group),
(viii) —C(=O)—OR$^{d2}$ wherein R$^{d2}$ is a hydrogen atom or a C$_{1-6}$ alkyl group (particularly, a methyl group, an ethyl group, a propyl group, an isopropyl group),
(ix) —C(=O)—NR$^{d3}$R$^{d4}$ wherein R$^{c13}$ and R$^{c14}$ are the same or different and each is a hydrogen atom or a C$_{1-6}$ alkyl group (particularly, a methyl group),
(x) —C(=O)—NR$^{d5}$—OR$^{d6}$ wherein R$^{d5}$ and R$^{d6}$ are the same or different and each is a hydrogen atom or a C$_{1-6}$ alkyl group (particularly, a methyl group),
(xi) —OR$^{d7}$ wherein R$^{d7}$ is a hydrogen atom or a C$_{1-6}$ alkyl group (particularly, a methyl group, an ethyl group),
(xii) —NR$^{d8}$R$^{d9}$ wherein R$^{d8}$ and R$^{d9}$ are the same or different and each is a hydrogen atom or a C$_{1-6}$ alkyl group (particularly, a methyl group),
(xiii) —NR$^{d10}$—C(=O)—R$^{d11}$ wherein R$^{d10}$ and R$^{d11}$ are the same or different and each is a hydrogen atom or a C$_{1-6}$ alkyl group (particularly, a methyl group), or
(xiv) —NR$^{d12}$—C(=O)—OR$^{d13}$ wherein R$^{d12}$ is a hydrogen atom or a C$_{1-6}$ alkyl group (particularly, a methyl group), and R$^{d13}$ is a C$_{1-6}$ alkyl group (particularly, a methyl group).

In type D, specifically preferable examples of R$^d$ include a hydrogen atom, a fluorine atom, a chlorine atom, a bromine atom, a methyl group, an ethyl group, a hydroxymethyl group, a 1-hydroxyethyl group, a 2-hydroxyethyl group, a 1-hydroxy-1-methylethyl group, a methoxymethyl group, a trifluoromethyl group, an aminomethyl group, a cyanomethyl group, a carboxymethyl group, a carbamoylmethyl group, a 1-methylvinyl group, an ethynyl group, a 3-hydroxypropynyl group, a cyano group, an acetyl group, a propionyl group, an isobutyryl group, a carboxy group, a methoxycarbonyl group, an ethoxycarbonyl group, a propoxycarbonyl group, an isopropoxycarbonyl group, a carbamoyl group, a methylcarbamoyl group, a dimethylcarbamoyl group, an N-methyl-N-methoxycarbamoyl group, a hydroxy group, a methoxy group, an ethoxy group, an amino group, a methylamino group, a dimethylamino group, an acetylamino group, a methoxycarbonylamino group and the like.

As $X^d$, type C and type D are preferable, and type C is more preferable.

$R^e$ $R^e$ is preferably the same or different and each is
(1) a halogen atom (particularly, a chlorine atom, a fluorine atom), or
(2) a alkyl group (particularly, a methyl group) optionally substituted by the same or different 1 to 5 substituents (particularly, a hydroxy group) selected from group C; more preferably, a fluorine atom, a chlorine atom, a methyl group, a hydroxymethyl group and the like.

n n is an integer of 0, or 1 to 3, preferably an integer of 0, or 1 to 2, particularly preferably 0.

As preferable embodiment of the compound represented by the formula [I], a compound represented by the following formula can be mentioned.

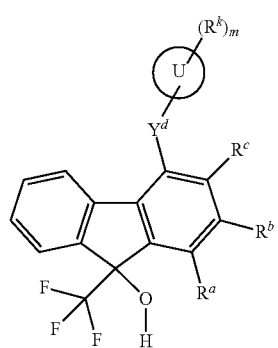

[II-C]

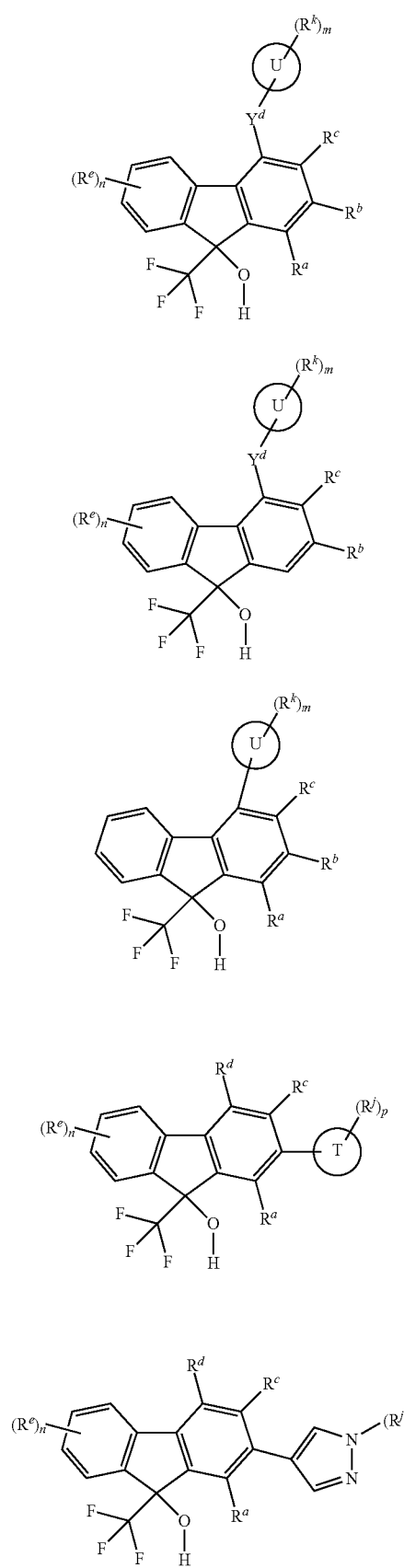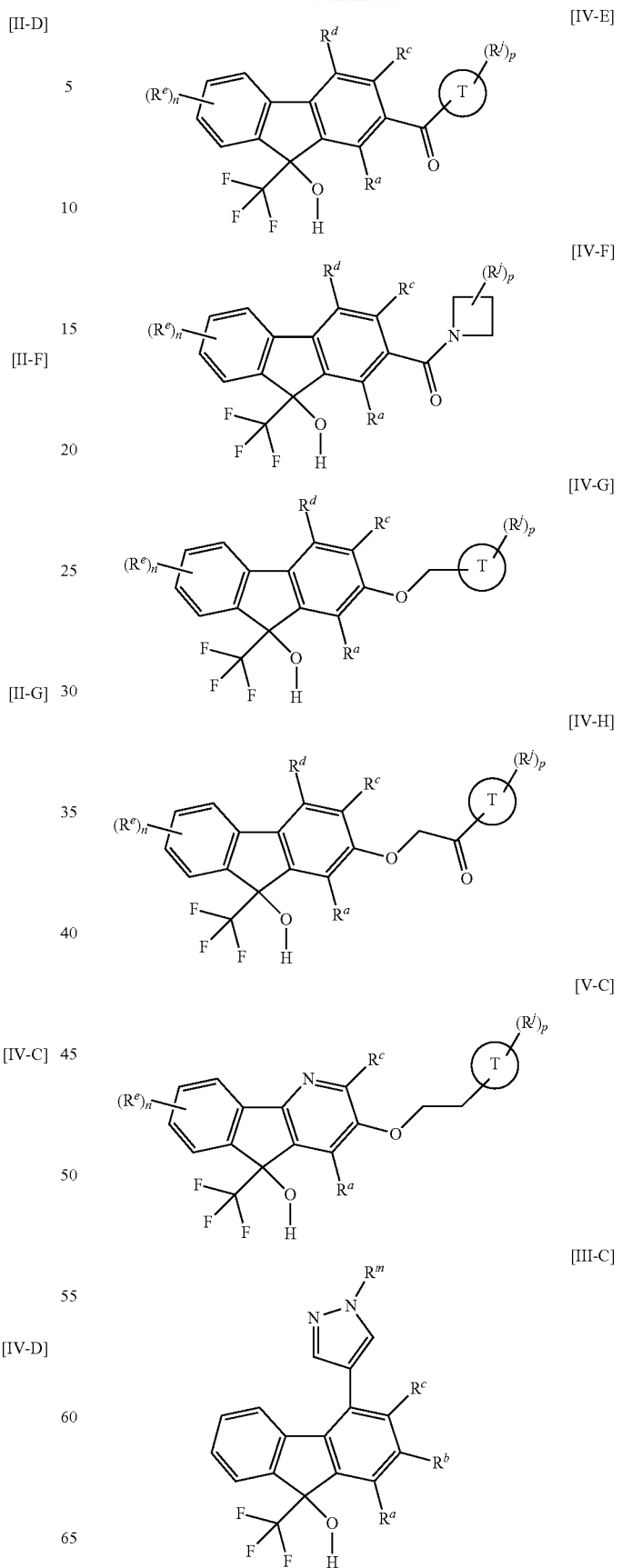

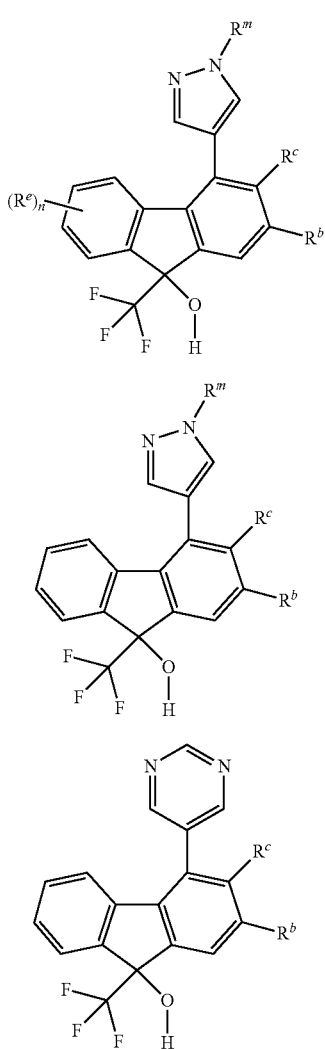

Here, as the compound represented by the formula [I], preferred is a compound represented by the formula [II], more preferred is a compound represented by the formula [III] or a compound represented by the formula [VI].

As a compound represented by the formula [III], preferred is the formula [III-E], and as a compound represented by the formula [VI], preferred is a compound represented by the formula [VI-A].

As a compound represented by the formula [IV], preferred is a compound represented by the formula [IV-D] or [IV-F].

As a compound represented by the formula [IV-D], preferred is a compound wherein $R^a$ is a hydrogen atom, $R^c$ is a hydrogen atom, $R^d$ is —$CH_3$, —$CH_2$—OH or —C(=O)—$NH_2$, and n=0.

As a compound represented by the formula [IV-F], preferred is a compound wherein $R^a$ is a hydrogen atom, $R^c$ is a hydrogen atom, $R^d$ is —$CH_3$, and n=0.

One example of preferable combination of each symbol in a compound represented by the formula [III] is explained in the following.

In a preferable combination, $R^a$ is a hydrogen atom, a fluorine atom or a chlorine atom, particularly a hydrogen atom, $R^b$ is
(1) a hydrogen atom,
(2) a halogen atom,
(3) a $C_{1-6}$ alkyl group optionally substituted by the same or different 1 to 5 substituents selected from group A,
(4) a $C_{2-6}$ alkenyl group optionally substituted by the same or different 1 to 5 substituents selected from group C,
(5) a $C_{2-6}$ alkynyl group optionally substituted by the same or different 1 to 5 substituents selected from group C,
(6) a cyano group,
(7) —C(=O)—$R^{b1}$ wherein $R^{b1}$ is a hydrogen atom or a $C_{1-6}$ alkyl group optionally substituted by the same or different 1 to 5 substituents selected from group B,
(8) —C(=O)—$OR^{b2}$ wherein $R^{b2}$ is a hydrogen atom or a $C_{1-6}$ alkyl group optionally substituted by the same or different 1 to 5 substituents selected from group B,
(9) —C(=O)—$NR^{b3}R^{b4}$ wherein $R^{b3}$ and $R^{b4}$ are the same or different and each is a hydrogen atom or a $C_{1-6}$ alkyl group optionally substituted by the same or different 1 to 5 substituents so selected from group B,
(10) —C(=O)—$NR^{b5}$—$OR^{b6}$ wherein $R^{b5}$ and $R^{b6}$ are the same or different and each is a hydrogen atom or a $C_{1-6}$ alkyl group optionally substituted by the same or different 1 to 5 substituents selected from group B,
(11) —$OR^{b7}$ wherein $R^{b7}$ is a hydrogen atom or a $C_{1-6}$ alkyl group optionally substituted by the same or different 1 to 5 substituents selected from group B,
(12) —$NR^{b8}R^{b9}$ wherein $R^{b8}$ and $R^{b9}$ are the same or different and each is a hydrogen atom or a $C_{1-6}$ alkyl group optionally substituted by the same or different 1 to 5 substituents selected from group B,
(13) —$NR^{b10}$—C(=O)—$R^{b11}$ wherein $R^{10}$ and $R^{11}$ are the same or different and each is a hydrogen atom or a $C_{1-6}$ alkyl group optionally substituted by the same or different 1 to 5 substituents selected from group B,
(14) —$NR^{b12}$—C(=O)—$OR^{b13}$ wherein $R^{b12}$ is a hydrogen atom or a $C_{1-6}$ alkyl group optionally substituted by the same or different 1 to 5 substituents selected from group B, and $R^{b13}$ is a $C_{1-6}$ alkyl group optionally substituted by the same or different 1 to 5 substituents selected from group B, or
(15) —O—C(=O)—$NR^{b14}R^{b15}$ wherein $R^{b14}$ and $R^{b15}$ are the same or different and each is a hydrogen atom or a $C_{1-6}$ alkyl group optionally substituted by the same or different 1 to 5 substituents selected from group B, particularly,
(1) a hydrogen atom,
(2) a halogen atom (particularly, a fluorine atom, a chlorine atom, a bromine atom),
(3) a $C_{1-6}$ alkyl group (particularly, a methyl group, an ethyl group, a propyl group, an isopropyl group, an isobutyl group, an isopentyl group, a neopentyl group, a 3,3-dimethylbutyl group) optionally substituted by the same or different 1 to 5 substituents selected from group A [particularly,
(i) —C(=O)—$OR^{42}$ wherein $R^{42}$ is a hydrogen atom or a $C_{1-6}$ alkyl group (particularly, a methyl group),
(ii) —C(=O)—$NR^{43}R^{44}$ wherein $R^{43}$ and $R^{44}$ are the same or different and each is a hydrogen atom or a $C_{1-6}$ alkyl group,
(iii) —$OR^{47}$ wherein $R^{47}$ is a hydrogen atom or a $C_{1-6}$ alkyl group (particularly, a methyl group),
(iv) —$NR^{48}R^{49}$ wherein $R^{48}$ and $R^{49}$ are the same or different and each is a hydrogen atom or a $C_{1-6}$ alkyl group (particularly, a methyl group),
(v) —$NR^{410}$—C(=O)—$R^{411}$ wherein $R^{410}$ and $R^{411}$ are the same or different and each is a hydrogen atom or a $C_{1-6}$ alkyl group (particularly, a methyl group), and (vi) —Si—(CH$_2$—CH$_3$)$_3$]
(particularly, a hydroxy group, a methoxy group, a carboxy group, a methoxycarbonyl group, a carbamoyl group, an acetylamino group, a methylamino group, an N-acetyl-N-methylamino group, a triethylsilyl group),
(4) a C$_{2-6}$ alkenyl group (particularly, a 1-propenyl group, a 2-methyl-1-propenyl group),
(5) a C$_{2-6}$ alkynyl group (particularly, an ethynyl group),
(6) a cyano group,
(7) —C(=O)—R$^{b1}$ wherein R$^{b1}$ is a hydrogen atom or a C$_{1-6}$ alkyl group (particularly, a methyl group),
(8) —C(=O)—OR$^{b2}$ wherein R$^{b2}$ is a hydrogen atom or a C$_{1-6}$ alkyl group (particularly, a methyl group),
(9) —C(=O)—NR$^{b3}$R$^{b4}$ wherein R$^{b3}$ and R$^{b4}$ are the same or different and each is a hydrogen atom or a C$_{1-6}$ alkyl group (particularly, a methyl group, an ethyl group, a propyl group, a butyl group) optionally substituted by the same or different 1 to 5 substituents selected from group B (particularly, a hydroxy group),
(10) —OR$^{b7}$ wherein R$^{b7}$ is a hydrogen atom or a C$_{1-6}$ alkyl group (particularly, a methyl group, an ethyl group, a propyl group, an isopropyl group, a butyl group, an isobutyl group, a tert-butyl group, a pentyl group, an isopentyl group, a neopentyl group, a hexyl group) optionally substituted by the same or different 1 to 5 substituents selected from group B [particularly,
(i) —C(=O)—OR$^{B2}$ wherein R$^{B2}$ is a hydrogen atom or a C$_{1-6}$ alkyl group (particularly, a methyl group, an ethyl group),
(ii) —C(=O)—NR$^{B3}$R$^{B4}$ wherein R$^{B3}$ and R$^{B4}$ are the same or different and each is a hydrogen atom or a C$_{1-6}$ alkyl group (particularly, a methyl group, an ethyl group) optionally substituted by the same or different 1 to 5 substituents selected from group C (particularly, a hydroxy group, a carboxyl group),
(iii) —OR$^{B7}$ wherein R$^{B7}$ is a hydrogen atom or a C$_{1-6}$ alkyl group,
(iv) —NR$^{B8}$R$^{B9}$ wherein R$^{B8}$ and R$^{B9}$ are the same or different and each is a hydrogen atom or a C$_{1-6}$ alkyl group (particularly, a methyl group) optionally substituted by the same or different 1 to 5 substituents selected from group C (particularly, a carboxyl group),
(v) —NR$^{B10}$—C(=O)—R$^{B11}$ wherein R$^{B10}$ and R$^{B11}$ are the same or different and each is a hydrogen atom or a C$_{1-6}$ alkyl group (particularly, a methyl group, an ethyl group, an isopropyl group, a tert-butyl group) optionally substituted by the same or different 1 to 5 substituents selected from group C (particularly, a hydroxy group, a carboxyl group, a trifluoroacetyl group),
(vi) —NR$^{B12}$—S(=O)$_2$—R$^{B13}$ wherein R$^{B12}$ and R$^{B13}$ are the same or different and each is a hydrogen atom or a C$_{1-6}$ alkyl group (particularly, a methyl group), and
(vii) —NR$^{B14}$—C(=O)—OR$^{B15}$ wherein R$^{B14}$ is a hydrogen atom or a C$_{1-6}$ alkyl group (particularly, a methyl group, a tert-butyl group), and R$^{B15}$ is a C$_{1-6}$ alkyl group (particularly, a methyl group, a tert-butyl group)]
(particularly, a carboxyl group, a methoxycarbonyl group, an ethoxycarbonyl group, a hydroxy group, a carbamoyl group, a methylcarbamoyl group, a dimethylcarbamoyl group, an amino group, a methylamino group, a dimethylamino group, a tert-butoxycarbonylamino group, an acetylamino group, an N-tert-butoxycarbonyl-N-methylamino group, an N-acetyl-N-methylamino group, an N-hydroxyacetyl-N-methylamino group, an N-acetyl-N-(2-hydroxyethyl)amino group, an N-(2-hydroxyethyl)carbamoyl group, an N-(2-hydroxyethyl)-N-methylcarbamoyl group, an N,N-bis(2-hydroxyethyl) carbamoyl group, an N-methyl-N-methanesulfonylamino group, an N-acetyl-N-(2-carboxyethyl)amino group, an N-carboxymethyl-N-methylamino group, an N-carboxymethyl-N-methylcarbamoyl group, an N-(2-carboxyethyl)-N-methylcarbamoyl group, a 3-(trifluoroacetyl)propionylamino group, an N-(2,2-dimethylpropionyl)-N-methylamino group, an N-(2,2-dimethyl-3-hydroxypropionyl)-N-methylamino group, an N-(2-hydroxy-2-methylpropionyl)-N-methylamino group),
(11) —NR$^{b8}$R$^{b9}$ wherein R$^{b8}$ and R$^{b9}$ are the same or different and each is a hydrogen atom or a C$_{1-6}$ alkyl group (particularly, a methyl group),
(12) —NR$^{b10}$—C(=O)—R$^{b11}$ wherein R$^{10}$ and R$^{b11}$ are the same or different and each is a hydrogen atom or a C$_{1-6}$ alkyl group (particularly, a methyl group), or
(13) —O—C(=O)—NR$^{b14}$R$^{b15}$ wherein R$^{b14}$ and R$^{b15}$ are the same or different and each is a hydrogen atom or a C$_{1-6}$ alkyl group (particularly, a methyl group),
R$^c$ is
(1) a hydrogen atom,
(2) a halogen atom (particularly, a fluorine atom, a chlorine atom),
(3) a methyl group,
(4) —C(=O)—OR$^{c1}$ wherein R$^{c1}$ is a hydrogen atom or a methyl group,
(5) —OR$^{c2}$ wherein R$^{c2}$ is a hydrogen atom, a methyl group or an ethyl group,
(6) —NH$_2$, or
(7) —NR$^{c5}$—C(=O)—R$^{c6}$ wherein R$^{c5}$ and R$^{c6}$ are the same or different and each is a hydrogen atom or a C$_{1-6}$ alkyl group (particularly, a methyl group, an ethyl group, an isopropyl group), particularly a hydrogen atom,
R$^m$ is
(1) a C$_{1-6}$ alkyl group optionally substituted by the same or different 1 to 5 substituents selected from group E,
(2) a C$_{1-6}$ alkyl group substituted by a C$_{6-10}$ aryl group optionally substituted by the same or different 1 to 5 substituents selected from group F,
(3) a C$_{1-6}$ alkyl group substituted by a C$_{3-10}$ cycloalkyl optionally substituted by the same or different 1 to 5 substituents selected from group F,
(4) a C$_{1-6}$ alkyl group substituted by a C$_{5-10}$ bridged cycloalkyl optionally substituted by the same or different 1 to 5 substituents selected from group F,
(5) a C$_{1-6}$ alkyl group substituted by a monocyclic aromatic heterocyclic group optionally substituted by the same or different 1 to 5 C$_{1-6}$ alkyl group (the monocyclic aromatic heterocyclic group contains, besides carbon atom, 1 to 4 hetero atoms selected from a nitrogen atom, an oxygen atom and a sulfur atom, and has 3 to 7 ring-constituting atoms),
(6) a C$_{3-10}$ cycloalkyl optionally substituted by the same or different 1 to 5 substituents selected from group F, or
(7) a C$_{5-10}$ bridged cycloalkyl optionally substituted by the same or different 1 to 5 substituents selected from group F,
more preferably,
(1) a C$_{1-6}$ alkyl group optionally substituted by the same or different 1 to 5 substituents selected from group E',
(2) a C$_{1-6}$ alkyl group substituted by a C$_{3-10}$ cycloalkyl optionally substituted by the same or different 1 to 5 substituents selected from group F,
(3) a C$_{1-6}$ alkyl group substituted by a C$_{5-10}$ bridged cycloalkyl optionally substituted by the same or different 1 to 5 substituents selected from group F,
(4) a C$_{3-10}$ cycloalkyl optionally substituted by the same or different 1 to 5 substituents selected from group F, or
(5) a C$_{5-10}$ bridged cycloalkyl optionally substituted by the same or different 1 to 5 substituents selected from group F, particularly,
(1) a $C_{1-6}$ alkyl group (particularly, a methyl group, an ethyl group, a propyl group, an isopropyl group, a butyl group, an isobutyl group, a tert-butyl group, a neopentyl group) optionally substituted by the same or different 1 to 5 substituents selected from
(i) —C(=O)—OR$^{E2}$ wherein R$^{E2}$ is a hydrogen atom or a $C_{1-6}$ alkyl group (particularly, a methyl group) optionally substituted by the same or different 1 to 5 substituents selected from group F,
(ii) —C(=O)—NR$^{E3}$R$^{E4}$ wherein R$^{E3}$ and R$^{E4}$ are the same or different and each is a hydrogen atom or a $C_{1-6}$ alkyl group (particularly, a methyl group, an ethyl group, an isopropyl group) optionally to substituted by the same or different 1 to 5 substituents selected from group F,
(iii) —OR$^{E7}$ wherein R$^{E7}$ is a hydrogen atom or a $C_{1-6}$ alkyl group (particularly, a methyl group) optionally substituted by the same or different 1 to 5 substituents selected from group F, and
(iv) —NR$^{E12}$—C(=O)—R$^{E13}$ wherein R$^{E12}$ and R$^{E13}$ are the same or different and each is a hydrogen atom or a $C_{1-6}$ alkyl group (particularly, a methyl group) optionally substituted by the same or different 1 to 5 substituents selected from group F,
(2) a $C_{3-10}$ cycloalkyl group (particularly, a cyclohexyl group, a cyclopentyl group) optionally substituted by the same or different 1 to 5 substituents selected from group F (particularly, a hydroxy group, a hydroxymethyl group, a carboxyl group), or
(3) a $C_{5-10}$ bridged cycloalkyl group (particularly, an adamantyl group) optionally substituted by the same or different 1 to 5 substituents selected from group F,
further particularly,
(1) a $C_{1-6}$ alkyl group (particularly, a methyl group, an ethyl group, a propyl group, an isopropyl group, a butyl group, an isobutyl group, a tert-butyl group, a neopentyl group) optionally substituted by the same or different 1 to 5 substituents selected from
(i) —C(=O)—OR$^{E2}$ wherein R$^{E2}$ is a hydrogen atom or a $C_{1-6}$ alkyl group (particularly, a methyl group) optionally substituted by the same or different 1 to 5 substituents selected from group F, and
(ii) —OR$^{E7}$ wherein R$^{E7}$ is a hydrogen atom or a $C_{1-6}$ alkyl group (particularly, a methyl group) optionally substituted by the same or different 1 to 5 substituents selected from group F,
(2) a $C_{3-10}$ cycloalkyl group (particularly, a cyclohexyl group, a cyclopentyl group) optionally substituted by the same or different 1 to 5 substituents selected from group F (particularly, a hydroxy group, a hydroxymethyl group, a carboxyl group), or
(3) a $C_{5-10}$ bridged cycloalkyl group (particularly, a 1-adamantyl group) optionally substituted by the same or different 1 to 5 substituents selected from group F,
particularly,

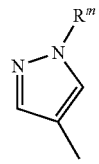

is a group represented by the following,

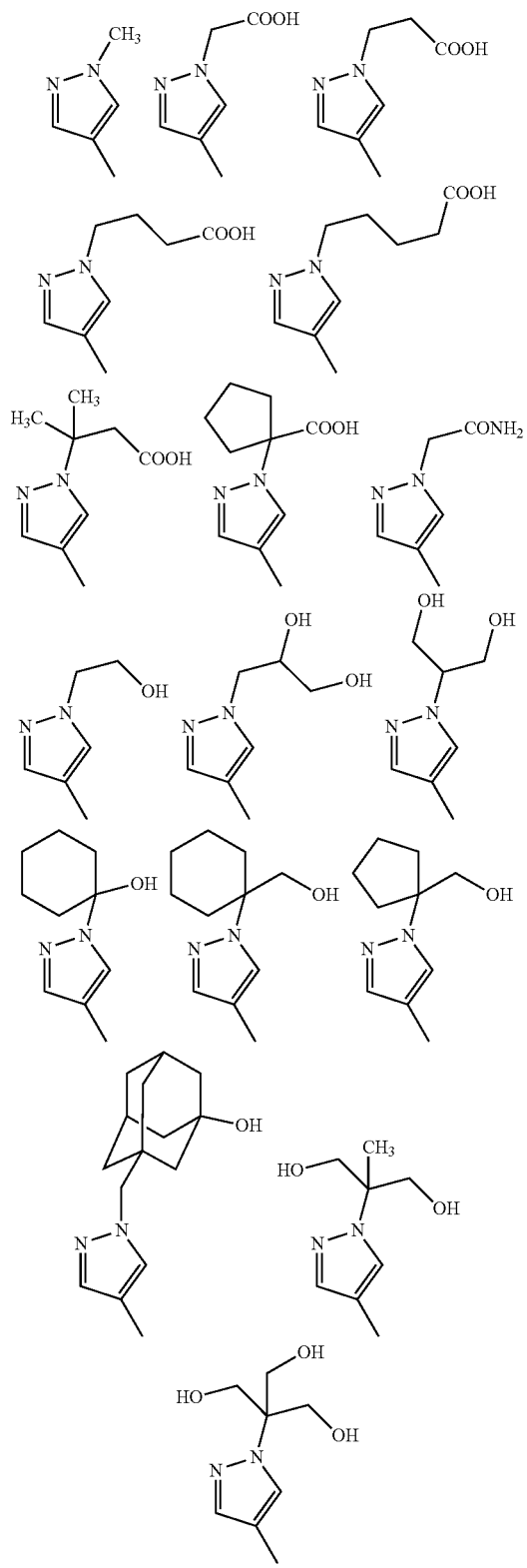

R$^e$ is the same or different and each is a fluorine atom, a chlorine atom, a methyl group, or a hydroxymethyl group,
n is an integer of 0, or 1 to 2, particularly 0.

As specifically preferable compounds of the compound represented by the formula [I], the following compounds can be mentioned.
1-(9-hydroxy-4-methyl-9-trifluoromethyl-9H-fluorene-2-carbonyl)-azetidine-3-carboxylic acid dimethylamide (compound No. 153)
1-[2-(5-hydroxy-5-trifluoromethyl-5H-indeno[1,2-b]pyridin-3-yloxy)-ethyl]-pyrrolidin-2-one (compound No. 430)
4-hydroxymethyl-2-(1-ethyl-1H-pyrazol-4-yl)-9-trifluoromethyl-9H-fluoren-9-ol (compound No. 629)
2-[1-(2,2-dimethyl-propyl)-1H-pyrazol-4-yl]-4-hydroxymethyl-9-trifluoromethyl-9H-fluoren-9-ol (compound No. 660)
(−)-2-(1-ethyl-1H-pyrazol-4-yl)-9-hydroxy-9-trifluoromethyl-9H-fluorene-4-carboxylic acid amide (compound No. 630)
2-[1-(2,2-dimethyl-propyl)-1H-pyrazol-4-yl]-9-hydroxy-9-trifluoromethyl-9H-fluorene-4-carboxylic acid amide (compound No. 659)
2-(1-cyclohexylmethyl-1H-pyrazol-4-yl)-9-hydroxy-9-trifluoromethyl-9H-fluorene-4-carboxylic acid amide (compound No. 667)
(+)-2-[4-(2-fluoro-9-hydroxy-9-trifluoromethyl-9H-fluoren-4-yl)-pyrazol-1-yl]-propane-1,3-diol (compound No. 595)
(+)-3-[4-(9-hydroxy-2-methyl-9-trifluoromethyl-9H-fluoren-4-yl)-pyrazol-1-yl]-propionic acid (compound No. 538)
(+)-4-[4-(9-hydroxy-2-methyl-9-trifluoromethyl-9H-fluoren-4-yl)-pyrazol-1-yl]-butyric acid (compound No. 539)

In addition, in the compound represented by the formula [I], various "isomers" are present. When an asymmetric carbon atom is present at the 9-position of the fluorene ring of the compound represented by the formula [I], enantiomers exist as a stereoisomer based thereon, and when an asymmetric carbon atom is further present in a substituent, diastereomers exist.

Specifically, an optical active form of the compound represented by the following chemical formulas and a mixture thereof are encompassed in the present invention.

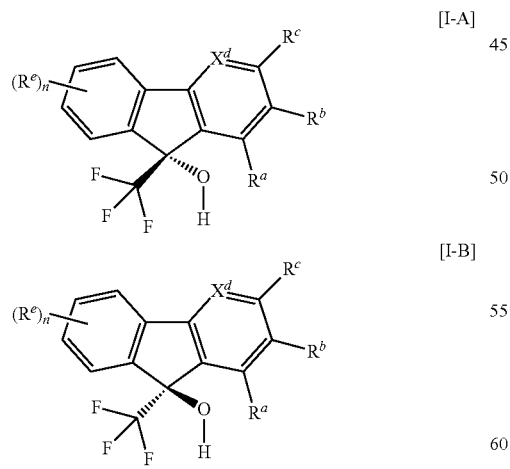

In addition, an optically active form of the compound represented by the following chemical formulas, which is a preferable embodiment of the compound of the present invention, and a mixture thereof are encompassed in the present invention.

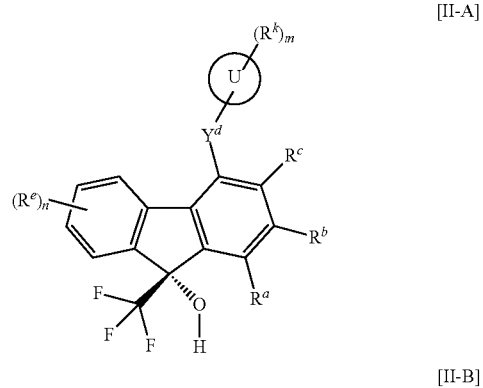

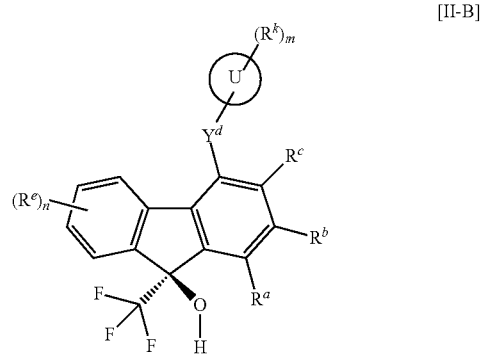

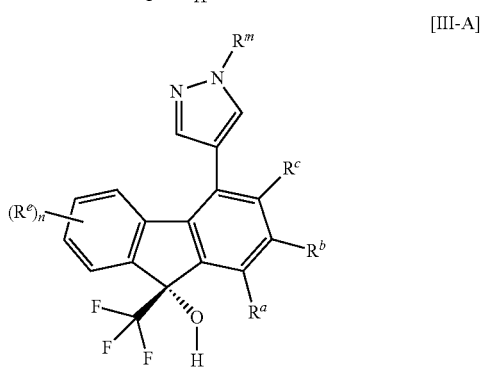

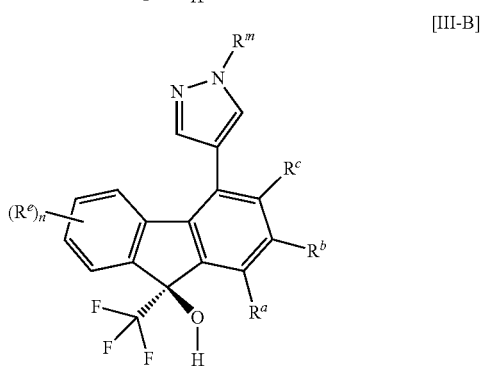

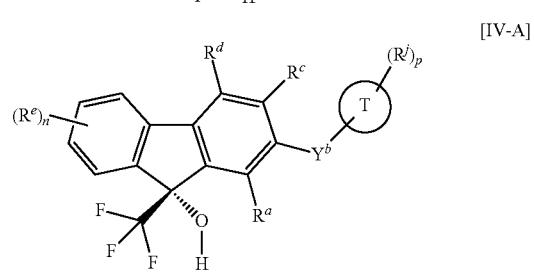

-continued

[IV-B]
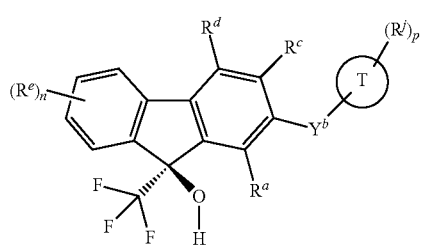

[V-A]
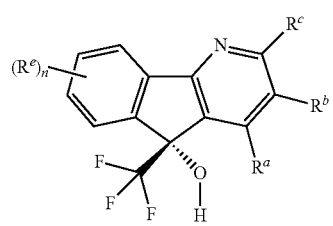

[V-B]
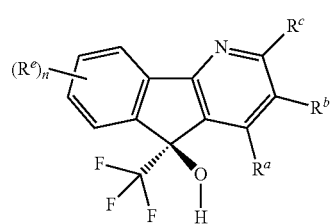

[VI-A]
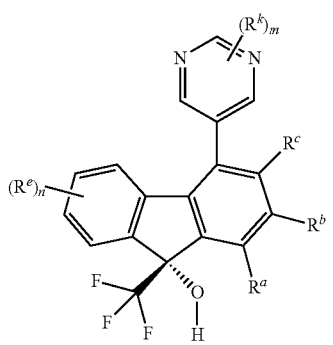

[VI-B]
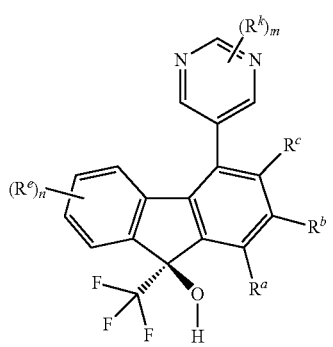

In addition, when E form and Z form exist as geometric isomers, and an axial chirality is present, stereoisomers based on these exist. In some cases, tautomers may exist. Therefore, all of these isomers and mixtures thereof are encompassed in the present invention.

As a compound represented by the formula [III], preferred is a compound represented by the formula [III-A].

As a compound represented by the formula [III-A], preferred is a compound wherein $R^m$ is (1) a alkyl group optionally substituted by the same or different 1 to 5 substituents selected from group E', (2) a $C_{1-6}$ alkyl group substituted by a $C_{3-10}$ cycloalkyl optionally substituted by the same or different 1 to 5 substituents selected from group F, (3) a $C_{1-6}$ alkyl group substituted by a $C_{5-10}$ bridged cycloalkyl optionally substituted by the same or different 1 to 5 substituents selected from group F, (4) a $C_{3-10}$ cycloalkyl optionally substituted by the same or different 1 to 5 substituents selected from group F, or (5) a $C_{5-10}$ bridged cycloalkyl optionally substituted by the same or different 1 to 5 substituents selected from group F.

In another embodiment, a specifically preferable compound of the compound represented by the formula [I] is the following compound.

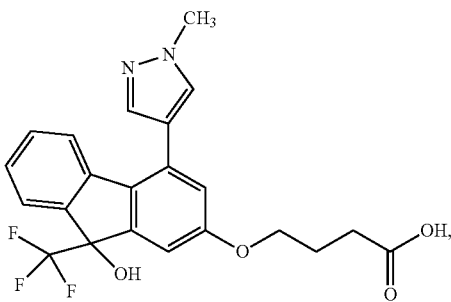

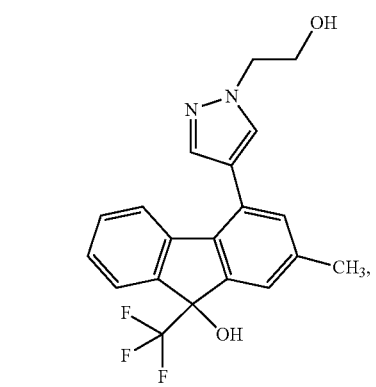

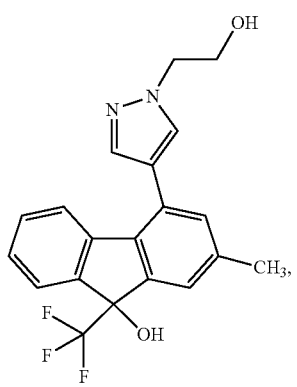

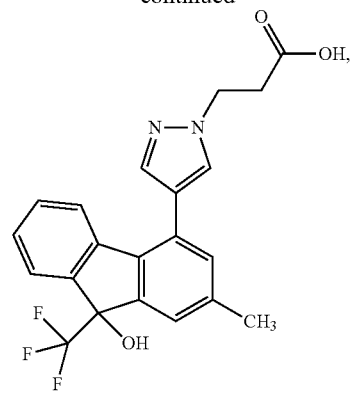
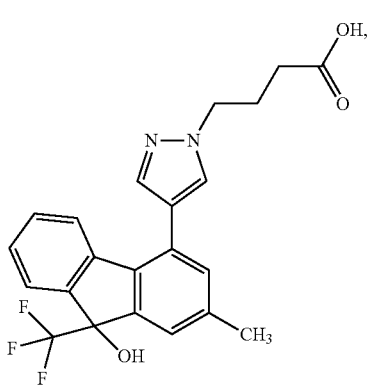
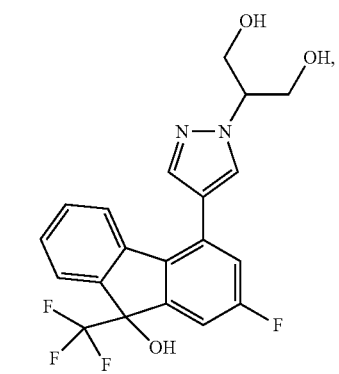
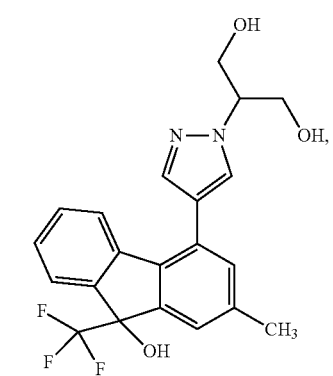
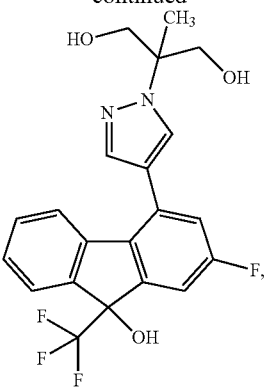
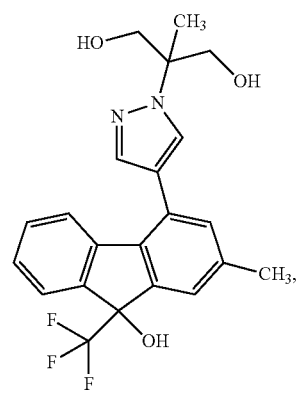
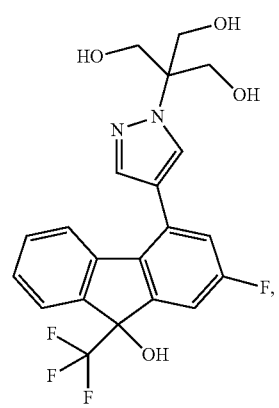
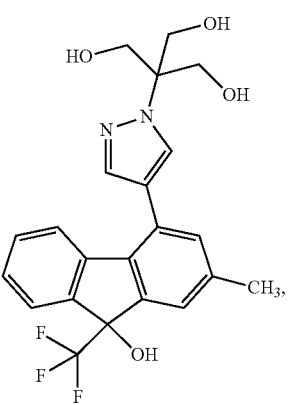

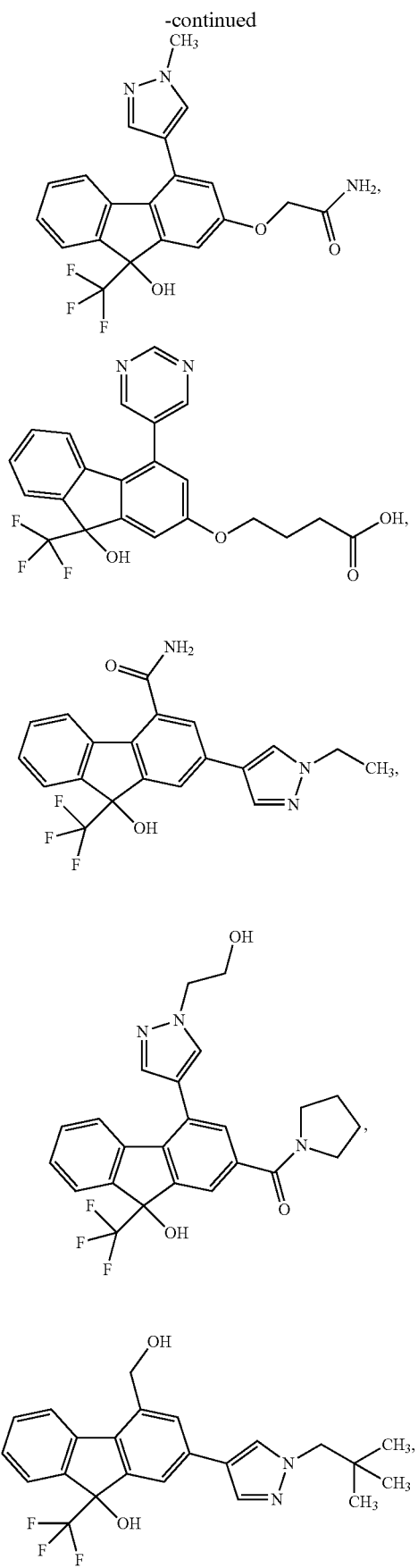
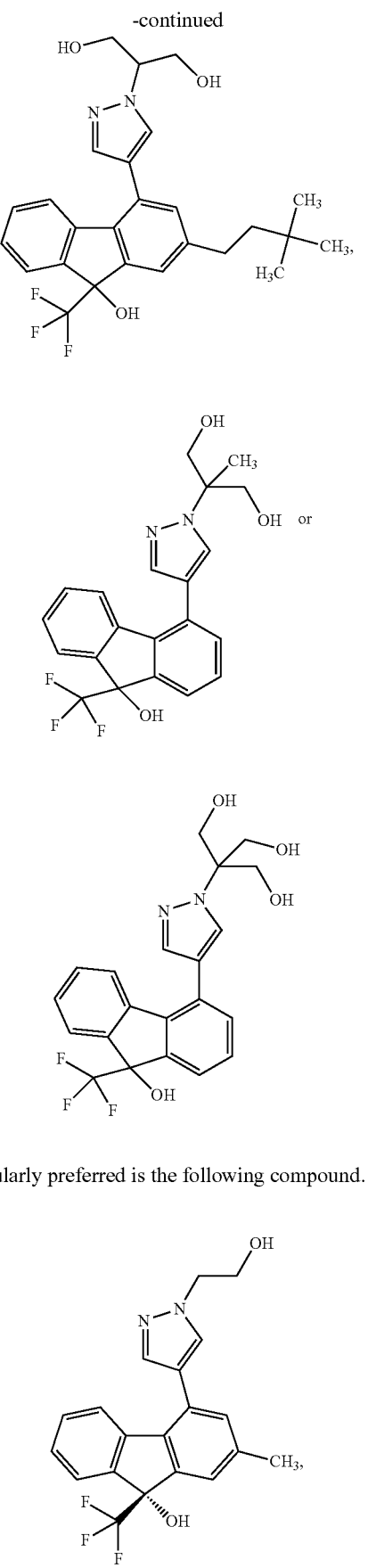
Particularly preferred is the following compound.

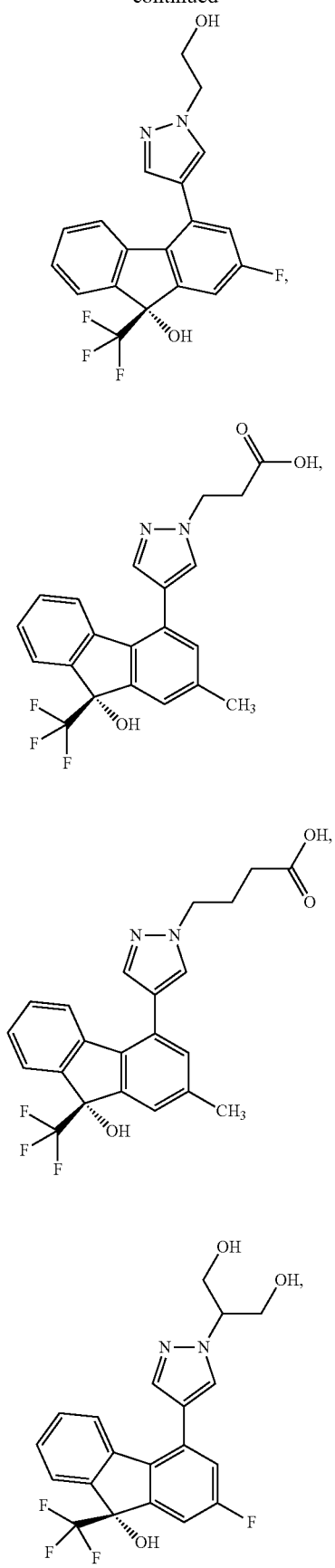
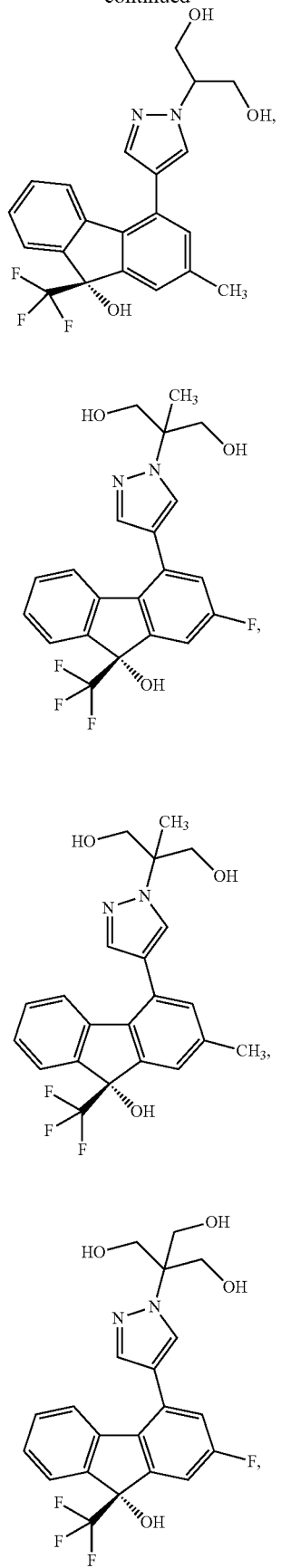

-continued

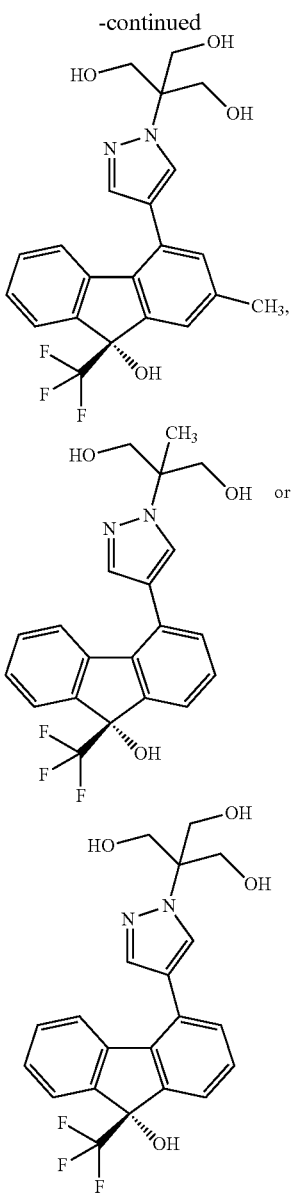

A pharmaceutically acceptable salt of the compound represented by the formula [I] (hereinafter to be also referred to as the compound of the present invention) may be any salt as long as it forms a nontoxic salt with the compound of the present invention. Examples thereof include salts with inorganic acids, salts with organic acids, salts with inorganic bases, salts with organic bases, salts with amino acids and the like.

Examples of the salt with inorganic acid include a salt with hydrochloric acid, nitric acid, sulfuric acid, phosphoric acid, hydrobromic acid and the like.

Examples of the salt with organic acid include salts with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salt with inorganic base include sodium salt, potassium salt, calcium salt, magnesium salt, ammonium salt and the like.

Examples of the salt with organic base include methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine and the like.

Examples of the salt with amino acid include salts with lysine, arginine, aspartic acid, glutamic acid and the like.

When a salt of the formula [I] is desired, each salt can be obtained by reacting a compound represented by the formula [I] with an inorganic base, organic base, inorganic acid, organic acid or amino acid according to a known method.

The "solvate" is a compound represented by the formula [I] or a pharmaceutically acceptable salt thereof wherein a molecule of the solvent is coordinated, and also includes hydrates. As the solvate, a pharmaceutically acceptable solvate is preferable and includes, for example, hydrate, ethanolate, dimethylsulfoxidate and the like of the compound represented by the formula [I] or a pharmaceutically acceptable salt thereof. Specific examples thereof include hemihydrate, monohydrate, dihydrate and monoethanolate of the compound represented by the formula [I], monohydrate of sodium salt, 2/3 ethanolate of dihydrochloride, and the like of the compound represented by the formula [I].

The solvate can be obtained according to a method known per se.

In addition, the compound represented by the formula [I] may be labeled with an isotope (e.g., $^3$H, $^{14}$C, $^{35}$S etc.).

The deuterium derivative wherein $^1$H of the compound represented by the formula [I] is substituted with $^2$H(D) is also encompassed in the compound represented by the formula [I].

As the compound represented by the formula [I] or a pharmaceutically acceptable salt thereof or a solvate thereof, a compound represented by the formula [I] or a pharmaceutically acceptable salt thereof or a solvate thereof, each of which is substantially purified, is preferable. More preferred is, a compound represented by the formula [I] or a pharmaceutically acceptable salt thereof or a solvate thereof, each of which is purified to a purity of not less than 80%.

In the present invention, a prodrug of the compound represented by the formula [I] can also be a useful medicament. The "prodrug" is a derivative of the compound of the present invention having a chemically or metabolically degradable group which, after administration to the body, restores to the original compound by, for example, hydrolysis, solvolysis or decomposition under physiological conditions, and shows inherent efficacy. It is considered to include a noncovalent complex, and a salt. Prodrug is utilized for, for example, improvement of absorption on oral administration, or targeting to a target moiety.

Examples of the modified moiety include, in the compound of the present invention, a highly reactive functional group such as a hydroxyl group, a carboxyl group, an amino group and the like.

Specific examples of the hydroxyl-modifying group include an acetyl group, a propionyl group, an isobutyryl group, a pivaloyl group, a palmitoyl group, a benzoyl group, a 4-methylbenzoyl group, a dimethylcarbamoyl group, a dimethylaminomethylcarbonyl group, a sulfo group, an alanyl group, a fumaryl group, a 3-carboxybenzoyl group, a 2-carboxyethylcarbonyl group and the like. In addition, sodium salt of 3-carboxybenzoyl group, 2-carboxyethylcarbonyl group and the like can be mentioned.

Specific examples of the carboxyl-modifying group include a methyl group, an ethyl group, a propyl group, an isopropyl group, a butyl group, an isobutyl group, a tert-butyl group, a pivaloyloxymethyl group, a carboxymethyl group, a dimethylaminomethyl group, a 1-(acetyloxy)ethyl group, a 1-(ethoxycarbonyloxy)ethyl group, a 1-(isopropyloxycarbonyloxy)ethyl group, a 1-(cyclohexyloxycarbonyloxy)ethyl group, a (5-methyl-2-oxo-1,3-dioxol-4-yl)methyl group, a benzyl group, a phenyl group, an o-tolyl group, a morpholinoethyl group, an N,N-diethylcarbamoylmethyl group, a phthalidyl group and the like.

Specific examples of the amino-modifying group include a tert-butyl group, a docosanoyl group, a pivaloyloxymethyl group, an alanyl group, a hexylcarbamoyl group, a pentylcarbamoyl group, a 3-methylthio-1-(acetylamino)propylcarbonyl group, a 1-sulfo-1-(3-ethoxy-4-hydroxyphenyl)methyl group, a (5-methyl-2-oxo-1,3-dioxol-4-yl)methyl group, a (5-methyl-2-oxo-1,3-dioxol-4-yl)methoxycarbonyl group, a tetrahydrofuranyl group, a pyrrolidylmethyl group and the like.

Examples of the "pharmaceutical composition" include oral preparations such as tablet, capsule, granule, powder, troche, syrup, emulsion, suspension and the like, and parenteral agents such as external preparation, suppository, injection, eye drop, nasal preparation, pulmonary preparation and the like.

The pharmaceutical composition of the present invention is produced according to a method known in the art of pharmaceutical preparations, by mixing a compound represented by the formula [I] or a pharmaceutically acceptable salt thereof or a solvate thereof with a suitable amount of at least one kind of pharmaceutically acceptable carrier and the like as appropriate. While the content of the compound represented by the formula [I] or a pharmaceutically acceptable salt thereof, or a solvate thereof in the pharmaceutical composition varies depending on the dosage form, dose and the like, it is, for example, 0.1 to 100 wt % of the whole composition.

Examples of the "pharmaceutically acceptable carrier" include various organic or inorganic carrier substances conventionally used as preparation materials, for example, excipient, disintegrant, binder, fluidizer, lubricant and the like for solid preparations, and solvent, solubilizing agent, suspending agent, isotonicity agent, buffering agent, soothing agent and the like for liquid preparations. Where necessary, moreover, additives such as preservative, antioxidant, colorant, sweetening agent and the like are used.

Examples of the "excipient" include lactose, sucrose, D-mannitol, D-sorbitol, cornstarch, dextrin, microcrystalline cellulose, crystalline cellulose, carmellose, carmellose calcium, sodium carboxymethyl starch, low-substituted hydroxypropylcellulose, gum arabic and the like.

Examples of the "disintegrant" include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose and the like.

Examples of the "binder" include hydroxypropylcellulose, hydroxypropylmethylcellulose, povidone, crystalline cellulose, sucrose, dextrin, starch, gelatin, carmellose sodium, gum arabic and the like.

Examples of the "fluidizer" include light anhydrous silicic acid, magnesium stearate and the like.

Examples of the "lubricant" include magnesium stearate, calcium stearate, talc and the like.

Examples of the "solvent" include purified water, ethanol, propylene glycol, macrogol, sesame oil, corn oil, olive oil and the like.

Examples of the "solubilizing agents" include propylene glycol, D-mannitol, benzyl benzoate, ethanol, triethanolamine, sodium carbonate, sodium citrate and the like.

Examples of the "suspending agent" include benzalkonium chloride, carmellose, hydroxypropylcellulose, propylene glycol, povidone, methylcellulose, glycerol monostearate and the like.

Examples of the "isotonicity agent" include glucose, D-sorbitol, sodium chloride, D-mannitol and the like.

Examples of the "buffering agent" include sodium hydrogenphosphate, sodium acetate, sodium carbonate, sodium citrate and the like.

Examples of the "soothing agent" include benzyl alcohol and the like.

Examples of the "preservative" include ethyl parahydroxybenzoate, chlorobutanol, benzyl alcohol, sodium dehydroacetate, sorbic acid and the like.

Examples of the "antioxidant" include sodium sulfite, ascorbic acid and the like.

Examples of the "colorant" include food colors (e.g., Food Color Red No. 2 or 3, Food Color yellow No. 4 or 5 etc.), β-carotene and the like.

Examples of the "sweetening agent" include saccharin sodium, dipotassium glycyrrhizinate, aspartame and the like.

The pharmaceutical composition of the present invention can be administered orally or parenterally (e.g., topical, rectal, intravenous administration etc.) to human as well as mammals other than human (e.g., mouse, rat, hamster, guinea pig, rabbit, cat, dog, swine, bovine, horse, sheep, monkey etc.). The dose varies depending on the subject of administration, disease, symptom, dosage form, administration route and the like. For example, the daily dose for oral administration to an adult patient (body weight: about 60 kg) is generally within the range of about 1 mg to 1 g, based on the compound of the present invention as the active ingredient. This amount can be administered in one to several portions.

The compound represented by the formula [I] or a pharmaceutically acceptable salt thereof, or a solvate thereof has inhibitory activity against pyruvate dehydrogenase kinase (PDHK, particularly PDHK2), and can activate pyruvate dehydrogenase (PDH) effectively. Therefore, the compound of the present invention or a pharmaceutically acceptable salt thereof, or a solvate thereof can be used as an active ingredient of an agent for the treatment or prophylaxis of diabetes (e.g., type 1 diabetes, type 2 diabetes etc.), insulin resistance syndrome, metabolic syndrome, hyperglycemia, dyslipidemia, atherosclerosis, cardiac failure, cardiomyopathy, myocardial ischemia, hyperlactacidemia, mitochondrial disease, mitochondrial encephalomyopathy or cancer. Furthermore, the compound can be used as an active ingredient of an agent for the treatment or prophylaxis of diabetic complications (e.g., neuropathy, retinopathy, nephropathy, cataract etc.), cerebral ischemia, cerebral apoplexy or pulmonary hypertension.

To "inhibit PDHK" means to specifically inhibit the function of PDHK and eliminate or attenuate the activity. To "inhibit PDHK", human PDHK is preferably inhibited. As a "PDHK inhibitor", preferred is a "human PDHK inhibitor".

To "inhibit PDHK2" means to specifically inhibit the function of PDHK2 and eliminate or attenuate the activity. For example, it means to specifically inhibit the function as PDHK2 based on the conditions in the below-mentioned Experimental Example 1. To "inhibit PDHK2", human PDHK2 is preferably inhibited. As a "PDHK2 inhibitor", preferred is a "human PDHK2 inhibitor".

To "activate PDH" means to activate PDH in a target organ (e.g., liver, skeletal muscle, adipose tissue, heart, brain) and the like, cancer or the like.

To "decrease blood glucose level" means to decrease the glucose concentration in blood (including in serum and plasma), preferably to decrease high blood glucose level, more preferably, to decrease the blood glucose level to normal level for human.

The above-mentioned compound represented by the formula [I] or a pharmaceutically acceptable salt thereof, or a solvate thereof can be used in combination with one or a plurality of other medicaments (hereinafter to be also referred to as a concomitant drug) according to a method generally employed in the medical field (hereinafter to be referred to as combined use).

The administration period of the above-mentioned compound represented by the formula [I] or a pharmaceutically acceptable salt thereof, or a solvate thereof, and a concomitant drug is not limited, and they may be administered to an administration subject as combination preparation, or the both preparations may be administered simultaneously or at given intervals. In addition, the pharmaceutical composition of the present invention and a concomitant drug may be used as a medicament in the form of a kit. The dose of the concomitant drug is similar to the clinically-employed dose and can be appropriately selected according to the subject of administration, disease, symptom, dosage form, administration route, administration time, combination and the like. The administration form of the concomitant drug is not particularly limited, and it only needs to be combined with the compound of the present invention or a salt thereof, or a solvate thereof.

Examples of the concomitant drug include an agent for the treatment and/or prophylaxis of diabetes and the like, and 1 to 3 agents therefrom and the compound represented by the formula [I] or a pharmaceutically acceptable salt thereof, or a solvate thereof can be used in combination.

Examples of the "agent for the treatment and/or prophylaxis of diabetes" include insulin preparation, sulfonylurea hypoglycemic agent and the like.

In the following, one example of the production method of the compound to be used for the embodiment of the present invention is explained. However, the production method of the compound of the present invention is not limited thereto.

Even if no directly corresponding disclosure is found in the following Production Methods, the steps may be modified for efficient production of the compound, such as introduction of a protecting group into a functional group with deprotection in a subsequent step, subjecting a functional group as a precursor to each step, followed by conversion to a desired functional group at a suitable stage, changing the order of Production Methods and steps, and the like.

The treatment after reaction in each step may be conventional ones, where isolation and purification can be performed as necessary according to a method appropriately selected from conventional methods such as crystallization, recrystallization, distillation, partitioning, silica gel chromatography, preparative HPLC and the like, or a combination of those methods.

Production Method 1 (Production Method of a Compound Represented by the Formula [I])

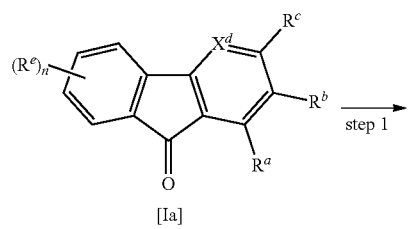

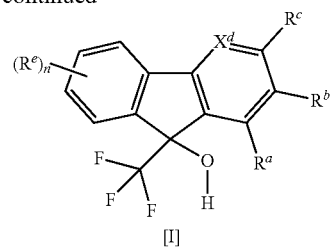

wherein each symbol is as defined above.

(Step 1)

Compound [Ia] is reacted with trimethyl(trifluoromethyl)silane in a solvent in the presence of a catalyst to allow trifluoromethylation to give trimethylsilyl ether of compound [1]. Then, the obtained trimethylsilyl ether is hydrolyzed to give compound [1] as a racemate.

Examples of the solvent to be used for the reaction include amide solvents such as dimethylformamide, N,N-dimethylacetamide etc. and the like. They can be used alone or two or more kinds thereof may be used in a mixture. Preferable solvent for this reaction is dimethylformamide.

Examples of the catalyst to be used for the trifluoromethylation reaction include alkali metal carbonates such as potassium carbonate and the like; alkali metal acetates such as lithium acetate and the like; fluorides such as tetrabutylammonium fluoride etc., and the like. Preferred is potassium carbonate or lithium acetate.

The reaction temperature of the trifluoromethylation is generally about 0 to 50° C., preferably about 0° C. to room temperature.

The reaction time of the trifluoromethylation is generally about 30 min to 1 day, preferably about 30 min to 3 hr.

The amount of trimethyl(trifluoromethyl)silane to be used is generally about 1 to 5 mol, preferably about 1 to 2.5 mol, per 1 mol of compound [Ia].

The amount of the catalyst of the trifluoromethylation reaction to be used is generally about 0.01 to 1 mol, preferably about 0.05 to 0.5 mol, per 1 mol of compound [Ia].

Examples of the reagent to be used for the hydrolysis of trimethylsilyl ether include alkali metal fluorides such as cesium fluoride and the like; ammonium fluoride salts such as tetrabutylammonium fluoride etc., and the like.

When trimethylsilyl ether is hydrolyzed, the reaction temperature is generally about −10 to 50° C., preferably about 0° C. to room temperature.

When trimethylsilyl ether is hydrolyzed, the reaction time is generally about 1 min to 1 day, preferably about 5 min to 2 hr.

The amount of the reagent to be used for the hydrolysis of trimethylsilyl ether is generally about 1 to 5 mol, preferably about 1 to 2 mol, per 1 mol of compound [Ia].

When optically active compound [I] is desired, the desired optically active compound [I] can be obtained by separating racemate according to preferential crystallization method, diastereomer method, optical resolution method using chiral stationary phase column and the like.

Production Method 2 (Production Method of a Compound Represented by the Formula [II] Wherein $Y^d$ is a Single Bond (Compound [IIo]))
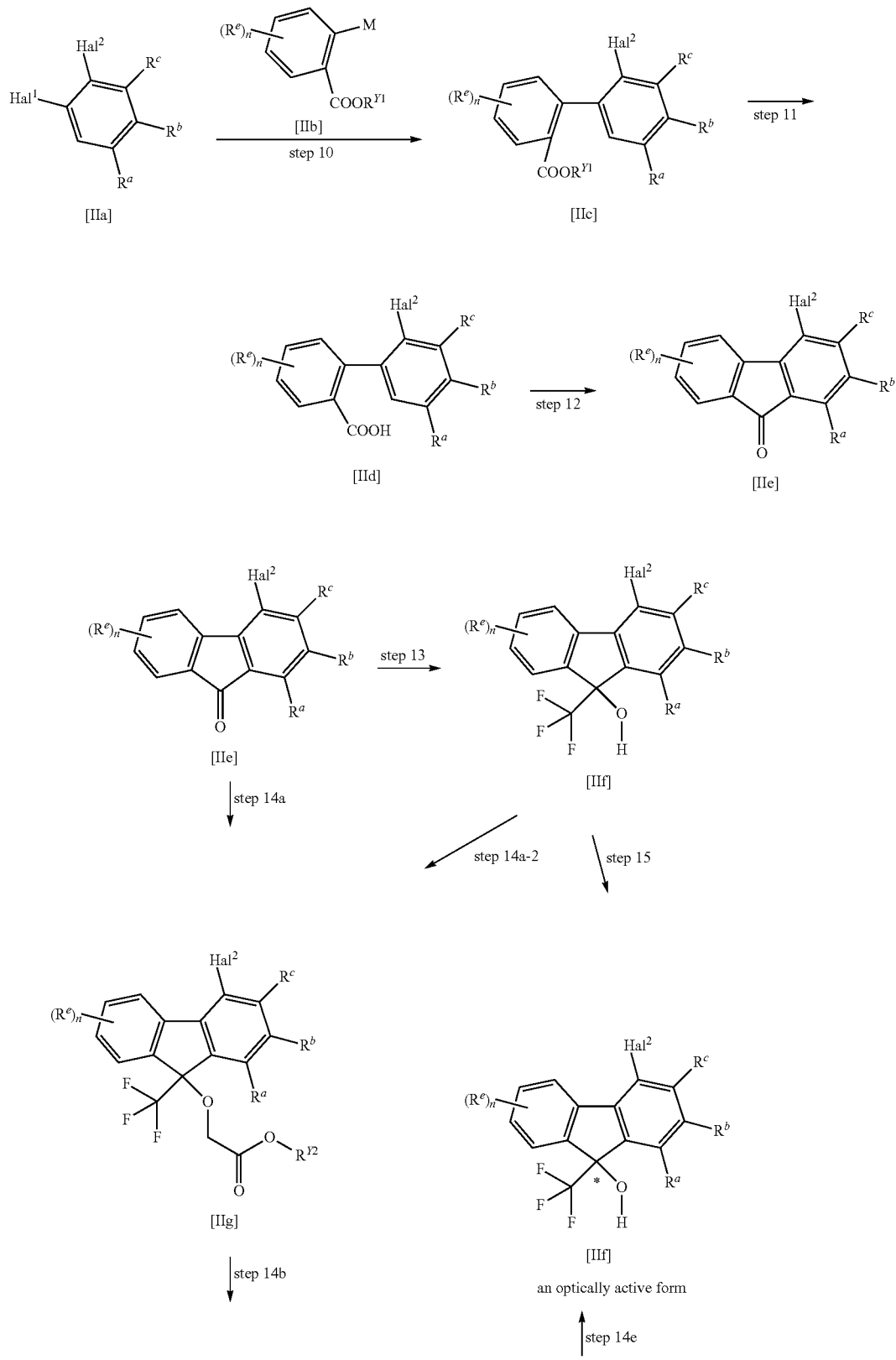

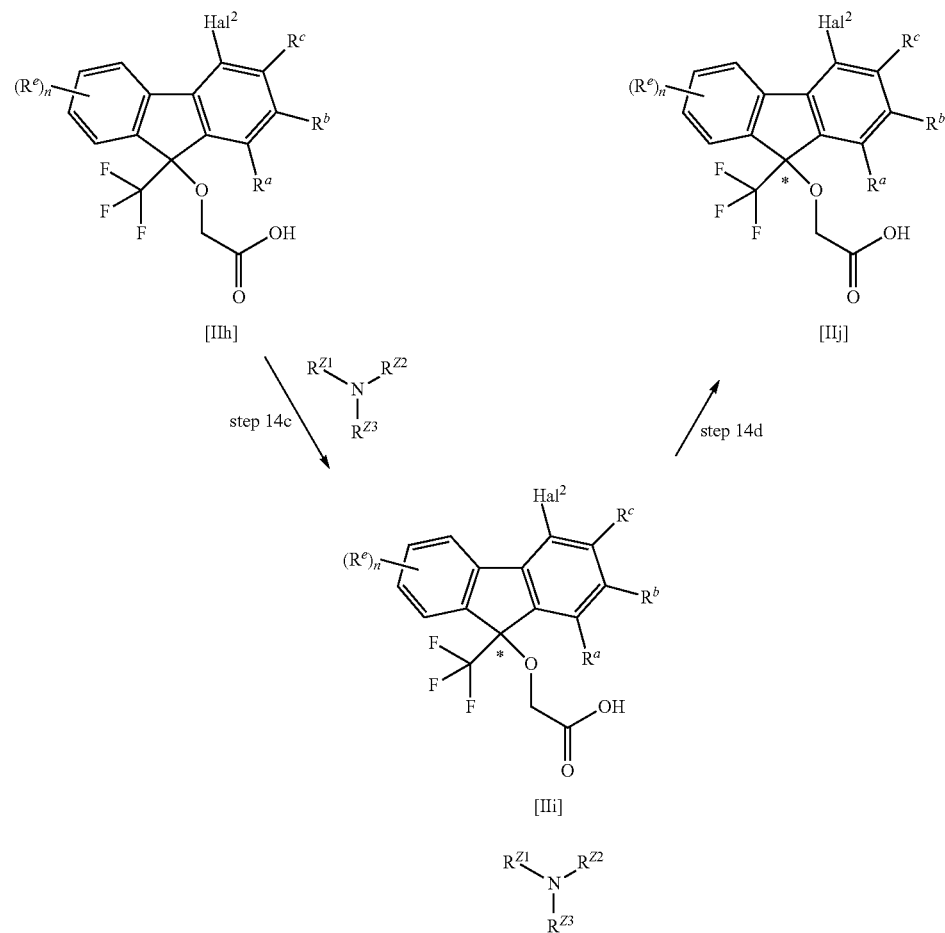
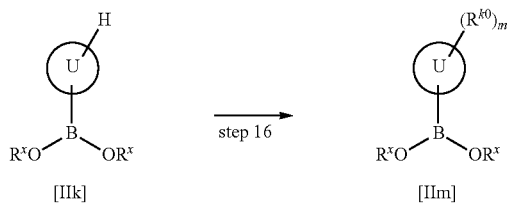
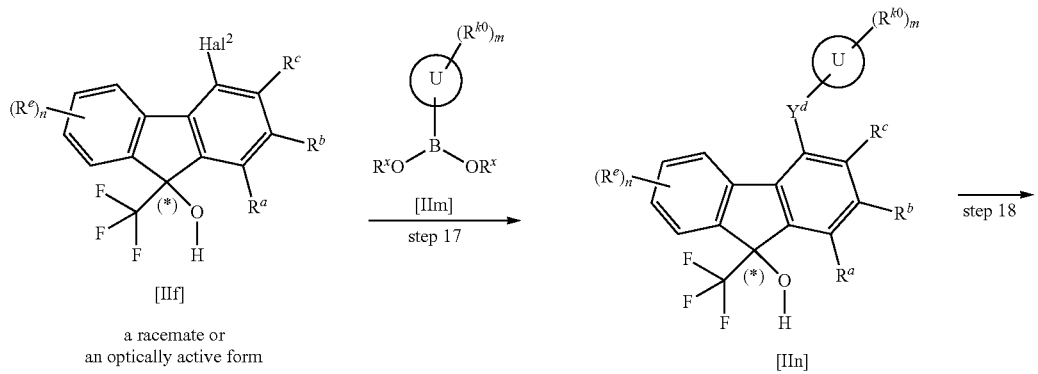

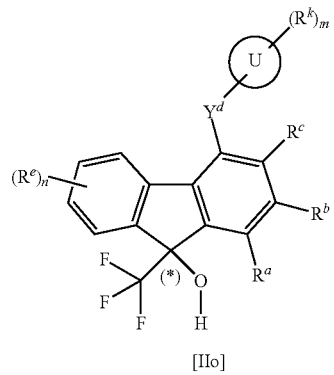

[IIo]

wherein
"Hal[1]" is a halogen atom, preferably a bromine atom, a chlorine atom or an iodine atom;
"Hal[2]" is a halogen atom, preferably a chlorine atom or a bromine atom;
"$R^{Y1}$" and "$R^{Y2}$" are the same or different and each is a carboxyl-protecting group such as a $C_{1-4}$ alkyl group (e.g., a methyl group, an ethyl group, t-butyl etc.), a benzyl group and the like;
at least one of the substituents "$R^{Z1}$" to "$R^{Z3}$" of amine has an asymmetric center and a single steric configuration (e.g., (R)-1-phenylethyl-1-yl, (S)-1-phenylethyl-1-yl, (R)-1-(1-naphthyl)ethyl-1-yl, (S)-1-(1-naphthyl)ethyl-1-yl etc.), and the rest is, for example, a hydrogen atom, alkyl groups such as a methyl group, an ethyl group and the like, an optionally substituted aralkyl group such as a benzyl group and the like, and the like;
"M" is a group including boron, zinc, tin or the like, for example, boronic acid, dialkoxyboron, halogenozinc, trialkyltin and the like;
the substituent "$R^X$" of the boron compound is, for example, a hydrogen atom, an alkyl group such as a methyl group and the like, or when it is "–B(OR$^X$)$_2$", two $R^X$, oxygen atoms and a boron atom bonded thereto in combination optionally form 4,4,5,5-tetramethyl-1,3,2-dioxaborolan-2-yl or the like;
"$R^{kO}$" is a substituent capable of conversion to "$R^k$" (e.g., (cyclo)alkyl group etc. substituted by carboxylic acid, carboxamide, alcohol etc.) by various functional group conversion reactions (e.g., (cyclo)alkyl group etc. substituted by ester, ether etc.);
"*" is an asymmetric center;
a compound having "*" is an optically active form;
a compound having "(*)" is a racemate or an optically active form; and
other symbols are as defined above.
(Step 10)
Compound [IIa] is reacted with compound [IIb] in a solvent in the presence of a metal catalyst and a base to give compound [IIc].
Here, M of compound [IIb] is a group containing boron, zinc, tin or the like. Examples thereof include boronic acid, dialkoxyboron, halogenozinc, trialkyltin and the like. Preferred are dialkoxyboron and boronic acid, and particularly preferred is 4,4,5,5-tetramethyl-1,3,2-dioxaborolan-2-yl.
Examples of the solvent to be used for the reaction include hydrocarbon solvents such as toluene and the like; ether solvents such as tetrahydrofuran, 1,2-dimethoxyethane, dioxane and the like; amide solvents such as dimethylformamide and the like; dimethyl sulfoxide; water and the like. They can be used alone or two or more kinds thereof may be used in a mixture. Preferable solvent for this reaction is a mixed solvent of toluene and water.
Examples of the metal catalyst to be used for the reaction include those having palladium or nickel, and preferred are palladium, particularly preferably palladium(II) acetate, dichlorobis(triphenylphosphine)palladium(II), 1,1'-bis(diphenylphosphino)ferrocene-palladium(II) dichloride, tetrakis(triphenylphosphine)palladium(0).
The amount of the metal catalyst to be used is generally about 0.001 to 1 mol, preferably about 0.01 to 0.2 mol, per 1 mol of compound [IIa].
Examples of the base to be used for the reaction include alkali metal phosphates such as tripotassium phosphate and the like; alkali metal carbonates such as sodium carbonate and the like; alkali metal acetate such as sodium acetate and the like; organic bases such as triethylamine and the like, preferably tripotassium phosphate.
The reaction temperature is generally about room temperature to 120° C., preferably about 90 to 110° C.
The reaction time is generally about 30 min to 1 day, preferably about 1-2 hr.
The amount of compound [IIb] to be used is generally about 1 to 5 mol, preferably about 1 to 2 mol, per 1 mol of compound [IIa].
The amount of the base to be used is generally about 1 to 5 mol, preferably about 1.5 to 3 mol, per 1 mol of compound [IIa].
(Step 11)
Compound [IId] can be obtained by subjecting compound [IIc] to ester hydrolysis in a solvent.
The ester hydrolysis may be performed under general conditions, for example, under alkaline conditions or acidic conditions.
When the hydrolysis is performed under alkaline conditions, compound [IIc] is reacted, for example, in the presence of about 1 to 20 mol of a base (alkali metal hydroxide such as potassium hydroxide, sodium hydroxide, lithium hydroxide etc., and the like) per 1 mol of compound [IIc] in, for example, water; alcohol solvents such as methanol, ethanol and the like; ether solvents such as tetrahydrofuran, dioxane etc., and the like, or a mixed solvent of two or more kinds thereof generally at about 0° C. to 100° C. for about 30 min to 1 day.
For reaction under acidic conditions, compound [IIc] is reacted in the presence of, for example, about 0.1 to 100 mol of an acid (hydrochloric acid, sulfuric acid etc.) per 1 mol of compound [IIc] in, for example, water; carboxylic acid solvents such as acetic acid and the like; ether solvents such as tetrahydrofuran, dioxane, etc., and the like, or a mixed solvent of two or more kinds thereof generally at about 0° C. to 100° C. for about 30 min to 2 days.

(Step 12)

Compound [IIe] can be obtained by cyclization reaction of compound [IId] in the presence of an acid without solvent or in a solvent.

Examples of the acid to be used for the reaction include phosphorus pentoxide, polyphosphoric acid and the like. The amount thereof to be used is generally about 1 mol to a large excess per 1 mol of compound [IId]. In addition, when a solvent is used, for example, methanesulfonic acid, sulfuric acid and the like can be mentioned. This reaction is preferably performed without a solvent or in methanesulfonic acid as a solvent.

The reaction temperature is generally about 50 to 200° C., preferably about 80 to 180° C.

The reaction time is generally about 30 min to 1 day, preferably about 1-3 hr.

(Step 13)

Compound [IIe] is reacted with trimethyl(trifluoromethyl) silane in a solvent in the presence of a catalyst to allow a trifluoromethylation reaction to give trimethylsilyl ether of compound [IIf], and the produced trimethylsilyl ether is hydrolyzed to give compound [IIf] as a racemate.

Examples of the solvent to be used for the reaction include amide solvents such as dimethylformamide, N,N-dimethylacetamide etc., and the like. They can be used alone or two or more kinds thereof may be used in a mixture. Preferable solvent for this reaction is dimethylformamide.

Examples of the catalyst to be used for the trifluoromethylation reaction include alkali metal carbonates such as potassium carbonate and the like; alkali metal acetates such as lithium acetate and the like; fluorides such as tetrabutylammonium fluoride etc., and the like. Preferred is potassium carbonate or lithium acetate.

The reaction temperature of the trifluoromethylation is generally about 0 to 50° C., preferably about 0° C. to room temperature.

The reaction time of the trifluoromethylation is generally about 30 min to 1 day, preferably about 30 min to 3 hr.

The amount of trimethyl(trifluoromethyl)silane to be used is generally about 1 to 5 mol, preferably about 1 to 2.5 mol, per 1 mol of compound [IIe].

The amount of the catalyst for the trifluoromethylation reaction to be used is generally about 0.01 to 1 mol, preferably about 0.05 to 0.5 mol, per 1 mol of compound [IIe].

Examples of the reagent to be used for hydrolysis of trimethylsilyl ether include alkali metal fluoride such as cesium fluoride and the like; ammonium fluoride salt such as tetrabutylammonium fluoride etc., and the like.

When trimethylsilyl ether is hydrolyzed, the reaction temperature is generally about −10 to 50° C., preferably about 0° C. to room temperature.

When trimethylsilyl ether is hydrolyzed, the reaction time is generally about 1 min to 1 day, preferably about 5 min to 2 hr.

The amount of the reagent to be used for hydrolysis of trimethylsilyl ether is generally about 1 to 5 mol, preferably about 1 to 2 mol, per 1 mol of compound [IIe].

(Step 14)

As a method for obtaining optically active compound [IIf], a method comprising steps 14a-14e from compound [IIe] or compound [IIf] can be mentioned. By selecting an appropriate optically active amine for this method, (+) or (−) form of compound [IIf] can be produced.

(Step 14a)

Compound [IIg] wherein an acetic acid ester moiety is introduced can be obtained by trifluoromethylation reaction and hydrolysis of trimethylsilyl ether in the same manner as in Step 13, followed by reaction with halogenated acetic acid ester.

Examples of the halogen atom of halogenated acetic acid ester to be used include a chlorine atom, a bromine atom and an iodine atom. In addition, examples of the carboxyl-protecting group ($R^{y2}$) include methyl, ethyl, t-butyl and the like. In this reaction, the halogenated acetic acid ester is preferably ethyl bromoacetate.

This acetic acid ester introduction reaction is performed by directly adding halogenated acetic acid ester to a mixture of the trifluoromethylation reaction product and the trimethylsilyl ether hydrolysis product.

The reaction temperature is generally about 0 to 50° C., preferably about 15 to 30° C.

The reaction time is generally about 30 min to 1 day, preferably about 1 hr to 5 hr.

The amount of the halogenated acetic acid ester to be used is generally about 1 to 5 mol, preferably about 1 to 2 mol, per 1 mol of compound [IIe].

(Step 14a-2)

Compound [IIg] wherein an acetic acid ester moiety is introduced can also be obtained by reacting isolated compound [IIf] with halogenated acetic acid ester. The reaction for introducing acetic acid ester is performed by reacting compound [IIf] with halogenated acetic acid ester in the presence of 1-5 equivalents (preferably, 2 equivalents) of a base (e.g., potassium carbonate etc.) at 0° C.-80° C. (preferably, room temperature) for 1-24 hr (preferably, overnight).

(Step 14b)

Compound [IIh] can be obtained by general ester hydrolysis of compound [IIg] in the same manner as in Step 11 in a solvent.

(Step 14c)

Compound [IIi], which is a salt of a single diastereomer, can be obtained as a solid by mixing compound [IIh] with an optically active amine in a solvent.

Examples of the optically active amine to be used include (R)-(+)-1-phenylethylamine, (S)-(−)-1-phenylethylamine, (R)-(+)-1-(1-naphthyl)-ethylamine, (S)-(−)-1-(1-naphthyl)-ethylamine and the like.

The amount of the optically active amine to be used is generally about 0.1 to 1 mol, preferably about 0.4 to 0.6 mol, per 1 mol of compound [IIh].

Examples of the solvent to be used include ketone solvents such as methyl ethyl ketone, methyl isobutyl ketone and the like; ester solvents such as ethyl acetate and the like; ether solvents such as isopropyl ether etc., and the like. They can be used alone or two or more kinds thereof may be used in a mixture. Preferable solvent for this step is methyl ethyl ketone, methyl isobutyl ketone.

The temperature for mixing is generally about 0 to 100° C., preferably about 20 to 70° C.

The time for the mixing is generally about 1 hr to 10 days, preferably about 1 to 5 days.

(Step 14d)

Compound [IIj] can be obtained by treating compound [IIi] with an acidic aqueous solution in a solvent to liberate carboxylic acid.

Examples of the solvent to be used include ester solvents such as ethyl acetate and the like; ether solvents such as ethyl ether and the like; hydrocarbon solvents such as toluene etc., and the like. They can be used alone or two or more kinds thereof may be used in a mixture. Preferable solvent for this reaction is ethyl acetate.

Examples of the acidic aqueous solution to be used include hydrochloric acid, sulfuric acid and the like.

The treatment temperature is generally about 0 to 50° C., preferably about 0° C. to room temperature.

The treatment time is generally about 1 min to 2 hr.

The amount of the acidic aqueous solution to be used is generally about 1 mol to large excess per 1 mol of compound [IIi].

(Step 14e)

Optically active compound [IIf] can be obtained by reacting compound [IIj] in a solvent.

Examples of the solvent to be used for the reaction include amide solvents such as dimethylformamide and the like; alcohol solvents such as t-butyl alcohol and the like; ether solvents such as dioxane and the like; hydrocarbon solvents such as toluene and the like and the like. They can be used alone or two or more kinds thereof may be used in a mixture. Preferable solvent for this reaction is a mixed solvent of dimethylformamide and t-butyl alcohol.

The reagent to be used for the reaction is preferably diphenylphosphoryl azide, and the base to be used for the reaction is a tertiary amine such as triethylamine, N-ethyldiisopropylamine and the like.

The reaction temperature is generally about 0 to 150° C., preferably about 0 to 100° C.

The reaction time is generally about 30 min to 1 day, preferably about 30 min to 5 hr.

The amount of diphenylphosphoryl azide to be used is generally about 1 to 3 mol, preferably about 1 to 1.5 mol, per 1 mol of compound [IIj].

The amount of the base to be used is generally about 1 to 3 mol, preferably about 1 to 1.5 mol, per 1 mol of compound [IIj].

(Step 15)

By treating racemic compound [IIf] using a chiral stationary phase column and the like, a desired optically active compound [IIf] can be separated from the other isomer.

(Step 16)

Compound [IIm] can be obtained by introducing $R^{k0}$ into compound [IIk] in a solvent in the presence of a base such as potassium carbonate, cesium fluoride and the like.

For example, when $R^{k0}$ is a (cyclo)alkyl group, compound [IIm] can be obtained by reacting compound [IIk] with (cyclo)alkyl halide such as (cyclo)alkyl iodide and (cyclo)alkyl bromide, (cyclo)alkyl sulfonic acid ester such as (cyclo)alkyl tosylate, or an α,β-unsaturated carbonyl compound such as acrylic acid ester and the like in amide solvents such as dimethylformamide, N,N-dimethylacetamide and the like or acetonitrile.

(Step 17)

Compound [IIn] can be obtained by reacting compound [IIf] in the form of a racemate or an optically active form with compound [IIm] in a solvent in the presence of a metal catalyst, a ligand and a base.

Boronic acid moiety of compound [IIm] is boronic acid per se, or boronic acid ester, preferably 4,4,5,5-tetramethyl-1,3,2-dioxaborolan-2-yl.

Examples of the solvent to be used for the reaction include hydrocarbon solvents such as toluene and the like; ether solvents such as tetrahydrofuran, 1,2-dimethoxyethane, dioxane and the like; amide solvents such as dimethylformamide and the like; dimethyl sulfoxide; water and the like. They can be used alone or two or more kinds thereof may be used in a mixture. Preferable solvent for this reaction is a mixed solvent of toluene and water.

The metal catalyst to be used for the reaction is palladium such as palladium(II) acetate, tris(dibenzylideneacetone)dipalladium(0), dichlorobis(triphenylphosphine)palladium(II) and tetrakis(triphenylphosphine)palladium(0), with preference given to palladium(II) acetate.

The amount of the metal catalyst to be used is generally about 0.001 to 1 mol, preferably about 0.01 to 0.2 mol, per 1 mol of compound [IIf].

The ligand to be used for the reaction is phosphine such as triphenylphosphine, tributylphosphine, 2-dicyclohexylphosphino-2',6'-dimethoxybiphenyl and the like, with preference given to 2-dicyclohexylphosphino-2',6'-dimethoxybiphenyl.

Examples of the base to be used for the reaction include alkali metal phosphate such as tripotassium phosphate and the like; alkali metal carbonate such as sodium carbonate and the like; alkali metal hydrogencarbonate such as sodium hydrogencarbonate and the like; alkali metal acetate such as sodium acetate and the like; organic base such as triethylamine and the like, with preference given to tripotassium phosphate.

The reaction temperature is generally about room temperature to 120° C., preferably about 90 to 110° C.

The reaction time is generally about 30 min to 1 day, preferably about 1-3 hr.

The amount of compound [IIm] to be used is generally about 1 to 5 mol, preferably about 1 to 2 mol, per 1 mol of compound [IIf].

The amount of the ligand to be used is generally about 1 to 5 mol, preferably about 1 to 3 mol, per 1 mol of the metal catalyst.

The amount of the base to be used is generally about 1 to 5 mol, preferably about 1 to 3 mol, per 1 mol of compound [IIf].

(Step 18)

The object compound [IIo] is obtained from compound [IIn] by general functional group conversion or deprotection.

For example, when compound [IIo] contains a hydroxyl group, the compound can be converted by removal of the hydroxyl-protecting group or reduction of an ester thereof, which is a precursor.

For example, in the case of the former, when a hydroxyl group is protected by a benzyl group, the compound can be converted by catalytic hydrogenation reaction. When the hydroxyl group is protected by a silyl group such as t-butyldimethylsilyl group and the like, the compound can be converted by deprotection with tetrabutylammonium fluoride or the like. When diol is protected by a ketal such as acetonide and the like, the compound can be converted by deprotection with acid such as pyridinium p-toluenesulfonate and the like. In the case of the latter, for example, the compound can be converted by a hydride reduction reaction using sodium borohydride, lithium aluminum hydride or the like in a single solvent such as tetrahydrofuran, tetrahydropyran, water and the like or a mixture thereof. Alternatively, conversion is possible by converting ester to carboxylic acid under general hydrolysis conditions, and reducing the acid with a reducing agent such as borane and the like.

Alternatively, compound [IIo] having a hydroxyl group can also be obtained by newly introducing a hydroxyl group. For example, a hydroxymethyl group can be introduced by reacting compound [IIn] having an ester with paraformaldehyde in the presence of a base such as tetrabutylammonium fluoride and the like. Alternatively, compound [IIo] having a hydroxyl group can also be obtained by introducing formyl group by reacting compound [IIn] having an ester with formic acid ester such as ethyl formate, t-butyl formate and the like in the presence of a base such as sodium hydride, potassium t-butoxide and the like, followed by hydride reduction.

When compound [IIo] has a carboxylic acid, compound [IIo] can be obtained by reacting an ester of compound [IIn] in the same manner as in Step 11 under general hydrolysis conditions. For example, when compound [IIn] is t-butyl ester, it can be converted to compound [IIo] under acidic conditions such as trifluoroacetic acid and the like.

When compound [IIo] has a tetrazole ring, the tetrazole ring can be introduced by reacting a cyano group with trimethylsilylazide or the like. A cyano group can be introduced by converting carboxylic acid and the like to an amide and dehydrating the amide with trifluoroacetic anhydride and the like, or by the use of an alkylating agent having a cyano group and the like.

When compound [IIo] has a sulfonamide group, a sulfonamide group can be introduced by amidating an amino group with sulfonyl chloride or the like. The amino group can be introduced by subjecting carboxylic acid to a rearrangement reaction, reacting alkyl halide with an amino source such as phthalimide potassium salt or the like.

The case wherein ring U is pyrazole in the step of obtaining compound [IIo] from compound [IIn] by a functional group conversion is exemplified below.

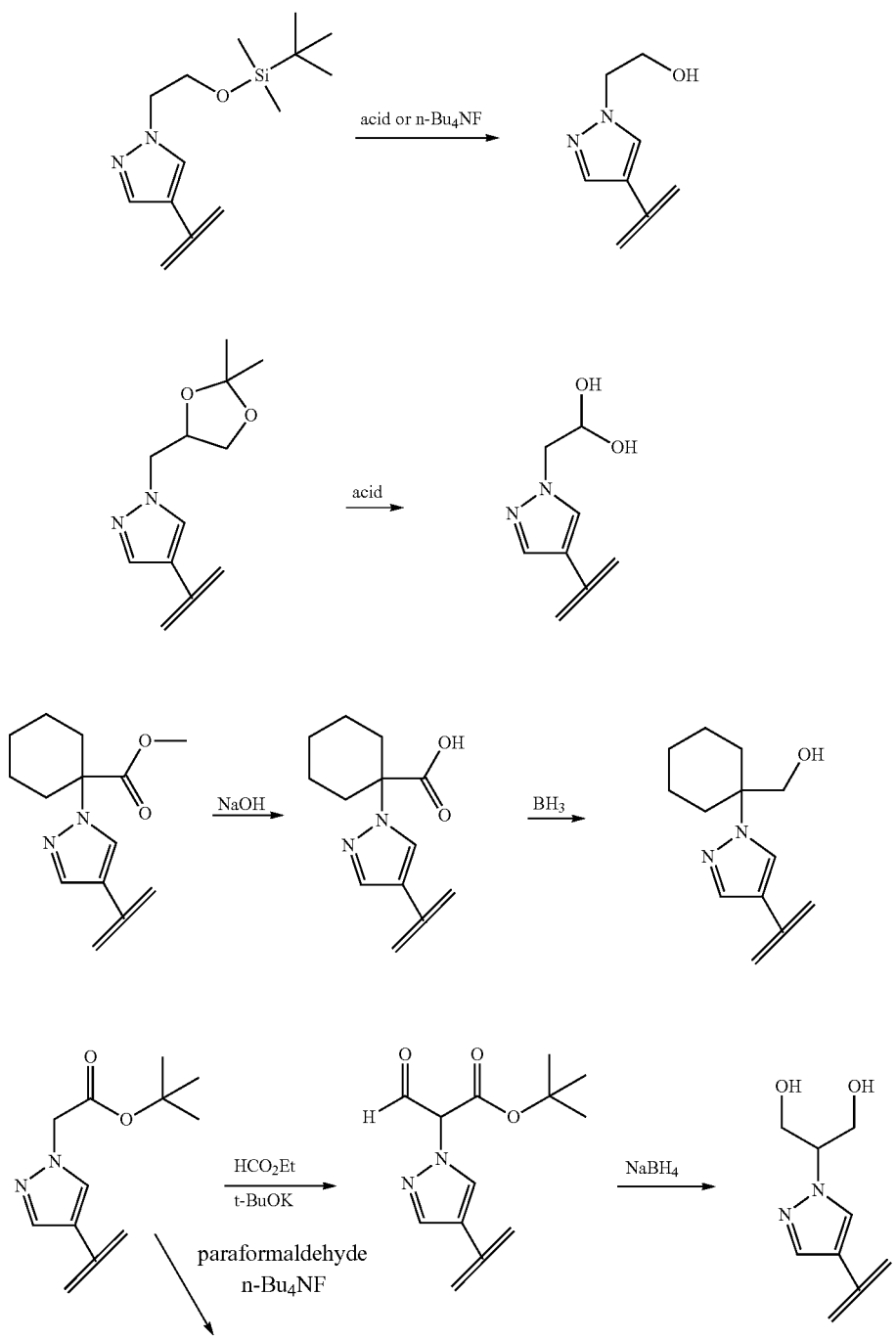

-continued
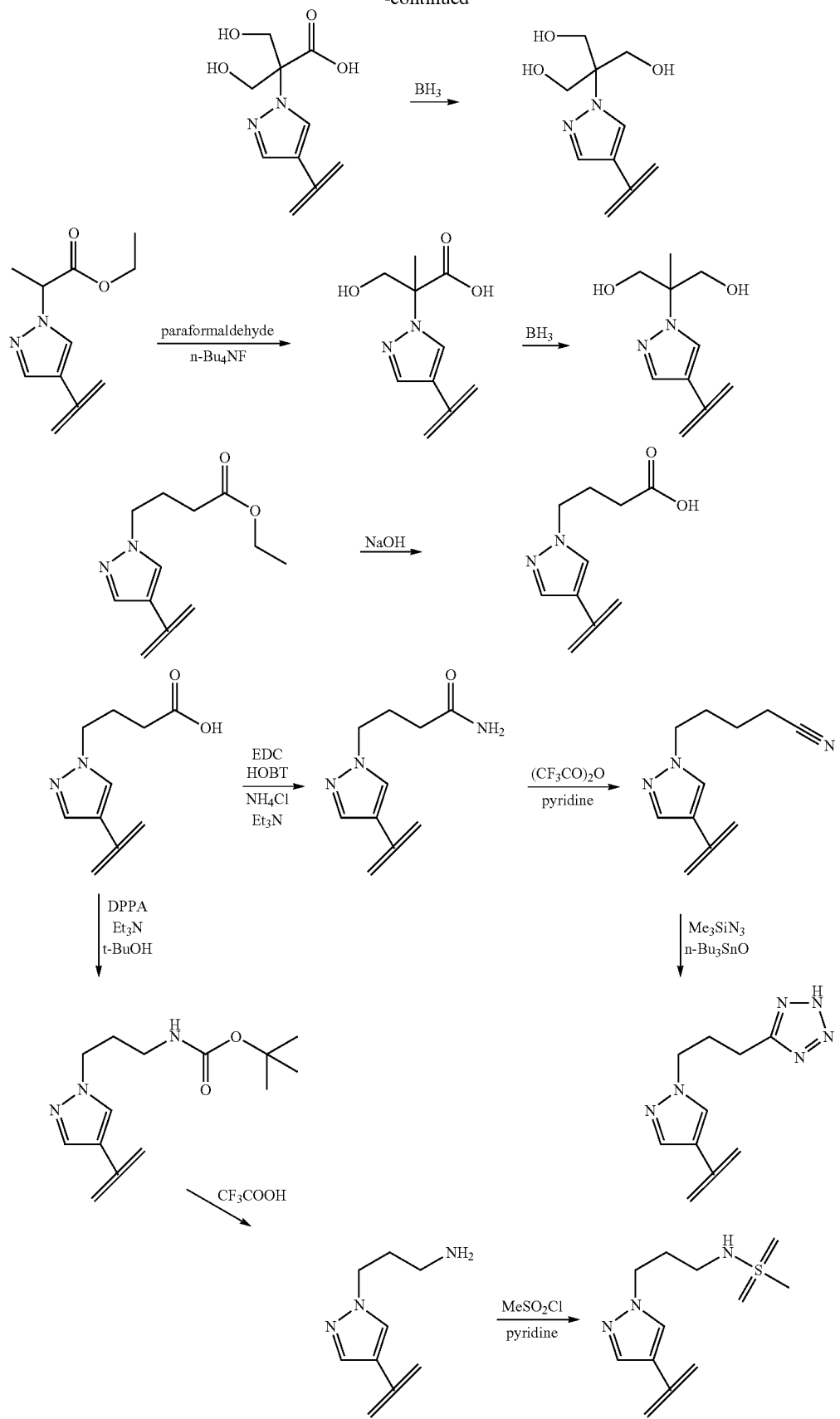

When $Y^d$ is —C(=O)— bond, the compound can be synthesized by an amidation reaction of the corresponding carboxylic acid or an activated derivative thereof with cyclic amine and the like, a reaction with a cyclic organometallic reagent or the like.

For example, various derivatives can be synthesized by the following step.

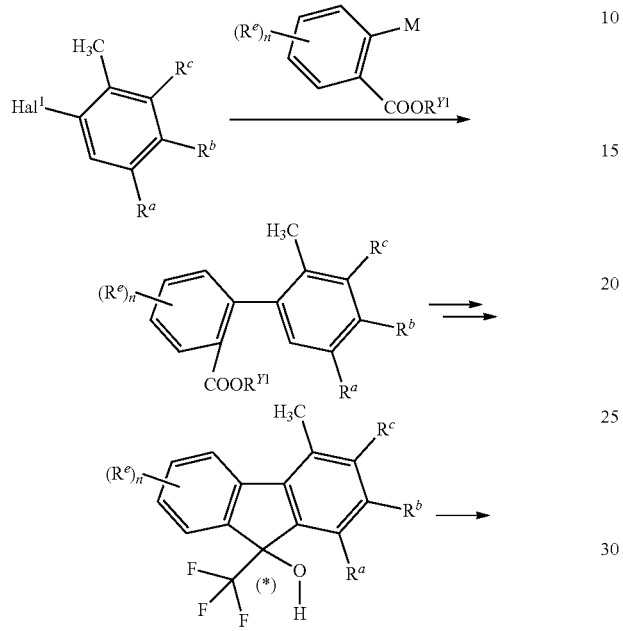

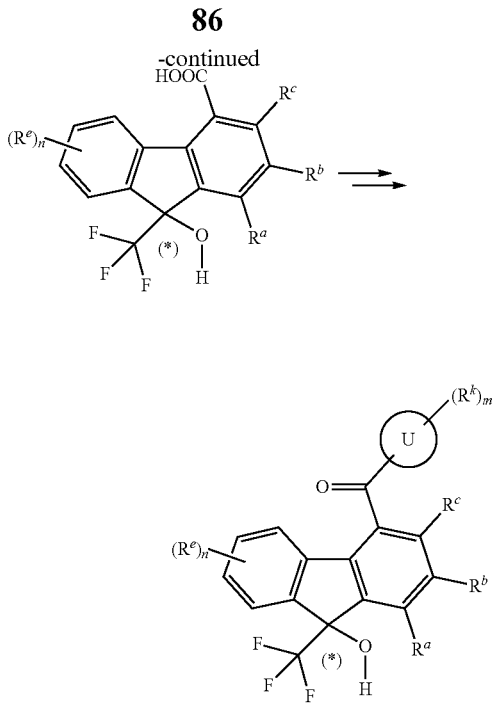

wherein each symbol is as defined above.

Production Method 3 (Production Method of a Compound Represented by the Formula [IV] Wherein $Y^b$ is a Single Bond (Compound [IVn]))

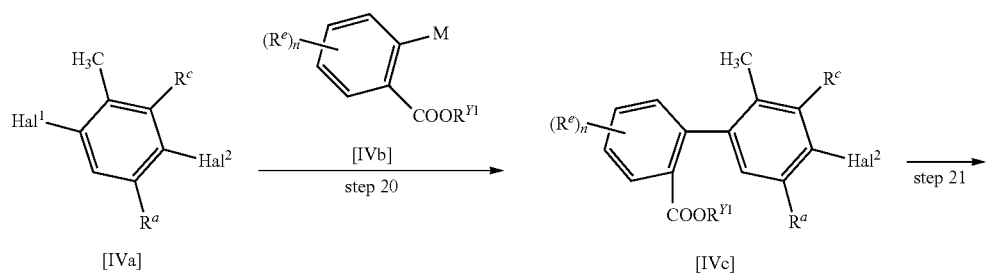

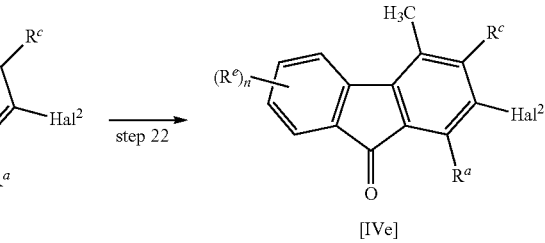

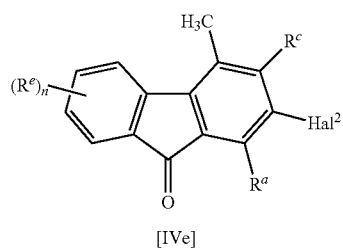
[IVe]
step 23
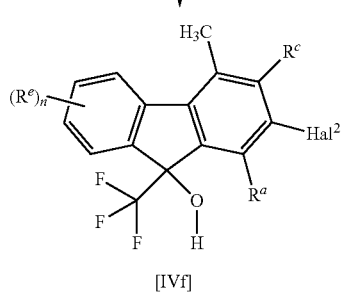
[IVf]
step 24
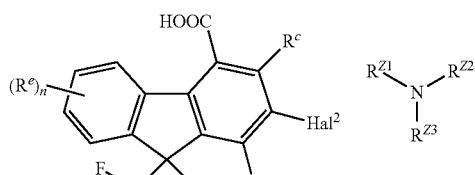
[IVh]
step 25a
step 25b
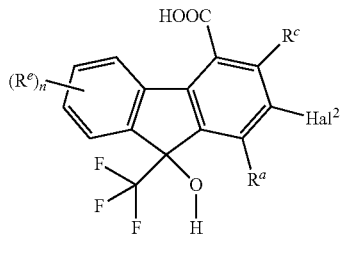
[IVh]
an optically active form
step 26
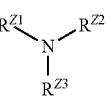
[IVg]
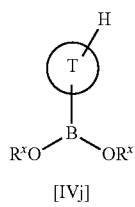
[IVj]
step 27
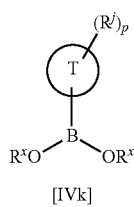
[IVk]
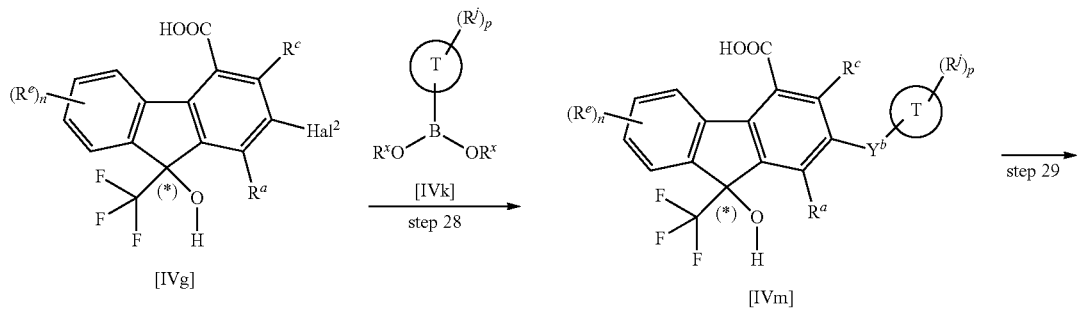
[IVg]
a racemate or
an optically active form
[IVk]
step 28
[IVm]
step 29

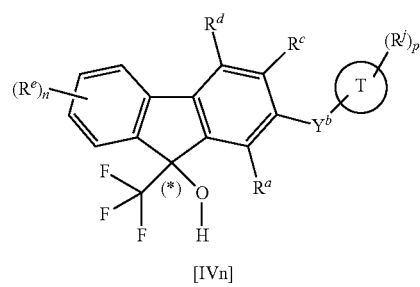

[IVn]

wherein each symbol is as defined above.

(Step 20)

Compound [IVc] can be obtained by reacting compound [IVa] with compound [IVb] in a solvent in the presence of a metal catalyst and a base.

Here, M in compound [IVb] is a group containing boron, zinc, tin or the like and, for example, boronic acid, dialkoxyboron, halogenozinc, trialkyltin and the like can be mentioned. It is preferably dialkoxyboron or boronic acid, particularly preferably 4,4,5,5-tetramethyl-1,3,2-dioxaborolan-2-yl.

Examples of the solvent to be used for the reaction include hydrocarbon solvents such as toluene and the like; ether solvents such as tetrahydrofuran, 1,2-dimethoxyethane, dioxane and the like; amide solvents such as dimethylformamide and the like; dimethyl sulfoxide; water and the like. They can be used alone or two or more kinds thereof may be used in a mixture. Preferable solvent for this reaction is a mixed solvent of toluene and water.

A metal catalyst to be used for the reaction is one containing palladium or nickel. Preferred is palladium, particularly preferably palladium(II) acetate, dichlorobis(triphenylphosphine)palladium(II), 1,1'-bis(diphenylphosphino)ferrocenepalladium(II) dichloride or tetrakis(triphenylphosphine)palladium(0).

The amount of the metal catalyst to be used is generally about 0.001 to 1 mol, preferably about 0.01 to 0.2 mol, per 1 mol of compound [IVa].

Examples of the base to be used for the reaction include alkali metal phosphates such as tripotassium phosphate and the like; alkali metal carbonates such as sodium carbonate and the like; alkali metal acetates such as sodium acetate and the like; organic bases such as triethylamine and the like, with preference given to tripotassium phosphate.

The reaction temperature is generally about room temperature to 120° C., preferably about 90 to 110° C.

The reaction time is generally about 30 min to 1 day, preferably about 1-2 hr.

The amount of compound [IVb] to be used is generally about 1 to 5 mol, preferably about 1 to 2 mol, per 1 mol of compound [IVa].

The amount of the base to be used is generally about 1 to 5 mol, preferably about 1.5 to 3 mol, per 1 mol of compound [IVa].

(Step 21)

Compound [IVd] can be obtained by subjecting compound [IVc] to ester hydrolysis in a solvent.

Ester hydrolysis can be performed under general conditions and, for example, under alkaline conditions or acidic conditions.

When it is performed under alkaline conditions, compound [IVc] is reacted, for example, in the presence of about 1 to 20 mol of a base (alkali metal hydroxide such as potassium hydroxide, sodium hydroxide, lithium hydroxide and the like etc.) per 1 mol of compound [IVc] in, for example, water; alcohol solvents such as methanol, ethanol and the like; ether solvents such as tetrahydrofuran, dioxane, etc., and the like, or a mixed solvent of two or more kinds thereof generally at about 0° C. to 100° C. for about 30 min to 1 day.

When it is performed under acidic conditions, compound [IVc] is reacted, for example, in the presence of about 0.1 to 100 mol of an acid (hydrochloric acid, sulfuric acid etc.) per 1 mol of compound [IVc] in the presence of, for example, water; carboxylic acid solvents such as acetic acid and the like; ether solvents such as tetrahydrofuran, dioxane, etc., and the like, or a mixed solvent of two or more kinds thereof generally at about 0° C. to 100° C. for about 30 min to 2 days.

(Step 22)

Compound [IVe] can be obtained by reacting compound [IVd] to cyclization in the presence of an acid with or without a solvent.

Examples of the acid to be used for the reaction include phosphorus pentoxide, polyphosphoric acid and the like. The amount thereof to be used is generally about 1 mol to a large excess, per 1 mol of compound [IVd]. When a solvent is used, for example, methanesulfonic acid, sulfuric acid and the like can be mentioned. This reaction is preferably performed without solvent or in methanesulfonic acid as a solvent.

The reaction temperature is generally about 50 to 200° C., preferably about 80 to 180° C.

The reaction time is generally about 30 min to 1 day, preferably about 1-3 hr.

(Step 23)

Compound [IVe] is reacted with trimethyl(trifluoromethyl)silane in a solvent in the presence of a catalyst to perform a trifluoromethylation reaction to give a trimethylsilyl ether of compound [IVf], then the resulting trimethylsilyl ether is hydrolyzed to give compound [IVf] as a racemate.

Examples of the solvent to be used for the reaction include amide solvents such as dimethylformamide, N,N-dimethylacetamide and the like and the like. They can be used alone or two or more kinds thereof may be used in a mixture. Preferable solvent for this reaction is dimethylformamide.

Examples of the catalyst to be used for the trifluoromethylation reaction include alkali metal carbonates such as potassium carbonate and the like; alkali metal acetates such as lithium acetate and the like; fluorides such as tetrabutylammonium fluoride and the like and the like, with preference given to potassium carbonate or lithium acetate.

The reaction temperature of trifluoromethylation is generally about 0 to 50° C., preferably about 0° C. to room temperature.

The reaction time of trifluoromethylation is generally about 30 min to 1 day, preferably about 30 min to 3 hr.

The amount of trimethyl(trifluoromethyl)silane to be used is generally about 1 to 5 mol, preferably about 1 to 2.5 mol, per 1 mol of compound [IVe].

The amount of the catalyst to be used for the trifluoromethylation reaction is generally for about 0.01 to 1 mol, preferably about 0.05 to 0.5 mol, per 1 mol of compound [IVe].

Examples of the reagent to be used for trimethylsilyl ether hydrolysis include alkali metal fluoride such as cesium fluoride and the like; ammonium fluoride salts such as tetrabutylammonium fluoride and the like and the like.

The reaction temperature when trimethylsilyl ether is hydrolyzed is generally about −10 to 50° C., preferably about 0° C. to room temperature.

The reaction time when trimethylsilyl ether is hydrolyzed is generally about 1 min to 1 day, preferably about 5 min to 2 hr.

The amount of the reagent to be used for trimethylsilyl ether hydrolysis is generally about 1 to 5 mol, preferably about 1 to 2 mol, per 1 mol of compound [IVe].

(Step 24)

Compound [IVg] can be obtained by reacting compound [IVf] in a solvent in the presence of an oxidant.

Examples of the solvent to be used for the reaction include water, pyridine, t-butyl alcohol, acetone, acetic acid, sulfuric acid and the like. They can be used alone or in a mixture with water. Preferable solvent for this reaction is a mixed solvent of water and pyridine.

Examples of the oxidant to be used for the reaction include permanganates such as potassium permanganate and the like, chromates such as sodium chromate and the like and the like, with preference given to potassium permanganate.

The reaction temperature is generally about 0 to 120° C., preferably 50 to 110° C.

The reaction time is generally about 30 min to 1 day, preferably about 1 to 8 hr.

The amount of potassium permanganate to be used is generally about 2 to 20 mol, preferably about 2 to 10 mol, per 1 mol of compound [IVf].

(Step 25)

As a method for obtaining optically active compound [IVg], a method includes Steps 25a-25b from a racemic compound [IVg]. In this method, (+) or (−) form of compound [IVg] can be produced by appropriately selecting an optically active amine.

(Step 25a)

Compound [IVh], which is a salt of single diastereomer, can be obtained as a solid by mixing compound [IVg] with optically active amine in a solvent.

Examples of the optically active amine to be used include (R)-(+)-1-phenylethylamine, (S)-(−)-1-phenylethylamine, (R)-(+)-1-(1-naphthyl)-ethylamine, (S)-(−)-1-(1-naphthyl)-ethylamine and the like.

The amount of the optically active amine to be used is generally about 0.1 to 1.5 mol, preferably about 0.4 to 1 mol, per 1 mol of compound [IVg].

Examples of the solvent to be used include ester solvents such as ethyl acetate and the like; ether solvents such as isopropyl ether and the like; ketone solvents such as methyl ethyl ketone, methyl isobutyl ketone and the like and the like. They can be used alone or two or more kinds thereof may be used in a mixture. Preferable solvent for this step is ethyl acetate.

The temperature for mixing is generally about 0 to 100° C., preferably about 15 to 30° C.

The time for mixing is generally about 1 hr to 10 days, preferably about 1 day to 3 days.

(Step 25b)

Optically active compound [IVg] can be obtained by treating compound [IVh] with acidic aqueous solution in a solvent, and liberating carboxylic acid.

Examples of the solvent to be used include ester solvents such as ethyl acetate and the like; ether solvents such as ethyl ether and the like; hydrocarbon solvents such as toluene and the like and the like. They can be used alone or two or more kinds thereof may be used in a mixture. Preferable solvent for this reaction is ethyl acetate.

Examples of the acidic aqueous solution to be used include hydrochloric acid, sulfuric acid and the like.

The treatment temperature is generally about 0 to 50° C., preferably about 0° C. to room temperature.

The treatment time is generally about 1 min to 2 hr.

The amount of the acidic aqueous solution to be used is generally about 1 mol to large excess per 1 mol of compound [IVh].

(Step 26)

By treating racemic compound [IVg] using a chiral stationary phase column and the like, a desired optically active compound [IVg] can be separated from the other isomer.

The chiral stationary phase column to be used is, for example, Daicel, CHIRALCEL OD-RH.

Examples of the solvent for separation include a mixed solution of acetonitrile and phosphate buffer wherein the composition ratio thereof is constant or varied.

For separation, a conventional high performance liquid chromatography apparatus is used, which is performed while monitoring with a detector such as ultraviolet absorption and the like.

(Step 27)

Compound [IVk] can be obtained by introducing $R^j$ into compound [IVj] in a solvent in the presence of a base such as potassium carbonate and the like.

For example, when $R^j$ is a (cyclo)alkyl group, compound [IVk] can be obtained by reacting compound [IVj] with (cyclo)alkyl halide such as (cyclo)alkyl iodide, (cyclo)alkyl sulfonic acid ester such as (cyclo)alkyl tosylate or the like in amide solvents such as dimethylformamide, N,N-dimethylacetamide and the like or acetonitrile.

(Step 28)

Compound [IVm] can be obtained by reacting compound [IVg] in the form of a racemate or an optically active form with compound [IVk] in a solvent in the presence of a metal catalyst, a ligand and a base.

Boronic acid moiety of compound [IVk] is boronic acid per se, or boronic acid ester, preferably 4,4,5,5-tetramethyl-1,3,2-dioxaborolan-2-yl.

Examples of the solvent to be used for the reaction include hydrocarbon solvents such as toluene and the like; ether solvents such as tetrahydrofuran, 1,2-dimethoxyethane, dioxane and the like; amide solvents such as dimethylformamide and the like; dimethyl sulfoxide; water and the like. They can be used alone or two or more kinds thereof may be used in a mixture. Preferable solvent for this reaction is a mixed solvent of dioxane and water.

The metal catalyst to be used for the reaction is palladium, for example, palladium(II) acetate, dichlorobis(triphenylphosphine)palladium(II), tetrakis(triphenylphosphine)palladium(0), with preference given to palladium(II) acetate.

The amount of the metal catalyst to be used is generally for about 0.001 to 1 mol, preferably about 0.01 to 0.2 mol, per 1 mol of compound [IVg].

The ligand to be used for the reaction is phosphine such as triphenylphosphine, tributylphosphine, 2-dicyclohexylphosphino-2',6'-dimethoxybiphenyl and the like. Preferred is 2-dicyclohexylphosphino-2',6'-dimethoxybiphenyl.

Examples of the base to be used for the reaction include alkali metal phosphates such as tripotassium phosphate and the like; alkali metal carbonates such as sodium carbonate and the like; alkali metal acetate such as sodium acetate and the like, with preference given to tripotassium phosphate.

The reaction temperature is generally about room temperature to 120° C., preferably about 90 to 110°.

The reaction time is generally about 30 min to 1 day, preferably about 1-3 hr.

The amount of compound [IVk] to be used is generally about 1 to 5 mol, preferably about 1 to 2 mol, per 1 mol of compound [IVg].

The amount of the ligand to be used is generally about 1 to 5 mol, preferably about 1 to 3 mol, per 1 mol of the metal catalyst.

The amount of the base to be used is generally about 1 to 5 mol, preferably about 1 to 3 mol, per 1 mol of compound [IVg].

(Step 29)

The object compound [IVn] is obtained from compound [IVm] by general functional group conversion or deprotection.

For example, when compound [IVn] contains carboxamide, the compound can be obtained by reacting carboxylic acid with amine to allow amidation with, for example, a condensation agent such as 1-(3-dimethylaminopropyl)-3-ethylcarbodiimide hydrochloride and the like in the presence of 1-hydroxybenzotriazole hydrate in a solvent such as dimethylformamide, chloroform and the like. In this case, carboxylic acid may be converted in advance to acid chloride, mixed acid anhydride or the like, and reacted with amine to allow amidation, whereby compound [IVn] containing carboxamide can be obtained.

When compound [IVn] has an ester, a general esterification reaction with alcohol needs to be performed. For example, carboxylic acid may be converted in advance to an acid chloride, and reacted with alcohol in the presence of a base such as pyridine and the like without solvent or in chloroform, whereby compound [IVn] having an ester can be obtained. Compound [IVn] having an ester can also be obtained by reacting carboxylic acid with alkyl halide in the presence of a base such as potassium carbonate in, for example, dimethylformamide.

When compound [IVn] contains a hydroxyl group, it can be obtained by reduction of carboxylic acid or a reaction with an organometallic reagent. In the case of the former, for example, compound [IVn] containing a hydroxyl group can be obtained by performing a hydride reduction reaction using borane, lithium aluminum hydride and the like in a single or mixed solvent of ethyl ether, tetrahydrofuran, tetrahydropyran and the like.

When $Y^b$ is an amine bond (—$NR^{b16}$—), compound [IVn] wherein $Y^b$ is an amine bond can be synthesized by subjecting compound [IVg] to a condensation reaction with amine compound or the like in the presence of a catalyst such as palladium and the like.

When $Y^b$ is alkanediyl, compound [IVn] wherein $Y^b$ is alkanediyl can be synthesized by subjecting compound [IVg] to a condensation reaction with an organic zinc compound and the like in the presence of a catalyst such as palladium and the like.

When $Y^b$ is alkenediyl, compound [IVn] wherein $Y^b$ is alkenediyl can be synthesized by subjecting compound [IVg] to a condensation reaction with an alkenylboron compound and the like in the presence of a catalyst such as palladium and the like.

Production Method 4 (Production Method of a Compound Represented by the Formula [IV] Wherein $Y^b$ is —C(=O)— Bond (Compound [IVz]))

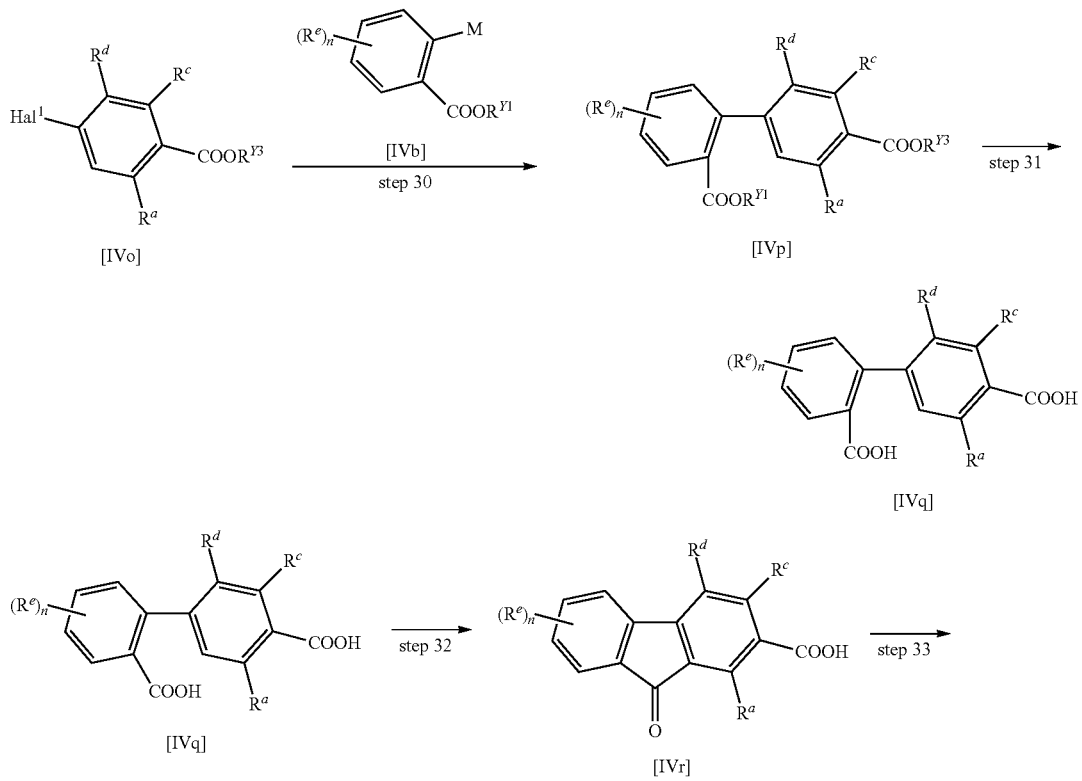

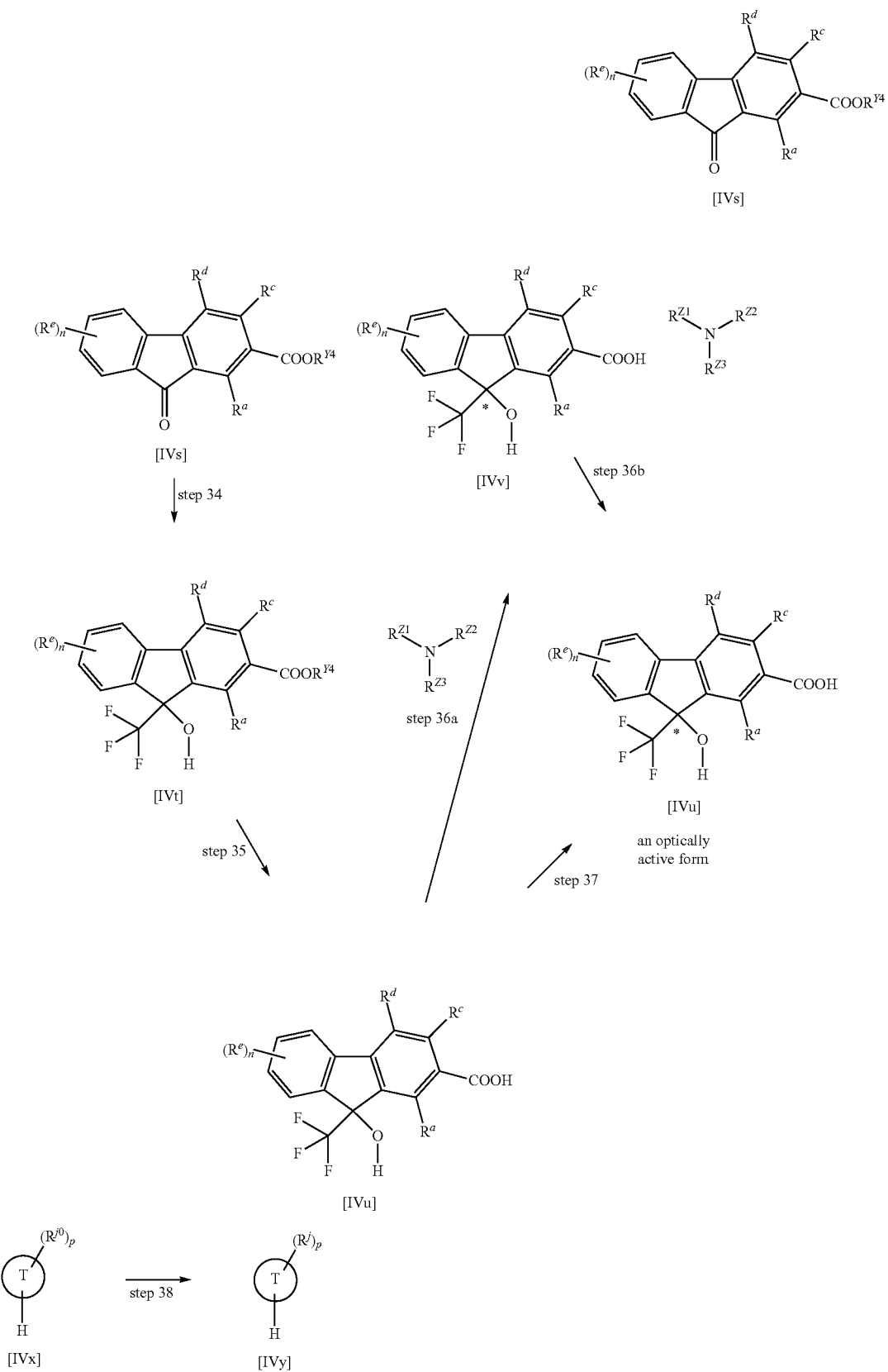

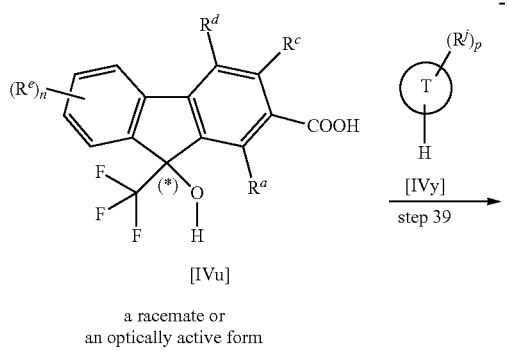 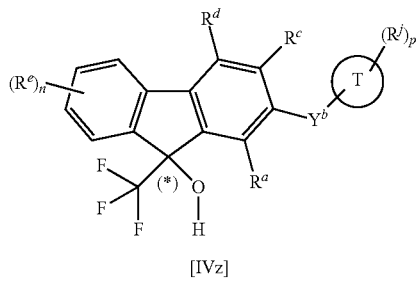

[IVu] a racemate or an optically active form

[IVz]

wherein
"$R^{Y3}$" and "$R^{Y4}$" are the same or different and each is a carboxyl-protecting group such as a $C_{1-4}$ alkyl group (e.g., a methyl group, an ethyl group, a t-butyl group etc.), a benzyl group and the like;
"$R^{j0}$" is a substituent (e.g., a carboxyl group etc.) that can be converted to "$R^{j}$" (e.g., a carbamoyl group etc.) by various functional group conversion reactions, and
other symbols are as defined above.
(Step 30)
Compound [IVp] can be obtained by reacting compound [IVo] with compound [IVb] in a solvent, in the presence of a metal catalyst and a base.

Here, M of compound [IVb] is a group containing boron, zinc, tin or the like. Examples thereof include boronic acid, dialkoxyboron, halogenozinc, trialkyltin and the like. Preferred are dialkoxyboron and boronic acid, and particularly preferred is 4,4,5,5-tetramethyl-1,3,2-dioxaborolan-2-yl.

Examples of the solvent to be used for the reaction include hydrocarbon solvents such as toluene and the like; ether solvents such as tetrahydrofuran, 1,2-dimethoxyethane, dioxane and the like; amide solvents such as dimethylformamide and the like; dimethyl sulfoxide; water and the like. They can be used alone or two or more kinds thereof may be used in a mixture. Preferable solvent for this reaction is a mixed solvent of toluene and water.

Examples of the metal catalyst to be used for the reaction include those having palladium or nickel, and preferred are palladium, and particularly preferred are palladium(II) acetate, dichlorobis(triphenylphosphine)palladium(II), 1,1'-bis(diphenylphosphino)ferrocene-palladium(II) dichloride, tetrakis(triphenylphosphine)palladium(0).

The amount of the metal catalyst to be used is generally about 0.001 to 1 mol, preferably about 0.01 to 0.2 mol, per 1 mol of compound [IVo].

Examples of the base to be used for the reaction include alkali metal phosphates such as tripotassium phosphate and the like; alkali metal carbonates such as sodium carbonate and the like; alkali metal acetates such as sodium acetate and the like; organic bases such as triethylamine and the like, with preference given to tripotassium phosphate.

The reaction temperature is generally about room temperature to 120° C., preferably about 90 to 110°.

The reaction time is generally about 30 min to 1 day, preferably about 1-2 hr.

The amount of compound [IVb] to be used is generally about 1 to 5 mol, preferably about 1 to 2 mol, per 1 mol of compound [IVo].

The amount of the base to be used is generally about 1 to 5 mol, preferably about 1.5 to 3 mol, per 1 mol of compound [IVo].

(Step 31)
Compound [IVq] can be obtained by subjecting compound [IVp] to ester hydrolysis in a solvent.

The ester hydrolysis may be performed under general conditions, for example, under alkaline conditions or acidic conditions.

When the hydrolysis is performed under alkaline conditions, compound [IVp] is reacted, for example, in the presence of about 1 to 20 mol of a base (alkali metal hydroxide such as potassium hydroxide, sodium hydroxide, lithium hydroxide etc., and the like) per 1 mol of compound [IVp] in, for example, water; alcohol solvents such as methanol, ethanol and the like; ether solvents such as tetrahydrofuran, dioxane etc., and the like, or a mixed solvent of two or more kinds thereof generally at about 0° C. to 100° C. for about 30 min to 1 day.

For reaction under acidic conditions, compound [IVp] is reacted in the presence of, for example, about 0.1 to 100 mol of an acid (hydrochloric acid, sulfuric acid etc.) per 1 mol of compound [IVp] in, for example, water; carboxylic acid solvents such as acetic acid and the like; ether solvents such as tetrahydrofuran, dioxane, etc., and the like, or a mixed solvent of two or more kinds thereof generally at about 0° C. to 100° C. for about 30 min to 2 days.

(Step 32)
Compound [IVr] can be obtained by cyclization reaction of compound [IVq] in the presence of an acid without solvent or in a solvent.

Examples of the acid to be used for the reaction include phosphorus pentoxide, polyphosphoric acid and the like. The amount thereof to be used is generally about 1 mol to a large excess per 1 mol of compound [IVq]. In addition, when a solvent is used, for example, methanesulfonic acid, sulfuric acid and the like can be mentioned. This reaction is preferably performed without a solvent or in methanesulfonic acid as a solvent.

The reaction temperature is generally about 50 to 200° C., preferably about 80 to 180° C.

The reaction time is generally about 30 min to 1 day, preferably about 1-3 hr.

(Step 33)
Compound [IVs] can be obtained by esterification reaction of compound [IVr] with alkyl halide in a solvent in the presence of a base.

Examples of the solvent to be used for the reaction include amide solvents such as dimethylformamide, N,N-dimethylacetamide and the like; dimethyl sulfoxide; water and the like. Preferable solvent for this reaction is dimethylformamide.

Examples of the base to be used for the reaction include alkali metal carbonates such as potassium carbonate and the like, alkali metal hydrides such as sodium hydride and the like; alkali metal hydroxides such as sodium hydroxide and the like, and the like; with preference given to potassium carbonate.

Examples of the halogen of the alkyl halide to be used for the reaction include iodine, bromine and the like, and examples of the alkyl include methyl, ethyl and the like. Preferred for this step is methyl iodide.

The reaction temperature is generally about 0 to 100° C., preferably about 0 to 80° C.

The reaction time is generally about 10 min to 1 day, preferably about 30 min to 12 hr.

The amount of the base to be used is generally about 1 to 5 mol, preferably about 1 to 3 mol, per 1 mol of compound [IVr].

The amount of the alkyl halide to be used is generally about 1 to 5 mol, preferably about 1 to 3 mol, per 1 mol of compound [IVr].

(Step 34)

Compound [IVs] is reacted with trimethyl(trifluoromethyl)silane in a solvent in the presence of a catalyst to perform a trifluoromethylation reaction to give a trimethylsilyl ether of compound [IVt], then the resulting trimethylsilyl ether is hydrolyzed to give compound [IVt] as a racemate.

Examples of the solvent to be used for the reaction include amide solvents such as dimethylformamide, N,N-dimethylacetamide and the like, and the like. They can be used alone or two or more kinds thereof may be used in a mixture. Preferable solvent for this reaction is dimethylformamide.

Examples of the catalyst to be used for the trifluoromethylation reaction include alkali metal carbonates such as potassium carbonate and the like; alkali metal acetates such as lithium acetate and the like; fluorides such as tetrabutylammonium fluoride and the like; and the like, with preference given to potassium carbonate and lithium acetate.

The reaction temperature of trifluoromethylation is generally about 0 to 50° C., preferably about 0° C. to room temperature.

The reaction time of trifluoromethylation is generally about 30 min to 1 day, preferably about 30 min to 3 hr.

The amount of trimethyl(trifluoromethyl)silane to be used is generally about 1 to 5 mol, preferably about 1 to 2.5 mol, per 1 mol of compound [IVs].

The amount of the catalyst to be used for the trifluoromethylation reaction is generally about 0.01 to 1 mol, preferably about 0.05 to 0.5 mol, per 1 mol of compound [IVs].

Examples of the reagent to be used for the trimethylsilyl ether hydrolysis include alkali metal fluoride such as cesium fluoride and the like; ammonium fluoride salts such as tetrabutylammonium fluoride and the like; and the like.

The reaction temperature when trimethylsilyl ether is hydrolyzed is generally about −10 to 50° C., preferably about 0° C. to room temperature.

The reaction time when trimethylsilyl ether is hydrolyzed is generally about 1 min to 1 day, preferably about 5 min to 2 hr.

The amount of the reagent to be used for trimethylsilyl ether hydrolysis is generally about 1 to 5 mol, preferably about 1 to 2 mol, per 1 mol of compound [IVs].

(Step 35)

Compound [IVu] can be obtained by subjecting compound [IVt] to ester hydrolysis in a solvent under alkaline conditions.

Examples of the solvent to be used for the reaction include water; alcohol solvents such as methanol, ethanol and the like; ether solvents such as tetrahydrofuran, dioxane and the like; and the like. They can be used alone or two or more kinds thereof may be used in a mixture. Preferable solvents for this reaction is a mixed solvent of water, methanol and tetrahydrofuran.

Examples of the alkali to be used for the reaction include alkali metal hydroxide such as potassium hydroxide, sodium hydroxide, lithium hydroxide and the like, and the like, with preference given to sodium hydroxide.

The reaction temperature is generally about 0 to 120° C., preferably about 0 to 90° C.

The reaction time is generally about 10 min to 1 day, preferably about 30 min to 12 hr.

The amount of the alkali to be used is generally about 1 mol to large excess, preferably about 1 to 10 mol, per 1 mol of compound [IVt].

(Step 36)

As a method for obtaining optically active compound [IVu], a method includes Steps 36a-36b from a racemic compound [IVu]. In this method, (+) or (−) form of compound [IVu] can be produced by appropriately selecting an optically active amine.

(Step 36a)

Compound [IVv], which is a salt of single diastereomer, can be obtained as a solid by mixing compound [IVu] with an optically active amine in a solvent.

Examples of the optically active amine to be used include (R)-(+)-1-phenylethylamine, (S)-(−)-1-phenylethylamine, (R)-(+)-1-(1-naphthyl)-ethylamine, (S)-(−)-1-(1-naphthyl)-ethylamine and the like.

The amount of the optically active amine to be used is generally about 0.1 to 1.5 mol, preferably about 0.4 to 1 mol, per 1 mol of compound [IVu].

Examples of the solvent to be used include ester solvents such as ethyl acetate and the like; ether solvents such as ethyl ether and the like; and the like. They can be used alone or two or more kinds thereof may be used in a mixture. Preferable solvent for this step is ethyl acetate.

The temperature for mixing is generally about 0 to 100° C., preferably about 15 to 80° C.

The time for mixing is generally about 1 hr to 10 days, preferably about 1 to 12 hr.

(Step 36b)

Optically active compound [IVu] can be obtained by treating compound [IVv] with acidic aqueous solution in a solvent, and liberating carboxylic acid.

Examples of the solvent to be used include ester solvents such as ethyl acetate and the like; ether solvents such as ethyl ether and the like; hydrocarbon solvents such as toluene and the like and the like. They can be used alone or two or more kinds thereof may be used in a mixture. Preferable solvent for this reaction is ethyl acetate.

Examples of the acidic aqueous solution to be used include hydrochloric acid, sulfuric acid and the like.

The treatment temperature is generally about 0 to 50° C., preferably about 0° C. to room temperature.

The treatment time is generally about 1 min to 2 hr.

The amount of the acidic aqueous solution to be used is generally about 1 mol to large excess per 1 mol of compound [IVv].

(Step 37)

By treating racemic compound [IVu] using a chiral stationary phase column and the like, a desired optically active compound [IVu] can be separated from the other isomer.

The chiral stationary phase column to be used is, for example, Daicel, CHIRALCEL OD-RH.

Examples of the solvent for separation include a mixed solution of acetonitrile and phosphate buffer wherein the composition ratio thereof is constant or varied.

For separation, a conventional high performance liquid chromatography apparatus is used, which is performed while monitoring with a detector such as ultraviolet absorption and the like.

(Step 38)

Compound [IVy] can be obtained by converting a precursor in $R^{j0}$ of compound [IVx] to a functional group in $R^j$ of compound [Ivy].

For example, when $R^j$ contains amide, compound [IVy] having amide in $R^j$ can be obtained by amidation reaction of compound [IVx] having carboxylic acid for $R^{j0}$ with amine in the presence of a condensation agent such as 1-(3-dimethylaminopropyl)-3-ethylcarbodiimide hydrochloride and the like and 1-hydroxybenzotriazole hydrate in a solvent such as dimethylformamide, chloroform and the like.

When a functional group influenced by conversion of a precursor in $R^{j0}$ of compound [IVx] to a functional group in $R^j$ of compound [Ivy] is present in other part of compound [IVx], a protecting group may be introduced as appropriate. For example, when an amino group is present in other part during production of compound [IVy] having amide in $R^j$ by amidation of compound [IVx] having carboxylic acid for $R^{j0}$, a protecting group such as t-butyloxycarbonyl group, benzyloxycarbonyl group and the like is introduced into the amino group by a conventional method, a desired amidation reaction is performed, and then deprotection is performed by a general method.

(Step 39)

Compound [IVz] can be obtained by reacting compound [IVu], which is a racemate or an optically active form, with compound [IVy].

When compound [IVy] is cyclic amine, compound [IVz] can be obtained by general amidation reaction. For example, compound [IVu] and compound [IVy] are reacted in a solvent in the presence of a condensation agent. Examples of the condensation agent include 1-(3-dimethylaminopropyl)-3-ethylcarbodiimide hydrochloride in the copresence of 1-hydroxybenzotriazole hydrate and the like, and examples of the solvent include dimethylfoimamide, chloroform and the like.

Alternatively, compound [IVu], which is a racemate or an optically active form, may be converted in advance to acid chloride, mixed acid anhydride or the like and reacted with compound [IVy], whereby compound [IVz] can be obtained.

In addition, compound [IVz] is obtained by reacting compound [IVy] with an organic base such as LDA and the like, and reacting the resultant with compound [IVu] or, for example, an amide compound thereof with N,O-dimethylhydroxyamine or the like.

When $Y^b$ is an ether bond etc., compound [IVz] wherein $Y^b$ is an ether bond etc. can be synthesized by subjecting the corresponding phenol compound to reactions such as Mitsunobu reaction, alkylation reaction with alkyl halide or alkyl sulfonate, and the like.

For example, various derivatives can be synthesized by the following steps.

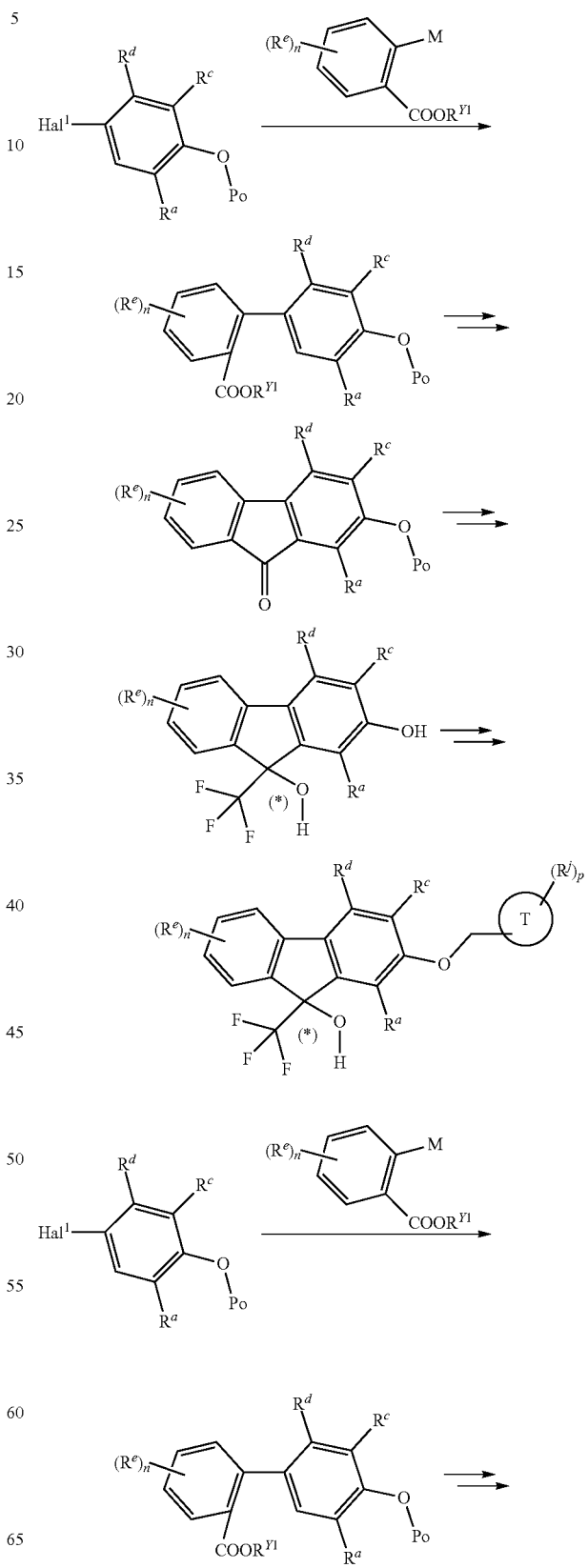

103
-continued

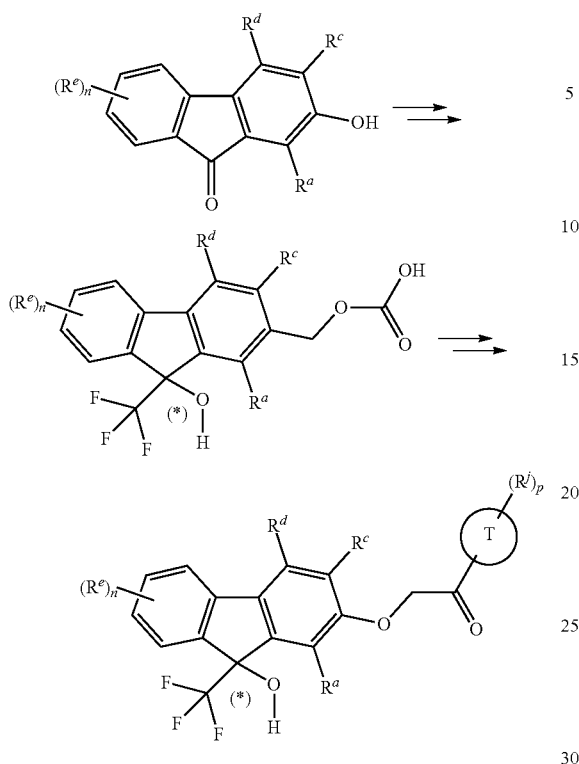

wherein
"Po" is a hydroxyl-protecting group (e.g., a methyl group etc.); and
other symbols are as defined above.

Production Method 5 (Production Method of a Compound Represented by the Formula [I] Wherein Xd is a Nitrogen Atom (Compound [V]))

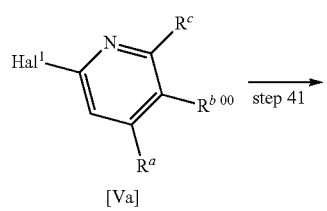

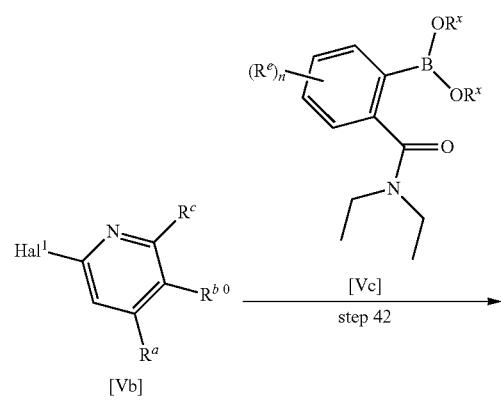

104
-continued

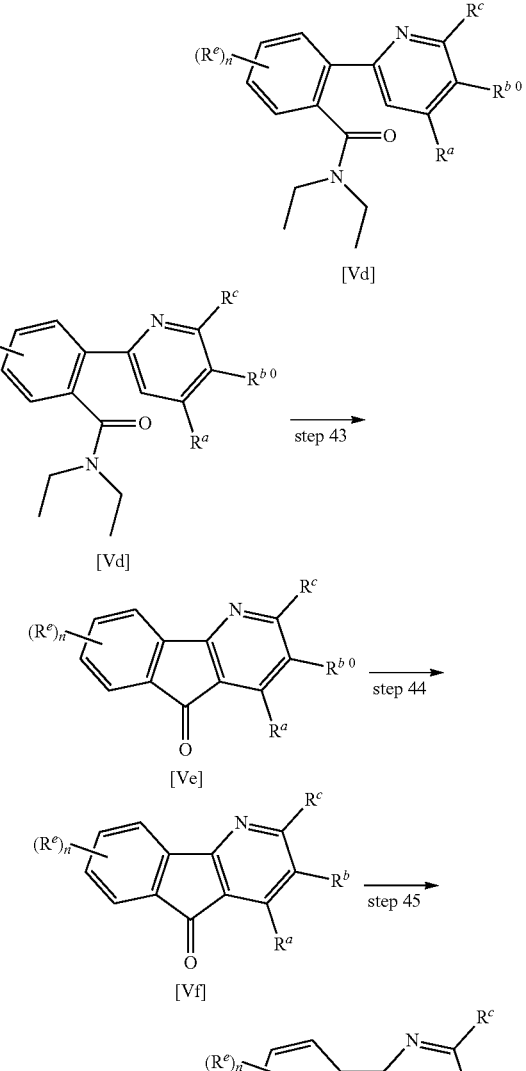

wherein
"$R^{b00}$" is a substituent (e.g., a hydroxy group etc.) that can be converted to "$R^{b0}$" (e.g., a methoxy group etc.) by various functional group conversion reactions;
"$R^{b0}$" is a substituent (e.g., a methoxy group etc.) that can be converted to "$R^b$" (e.g., carboxamide, an alkoxy group substituted by lactam and the like, an alkyl group etc.) by various functional group conversion reactions; and
other symbols are as defined above.

(Step 41)

When a functional group influenced by the reaction in the next Step 42 is present in compound [Va], a protecting group may be introduced into the functional group as appropriate to give compound [Vb].

For example, when the functional group influenced by the reaction is a hydroxyl group, compound [Va] is subjected to alkylation reaction with an alkylating agent in a solvent in the presence of a base to give compound [Vb].

Examples of the solvent to be used for the reaction include amide solvents such as dimethylformamide and the like; ether solvents such as tetrahydrofuran and the like; dimethylsulfoxide and the like. They can be used alone or two or more kinds thereof may be used in a mixture. Preferable solvent for this reaction is dimethylformamide.

Examples of the alkylating agent to be used for the reaction include alkyl halide such as methyl iodide and the like; alkyl sulfonates such as ethyl tosylate and the like; sulfuric acid esters such as methyl sulfate and the like; and the like, with preference given to methyl iodide.

Examples of the base to be used for the reaction include alkali metal carbonates such as potassium carbonate and the like; alkali metal hydrides such as sodium hydride and the like; alkali metal hydroxides such as sodium hydroxide and the like; and the like, with preference given to potassium carbonate.

The reaction temperature is generally about 0 to 120° C., preferably about 0 to 80° C.

The reaction time is generally about 30 min to 1 day, preferably about 1 hr to 1 day.

The amount of the alkylating agent to be used is generally about 1 to 3 mol, preferably about 1 to 2 mol, per 1 mol of compound [Va].

The amount of the base to be used is generally about 1 to 10 mol, preferably about 1 to 5 mol, per 1 mol of compound [Va].
(Step 42)

Compound [Vd] can be obtained by reacting compound [Vb] with compound [Vc] in a solvent in the presence of a metal catalyst and a base.

The boronic acid moiety of compound [Vc] is boronic acid per se, or boronic acid ester, preferably boronic acid per se.

Examples of the solvent to be used for the reaction include hydrocarbon solvents such as toluene and the like; ether solvents such as tetrahydrofuran, 1,2-dimethoxyethane, dioxane and the like; amide solvents such as dimethylformamide and the like; dimethyl sulfoxide; water and the like. They can be used alone or two or more kinds thereof may be used in a mixture. Preferable solvent for this reaction is a mixed solvent of so toluene and water.

Examples of the metal catalyst to be used for the reaction include one containing palladium. Particularly preferred is 1,1'-bis(diphenylphosphino)ferrocene-palladium(II) dichloride.

The amount of the metal catalyst to be used is generally about 0.001 to 1 mol, preferably about 0.01 to 0.2 mol, per 1 mol of compound [Vb].

Examples of the base to be used for the reaction include alkali metal phosphates such as tripotassium phosphate and the like; alkali metal carbonates such as sodium carbonate and the like; alkali metal acetates such as sodium acetate and the like, with preference given to tripotassium phosphate.

The reaction temperature is generally about room temperature to 120° C., preferably about 70 to 110° C.

The reaction time is generally about 30 min to 1 day, preferably about 1-3 hr.

The amount of compound [Vc] to be used is generally about 1 to 5 mol, preferably about 1 to 2 mol, per 1 mol of compound [Vb].

The amount of the base to be used is generally about 1 to 5 mol, preferably about 1.5 to 3 mol, per 1 mol of compound [Vb].
(Step 43)

Compound [Ve] can be obtained by cyclization reaction of compound [Vd] in a solvent in the presence of a base.

Examples of the solvent to be used for the reaction include hydrocarbon solvents such as n-hexane and the like; ether solvents such as tetrahydrofuran and the like; amide solvents such as N-methylpyrrolidone and the like; and the like. They can be used alone or two or more kinds thereof may be used in a mixture. Preferable solvent for this reaction is tetrahydrofuran.

Examples of the base to be used for the reaction include amide bases such as lithium N,N-diisopropylamide, lithium hexamethyldisilazide and the like; organometalllics such as butyllithium and the like; and the like, with preference given to lithium N,N-diisopropylamide.

The reaction temperature is generally about −78 to 100° C., preferably about −10 to 50° C.

The reaction time is generally about 10 min to 1 day, preferably about 10 min to 3 hr.

The amount of the base to be used is generally about 1 to 10 mol, preferably about 1 to 3 mol, per 1 mol of compound [Vd].
(Step 44)

Compound [Vf] is obtained from compound [Ve] by general functional group conversion or deprotection.

For example, when $R^b$ is a (substituted) alkoxy group and $R^{b00}$ of compound [Va] is a hydroxyl group which is subjected to alkyl group protection in the earlier Step 41, compound [Vf] wherein $R^b$ is a (substituted) alkoxy group can be obtained by deprotection to regenerate the hydroxyl group according to a conventional method, for example, by fusing compound [Ve] and pyridinium chloride and the like and, alkylation by, for example, Mitsunobu reaction and the like.

When $R^b$ is a (substituted) alkyl group and $R^{b00}$ of compound [Va] is a hydroxyl group which is subjected to alkyl group protection in the earlier Step 41, compound [Vf] wherein $R^b$ is a (substituted) alkyl group can be obtained by deprotection according to a conventional method to regenerate the hydroxyl group, conversion to trifluoromethanesulfonate, a reaction of the trifluoromethanesulfonate compound with a terminal acetylene compound or an alkenyl metal compound such as an alkenylboron compound and the like in the presence of a metal catalyst such as palladium and the like, and a hydrogenation reaction.
(Step 45)

Compound [V] can be obtained as a racemate by reacting compound [Vf] with trimethyl(trifluoromethyl)silane in a solvent in the presence of a catalyst to cause trifluoromethylation reaction, whereby a trimethylsilyl ether of compound [V] is obtained, then hydrolyzing the resulting trimethylsilyl ether.

Examples of the solvent to be used for the reaction include amide solvents such as dimethylformamide, N,N-dimethylacetamide and the like, and the like. They can be used alone or two or more kinds thereof may be used in a mixture. Preferable solvent for this reaction is dimethylformamide.

Examples of the catalyst to be used for the trifluoromethylation reaction include alkali metal carbonates such as potassium carbonate and the like; alkali metal acetates such as lithium acetate and the like; fluorides such as tetrabutylammonium fluoride and the like; and the like, with preference given to potassium carbonate and lithium acetate.

The reaction temperature of trifluoromethylation is generally about 0 to 50° C., preferably about 0° C. to room temperature.

The reaction time of trifluoromethylation is generally about 30 min to 1 day, preferably about 30 min to 3 hr.

The amount of trimethyl(trifluoromethyl)silane to be used is generally about 1 to 5 mol, preferably about 1 to 2.5 mol, per 1 mol of compound [Vf].

The amount of the catalyst to be used for the trifluoromethylation reaction is generally for about 0.01 to 1 mol, preferably about 0.05 to 0.5 mol, per 1 mol of compound [Vf].

Examples of the reagent to be used for the trimethylsilyl ether hydrolysis include alkali metal fluorides such as cesium fluoride and the like; ammonium fluoride salts such as tetrabutylammonium fluoride and the like; and the like.

The reaction temperature when trimethylsilyl ether is hydrolyzed is generally about −10 to 50° C., preferably about 0° C. to room temperature.

The reaction time when trimethylsilyl ether is hydrolyzed is generally about 1 min to 1 day, preferably about 5 min to 2 hr.

The amount of the reagent to be used for trimethylsilyl ether hydrolysis is generally about 1 to 5 mol, preferably about 1 to 2 mol, per 1 mol of compound [Vf].

As for compound [V], a desired optically active compound [V] can be separated from the other isomer by a preferential crystallization method, a diastereomer method, an optical resolution method using a chiral stationary phase column, or the like.

EXAMPLES

The production of the compound of the present invention is specifically explained by Examples. However, the present invention is not limited by these Examples.

The room temperature in the Examples means 1-40° C.
(Derivatization Method a for Determination of Optical Purity)

A solid (0.002-0.003 g) to be analyzed is shaken with ethyl acetate (0.1 ml) and 1N hydrochloric acid (0.1 ml), the mixture was stood still to separate layers. The upper layer (0.010 ml) was added to the following preparation solution (0.1 ml), and the mixture was shaken at 50° C. for 30 min. The obtained mixture was analyzed by HPLC.
(Preparation Solution)

Dimethylformamide was added to 1-(3-dimethylaminopropyl)-3-ethylcarbodiimide hydrochloride (0.191 g) and 1-hydroxybenzotriazole hydrate (0.153 g) to a total amount of 10 ml. (S)-(−)-1-(1-Naphthyl)-ethylamine (0.258 ml) was added to the mixture to give the title preparation solution.
(10 mM Phosphate Buffer (pH 2.0))

Potassium dihydrogen phosphate (4.08 g) was dissolved in water (3000 mL) and adjusted to pH 2.0 with phosphoric acid to give the title buffer.
HPLC Analysis Conditions
Analysis Condition 1
instrument: HPLC system SHIMADZU Corporation high-speed liquid
Chromatography Prominence
column: Daicel CHIRALCEL OD-RH 4.6 mmϕ×150 mm
column temperature: 40° C.
mobile phase: (SOLUTION A) 10 mM phosphate buffer (pH 2.0), (SOLUTION B) acetonitrile
the composition (SOLUTION A:SOLUTION B) of the mobile phase was changed linearly from 50:50 to 20:80 over 20 min, thereafter, kept constant at 20:80 for 5 min.
flow rate: 0.5 ml/min
detection: UV (220 nm)
Analysis Condition 2
instrument: HPLC system SHIMADZU Corporation high-speed liquid
Chromatography Prominence
column: Daicel CHIRALCEL OD-RH 4.6 mmϕ×150 mm
column temperature: 40° C.
mobile phase: (SOLUTION A) 10 mM phosphate buffer (pH 2.0), (SOLUTION B) acetonitrile
the composition (SOLUTION A:SOLUTION B) of the mobile phase was changed linearly from 70:30 to 40:60 over 20 min, thereafter, kept constant at 40:60 for 5 min.
flow rate: 0.5 ml/min
detection: UV (220 nm)
Analysis Condition 3
instrument: HPLC system SHIMADZU Corporation high-speed liquid
Chromatography Prominence
column: Daicel CHIRALCEL OJ-RH 4.6 mmϕ×150 mm
column temperature: 40° C.
mobile phase: (SOLUTION A) 10 mM phosphate buffer (pH 2.0), (SOLUTION B) acetonitrile
the composition (SOLUTION A:SOLUTION B) of the mobile phase was kept constant at 70:30 for 25 min, thereafter, at 40:60 for 10 min.
flow rate: 0.5 ml/min
detection: UV (294 nm)
Analysis Condition 4
instrument: HPLC system SHIMADZU Corporation high-speed liquid
Chromatography Prominence
column: Daicel CHIRALPAK AD-RH 4.6 mmϕ×150 mm
column temperature: 40° C.
mobile phase: (SOLUTION A) 10 mM phosphate buffer (pH 2.0), (SOLUTION B) acetonitrile
the composition (SOLUTION A:SOLUTION B) of the mobile phase was changed linearly from 70:30 to 50:50 over 20 min, thereafter, kept constant at 50:50 for 5 min.
flow rate: 0.5 ml/min
detection: UV (220 nm)

Example 1

Synthesis of (+)-4-chloro-2-fluoro-9-trifluoromethyl-9H-fluoren-9-ol (Compound No. 526)

Step 1

2'-chloro-4'-fluoro-biphenyl-2-carboxylic acid ethyl ester

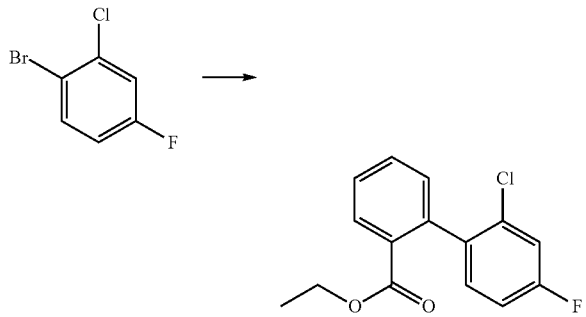

To a reaction vessel were added 1-bromo-2-chloro-4-fluorobenzene (25 g), ethyl 2-(4,4,5,5-tetramethyl-1,3,2-dioxaborolan-2-yl)benzoate (46 g), toluene (125 ml), water (125 ml) and tripotassium phosphate (50.5 g), and purged with argon. To this mixture was added dichlorobis(triphenylphosphine)palladium(II) (1.67 g) and the mixture was stirred in an oil bath at 110° C. for 3 hr. The oil bath was removed, and water (125 ml) was added to the reaction mixture. The mixture was stirred at room temperature for 1 hr, and filtered through celite. The filtrate was partitioned in a separatory funnel. The aqueous layer was extracted with toluene, and the organic layers were combined. The organic layer was washed twice with water (125 ml), dried over anhydrous magnesium sulfate and filtered. The filtrate was concentrated under reduced pressure to give the title compound (41.8 g). The obtained solid was directly used for the next reaction without further purification.

$^1$H-NMR (CDCl$_3$) δ: 8.06-8.02 (1H, m), 7.60-7.54 (1H, m), 7.52-7.45 (1H, m), 7.27-7.16 (3H, m), 7.06-7.00 (1H, m), 4.18-4.09 (2H, m), 1.11-1.06 (3H, m).

Step 2

2'-chloro-4'-fluoro-biphenyl-2-carboxylic acid

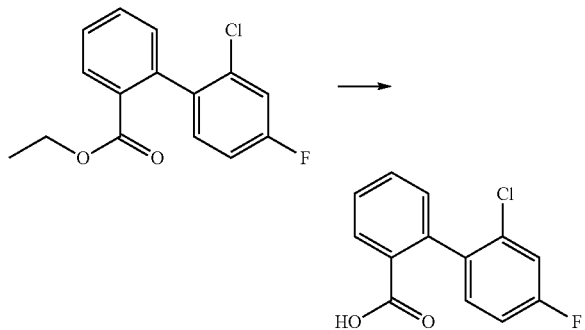

To a mixture of ethanol (179 ml) and 2'-chloro-4'-fluoro-biphenyl-2-carboxylic acid ethyl ester (41.8 g) was added 2N aqueous sodium hydroxide solution (179 ml), and the mixture was stirred in an oil bath at 80° C. for 2 hr. The reaction mixture was cooled to room temperature, activated carbon (2.5 g) was added and the mixture was stirred for 2.5 hr. The activated carbon was filtered off through celite and washed with 50 v/v % ethanol-water (100 ml). The filtrate was acidified with 2N hydrochloric acid (196 ml). Then, to this mixture was added water (33 ml) and the mixture was stirred at room temperature for 2 hr. This suspension was filtered, and the obtained solid was air-dried for 2 hr, and dried under reduced pressure at 60° C. to give the title compound (28.6 g, 2 steps 93%).

$^1$H-NMR (CDCl$_3$) δ: 8.12-8.08 (1H, m), 7.64-7.59 (1H, m), 7.52-7.47 (1H, m), 7.27-7.24 (1H, m), 7.22-7.16 (2H, m), 7.05-7.00 (1H, m).

Step 3

4-chloro-2-fluoro-fluoren-9-one

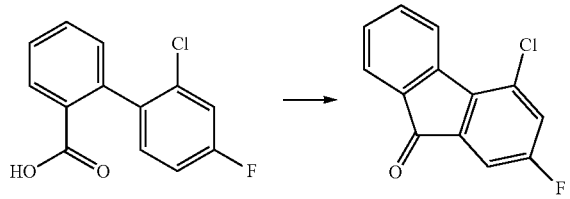 [SMILES: O=C(O)c1ccccc1-c1ccc(F)cc1Cl ; O=C1c2ccccc2-c2c(Cl)cc(F)cc21]

To a mixture of phosphorus pentoxide (133 g) and methanesulfonic acid (1300 ml) was added 2'-chloro-4'-fluoro-biphenyl-2-carboxylic acid (132.9 g), and the mixture was stirred at 80° C. for 2.5 hr. The reaction mixture was ice-cooled, water (1300 ml) was slowly added dropwise, and the mixture was further stirred at room temperature for 1 hr. This suspension was filtered, and the obtained solid was washed with water (300 ml). The solid was mixed with 50 v/v % ethanol-water (1300 ml), and the slurry was stirred at room temperature for 1.5 hr, and filtered. The obtained solid was washed with 50 v/v % ethanol-water (200 ml), air-dried for 3 hr, and dried under reduced pressure at 60° C. to give the title compound (121.6 g, 99%).

$^1$H-NMR (CDCl$_3$) δ: 8.13-8.10 (1H, m), 7.72-7.69 (1H, m), 7.57-7.53 (1H, m), 7.36-7.30 (2H, m), 7.20-7.17 (1H, m).

Step 4

(4-chloro-2-fluoro-9-trifluoromethyl-9H-fluoren-9-yloxy)-acetic acid ethyl ester

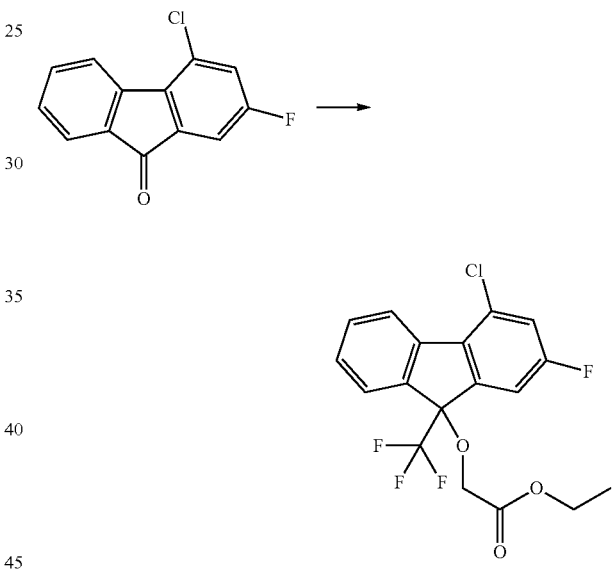

To a mixture of dimethylformamide (1000 ml) and 4-chloro-2-fluoro-fluoren-9-one (204 g) was added potassium carbonate (36.4 g), and the mixture was stirred in a water bath. To this mixture was added dropwise trimethyl(trifluoromethyl)silane (156 ml) over 30 min, and the mixture was further stirred at room temperature for 30 min. To the reaction mixture was added cesium fluoride (173 g), ethyl bromoacetate (75 ml) was added dropwise over 20 min, and the mixture was stirred at room temperature. Water (1000 ml) was added to the reaction mixture, and the mixture was placed in a separatory funnel, and extracted with ethyl acetate (1000 ml). The organic layer was washed twice with brine (water: saturated brine=4:1, 1000 ml) and once with saturated brine (500 ml), dried over anhydrous sodium sulfate, and filtered. The filtrate was concentrated under reduced pressure to give the title compound (360 g). The obtained residue was directly used for the next reaction without further purification.

$^1$H-NMR (CDCl$_3$) δ: 8.30-8.27 (1H, m), 7.73-7.69 (1H, m), 7.57-7.52 (1H, m), 7.43-7.37 (2H, m), 7.25-7.21 (1H, m), 4.11 (2H, q, J=7.1 Hz), 3.60 (1H, d, J=15.5 Hz), 3.53 (1H, d, J=15.3 Hz), 1.19 (3H, t, J=7.2 Hz).

Step 5

(4-chloro-2-fluoro-9-trifluoromethyl-9H-fluoren-9-yloxy)-acetic acid

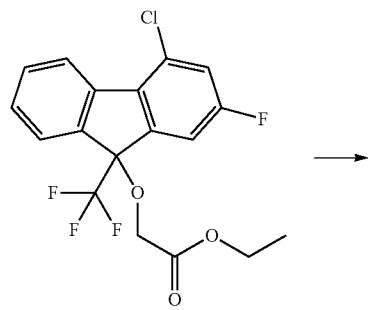

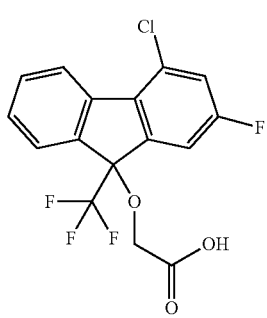

To a mixture of ethanol (440 ml) and (4-chloro-2-fluoro-9-trifluoromethyl-9H-fluoren-9-yloxy)-acetic acid ethyl ester (360 g) was added 2N aqueous sodium hydroxide solution (877 ml), and the mixture was stirred at 80° C. for 3.5 hr. The reaction mixture was cooled to room temperature, insoluble material was filtered off through celite, and washed with water (500 ml) and ethanol (60 ml). Water (120 ml) was added to the filtrate and the mixture was ice-cooled, and formic acid (199 ml) was added dropwise. This suspension was stirred at room temperature overnight, and filtered. The obtained solid was washed with 25 v/v % ethanol-water (400 ml), air-dried overnight, and dried under reduced pressure at 60° C. to give the title compound (285 g, 2 steps 90%).

$^1$H-NMR (CDCl$_3$) δ: 8.32-8.29 (1H, m), 7.71-7.67 (1H, m), 7.59-7.54 (1H, m), 7.45-7.40 (1H, m), 7.38-7.34 (1H, m), 7.27-7.23 (1H, m), 3.65 (1H, d, J=16.0 Hz), 3.60 (1H, d, J=16.0 Hz).

Step 6

Salt of Optically Active Form of (4-chloro-2-fluoro-9-trifluoromethyl-9H-fluoren-9-yloxy)-acetic acid and (R)-(+)-1-(1-naphthyl)-ethylamine

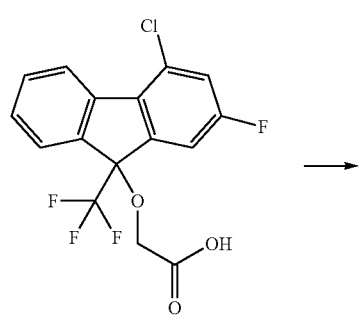

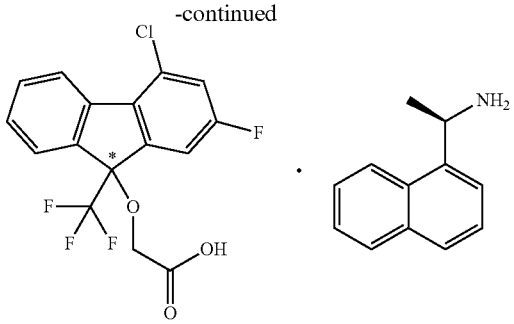

To a mixture of methyl ethyl ketone (250 ml) and (4-chloro-2-fluoro-9-trifluoromethyl-9H-fluoren-9-yloxy)-acetic acid (50 g) was added (R)-(+)-1-(1-naphthyl)-ethylamine (11.1 ml), and the mixture was stirred at 50° C. for 3 days. This suspension was cooled to room temperature, further stirred for 4 days, and filtered. The obtained solid was dried under reduced pressure to give the title compound (25.5 g, 35%). The solid was subjected to derivatization method A for determining the optical purity, and the obtained mixture was analyzed under HPLC analysis condition 1 to find that an isomer with a long retention time was the main component.

isomer with short retention time (retention time 22.58 min)
isomer with long retention time (retention time 22.73 min)

Step 7

Optically Active Form of (4-chloro-2-fluoro-9-trifluoromethyl-9H-fluoren-9-yloxy)-acetic acid

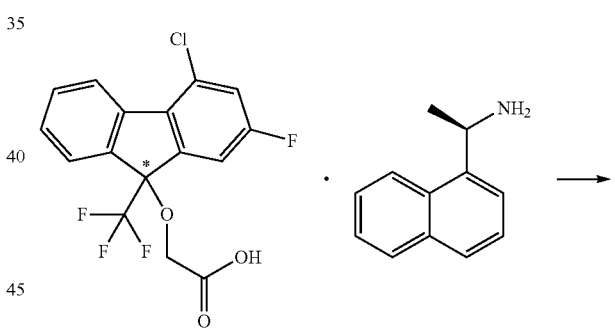

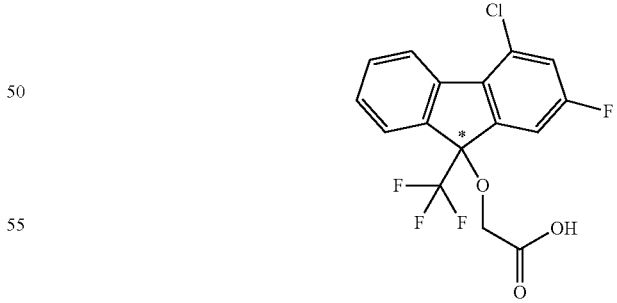

To a mixture of ethyl acetate (178 ml), and a salt (25.45 g) of an optically active form of (4-chloro-2-fluoro-9-trifluoromethyl-9H-fluoren-9-yloxy)-acetic acid and (R)-(+)-1-(1-naphthyl)-ethylamine were added 2N hydrochloric acid (51 ml) and water (127 ml), and the mixture was stirred at room temperature for 1 hr. The mixture was partitioned in a separatory funnel. The organic layer was washed twice with water (100 ml) and then with saturated brine (100 ml), dried over anhydrous sodium sulfate, and filtered. The filtrate was concentrated under reduced pressure, n-hexane (127 ml) was added to the obtained residue and the mixture was stirred at room temperature for 1 hr. This slurry was filtered, and the obtained solid was washed with hexane, and dried under reduced pressure to give the title compound (16.33 g, 95%).

$^1$H-NMR (DMSO-D$_6$) δ: 12.78 (1H, br s), 8.31-8.28 (1H, m), 7.73-7.65 (3H, m), 7.56-7.49 (2H, m), 3.57 (1H, d, J=15.8 Hz), 3.51 (1H, d, J=15.5 Hz).

Step 8

(+)-4-chloro-2-fluoro-9-trifluoromethyl-9H-fluoren-9-ol

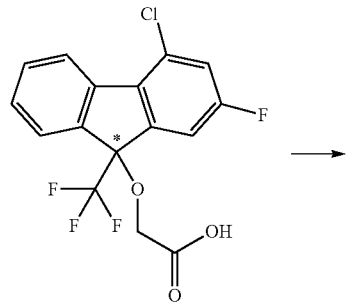

To a mixture of dimethylformamide (184 ml) and an optically active form (36.74 g) of (4-chloro-2-fluoro-9-trifluoromethyl-9H-fluoren-9-yloxy)-acetic acid was added N-ethyldiisopropylamine (20.9 ml), and the mixture was stirred at 0° C. Thereto, diphenylphosphoryl azide (23.7 ml) was added dropwise over 30 min, and the mixture was further stirred at 0° C. for 2 hr. To the reaction mixture was added acetic acid (2.86 ml) and the mixture was warmed to room temperature. t-Butyl alcohol (96 ml) was added, and the mixture was stirred at 100° C. for 1 hr. The reaction mixture was ice-cooled, 2N hydrochloric acid (367 ml) was added, placed in a separatory funnel and the mixture was extracted 3 times with toluene (180 ml). The combined organic layer was successively washed with water (180 ml), 1N aqueous sodium hydroxide solution (180 ml), water (180 ml) and saturated brine (180 ml), dried over anhydrous sodium sulfate, and filtered. The filtrate was concentrated under reduced pressure, and the obtained residue, ethanol (37 ml), tetrahydrofuran (37 ml) and 2N aqueous sodium hydroxide solution (37 ml) were mixed, and the mixture was stirred at 60° C. for 3 hr. The reaction mixture was cooled to room temperature, water (180 ml) was added, and the mixture was placed in a separatory funnel, and extracted twice with toluene (180 ml). The organic layer was washed twice with water (180 ml) and once with saturated brine (180 ml), dried over anhydrous sodium sulfate, and filtered. The filtrate was concentrated under reduced pressure and the obtained residue was purified by silica gel column chromatography (eluent: n-hexane/ethyl acetate=9/1 to 8/2) to give the title compound (21.69 g, 70%).

[α]D=+30.60° (20° C., c=1.00, methanol)

$^1$H-NMR (CDCl$_3$) δ: 8.29-8.26 (1H, m), 7.73-7.69 (1H, m), 7.55-7.50 (1H, m), 7.43-7.35 (2H, m), 7.21-7.18 (1H, m), 2.82 (1H, s).

Example 2

Synthesis of (+)-2-[4-(2-fluoro-9-hydroxy-9-trifluoromethyl-9H-fluoren-4-yl)-pyrazol-1-yl]-propane-1,3-diol (Compound No. 595)

Step 1

[4-(4,4,5,5-tetramethyl-[1,3,2]dioxaborolan-2-yl)-pyrazol-1-yl]-acetic acid t-butyl ester

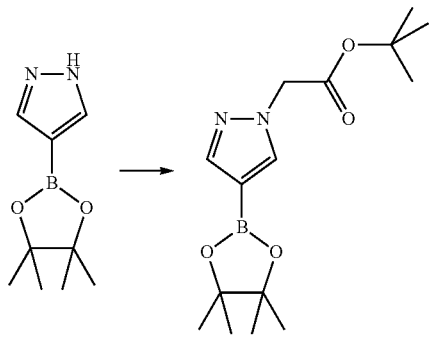

4,4,5,5-Tetramethyl-2-(1H-pyrazol-4-yl)-1,3,2-dioxaborolane (10 g), N,N-dimethylacetamide (100 ml), potassium carbonate (17.8 g) and t-butyl bromoacetate (9.9 ml) were mixed, and the mixture was stirred at room temperature for 4 hr. The reaction mixture was filtered through celite. Water and ethyl ether were added to the filtrate, and the mixture was partitioned in a separatory funnel. The aqueous layer was extracted with ethyl ether, and the organic layers were combined. The organic layer was washed 3 times with water and once with saturated brine, dried over anhydrous sodium sulfate, and filtered. The filtrate was concentrated under reduced pressure, hexane (50 ml) was added to the obtained residue and the mixture was stirred. This slurry was filtered, and the obtained solid was washed with hexane, and dried under reduced pressure to give the title compound (12.23 g, 77%).

$^1$H-NMR (DMSO-D$_6$) δ: 7.92 (1H, d, J=0.7 Hz), 7.59 (1H, d, J=0.5 Hz), 4.95 (2H, s), 1.42 (9H, s), 1.25 (12H, s).

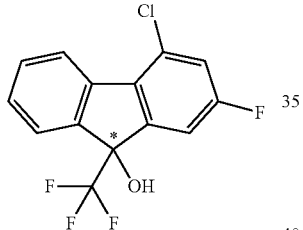

Step 2

Optically Active Form of t-butyl[4-(2-fluoro-9-hydroxy-9-trifluoromethyl-9H-fluoren-4-yl)-pyrazol-1-yl]-acetate

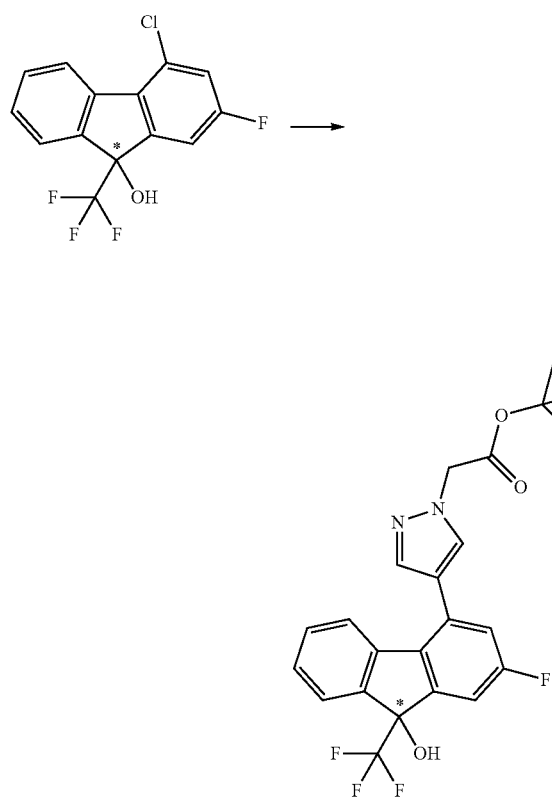

Sodium hydrogen carbonate (5.54 g), water (33 ml), toluene (100 ml), (+)-4-chloro-2-fluoro-9-trifluoromethyl-9H-fluoren-9-ol (10.0 g), t-butyl[4-(4,4,5,5-tetramethyl-[1,3,2]dioxoborolan-2-yl)-pyrazol-1-yl]-acetate (15.3 g), palladium (II) acetate (370 mg) and 2-dicyclohexylphosphino-2',6'-dimethoxybiphenyl (1.35 g) were mixed, and purged with argon. The mixture was stirred at 100° C. for 180 min. The reaction mixture was cooled to room temperature, water was added, and the mixture was filtered through celite. The filtered substance was further washed with toluene and water. The filtrate was partitioned in a separatory funnel. The aqueous layer was extracted with toluene. The combined organic layer was washed three times with water and once with saturated brine, dried over anhydrous sodium sulfate, and filtered. The filtrate was concentrated under reduced pressure, and the obtained residue was recrystallized from n-hexane/2-propanol (10:1, 165 ml) to give the title compound (11.1 g, 60%).

$^1$H-NMR (CDCl$_3$) δ: 7.69-7.66 (1H, m), 7.66 (1H, d, J=0.7 Hz), 7.63 (1H, d, J=0.7 Hz), 7.42-7.37 (2H, m), 7.31-7.25 (2H, m), 7.03 (1H, dd, J=9.5, 2.6 Hz), 4.94 (1H, d, J=17.2 Hz), 4.89 (1H, d, J=17.4 Hz), 2.85 (1H, br s), 1.52 (9H, s).

Step 3

Optically Active Form of ethyl 2-[4-(2-fluoro-9-hydroxy-9-trifluoromethyl-9H-fluoren-4-yl)-pyrazol-1-yl]-3-oxo-propionate

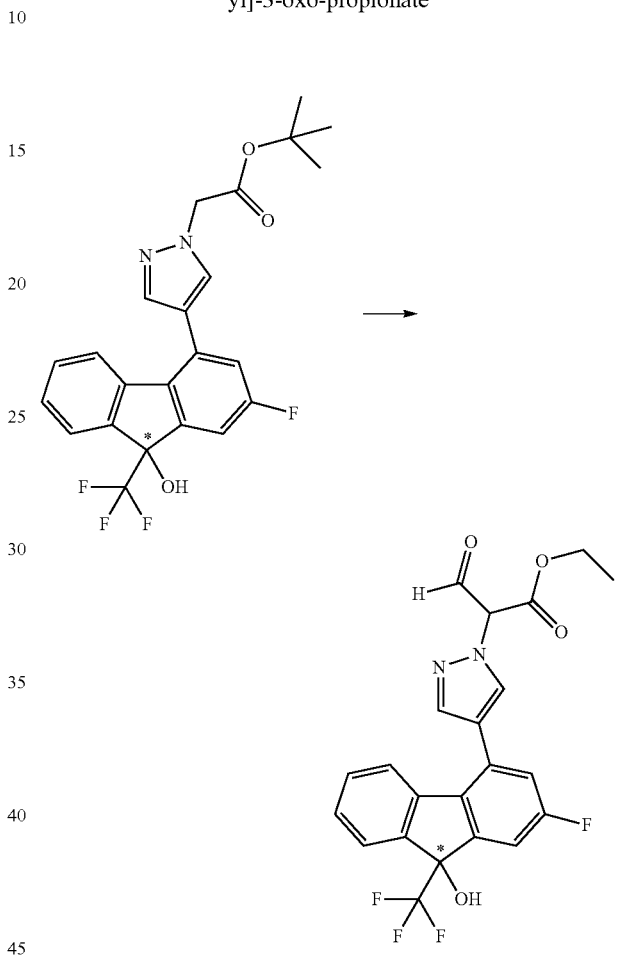

To a mixture of tetrahydrofuran (80 ml) and an optically active form (10.1 g) of t-butyl[4-(2-fluoro-9-hydroxy-9-trifluoromethyl-9H-fluoren-4-yl)-pyrazol-1-yl]-acetate was added ethyl formate (4.13 ml), and the mixture was stirred at 0° C. To this mixture was added sodium hydride (60 w/w % mineral oil dispersion, 2.57 g). The reaction mixture was warmed to room temperature and stirred for 3 hr. The reaction mixture was ice-cooled, 1N hydrochloric acid was added and the mixture was stirred. Ethyl acetate and water were added thereto, and the mixture was partitioned in a separatory funnel. The aqueous layer was further extracted with ethyl acetate, and the extract was combined with the organic layer obtained earlier. The organic layer was successively washed with water and saturated brine, dried over anhydrous sodium sulfate, and filtered. The filtrate was concentrated under reduced pressure to give the title compound (13.2 g). The obtained residue was directly used for the next reaction without further purification.

$^1$H-NMR (DMSO-D$_6$) δ: 11.98 (1H, br s), 7.98 (1H, br s), 7.97 (1H, d, J=0.5 Hz), 7.77 (1H, d, J=0.7 Hz), 7.66-7.62 (1H, m), 7.44-7.39 (3H, m), 7.36-7.32 (1H, m), 7.30-7.24 (1H, m), 7.21 (1H, dd, J=9.9, 2.4 Hz), 4.18 (2H, q, J=7.1 Hz), 1.22 (3H, t, J=7.1 Hz).

Step 4

(+)-2-[4-(2-fluoro-9-hydroxy-9-trifluoromethyl-9H-fluoren-4-yl)-pyrazol-1-yl]-propane-1,3-diol

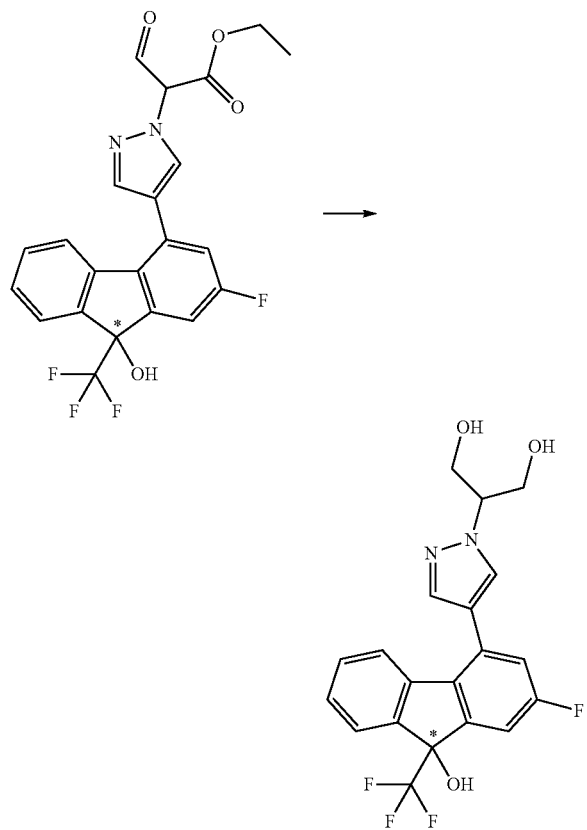

To a mixture of ethanol (80 ml) and sodium borohydride (16.2 g), a solution of an optically active form (13.2 g) of ethyl 2-[4-(2-fluoro-9-hydroxy-9-trifluoromethyl-9H-fluoren-4-yl)-pyrazol-1-yl]-3-oxo-propionate in tetrahydrofuran (80 ml) was added dropwise over 25 min. At this time, the temperature of the reaction mixture was controlled with an ice-bath not to exceed 30° C. The ice-bath was changed to a water-bath, and the mixture was stirred for 17 hr. Then, the water-bath was removed and the mixture was further stirred for 4 hr. The reaction mixture was ice-cooled, 2N hydrochloric acid was added and the mixture was stirred. To this mixture were added ethyl acetate and water, and the mixture was partitioned in a separatory funnel. The aqueous layer was further extracted with ethyl acetate, and the extract was combined with the organic layer obtained earlier. The organic layer was successively washed with water and saturated brine, dried over anhydrous sodium sulfate, and filtered. The filtrate was concentrated under reduced pressure and the obtained residue was purified by silica gel column chromatography (eluent: chloroform/methanol=30/1 to 15/1) to give the title compound (7.38 g, 84%).

[α]D=+67.50° (20° C., c=1.00, methanol)

$^1$H-NMR (DMSO-D$_6$) δ: 8.02 (1H, s), 7.68 (1H, s), 7.66-7.61 (1H, m), 7.44-7.37 (3H, m), 7.36-7.31 (1H, m), 7.30-7.26 (1H, m), 7.18 (1H, dd, J=10.0, 2.6 Hz), 4.99-4.94 (2H, m), 4.39-4.32 (1H, m), 3.86-3.76 (4H, m).

The obtained title compound can be crystallized from a solvent (toluene/ethyl acetate (7:1)) containing 1 mol of water per 1 mol of the compound.

Using the above-mentioned (+)-4-chloro-2-fluoro-9-trifluoromethyl-9H-fluoren-9-ol as an intermediate and by a similar method, compound Nos. 531, 534, 537, 543, 544, 545, 548, 549, 551, 565, 566, 607, 610, 672, 674, 675, 682, 685, 687, 692, 693, 694, 695, 704 and 705 were synthesized.

Example 3

Synthesis of (+)-3-[4-(9-hydroxy-2-methyl-9-trifluoromethyl-9H-fluoren-4-yl)-pyrazol-1-yl]-propionic acid (Compound No. 538)

Step 1

2'-chloro-4'-methyl-biphenyl-2-carboxylic acid ethyl ester

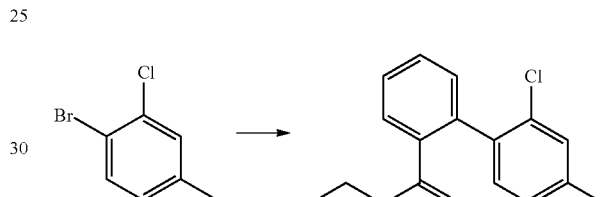

Under an argon atmosphere, 4-bromo-3-chlorotoluene (200 g), ethyl 2-(4,4,5,5-tetramethyl-1,3,2-dioxaborolan-2-yl)benzoate (376 g), toluene (1000 ml), water (1000 ml), tripotassium phosphate (412 g) and dichlorobis(triphenylphosphine)palladium(II) (14 g) were added to a reaction vessel and the mixture was stirred at 110° C. for 2 hr. The reaction mixture was cooled to room temperature. The insoluble material was filtered off, and washed with water (500 ml) and toluene (500 ml). The filtrate was partitioned in a separatory funnel. The organic layer was washed twice with water (1000 ml), dried over anhydrous sodium sulfate, and filtered. The filtrate was concentrated under reduced pressure to give the title compound (337 g). The obtained residue was directly used for the next reaction without further purification.

$^1$H-NMR (CDCl$_3$) δ: 8.02-7.99 (1H, m), 7.58-7.53 (1H, m), 7.48-7.43 (1H, m), 7.28-7.23 (2H, m), 7.13-7.11 (2H, m), 4.17-4.08 (2H, m), 2.38 (3H, s), 1.06 (3H, t, J=7.1 Hz).

Step 2

2'-chloro-4'-methyl-biphenyl-2-carboxylic acid

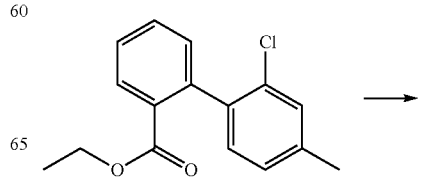

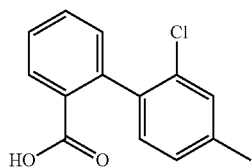

To a mixture of ethanol (728 ml) and 2'-chloro-4'-methyl-biphenyl-2-carboxylic acid ethyl ester (337 g) was added 4N aqueous sodium hydroxide solution (728 ml), and the mixture was stirred at 80° C. for 2 hr. The reaction mixture was cooled to room temperature, activated carbon (17 g) was added and the mixture was stirred overnight. The activated carbon was filtered off, and washed with 50 v/v % ethanol-water (200 ml). The filtrate was acidified by dropwise addition of acetic acid (500 ml) at room temperature. To this mixture, water (414 ml) was added dropwise at room temperature, and the mixture was stirred for 2 hr. This suspension was filtered, and the obtained solid was washed with 40 v/v % ethanol-water (250 ml), and dried under reduced pressure at 80° C. to give the title compound (203 g, 2 steps 85%).

$^1$H-NMR (DMSO-D$_6$) δ: 12.60 (1H, br s), 7.93-7.89 (1H, m), 7.64-7.58 (1H, m), 7.53-7.47 (1H, m), 7.32-7.29 (1H, m), 7.25-7.21 (1H, m), 7.20-7.13 (2H, m), 2.34 (3H, s).

Step 3

4-chloro-2-methyl-fluoren-9-one

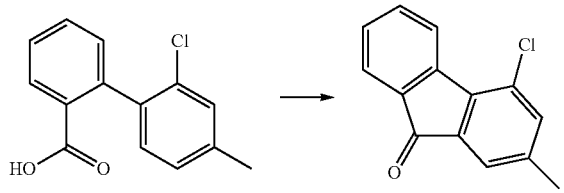 [SMILES: Cc1ccc(-c2ccccc2C(=O)O)c(Cl)c1 ; Cc1cc(Cl)c2c(c1)C(=O)c1ccccc1-2]

To a mixture of phosphorus pentoxide (150 g) and methanesulfonic acid (1500 ml) was added 2'-chloro-4'-methyl-biphenyl-2-carboxylic acid (153 g), and the mixture was stirred at 80° C. for 2 hr. The reaction mixture was cooled to 0° C. While keeping the temperature of the reaction mixture at 90° C. or below, water (1500 ml) was added dropwise, and the mixture was further stirred at room temperature for 2 hr. This suspension was filtered, and the obtained solid was washed with water (1000 ml). The solid was suspended in 50 v/v % ethanol-water (1500 ml), and the slurry was stirred at room temperature for 2 hr, and filtered. The obtained solid was air-dried for 1 hr and dried under reduced pressure at 80° C. to give the title compound (140.12 g, 99%).

$^1$H-NMR (DMSO-D$_6$) δ: 8.10-8.07 (1H, m), 7.69-7.64 (2H, m), 7.49-7.41 (3H, m), 2.36 (3H, s).

Step 4

(4-chloro-2-methyl-9-trifluoromethyl-9H-fluoren-9-yloxy)-acetic acid

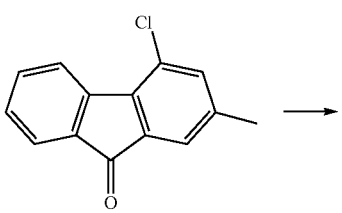

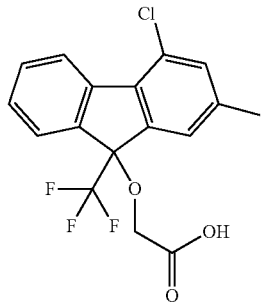

Under an argon stream, potassium carbonate (18 g) was added to a mixture of dimethylformamide (500 ml) and 4-chloro-2-methyl-fluoren-9-one (100 g). To this mixture, trimethyl(trifluoromethyl)silane (78 ml) was added dropwise over 80 min, and the mixture was further stirred at room temperature for 1 hr. To the reaction mixture was added cesium fluoride (87 g) at room temperature, then ethyl bromoacetate (63 ml) was added dropwise over 15 min, and the mixture was further stirred at room temperature for 4 hr. To the reaction mixture was added water (500 ml), and the aqueous layer was extracted twice with toluene (500 ml). The combined organic layer was washed with water (500 ml) and saturated brine (500 ml), dried over anhydrous sodium sulfate, and filtered. The filtrate was concentrated under reduced pressure. To the obtained residue were added ethanol (220 ml) and 2N aqueous sodium hydroxide solution (440 ml), and the mixture was stirred at 80° C. for 1 hr. The reaction mixture was cooled to room temperature, activated carbon (15 g) was added, and the mixture was stirred at room temperature overnight. The activated carbon was filtered off, and washed with 33 v/v % ethanol-water (120 ml). The filtrate was acidified by dropwise addition of acetic acid (151 ml), and the mixture was stirred at room temperature overnight. This suspension was filtered, the obtained solid was washed with 33 v/v % ethanol-water (150 ml), and dried under reduced pressure at 80° C. to give the title compound (136.40 g, 87%).

$^1$H-NMR (DMSO-D$_6$) δ: 12.76 (1H, br s), 8.26 (1H, d, J=7.7 Hz), 7.69-7.62 (2H, m), 7.53-7.45 (3H, m), 3.50 (1H, d, J=15.5 Hz), 3.43 (1H, d, J=15.5 Hz), 2.41 (3H, s).

Step 5

Salt of Optically Active Form of (4-chloro-2-methyl-9-trifluoromethyl-9H-fluoren-9-yloxy)-acetic acid and (R)-(+)-1-phenylethylamine

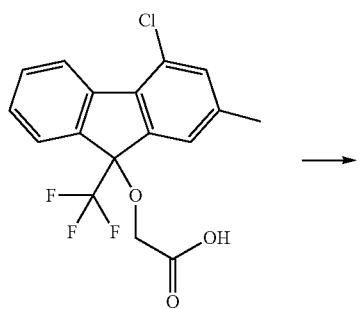

Step 5-1 Synthesis of Seed Crystal

To a mixture of isopropyl ether (16 ml) and (4-chloro-2-methyl-9-trifluoromethyl-9H-fluoren-9-yloxy)-acetic acid (0.400 g) was added (R)-(+)-1-phenylethylamine (0.058 ml). The mixture was stirred at room temperature for 1 hr 40 min. This suspension was filtered, and the obtained filtrate was dried under reduced pressure to give a solid (0.240 g). The solid (0.210 g) was suspended in ethyl acetate (4.2 ml), and the suspension was stirred at room temperature for 1 hr. This suspension was filtered, and the obtained filtered substance was dried under reduced pressure to give a solid (0.178 g). The solid (0.170 g) was resuspended in ethyl acetate (3.4 ml), and the mixture was stirred at 50° C. for 1 hr. This suspension was filtered, and the obtained solid was dried under reduced pressure to give the title compound (0.137 g). The solid was subjected to derivatization method A for determining the optical purity, and the obtained mixture was analyzed under HPLC analysis condition 1 to find that an isomer with a long retention time was the main component.
isomer with short retention time (retention time 20.19 min)
isomer with long retention time (retention time 21.41 min)

Step 5-2

To a mixture of methyl isobutyl ketone (575 ml) and (4-chloro-2-methyl-9-trifluoromethyl-9H-fluoren-9-yloxy)-acetic acid (191.60 g) was added (R)-(+)-1-phenylethylamine (34.81 ml). To this mixture was added a seed crystal, and the mixture was stirred at 50° C. for 3 days. This suspension was filtered, and the obtained solid was washed with methyl isobutyl ketone (192 ml), and dried under reduced pressure to give the title compound (71.10 g, 28%). The solid was subjected to derivatization method A for determining the optical purity, and the obtained mixture was analyzed under HPLC analysis condition 1 to find that an isomer with a long retention time was the main component.
isomer with short retention time (retention time 24.11 min)
isomer with long retention time (retention time 25.43 min)

Step 6

Optically Active Form of (4-chloro-2-methyl-9-trifluoromethyl-9H-fluoren-9-yloxy)-acetic acid

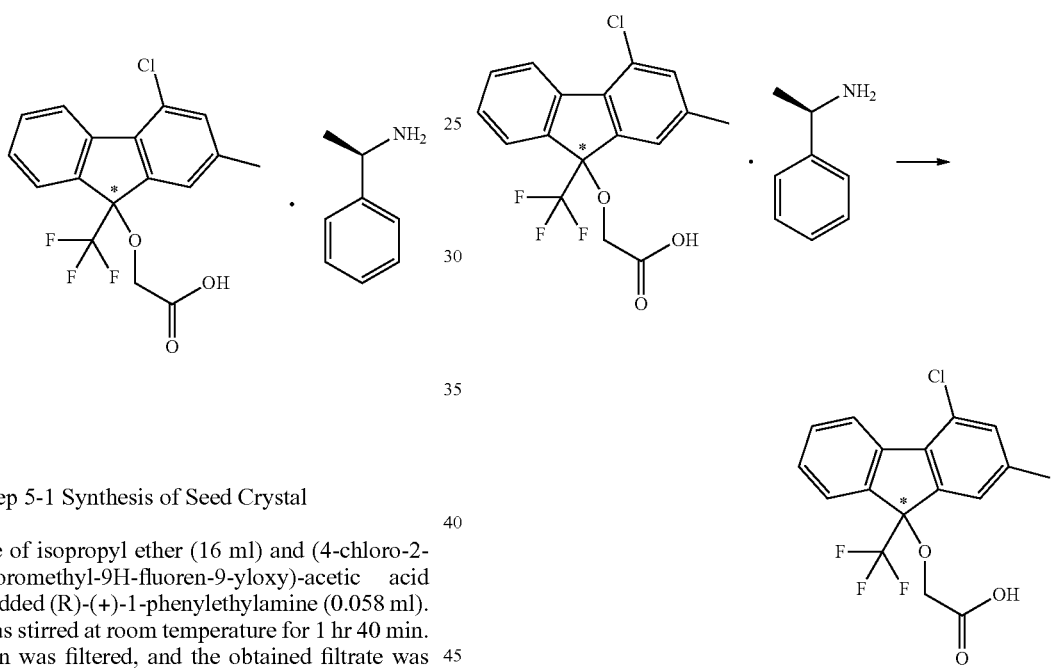

To a mixture of ethyl acetate (796 ml) and a salt (159.16 g) of an optically active form of (4-chloro-2-methyl-9-trifluoromethyl-9H-fluoren-9-yloxy)-acetic acid and (R)-(+)-1-phenylethylamine was added 2N hydrochloric acid (318 ml), and the mixture was stirred at room temperature for 2 hr. The mixture was partitioned in a separatory funnel. The organic layer was washed twice with water (600 ml) and once with saturated brine (300 ml), dried over anhydrous sodium sulfate, and filtered. The filtrate was concentrated under reduced pressure. n-Hexane was added to the obtained residue and the mixture was stirred at room temperature for 1 hr. This slurry was filtered, and the obtained solid was washed with hexane, and dried under reduced pressure to give the title compound (112.33 g, 95%).

$^1$H-NMR (DMSO-D$_6$) δ: 12.75 (1H, br s), 8.26 (1H, d, J=7.7 Hz), 7.71-7.62 (2H, m), 7.54-7.45 (3H, m), 3.50 (1H, d, J=15.5 Hz), 3.43 (1H, d, J=15.5 Hz), 2.41 (3H, s).

Step 7

(+)-4-chloro-2-methyl-9-trifluoromethyl-9H-fluoren-9-ol

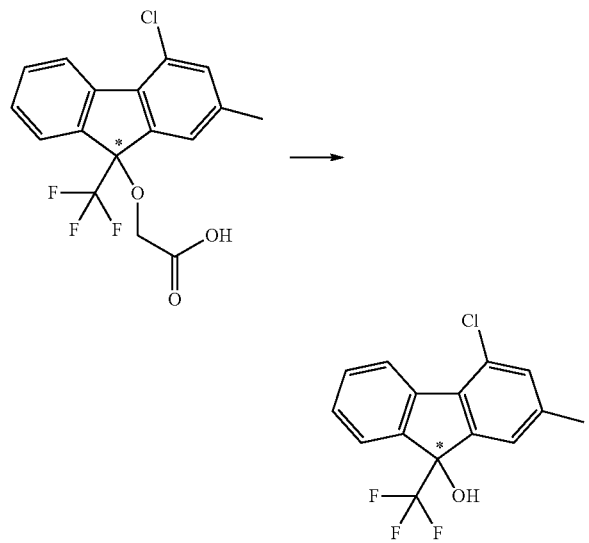

To a mixture of dimethylformamide (90 ml) and an optically active form (30 g) of (4-chloro-2-methyl-9-trifluoromethyl-9H-fluoren-9-yloxy)-acetic acid was added triethylamine (14.1 ml), and the mixture was stirred at 0° C. A solution of diphenylphosphoryl azide (20.0 ml) in dimethylformamide (60 ml) was added dropwise over 20 min, and the mixture was further stirred at 0° C. for 2 hr. To the reaction mixture was added t-butyl alcohol (75 ml), and the mixture was stirred at 100° C. for 1 hr. The reaction mixture was ice-cooled, 2N hydrochloric acid (300 ml) was added and the mixture was stirred at room temperature overnight. To this mixture was added water (100 ml) and the mixture was placed in a separatory funnel. The aqueous layer was extracted twice with toluene (300 ml, 200 ml). The combined organic layer was successively washed twice with water (200 ml), twice with 1N aqueous sodium hydroxide solution (150 ml) and once with saturated brine (150 ml), and dried over anhydrous sodium sulfate. Thereto was added silica gel (6 g) and the mixture was stirred at room temperature. The insoluble material was filtered off, and washed with toluene (500 ml). The filtrate was concentrated under reduced pressure to give the title compound (28.58 g).

[α]D=+22.50° (20° C., c=1.00, methanol)
$^1$H-NMR (CDCl$_3$) δ: 8.27 (1H, d, J=7.7 Hz), 7.70-7.69 (1H, m), 7.52-7.47 (1H, m), 7.44-7.42 (1H, m), 7.40-7.35 (1H, m), 7.25 (1H, s), 2.82 (1H, br s), 2.41 (3H, s).

Step 8 t-butyl 3-[4-(4,4,5,5-tetramethyl-[1,3,2]dioxaborolan-2-yl)-pyrazol-1-yl]-propionate

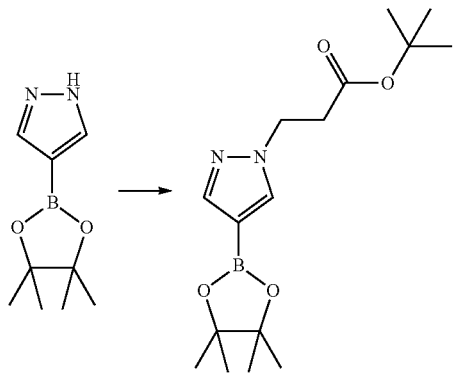

4,4,5,5-Tetramethyl-2-(1H-pyrazol-4-yl)-1,3,2-dioxaborolane (5.82 g), acetonitrile (50 ml), cesium fluoride (455.7 mg) and t-butyl acrylate (5.7 ml) were mixed at room temperature, and the mixture was stirred at 80° C. for 17.5 hr. The reaction mixture was cooled to room temperature, and concentrated under reduced pressure. To the obtained residue were added water and ethyl ether, and the mixture was partitioned in a separatory funnel. The aqueous layer was further extracted with ethyl ether, and the organic layers were combined. The organic layer was washed with water and saturated brine, dried over anhydrous sodium sulfate, and filtered. The filtrate was concentrated under reduced pressure, and the obtained residue was purified by silica gel column chromatography (eluent: n-hexane/ethyl acetate=9/1 to 4/6) to give the title compound (8.38 g, 87%).

$^1$H-NMR (CDCl$_3$) δ: 7.77 (1H, s), 7.71 (1H, s), 4.38 (2H, t, J=6.9 Hz), 2.80 (2H, t, J=6.8 Hz), 1.41 (9H, s), 1.31 (12H, s).

Step 9

Optically Active Form of t-butyl 3-[4-(9-hydroxy-2-methyl-9-trifluoromethyl-9H-fluoren-4-yl)-pyrazol-1-yl]-propionate

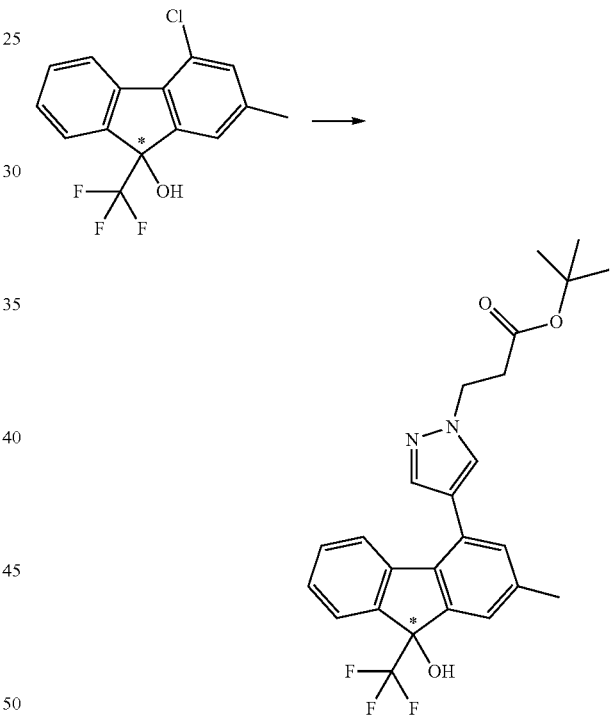

Tripotassium phosphate (35.7 g), water (60 ml), toluene (240 ml), (+)-4-chloro-2-methyl-9-trifluoromethyl-9H-fluoren-9-ol (28.58 g), t-butyl 3-[4-(4,4,5,5-tetramethyl-[1,3,2]dioxoborolan-2-yl)-pyrazol-1-yl]-propionate (41.9 g), palladium(II) acetate (1.89 g) and 2-dicyclohexylphosphino-2',6'-dimethoxybiphenyl (6.905 g) were mixed in a reaction vessel, and purged with argon. The mixture was stirred at 100° C. for 3 hr. The reaction mixture was cooled to room temperature, water (180 ml) was added and the mixture was stirred overnight. Insoluble material was filtered off through celite, and washed with ethyl acetate (500 ml). The filtrate was partitioned in a separatory funnel. The aqueous layer was extracted with ethyl acetate, and the organic layers were combined. The organic layer was successively washed with water (250 ml), saturated aqueous sodium hydrogen carbonate (250 ml) and saturated brine (200 ml), dried over anhydrous sodium sulfate and filtered. The filtrate was concentrated under reduced pressure, and the obtained residue was dissolved in toluene/ethyl acetate (3:1, 270 ml). Silica gel (30 g) was added and the mixture was stirred at room temperature for 3 hr. The mixture was filtered, and washed with toluene/ethyl acetate (3:1, 500 ml). The filtrate was concentrated under reduced pressure, isopropyl ether (100 ml) was added to the obtained residue and the mixture was stirred at room temperature for 4 hr. This slurry was filtered, and the obtained solid was washed with isopropyl ether (40 ml), and dried under reduced pressure at 50° C. The solid was mixed with chloroform (27 ml) and the mixture was stirred at room temperature for 5 min. Hexane (107 ml) was added, and the mixture was further stirred for 2 hr 50 min. This suspension was filtered, and the filtered substance was washed with hexane/chloroform (4:1, 40 ml), and dried under reduced pressure at 50° C. to give the title compound (24.75 g, 64%).

$^1$H-NMR (CDCl$_3$) δ: 7.69-7.65 (1H, m), 7.54 (1H, s), 7.51-7.47 (1H, m), 7.50 (1H, s), 7.28-7.19 (3H, m), 7.06-7.03 (1H, m), 4.44 (2H, t, J=6.6 Hz), 3.16 (1H, br s), 2.88 (2H, t, J=6.5 Hz), 2.41 (3H, s), 1.43 (9H, s).

Step 10

(+)-3-[4-(9-hydroxy-2-methyl-9-trifluoromethyl-9H-fluoren-4-yl)-pyrazol-1-yl]-propionic acid

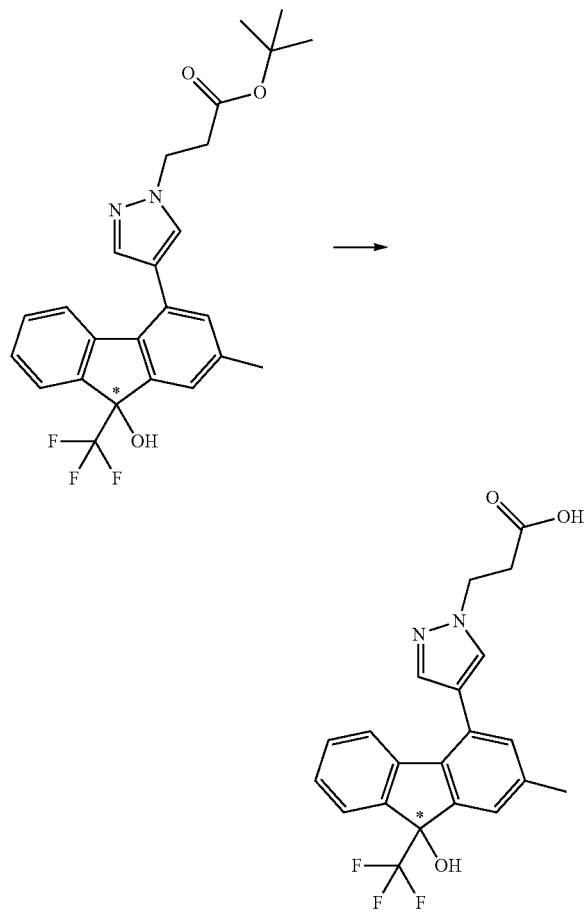

To a mixture of 1,4-dioxane (6.7 ml) and an optically active form (1.34 g) of t-butyl 3-[4-(9-hydroxy-2-methyl-9-trifluoromethyl-9H-fluoren-4-yl)-pyrazol-1-yl]-propionate was added trifluoroacetic acid (6.7 ml), and the mixture was stirred at room temperature for 4 hr. The reaction mixture was concentrated under reduced pressure. Toluene was added to the obtained residue and the mixture was concentrated under reduced pressure. To the residue was added water (10 ml) and the mixture was extracted twice with ethyl acetate (10 ml). The combined organic layer was washed twice with water (10 ml) and once with saturated brine (10 ml), and dried over anhydrous sodium sulfate. Insoluble material was filtered off, and the obtained filtrate was concentrated under reduced pressure. Toluene was added to the obtained residue and the mixture was concentrated under reduced pressure. n-Hexane (10 ml) was added to the concentrated residue, and the slurry was stirred and filtered. The obtained solid was washed with n-hexane, and dried under reduced pressure to give the title compound (1.12 g, 96%).

[α]D=+65.10° (25° C., c=1.00, methanol)
$^1$H-NMR (DMSO-D$_6$) δ: 12.40 (1H, br s), 7.93 (1H, s), 7.61-7.56 (1H, m), 7.57 (1H, s), 7.41-7.39 (1H, m), 7.30-7.21 (3H, m), 7.13 (1H, br s), 7.09-7.08 (1H, m), 4.40 (2H, t, J=6.6 Hz), 2.87 (2H, t, J=6.6 Hz), 2.36 (3H, s).

Example 4

Synthesis of (+)-4-[4-(9-hydroxy-2-methyl-9-trifluoromethyl-9H-fluoren-4-yl)-pyrazol-1-yl]-butyric acid (Compound No. 539)

Step 1

4-[4-(4,4,5,5-tetramethyl-[1,3,2]dioxaborolan-2-yl)-pyrazol-1-yl]-butyric acid ethyl ester

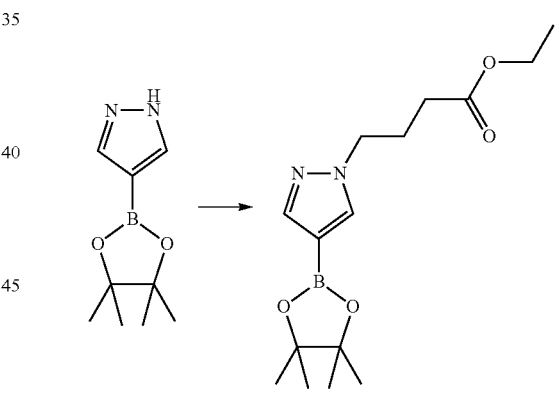

4,4,5,5-Tetramethyl-2-(1H-pyrazol-4-yl)-1,3,2-dioxaborolane (25.0 g), dimethylformamide (200 ml), potassium carbonate (44.5 g) and ethyl 4-bromobutyrate (36.9 ml) were mixed at room temperature and stirred at 75° C. for 6 hr. The reaction mixture was cooled to room temperature, and the insoluble material was filtered off through celite. To the filtrate was added water (150 ml) and the mixture was extracted twice with ethyl acetate (100 ml, 50 ml). To the aqueous layer was added water (100 ml) again and the mixture was extracted twice with ethyl acetate (50 ml). To the combined organic layer was added n-hexane (100 ml), and the mixture was washed 3 times with water (100 ml) and once with saturated brine, dried over anhydrous sodium sulfate, and filtered. The filtrate was concentrated under reduced pressure, and the obtained residue was purified by silica gel column chromatography (eluent: n-hexane/ethyl acetate-5/1 to 1/1) to give the title compound (33.4 g, 84%).

$^1$H-NMR (DMSO-D$_6$) δ: 7.92 (1H, d, J=0.4 Hz), 7.58 (1H, d, J=0.7 Hz), 4.14 (2H, t, J=6.7 Hz), 4.03 (2H, q, J=7.1 Hz), 2.22 (2H, t, J=7.4 Hz), 2.04-1.96 (2H, m), 1.25 (12H, s), 1.17 (3H, t, J=7.2 Hz).

Step 2

Optically Active Form of 4-[4-(9-hydroxy-2-methyl-9-trifluoromethyl-9H-fluoren-4-yl)-pyrazol-1-yl]-butyric acid ethyl ester

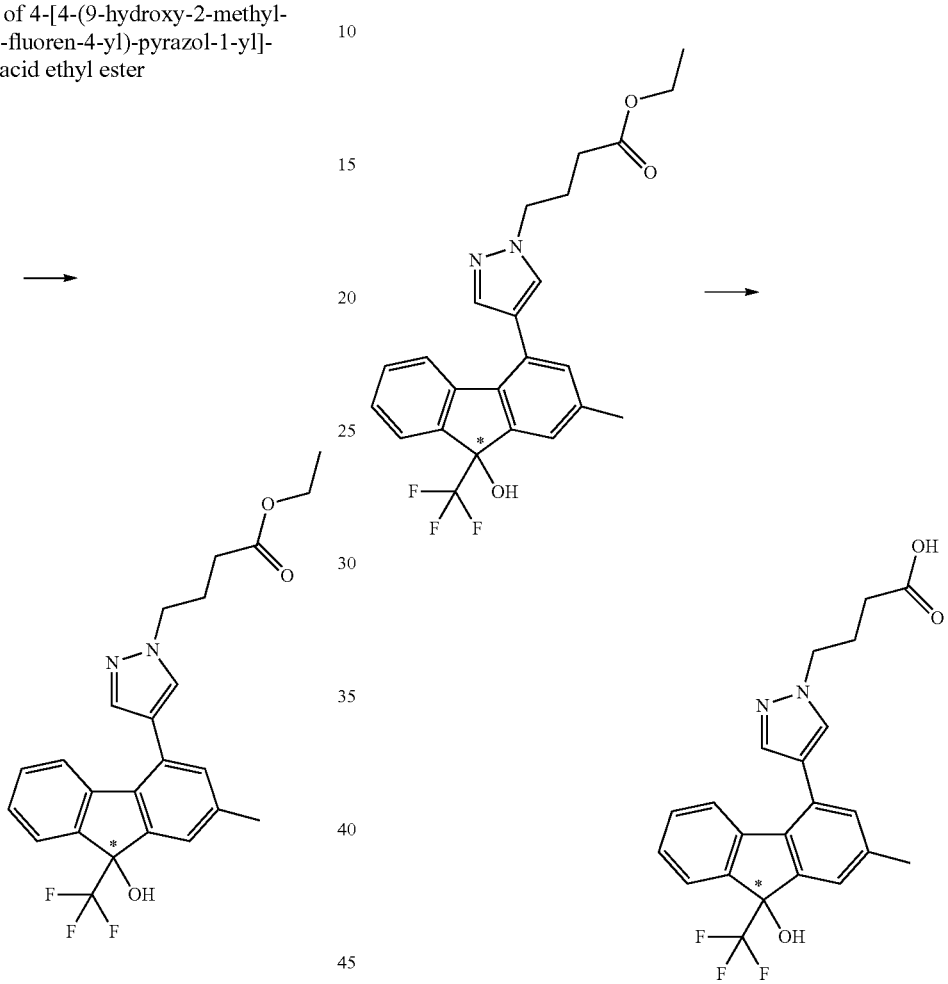

Tripotassium phosphate (14.86 g), water (30 ml), toluene (60 ml), (+)-4-chloro-2-methyl-9-trifluoromethyl-9H-fluoren-9-ol (9.583 g) and 4-[4-(4,4,5,5-tetramethyl-[1,3,2]dioxoborolan-2-yl)-pyrazol-1-yl]-butyric acid ethyl ester (12.08 g) were added to a reaction vessel, and purged with argon. To this mixture were added palladium(II) acetate (314 mg) and a solution (30 ml) of 2-dicyclohexylphosphino-2',6'-dimethoxybiphenyl (1.149 g) in toluene and the mixture was stirred at 90° C. for 2 hr. The reaction mixture was cooled to room temperature, activated carbon (2 g) was added and the mixture was stirred for 30 min. The insoluble material was filtered off. The filtrate was partitioned in a separatory funnel. The organic layer was washed twice with water (50 ml) and once with saturated brine, dried over anhydrous sodium sulfate, and filtered. The filtrate was concentrated under reduced pressure, and the obtained residue was recrystallized from isopropyl ether (50 ml) to give the title compound (7.926 g, 64%).

$^1$H-NMR (CDCl$_3$) δ: 7.70-7.66 (1H, m), 7.53-7.51 (1H, m), 7.42 (1H, s), 7.27-7.21 (2H, m), 7.20-7.15 (1H, m), 7.12-7.08 (1H, m), 7.04-7.02 (1H, m), 4.18 (2H, t, J=6.7 Hz), 4.14 (2H, q, J=7.1 Hz), 4.03 (1H, brs), 2.41 (3H, s), 2.34-2.28 (2H, m), 2.23-2.15 (2H, m), 1.25 (3H, t, J=7.2 Hz).

Step 3

(+)-4-[4-(9-hydroxy-2-methyl-9-trifluoromethyl-9H-fluoren-4-yl)-pyrazol-1-yl]-butyric acid To a mixture of ethanol (5.4 ml) and an optically active form (3.55 g) of 4-[4-(9-hydroxy-2-methyl-9-trifluoromethyl-9H-fluoren-4-yl)-pyrazol-1-yl]-butyric acid ethyl ester was added 2N aqueous sodium hydroxide solution (18 ml), and the mixture was stirred at room temperature for 1.5 hr. The reaction mixture was acidified with 2N hydrochloric acid (36 ml). To this mixture was added water (36 ml), and the mixture was extracted 3 times with ethyl acetate (30 ml). The combined organic layer was washed 3 times with water (50 ml) and once with saturated brine (50 ml), dried over anhydrous sodium sulfate, and filtered. The filtrate was concentrated under reduced pressure to give the title compound (3.40 g, 100%).

[α]D=+63.00° (20° C., c=1.00, methanol)

$^1$H-NMR (DMSO-D$_6$) δ: 12.21 (1H, br s), 7.98 (1H, s), 7.64-7.59 (1H, m), 7.60 (1H, s), 7.44-7.42 (1H, m), 7.33-7.22 (3H, m), 7.17 (1H, br s), 7.14-7.12 (1H, m), 4.24 (2H, t, J=6.7 Hz), 2.39 (3H, s), 2.27 (2H, t, J=7.3 Hz), 2.12-2.05 (2H, m).

The obtained compound was crystallized from toluene/ethyl acetate (20:1).

Using the above-mentioned (+)-4-chloro-2-methyl-9-trifluoromethyl-9H-fluoren-9-ol as an intermediate and by a similar method, compound Nos. 529, 532, 533, 546, 550, 574, 575, 576, 605, 606, 663, 686, 690, 691, 696, 697, 699, 700, 701, 702, 706 and 707 were synthesized.

Example 5

Synthesis of (−)-2-(1-ethyl-1H-pyrazol-4-yl)-9-hydroxy-9-trifluoromethyl-9H-fluorene-4-carboxamide (Compound No. 630)

Step 1 ethyl 4'-chloro-2'-methyl-biphenyl-2-carboxylate

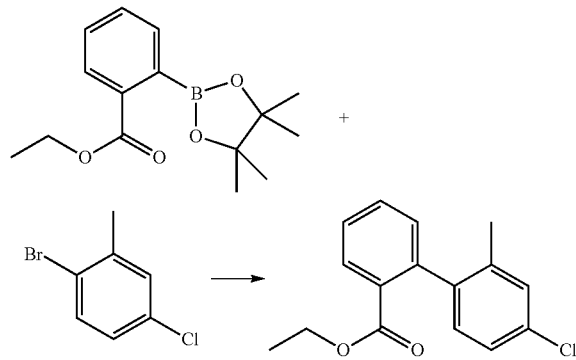

Under an argon atmosphere, a mixture of 2-bromo-5-chloro-toluene (20.55 g), ethyl 2-(4,4,5,5-tetramethyl-1,3,2-dioxaborolan-2-yl)benzoate (55.23 g), toluene (200 ml), water (125 ml), tripotassium phosphate (53.07 g) and 1,1'-bis(diphenylphosphino)ferrocene-palladium(II) dichloride-dichloromethane complex (1.633 g) was stirred with heating under reflux for 1 hr. The reaction mixture was cooled to room temperature, activated carbon (1 g) was added and the mixture was stirred for 10 min at room temperature. The insoluble material was filtered off, and the filtrate was partitioned in a separatory funnel. The organic layer was washed twice with water, dried over anhydrous sodium sulfate, and filtered. The filtrate was concentrated under reduced pressure and the obtained residue was purified by silica gel column chromatography (eluent: n-hexane/ethyl acetate=98/2) to give the title compound (27.20 g, 99%).

$^1$H-NMR (CDCl$_3$) δ: 7.98 (1H, dd, J=7.7, 1.1 Hz), 7.56-7.51 (1H, m), 7.46-7.42 (1H, m), 7.23-7.22 (1H, m), 7.20-7.16 (2H, m), 7.00 (1H, d, J=7.9 Hz), 4.07 (2H, q, J=7.1 Hz), 2.04 (3H, s), 1.02 (3H, t, J=7.2 Hz).

Step 2

4'-chloro-2'-methyl-biphenyl-2-carboxylic acid

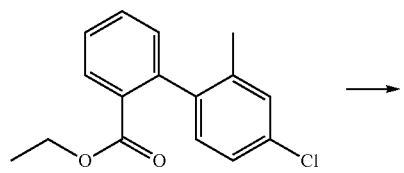

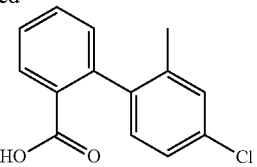

A mixture of ethyl 4'-chloro-2'-methyl-biphenyl-2-carboxylate (27.10 g), ethanol (60 ml) and 1N aqueous sodium hydroxide solution (120 ml) was stirred at 100° C. for 2 hr. To the reaction mixture was added 8N aqueous sodium hydroxide m solution (10 ml), and the mixture was further stirred at 100° C. for 1 hr. The reaction mixture was cooled to room temperature. The insoluble material was filtered off, and washed with 33 v/v % ethanol-water (100 ml). The filtrate was adjusted to pH 2 with formic acid (23 ml) and the mixture was stirred at room temperature for 1 hr. This suspension was filtered, and the obtained solid was air-dried for 1 hr and dried under reduced pressure at 60° C. to give the title compound (22.082 g, 91%).

$^1$H-NMR (DMSO-D$_6$) δ: 12.64 (1H, s), 7.89 (1H, dd, J=7.8, 1.0 Hz), 7.63-7.58 (1H, m), 7.52-7.48 (1H, m), 7.33-7.32 (1H, m), 7.26-7.19 (2H, m), 7.05 (1H, d, J=8.2 Hz), 2.00 (3H, s).

Step 3

2-chloro-4-methyl-fluoren-9-one

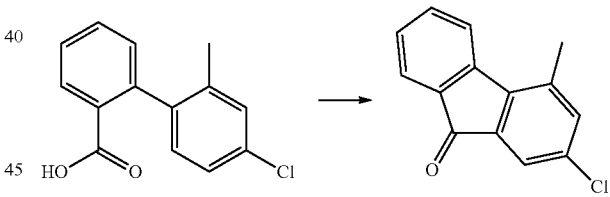

Under anhydrous calcium chloride drying conditions, a mixture of 4'-chloro-2'-methyl-biphenyl-2-carboxylic acid (21.60 g) and Eaton's reagent (7.7 w/w % solution of phosphorus pentoxide in methanesulfonic acid) (170 ml) was stirred at 100° C. for 2.5 hr. The reaction mixture was ice-cooled, water (500 ml) was slowly added dropwise, and the mixture was further stirred at room temperature for 10 min. This suspension was filtered, the obtained solid was mixed with 30 v/v % aqueous ethanol solution (200 ml), and the slurry was stirred at room temperature for 10 min, and filtered. The obtained solid was air-dried and dried under reduced pressure at 80° C. to give the title compound (19.744 g, 99%).

$^1$H-NMR (CDCl$_3$) δ: 7.69-7.66 (1H, m), 7.60-7.57 (1H, m), 7.52-7.46 (2H, m), 7.32-7.27 (1H, m), 7.25-7.23 (1H, m), 2.56 (3H, s).

Step 4

2-chloro-4-methyl-9-trifluoromethyl-9H-fluoren-9-ol

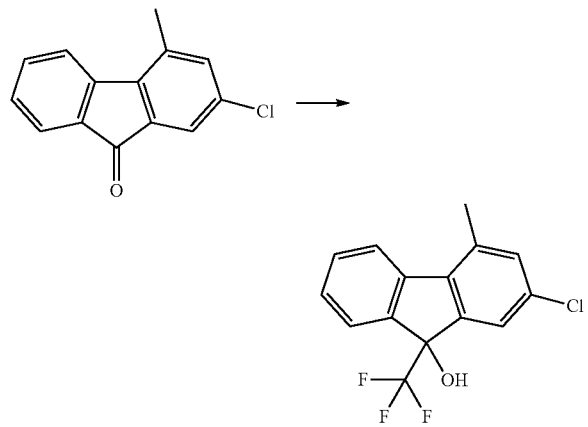

Under anhydrous calcium chloride drying conditions, 2-chloro-4-methyl-fluoren-9-one (18.627 g), potassium carbonate (3.372 g) and dimethylformamide (100 ml) were mixed, trimethyl(trifluoromethyl)silane (16 ml) was added dropwise over 25 min at room temperature with stirring, and the mixture was further stirred at room temperature for 14 min. To this mixture, a 1M solution (122 ml) of tetrabutylammonium fluoride in tetrahydrofuran was added dropwise over 6 min. To the reaction mixture was added aqueous ammonium chloride (400 ml), and the mixture was extracted with ethyl acetate (200 ml). The organic layer was washed once with water (100 ml), once with saturated aqueous sodium hydrogen carbonate and 3 times with water, and concentrated under reduced pressure. The obtained residue was dissolved in methanol (200 ml), activated carbon (1.5 g) was added, and the mixture was stirred at room temperature for 10 min. The mixture was filtered, and the filtrate was concentrated under reduced pressure to give the title compound (24.689 g). The obtained residue was directly used for the next reaction without further purification.

$^1$H-NMR (CDCl$_3$) δ: 7.78-7.75 (1H, m), 7.74-7.70 (1H, m), 7.55-7.53 (1H, m), 7.52-7.47 (1H, m), 7.40-7.35 (1H, m), 7.27-7.25 (1H, m), 2.80 (1H, brs), 2.64 (3H, s).

Step 5

2-chloro-9-hydroxy-9-trifluoromethyl-9H-fluorene-4-carboxylic acid

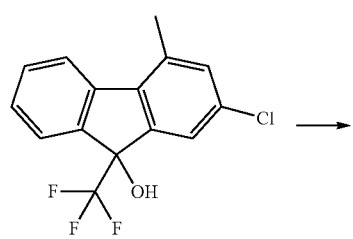

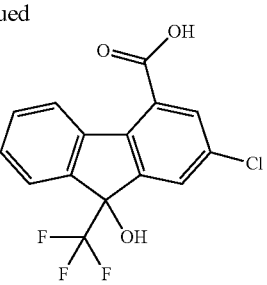

To a mixture of 2-chloro-4-methyl-9-trifluoromethyl-9H-fluoren-9-ol (2.987 g), pyridine (6 ml) and water (24 ml) was added potassium permanganate (7.902 g) at 100° C., and the mixture was stirred for 2 hr. To this mixture were added further potassium permanganate (4.70 g) and pyridine (6 ml) and the mixture was stirred at 100° C. for 2 hr. Potassium permanganate (4.70 g) was further added and the mixture was stirred at 100° C. for 2 hr. This operation was repeated twice. The reaction mixture was cooled to room temperature, and the insoluble material was filtered off and washed with water (50 ml). The filtrate was adjusted to pH 1 with 6N hydrochloric acid, and extracted with ethyl acetate (200 ml). The organic layer was successively washed with water and saturated brine, dried over anhydrous sodium sulfate, and filtered. The filtrate was concentrated under reduced pressure and the obtained residue was treated with hexane/ethyl acetate mixed solution (hexane:ethyl acetate=9:1) (30 ml). This slurry was filtered, and the obtained solid was dried to give the title compound (2.509 g, 76%).

$^1$H-NMR (DMSO-D$_6$) δ: 13.91 (1H, br s), 8.22-8.19 (1H, m), 7.87 (1H, d, J=2.0 Hz), 7.81-7.79 (1H, m), 7.72-7.68 (1H, m), 7.57-7.51 (2H, m), 7.51-7.46 (1H, m).

Step 6

Salt of Optically Active Form of 2-chloro-9-hydroxy-9-trifluoromethyl-9H-fluorene-4-carboxylic acid and (S)-(−)-1-phenylethylamine

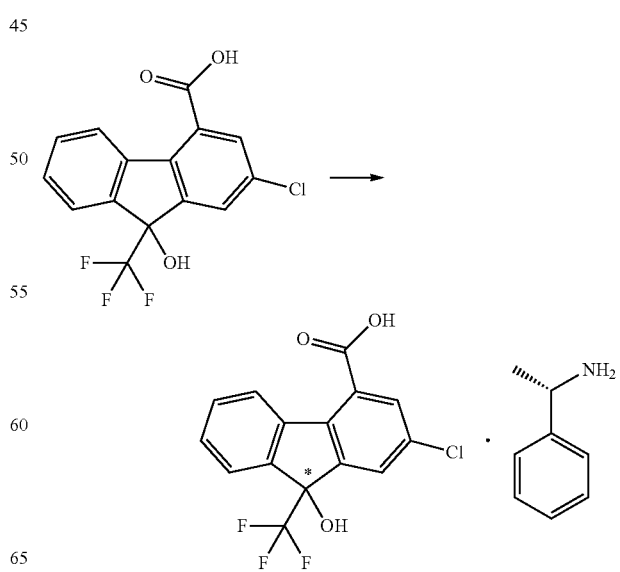

Step 6-1 Synthesis of Seed Crystal

To a solution of 2-chloro-9-hydroxy-9-trifluoromethyl-9H-fluorene-4-carboxylic acid (0.100 g) in ethyl acetate (0.50 ml) was added (S)-(−)-1-phenylethylamine (0.040 ml), and the mixture was stirred at room temperature for 2 days. This suspension was filtered, and the obtained solid was dried under reduced pressure to give the title compound (0.062 g, containing 8 w/w % ethyl acetate, 41%). The solid was analyzed under HPLC analysis condition 2 to find that the isomer with a short retention time was the main component.

isomer with short retention time (retention time 20.35 min)
isomer with long retention time (retention time 21.10 min)

$^1$H-NMR (DMSO-D$_6$) δ: 8.38 (1H, d, J=7.2 Hz), 8.29 (3H, br s), 7.61-7.57 (1H, m), 7.51-7.48 (2H, m), 7.45-7.32 (7H, m), 7.30 (1H, br s), 4.38 (1H, q, J=6.8 Hz), 1.49 (3H, d, J=6.7 Hz).

Step 6-2

To a solution of 2-chloro-9-hydroxy-9-trifluoromethyl-9H-fluorene-4-carboxylic acid (0.972 g) in ethyl acetate (5.0 ml) were added (S)-(−)-1-phenylethylamine (0.38 ml) and a seed crystal of a salt of an optically active form of 2-chloro-9-hydroxy-9-trifluoromethyl-9H-fluorene-4-carboxylic acid and (S)-(−)-1-phenylethylamine, and the mixture was stirred at room temperature for 2 days. This suspension was filtered, and the obtained solid was dried under reduced pressure to give the title compound (0.608 g, containing 16 w/w % ethyl acetate, 38%). The solid was analyzed under HPLC analysis condition 2 to find that the isomer with a short retention time was the main component.

isomer with short retention time (retention time 20.31 min)
isomer with long retention time (retention time 21.06 min)

$^1$H-NMR (DMSO-D$_6$) δ: 8.38 (1H, d, J=7.1 Hz), 8.34 (3H, br s), 7.61-7.57 (1H, m), 7.51-7.48 (2H, m), 7.46-7.32 (7H, m), 7.30 (1H, br s), 4.38 (1H, q, J=6.8 Hz), 1.50 (3H, d, J=6.8 Hz).

Step 7

Optically Active Form of 2-chloro-9-hydroxy-9-trifluoromethyl-9H-fluorene-4-carboxylic acid

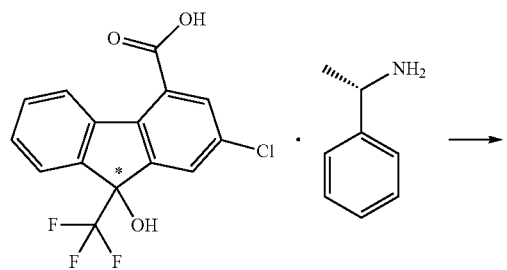

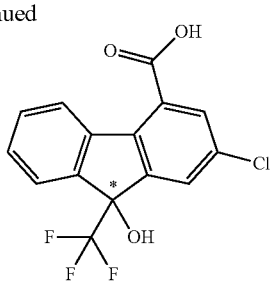

A salt of an optically active form of 2-chloro-9-hydroxy-9-trifluoromethyl-9H-fluorene-4-carboxylic acid and (S)-(−)-1-phenylethylamine (0.575 g) was dissolved in ethyl acetate, and the mixture was placed in a separatory funnel, hydrochloric acid was added, and the mixture was partitioned. The organic layer was washed with water, dried over anhydrous sodium sulfate, and filtered. The filtrate was concentrated under reduced pressure to give the title compound (0.357 g).

$^1$H-NMR (DMSO-D$_6$) δ: 13.90 (1H, br s), 8.22-8.19 (1H, m), 7.87 (1H, d, J=2.0 Hz), 7.81-7.79 (1H, m), 7.72-7.68 (1H, m), 7.57-7.46 (3H, m).

Step 8

1-ethyl-4-(4,4,5,5-tetramethyl-[1,3,2]dioxaborolan-2-yl)-1H-pyrazole

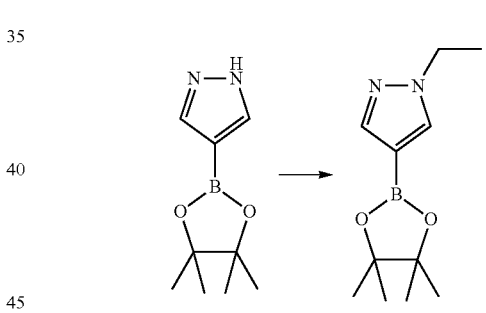

4,4,5,5-Tetramethyl-2-(1H-pyrazol-4-yl)-1,3,2-dioxaborolane (5.0 g), N,N-dimethylacetamide (50 ml), potassium carbonate (5.3 g) and ethyl iodide (2.1 ml) were mixed, and the mixture was stirred at 60° C. overnight. The reaction mixture was cooled to room temperature, water (100 ml) and ethyl ether (100 ml) were added, and the mixture was partitioned in a separatory funnel. The aqueous layer was further extracted with ethyl ether (100 ml), and the organic layers were combined. The organic layer was washed 3 times with water (100 ml) and once with saturated brine (100 ml), dried over anhydrous sodium sulfate, and filtered. The filtrate was concentrated under reduced pressure, hexane (50 ml) was added to the obtained residue and the mixture was partitioned in a separatory funnel. The organic layer was washed 3 times with water (40 ml) and once with saturated brine (40 ml), dried over anhydrous sodium sulfate, and filtered. The filtrate was concentrated under reduced pressure to give the title compound (2.1691 g, 38%).

$^1$H-NMR (CDCl$_3$) δ: 7.79 (1H, s), 7.70 (1H, s), 4.19 (2H, q, J=7.3 Hz), 1.49 (3H, t, J=7.3 Hz), 1.32 (12H, s).

Step 9

Optically Active Form of 2-(1-ethyl-1H-pyrazol-4-yl)-9-hydroxy-9-trifluoromethyl-9H-fluorene-4-carboxylic acid

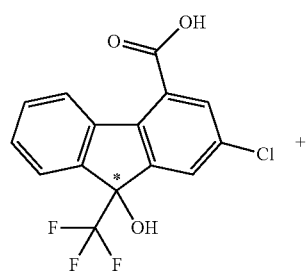

Under an argon atmosphere, an optically active form (0.100 g) of 2-chloro-9-hydroxy-9-trifluoromethyl-9H-fluorene-4-carboxylic acid, 1-ethyl-4-(4,4,5,5-tetramethyl-[1,3,2]dioxaborolan-2-yl)-1H-pyrazole (0.133 g), tripotassium phosphate (0.191 g), palladium(II) acetate (0.0034 g), 2-dicyclohexylphosphino-2',6'-dimethoxybiphenyl (0.0123 g), dioxane (3 ml) and water (0.6 ml) were mixed, and the mixture was stirred at 100° C. for 1 hr. The reaction mixture was cooled to room temperature, hydrochloric acid and ethyl acetate were added, and the mixture was partitioned in a separatory funnel. The organic layer was washed twice with water and once with saturated brine, dried over anhydrous sodium sulfate, and filtered. The filtrate was concentrated under reduced pressure, and the obtained residue was treated with hexane/ethyl acetate mixed solution (hexane:ethyl acetate=1:2, 2 ml). This slurry was filtered, and the obtained solid was dried to give the title compound (0.075 g, 63%).
$^1$H-NMR (DMSO-D$_6$) δ: 13.60 (1H, s), 8.43 (1H, s), 8.18-8.15 (1H, m), 8.01 (1H, d, J=0.7 Hz), 8.00 (1H, d, J=1.6 Hz), 7.97-7.95 (1H, m), 7.70-7.66 (1H, m), 7.53-7.48 (1H, m), 7.45-7.40 (1H, m), 7.35 (1H, s), 4.17 (2H, q, J=7.3 Hz), 1.43 (3H, t, J=7.3 Hz).

Step 10

(−)-2-(1-ethyl-1H-pyrazol-4-yl)-9-hydroxy-9-trifluoromethyl-9H-fluorene-4-carboxamide

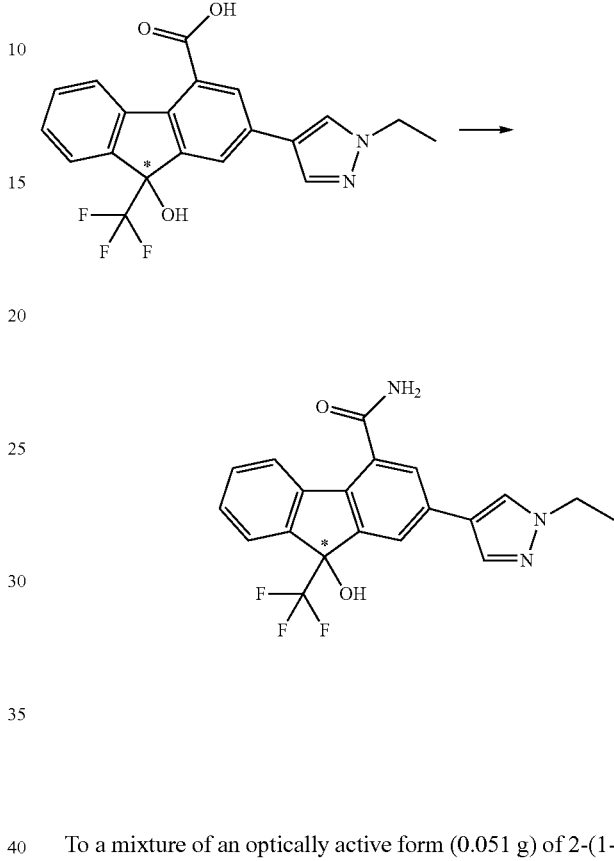

To a mixture of an optically active form (0.051 g) of 2-(1-ethyl-1H-pyrazol-4-yl)-9-hydroxy-9-trifluoromethyl-9H-fluorene-4-carboxylic acid, 1-(3-dimethylaminopropyl)-3-ethylcarbodiimide hydrochloride (0.038 g), 1-hydroxybenzotriazole hydrate (0.030 g), ammonium chloride (0.022 g) and dimethylformamide (1 ml) was added triethylamine (0.055 ml), and the mixture was stirred at room temperature overnight. To the reaction mixture was added ethyl acetate (10 ml), and the organic layer was successively washed once with hydrochloric acid, once with water, twice with saturated aqueous sodium hydrogen carbonate, 3 times with water and once with saturated brine. The organic layer was dried over anhydrous sodium sulfate, and filtered. The filtrate was concentrated under reduced pressure to give the title compound (0.043 g, 85%).

[α]D=−3.00° (20° C., c=0.20, methanol)

$^1$H-NMR (DMSO-D$_6$) δ: 8.37 (1H, s), 8.14 (1H, br s), 7.98 (1H, J=0.7 Hz), 7.93-7.90 (1H, m), 7.85-7.83 (1H, m), 7.74 (1H, br s), 7.70 (1H, d, J=1.5 Hz), 7.67-7.64 (1H, m), 7.49-7.44 (1H, m), 7.40-7.35 (1H, m), 7.30 (1H, s), 4.17 (2H, q, J=7.3 Hz), 1.42 (3H, t, J=7.3 Hz).

Using the above-mentioned optically active form of 2-chloro-9-hydroxy-9-trifluoromethyl-9H-fluorene-4-carboxylic acid as an intermediate and by a similar method, compound Nos. 629, 659, 660, 667 and 668 where synthesized.

Example 6

Synthesis of (−)-1-(9-hydroxy-4-methyl-9-trifluoromethyl-9H-fluorene-2-carbonyl)-azetidine-3-carboxylic acid dimethylamide (Compound No. 153)

Step 1

2-ethyl 4'-methyl 2'-methyl-biphenyl-2,4'-dicarboxylate

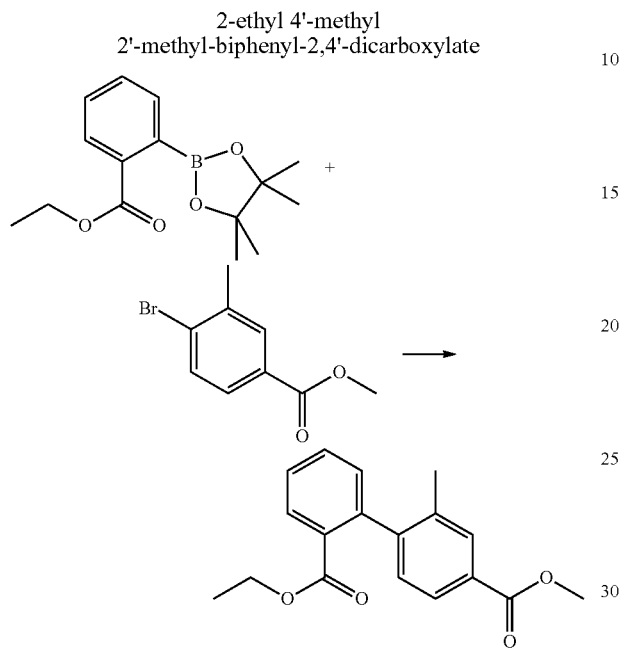

Under a nitrogen atmosphere, to a mixture of methyl 4-bromo-3-methylbenzoate (2.291 g), ethyl 2-(4,4,5,5-tetramethyl-1,3,2-dioxaborolan-2-yl)benzoate (3.313 g), toluene (20 ml), water (10 ml) and tripotassium phosphate (4.246 g) was added tetrakis(triphenylphosphine)palladium(0) (0.578 g) at room temperature, and the mixture was stirred with heating under reflux overnight. The reaction mixture was cooled to room temperature, and partitioned in a separatory funnel. The organic layer was successively washed with water and saturated brine, dried over anhydrous sodium sulfate, and filtered. The filtrate was concentrated under reduced pressure and the obtained residue was purified by silica gel column chromatography (eluent: n-hexane/ethyl acetate=95/5) to give the title compound (2.404 g, 81%)

$^1$H-NMR (CDCl$_3$) δ: 8.03-7.99 (1H, m), 7.94-7.91 (1H, m), 7.89-7.85 (1H, m), 7.59-7.53 (1H, m), 7.49-7.43 (1H, m), 7.21-7.18 (1H, m), 7.17-7.14 (1H, m), 4.07-4.01 (2H, m), 3.93 (3H, s), 2.11 (3H, s), 0.98-0.93 (3H, m).

Step 2

2'-methyl-biphenyl-2,4'-dicarboxylic acid

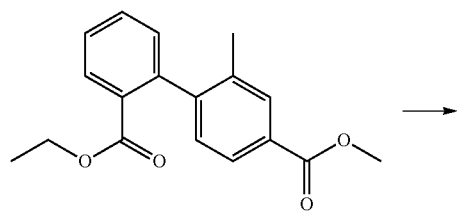

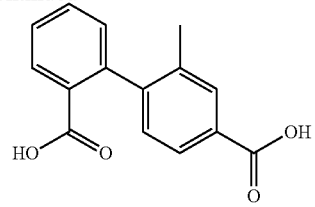

A mixture of 2-ethyl 4'-methyl 2'-methyl-biphenyl-2,4'-dicarboxylate (2.404 g), ethanol (12 ml) and 4N aqueous sodium hydroxide solution (6 ml) was stirred at 100° C. overnight. After completion of the reaction, the reaction mixture was concentrated under reduced pressure, and water (50 ml) was added to the obtained residue. This mixture was adjusted to pH 1 with 6N hydrochloric acid (5 ml), ethanol (10 ml) was added, and the mixture was stirred at room temperature for 10 min. This suspension was filtered, the obtained solid was washed with 20 v/v % ethanol-water (10 ml), air-dried, and dried under reduced pressure at 80° C. to give the title compound (1.957 g, 95%).

$^1$H-NMR (DMSO-D$_6$) δ: 12.74 (2H, br s), 7.92 (1H, dd, J=7.8, 1.3 Hz), 7.82-7.80 (1H, m), 7.76 (1H, dd, J=7.9, 1.6 Hz), 7.65-7.60 (1H, m), 7.54-7.49 (1H, m), 7.22 (1H, dd, J=7.7, 1.2 Hz), 7.15 (1H, d, J=7.9 Hz), 2.06 (3H, s).

Step 3

4-methyl-9-oxo-9H-fluorene-2-carboxylic acid

A mixture of 2'-methyl-biphenyl-2,4'-dicarboxylic acid (1.94 g) and polyphosphoric acid (50 g) was stirred at 180° C. for 3 hr. The reaction mixture was cooled to room temperature, water (100 ml) was slowly added dropwise, and the mixture was further stirred at room temperature for 10 min. This suspension was filtered, and the obtained solid was successively washed with water (50 ml) and 50 v/v % aqueous methanol solution (50 ml). The obtained solid was air-dried, and dried under reduced pressure at 80° C. to give the title compound (1.745 g, 97%).

$^1$H-NMR (DMSO-D$_6$) δ: 12.98 (1H, br s), 8.00-7.99 (1H, m), 7.88 (1H, d, J=1.6 Hz), 7.86 (1H, d, J=7.4 Hz), 7.71-7.66 (2H, m), 7.49-7.45 (1H, m), 2.65 (3H, s).

Step 4 methyl 4-methyl-9-oxo-9H-fluorene-2-carboxylate

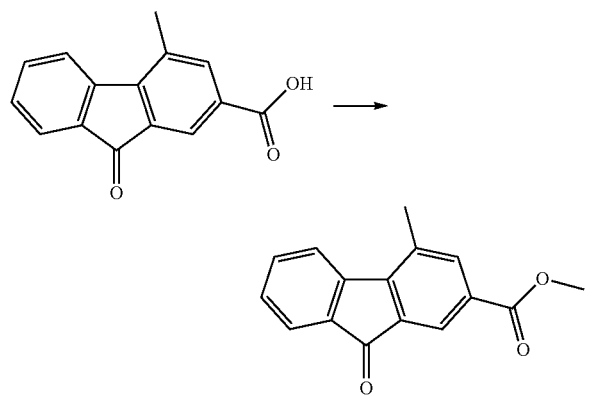

Under anhydrous calcium chloride drying conditions, 4-methyl-9-oxo-9H-fluorene-2-carboxylic acid (1.745 g), potassium carbonate (3.03 g) and dimethylformamide (20 ml) were mixed. To this mixture was added methyl iodide (0.92 ml) at room temperature, and the mixture was stirred for 3 hr 15 min. To the reaction mixture was added water (60 ml), and the mixture was stirred at room temperature for 30 min. The mixture was filtered and the obtained solid was air-dried and dried under reduced pressure at 80° C. to give the title compound (1.778 g, 96%).

$^1$H-NMR (CDCl$_3$) δ: 8.17 (1H, s), 8.01 (1H, s), 7.76-7.70 (2H, m), 7.58-7.52 (1H, m), 7.40-7.35 (1H, m), 3.94 (3H, s), 2.67 (3H, s).

Step 5 methyl 9-hydroxy-4-methyl-9-trifluoromethyl-9H-fluorene-2-carboxylate

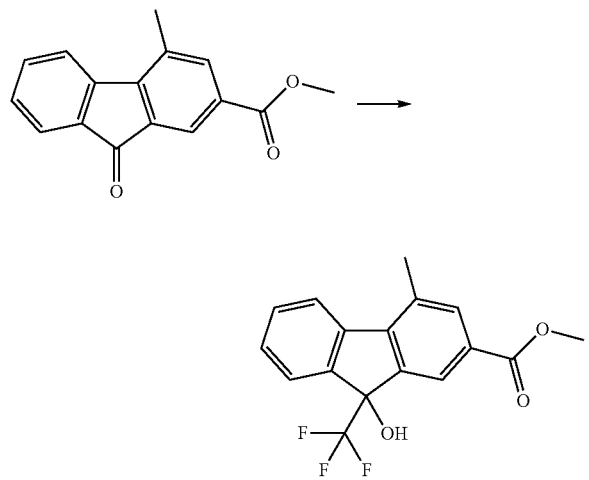 [SMILES: COC(=O)c1cc(C)c2c(c1)C(=O)c1ccccc1-2 ; COC(=O)c1cc(C)c2c(c1)C(O)(C(F)(F)F)c1ccccc1-2]

Under an argon atmosphere, methyl 4-methyl-9-oxo-9H-fluorene-2-carboxylate (1.009 g), trimethyl(trifluoromethyl)silane (0.89 ml) and dimethylformamide (50 ml) were mixed, lithium acetate (0.027 g) was added with stirring at room temperature, and the mixture was further stirred at room temperature for 30 min. Acetic acid (0.7 ml) and a 1M solution (6 ml) of tetrabutylammonium fluoride in tetrahydrofuran were added, and the mixture was further stirred at room temperature for 15 min. To the reaction mixture was added aqueous sodium hydrogen carbonate (300 ml), and the mixture was extracted twice with ethyl acetate (50 ml). The combined organic layer was washed once with saturated aqueous sodium hydrogen carbonate, 4 times with water and once with saturated brine, and concentrated under reduced pressure. To the obtained residue was added hexane/ethyl acetate (8:2, 10 ml) and the mixture was stirred for 10 min. This slurry was filtered, and the obtained solid was dried to give the title compound (1.000 g, 78%).

$^1$H-NMR (CDCl$_3$) δ: 8.20-8.19 (1H, m), 7.98-7.96 (1H, m), 7.86 (1H, d, J=7.7 Hz), 7.79-7.75 (1H, m), 7.56-7.51 (1H, m), 7.46-7.40 (1H, m), 3.93 (3H, s), 2.84 (1H, s), 2.71 (3H, s).

Step 6

9-hydroxy-4-methyl-9-trifluoromethyl-9H-fluorene-2-carboxylic acid

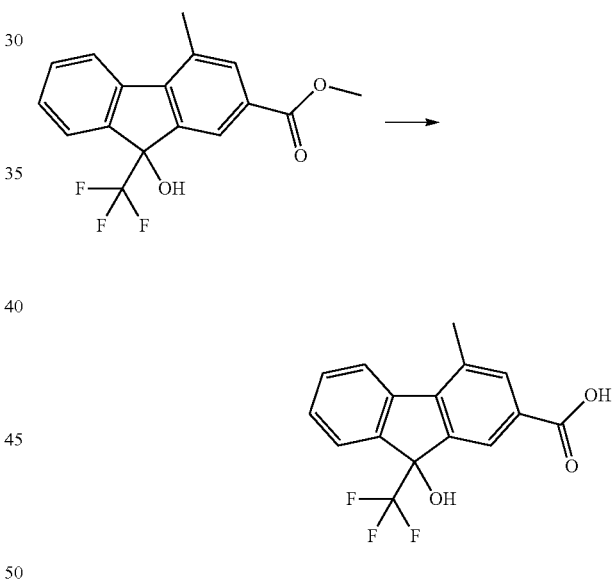

A mixture of methyl 9-hydroxy-4-methyl-9-trifluoromethyl-9H-fluorene-2-carboxylate (1.000 g), tetrahydrofuran (4 ml), methanol (6 ml) and 4N aqueous sodium hydroxide solution (1.6 ml) was stirred with heating under reflux for 3 hr. The reaction mixture was cooled to room temperature, and concentrated under reduced pressure. Water (30 ml) was added to the obtained residue, and the mixture was adjusted to pH 1 with 6N hydrochloric acid (2 ml), and extracted with ethyl acetate (30 ml). The organic layer was successively washed with water and saturated brine. After addition of anhydrous magnesium sulfate and activated carbon (0.2 g), the mixture was stirred at room temperature for 10 min. The insoluble material was filtered off, and the filtrate was concentrated under reduced pressure to give the title compound (1.053 g). The residue was directly used for the next reaction without further purification.

¹H-NMR (DMSO-D₆) δ: 13.07 (1H, br s), 8.06-8.03 (1H, m), 7.97-7.91 (2H, m), 7.74-7.71 (1H, m), 7.61-7.56 (1H, m), 7.51-7.46 (1H, m), 7.33 (1H, s), 2.70 (3H, s).

Step 7

Salt of racemic 9-hydroxy-4-methyl-9-trifluoromethyl-9H-fluorene-2-carboxylic acid and (R)-(+)-1-phenylethylamine

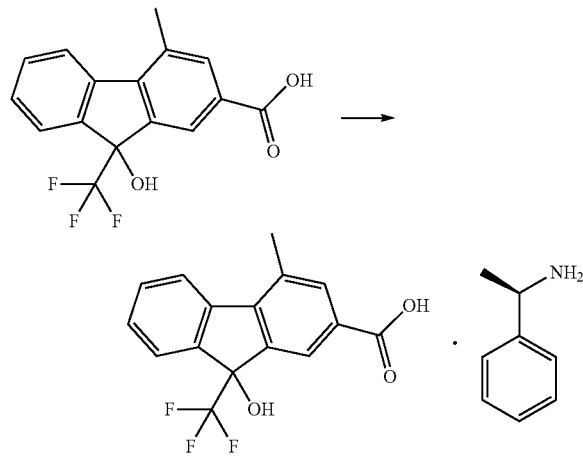

A mixture of 9-hydroxy-4-methyl-9-trifluoromethyl-9H-fluorene-2-carboxylic acid (0.159 g), (R)-(+)-1-phenylethylamine (0.066 ml), and ethyl acetate (2 ml) was concentrated under reduced pressure, ethyl acetate was added to the residue and the mixture was concentrated under reduced pressure again to give the title compound (0.229 g).

Step 8

Salt of Optically Active Form (Enantiomer with Long Retention Time Under HPLC Analysis Condition 3) of 9-hydroxy-4-methyl-9-trifluoromethyl-9H-fluorene-2-carboxylic acid and (R)-(+)-1-phenylethylamine

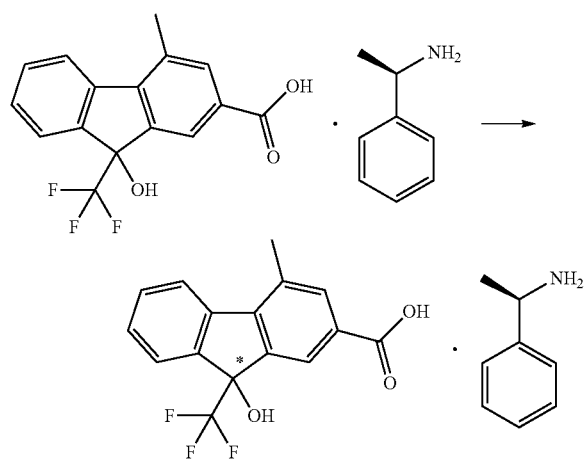

Salt (0.010 g) of the racemic 9-hydroxy-4-methyl-9-trifluoromethyl-9H-fluorene-2-carboxylic acid and (R)-(+)-1-phenylethylamine obtained in Step 7 was dissolved in ethyl acetate (0.2 ml) and the mixture was stood at room temperature overnight. The obtained solid was collected by filtration, and dried under reduced pressure to give the title compound (0.0017 g). The solid was analyzed under HPLC analysis condition 3 to find that an isomer with a long retention time was the main component.
isomer with short retention time (retention time 23.27 min)
isomer with long retention time (retention time 25.39 min)

Step 9

Salt of Optically Active Form (Enantiomer with Short Retention Time Under HPLC Analysis Condition 3) of 9-hydroxy-4-methyl-9-trifluoromethyl-9H-fluorene-2-carboxylic acid and (S)-(−)-1-phenylethylamine

Step 9-1 Synthesis of Seed Crystal

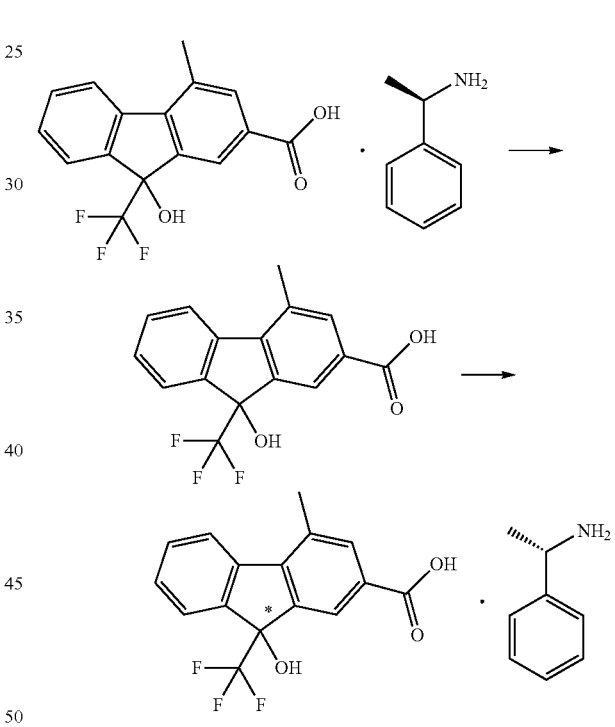

To a mixture of a salt (0.141 g) of the racemic 9-hydroxy-4-methyl-9-trifluoromethyl-9H-fluorene-2-carboxylic acid and (R)-(+)-1-phenylethylamine obtained in Step 7 and ethyl acetate (0.70 ml) was added a salt of an optically active form (enantiomer with long retention time under HPLC analysis condition 3) of 9-hydroxy-4-methyl-9-trifluoromethyl-9H-fluorene-2-carboxylic acid and (R)-(+)-1-phenylethylamine obtained in Step 8 as a seed crystal, and the mixture was stirred at room temperature for 30 min. Ethyl acetate (0.7 ml) was added to the mixture, and the mixture was further stirred at room temperature for 2 hr. This suspension was filtered, and the obtained solid was washed with ethyl acetate (4 ml). The filtrate was successively washed with 1N hydrochloric acid and water, dried over anhydrous sodium sulfate, and filtered. The filtrate was concentrated under reduced pressure to give a residue (0.046 g). The residue was dissolved in ethyl acetate (0.50 ml), (S)-(−)-1-phenylethylamine (0.019 ml) was added, and the mixture was stirred at room temperature overnight. This suspension was filtered, and the obtained solid was washed with ethyl acetate (2 ml), and dried. The solid was further mixed with ethyl acetate (0.5 ml), and the mixture was stirred at 70° C. for 30 min, and further at room temperature for 2 hr. This suspension was filtered, and the obtained solid was washed with ethyl acetate (2 ml), and dried to give the title compound (0.0357 g). The solid was analyzed under HPLC analysis condition 3 to find that an isomer with a short retention time was the main component.
isomer with short retention time (retention time 23.57 min)
isomer with long retention time (retention time 25.65 min)

Step 9-2

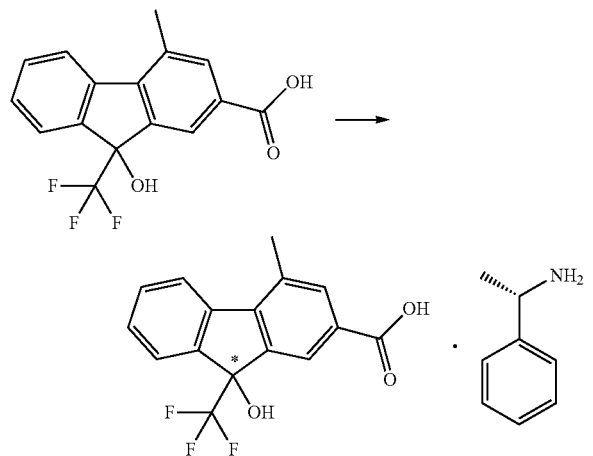

To a solution of 9-hydroxy-4-methyl-9-trifluoromethyl-9H-fluorene-2-carboxylic acid (1.053 g) in ethyl acetate (15 ml) were added at 50° C. (S)-(−)-1-phenylethylamine (0.200 ml) and a seed crystal of a salt of an optically active form (enantiomer with short retention time under HPLC analysis condition 3) of 9-hydroxy-4-methyl-9-trifluoromethyl-9H-fluorene-2-carboxylic acid and (S)-(−)-1-phenylethylamine obtained in Step 9-1, and the mixture was stirred at 50° C. for 5 min and at room temperature for 4 hr. This suspension was filtered, and the obtained solid was dried under reduced pressure to give the title compound (0.400 g). The solid was analyzed under HPLC analysis condition 3 to find that an isomer with a short retention time was the main component.
isomer with short retention time (retention time 23.49 min)
isomer with long retention time (retention time 25.52 min)

Step 10

Optically Active Form of 9-hydroxy-4-methyl-9-trifluoromethyl-9H-fluorene-2-carboxylic acid

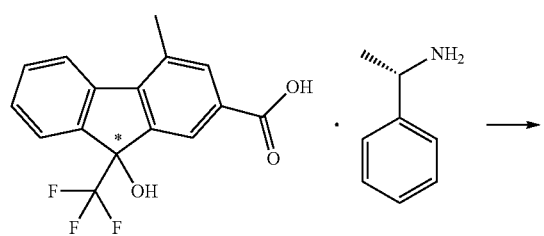

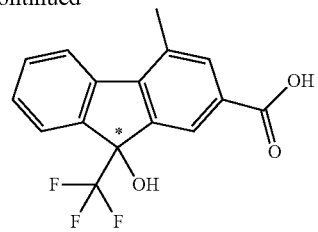

Salt (0.390 g) of an optically active form (enantiomer with short retention time under HPLC analysis condition 3) of 9-hydroxy-4-methyl-9-trifluoromethyl-9H-fluorene-2-carboxylic acid and (S)-(−)-1-phenylethylamine was mixed with ethyl acetate (10 ml), hydrochloric acid was added, and the mixture was partitioned. The organic layer was successively washed with water and saturated brine, dried over anhydrous sodium sulfate, and filtered. The filtrate was concentrated under reduced pressure to give the title compound (0.310 g).
$^1$H-NMR (DMSO-D$_6$) δ: 13.10 (1H, br s), 8.06-8.03 (1H, m), 7.97-7.91 (2H, m), 7.75-7.71 (1H, m), 7.61-7.56 (1H, m), 7.51-7.46 (1H, m), 7.35 (1H, s), 2.70 (3H, s).

Step 11 t-butyl 3-dimethylcarbamoyl-azetidine-1-carboxylate

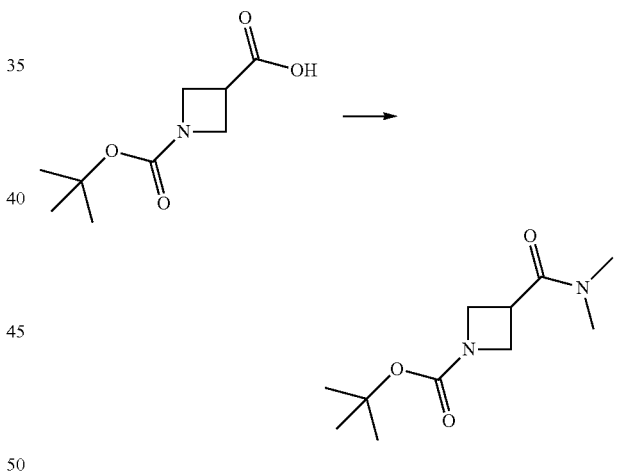

Under a nitrogen atmosphere, triethylamine (1.2 ml) was added to a mixture of 1-(t-butyloxycarbonyl)-azetidine-3-carboxylic acid (0.804 g), dimethylamine hydrochloride (0.489 g), 1-(3-dimethylaminopropyl)-3-ethylcarbodiimide hydrochloride (0.997 g), 1-hydroxybenzotriazole hydrate (0.796 g), and dimethylformamide (8 ml), and the mixture was stirred at room temperature for 3 days. To the reaction mixture was added ethyl acetate (30 ml), and the mixture was successively washed once with water, once with hydrochloric acid, once with water, twice with saturated aqueous sodium hydrogen carbonate and twice with water. The organic layer was dried over anhydrous sodium sulfate, and filtered. The filtrate was concentrated under reduced pressure to give the title compound (0.364 g, 40%).
$^1$H-NMR (CDCl$_3$) δ: 4.17 (2H, br s), 4.05 (2H, t, J=8.5 Hz), 3.52-3.43 (1H, m), 2.97 (3H, s), 2.88 (3H, s), 1.43 (9H, s).

Step 12 azetidine-3-carboxylic acid dimethylamide hydrochloride

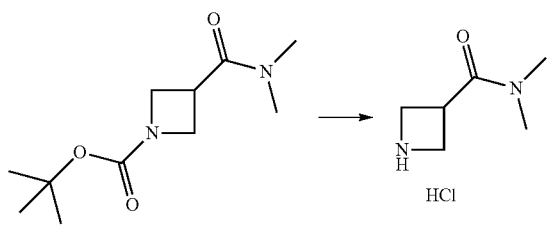

A mixture of t-butyl 3-dimethylcarbamoyl-azetidine-1-carboxylate (0.365 g) and 4N hydrogen chloride/dioxane solution (5 ml) was stirred at room temperature for 5 hr 15 min. The reaction mixture was concentrated under reduced pressure, dioxane was added to the obtained residue and the mixture was concentrated again under reduced pressure. The obtained residue was dried under reduced pressure at 60° C. to give the title compound (0.290 g). The obtained residue was directly used for the next reaction without further purification.

¹H-NMR (DMSO-D₆) δ: 9.38 (1H, br s), 8.95 (1H, br s), 4.10-3.99 (4H, m), 3.94-3.85 (1H, m), 2.85 (3H, s), 2.82 (3H, s).

Step 13

(−)-1-(9-hydroxy-4-methyl-9-trifluoromethyl-9H-fluorene-2-carbonyl)-azetidine-3-carboxylic acid dimethylamide

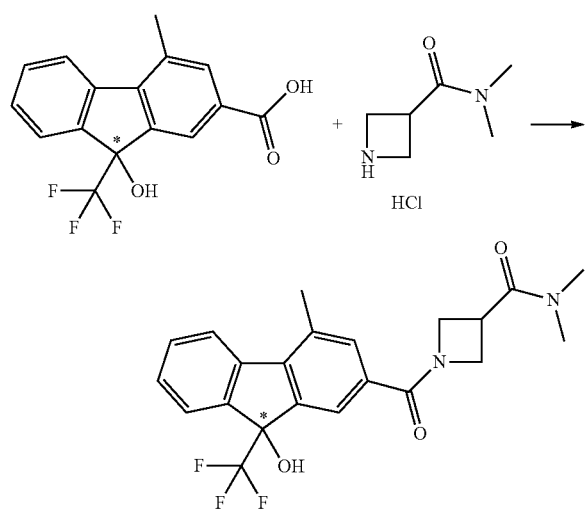

To a mixture of an optically active form (0.080 g) of 9-hydroxy-4-methyl-9-trifluoromethyl-9H-fluorene-2-carboxylic acid, azetidine-3-carboxylic acid dimethylamide hydrochloride (0.060 g), 1-(3-dimethylaminopropyl)-3-ethylcarbodiimide hydrochloride (0.065 g), 1-hydroxybenzotriazole hydrate (0.052 g) and dimethylformamide (2 ml) was added triethylamine (0.073 ml), and the mixture was stirred at room temperature for 3 hr. To the reaction mixture was added ethyl acetate (15 ml), and the mixture was successively washed once with hydrochloric acid, once with water, twice with saturated aqueous sodium hydrogen carbonate and 3 times with water. The organic layer was dried over anhydrous sodium sulfate, and filtered. The filtrate was concentrated under reduced pressure, and the obtained residue was treated with ethyl ether. This slurry was filtered and the obtained solid was dried to give the title compound (0.054 g, 50%).

[α]D=−12.53° (25° C., c=0.744, methanol)

¹H-NMR (CDCl₃) δ: 7.85-7.74 (3H, m), 7.54-7.48 (1H, m), 7.45-7.38 (2H, m), 4.74-4.64 (1H, m), 4.43-4.32 (2H, m), 4.25-4.11 (1H, m), 3.94-3.86 (1H, m), 3.65-3.54 (1H, m), 2.98 (3H, s), 2.91 (3H, s), 2.64 (3H, s).

Using the above-mentioned optically active form of 9-hydroxy-4-methyl-9-trifluoromethyl-9H-fluorene-2-carboxylic acid as an intermediate and by a similar method, compound Nos. 136 and 152 were synthesized.

Example 7

Synthesis of 1-[2-(5-hydroxy-5-trifluoromethyl-5-H-indeno[1,2-b]pyridin-3-yloxy)-ethyl]-pyrrolidin-2-one (Compound No. 430)

Step 1

2-chloro-5-methoxy-pyridine

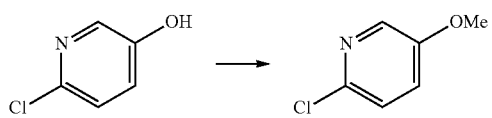 [SMILES: Oc1ccc(Cl)nc1 ; COc1ccc(Cl)nc1]

Under a nitrogen atmosphere, potassium carbonate (5.52 g) was added to a mixture of 2-chloro-5-hydroxy-pyridine (2.591 g), methyl iodide (1.50 ml) and dimethylformamide (26 ml), and the mixture was stirred at room temperature for 18 hr. To the reaction mixture was added ethyl acetate and the mixture was placed in a separatory funnel. The organic layer was washed 4 times with aqueous ammonium chloride, dried over anhydrous sodium sulfate, and filtered. The filtrate was concentrated under reduced pressure to give the title compound (2.403 g, 84%).

¹H-NMR (CDCl₃) δ: 8.07 (1H, d, J=3.0 Hz), 7.24 (1H, dd, J=8.8, 0.7 Hz), 7.20 (1H, dd, J=8.6, 3.0 Hz), 3.87 (3H, s).

Step 2

2-(5-methoxy-pyridin-2-yl)-benzoic acid diethylamide

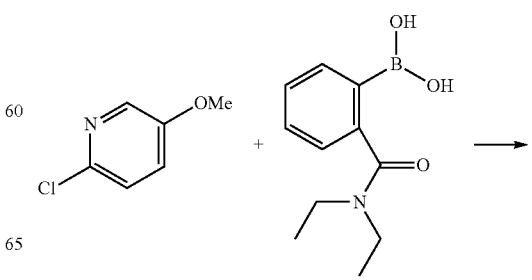

-continued

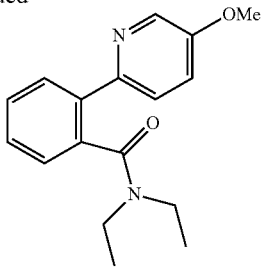

Under an argon atmosphere, a mixture of tripotassium phosphate (6.24 g) and water (15 ml) was added to a mixture of 2-chloro-5-methoxy-pyridine (2.05 g), 2-(diethylcarbamoyl)benzeneboronic acid (4.65 g), 1,1'-bis(diphenylphosphino)ferrocene-palladium(II) dichloride-dichloromethane complex (0.584 g) and toluene (30 ml), and the mixture was stirred at 80° C. for 2 hr. The reaction mixture was cooled to room temperature, water (20 ml), citric acid (2.2 g) and ethyl acetate were added and the mixture was stirred and filtered through celite. The filtrate was partitioned in a separatory funnel. The organic layer was washed with saturated brine, dried over anhydrous sodium sulfate, and filtered. The filtrate was concentrated under reduced pressure and the obtained residue was purified by silica gel column chromatography (eluent: n-hexane/ethyl acetate=1/1 to 1/2) to give a roughly purified product (1.144 g) of the title compound. This product was directly used for the next reaction without further purification.

$^1$H-NMR (CDCl$_3$) δ: 8.33 (1H, d, J=2.9 Hz), 7.68 (1H, dd, J=7.7, 1.3 Hz), 7.60 (1H, d, J=8.6 Hz), 7.48-7.32 (3H, m), 7.25-7.15 (1H, m), 3.88 (3H, s), 3.32-2.78 (4H, m), 1.07 (3H, t, J=7.1 Hz), 0.81 (3H, t, J=7.2 Hz).

Step 3

3-methoxy-indeno[1,2-b]pyridin-5-one

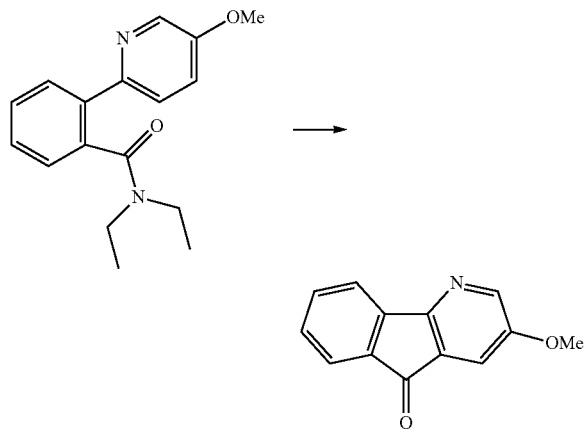

Under an argon atmosphere, a 2.66M solution (1.96 ml) of n-butyllithium in n-hexane was added to a solution of N,N-diisopropylamine (0.734 ml) in tetrahydrofuran (20 ml) at 0° C., and the mixture was stirred at 0° C. for 30 min. To this mixture was added a solution (10 ml) of 2-(5-methoxy-pyridin-2-yl)-benzoic acid diethylamide (1.14 g) in tetrahydrofuran at 0° C. and the mixture was stirred at 0° C. for 30 min, and further at room temperature for 1 hr. To the reaction mixture was added aqueous ammonium chloride solution and the mixture was placed in a separatory funnel, and separated into layers by adding ethyl acetate. The organic layer was successively washed with water and saturated brine, dried over anhydrous sodium sulfate, and filtered. The filtrate was concentrated under reduced pressure and the obtained residue was treated with ethyl ether at room temperature for 1 hr. This slurry was filtered, and the obtained solid was dried to give the title compound (0.183 g, 22%). The filtrate was concentrated under reduced pressure and the obtained residue was treated with ethyl ether at room temperature for 20 min. This slurry was filtered, and the obtained solid was dried to further give the title compound (0.128 g, 15%). The filtrate was concentrated under reduced pressure and the obtained residue was purified by silica gel column chromatography (eluent: n-hexane/ethyl acetate=3/1) to further give the title compound (0.134 g, 16%).

$^1$H-NMR (DMSO-D$_6$) δ: 8.37 (1H, d, J=2.8 Hz), 7.73-7.64 (3H, m), 7.60 (1H, d, J=3.0 Hz), 7.46-7.42 (1H, m), 3.91 (3H, s).

Step 4

3-hydroxy-indeno[1,2-b]pyridin-5-one

[化118]

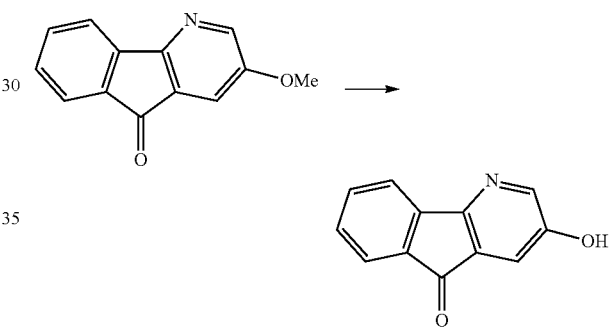

Under an argon atmosphere, 3-methoxy-indeno[1,2-b]pyridin-5-one (0.545 g) and pyridinium chloride (5.89 g) were mixed with pyridine (1.0 ml). The reaction mixture was stirred with heating at 180° C. for 30 min while evaporating pyridine, and further stirred with heating at 200° C. for 4 hr. The mixture was cooled to room temperature, water was added and the mixture was stirred for 30 min. This slurry was filtered, and the obtained solid was dried under reduced pressure to give the title compound (0.054 g). The obtained solid was used for the next reaction without further purification.

$^1$H-NMR (DMSO-D$_6$) δ: 10.53 (1H, br s), 8.19 (1H, d, J=2.8 Hz), 7.68-7.61 (3H, m), 7.43-7.38 (1H, m), 7.29 (1H, d, J=2.6 Hz).

Step 5

3-[2-(2-oxo-pyrrolidin-1-yl)-ethoxy]-indeno[1,2-b]pyridin-5-one

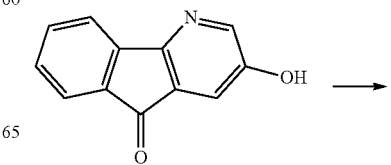

-continued

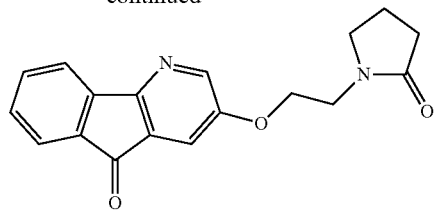

3-Hydroxy-indeno[1,2-b]pyridin-5-one (0.0500 g), di-t-butyl azodicarboxylate (0.087 g) and triphenylphosphine (0.10 g) were mixed with tetrahydrofuran (1.0 ml), 1-(2-hydroxy-ethyl)-2-pyrrolidone (0.043 ml) was added thereto, and the mixture was stirred at room temperature for 1 day. The mixture was purified by preparative thin layer chromatography (silica gel, eluent:ethyl acetate/methanol=10/1) to give the title compound (0.0386 g, 49%).

$^1$H-NMR (DMSO-D$_6$) δ: 8.36 (1H, d, J=2.8 Hz), 7.73-7.64 (3H, m), 7.63 (1H, d, J=2.8 Hz), 7.47-7.42 (1H, m), 4.27 (2H, t, J=5.4 Hz), 3.57 (2H, t, J=5.4 Hz), 3.49-3.44 (2H, m), 2.25-2.19 (2H, m), 1.97-1.87 (2H, m).

Step 6

1-[2-(5-hydroxy-5-trifluoromethyl-5-H-indeno[1,2-b]pyridin-3-yloxy)-ethyl]-pyrrolidin-2-one

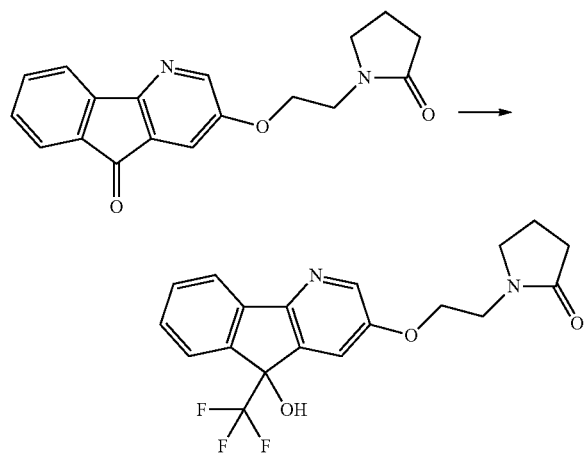

3-[2-(2-oxo-pyrrolidin-1-yl)-ethoxy]-indeno[1,2-b]pyridin-5-one (0.0376 g) and potassium carbonate (0.001 g) were mixed with dimethylformamide (1.0 ml), and the mixture was stirred at 0° C. To this mixture was added trimethyl(trifluoromethyl)silane (0.035 ml), and the mixture was stirred at 0° C. for 1 hr. Trimethyl(trifluoromethyl)silane (0.018 ml) was further added, and the mixture was stirred at 0° C. for 1 hr. To the reaction mixture was added acetic acid (0.010 ml), then a 1M solution (0.12 ml) of tetrabutylammonium fluoride in tetrahydrofuran was added, and the mixture was stirred at 0° C. for 30 min. To the reaction mixture was added ethyl acetate (20 ml), and the mixture was placed in a separatory funnel. The organic layer was washed 3 times with water (10 ml) and once with saturated brine (10 ml). The organic layer was dried over anhydrous sodium sulfate, and filtered. The filtrate was concentrated under reduced pressure, and the residue was purified by preparative thin layer chromatography (silica gel, eluent: n-hexane/ethyl acetate=7/3) to give the title compound (0.0389 g, 68%).

$^1$H-NMR (DMSO-D$_6$) δ: 8.36 (1H, d, J=2.8 Hz), 7.82-7.78 (1H, m), 7.71-7.66 (1H, m), 7.60-7.54 (2H, m), 7.50 (1H, s), 7.48-7.43 (1H, m), 4.25 (2H, t, J=5.4 Hz), 3.59 (2H, t, J=5.4 Hz), 3.51-3.45 (2H, m), 2.26-2.19 (2H, m), 1.97-1.88 (2H, m).

Example 8

Synthesis of optically active form of (4-bromo-9-hydroxy-9-trifluoromethyl-9H-fluoren-2-yloxy)-acetic acid methyl ester (Compound No. 451) and the like Step 1

Salt of Optically Active Form of (4-bromo-9-hydroxy-9-trifluoromethyl-9H-fluoren-2-yloxy)-acetic acid and (S)-(−)-1-phenylethylamine

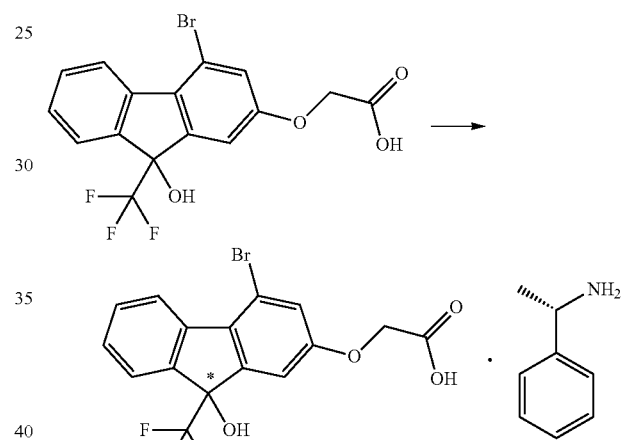

(4-Bromo-9-hydroxy-9-trifluoromethyl-9H-fluoren-2-yloxy)-acetic acid (0.176 g) and (S)-(−)-1-phenylethylamine (0.057 ml) were mixed with ethyl acetate (1 ml). The mixture was concentrated under reduced pressure. To the obtained residue was added ethyl acetate, and the mixture was concentrated under reduced pressure to give a residue (0.233 g). Under a nitrogen atmosphere, the residue (0.160 g) and ethyl acetate (2.0 ml) were mixed. The mixture was stirred with heating at 80° C. until insoluble material was solved, and stirred at room temperature overnight. This suspension was filtered to give a solid (0.044 g). The solid was mixed with ethyl ether/ethyl acetate (1:1, 1 ml), and the mixture was stirred at room temperature for 1 hr. This suspension was filtered, and the obtained solid was washed with ethyl ether/ethyl acetate (1:1, 2 ml). The obtained solid was dried under reduced pressure to give the title compound (0.023 g). The solid was analyzed under HPLC analysis condition 2 to find that an isomer with a long retention time was the main component.

isomer with short retention time (retention time 16.50 min)

isomer with long retention time (retention time 17.58 min)

Using the salt as an intermediate, compound Nos. 451, 467, 474, 475 and 477 were synthesized.

Example 9

Synthesis of Optically Active Form of 4-[9-hydroxy-4-(1-methyl-1H-pyrazol-4-yl)-9-trifluoromethyl-9H-fluoren-2-yloxy]-butyric acid (Compound No. 504) and the Like

Step 1

Salt of Optically Active Form of 4-(4-chloro-9-hydroxy-9-trifluoromethyl-9H-fluoren-2-yloxy)-butyric acid and (S)-(−)-1-(4-methylphenyl)ethylamine

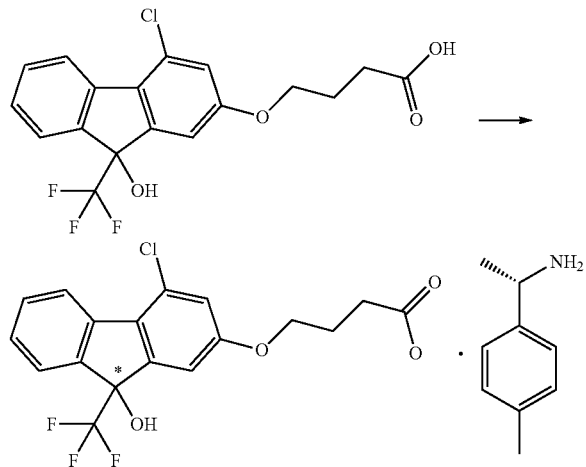

4-(4-Chloro-9-hydroxy-9-trifluoromethyl-9H-fluoren-2-yloxy)-butyric acid (0.100 g) and isopropyl ether (2.0 ml) were mixed, (S)-(−)-1-(4-methylphenyl)ethylamine (0.0189 ml) was added, and the mixture was stirred at room temperature for 17 hr. This suspension was filtered to give a salt (0.0403 g) of an optically active form of 4-(4-chloro-9-hydroxy-9-trifluoromethyl-9H-fluoren-2-yloxy)-butyric acid and (S)-(−)-1-(4-methylphenyl)ethylamine. The solid was analyzed under HPLC analysis condition 2 to find that an isomer with a long retention time was the main component.
isomer with short retention time (retention time 19.97 min)
isomer with long retention time (retention time 22.06 min)

Using this salt as an intermediate, compound Nos. 504, 553, 554, 561, 573, 577, 604, 624, 669, 676, 678, 679, 680, 681, 683, 684, 688, 689 and 698 were synthesized.

Example 10

Synthesis of Optically Active Form of (4-chloro-9-hydroxy-9-trifluoromethyl-9H-fluoren-2-yloxy)-acetic acid methyl ester (Compound No. 481) and the Like

Step 1

Salt of Optically Active Form of (4-chloro-9-hydroxy-9-trifluoromethyl-9H-fluoren-2-yloxy)-acetic acid and (S)-(−)-1-phenylethylamine

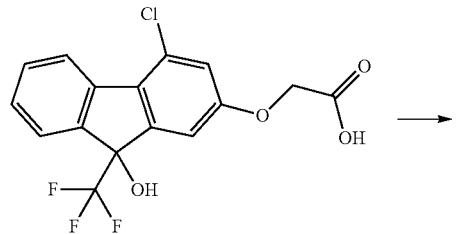

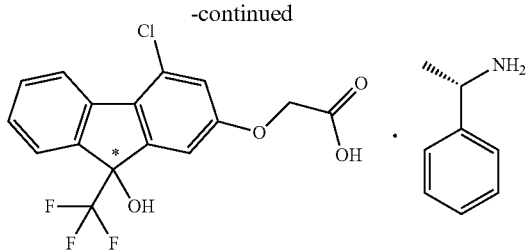

Under a nitrogen atmosphere, (S)-(−)-1-phenylethylamine (0.011 ml) was added to a mixture of (4-chloro-9-hydroxy-9-trifluoromethyl-9H-fluoren-2-yloxy)-acetic acid (0.100 g) and isopropyl ether (5.0 ml), and the mixture was stirred at room temperature overnight. This suspension was filtered, and the obtained solid was dried under reduced pressure to give the title compound (0.0414 g). The solid was analyzed under HPLC analysis condition 2 to find that an isomer with a long retention time was the main component.
isomer with short retention time (retention time 15.67 min)
isomer with long retention time (retention time 16.39 min)

Using this salt as an intermediate, compound Nos. 481, 540, 541, 542, 552, 581, 582, 588, 589, 614 and 619 were synthesized.

Example 11

Synthesis of Optically Active Form of 4-chloro-9-hydroxy-9-trifluoromethyl-9H-fluorene-2-carboxylic acid methyl ester (Compound No. 647) and the Like Salt of Optically Active Form of 4-chloro-9-hydroxy-9-trifluoromethyl-9H-fluorene-2-carboxylic acid and (S)-(−)-1-phenylethylamine

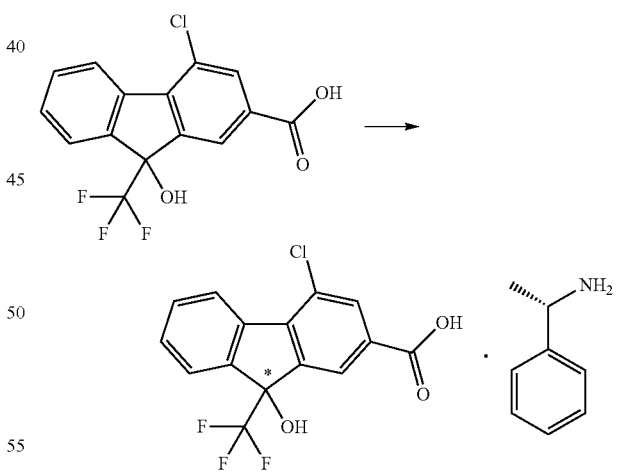

Step 1-1 Synthesis of Seed Crystal

To a mixture of 4-chloro-9-hydroxy-9-trifluoromethyl-9H-fluorene-2-carboxylic acid (0.050 g) and isopropyl ether (0.250 ml) was added (S)-(−)-1-phenylethylamine (0.020 ml), and the mixture was stirred at room temperature overnight. This suspension was filtered to give a solid (0.060 g). The solid was added as a seed crystal to a mixture of 4-chloro-9-hydroxy-9-trifluoromethyl-9H-fluorene-2-carboxylic acid (0.050 g), (S)-(-)-1-phenylethylamine (0.020 ml) and ethyl acetate (0.250 ml), which had been stirred overnight at room temperature in advance, and the mixture was further stirred at room temperature overnight. The resulting suspension was filtered, and the obtained solid was washed with ethyl acetate. The solid was dried under reduced pressure to give the title compound (0.019 g). The solid was analyzed under HPLC analysis condition 4 to find that an isomer with a long retention time was the main component.

isomer with short retention time (retention time 20.09 min)
isomer with long retention time (retention time 21.19 min)

Step 1-2

Under an argon atmosphere, (S)-(-)-1-phenylethylamine (0.392 ml) and a seed crystal of a salt of an optically active form of 4-chloro-9-hydroxy-9-trifluoromethyl-9H-fluorene-2-carboxylic acid and (S)-(-)-1-phenylethylamine were added to a mixture of 4-chloro-9-hydroxy-9-trifluoromethyl-9H-fluorene-2-carboxylic acid (1.000 g) and ethyl acetate (5 ml), and the mixture was stirred at room temperature for 3 days. This suspension was filtered, and the obtained solid was washed with ethyl acetate (3 ml). The solid was dried under reduced pressure to give the title compound (0.466 g). The solid was analyzed under HPLC analysis condition 4 to find that an isomer with a long retention time was the main component.

isomer with short retention time (retention time 19.91 min)
isomer with long retention time (retention time 21.00 min)

Using this salt as an intermediate, compound Nos. 647, 657, 664 and 665 were synthesized.

Example 12

Synthesis of (+)-2-[4-(2-fluoro-9-hydroxy-9-trifluoromethyl-9H-fluoren-4-yl)-pyrazol-1-yl]-2-hydroxymethyl-propane-1,3-diol (Compound No. 703)

Step 1

Optically Active Form of 2-[4-(2-fluoro-9-hydroxy-9-trifluoromethyl-9H-fluoren-4-yl)-pyrazol-1-yl]-3-hydroxy-2-hydroxymethyl-propionic acid

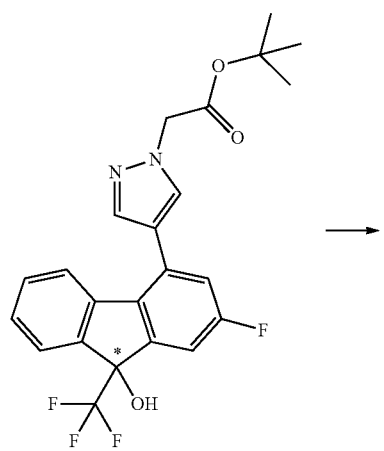

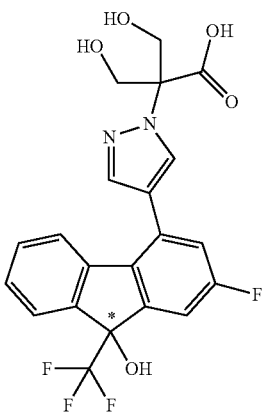

To a solution of an optically active form (33.3 g) of t-butyl [4-(2-fluoro-9-hydroxy-9-trifluoromethyl-9H-fluoren-4-yl)-pyrazol-1-yl]-acetate and paraformaldehyde (18.3 g) in dimethylformamide (100 ml) was added at room temperature a 1M solution (244 ml) of tetrabutylammonium fluoride in tetrahydrofuran, and the mixture was stirred at 90° C. for 4 hr. To the reaction mixture was added 1N hydrochloric acid (400 ml), m and the mixture was extracted with ethyl acetate (200 ml). The separated aqueous layer was extracted twice with ethyl acetate (100 ml). The combined organic layer was successively washed once with 1N hydrochloric acid (100 ml), twice with brine (water/saturated brine=100 ml/10 ml) and once with saturated brine (100 ml), dried over anhydrous sodium sulfate and concentrated under reduced pressure. The obtained residue was azeotroped twice with toluene to give the title compound (28.3 g).

$^1$H-NMR (DMSO-D$_6$) δ: 13.13 (1H, br s), 8.12 (1H, d, J=0.7 Hz), 7.73 (1H, d, J=0.5 Hz), 7.66-7.61 (1H, m), 7.48-7.45 (1H, m), 7.42-7.38 (2H, m), 7.36-7.31 (1H, m), 7.28-7.19 (2H, m), 5.15 (2H, br s), 4.24-4.07 (4H, m).

Step 2

(+)-2-[4-(2-fluoro-9-hydroxy-9-trifluoromethyl-9H-fluoren-4-yl)-pyrazol-1-yl]-2-hydroxymethyl-propane-1,3-diol

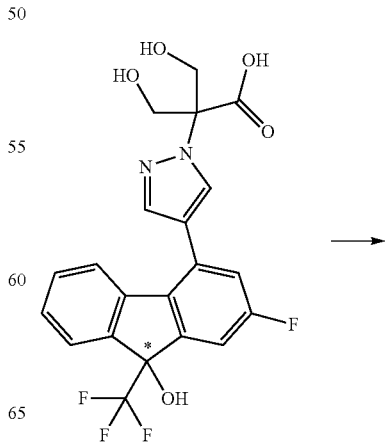

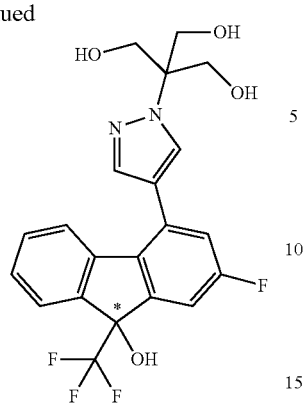

To a solution of an optically active form (28.3 g) of 2-[4-(2-fluoro-9-hydroxy-9-trifluoromethyl-9H-fluoren-4-yl)-pyrazol-1-yl]-3-hydroxy-2-hydroxymethyl-propionic acid in tetrahydrofuran (40 ml) were successively added dropwise at room temperature a 0.93M solution (225 ml) of borane-tetrahydrofuran complex in tetrahydrofuran and a 1.09M solution (32 ml) of borane-tetrahydrofuran complex in tetrahydrofuran, and the mixture was stirred for 3 hr. To the reaction mixture, ethanol (57 ml) was added dropwise at room temperature and the mixture was stirred at 80° C. for 1 hr. To this mixture were added water (150 ml) and saturated aqueous sodium hydrogen carbonate (100 ml), and the mixture was extracted twice with ethyl acetate (100 ml, 50 ml). The combined organic layer was successively washed twice with water (100 ml) and once with saturated brine (100 ml), dried over anhydrous sodium sulfate and concentrated under reduced pressure. A solution of the obtained residue in ethanol (50 ml) was cooled to 0° C., sodium borohydride (2.3 g) was added thereto, and the mixture was stirred at room temperature for 2 hr. To the reaction mixture was added 1N hydrochloric acid (100 ml), and the mixture was extracted with ethyl acetate (100 ml). The separated aqueous layer was extracted again with ethyl acetate (50 ml). The combined organic layer was successively washed with water (100 ml), saturated aqueous sodium hydrogen carbonate (100 ml) and saturated brine (100 ml), dried over anhydrous sodium sulfate and concentrated under reduced pressure. The obtained residue was purified by silica gel column chromatography (eluent: chloroform/methanol=20/1 to 9/1) to give the title compound (21.6 g).

[α]D=+71.5° (25° C., c=1.000, methanol)
$^1$H-NMR (DMSO-D$_6$) δ: 8.05 (1H, d, J=0.7 Hz), 7.70 (1H, d, J=0.7 Hz), 7.65-7.61 (1H, m), 7.51-7.47 (1H, m), 7.40-7.36 (2H, m), 7.35-7.30 (1H, m), 7.29-7.24 (1H, m), 7.21-7.17 (1H, m), 4.83 (3H, t, J=5.4 Hz), 3.90 (6H, d, J=5.6 Hz).

Example 13

Synthesis of (+)-2-[4-(2-fluoro-9-hydroxy-9-trifluoromethyl-9H-fluoren-4-yl)-pyrazol-1-yl]-2-methyl-propane-1,3-diol (Compound No. 673)

Step 1

2-[4-(4,4,5,5-tetramethyl-[1,3,2]dioxaborolan-2-yl)-pyrazol-1-yl]-propionic acid ethyl ester

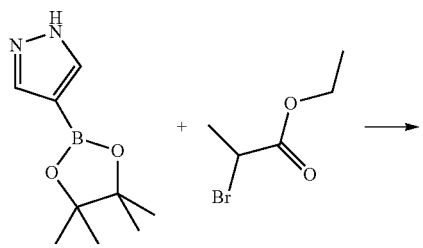

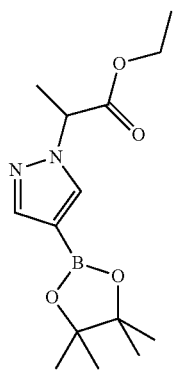

To a suspension of 4-(4,4,5,5-tetramethyl-[1,3,2]dioxaborolan-2-yl)-1H-pyrazole (21.3 g) and potassium carbonate (20.7 g) in dimethylformamide (100 ml) was added 2-bromo-propionic acid ethyl ester (13 ml) and the mixture was stirred at 80° C. for 14 hr. The reaction mixture was cooled to 0° C., and toluene (100 ml) and water (150 ml) were successively added dropwise. The mixture was partitioned, and the aqueous layer was extracted with toluene (50 ml). The combined organic layer was successively washed once with 10% aqueous potassium carbonate (50 ml), twice with water (50 ml) and once with saturated brine (50 ml), dried over anhydrous sodium sulfate, and concentrated under reduced pressure to give the title compound (21.6 g).
$^1$H-NMR (CDCl$_3$) δ: 7.85 (1H, s), 7.81 (1H, s), 5.10 (1H, q, J=7.3 Hz), 4.19 (2H, q, J=7.1 Hz), 1.78 (3H, d, J=7.4 Hz), 1.32 (12H, s), 1.25 (3H, t, J=7.2 Hz).

Step 2

Optically Active Form of 2-[4-(2-fluoro-9-hydroxy-9-trifluoromethyl-9H-fluoren-4-yl)-pyrazol-1-yl]-propionic acid ethyl ester

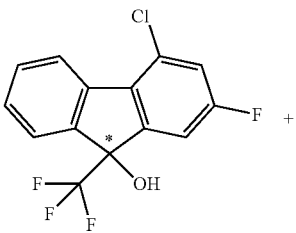

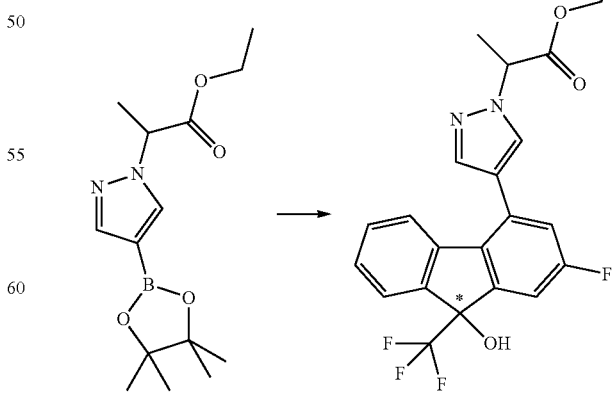

To a suspension of 2-[4-(4,4,5,5-tetramethyl-[1,3,2]dioxaborolan-2-yl)-pyrazol-1-yl]-propionic acid ethyl ester (29.2 g), (+)-4-chloro-2-fluoro-9-trifluoromethyl-9H-fluoren-9-ol (20.4 g), and sodium hydrogen carbonate (11.1 g) in toluene/water (200 ml/66 ml) were added palladium acetate (743 mg) and 2-dicyclohexylphosphino-2',6'-dimethoxybiphenyl (2.72 g) at room temperature, and the mixture was stirred at 115° C. for 8 hr. To the reaction mixture were added activated carbon (10 g) and Celite (10 g) at room temperature and the mixture was stirred for 1 hr. The mixture was filtered through celite, and the solid was washed with toluene (100 ml). The filtrate was partitioned, and the aqueous layer was extracted with toluene (60 ml). The combined organic layer was washed 3 times with water (100 ml), and once with saturated brine (100 ml), dried over anhydrous sodium sulfate and concentrated under reduced pressure. To a solution of the obtained residue in toluene/ethyl acetate (3/1, 130 ml) was added silica gel (40 g), and the mixture was stirred at room temperature for 1 hr. The mixture was filtered, and concentrated under reduced pressure. The obtained residue was purified by silica gel column chromatography (eluent: n-hexane/ethyl acetate=5/1 to 2/1) to give the title compound (27.9 g).

$^1$H-NMR (DMSO-D$_6$) δ: 8.20-8.18 (1H, m), 7.72-7.71 (1H, m), 7.67-7.63 (1H, m), 7.44-7.40 (2H, m), 7.37-7.23 (4H, m), 5.40-5.34 (1H, m), 4.22-4.15 (2H, m), 1.78-1.75 (3H, m), 1.23-1.18 (3H, m).

Step 3

Optically Active Form of 2-[4-(2-fluoro-9-hydroxy-9-trifluoromethyl-9H-fluoren-4-yl)-pyrazol-1-yl]-3-hydroxy-2-methyl-propionic acid To a solution of an optically active form (27.9 g) of 2-[4-(2-fluoro-9-hydroxy-9-trifluoromethyl-9H-fluoren-4-yl)-pyrazol-1-yl]-propionic acid ethyl ester and paraformaldehyde (17.0 g) in dimethylformamide (100 ml) was added at room temperature a 1M solution (170 ml) of tetrabutylammonium fluoride in tetrahydrofuran, and the mixture was stirred at 100° C. for 6 hr. The reaction mixture was filtered through celite, and the solid was washed with ethyl acetate (100 ml). To the filtrate was added 1N hydrochloric acid (400 ml), and the mixture was extracted with ethyl acetate (100 ml). The separated aqueous layer was extracted twice with ethyl acetate (100 ml). The combined organic layer was successively washed once with 1N hydrochloric acid (100 ml), twice with brine (water/saturated brine=100 ml/10 ml) and once with saturated brine, dried over anhydrous sodium sulfate and concentrated under reduced pressure. The obtained residue was azeotroped twice with toluene to give the title compound (26.6 g).

$^1$H-NMR (DMSO-D$_6$) δ: 8.19-8.17 (1H, m), 7.71-7.70 (1H, m), 7.66-7.61 (1H, m), 7.46-7.19 (7H, m), 5.35-5.22 (1H, m), 4.21-4.12 (1H, m), 3.96-3.88 (1H, m), 1.80 (3H, s).

Step 4

(+)-2-[4-(2-fluoro-9-hydroxy-9-trifluoromethyl-9H-fluoren-4-yl)-pyrazol-1-yl]-2-methyl-propane-1,3-diol

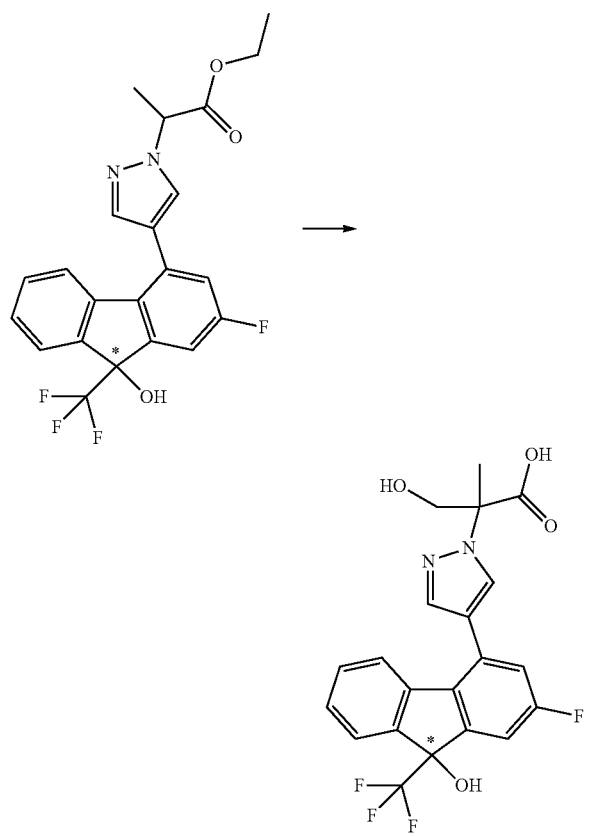

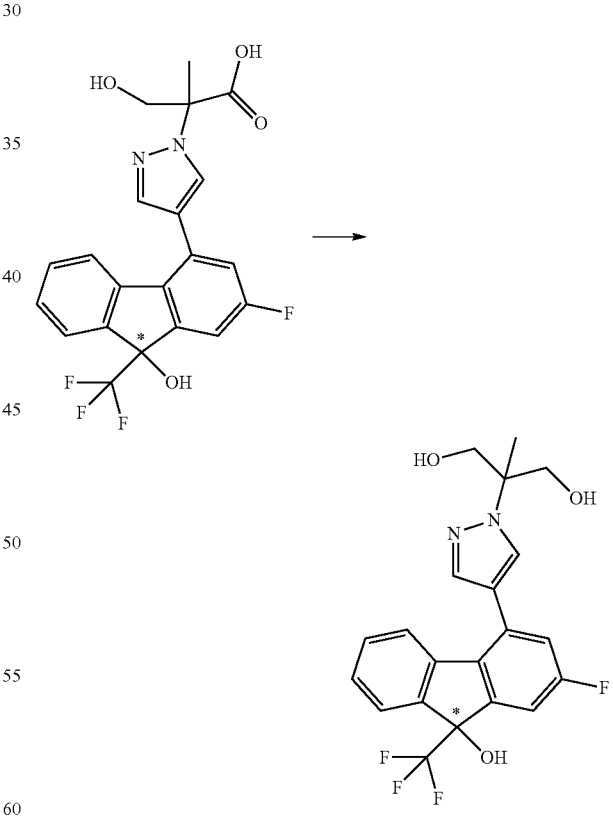

To a solution of an optically active form (26.6 g) of 2-[4-(2-fluoro-9-hydroxy-9-trifluoromethyl-9H-fluoren-4-yl)-pyrazol-1-yl]-3-hydroxy-2-methyl-propionic acid in tetrahydrofuran (40 ml) was added dropwise at room temperature a 1.09M solution (200 ml) of borane-tetrahydrofuran complex in tetrahydrofuran, and the mixture was stirred for 3 hr. To the reaction mixture was added dropwise ethanol (25 ml) at room temperature and the mixture was stirred at 80° C. for 1 hr. To this mixture were added water (200 ml) and saturated aqueous sodium hydrogen carbonate (100 ml) and the mixture was extracted twice with ethyl acetate (100 ml). The combined organic layer was successively washed twice with water (100 ml) and once with saturated brine (100 ml), dried over anhydrous sodium sulfate and concentrated under reduced pressure. The obtained residue was purified by silica gel column chromatography (eluent: chloroform/methanol=20/1 to 10/1) to give the title compound (17.4 g).

[α]D=+72.4° (25° C., c=1.004, methanol)

$^1$H-NMR (DMSO-D$_6$) δ: 8.05 (1H, d, J=0.7 Hz), 7.68 (1H, d, J=0.7 Hz), 7.65-7.62 (1H, m), 7.44-7.42 (1H, m), 7.40-7.36 (2H, m), 7.35-7.26 (2H, m), 7.21-7.17 (1H, m), 4.98-4.93 (2H, m), 3.84-3.79 (2H, m), 3.76-3.70 (2H, m), 1.52 (3H, s).

Example 14

Synthesis of (+)-2-hydroxymethyl-2-[4-(9-hydroxy-2-methyl-9-trifluoromethyl-9H-fluoren-4-yl)-pyrazol-1-yl]-propane-1,3-diol (Compound No. 707)

Step 1

Optically Active Form of [4-(9-hydroxy-2-methyl-9-trifluoromethyl-9H-fluoren-4-yl)-pyrazol-1-yl]-acetic acid t-butyl ester

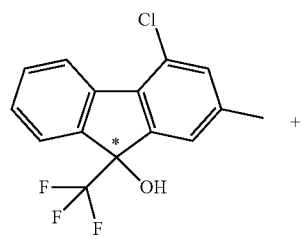

+

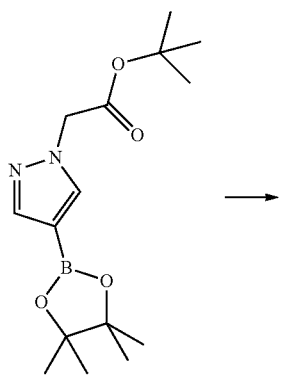

→

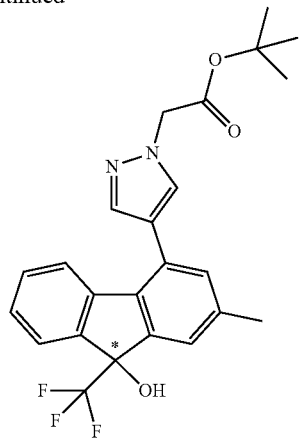

To a suspension of t-butyl[4-(4,4,5,5-tetramethyl-[1,3,2]dioxaborolan-2-yl)-pyrazol-1-yl]-acetate (24.8 g), (+)-4-chloro-2-methyl-9-trifluoromethyl-9H-fluoren-9-ol (20.0 g), and sodium hydrogen carbonate (11.3 g) in toluene/water (200 ml/60 ml) were added palladium acetate (750 mg) and 2-dicyclohexylphosphino-2',6'-dimethoxybiphenyl (2.75 g) at room temperature and the mixture was stirred at 110° C. for 2 hr. To I° the reaction mixture were added water (80 ml) and activated carbon (2.0 g) at room temperature and the mixture was stirred for 1 hr. The mixture was filtered through celite, and the solid was washed with tetrahydrofuran (100 ml). The filtrate was partitioned and the aqueous layer was extracted with ethyl acetate (100 ml). The combined organic layer was successively washed twice with water (100 ml) and once with saturated brine (100 ml), anhydrous sodium sulfate and silica gel (40 g) were added, and the mixture was stirred overnight. The mixture was filtered, and the filtrate was concentrated under reduced pressure. The obtained residue was treated with n-hexane/ethyl acetate (2/1, 120 ml) solution, and the resulting slurry was filtered to give the title compound (17.8 g).

$^1$H-NMR (CDCl$_3$) δ: 7.68-7.64 (1H, m), 7.65 (1H, d, J=0.7 Hz), 7.60 (1H, d, J=0.7 Hz), 7.51-7.49 (1H, m), 7.40-7.37 (1H, m), 7.28-7.23 (2H, m), 7.14-7.13 (1H, m), 4.93 (1H, d, J=17.4 Hz), 4.88 (1H, d, J=17.4 Hz), 4.80 (1H, s), 2.42 (3H, s), 1.52 (9H, s).

Step 2

Optically Active Form of 3-hydroxy-2-hydroxymethyl-2-[4-(9-hydroxy-2-methyl-9-trifluoromethyl-9H-fluoren-4-yl)-pyrazol-1-yl]-propionic acid

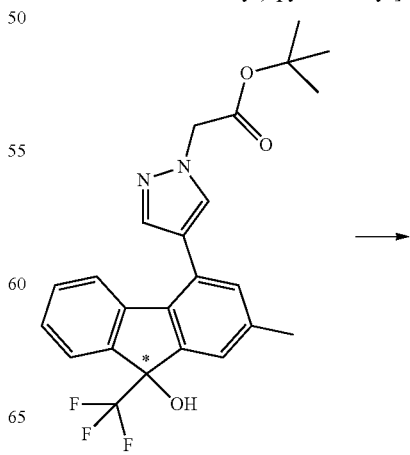

→

161

-continued

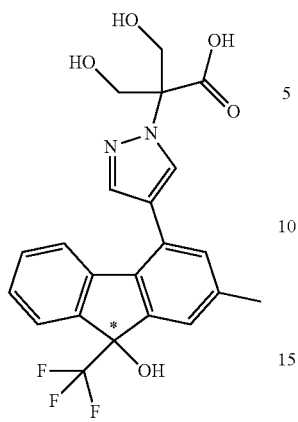

To a solution of an optically active form (17.8 g) of t-butyl [4-(9-hydroxy-2-methyl-9-trifluoromethyl-9H-fluoren-4-yl)-pyrazol-1-yl]-acetate and paraformaldehyde (12.0 g) in dimethylformamide (60 ml) was added at room temperature a 1M solution (120 ml) of tetrabutylammonium fluoride in tetrahydrofuran, and the mixture was stirred at 95° C. for 3 hr. To the reaction mixture were added 1N hydrochloric acid (180 ml) and water (90 ml), and the mixture was extracted with ethyl acetate (180 ml). The separated aqueous layer was extracted twice with ethyl acetate (90 ml). The combined organic layer was successively washed once with 1N hydrochloric acid (90 ml), twice with water (90 ml) and once with saturated brine (90 ml), dried over anhydrous sodium sulfate, and concentrated under reduced pressure to give the title compound (15.5 g).

$^1$H-NMR (DMSO-D$_6$) δ: 13.10 (1H, br s), 8.03 (1H, s), 7.65 (1H, s), 7.63-7.59 (1H, m), 7.44-7.40 (2H, m), 7.31-7.27 (1H, m), 7.25-7.20 (1H, m), 7.15 (2H, s), 5.14 (2H, br s), 4.21-4.09 (4H, m), 2.39 (3H, s).

Step 3

(+)-2-hydroxymethyl-2-[4-(9-hydroxy-2-methyl-9-trifluoromethyl-9H-fluoren-4-yl)-pyrazol-1-yl]-propane-1,3-diol

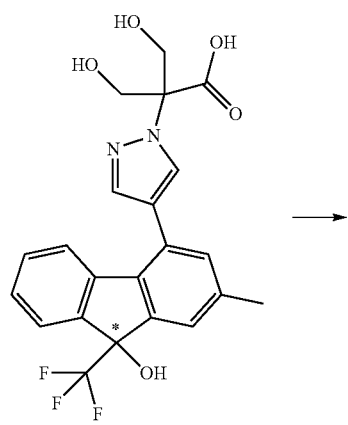

162

-continued

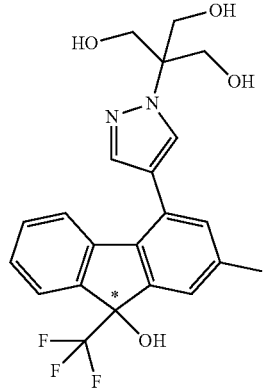

To a solution of an optically active form (15.5 g) of 3-hydroxy-2-hydroxymethyl-2-[4-(9-hydroxy-2-methyl-9-trifluoromethyl-9H-fluoren-4-yl)-pyrazol-1-yl]-propionic acid in tetrahydrofuran (31 ml) was added dropwise at room temperature a 1.09M solution (127 ml) of borane-tetrahydrofuran complex in tetrahydrofuran, and the mixture was stirred for 5 hr. To the reaction mixture was added dropwise ethanol (15 ml) at room temperature and the mixture was stirred at 75° C. for 1 hr. To this mixture were added water (90 ml) and saturated aqueous sodium hydrogen carbonate (150 ml), and the mixture was extracted twice with ethyl acetate (150 ml, 75 ml). The combined organic layer was successively washed once with saturated aqueous sodium hydrogen carbonate (75 ml), twice with water (75 ml) and once with saturated brine (75 ml), dried over anhydrous sodium sulfate and concentrated under reduced pressure. To a solution of the obtained residue in ethanol (45 ml) was added sodium borohydride (1.3 g) at room temperature, and the mixture was stirred for 1 hr. To the reaction mixture was added 1N hydrochloric acid (150 ml), and the mixture was extracted with ethyl acetate (150 ml). The separated aqueous layer was extracted again with ethyl acetate (75 ml). The combined organic layer was successively washed with water (75 ml), saturated aqueous sodium hydrogen carbonate (75 ml), water (75 ml) and saturated brine (75 ml), dried over anhydrous sodium sulfate and concentrated under reduced pressure. The obtained residue was purified by silica gel column chromatography (eluent: chloroform/methanol=20/1 to 10/1) to give the title compound (12.6 g).

[α]D=+65.6° (25° C., c=1.008, methanol)

$^1$H-NMR (DMSO-D$_6$) δ: 7.96 (1H, d, J=0.7 Hz), 7.63-7.59 (1H, m), 7.62 (1H, d, J=0.7 Hz), 7.46-7.40 (2H, m), 7.31-7.21 (2H, m), 7.14 (2H, s), 4.82 (3H, t, J=5.6 Hz), 3.91 (6H, d, J=5.6 Hz), 2.39 (3H, s).

In the same manner as in the above-mentioned Examples, the compound Nos. 1 to 707 including the compounds shown in the above-mentioned Examples were obtained. The structural formulas and $^1$H-NMR spectrum data of the obtained compounds are shown in Table 1-1 to Table 1-106.

In the Tables, optically active compounds are indicated with (optically active form) under compound No. Among them, those measured for optical rotation are marked with (+) or (−) in the structural formulas.

$^1$H-NMR spectrum was measured in CDCl$_3$ or DMSO-D$_6$ using tetramethylsilane as an internal standard, and all δ values are shown in ppm.

The symbols in the Tables mean the following.
s: singlet
d: doublet
t: triplet
q: quartet
dd: double doublet
ddd: double double doublet
brs: broad singlet
m: multiplet
J: coupling constant

TABLE 1-1

| compound No. | structural formula | NMR |
|---|---|---|
| 1 | fluorene with pyridyl N at 4-position, 9-CF3, 9-OH | $^1$H-NMR (DMSO-D$_6$) δ: 8.65 (1H, dd, J = 5.1, 1.6 Hz), 8.04-8.01 (1H, m), 7.92-7.90 (1H, m), 7.75-7.72 (1H, m), 7.63-7.59 (1H, m), 7.57-7.52 (1H, m), 7.50 (1H, s), 7.39 (1H, dd, J = 7.7, 4.9 Hz). |
| 2 | 4-methyl fluorene, 9-CF3, 9-OH | $^1$H-NMR (DMSO-D$_6$) δ: 7.85 (1H, d, J = 7.7 Hz), 7.70-7.66 (1H, m), 7.55-7.49 (2H, m), 7.42-7.38 (1H, m), 7.32-7.27 (2H, m), 7.17 (1H, s), 2.64 (3H, s). |
| 3 | 2-methyl fluorene, 9-CF3, 9-OH | $^1$H-NMR (DMSO-D$_6$) δ: 7.79 (1H, d, J = 7.5 Hz), 7.73 (1H, d, J = 7.7 Hz), 7.63-7.59 (1H, m), 7.50-7.44 (2H, m), 7.37-7.30 (2H, m), 7.17 (1H, s), 2.39 (3H, s). |
| 4 | 2-fluoro fluorene, 9-CF3, 9-OH | $^1$H-NMR (DMSO-D$_6$) δ: 7.92 (1H, dd, J = 8.4, 5.1 Hz), 7.86 (1H, d, J = 7.5 Hz), 7.66-7.62 (1H, m), 7.54-7.49 (1H, m), 7.44-7.34 (4H, m). |
| 5 | 2-chloro fluorene, 9-CF3, 9-OH | $^1$H-NMR (CDCl$_3$) δ: 7.71-7.67 (2H, m), 7.65-7.63 (1H, m), 7.59 (1H, d, J = 7.9 Hz), 7.51-7.44 (2H, m), 7.40-7.36 (1H, m), 2.71 (1H, s). |
| 6 | 4-chloro fluorene, 9-CF3, 9-OH | $^1$H-NMR (CDCl$_3$) δ: 8.34 (1H, d, J = 7.7 Hz), 7.75-7.71 (1H, m), 7.65-7.61 (1H, m), 7.55-7.51 (1H, m), 7.46-7.40 (2H, m), 7.32-7.27 (1H, m), 2.71 (1H, brs). |

TABLE 1-1-continued

| compound No. | structural formula | NMR |
|---|---|---|
| 7 | 2-bromo fluorene, 9-CF3, 9-OH | $^1$H-NMR (CDCl$_3$) δ: 7.86-7.83 (1H, m), 7.72-7.61 (3H, m), 7.56-7.48 (2H, m), 7.43-7.38 (1H, m), 2.73 (1H, s). |

TABLE 1-2

| compound No. | structural formula | NMR |
|---|---|---|
| 8 | 1-chloro fluorene, 9-CF3, 9-OH | $^1$H-NMR (CDCl$_3$) δ: 7.74-7.71 (1H, m), 7.66-7.63 (1H, m), 7.60-7.57 (1H, m), 7.51-7.46 (1H, m), 7.43-7.37 (2H, m), 7.29-7.26 (1H, m), 3.73 (1H, s). |
| 9 | 3-chloro fluorene, 9-CF3, 9-OH | $^1$H-NMR (CDCl$_3$) δ: 7.72-7.68 (1H, m), 7.65-7.60 (3H, m), 7.52-7.47 (1H, m), 7.42-7.37 (1H, m), 7.33 (1H, dd, J = 8.1, 1.9 Hz), 2.69 (1H, s). |
| 10 | 3-methyl fluorene, 9-CF3, 9-OH | $^1$H-NMR (DMSO-D$_6$) δ: 7.81 (1H, d, J = 7.5 Hz), 7.68-7.66 (1H, m), 7.64-7.60 (1H, m), 7.53-7.47 (2H, m), 7.39-7.35 (1H, m), 7.21-7.17 (1H, m), 7.15 (1H, s), 2.40 (3H, s). |
| 11 | 4-fluoro fluorene, 9-CF3, 9-OH | $^1$H-NMR (DMSO-D$_6$) δ: 7.81-7.78 (1H, m), 7.71-7.68 (1H, m), 7.59-7.54 (1H, m), 7.53-7.50 (1H, m), 7.49-7.43 (2H, m), 7.44 (1H, s), 7.41-7.36 (1H, m). |
| 12 | 3-fluoro fluorene, 9-CF3, 9-OH | $^1$H-NMR (DMSO-D$_6$) δ: 7.93-7.90 (1H, m), 7.79 (1H, dd, J = 9.0, 2.3 Hz), 7.67-7.63 (2H, m), 7.56-7.52 (1H, m), 7.45-7.41 (1H, m), 7.31 (1H, s), 7.23-7.17 (1H, m). |

TABLE 1-2-continued

| compound No. | structural formula | NMR |
|---|---|---|
| 13 | fluorene with F, OH, CF2, F substituents | $^1$H-NMR (DMSO-D$_6$) δ: 7.90 (1H, d, J = 7.4 Hz), 7.73 (1H, d, J = 7.7 Hz), 7.68-7.65 (1H, m), 7.60-7.52 (2H, m), 7.46-7.41 (1H, m), 7.40 (1H, s), 7.21-7.15 (1H, m). |
| 14 | 2,7-dichlorofluorene with CF2-OH | $^1$H-NMR (CDCl$_3$) δ: 7.67-7.65 (2H, m), 7.55 (2H, d, J = 8.1 Hz), 7.46 (2H, dd, J = 8.1, 2.1 Hz), 2.77 (1H, s). |

TABLE 1-3

| compound No. | structural formula | NMR |
|---|---|---|
| 15 | CH$_3$-azafluorene with CF2-OH | $^1$H-NMR (DMSO-D$_6$) δ: 8.67 (1H, dd, J = 5.1, 1.5 Hz), 8.03-7.99 (1H, m), 7.57-7.53 (1H, m), 7.43-7.34 (4H, m), 2.80 (3H, s). |
| 16 | H$_3$C-azafluorene with CF2-OH | $^1$H-NMR (DMSO-D$_6$) δ: 8.61 (1H, dd, J = 5.1, 1.3 Hz), 7.98 (1H, d, J = 7.5 Hz), 7.78 (1H, d, J = 7.7 Hz), 7.56-7.53 (1H, m), 7.44-7.40 (2H, m), 7.35 (1H, dd, J = 7.6, 5.0 Hz), 2.43 (3H, s). |
| 17 | dimethyl fluorene with CF2-OH | $^1$H-NMR (CDCl$_3$) δ: 7.67 (1H, d, J = 7.9 Hz), 7.56-7.53 (2H, m), 7.30-7.27 (1H, m), 7.24-7.22 (2H, m), 2.66 (1H, br s), 2.64 (3H, s), 2.44 (3H, s). |

TABLE 1-3-continued

| compound No. | structural formula | NMR |
|---|---|---|
| 18 | dimethyl fluorene with CF2-OH | $^1$H-NMR (CDCl$_3$) δ: 7.74 (1H, d, J = 7.7 Hz), 7.72-7.69 (1H, m), 7.49-7.44 (1H, m), 7.38-7.36 (1H, m), 7.34-7.30 (1H, m), 7.08-7.06 (1H, m), 2.66 (1H, br s), 2.62 (3H, s), 2.39 (3H, s). |
| 19 | acetamido fluorene with CF2-OH | $^1$H-NMR (DMSO-D$_6$) δ: 9.95 (1H, br s), 7.77 (1H, d, J = 7.5 Hz), 7.67-7.62 (1H, m), 7.54-7.48 (2H, m), 7.42-7.35 (3H, m), 7.26 (1H, s), 2.17 (3H, br s). |
| 20 | amino fluorene HCl with CF2-OH | $^1$H-NMR (DMSO-D$_6$) δ: 7.89 (1H, d, J = 7.5 Hz), 7.64-7.60 (1H, m), 7.50-7.45 (1H, m), 7.35-7.31 (1H, m), 7.21-7.17 (1H, m), 7.15-7.07 (1H, m), 7.05-6.98 (1H, m), 6.13 (3H, br s). |
| 21 | dichloro fluorene with CF2-OH | $^1$H-NMR (DMSO-D$_6$) δ: 8.28-8.25 (1H, m), 7.80 (1H, d, J = 1.8 Hz), 7.74-7.71 (1H, m), 7.66-7.64 (1H, m), 7.64-7.59 (1H, m), 7.61 (1H, s), 7.55-7.51 (1H, m). |

TABLE 1-4

| compound No. | structural formula | NMR |
|---|---|---|
| 22 | acetamido fluorene with CF2-OH | $^1$H-NMR (DMSO-D$_6$) δ: 10.14 (1H, br s), 7.97-7.96 (1H, m), 7.77-7.74 (2H, m), 7.71-7.68 (1H, m), 7.62-7.59 (1H, m), 7.49-7.45 (1H, m), 7.34-7.30 (1H, m), 7.22 (1H, s), 2.07 (3H, s). |

TABLE 1-4-continued
| compound No. | structural formula | NMR |
|---|---|---|
| 23 | 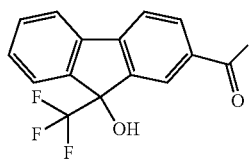 | ¹H-NMR (DMSO-D₆) δ: 8.20-8.18 (1H, m), 8.14 (1H, dd, J = 8.0, 1.5 Hz), 8.03 (1H, d, J = 7.7 Hz), 8.00-7.97 (1H, m), 7.72-7.68 (1H, m), 7.60-7.56 (1H, m), 7.51-7.47 (1H, m), 7.48 (1H, s), 3.90 (3H, s). |
| 24 | 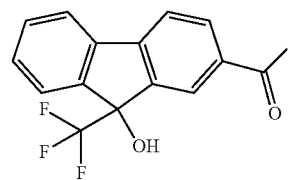 | ¹H-NMR (DMSO-D₆) δ: 13.18 (1H, br s), 8.19-8.17 (1H, m), 8.11 (1H, dd, J = 8.0, 1.5 Hz), 8.00 (1H, d, J = 8.1 Hz), 7.98-7.95 (1H, m), 7.71-7.68 (1H, m), 7.59-7.55 (1H, m), 7.50-7.45 (1H, m), 7.43 (1H, s). |
| 25 | 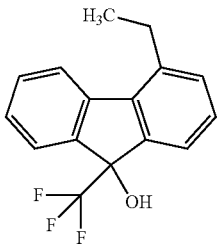 [SMILES: CCc1cccc2c1-c1ccccc1C2(O)C(F)(F)F] | ¹H-NMR (DMSO-D₆) δ: 7.83 (1H, d, J = 7.7 Hz), 7.70-7.66 (1H, m), 7.56-7.49 (2H, m), 7.42-7.37 (1H, m), 7.33 (2H, d, J = 4.9 Hz), 7.16 (1H, s), 3.09-2.95 (2H, m), 1.28 (3H, t, J = 7.5 Hz). |
| 26 | 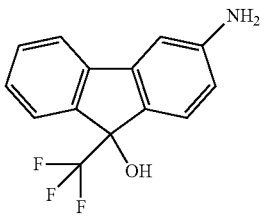 [SMILES: Nc1ccc2c(c1)-c1ccccc1C2(O)C(F)(F)F] | ¹H-NMR (DMSO-D₆) δ: 7.62 (1H, d, J = 7.5 Hz), 7.57-7.54 (1H, m), 7.47-7.41 (1H, m), 7.34-7.29 (1H, m), 7.28-7.24 (1H, m), 6.92 (1H, d, J = 2.0 Hz), 6.83 (1H, s), 6.53 (1H, dd, J = 8.3, 2.1 Hz), 5.44 (2H, br s). |
| 27 | 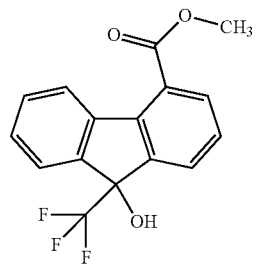 [SMILES: COC(=O)c1cccc2c1-c1ccccc1C2(O)C(F)(F)F] | ¹H-NMR (DMSO-D₆) δ: 8.07-8.04 (1H, m), 7.88-7.82 (2H, m), 7.72-7.68 (1H, m), 7.55-7.44 (3H, m), 7.36 (1H, s), 3.97 (3H, s). |
| 28 | 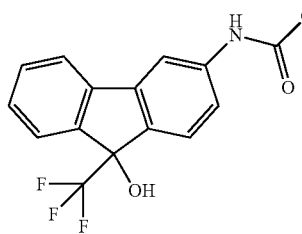 | ¹H-NMR (DMSO-D₆) δ: 10.17 (1H, br s), 8.06 (1H, d, J = 1.6 Hz), 7.73-7.70 (1H, m), 7.64-7.61 (1H, m), 7.57-7.53 (1H, m), 7.53-7.47 (2H, m), 7.41-7.37 (1H, m), 7.16 (1H, s), 2.09 (3H, s). |

TABLE 1-5

| compound No. | structural formula | NMR |
|---|---|---|
| 29 | (fluorene with 9-OH, 9-CF3, 2-C(O)NH2) | $^1$H-NMR (DMSO-D$_6$) δ: 8.18-8.16 (1H, m), 8.12 (1H, br s), 8.05 (1H, dd, J = 8.0, 1.5 Hz), 7.96-7.92 (2H, m), 7.69-7.66 (1H, m), 7.57-7.53 (1H, m), 7.47-7.42 (2H, m), 7.35 (1H, s). |
| 30 | (fluorene with 9-OH, 9-CF3, 2-C(O)NHCH3) | $^1$H-NMR (DMSO-D$_6$) δ: 8.63-8.55 (1H, m), 8.15-8.11 (1H, m), 8.00 (1H, dd, J = 7.9, 1.6 Hz), 7.96-7.91 (2H, m), 7.69-7.66 (1H, m), 7.57-7.52 (1H, m), 7.46-7.42 (1H, m), 7.36 (1H, s), 2.81 (3H, d, J = 4.6 Hz). |
| 31 | (fluorene with 9-OH, 9-CF3, 2-C(O)N(CH3)2) | $^1$H-NMR (DMSO-D$_6$) δ: 7.94-7.91 (2H, m), 7.68-7.65 (1H, m), 7.63-7.62 (1H, m), 7.58-7.52 (2H, m), 7.46-7.41 (1H, m), 7.37 (1H, s), 3.00 (3H, br s), 2.96 (3H, br s). |
| 32 | (fluorene with 9-OH, 9-CF3, 4-COOH) | $^1$H-NMR (DMSO-D$_6$) δ: 13.52 (1H, br s), 8.23 (1H, d, J = 7.5 Hz), 7.84-7.60 (2H, m), 7.71-7.67 (1H, m), 7.54-7.42 (3H, m), 7.31 (1H, br s). |
| 33 | (fluorene with 9-OH, 9-CF3, 4-C(O)NH2) | $^1$H-NMR (DMSO-D$_6$) δ: 8.11 (1H, br s), 7.94 (1H, d, J = 7.7 Hz), 7.72-7.64 (3H, m), 7.50-7.38 (4H, m), 7.28 (1H, s). |
| 34 | (fluorene with 9-OH, 9-CF3, 4-C(O)NHCH3) | $^1$H-NMR (DMSO-D$_6$) δ: 8.62-8.54 (1H, m), 7.77-7.74 (1H, m), 7.72-7.69 (1H, m), 7.68-7.64 (1H, m), 7.50-7.38 (4H, m), 7.29 (1H, s), 2.86 (3H, d, J = 4.4 Hz). |

TABLE 1-5-continued

| compound No. | structural formula | NMR |
|---|---|---|
| 35 | [structure: N,N-dimethylcarboxamide-substituted 9-(trifluoromethyl)-9H-fluoren-9-ol] | $^1$H-NMR (DMSO-D$_6$) δ: 7.71-7.66 (2H, m), 7.53-7.34 (5H, m), 7.33 (1H, br s), 3.14 (3H, s), 2.76 (3H, s). |

TABLE 1-6

| compound No. | structural formula | NMR |
|---|---|---|
| 36 | [structure: 3-chloro-azafluorene with C(CF$_3$)(OH)] | $^1$H-NMR (DMSO-D$_6$) δ: 8.73 (1H, d, J = 2.2 Hz), 8.11 (1H, d, J = 1.5 Hz), 7.93-7.89 (1H, m), 7.76-7.73 (1H, m), 7.67-7.56 (2H, m), 7.66 (1H, s). |
| 37 | [structure: 2-methoxy-9-(trifluoromethyl)-9H-fluoren-9-ol] | $^1$H-NMR (DMSO-D$_6$) δ: 7.78-7.73 (2H, m), 7.60-7.57 (1H, m), 7.48-7.44 (1H, m), 7.32-7.28 (1H, m), 7.25 (1H, s), 7.17-7.15 (1H, m), 7.07 (1H, dd, J = 8.3, 2.6 Hz), 3.83 (3H, s). |
| 38 | [structure: 2-hydroxy-9-(trifluoromethyl)-9H-fluoren-9-ol] | $^1$H-NMR (DMSO-D$_6$) δ: 9.82 (1H, s), 7.67 (1H, d, J = 7.4 Hz), 7.63 (1H, d, J = 8.3 Hz), 7.58-7.54 (1H, m), 7.45-7.40 (1H, m), 7.28-7.23 (1H, m), 7.15 (1H, s), 7.07-7.04 (1H, m), 6.87 (1H, dd, J = 8.1, 2.3 Hz). |
| 39 | [structure: 2-ethyl-9-(trifluoromethyl)-9H-fluoren-9-ol] | $^1$H-NMR (DMSO-D$_6$) δ: 7.80 (1H, d, J = 7.4 Hz), 7.75 (1H, d, J = 7.7 Hz), 7.63-7.59 (1H, m), 7.50-7.46 (2H, m), 7.37-7.32 (2H, m), 7.19 (1H, s), 2.69 (2H, q, J = 7.6 Hz), 1.22 (3H, t, J = 7.5 Hz). |
| 40 | [structure: methyl ester of fluorene carboxylic acid with C(CF$_3$)(OH)] | $^1$H-NMR (DMSO-D$_6$) δ: 8.41 (1H, d, J = 0.9 Hz), 8.05-7.99 (2H, m), 7.81-7.77 (1H, m), 7.70-7.66 (1H, m), 7.57-7.53 (1H, m), 7.47-7.42 (1H, m), 7.44 (1H, s), 3.92 (3H, s). |
| 41 | [structure: fluorene carboxylic acid with C(CF$_3$)(OH)] | $^1$H-NMR (DMSO-D$_6$) δ: 13.23 (1H, br s), 8.38 (1H, d, J = 0.9 Hz), 8.02-7.97 (2H, m), 7.78-7.74 (1H, m), 7.69-7.65 (1H, m), 7.57-7.52 (1H, m), 7.46-7.41 (1H, m), 7.41 (1H, s). |
| 42 | [structure: fluorene carboxamide with C(CF$_3$)(OH)] | $^1$H-NMR (DMSO-D$_6$) δ: 8.32 (1H, d, J = 1.1 Hz), 8.08 (1H, br s), 7.90-7.86 (2H, m), 7.71-7.65 (2H, m), 7.57-7.53 (1H, m), 7.51 (1H, br s), 7.45-7.41 (1H, m), 7.35 (1H, s). |

TABLE 1-7

| compound No. | structural formula | NMR |
|---|---|---|
| 43 | (fluorene with 9-OH, 9-CF3, and 3-C(=O)NHCH3) | $^1$H-NMR (DMSO-D$_6$) δ: 8.59-8.53 (1H, m), 8.26 (1H, d, J = 1.1 Hz), 7.89 (1H, d, J = 7.5 Hz), 7.82 (1H, dd, J = 7.9, 1.5 Hz), 7.72-7.69 (1H, m), 7.68-7.65 (1H, m), 7.58-7.53 (1H, m), 7.45-7.40 (1H, m), 7.35 (1H, s), 2.83 (3H, d, J = 4.6 Hz). |
| 44 | (fluorene with 9-OH, 9-CF3, and 3-C(=O)N(CH3)2) | $^1$H-NMR (DMSO-D$_6$) δ: 7.96-7.91 (2H, m), 7.69-7.64 (2H, m), 7.55-7.50 (1H, m), 7.44-7.37 (2H, m), 7.33 (1H, s), 3.03 (3H, br s), 2.94 (3H, br s). |
| 45 | (fluorene with 9-OH, 9-CF3, 4-CH3, and 2-CO2CH3) | $^1$H-NMR (DMSO-D$_6$) δ: 8.07-8.04 (1H, m), 7.98-7.94 (2H, m), 7.76-7.71 (1H, m), 7.62-7.57 (1H, m), 7.52-7.47 (1H, m), 7.41 (1H, s), 3.89 (3H, s), 2.71 (3H, s). |
| 46 | (fluorene with 9-OH, 9-CF3, and 4-OCH3) | $^1$H-NMR (DMSO-D$_6$) δ: 7.93 (1H, d, J = 7.5 Hz), 7.64-7.60 (1H m), 7.50-7.45 (1H, m), 7.40-7.32 (2H, m), 7.27-7.23 (1H, m), 7.20 (1H, s), 7.17 (1H, d J = 8.4 Hz), 3.98 (3H, s). |
| 47 | (fluorene with 9-OH, 9-CF3, and 3-OCH3) | $^1$H-NMR (DMSO-D$_6$) δ: 7.87 (1H, d, J = 7.5 Hz), 7.63-7.59 (1H, m), 7.54-7.47 (2H, m), 7.46 (1H, d, J = 2.4 Hz), 7.40-7.35 (1H, m), 7.10 (1H, s), 6.92 (1H, dd, J = 8.4, 2.4 Hz), 3.85 (3H, s). |
| 48 | (fluorene with 9-OH, 9-CF3, and 4-CO2CH2CH3) | $^1$H-NMR (CDCl$_3$) δ: 8.29 (1H, d, J = 7.9 Hz), 7.91-7.84 (2H, m), 7.75-7.70 (1H, m), 7.50-7.45 (1H, m), 7.42-7.38 (2H, m), 4.48 (2H, q, J = 7.1 Hz), 2.72 (1H, s), 1.45 (3H, t, J = 7.2 Hz). |

TABLE 1-7-continued

| compound No. | structural formula | NMR |
|---|---|---|
| 49 | (fluorene with CN at position 4, C(CF3)(OH) at 9) | $^1$H-NMR (DMSO-D$_6$) δ: 8.23-8.19 (1H, m), 7.98 (2H, d, J = 7.9 Hz), 7.79-7.75 (1H, m), 7.71-7.66 (1H, m), 7.63-7.54 (2H, m), 7.55 (1H, s). |

TABLE 1-8

| compound No. | structural formula | NMR |
|---|---|---|
| 50 | (fluorene with two methyl ester groups and C(CF3)(OH) at 9) | $^1$H-NMR (CDCl$_3$) δ: 8.54 (1H, d, J = 1.5 Hz), 8.45 (1H, br s), 8.37-8.33 (1H, m), 7.79-7.74 (1H, m), 7.54-7.44 (2H, m), 4.03 (3H, s), 3.96 (3H, s), 3.03 (0H, s). |
| 51 | (fluorene with N-ethyl-N-methyl amide and C(CF3)(OH) at 9) | $^1$H-NMR (CDCl$_3$) δ: 7.76-7.72 (1H, m), 7.68-7.65 (1H, m), 7.64-7.61 (1H, m), 7.59 (1H, d, J = 7.7 Hz), 7.52-7.47 (1H, m), 7.42-7.34 (2H, m), 3.97 (1H, br s), 3.53 (1H, br s), 3.26 (1H, br s), 3.03-2.91 (3H, m), 1.26-1.10 (3H, m). |
| 52 | (fluorene with piperidine amide and C(CF3)(OH) at 9) | $^1$H-NMR (CDCl$_3$) δ: 7.75-7.72 (1H, m), 7.68-7.65 (1H, m), 7.63-7.61 (1H, m), 7.60 (1H, d, J = 7.7 Hz), 7.52-7.47 (1H, m), 7.42-7.36 (2H, m), 3.87 (1H, s), 3.75-3.22 (4H, m), 1.73-1.43 (6H, m). |
| 53 | (fluorene with pyrrolidine amide and C(CF3)(OH) at 9) | $^1$H-NMR (CDCl$_3$) δ: 7.77-7.72 (2H, m), 7.69-7.65 (1H, m), 7.60-7.57 (1H, m), 7.52-7.47 (2H, m), 7.43-7.38 (1H, m), 4.36 (1H, br s), 3.62-3.35 (4H, m), 1.98-1.90 (4H, m). |
| 54 | (fluorene with N,N-diethyl amide and C(CF3)(OH) at 9) | $^1$H-NMR (CDCl$_3$) δ: 7.76-7.72 (1H, m), 7.68-7.65 (1H, m), 7.63-7.57 (2H, m), 7.52-7.47 (1H, m), 7.42-7.37 (1H, m), 7.36-7.32 (1H, m), 3.93 (1H, br s), 3.50 (2H, br s), 3.25 (2H, br s), 1.22 (3H, br s), 1.12 (3H, br s). |

TABLE 1-8-continued

| compound No. | structural formula | NMR |
| --- | --- | --- |
| 55 | (fluorene with NH2 at 2-position, C(CF3)(OH) at 9-position) · HCl | ¹H-NMR (DMSO-D₆) δ: 7.84 (1H, d, J = 8.1 Hz), 7.81 (1H, d, J = 7.4 Hz), 7.65-7.61 (1H, m), 7.53-7.48 (1H, m), 7.46-7.43 (1H, m), 7.39-7.34 (1H, m), 7.31-7.27 (1H, m). |
| 56 | (fluorene with N(CH3)(phenyl) amide at 2-position, C(CF3)(OH) at 9-position) | ¹H-NMR (CDCl₃) δ: 7.67-7.64 (1H, m), 7.61-7.58 (1H, m), 7.53-7.42 (4H, m), 7.37-7.33 (1H, m), 7.25-7.20 (2H, m), 7.17-7.12 (1H, m), 7.07-7.02 (2H, m), 3.50 (3H, s), 2.84 (1H, br s). |

TABLE 1-9

| compound No. | structural formula | NMR |
| --- | --- | --- |
| 57 | (fluorene with N(CH3)(cyclobutyl) amide at 2-position, C(CF3)(OH) at 9-position) | ¹H-NMR (CDCl₃) δ: 7.76-7.72 (1H, m), 7.69-7.66 (1H, m), 7.65-7.60 (2H, m), 7.53-7.48 (1H, m), 7.43-7.37 (2H, m), 4.33-3.47 (1H, m), 3.13-2.80 (3H, m), 2.33-1.93 (4H, m), 1.79-1.37 (2H, m). |
| 58 | (fluorene with azetidinyl amide at 2-position, C(CF3)(OH) at 9-position) | ¹H-NMR (CDCl₃) δ: 7.83-7.80 (1H, m), 7.78-7.73 (1H, m), 7.71-7.67 (2H, m), 7.66-7.62 (1H, m), 7.52-7.47 (1H, m), 7.43-7.39 (1H, m), 4.39-3.99 (5H, m), 2.37-2.26 (2H, m). |
| 59 | (fluorene with propyl ester at 4-position, C(CF3)(OH) at 9-position) | ¹H-NMR (DMSO-D₆) δ: 8.07 (1H, d, J = 7.7 Hz), 7.87-7.84 (1H, m), 7.83 (1H, dd, J = 7.8, 1.0 Hz), 7.72-7.68 (1H, m), 7.54-7.44 (3H, m), 7.36 (1H, s), 4.36 (2H, t, J = 6.6 Hz), 1.83-1.73 (2H, m), 0.99 (3H, t, J = 7.4 Hz). |
| 60 | (fluorene with isopropyl ester at 4-position, C(CF3)(OH) at 9-position) | ¹H-NMR (DMSO-D₆) δ: 8.09 (1H, d, J = 7.4 Hz), 7.86-7.83 (1H, m), 7.79 (1H, dd, J = 7.9, 1.2 Hz), 7.71-7.68 (1H, m), 7.55-7.44 (3H, m), 7.35 (1H, s), 5.33-5.23 (1H, m), 1.40 (3H, d, J = 3.7 Hz), 1.38 (3H, d, J = 3.7 Hz). |

TABLE 1-9-continued

| compound No. | structural formula | NMR |
|---|---|---|
| 61 | (fluorene with Cl at top, C(CF3)(OH) at bottom, CO2CH3 substituent) | $^1$H-NMR (DMSO-D$_6$) δ: 8.36 (1H, d, J = 7.4 Hz), 8.14-8.13 (1H, m), 8.09 (1H, d, J = 1.4 Hz), 7.79-7.76 (1H, m), 7.68-7.64 (1H, m), 7.66 (1H, s), 7.61-7.57 (1H, m), 3.92 (3H, s). |
| 62 | (fluorene with OH substituent, C(CF3)(OH) at bottom) | $^1$H-NMR (DMSO-D$_6$) δ: 9.81 (1H, s), 7.74 (1H, d, J = 7.5 Hz), 7.61-7.57 (1H, m), 7.49-7.44 (1H, m), 7.43-7.39 (1H, m), 7.38-7.33 (1H, m), 7.18 (1H, d, J = 2.2 Hz), 6.99 (1H, s), 6.75 (1H, dd, J = 8.3, 2.3 Hz). |
| 63 | (fluorene with HO substituent, C(CF3)(OH) at bottom) | $^1$H-NMR (DMSO-D$_6$) δ: 10.27 (1H, s), 7.94 (1H, d, J = 7.4 Hz), 7.61-7.57 (1H, m), 7.48-7.43 (1H, m), 7.33-7.28 (1H, m), 7.21-7.17 (1H, m), 7.12-7.08 (2H, m), 6.94 (1H, dd, J = 8.1, 0.9 Hz). |

TABLE 1-10

| compound No. | structural formula | NMR |
|---|---|---|
| 64 | (fluorene with CF3 substituent at top, C(CF3)(OH) at bottom) | $^1$H-NMR (DMSO-D$_6$) δ: 8.00-7.97 (1H, m), 7.92-7.89 (2H, m), 7.78-7.75 (1H, m), 7.66-7.60 (2H, m), 7.56-7.52 (1H, m), 7.48 (1H, s). |
| 65 | (fluorene with C(O)N(CH3)(OCH3) substituent, C(CF3)(OH) at bottom) | $^1$H-NMR (DMSO-D$_6$) δ: 7.74-7.65 (2H, m), 7.53-7.39 (5H, m), 7.35 (1H, s), 3.42 (3H, br s), 3.36 (3H, br s). |

TABLE 1-10-continued

| compound No. | structural formula | NMR |
|---|---|---|
| 66 | | ¹H-NMR (DMSO-D₆) δ: 7.96 (1H, d, J = 7.5 Hz), 7.64-7.60 (1H, m), 7.51-7.46 (1H, m), 7.37-7.32 (2H, m), 7.25-7.22 (1H, m), 7.18 (1H, s), 7.14 (1H, d, J = 8.2 Hz), 4.23 (2H, q, J = 7.0 Hz), 1.48 (3H, t, J = 6.9 Hz). |
| 67 | | ¹H-NMR (DMSO-D₆) δ: 7.85 (1H, d, J = 7.5 Hz), 7.62-7.59 (1H, m), 7.53-7.47 (2H, m), 7.45 (1H, d, J = 2.4 Hz), 7.39-7.35 (1H, m), 7.08 (1H, s), 6.90 (1H, dd, J = 8.4, 2.4 Hz), 4.13 (2H, q, J = 6.9 Hz), 1.37 (3H, t, J = 6.9 Hz). |
| 68 | | ¹H-NMR (DMSO-D₆) δ: 7.89-7.79 (3H, m), 7.70-7.66 (1H, m), 7.54-7.40 (3H, m), 7.31 (1H, s), 2.71 (3H, s). |
| 69 | | ¹H-NMR (DMSO-D₆) δ: 7.82 (1H, d, J = 7.7 Hz), 7.79 (1H, d, J = 7.9 Hz), 7.65-7.61 (2H, m), 7.52-7.47 (1H, m), 7.45-7.41 (1H, m), 7.39-7.34 (1H, m), 7.21 (1H, s), 5.33 (1H, t, J = 5.7 Hz), 4.57 (2H, d, J = 5.6 Hz). |
| 70 | | ¹H-NMR (CDCl₃) δ: 7.70-7.66 (1H, m), 7.64-7.60 (1H, m), 7.56 (1H, d, J = 7.9 Hz), 7.52-7.50 (1H, m), 7.47-7.43 (1H, m), 7.34-7.27 (2H, m), 2.70 (1H, br s), 2.69-2.63 (2H, m), 1.74-1.64 (2H, m), 0.97 (3H, t, J = 7.3 Hz). |

TABLE 1-11

| compound No. | structural formula | NMR |
|---|---|---|
| 71 | | ¹H-NMR (CDCl₃) δ: 7.70-7.66 (1H, m), 7.64-7.61 (1H, m), 7.59-7.55 (2H, m), 7.48-7.43 (1H, m), 7.35-7.30 (2H, m), 3.05-2.93 (1H, m), 2.70 (1H, s), 1.31 (3H, d, J = 1.4 Hz), 1.29 (3H, d, J = 1.4 Hz). |

TABLE 1-11-continued

| compound No. | structural formula | NMR |
|---|---|---|
| 72 | (fluorene with 9-C(CF₃)(OH), 3-C(=O)NH-CH₂CH₃) | ¹H-NMR (DMSO-D₆) δ: 8.59-8.55 (1H, m), 8.26 (1H, d, J = 1.3 Hz), 7.90 (1H, d, J = 7.5 Hz), 7.83 (1H, dd, J = 7.9, 1.5 Hz), 7.72-7.65 (2H, m), 7.57-7.53 (1H, m), 7.45-7.40 (1H, m), 7.35 (1H, s), 3.37-3.29 (2H, m), 1.16 (3H, t, J = 7.2 Hz). |
| 73 | (fluorene with 9-C(CF₃)(OH), 3-C(=O)NH-CH(CH₃)₂) | ¹H-NMR (DMSO-D₆) δ: 8.35-8.31 (1H, m), 8.27-8.25 (1H, m), 7.91 (1H, d, J = 7.5 Hz), 7.83 (1H, dd, J = 7.9, 1.5 Hz), 7.72-7.65 (2H, m), 7.57-7.53 (1H, m), 7.45-7.40 (1H, m), 7.35 (1H, s), 4.17-4.08 (1H, m), 1.21 (3H, s), 1.19 (3H, s). |
| 74 | (fluorene with 9-C(CF₃)(OH), CH₂OH substituent) | ¹H-NMR (DMSO-D₆) δ: 7.83 (1H, d, J = 7.7 Hz), 7.69-7.65 (1H, m), 7.58-7.50 (3H, m), 7.41-7.35 (2H, m), 7.17 (1H, s), 5.43 (1H, t, J = 5.4 Hz), 4.91-4.81 (2H, m). |
| 75 | (fluorene with 9-C(CF₃)(OH), 2-CH₂-O-CH₃) | ¹H-NMR (DMSO-D₆) δ: 7.86-7.81 (2H, m), 7.66-7.62 (1H, m), 7.61-7.58 (1H, m), 7.53-7.48 (1H, m), 7.46-7.43 (1H, m), 7.40-7.36 (1H, m), 7.24 (1H, s), 4.49 (2H, s), 3.34 (3H, s). |
| 76 | (fluorene with 9-C(CF₃)(OH), 2-C(=O)CH₃) | ¹H-NMR (DMSO-D₆) δ: 8.18-8.15 (2H, m), 8.05-7.98 (2H, m), 7.72-7.68 (1H, m), 7.60-7.55 (1H, m), 7.51-7.46 (1H, m), 7.44 (1H, s), 2.64 (3H, s). |
| 77 | (fluorene with 9-C(CF₃)(OH), 2-C(=O)-(2-methylpyrrolidin-1-yl)) | ¹H-NMR (DMSO-D₆) δ: 7.92 (2H, d, J = 7.4 Hz), 7.73-7.61 (3H, m), 7.57-7.52 (1H, m), 7.46-7.41 (1H, m), 7.39 (0.5H, s), 7.35 (0.5H, s), 4.23-3.94 (1H, m), 3.60-3.47 (1H, m), 3.38-3.29 (1H, m), 2.14-2.03 (1H, m), 1.97-1.82 (1H, m), 1.78-1.66 (1H, m), 1.62-1.50 (1H, m), 1.33-1.20 (2H, m), 0.95-0.77 (1H, m). |

TABLE 1-12

| compound No. | structural formula | NMR |
|---|---|---|
| 78 | | ¹H-NMR (DMSO-D₆) δ: 8.13-8.11 (1H, m), 8.03-7.92 (3H, m), 7.69-7.66 (1H, m), 7.58-7.53 (1H, m), 7.48-7.43 (1H, m), 7.41 (1H, s), 4.48-4.42 (2H, m), 4.02-3.97 (2H, m). |
| 79 | | ¹H-NMR (DMSO-D₆) δ: 7.96-7.91 (2H, m), 7.87-7.85 (1H, m), 7.78-7.74 (1H, m), 7.69-7.65 (1H, m), 7.57-7.53 (1H, m), 7.47-7.43 (1H, m), 7.39 (1H, s), 5.76 (1H, d, J = 6.0 Hz), 4.56-4.43 (2H, m), 4.34-4.22 (1H, m), 4.13-4.00 (1H, m), 3.89-3.71 (1H, m). |
| 80 | | ¹H-NMR (CDCl₃) δ: 7.64-7.60 (1H, m), 7.51-7.47 (2H, m), 7.42-7.37 (1H, m), 7.23-7.18 (1H, m), 7.06-7.03 (1H, m), 6.76 (1H, dd, J = 8.5, 2.4 Hz), 3.03 (6H, s), 2.69 (1H, br s). |
| 81 | | ¹H-NMR (DMSO-D₆) δ: 7.80-7.76 (2H, m), 7.69-7.66 (1H, m), 7.64-7.61 (1H, m), 7.52-7.40 (3H, m), 7.32 (1H, s), 3.16-2.97 (2H, m), 1.17 (3H, t, J = 7.2 Hz). |
| 82 | | ¹H-NMR (DMSO-D₆) δ: 7.75 (1H, d, J = 7.7 Hz), 7.69-7.65 (1H, m), 7.64-7.60 (1H, m), 7.56-7.48 (2H, m), 7.43-7.36 (2H, m), 7.22 (1H, s), 4.79 (1H, d, J = 12.3 Hz), 4.74 (1H, d, J = 12.3 Hz), 3.40 (3H, s). |
| 83 | | ¹H-NMR (DMSO-D₆) δ: 7.83-7.78 (2H, m), 7.72-7.66 (2H, m), 7.55-7.51 (1H, m), 7.49-7.40 (2H, m), 7.33 (1H, s), 2.62-2.55 (1H, m), 1.26-1.14 (4H, m). |

TABLE 1-12-continued
| compound No. | structural formula | NMR |
|---|---|---|
| 84 | 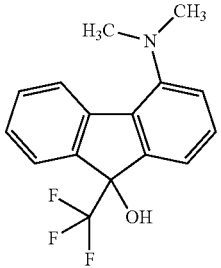 | ¹H-NMR (DMSO-D$_6$) δ: 7.96-7.92 (1H, m), 7.65-7.62 (1H, m), 7.54-7.49 (1H, m), 7.38-7.30 (3H, m), 7.23 (1H, dd, J = 7.1, 2.0 Hz), 7.13 (1H, s), 2.76 (6H, s). |
TABLE 1-13
| compound No. | structural formula | NMR |
|---|---|---|
| 85 | 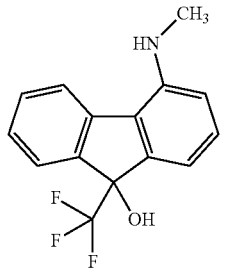 [SMILES: OCc1cccc2c1-c1ccccc1C2(O)C(F)(F)F] | ¹H-NMR (DMSO-D$_6$) δ: 7.96 (1H, d, J = 7.7 Hz), 7.63-7.61 (1H, m), 7.49-7.44 (1H, m), 7.33-7.24 (2H, m), 7.05-7.00 (1H, m), 6.82 (2H, br s), 6.67 (2H, s), 2.88 (3H, s). |
| 86 | 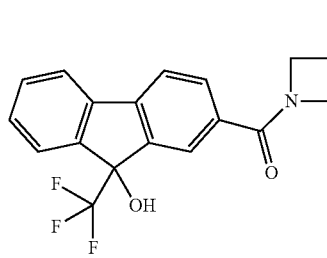 | ¹H-NMR (DMSO-D$_6$) δ: 7.96-7.92 (2H, m), 7.90-7.87 (1H, m), 7.80-7.76 (1H, m), 7.70-7.66 (1H, m), 7.58-7.53 (1H, m), 7.48-7.43 (1H, m), 7.40 (1H, br s), 4.55-4.40 (1H, m), 4.32-4.23 (2H, m), 4.22-4.11 (1H, m), 3.97-3.78 (1H, m), 3.24 (3H, s). |
| 87 | 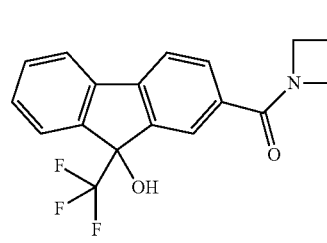 | ¹H-NMR (DMSO-D$_6$) δ: 7.94 (2H, d, J = 7.9 Hz), 7.88-7.86 (1H, m), 7.80-7.76 (1H, m), 7.69-7.65 (1H, m), 7.57-7.53 (1H, m), 7.47-7.42 (1H, m), 7.40 (1H, s), 4.83 (1H, t, J = 5.3 Hz), 4.40-4.31 (1H, m), 4.10-4.03 (2H, m), 3.84-3.78 (1H, m), 3.56 (2H, t, J = 5.7 Hz), 2.80-2.69 (1H, m). |
| 88 | 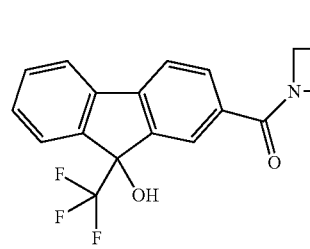 | ¹H-NMR (DMSO-D$_6$) δ: 8.14-8.11 (1H, m), 8.01-7.96 (1H, m), 7.92-7.86 (2H, m), 7.69-7.63 (1H, m), 7.57-7.50 (1H, m), 7.45-7.39 (1H, m), 7.32 (1H, s), 4.41-4.33 (1H, m), 3.95-3.85 (1H, m), 3.65-3.54 (1H, m), 3.19-3.07 (1H, m), 2.11-1.94 (1H, m), 0.95 (3H, d, J = 6.4 Hz). |

TABLE 1-13-continued
| compound No. | structural formula | NMR |
|---|---|---|
| 89 | 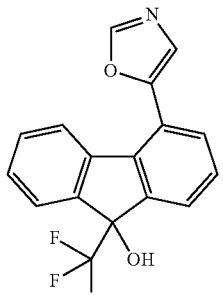 | ¹H-NMR (CDCl₃) δ: 7.67-7.63 (1H, m), 7.57-7.53 (2H, m), 7.45-7.41 (1H, m), 7.30-7.23 (2H, m), 6.98 (1H, dd, J = 8.3, 2.3 Hz), 4.10 (2H, q, J = 7.0 Hz), 2.67 (1H, s), 1.44 (3H, t, J = 6.9 Hz). |
| 90 | | ¹H-NMR (DMSO-D₆) δ: 7.95-7.91 (2H, m), 7.87-7.71 (2H, m), 7.69-7.65 (1H, m), 7.57-7.52 (1H, m), 7.47-7.42 (1H, m), 7.40 (0.5H, s), 7.36 (0.5H, s), 4.84-3.87 (3H, m), 2.46-2.31 (1H, m), 1.94-1.74 (1H, m), 1.55-1.35 (2H, m), 1.21-1.00 (1H, m). |
| 91 | | ¹H-NMR (DMSO-D₆) δ: 7.93-7.88 (1H, m), 7.74-7.68 (2H, m), 7.60-7.54 (2H, m), 7.48-7.43 (1H, m), 7.32 (1H, s), 4.39-4.29 (2H, m), 4.12-4.02 (2H, m), 2.68 (3H, s), 2.34-2.23 (2H, m). |
TABLE 1-14
| compound No. | structural formula | NMR |
|---|---|---|
| 92 | 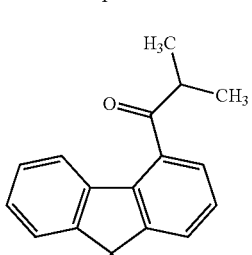 | ¹H-NMR (DMSO-D₆) δ: 8.64 (1H, s), 7.79 (1H, d, J = 7.3 Hz), 7.72-7.68 (1H, m), 7.59-7.56 (2H, m), 7.53-7.49 (1H, m), 7.44-7.40 (2H, m), 7.35 (1H, s), 7.11-7.06 (1H, m). |
| 93 | | ¹H-NMR (DMSO-D₆) δ: 7.80-7.76 (1H, m), 7.75-7.71 (1H, m), 7.69-7.66 (1H, m), 7.52-7.39 (4H, m), 7.32 (1H, s), 3.50-3.42 (1H, m), 1.18 (3H, d, J = 7.0 Hz), 1.13 (3H, d, J = 7.0 Hz). |

TABLE 1-14-continued

| compound No. | structural formula | NMR |
| --- | --- | --- |
| 94 | (4-chloro-9-hydroxy-9-(trifluoromethyl)-9H-fluoren-2-yl)(azetidin-1-yl)methanone | $^1$H-NMR (DMSO-D$_6$) δ: 8.32 (1H, d, J = 7.7 Hz), 7.83-7.81 (1H, m), 7.78-7.73 (2H, m), 7.65-7.61 (1H, m), 7.58-7.52 (1H, m), 7.57 (1H, s), 4.39-4.33 (2H, m), 4.11-4.04 (2H, m), 2.34-2.24 (2H, m). |
| 95 | 9-hydroxy-N-methyl-9-(trifluoromethyl)-9H-fluoren-2-amine HCl | $^1$H-NMR (DMSO-D$_6$) δ: 7.73-7.66 (2H, m), 7.59-7.54 (1H, m), 7.46-7.41 (1H, m), 7.29-7.23 (1H, m), 7.17 (1H, br s), 6.99 (1H, br s), 4.64 (2H, br s), 2.81 (3H, br s). |
| 96 | N-(9-hydroxy-9-(trifluoromethyl)-9H-fluoren-2-yl)-N-methylacetamide | $^1$H-NMR (CDCl$_3$) δ: 7.74-7.65 (3H, m), 7.54-7.48 (2H, m), 7.43-7.37 (1H, m), 7.32-7.27 (1H, m), 3.29 (3H, br s), 3.10 (1H, br s), 1.91 (3H, br s). |
| 97 | 2-phenyl-9-(trifluoromethyl)-9H-fluoren-9-ol | $^1$H-NMR (DMSO-D$_6$) δ: 7.96 (1H, d, J = 7.9 Hz), 7.91 (1H, d, J = 7.4 Hz), 7.89-7.87 (1H, m), 7.83 (1H, dd, J = 7.9, 1.6 Hz), 7.73-7.69 (2H, m), 7.68-7.64 (1H, m), 7.56-7.49 (3H, m), 7.44-7.38 (2H, m), 7.35 (1H, s). |
| 98 | (9-hydroxy-9-(trifluoromethyl)-9H-fluoren-2-yl)(phenyl)methanone | $^1$H-NMR (DMSO-D$_6$) δ: 8.06 (1H, d, J = 7.9 Hz), 8.02-7.99 (2H, m), 7.92 (1H, dd, J = 7.9, 1.6 Hz), 7.79-7.75 (2H, m), 7.74-7.69 (2H, m), 7.63-7.57 (3H, m), 7.52-7.47 (2H, m). |

TABLE 1-15

| compound No. | structural formula | NMR |
| --- | --- | --- |
| 99 | (9-hydroxy-9-(trifluoromethyl)-9H-fluoren-2-yl)(thiophen-2-yl)methanone | $^1$H-NMR (DMSO-D$_6$) δ: 8.18-8.16 (1H, m), 8.09-8.00 (4H, m), 7.79-7.77 (1H, m), 7.73-7.70 (1H, m), 7.62-7.57 (1H, m), 7.52-7.47 (2H, m), 7.36-7.33 (1H, m). |

TABLE 1-15-continued

| compound No. | structural formula | NMR |
|---|---|---|
| 100 | (fluorene with 9-OH, 9-CF3, 2-NHC(O)CH2CH3) | ¹H-NMR (DMSO-D6) δ: 10.09 (1H, s), 8.10-8.08 (1H, m), 7.71 (1H, d, J = 7.4 Hz), 7.64-7.61 (1H, m), 7.57-7.47 (3H, m), 7.41-7.36 (1H, m), 7.14 (1H, s), 2.37 (2H, q, J = 7.6 Hz), 1.11 (3H, t, J = 7.5 Hz). |
| 101 | (fluorene with 9-OH, 9-CF3, 2-NHC(O)CH(CH3)2) | ¹H-NMR (DMSO-D$_6$) δ: 10.05 (1H, s), 8.12 (1H, d, J = 1.6 Hz), 7.72 (1H, d, J = 7.7 Hz), 7.63 (1H, d, J = 7.4 Hz), 7.57-7.48 (3H, m), 7.41-7.37 (1H, m), 7.15 (1H, s), 2.69-2.58 (1H, m), 1.13 (6H, d, J = 6.7 Hz). |
| 102 | (fluorene with 9-OH, 9-CF3, 2-(pyridin-3-yl)) | ¹H-NMR (CDCl$_3$) δ: 8.61 (1H, d, J = 2.3 Hz), 8.44-8.42 (1H, m), 7.89-7.85 (2H, m), 7.77 (1H, d, J = 13.9 Hz), 7.72 (1H, d, J = 7.9 Hz), 7.69 (1H, d, J = 7.7 Hz), 7.60-7.57 (1H, m), 7.53-7.49 (1H, m), 7.43-7.38 (1H, m), 7.33 (1H, dd, J = 8.0, 4.8 Hz), 4.49 (1H, br s). |
| 103 | (fluorene with 9-OH, 9-CF3, 2-(pyridin-4-yl)) | ¹H-NMR (CDCl$_3$) δ: 8.58-8.55 (2H, m), 7.87-7.85 (1H, m), 7.78-7.69 (4H, m), 7.54-7.47 (3H, m), 7.43-7.38 (1H, m), 4.19 (1H, br s). |
| 104 | (fluorene with 9-OH, 9-CF3, 2-C(O)-N-azetidine-3-O-CH2CH3) | ¹H-NMR (DMSO-D$_6$) δ: 7.96-7.90 (2H, m), 7.87 (1H, s), 7.79-7.74 (1H, m), 7.69-7.64 (1H, m), 7.57-7.52 (1H, m), 7.47-7.41 (1H, m), 7.38 (1H, s), 4.52-4.43 (1H, m), 4.37-4.23 (2H, m), 4.21-4.11 (1H, m), 3.89-3.82 (1H, m), 3.42 (2H, q, J = 6.9 Hz), 1.13 (3H, t, J = 7.0 Hz). |
| 105 | (fluorene with 9-OH, 9-CF3, 2-C(O)-N-azetidine-3-O-CH2CH2CH3) | ¹H-NMR (DMSO-D$_6$) δ: 7.97-7.91 (2H, m), 7.88 (1H, s), 7.80-7.76 (1H, m), 7.69-7.65 (1H, m), 7.58-7.53 (1H, m), 7.47-7.42 (1H, m), 7.39 (1H, br s), 4.54-4.43 (1H, m), 4.37-4.24 (2H, m), 4.22-4.12 (1H, m), 3.90-3.83 (1H, m), 3.36-3.27 (2H, m), 1.58-1.48 (2H, m), 0.88 (3H, t, J = 7.4 Hz). |

TABLE 1-16

| compound No. | structural formula | NMR |
|---|---|---|
| 106 | | $^1$H-NMR (DMSO-D$_6$) δ: 7.97-7.91 (2H, m), 7.90-7.86 (1H, m), 7.80-7.76 (1H, m), 7.69-7.65 (1H, m), 7.58-7.52 (1H, m), 7.48-7.42 (1H, m), 7.39 (1H, br s), 4.53-4.42 (1H, m), 4.41-4.34 (1H, m), 4.32-4.24 (1H, m), 4.21-4.12 (1H, m), 3.92-3.82 (1H, m), 3.55-3.49 (2H, m), 3.48-3.43 (2H, m), 3.25 (3H, s). |
| 107 | | $^1$H-NMR (DMSO-D$_6$) δ: 12.73 (1H, br s), 7.97-7.92 (2H, m), 7.89-7.86 (1H, m), 7.80-7.75 (1H, m), 7.69-7.65 (1H, m), 7.58-7.53 (1H, m), 7.48-7.42 (1H, m), 7.40 (1H, br s), 4.53-4.42 (2H, m), 4.33-4.19 (2H, m), 4.07 (2H, s), 3.98-3.90 (1H, m). |
| 108 | | $^1$H-NMR (DMSO-D$_6$) δ: 7.96-7.92 (2H, m), 7.89-7.86 (1H, m), 7.79-7.76 (1H, m), 7.70-7.65 (1H, m), 7.58-7.53 (1H, m), 7.48-7.43 (1H, m), 7.40 (1H, s), 4.67 (1H, t, J = 5.3 Hz), 4.54-4.45 (1H, m), 4.41-4.35 (1H, m), 4.32-4.24 (1H, m), 4.21-4.13 (1H, m), 3.94-3.84 (1H, m), 3.53-3.48 (2H, m), 3.45-3.40 (2H, m). |
| 109 | | $^1$H-NMR (DMSO-D$_6$) δ: 8.21-8.17 (2H, m), 8.02 (1H, d, J = 8.3 Hz), 8.00-7.97 (1H, m), 7.71-7.68 (1H, m), 7.60-7.55 (1H, m), 7.51-7.46 (1H, m), 7.43 (1H, s), 3.92-3.83 (1H, m), 1.99-1.88 (2H, m), 1.84-1.70 (2H, m), 1.66-1.61 (4H, m). |
| 110 | | $^1$H-NMR (DMSO-D$_6$) δ: 7.73 (2H, d, J = 8.1 Hz), 7.60-7.56 (1H, m), 7.47-7.43 (1H, m), 7.31-7.27 (1H, m), 7.21 (1H, s), 7.14-7.11 (1H, m), 7.04 (1H, dd, J = 8.3, 2.3 Hz), 4.71-4.61 (1H, m), 1.31 (3H, d, J = 4.6 Hz), 1.29 (3H, d, J = 4.4 Hz). |
| 111 | | $^1$H-NMR (DMSO-D$_6$) δ: 8.20 (1H, d, J = 7.9 Hz), 7.81-7.78 (1H, m), 7.74-7.71 (1H, m), 7.70-7.66 (1H, m), 7.52-7.41 (3H, m), 7.32 (1H, s), 4.55-4.49 (2H, m), 4.16-4.10 (2H, m). |

TABLE 1-16-continued

| compound No. | structural formula | NMR |
|---|---|---|
| 112 | (fluorene with C(CF3)OH at 9-position and 2-pyridyl substituent) | ¹H-NMR (CDCl₃) δ: 8.54-8.52 (1H, m), 8.18-8.16 (1H, m), 8.04 (1H, dd, J = 7.9, 1.8 Hz), 7.77-7.64 (4H, m), 7.61-7.58 (1H, m), 7.47-7.43 (1H, m), 7.39-7.35 (1H, m), 7.17-7.13 (1H, m), 4.05 (1H, br s). |

TABLE 1-17

| compound No. | structural formula | NMR |
|---|---|---|
| 113 | (4-bromo fluorene with C(CF3)OH at 9-position) | ¹H-NMR (DMSO-D₆) δ: 8.45 (1H, d, J = 7.7 Hz), 7.76-7.67 (3H, m), 7.63-7.58 (1H, m), 7.53-7.48 (1H, m), 7.40 (1H, br s), 7.37-7.33 (1H, m). |
| 114 | (4-bromo fluorene with C(CF3)OH at 9-position and 2-(azetidin-1-ylcarbonyl) substituent) | ¹H-NMR (DMSO-D₆) δ: 8.50-8.47 (1H, m), 7.91 (1H, d, J = 1.3 Hz), 7.87-7.84 (1H, m), 7.76-7.73 (1H, m), 7.67-7.62 (1H, m), 7.58-7.53 (1H, m), 7.55 (1H, s), 4.41-4.30 (2H, m), 4.14-4.02 (2H, m), 2.34-2.23 (2H, m). |
| 115 | (fluorene with C(CF3)OH at 9-position and 2-[(3-(methoxycarbonylmethoxy)azetidin-1-yl)carbonyl] substituent) | ¹H-NMR (CDCl₃) δ: 7.78-7.64 (3H, m), 7.61-7.57 (2H, m), 7.51-7.46 (1H, m), 7.44-7.38 (1H, m), 5.34 (0.5H, br s), 5.16 (0.5H, br s), 4.48-3.93 (7H, m), 3.76 (3H, s). |
| 116 | (fluorene with C(CF3)OH at 9-position and 2-[(3-(carbamoylmethoxy)azetidin-1-yl)carbonyl] substituent) | ¹H-NMR (DMSO-D₆) δ: 7.94 (2H, d, J = 7.7 Hz), 7.88-7.87 (1H, m), 7.79-7.76 (1H, m), 7.69-7.65 (1H, m), 7.58-7.53 (1H, m), 7.47-7.43 (1H, m), 7.40 (1H, s), 7.36 (1H, br s), 7.27 (1H, br s), 4.55-4.45 (1H, m), 4.45-4.39 (1H, m), 4.31-4.21 (2H, m), 4.01-3.92 (1H, m), 3.83 (2H, s). |

TABLE 1-17-continued
| compound No. | structural formula | NMR |
|---|---|---|
| 117 | | ¹H-NMR (DMSO-D₆) δ: 7.96-7.93 (2H, m), 7.89-7.87 (1H, m), 7.84 (1H, br s), 7.80-7.76 (1H, m), 7.69-7.66 (1H, m), 7.58-7.53 (1H, m), 7.48-7.43 (1H, m), 7.40 (1H, br s), 4.58-4.46 (1H, m), 4.45-4.38 (1H, m), 4.34-4.17 (2H, m), 4.01-3.91 (1H, m), 3.87 (2H, s), 2.62 (3H, d, J = 4.6 Hz). |
| 118 | | ¹H-NMR (DMSO-D₆) δ: 7.96-7.92 (2H, m), 7.88-7.87 (1H, m), 7.79-7.76 (1H, m), 7.69-7.66 (1H, m), 7.58-7.53 (1H, m), 7.47-7.43 (1H, m), 7.40 (1H, br s), 4.54-4.39 (2H, m), 4.32-4.17 (2H, m), 4.20 (2H, s), 3.99-3.87 (1H, m), 2.89 (3H, s), 2.81 (3H, s). |
| 119 | | ¹H-NMR (DMSO-D₆) δ: 8.15-8.11 (1H, m), 8.08-8.05 (1H, m), 8.03-7.96 (2H, m), 7.72-7.68 (1H, m), 7.60-7.55 (1H, m), 7.51-7.46 (1H, m), 7.44 (1H, s), 4.23-4.14 (1H, m), 2.33-2.23 (4H, m), 2.13-2.00 (1H, m), 1.87-1.75 (1H, m). |
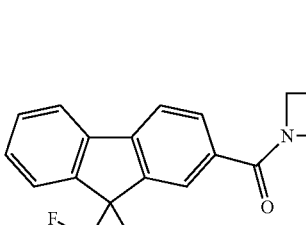
TABLE 1-18
| compound No. | structural formula | NMR |
|---|---|---|
| 120 | | ¹H-NMR (CDCl₃) δ: 7.83-7.63 (5H, m), 7.53-7.48 (1H, m), 7.44-7.39 (1H, m), 4.58-4.06 (5H, m), 3.82-3.72 (3H, m), 3.52-3.40 (1H, m). |
| 121 | | ¹H-NMR (DMSO-D₆) δ: 7.94 (2H, d, J = 7.7 Hz), 7.88-7.86 (1H, m), 7.80-7.76 (1H, m), 7.69-7.66 (1H, m), 7.58-7.53 (1H, m), 7.48-7.43 (1H, m), 7.41 (1H, br s), 4.58-3.99 (4H, m), 3.55-3.43 (1H, m). |
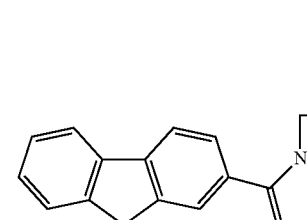

TABLE 1-18-continued

| compound No. | structural formula | NMR |
|---|---|---|
| 122 | | ¹H-NMR (DMSO-D₆) δ: 8.03 (1H, d, J = 1.5 Hz), 7.98 (1H, br s), 7.86-7.83 (1H, m), 7.73-7.68 (1H, m), 7.53-7.46 (3H, m), 4.43-4.34 (2H, m), 4.13-4.06 (2H, m), 2.75 (3H, s), 2.34-2.26 (2H, m). |
| 123 | | ¹H-NMR (DMSO-D₆) δ: 7.94 (2H, d, J = 7.9 Hz), 7.89-7.86 (1H, m), 7.80-7.75 (1H, m), 7.69-7.66 (1H, m), 7.58-7.53 (1H, m), 7.52 (1H, s), 7.48-7.43 (1H, m), 7.42-7.40 (1H, m), 7.09 (1H, br s), 4.48-4.40 (1H, m), 4.37-4.30 (1H, m), 4.22-4.14 (1H, m), 4.08-4.00 (1H, m), 3.42-3.35 (1H, m). |
| 124 | | ¹H-NMR (DMSO-D₆) δ: 8.02-7.97 (1H, m), 7.94 (2H, d, J = 7.7 Hz), 7.88-7.86 (1H, m), 7.80-7.75 (1H, m), 7.69-7.65 (1H, m), 7.58-7.53 (1H, m), 7.47-7.43 (1H, m), 7.42-7.39 (1H, m), 4.49-4.40 (1H, m), 4.37-4.29 (1H, m), 4.22-4.14 (1H, m), 4.08-4.01 (1H, m), 3.41-3.34 (1H, m), 2.62 (3H, d, J = 4.6 Hz). |
| 125 | | ¹H-NMR (CDCl₃) δ: 7.89 (0.5H, br s), 7.81 (0.5H, br s), 7.78-7.63 (4H, m), 7.51-7.46 (1H, m), 7.43-7.37 (1H, m), 4.71-4.62 (1H, m), 4.49 (0.5H, br s), 4.38-3.98 (3.5H, m), 3.63-3.48 (1H, m), 2.97 (3H, s), 2.92-2.85 (3H, m). |
| 126 | | ¹H-NMR (CDCl₃) δ: 7.72 (1H, d, J = 7.4 Hz), 7.68 (1H, d, J = 7.7 Hz), 7.54-7.36 (6H, m), 7.32 (1H, dd, J = 7.7, 0.7 Hz), 7.29-7.24 (1H, m), 7.17-7.12 (1H, m), 6.82 (1H, d, J = 7.9 Hz), 2.04 (1H, br s). |

TABLE 1-19

| compound No. | structural formula | NMR |
|---|---|---|
| 127 | | $^1$H-NMR (DMSO-D$_6$) δ: 7.96-7.91 (2H, m), 7.68-7.63 (2H, m), 7.59-7.52 (2H, m), 7.46-7.41 (1H, m), 7.39 (1H, br s), 3.82-3.35 (8H, m). |
| 128 | | $^1$H-NMR (DMSO-D$_6$) δ: 7.73 (2H, d, J = 8.1 Hz), 7.60-7.57 (1H, m), 7.48-7.43 (1H, m), 7.32-7.27 (1H, m), 7.22 (1H, s), 7.08-7.05 (1H, m), 6.96 (1H, dd, J = 8.3, 2.3 Hz), 4.79-4.71 (1H, m), 2.48-2.41 (2H, m), 2.13-2.01 (2H, m), 1.85-1.75 (1H, m), 1.74-1.64 (1H, m). |
| 129 | | $^1$H-NHR (DMSO-D$_6$) δ: 7.98 (1H, d, J = 7.9 Hz), 7.94-7.90 (2H, m), 7.87 (1H, dd, J = 8.0, 1.7 Hz), 7.69-7.65 (1H, m), 7.59-7.51 (4H, m), 7.44-7.40 (1H, m), 7.36 (1H, s), 7.28-7.21 (1H, m). |
| 130 | | $^1$H-NMR (DMSO-D$_6$) δ: 9.46 (1H, br s), 7.76-7.72 (1H, m), 7.67-7.63 (1H, m), 7.54-7.48 (2H, m), 7.41-7.35 (3H, m), 7.26 (1H, s), 3.32 (1.5H, s), 3.29 (1.5H, s). |
| 131 | | $^1$H-NMR (DMSO-D$_6$) δ: 8.39 (1H, d, J = 0.9 Hz), 8.10-8.07 (1H, m), 7.88 (1H, dd, J = 7.8, 1.2 Hz), 7.86-7.82 (1H, m), 7.73-7.69 (1H, m), 7.59-7.54 (2H, m), 7.49-7.42 (2H, m), 7.36 (1H, s). |
| 132 | | $^1$H-NMR (DMSO-D$_6$) δ: 7.98 (1H, d, J = 7.9 Hz), 7.94-7.86 (3H, m), 7.78-7.76 (1H, m), 7.71-7.65 (2H, m), 7.57-7.52 (2H, m), 7.49-7.46 (1H, m), 7.44-7.40 (1H, m), 7.36 (1H, s). |

TABLE 1-19-continued
| compound No. | structural formula | NMR |
|---|---|---|
| 133 | 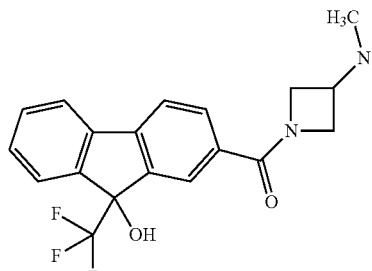 | $^1$H-NMR (CDCl$_3$) δ: 7.92-7.58 (5H, m), 7.52-7.47 (1H, m), 7.43-7.38 (1H, m), 5.81 (0.5H, br s), 5.54 (0.5H, br s), 4.22-4.09 (1H, m), 4.06-3.93 (2H, m), 3.82-3.77 (0.5H, m), 3.68-3.62 (0.5H, m), 3.05-2.89 (1H, m), 2.05 (3H, s), 1.97 (3H, s). |
TABLE 1-20
| compound No. | structural formula | NMR |
|---|---|---|
| 134 | 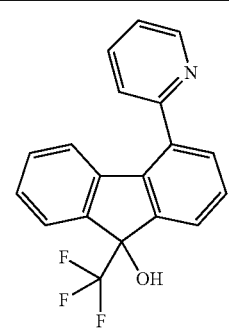 | $^1$H-NMR (CDCl$_3$) δ: 8.79-8.75 (1H, m), 7.83-7.77 (1H, m), 7.73-7.66 (2H, m), 7.51-7.47 (1H, m), 7.41-7.37 (1H, m), 7.31-7.20 (3H, m), 7.14-7.07 (1H, m), 6.66 (1H, d, J = 7.9 Hz). |
| 135 (optically active form) | 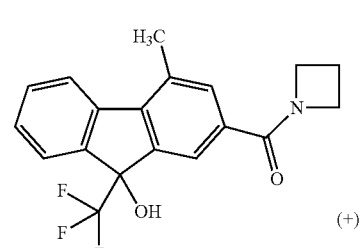 (+) | $^1$H-NMR (DMSO-D$_6$) δ: 7.92-7.89 (1H, m), 7.72-7.69 (2H, m), 7.59-7.54 (2H, m), 7.48-7.43 (1H, m), 7.31 (1H, s), 4.38-4.29 (2H, m), 4.12-4.03 (2H, m), 2.68 (3H, s), 2.32-2.24 (2H, m). |
| 136 (optically active form) | 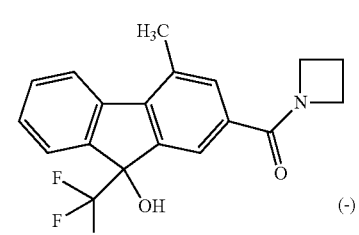 (-) | $^1$H-NMR (DMSO-D$_6$) δ: 7.92-7.89 (1H, m), 7.73-7.68 (2H, m), 7.59-7.54 (2H, m), 7.48-7.43 (1H, m), 7.31 (1H, s), 4.39-4.28 (2H, m), 4.11-4.02 (2H, m), 2.68 (3H, s), 2.32-2.23 (2H, m). |
| 137 | 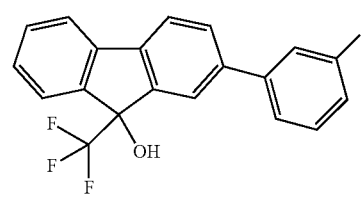 | $^1$H-NMR (DMSO-D$_6$) δ: 7.96-7.92 (1H, m), 7.92-7.85 (2H, m), 7.83-7.79 (1H, m), 7.69-7.64 (1H, m), 7.56-7.47 (3H, m), 7.43-7.37 (2H, m), 7.33 (1H, s), 7.24-7.20 (1H, m), 2.41 (3H, s). |

TABLE 1-20-continued
| compound No. | structural formula | NMR |
|---|---|---|
| 138 | 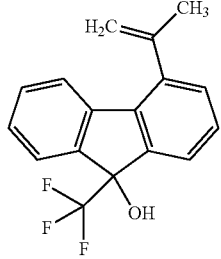 [SMILES: C=C(C)c1cccc2c1-c1ccccc1C2(O)C(F)(F)F] | $^1$H-NMR (CDCl$_3$) δ: 7.88-7.84 (1H, m), 7.73-7.68 (1H, m), 7.64-7.59 (1H, m), 7.44-7.38 (1H, m), 7.35-7.28 (2H, m), 7.22-7.19 (1H, m), 5.36-5.33 (1H, m), 5.09-5.07 (1H, m), 2.66 (1H, br s), 2.16 (3H, s). |
| 139 | 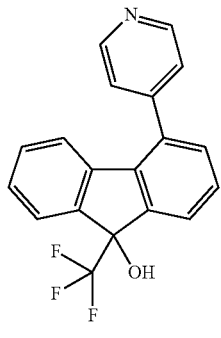 [SMILES: OC1(C(F)(F)F)c2ccccc2-c2c(-c3ccncc3)cccc21] | $^1$H-NMR (DMSO-D$_6$) δ: 8.76 (2H, d, J = 5.5 Hz), 7.75 (1H, d, J = 7.5 Hz), 7.67 (1H, d, J = 7.5 Hz), 7.54-7.47 (3H, m), 7.37-7.32 (2H, m), 7.32 (1H, s), 7.28-7.23 (1H, m), 6.79 (1H, d, J = 7.7 Hz). |
| 140 | 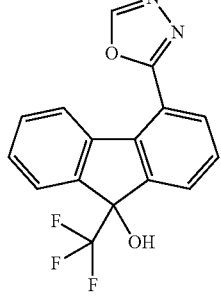 | $^1$H-NMR (DMSO-D$_6$) δ: 9.52 (1H, s), 8.05-8.02 (1H, m), 7.94-7.90 (2H, m), 7.75-7.70 (1H, m), 7.64-7.59 (1H, m), 7.52-7.45 (2H, m), 7.44 (1H, s). |
TABLE 1-21
| compound No. | structural formula | NMR |
|---|---|---|
| 141 | 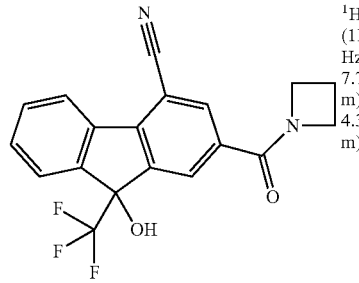 | $^1$H-NMR (DMSO-D$_6$) δ: 8.26-8.23 (1H, m), 8.17 (1H, d, J = 1.4 Hz), 8.14-8.11 (1H, m), 7.82-7.78 (1H, m), 7.74-7.69 (2H, m), 7.65-7.61 (1H, m), 4.45-4.34 (2H, m), 4.14-4.05 (2H, m), 2.34-2.24 (2H, m). |

TABLE 1-21-continued

| compound No. | structural formula | NMR |
|---|---|---|
| 142 | | ¹H-NMR (DMSO-D₆) δ: 7.98-7.94 (3H, m), 7.75-7.71 (1H, m), 7.65-7.60 (1H, m), 7.53-7.48 (2H, m), 7.46 (1H, s), 2.54 (3H, s). |
| 143 | | ¹H-NMR (CDCl₃) δ: 8.60-8.57 (1H, m), 8.21-8.18 (1H, m), 8.03-8.00 (1H, m), 7.81-7.77 (1H, m), 7.60-7.54 (2H, m), 7.51-7.47 (1H, m), 3.21 (3H, s), 2.96 (1H, br s) |
| 144 | | ¹H-NMR (CDCl₃) δ: 7.95-7.92 (1H, m), 7.74-7.70 (2H, m), 7.68-7.64 (2H, m), 7.51-7.47 (1H, m), 7.40-7.31 (3H, m), 7.11 (1H, dd, J = 5.1, 3.7 Hz), 2.79 (1H, br s). |
| 145 | | ¹H-NMR (CDCl₃) δ: 7.91-7.89 (1H, m), 7.70-7.66 (2H, m), 7.65-7.61 (2H, m), 7.52-7.49 (1H, m), 7.48-7.43 (1H, m), 7.43-7.38 (2H, m), 7.36-7.31 (1H, m), 2.91 (1H, br s). |
| 146 | | ¹H-NMR (DMSO-D₆) δ: 8.74 (1H, dd, J = 4.9, 1.5 Hz), 8.65 (1H, br s), 7.94-7.86 (1H, m), 7.74 (1H, d, J = 7.5 Hz), 7.67 (1H, d, J = 7.3 Hz), 7.60 (1H, dd, J = 7.9, 5.1 Hz), 7.52-7.48 (1H, m), 7.39-7.32 (2H, m), 7.31 (1H, s), 7.26-7.22 (1H, m), 6.66 (1H, d, J = 7.7 Hz). |
| 147 | | ¹H-NMR (DMSO-D₆) δ: 8.13-8.11 (1H, m), 7.84 (1H, d, J = 8.3 Hz), 7.82-7.79 (1H, m), 7.65 (1H, dd, J = 8.5, 2.0 Hz), 7.64-7.61 (1H, m), 7.51-7.47 (1H, m), 7.37-7.32 (1H, m), 7.27 (1H, s), 3.95-3.83 (2H, m), 2.56-2.51 (2H, m), 2.13-2.05 (2H, m). |

TABLE 1-22

| compound No. | structural formula | NMR |
|---|---|---|
| 148 | | ¹H-NMR (CDCl₃) δ: 7.65-7.62 (1H, m), 7.53-7.50 (1H, m), 7.48 (1H, d, J = 8.4 Hz), 7.43-7.38 (1H, m), 7.26-7.20 (2H, m), 6.96 (1H, dd, J = 8.4, 2.4 Hz), 3.24-3.20 (4H, m), 2.78 (1H, br s), 1.76-1.68 (4H, m), 1.63-1.57 (2H, m). |
| 149 | | ¹H-NMR (DMSO-D₆) δ: 7.98 (1H, d, J = 7.9 Hz), 7.93-7.90 (1H, m), 7.80-7.78 (1H, m), 7.73-7.65 (2H, m), 7.62-7.52 (2H, m), 7.50-7.33 (5H, m). |
| 150 | | ¹H-NMR (CDCl₃) δ: 7.98-7.90 (2H, m), 7.70-7.65 (2H, m), 7.64-7.52 (3H, m), 7.84-7.40 (4H, m), 7.34 (1H, s). |
| 151 | | ¹H-NMR (CDCl₃) δ: 7.74-7.67 (4H, m), 7.52-7.43 (2H, m), 7.39-7.35 (1H, m), 7.32-7.27 (4H, m), 2.76 (1H, br s), 2.31 (3H, s). |
| 152 (optically active form) | (-) | ¹H-NMR (CDCl₃) δ: 7.82-7.76 (2H, m), 7.75-7.64 (1H, m), 7.53-7.48 (1H, m), 7.44-7.38 (2H, m), 4.48-3.99 (6H, m), 3.80-3.71 (2H, m), 3.53 (2H, br s), 2.66-2.50 (3H, m), 2.31 (0.5H, br s), 2.03 (0.5H, br s). |
| 153 (optically active form) | (-) | ¹H-NMR (CDCl₃) δ: 7.83-7.73 (3H, m), 7.53-7.38 (3H, m), 4.73-4.65 (1H, m), 4.43-4.32 (2H, m), 4.24-4.11 (1H, m), 3.93-3.86 (1H, m), 3.64-3.56 (1H, m), 2.98 (3H, s), 2.91 (3H, s), 2.64 (3H, s). |

TABLE 1-22-continued

| compound No. | structural formula | NMR |
|---|---|---|
| 154 | (fluorene with C(CF3)(OH) at 9-position, 2-aryl = 3-(methoxycarbonyl)phenyl) | $^1$H-NMR (CDCl$_3$) δ: 8.31-8.30 (1H, m), 8.06-8.03 (1H, m), 7.96-7.94 (1H, m), 7.85-7.81 (1H, m), 7.75-7.69 (4H, m), 7.57-7.48 (2H, m), 7.41-7.36 (1H, m), 3.96 (3H, s), 2.94 (1H, br s). |

TABLE 1-23

| compound No. | structural formula | NMR |
|---|---|---|
| 155 | (fluorene with C(CF3)(OH) at 9-position, 2-aryl = 3-carboxyphenyl) | $^1$H-NMR (CDCl$_3$) δ: 8.40-8.38 (1H, m), 8.14-8.11 (1H, m), 7.98-7.95 (1H, m), 7.91-7.88 (1H, m), 7.77-7.69 (4H, m), 7.62-7.57 (1H, m), 7.54-7.49 (1H, m), 7.42-7.36 (1H, m), 2.04 (1H, br s). |
| 156 | (fluorene with C(CF3)(OH) at 9-position, 2-aryl = 3-carbamoylphenyl) | $^1$H-NMR (DMSO-D$_6$) δ: 8.22-8.20 (1H, m), 8.18 (1H, br s), 8.00-7.97 (2H, m), 7.94-7.85 (4H, m), 7.70-7.66 (1H, m), 7.61-7.52 (2H, m), 7.47 (1H, br s), 7.44-7.39 (1H, m), 7.38 (1H, s). |
| 157 | (fluorene with C(CF3)(OH) at 9-position, 2-aryl = 3-(N-methylcarbamoyl)phenyl) | $^1$H-NMR (DMSO-D$_6$) δ: 8.65-8.60 (1H, m), 8.17-8.14 (1H, m), 8.01-7.96 (2H, m), 7.94-7.84 (4H, m), 7.70-7.66 (1H, m), 7.61-7.57 (1H, m), 7.56-7.52 (1H, m), 7.44-7.40 (1H, m), 7.39 (1H, s), 2.83 (3H, d, J = 4.4 Hz). |
| 158 | (fluorene with C(CF3)(OH) at 9-position, 2-aryl = 3-(N,N-dimethylcarbamoyl)phenyl) | $^1$H-NMR (DMSO-D$_6$) δ: 7.97 (1H, d, J = 7.9 Hz), 7.93-7.90 (2H, m), 7.37 (1H, dd, J = 7.9, 1.9 Hz), 7.81-7.77 (1H, m), 7.71-7.69 (1H, m), 7.69-7.65 (1H, m), 7.59-7.51 (2H, m), 7.44-7.39 (2H, m), 7.36 (1H, br s), 3.05-2.94 (6H, m). |
| 159 | (4-chloro-fluorene with C(CF3)(OH) at 9-position, 2-phenyl) | $^1$H-NMR (DMSO-D$_6$) δ: 8.29 (1H, d, J = 7.7 Hz), 7.89 (2H, s), 7.78-7.72 (3H, m), 7.63-7.59 (1H, m), 7.55-7.42 (5H, m). |

TABLE 1-23-continued

| compound No. | structural formula | NMR |
|---|---|---|
| 160 | | $^1$H-NMR (CDCl$_3$) δ: 7.63-7.59 (1H, m), 7.49-7.45 (2H, m), 7.40-7.36 (1H, m), 7.20-7.15 (1H, m), 6.89-6.87 (1H, m), 6.60 (1H, dd, J = 8.4, 2.2 Hz), 3.38-3.33 (4H, m), 2.67 (1H, s), 2.07-1.99 (4H, m). |
| 161 | | $^1$H-NMR (DMSO-D$_6$) δ: 7.70-7.66 (2H, m), 7.58-7.55 (1H, m), 7.45-7.40 (1H, m), 7.27-7.23 (1H, m), 7.19-7.18 (1H, m), 7.12 (1H, s), 7.06 (1H, dd, J = 8.4, 2.4 Hz), 3.78-3.74 (4H, m), 3.20-3.16 (4H, m). |

TABLE 1-24

| compound No. | structural formula | NMR |
|---|---|---|
| 162 | | $^1$H-NMR (DMSO-D$_6$) δ: 7.69-7.63 (2H, m), 7.57-7.54 (1H, m), 7.44-7.40 (1H, m), 7.27-7.22 (1H, m), 7.19-7.16 (1H, m), 7.10 (1H, s), 7.05 (1H, dd, J = 8.5, 2.3 Hz), 3.23-3.18 (4H, m), 2.49-2.45 (4H, m), 2.23 (3H, s). |
| 163 | | $^1$H-NMR (CDCl$_3$) δ: 7.67-7.63 (1H, m), 7.56-7.51 (2H, m), 7.45-7.40 (1H, m), 7.28-7.24 (2H, m), 6.97 (1H, dd, J = 8.3, 2.3 Hz), 3.62-3.57 (4H, m), 3.23-3.18 (4H, m), 2.77 (1H, br s), 1.49 (9H, s). |
| 164 | 2HCl | $^1$H-NMR (DMSO-D$_6$) δ: 9.11 (2H, br s), 7.72 (2H, d, J = 8.2 Hz), 7.60-7.56 (1H, m), 7.47-7.42 (1H, m), 7.30-7.26 (1H, m), 7.25-7.22 (1H, m), 7.11 (1H, dd, J = 8.5, 2.3 Hz), 4.96 (2H, br s), 3.46-3.41 (4H, m), 3.28-3.21 (4H, m). |
| 165 | | $^1$H-NMR (DMSO-D$_6$) δ: 7.71-7.66 (2H, m), 7.58-7.54 (1H, m), 7.45-7.40 (1H, m), 7.28-7.23 (1H, m), 7.22-7.19 (1H, m), 7.15 (1H, s), 7.07 (1H, dd, J = 8.3, 2.1 Hz), 3.63-3.58 (4H, m), 3.30-3.11 (4H, m), 2.05 (3H, s). |

TABLE 1-24-continued

| compound No. | structural formula | NMR |
|---|---|---|
| 166 | | $^1$H-NMR (DMSO-D$_6$) δ: 8.49 (1H, s), 7.69-7.65 (2H, m), 7.58-7.55 (1H, m), 7.46-7.41 (1H, m), 7.37-7.35 (1H, m), 7.31-7.23 (3H, m), 7.18-7.11 (4H, m), 6.91-6.87 (1H, m). |
| 167 | | $^1$H-NMR (CDCl$_3$) δ: 7.86-7.32 (7H, m), 4.63-4.49 (1H, m), 3.76 (3H, s), 3.73-3.47 (2H, m), 2.38-2.16 (1H, m), 2.09-1.82 (3H, m). |
| 168 | | $^1$H-NMR (DMSO-D$_6$) δ: 12.57 (1H, br s), 7.97-7.87 (2H, m), 7.77-7.73 (1H, m), 7.72-7.61 (2H, m), 7.58-7.50 (1H, m), 7.48-7.38 (2H, m), 4.47-4.37 (1H, m), 3.65-3.46 (2H, m), 2.35-2.22 (1H, m), 2.04-1.77 (3H, m). |

TABLE 1-25

| compound No. | structural formula | NMR |
|---|---|---|
| 169 | | $^1$H-NMR (CDCl$_3$) δ: 7.59-7.66 (1H, m), 7.63-7.60 (1H, m), 7.57 (1H, d, J = 7.9 Hz), 7.55-7.54 (1H, m), 7.47-7.43 (1H, m), 7.34-7.29 (2H, m), 2.65 (1H, br s), 2.62-2.54 (1H, m), 1.95-1.83 (4H, m), 1.80-1.74 (1H, m), 1.49-1.38 (4H, m), 1.34-1.23 (1H, m). |
| 170 | | $^1$H-NMR (DMSO-D$_6$) δ: 7.90-7.86 (2H, m), 7.75-7.74 (1H, m), 7.67-7.61 (2H, m), 7.54-7.50 (1H, m), 7.42-7.33 (3H, m), 7.28 (1H, br s), 7.15 (1H, d, J = 8.1 Hz), 7.09-7.05 (1H, m), 3.80 (3H, s). |
| 171 | | $^1$H-NMR (CDCl$_3$) δ: 7.88-7.87 (1H, m), 7.74-7.64 (4H, m), 7.63-7.57 (2H, m), 7.52-7.48 (1H, m), 7.40-7.36 (1H, m), 7.19-7.13 (2H, m), 2.75 (1H, br s). |

TABLE 1-25-continued

| compound No. | structural formula | NMR |
|---|---|---|
| 172 | | ¹H-NMR (CDCl₃) δ: 7.89-7.87 (1H, m), 7.73-7.64 (4H, m), 7.60-7.56 (2H, m), 7.51-7.46 (1H, m), 7.38-7.33 (1H, m), 7.02-6.98 (2H, m), 3.87 (3H, s), 2.75 (1H, br s). |
| 173 | | ¹H-NMR (CDCl₃) δ: 7.88 (1H, d, J = 7.7 Hz), 7.73-7.67 (3H, m), 7.65-7.63 (1H, m), 7.58-7.53 (1H, m), 7.52-7.35 (5H, m), 4.15-4.05 (2H, m), 2.92 (1H, s), 1.04-0.99 (3H, m). |
| 174 | | ¹H-NMR (DMSO-D₆) δ: 8.22 (1H, br s), 7.97 (1H, d, J = 7.7 Hz), 7.90 (1H, br s), 7.80 (1H, br s), 7.71-7.67 (2H, m), 7.54-7.49 (1H, m), 7.48-7.43 (1H, m), 7.45 (1H, s), 4.40-4.32 (2H, m), 4.13-4.04 (2H, m), 2.34-2.25 (2H, m). |
| 175 | | ¹H-NMR (CDCl₃) δ: 8.15-8.11 (2H, m), 7.96-7.95 (1H, m), 7.75-7.74 (2H, m), 7.73-7.69 (4H, m), 7.53-7.49 (1H, m), 7.42-7.37 (1H, m), 4.41 (2H, q, J = 7.1 Hz), 2.85 (1H, s), 1.42 (3H, t, J = 7.2 Hz). |

TABLE 1-26

| compound No. | structural formula | NMR |
|---|---|---|
| 176 | | ¹H-NMR (DMSO-D₆) δ: 7.95-7.23 (9H, m), 7.01-6.92 (1H, m), 4.41-4.36 (0.8H, m), 4.25-4.17 (0.2H, m), 3.66-3.56 (1.2H, m), 3.49-3.38 (0.8H, m), 2.26-2.11 (1H, m), 1.95-1.75 (3H, m). |
| 177 | | ¹H-NMR (DMSO-D₆) δ: 7.95-7.30 (8H, m), 4.45-4.39 (0.7H, m), 4.21-4.13 (0.3H, m), 3.68-3.55 (1.4H, m), 3.49-3.38 (0.6H, m), 2.63-2.62 (2.1H, m), 2.52-2.49 (0.4H, m), 2.40-2.39 (0.5H, m), 2.23-2.11 (1H, m), 1.97-1.74 (3H, m). |

TABLE 1-26-continued

| compound No. | structural formula | NMR |
|---|---|---|
| 178 | | $^1$H-NMR (DMSO-D$_6$) δ: 7.95-7.86 (2H, m), 7.75-7.71 (0.7H, m), 7.69-7.64 (2H, m), 7.57-7.38 (3H, m), 7.31 (0.3H, d, J = 7.4 Hz), 4.98-4.93 (0.7H, m), 4.78-4.69 (0.3H, m), 3.70-3.45 (2H, m), 3.11 (2.1H, s), 2.86 (2.1H, s), 2.67 (0.4H, s), 2.64 (0.4H, s), 2.62 (0.5H, s), 2.58 (0.5H, s), 2.34-2.23 (1H, m), 1.97-1.71 (3H, m). |
| 179 | | $^1$H-NMR (DMSO-D$_6$) δ: 7.96 (1H, d, J = 7.9 Hz), 7.92-7.89 (1H, m), 7.88 (1H, br s), 7.83 (1H, dd, J = 7.9, 1.8 Hz), 7.76-7.73 (2H, m), 7.69-7.65 (1H, m), 7.58-7.51 (3H, m), 7.44-7.39 (1H, m), 7.35 (1H, br s). |
| 180 | | $^1$H-NMR (DMSO-D$_6$) δ: 12.88 (1H, br s), 7.89 (2H, d, J = 7.9 Hz), 7.79-7.75 (1H, m), 7.67-7.64 (1H, m), 7.63-7.58 (2H, m), 7.55-7.46 (3H, m), 7.44-7.38 (2H, m), 7.31 (1H, br s). |
| 181 | | $^1$H-NMR (CDCl$_3$) δ: 7.91-7.90 (1H, m), 7.73-7.66 (4H, m), 7.54 (2H, d, J = 8.1 Hz), 7.51-7.46 (1H, m), 7.38-7.34 (1H, m), 7.28 (2H, d, J = 8.6 Hz), 2.76 (1H, s), 2.41 (3H, s). |
| 182 | | $^1$H-NMR (DMSO-D$_6$) δ: 7.88 (2H, d, J = 7.7 Hz), 7.76 (1H, br s), 7.70 (1H, br s), 7.67-7.64 (1H, m), 7.57 (1H, dd, J = 7.9, 1.6 Hz), 7.55-7.37 (6H, m), 7.34 (1H, br s), 7.29 (1H, s). |

TABLE 1-27

| compound No. | structural formula | NMR |
|---|---|---|
| 183 | | $^1$H-NMR (DMSO-D$_6$) δ: 8.19-8.14 (1H, m), 7.91-7.86 (2H, m), 7.67-7.63 (2H, m), 7.56-7.50 (3H, m), 7.47-7.42 (3H, m), 7.42-7.37 (1H, m), 7.26 (1H, s), 2.59 (3H, d, J = 4.6 Hz). |

TABLE 1-27-continued

| compound No. | structural formula | NMR |
|---|---|---|
| 184 | | $^1$H-NMR (DMSO-D$_6$) δ: 7.92 (1H, d, J = 7.7 Hz), 7.90 (1H, d, J = 7.5 Hz), 7.68-7.64 (1H, m), 7.63 (1H, br s), 7.57-7.45 (5H, m), 7.43-7.39 (1H, m), 7.38-7.36 (1H, m), 7.26 (1H, s), 2.77 (3H, br s), 2.52-2.43 (3H, m). |
| 185 | | $^1$H-NMR (DMSO-D$_6$) δ: 8.71-8.68 (2H, m), 8.34-8.31 (1H, m), 8.06 (1H, d, J = 1.5 Hz), 8.01-8.00 (1H, m), 7.83-7.80 (2H, m), 7.78-7.74 (1H, m), 7.66-7.61 (1H, m), 7.58 (1H, s), 7.57-7.52 (1H, m). |
| 186 | | $^1$H-NMR (DMSO-D$_6$) δ: 7.72-7.68 (2H, m), 7.58-7.55 (1H, m), 7.46-7.42 (1H, m), 7.38-7.33 (2H, m), 7.29-7.25 (1H, m), 7.19-7.17 (1H, m), 7.16 (1H, s), 7.15-7.11 (2H, m), 7.08-7.03 (2H, m), 3.32 (3H, s). |
| 187 | | $^1$H-NMR (CDCl$_3$) δ: 7.69-7.66 (1H, m), 7.62-7.58 (2H, m), 7.49-7.44 (1H, m), 7.40-7.35 (3H, m), 7.34-7.30 (1H, m), 7.18-7.13 (1H, m), 7.09 (1H, dd, J = 8.3, 2.3 Hz), 7.07-7.04 (2H, m), 2.69 (1H, s). |
| 188 | | $^1$H-NMR (DMSO-D$_6$) δ: 8.08-8.05 (2H, m), 8.01-7.99 (1H, m), 7.96-7.89 (3H, m), 7.87-7.83 (2H, m), 7.69-7.66 (1H, m), 7.57-7.52 (1H, m), 7.45-7.40 (1H, m), 7.39 (1H, br s). |
| 189 | | $^1$H-NMR (CDCl$_3$) δ: 7.74-7.68 (4H, m), 7.58-7.54 (1H, m), 7.52-7.47 (2H, m), 7.45-7.33 (4H, m), 4.64 (1H, d, J = 13.2 Hz), 4.60 (1H, d, J = 12.8 Hz), 1.78 (1H, br s). |

TABLE 1-28

| compound No. | structural formula | NMR |
|---|---|---|
| 190 | | ¹H-NMR (DMSO-D₆) δ: 9.39 (1H, br s), 7.92 (1H, d, J = 7.7 Hz), 7.89 (1H, d, J = 7.3 Hz), 7.67-7.64 (2H, m), 7.55-7.50 (2H, m), 7.43-7.30 (5H, m), 7.27 (1H, s), 1.88 (3H, br s). |
| 191 | | ¹H-NMR (DMSO-D₆) δ: 8.54-8.49 (1H, m), 8.00-7.88 (6H, m), 7.83-7.79 (2H, m), 7.69-7.66 (1H, m), 7.57-7.52 (1H, m), 7.45-7.40 (1H, m), 7.37 (1H, s), 2.82 (3H, d, J = 4.6 Hz). |
| 192 | | ¹H-NMR (DMSO-D₆) δ: 7.98 (1H, d, J = 7.9 Hz), 7.93-7.90 (2H, m), 7.87 (1H, dd, J = 7.9, 1.6 Hz), 7.79-7.76 (2H, m), 7.69-7.66 (1H, m), 7.56-7.52 (3H, m), 7.44-7.40 (1H, m), 7.37 (1H, s), 3.06-2.92 (6H, m). |
| 193 | | ¹H-NMR (DMSO-D₆) δ: 7.85-7.82 (2H, m), 7.77-7.75 (1H, m), 7.68 (1H, dd, J = 7.9, 1.6 Hz), 7.65-7.61 (1H, m), 7.52-7.47 (1H, m), 7.43-7.39 (2H, m), 7.38-7.33 (1H, m), 7.25 (1H, s), 6.69-6.65 (2H, m), 5.31 (2H, s). |
| 194 | | ¹H-NMR (CDCl₃) δ: 7.93-7.91 (1H, m), 7.75-7.63 (6H, m), 7.52-7.45 (3H, m), 7.40-7.35 (1H, m), 4.77 (2H, d, J = 5.5 Hz), 2.82 (1H, s), 1.69 (1H, t, J = 6.0 Hz). |
| 195 | | ¹H-NMR (DMSO-D₆) δ: 7.94-7.90 (2H, m), 7.77-7.72 (1H, m), 7.69-7.61 (2H, m), 7.56-7.52 (1H, m), 7.46-7.41 (1H, m), 7.37 (0.5H, s), 7.33 (0.5H, s), 4.83-4.78 (0.5H, m), 4.21-4.12 (0.5H, m), 3.65-3.00 (5H, m), 2.01-1.64 (4H, m). |
| 196 | | ¹H-NMR (DMSO-D₆) δ: 8.50-8.47 (1H, m), 7.88-7.83 (2H, m), 7.73-7.69 (1H, m), 7.60-7.56 (1H, m), 7.52-7.48 (1H, m), 7.42 (1H, s), 2.39 (3H, s). |

TABLE 1-29

| compound No. | structural formula | NMR |
|---|---|---|
| 197 | | $^1$H-NMR (DMSO-D$_6$) δ: 10.07 (1H, br s), 7.92 (1H, d, J = 7.9 Hz), 7.88 (1H, d, J = 7.4 Hz), 7.87-7.85 (1H, m), 7.79 (1H, dd, J = 7.9, 1.6 Hz), 7.74-7.70 (2H, m), 7.68-7.64 (3H, m), 7.54-7.50 (1H, m), 7.42-7.37 (1H, m), 7.32 (1H, s), 2.08 (3H, s). |
| 198 | | $^1$H-NMR (DMSO-D$_6$) δ: 8.53 (1H, d, J = 5.1 Hz), 8.03-7.93 (4H, m), 7.70-7.67 (1H, m), 7.64-7.62 (1H, m), 7.58-7.53 (2H, m), 7.46-7.42 (1H, m), 7.40 (1H, s), 2.56 (3H, s). |
| 199 | | $^1$H-NMR (DMSO-D$_6$) δ: 8.04 (1H, br s), 8.03-7.97 (3H, m), 7.95-7.88 (3H, m), 7.82-7.78 (2H, m), 7.69-7.66 (1H, m), 7.56-7.52 (1H, m), 7.44-7.40 (1H, m), 7.39 (1H, br s), 7.36 (1H, s). |
| 200 | | $^1$H-NMR (DMSO-D$_6$) δ: 7.96-7.92 (2H, m), 7.89-7.86 (1H, m), 7.80-7.76 (1H, m), 7.69-7.65 (1H, m), 7.58-7.53 (1H, m), 7.47-7.43 (1H, m), 7.41 (1H, br s), 4.54-4.38 (2H, m), 4.31-4.22 (1H, m), 4.13-4.05 (1H, m), 3.81-3.73 (1H, m), 3.33-3.27 (2H, m), 3.21-3.16 (2H, m), 1.10-1.01 (6H, m). |
| 201 | | $^1$H-NMR (DMSO-D$_6$) δ: 7.96-7.93 (2H, m), 7.88-7.86 (1H, m), 7.80-7.76 (1H, m), 7.69-7.65 (1H, m), 7.58-7.53 (1H, m), 7.47-7.43 (1H, m), 7.41 (1H, br s), 4.55-4.38 (2H, m), 4.30-4.21 (1H, m), 4.17-4.09 (1H, m), 3.72-3.64 (1H, m), 3.34-3.27 (4H, m), 1.90-1.82 (2H, m), 1.81-1.73 (2H, m). |
| 202 | | $^1$H-NMR (DMSO-D$_6$) δ: 7.97-7.93 (2H, m), 7.89-7.86 (1H, m), 7.80-7.76 (1H, m), 7.69-7.66 (1H, m), 7.58-7.53 (1H, m), 7.47-7.43 (1H, m), 7.42 (1H, br s), 4.55-4.41 (2H, m), 4.31-4.23 (1H, m), 4.17-4.07 (1H, m), 3.81-3.72 (1H, m), 3.48-3.43 (2H, m), 3.25-3.20 (2H, m), 1.61-1.54 (2H, m), 1.50-1.41 (4H, m). |

TABLE 1-30
| compound No. | structural formula | NMR |
|---|---|---|
| 203 | 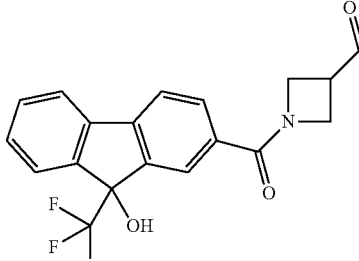 | $^1$H-NMR (DMSO-D$_6$) δ: 7.96-7.93 (2H, m), 7.88-7.86 (1H, m), 7.80-7.76 (1H, m), 7.69-7.65 (1H, m), 7.58-7.53 (1H, m), 7.48-7.43 (1H, m), 7.42 (1H, br s), 4.74 (1H, d, J = 3.9 Hz), 4.55-4.39 (2H, m), 4.32-4.23 (1H, m), 4.16-4.07 (1H, m), 3.94-3.86 (1H, m), 3.82-3.74 (1H, m), 3.73-3.65 (1H, m), 3.49-3.41 (1H, m), 3.12-3.01 (2H, m), 1.76-1.66 (2H, m), 1.36-1.22 (2H, m). |
| 204 | 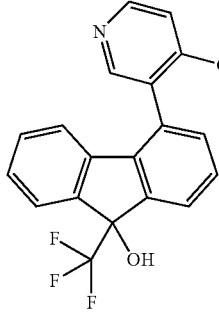 | $^1$H-NMR (DMSO-D$_6$) δ: 8.61 (1H, d, J = 4.6 Hz), 8.39 (1H, d, J = 5.1 Hz), 7.75 (1H, d, J = 6.8 Hz), 7.67 (1H, d, J = 7.3 Hz), 7.56-7.44 (2H, m), 7.38-7.28 (3H, m), 7.26-7.19 (1H, m), 6.38-6.29 (1H, m), 2.07-1.99 (3H, m). |
| 205 | 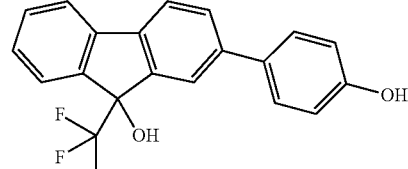 | $^1$H-NMR (CDCl$_3$) δ: 7.88-7.85 (1H, m), 7.73-7.63 (4H, m), 7.55-7.51 (2H, m), 7.51-7.46 (1H, m), 7.38-7.34 (1H, m), 6.95-6.91 (2H, m), 4.82 (1H, s), 2.74 (1H, s). |
| 206 | 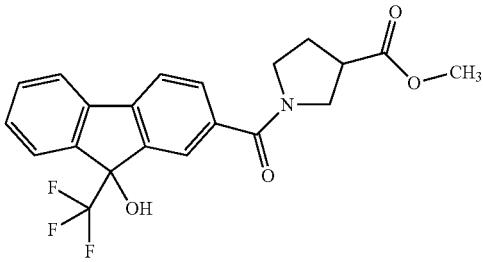 [SMILES: COC(=O)C1CCN(C(=O)c2ccc3c(c2)C(O)(C(F)(F)F)c2ccccc2-3)C1] | $^1$H-NMR (DMSO-D$_6$) δ: 7.95-7.91 (2H, m), 7.75-7.73 (1H, m), 7.70-7.65 (2H, m), 7.57-7.52 (1H, m), 7.46-7.41 (1H, m), 7.41-7.37 (1H, m), 3.79-3.47 (7H, m), 3.30-3.18 (1H, m), 2.26-2.00 (2H, m). |
| 207 | 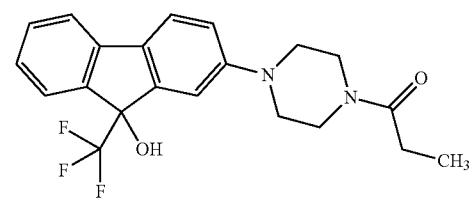 [SMILES: CCC(=O)N1CCN(c2ccc3c(c2)C(O)(C(F)(F)F)c2ccccc2-3)CC1] | $^1$H-NMR (DMSO-D$_6$) δ: 7.70-7.66 (2H, m), 7.58-7.54 (1H, m), 7.45-7.40 (1H, m), 7.28-7.23 (1H, m), 7.21-7.19 (1H, m), 7.15 (1H, s), 7.07 (1H, dd, J = 8.6, 2.3 Hz), 3.67-3.56 (4H, m), 3.27-3.13 (4H, m), 2.37 (2H, q, J = 7.4 Hz), 1.02 (3H, t, J = 7.4 Hz). |
| 208 | 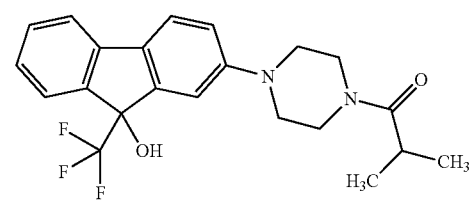 [SMILES: CC(C)C(=O)N1CCN(c2ccc3c(c2)C(O)(C(F)(F)F)c2ccccc2-3)CC1] | $^1$H-NMR (DMSO-D$_6$) δ: 7.71-7.67 (2H, m), 7.58-7.55 (1H, m), 7.45-7.40 (1H, m), 7.28-7.23 (1H, m), 7.22-7.20 (1H, m), 7.15 (1H, s), 7.08 (1H, dd, J = 8.5, 2.2 Hz), 3.74-3.58 (4H, m), 3.27-3.13 (4H, m), 2.96-2.88 (1H, m), 1.04 (3H, s), 1.02 (3H, s). |

TABLE 1-30-continued

| compound No. | structural formula | NMR |
|---|---|---|
| 209 | 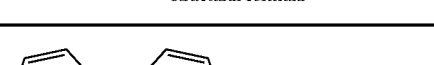 | $^1$H-NMR (DMSO-D$_6$) δ: 7.71-7.66 (2H, m), 7.58-7.54 (1H, m), 7.45-7.41 (1H, m), 7.28-7.23 (1H, m), 7.21-7.19 (1H, m), 7.14 (1H, s), 7.07 (1H, dd, J = 8.3, 2.3 Hz), 3.75-3.69 (4H, m), 3.23-3.16 (4H, m), 1.23 (9H, s). |

TABLE 1-31

| compound No. | structural formula | NMR |
|---|---|---|
| 210 | | $^1$H-NMR (DMSO-D$_6$) δ: 7.71-7.66 (2H, m), 7.58-7.54 (1H, m), 7.45-7.40 (1H, m), 7.28-7.23 (1H, m), 7.21-7.19 (1H, m), 7.15 (1H, s), 7.07 (1H, dd, J = 8.5, 2.2 Hz), 3.64 (3H, s), 3.56-3.51 (4H, m), 3.23-3.18 (4H, m). |
| 211 | | $^1$H-NMR (DMSO-D$_6$) δ: 7.70-7.66 (2H, m), 7.58-7.55 (1H, m), 7.45-7.40 (1H, m), 7.28-7.23 (1H, m), 7.21-7.19 (1H, m), 7.15 (1H, s), 7.07 (1H, dd, J = 8.3, 2.3 Hz), 4.08 (2H, q, J = 7.1 Hz), 3.57-3.50 (4H, m), 3.24-3.17 (4H, m), 1.21 (3H, t, J = 7.1 Hz). |
| 212 | | $^1$H-NMR (DMSO-D$_6$) δ: 7.71-7.66 (2H, m), 7.58-7.55 (1H, m), 7.45-7.40 (1H, m), 7.28-7.23 (1H, m), 7.21-7.19 (1H, m), 7.15 (1H, s), 7.06 (1H, dd, J = 8.3, 2.1 Hz), 4.86-4.74 (1H, m), 3.55-3.49 (4H, m), 3.24-3.15 (4H, m), 1.21 (6H, d, J = 6.3 Hz). |
| 213 | | $^1$H-NMR (DMSO-D$_6$) δ: 8.88 (1H, d, J = 2.0 Hz), 8.17-8.16 (1H, m), 7.97-7.94 (1H, m), 7.78-7.75 (1H, m), 7.68-7.58 (2H, m), 7.64 (1H, s), 4.45-4.35 (2H, m), 4.15-4.06 (2H, m), 2.34-2.26 (2H, m). |
| 214 | | $^1$H-NMR (CDCl$_3$) δ: 7.92-7.85 (3H, m), 7.78-7.65 (5H, m), 7.61-7.56 (1H, m), 7.54-7.49 (1H, m), 7.43-7.38 (1H, m), 2.87 (1H, br s). |

TABLE 1-31-continued

| compound No. | structural formula | NMR |
|---|---|---|
| 215 | (fluorene with C(CF3)(OH) at 9-position, and C(=O)-N(pyrrolidine-3-OH) substituent) | ¹H-NMR (DMSO-D₆) δ: 7.94-7.91 (2H, m), 7.77-7.73 (1H, m), 7.70-7.65 (2H, m), 7.57-7.52 (1H, m), 7.46-7.41 (1H, m), 7.40-7.35 (1H, m), 5.03 (0.5H, d, J = 3.7 Hz), 4.97 (0.5H, d, J = 3.3 Hz), 4.37-4.32 (0.5H, m), 4.29-4.24 (0.5H, m), 3.69-3.50 (2H, m), 3.49-3.20 (2H, m), 2.03-1.76 (2H, m). |
| 216 | (fluorene with C(CF3)(OH) at 9-position, and C(=O)-N(pyrrolidine-3-N(CH3)2) substituent) | ¹H-NMR (DMSO-D₆) δ: 7.94-7.90 (2H, m), 7.76-7.72 (1H, m), 7.71-7.64 (2H, m), 7.57-7.52 (1H, m), 7.46-7.41 (1H, m), 7.40-7.34 (1H, m), 3.77-3.60 (1H, m), 3.57-3.43 (2H, m), 3.30-3.20 (1H, m), 2.78-2.63 (1H, m), 2.19 (3H, s), 2.10-2.09 (3H, m), 2.07-1.98 (1H, m), 1.81-1.68 (1H, m). |

TABLE 1-32

| compound No. | structural formula | NMR |
|---|---|---|
| 217 | (fluorene with C(CF3)(OH) at 9-position, and C(=O)-N(pyrrolidine-3-COOH) substituent) | ¹H-NMR (DMSO-D₆) δ: 12.52 (1H, br s), 7.95-7.91 (2H, m), 7.76-7.73 (1H, m), 7.71-7.64 (2H, m), 7.57-7.52 (1H, m), 7.46-7.41 (1H, m), 7.40-7.35 (1H, m), 3.77-3.47 (4H, m), 3.20-3.05 (1H, m), 2.24-1.96 (2H, m). |
| 218 | (fluorene with C(CF3)(OH) at 9-position, and N(piperidine-4-C(=O)OCH3) substituent) | ¹H-NMR (DMSO-D₆) δ: 7.69-7.62 (2H, m), 7.57-7.53 (1H, m), 7.44-7.39 (1H, m), 7.27-7.22 (1H, m), 7.20-7.16 (1H, m), 7.11 (1H, s), 7.06 (1H, dd, J = 8.6, 2.4 Hz), 3.74-3.66 (2H, m), 3.63 (3H, s), 2.90-2.82 (2H, m), 2.61-2.52 (1H, m), 2.00-1.90 (2H, m), 1.74-1.62 (2H, m). |
| 219 | (fluorene with C(CF3)(OH) at 9-position, F substituent, and C(=O)OCH3 substituent) | ¹H-NMR (CDCl₃) δ: 8.37 (1H, dd, J = 8.8, 5.1 Hz), 7.93 (1H, dd, J = 7.8, 1.2 Hz), 7.87-7.84 (1H, m), 7.44-7.37 (2H, m), 7.19-7.13 (1H, m), 4.01 (3H, s), 2.77 (1H, s). |

TABLE 1-32-continued

| compound No. | structural formula | NMR |
|---|---|---|
| 220 | | ¹H-NMR (CDCl₃) δ: 8.12 (1H, dd, J = 10.4, 2.4 Hz), 7.95 (1H, dd, J = 7.9, 1.1 Hz), 7.89-7.86 (1H, m), 7.70-7.65 (1H, m), 7.47-7.41 (1H, m), 7.12-7.07 (1H, m), 4.02 (3H, s), 2.72 (1H, s). |
| 221 | | ¹H-NMR (CDCl₃) δ: 8.36-8.32 (1H, m), 7.94 (1H, dd, J = 8.7, 5.2 Hz), 7.75-7.72 (1H, m), 7.53-7.48 (1H, m), 7.47-7.42 (1H, m), 7.09-7.04 (1H, m), 4.01 (3H, s), 3.21-3.19 (1H, m). |
| 222 | | ¹H-NMR (DMSO-D₆) δ: 7.78-7.71 (2H, m), 7.61-7.57 (1H, m), 7.48-7.43 (2H, m), 7.34-7.25 (2H, m), 3.72-3.63 (2H, m), 3.08 (2H, br s), 2.57-2.46 (1H, m), 2.04-1.96 (2H, m), 1.89-1.72 (2H, m). |
| 223 | | ¹H-NMR (DMSO-D₆) δ: 7.68-7.63 (2H, m), 7.57-7.53 (1H, m), 7.44-7.39 (1H, m), 7.26-7.22 (1H, m), 7.19-7.17 (1H, m), 7.11 (1H, s), 7.06 (1H, dd, J = 8.5, 2.3 Hz), 4.09 (2H, q, J = 7.1 Hz), 3.74-3.66 (2H, m), 2.90-2.82 (2H, m), 2.58-2.48 (1H, m), 1.98-1.90 (2H, m), 1.73-1.62 (2H, m), 1.20 (3H, t, J = 7.1 Hz). |

TABLE 1-33

| compound No. | structural formula | NMR |
|---|---|---|
| 224 | | ¹H-NMR (CDCl₃) δ: 7.93-7.91 (1H, m), 7.79-7.70 (8H, m), 7.54-7.50 (1H, m), 7.43-7.39 (1H, m), 2.81 (1H, br s). |
| 225 | | ¹H-NMR (DMSO-D₆) δ: 7.92 (2H, d, J = 7.7 Hz), 7.75-7.72 (1H, m), 7.69-7.65 (2H, m), 7.57-7.52 (1H, m), 7.46-7.41 (1H, m), 7.40-7.35 (1H, m), 4.75-4.63 (1H, m), 3.64-3.21 (6H, m), 2.42-2.24 (1H, m), 2.00-1.85 (1H, m), 1.72-1.59 (1H, m). |

TABLE 1-33-continued

| compound No. | structural formula | NMR |
|---|---|---|
| 226 | | ¹H-NMR (DMSO-D₆) δ: 7.92 (2H, d, J = 7.4 Hz), 7.76-7.73 (1H, m), 7.70-7.64 (2H, m), 7.56-7.36 (4H, m), 7.00-6.91 (1H, m), 3.75-3.43 (4H, m), 3.04-2.90 (1H, m), 2.17-1.91 (2H, m). |
| 227 | | ¹H-NMR (DMSO-D₆) δ: 8.01-7.96 (0.5H, m), 7.92 (2H, d, J = 7.7 Hz), 7.90-7.85 (0.5H, m), 7.75-7.72 (1H, m), 7.70-7.64 (2H, m), 7.57-7.52 (1H, m), 7.46-7.35 (2H, m), 3.73-3.43 (4H, m), 3.03-2.88 (1H, m), 2.62 (1.5H, d, J = 4.4 Hz), 2.55 (1.5H, d, J = 4.4 Hz), 2.16-1.91 (2H, m). |
| 228 | | ¹H-NMR (DMSO-D₆) δ: 7.94-7.90 (2H, m), 7.75-7.72 (1H, m), 7.69-7.64 (2H, m), 7.57-7.52 (1H, m), 7.46-7.41 (1H, m), 7.38-7.36 (1H, m), 3.62-3.37 (3H, m), 3.24-3.08 (2H, m), 2.30 (1.4H, s), 2.18 (1.6H, d, J = 4.9 Hz), 2.05-1.87 (1H, m), 1.79-1.68 (1H, m). |
| 229 | | ¹H-NMR (DMSO-D₆) δ: 7.94-7.91 (2H, m), 7.76-7.72 (1H, m), 7.71-7.64 (2H, m), 7.57-7.52 (1H, m), 7.46-7.36 (2H, m), 3.77-3.40 (5H, m), 3.07 (1.5H, s), 2.98 (1.5H, s), 2.86 (1.5H, s), 2.80 (1.5H, s), 2.22-2.03 (1H, m), 2.01-1.89 (1H, m). |
| 230 | | ¹H-NMR (DMSO-D₆) δ: 7.66 (1H, d, J = 7.3 Hz), 7.64 (1H, d, J = 8.6 Hz), 7.57-7.53 (1H, m), 7.44-7.39 (1H, m), 7.29 (1H, s), 7.26-7.21 (1H, m), 7.19-7.16 (1H, m), 7.11 (1H, s), 7.05 (1H, dd, J = 8.5, 2.3 Hz), 6.77 (1H, br s), 3.81-3.73 (2H, m), 2.81-2.73 (2H, m), 2.33-2.24 (1H, m), 1.84-1.77 (2H, m), 1.71-1.60 (2H, m). |

TABLE 1-34

| compound No. | structural formula | NMR |
|---|---|---|
| 231 | | ¹H-NMR (DMSO-D₆) δ: 7.77-7.72 (1H, m), 7.68-7.62 (2H, m), 7.57-7.53 (1H, m), 7.44-7.39 (1H, m), 7.26-7.21 (1H, m), 7.19-7.16 (1H, m), 7.11 (1H, s), 7.05 (1H, dd, J = 8.6, 2.4 Hz), 3.82-3.73 (2H, m), 2.81-2.72 (2H, m), 2.58 (3H, d, J = 4.6 Hz), 2.34-2.24 (1H, m), 1.81-1.74 (2H, m), 1.73-1.61 (2H, m). |

TABLE 1-34-continued

| compound No. | structural formula | NMR |
|---|---|---|
| 232 | | $^1$H-NMR (DMSO-D$_6$) δ: 7.68-7.62 (2H, m), 7.57-7.53 (1H, m), 7.45-7.39 (1H, m), 7.27-7.21 (1H, m), 7.19-7.16 (1H, m), 7.11 (1H, s), 7.05 (1H, dd, J = 8.4, 2.2 Hz), 3.83-3.74 (2H, m), 3.06 (3H, s), 2.90-2.78 (3H, m), 2.82 (3H, s), 1.77-1.60 (4H, m). |
| 233 | | $^1$H-NMR (DMSO-D$_6$) δ: 8.33-8.30 (1H, m), 8.11-8.07 (2H, m), 7.99 (1H, d, J = 1.5 Hz), 7.97-7.92 (3H, m), 7.77-7.74 (1H, m), 7.65-7.60 (1H, m), 7.58 (1H, s), 7.56-7.51 (1H, m), 4.36 (2H, q, J = 7.1 Hz), 1.36 (3H, t, J = 7.2 Hz). |
| 234 | | $^1$H-NMR (DMSO-D$_6$) δ: 13.08 (1H, br s), 8.32-8.29 (1H, m), 8.09-8.05 (2H, m), 7.98 (1H, d, J = 1.5 Hz), 7.96-7.94 (1H, m), 7.92-7.88 (2H, m), 7.77-7.73 (1H, m), 7.65-7.60 (1H, m), 7.59-7.50 (2H, m). |
| 245 | | $^1$H-NMR (DMSO-D$_6$) δ: 7.92 (1H, s), 7.88-7.85 (1H, m), 7.73-7.70 (1H, m), 7.63-7.59 (1H, m), 7.58-7.53 (1H, m), 7.45 (1H, s), 4.08 (3H, s), 4.06-3.95 (4H, m), 2.30-2.20 (2H, m). |
| 236 | | $^1$H-NMR (DMSO-D$_6$) δ: 8.01 (1H, d, J = 7.9 Hz), 7.99-7.92 (5H, m), 7.83 (1H, dd, J = 8.1, 1.6 Hz), 7.70-7.67 (1H, m), 7.58-7.53 (1H, m), 7.46-7.42 (1H, m), 7.40 (1H, s), 3.90 (3H, s). |
| 237 | | $^1$H-NMR (DMSO-D$_6$) δ: 7.87-7.83 (2H, m), 7.65-7.61 (1H, m), 7.53-7.49 (1H, m), 7.40-7.33 (2H, m), 7.34 (1H, s), 7.26 (1H, dd, J = 8.2, 2.2 Hz), 3.07 (3H, s), 2.93 (3H, s). |

TABLE 1-35

| compound No. | structural formula | NMR |
|---|---|---|
| 238 | | ¹H-NMR (DMSO-D₆) δ: 13.44 (1H, br s), 8.02-7.99 (1H, m), 7.97-7.92 (4H, m), 7.89-7.86 (1H, m), 7.80-7.77 (1H, m), 7.70-7.66 (1H, m), 7.57-7.52 (1H, m), 7.46-7.41 (1H, m), 7.39 (1H, br s). |
| 239 | | ¹H-NMR (DMSO-D₆) δ: 7.99 (1H, d, J = 7.9 Hz), 7.95-7.88 (4H, m), 7.81 (1H, d, J = 1.6 Hz), 7.73 (1H, dd, J = 8.0, 1.5 Hz), 7.69-7.62 (2H, m), 7.59-7.57 (1H, m), 7.55-7.52 (1H, m), 7.45-7.40 (1H, m), 7.38 (1H, s). |
| 240 | | ¹H-NMR (DMSO-D₆) δ: 8.43-8.37 (1H, m), 8.01-7.97 (1H, m), 7.96-7.88 (3H, m), 7.83-7.81 (1H, m), 7.75-7.71 (1H, m), 7.70-7.66 (1H, m), 7.58-7.52 (2H, m), 7.45-7.40 (1H, m), 7.37 (1H, s), 2.79 (3H, d, J = 4.4 Hz). |
| 241 | | ¹H-NMR (DMSO-D₆) δ: 7.99 (1H, d, J = 7.9 Hz), 7.95-7.90 (3H, m), 7.86 (1H, d, J = 1.6 Hz), 7.76 (1H, dd, J = 8.1, 1.6 Hz), 7.69-7.66 (1H, m), 7.57-7.52 (1H, m), 7.48 (1H, d, J = 7.9 Hz), 7.45-7.40 (1H, m), 7.38 (1H, s), 3.04 (3H, s), 2.84 (3H, s). |
| 242 | | ¹H-NMR (DMSO-D₆) δ: 8.77 (1H, dd, J = 4.9, 1.8 Hz), 8.68 (1H, br s), 7.94 (2H, br s), 7.72-7.68 (1H, m), 7.64-7.59 (1H, m), 7.58 (1H, d, J = 1.5 Hz), 7.48 (1H, s), 7.42-7.37 (1H, m), 7.31-7.26 (1H, m), 6.71 (1H, d, J = 7.5 Hz), 4.42-4.33 (2H, m), 4.13-4.05 (2H, m), 2.34-2.24 (2H, m). |
| 243 | | ¹H-NMR (DMSO-D₆) δ: 8.78-8.76 (1H, m), 8.70-8.66 (1H, m), 7.98-7.91 (1H, m), 7.72 (1H, d, J = 1.1 Hz), 7.68 (1H, d, J = 7.5 Hz), 7.63-7.59 (1H, m), 7.54-7.50 (2H, m), 7.40-7.35 (1H, m), 7.29-7.24 (1H, m), 6.63 (1H, d, J = 7.7 Hz). |

TABLE 1-35-continued

| compound No. | structural formula | NMR |
|---|---|---|
| 244 | | ¹H-NMR (DMSO-D₆) δ: 7.79-7.76 (1H, m), 7.71 (1H, d, J = 7.9 Hz), 7.62-7.58 (1H, m), 7.49-7.45 (1H, m), 7.36-7.30 (2H, m), 7.19 (1H, dd, J = 7.9, 1.5 Hz), 7.16 (1H, s), 2.06-1.98 (1H, m), 1.04-0.98 (2H, m), 0.75-0.68 (2H, m). |

TABLE 1-36

| compound No. | structural formula | NMR |
|---|---|---|
| 245 | | ¹H-NMR (CDCl₃) δ: 7.98-7.96 (1H, m), 7.93 (1H, s), 7.79-7.76 (1H, m), 7.75-7.67 (3H, m), 7.53-7.49 (1H, m), 7.42-7.37 (2H, m), 2.96 (1H, br s). |
| 246 | | ¹H-NMR (DMSO-D₆) δ: 7.95-7.90 (2H, m), 7.80-7.64 (3H, m), 7.57-7.52 (1H, m), 7.46-7.41 (1H, m), 7.39-7.34 (1H, m), 5.16-4.47 (1H, m), 3.77-3.34 (4H, m), 2.92-2.71 (3H, m), 2.14-1.91 (5H, m). |
| 247 | | ¹H-NMR (CDCl₃) δ: 8.42 (1H, s), 8.21-8.18 (1H, m), 7.80-7.76 (2H, m), 7.75-7.72 (1H, m), 7.56-7.52 (1H, m), 7.49-7.44 (1H, m), 3.48 (1H, br s), 2.37 (3H, s). |
| 248 | | ¹H-NMR (CDCl₃) δ: 7.70-7.67 (2H, m), 7.63 (1H, d, J = 7.7 Hz), 7.58 (1H, d, J = 7.9 Hz), 7.48-7.44 (1H, m), 7.43-7.40 (1H, m), 7.36-7.31 (1H, m), 6.49-6.43 (1H, m), 6.38-6.29 (1H, m), 2.70 (1H, s), 1.92 (3H, d, J = 6.3 Hz). |
| 249 | | ¹H-NMR (CDCl₃) δ: 7.67-7.64 (1H, m), 7.57-7.53 (2H, m), 7.46-7.41 (1H, m), 7.30-7.23 (2H, m), 7.00-6.96 (1H, m), 4.02 (2H, t, J = 6.4 Hz), 2.70 (1H, s), 1.84-1-76 (2H, m), 1.57-1.47 (2H, m), 1.02-0.97 (3H, m). |

TABLE 1-36-continued
| compound No. | structural formula | NMR |
|---|---|---|
| 250 | 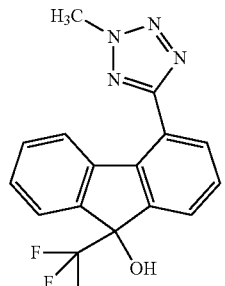 | ¹H-NMR (DMSO-D$_6$) δ: 7.85 (1H, d, J = 7.7 Hz), 7.73 (1H, d, J = 7.7 Hz), 7.70 (1H, d, J = 7.2 Hz), 7.60-7.54 (2H, m), 7.45-7.36 (2H, m), 7.37 (1H, s), 4.54 (3H, s). |
| 251 | | ¹H-NMR (DMSO-D$_6$) δ: 7.93 (1H, d, J = 7.7 Hz), 7.73-7.68 (2H, m), 7.66-7.61 (1H, m), 7.48 (1H, s), 7.45-7.41 (1H, m), 7.39-7.34 (1H, m), 6.44 (1H, d, J = 7.4 Hz), 3.92 (3H, s). |
TABLE 1-37
| compound No. | structural formula | NMR |
|---|---|---|
| 252 | 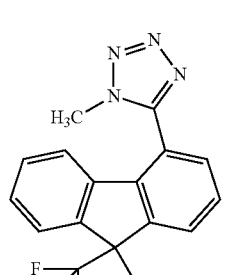 | ¹H-NMR (CDCl$_3$) δ: 7.88-7.86 (1H, m), 7.73-7.69 (1H, m), 7.67-7.58 (3H, m), 7.56-7.53 (2H, m), 7.50-7.46 (1H, m), 7.41-7.33 (3H, m), 7.30-7.26 (1H, m), 7.20 (1H, d, J = 16.5 Hz), 7.15 (1H, d, J = 16.3 Hz), 2.75 (1H, br s). |
| 253 | | ¹H-NMR (DMSO-D$_6$) δ: 7.75-7.72 (2H, m), 7.60-7.57 (1H, m), 7.47-7.43 (1H, m), 7.31-7.27 (1H, m), 7.20 (1H, s), 7.15-7.13 (1H, m), 7.05 (1H, dd, J = 8.4, 2.4 Hz), 3.84 (2H, d, J = 6.2 Hz), 1.86-1.64 (6H, m), 1.32-1.02 (5H, m). |
| 254 | | ¹H-NMR (DMSO-D$_6$) δ: 7.76-7.72 (2H, m), 7.60-7.56 (1H, m), 7.47-7.43 (1H, m), 7.31-7.27 (1H, m), 7.20 (1H, s), 7.16-7.14 (1H, m), 7.06 (1H, dd, J = 8.4, 2.4 Hz), 3.91 (2H, d, J = 7.1 Hz), 2.39-2.27 (1H, m), 1.84-1.74 (2H, m), 1.68-1.50 (4H, m), 1.41-1.31 (2H, m). |

TABLE 1-37-continued

| compound No. | structural formula | NMR |
|---|---|---|
| 255 | | ¹H-NMR (DMSO-D₆) δ: 7.76-7.72 (2H, m), 7.60-7.56 (1H, m), 7.48-7.43 (1H, m), 7.32-7.27 (1H, m), 7.21 (1H, s), 7.16-7.14 (1H, m), 7.06 (1H, dd, J = 8.4, 2.4 Hz), 4.01 (2H, d, J = 6.6 Hz), 2.78-2.70 (1H, m), 2.14-2.04 (2H, m), 1.97-1.80 (4H, m). |
| 256 | | ¹H-NMR (DMSO-D₆) δ: 7.76-7.72 (2H, m), 7.60-7.56 (1H, m), 7.48-7.43 (1H, m), 7.31-7.26 (1H, m), 7.21 (1H, s), 7.15-7.13 (1H, m), 7.05 (1H, dd, J = 8.3, 2.3 Hz), 3.88 (2H, d, J = 7.0 Hz), 1.29-1.19 (1H, m), 0.61-0.56 (2H, m), 0.38-0.33 (2H, m). |
| 257 | | ¹H-NMR (CDCl₃) δ: 7.67-7.64 (1H, m), 7.57-7.53 (2H, m), 7.46-7.41 (1H, m), 7.30-7.25 (1H, m), 7.24-7.22 (1H, m), 6.99-6.95 (1H, m), 4.18-4.12 (2H, m), 4.07 (2H, t, J = 6.0 Hz), 2.77 (1H, s), 2.53 (2H, t, J = 7.3 Hz), 2.17-2.10 (2H, m), 1.29-1.24 (3H, m). |
| 258 | | ¹H-NMR (DMSO-D₆) δ: 12.16 (1H, br s), 7.76-7.73 (2H, m), 7.61-7.56 (1H, m), 7.48-7.43 (1H, m), 7.32-7.27 (1H, m), 7.25-7.21 (1H, m), 7.18-7.14 (1H, m), 7.06 (1H, dd, J = 8.2, 2.0 Hz), 4.05 (2H, t, J = 6.4 Hz), 2.41 (2H, t, J = 7.3 Hz), 2.01-1.93 (2H, m). |

TABLE 1-38

| compound No. | structural formula | NMR |
|---|---|---|
| 259 | | ¹H-NMR (DMSO-D₆) δ: 7.75-7.71 (2H, m), 7.60-7.56 (1H, m), 7.48-7.43 (1H, m), 7.32-7.27 (1H, m), 7.21 (1H, s), 7.15-7.12 (1H, m), 7.08-7.05 (1H, m), 4.43-4.37 (1H, m), 2.00-1.91 (2H, m), 1.77-1.68 (2H, m), 1.59-1.22 (6H, m). |
| 260 | | ¹H-NMR (DMSO-D₆) δ: 7.75-7.71 (2H, m), 7.60-7.56 (1H, m), 7.48-7.43 (1H, m), 7.32-7.27 (1H, m), 7.21 (1H, s), 7.15-7.12 (1H, m), 7.08-7.05 (1H, m), 4.43-4.37 (1H, m), 2.00-1.91 (2H, m), 1.77-1.68 (2H, m), 1.59-1.22 (6H, m). |

TABLE 1-38-continued

| compound No. | structural formula | NMR |
|---|---|---|
| 261 | (fluorene with CF3, OH, and O-CH2-thiophene substituent) | $^1$H-NMR (DMSO-D$_6$) δ: 7.78-7.74 (2H, m), 7.61-7.56 (2H, m), 7.49-7.44 (1H, m), 7.33-7.28 (1H, m), 7.26-7.23 (2H, m), 7.23 (1H, s), 7.17 (1H, dd, J = 8.4, 2.4 Hz), 7.05 (1H, dd, J = 5.1, 3.5 Hz), 5.38 (1H, d, J = 12.1 Hz), 5.35 (1H, d, J = 12.1 Hz). |
| 262 | (fluorene with CF3, OH, and O-benzyl substituent) | $^1$H-NMR (DMSO-D$_6$) δ: 7.79-7.73 (2H, m), 7.61-7.57 (1H, m), 7.51-7.23 (9H, m), 7.16 (1H, dd, J = 8.3, 2.3 Hz), 5.17 (2H, s). |
| 263 | (fluorene with CF3, OH, and N-methylpyrazole substituent) | $^1$H-NMR (CDCl$_3$) δ: 7.72-7.67 (2H, m), 7.48 (1H, s), 7.47 (1H, s), 7.36-7.22 (5H, m), 4.00 (3H, s), 3.20 (1H, br s). |
| 264 | (fluorene with CF3, OH, and O-isobutyl substituent) | $^1$H-NMR (CDCl$_3$) δ: 7.67-7.63 (1H, m), 7.57-7.53 (2H, m), 7.45-7.41 (1H, m), 7.29-7.25 (1H, m), 7.24-7.23 (1H, m), 6.98 (1H, dd, J = 8.3, 2.3 Hz), 3.78 (2H, d, J = 6.6 Hz), 2.66 (1H, s), 2.17-2.05 (1H, m), 1.06 (3H, d, J = 0.9 Hz), 1.04 (3H, d, J = 0.9 Hz). |
| 265 | (fluorene with CF3, OH, and O-propyl substituent) | $^1$H-NMR (CDCl$_3$) δ: 7.67-7.63 (1H, m), 7.57-7.53 (2H, m), 7.46-7.41 (1H, m), 7.30-7.23 (2H, m), 6.99 (1H, dd, J = 8.2, 2.4 Hz), 3.98 (2H, t, J = 6.5 Hz), 2.66 (1H, s), 1.89-1.79 (2H, m), 1.06 (3H, t, J = 7.4 Hz). |

TABLE 1-39

| compound No. | structural formula | NMR |
|---|---|---|
| 266 | (fluorene with CF3, OH, and 3,5-dichlorophenyl substituent) | $^1$H-NMR (CDCl$_3$) δ: 7.87-7.85 (1H, m), 7.76-7.64 (4H, m), 7.54-7.49 (3H, m), 7.43-7.36 (2H, m), 2.77 (1H, s). |

TABLE 1-39-continued

| compound No. | structural formula | NMR |
|---|---|---|
| 267 | (fluorene with 5-methyl-1,3,4-oxadiazol-2-yl substituent and C(CF$_3$)(OH) at 9-position) | $^1$H-NMR (DMSO-D$_6$) δ: 8.17-8.13 (1H, m), 7.92-7.89 (1H, m), 7.88 (1H, dd, J = 7.9, 1.1 Hz), 7.74-7.71 (1H, m), 7.63-7.58 (1H, m), 7.53-7.45 (2H, m), 7.42 (1H, s), 2.66 (3H, s). |
| 268 | (fluorene with cyclopropyl substituent and C(CF$_3$)(OH) at 9-position) | $^1$H-NMR (DMSO-D$_6$) δ: 8.18 (1H, d, J = 7.7 Hz), 7.70-7.66 (1H, m), 7.56-7.48 (2H, m), 7.43-7.38 (1H, m), 7.33-7.25 (2H, m), 7.15 (1H, s), 2.37-2.29 (1H, m), 1.17-1.05 (2H, m), 0.85-0.79 (1H, m), 0.72-0.65 (1H, m). |
| 269 | (fluorene with 3-methylpyrrolidin-1-yl substituent and C(CF$_3$)(OH) at 9-position) | $^1$H-NMR (CDCl$_3$) δ: 7.63-7.59 (1H, m), 7.47 (2H, d, J = 8.1 Hz), 7.41-7.36 (1H, m), 7.20-7.16 (1H, m), 6.87-6.85 (1H, m), 6.58 (1H, dd, J = 8.5, 2.0 Hz), 3.55-3.34 (3H, m), 2.97-2.91 (1H, m), 2.63 (1H, s), 2.48-2.38 (1H, m), 2.20-2.12 (1H, m), 1.71-1.61 (1H, m), 1.15 (3H, d, J = 6.7 Hz). |
| 270 | (fluorene with O-(CH$_2$)$_4$-OH substituent and C(CF$_3$)(OH) at 9-position) | $^1$H-NMR (DMSO-D$_6$) δ: 7.76-7.72 (2H, m), 7.60-7.57 (1H, m), 7.48-7.43 (1H, m), 7.32-7.27 (1H, m), 7.23 (1H, s), 7.16-7.14 (1H, m), 7.06 (1H, dd, J = 8.3, 2.1 Hz), 4.46 (1H, t, J = 5.1 Hz), 4.04 (2H, t, J = 6.5 Hz), 3.50-3.44 (2H, m), 1.82-1.73 (2H, m), 1.63-1.54 (2H, m). |
| 271 | (fluorene with Cl, piperazinyl-isobutyryl substituent and C(CF$_3$)(OH) at 9-position) | $^1$H-NMR (DMSO-D$_6$) δ: 8.07 (1H, d, J = 7.5 Hz), 7.65-7.61 (1H, m), 7.53-7.47 (1H, m), 7.37-7.33 (1H, m), 7.31 (1H, s), 7.20-7.18 (1H, m), 7.03 (1H, d, J = 2.2 Hz), 3.74-3.68 (4H, m), 3.29-3.24 (4H, m), 1.23 (9H, s). |
| 272 | (fluorene with Br, Cl substituents and C(CF$_3$)(OH) at 9-position) | $^1$H-NMR (CDCl$_3$) δ: 8.47 (1H, d, J = 7.7 Hz), 7.73-7.70 (1H, m), 7.65 (2H, s), 7.57-7.52 (1H, m), 7.46-7.42 (1H, m), 2.70 (1H, s). |

TABLE 1-40
| compound No. | structural formula | NMR |
|---|---|---|
| 273 | 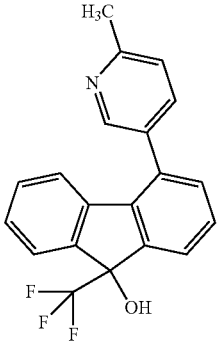 [SMILES: Cc1ccc(-c2cccc3c2-c2ccccc2C3(O)C(F)(F)F)cn1] | ¹H-NMR (DMSO-D₆) δ: 8.53-8.47 (1H, m), 7.82-7.75 (1H, m), 7.72 (1H, d, J = 7.5 Hz), 7.67 (1H, d, J = 7.5 Hz), 7.50-7.46 (1H, m), 7.46-7.42 (1H, m), 7.36-7.31 (2H, m), 7.29 (1H, s), 7.28-7.23 (1H, m), 6.76 (1H, d, J = 7.5 Hz), 2.60 (3H, s). |
| 274 | 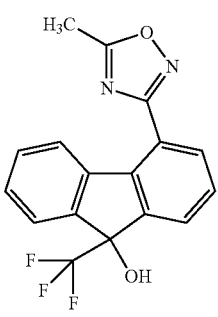 [SMILES: Cc1nc(-c2cccc3c2-c2ccccc2C3(O)C(F)(F)F)no1] | ¹H-NMR (DMSO-D₆) δ: 7.90-7.86 (1H, m), 7.79-7.68 (3H, m), 7.59-7.54 (1H, m), 7.48-7.41 (2H, m), 7.39 (1H, s), 2.77 (3H, s). |
| 275 | 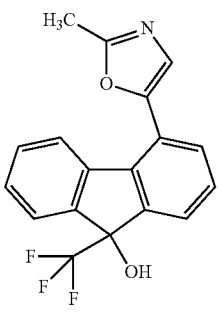 [SMILES: Cc1ncc(-c2cccc3c2-c2ccccc2C3(O)C(F)(F)F)o1] | ¹H-NMR (DMSO-D₆) δ: 7.77-7.74 (1H, m), 7.71-7.67 (1H, m), 7.54 (1H, dd, J = 7.7, 1.3 Hz), 7.51-7.47 (1H, m), 7.47-7.39 (2H, m), 7.39 (1H, s), 7.33 (1H, s), 7.25 (1H, dd, J = 6.5, 2.1 Hz), 2.55 (3H, s). |
| 276 | 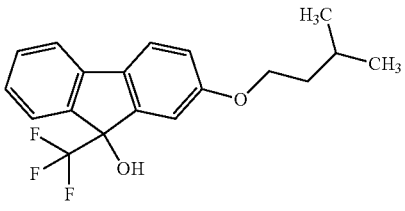 [SMILES: CC(C)CCOc1ccc2c(c1)C(O)(C(F)(F)F)c1ccccc1-2] | ¹H-NMR (CDCl₃) δ: 7.68-7.64 (1H, m), 7.57-7.53 (2H, m), 7.46-7.41 (1H, m), 7.30-7.23 (2H, m), 7.00-6.97 (1H, m), 4.07-4.02 (2H, m), 2.69 (1H, s), 1.92-1.81 (1H, m), 1.74-1.68 (2H, m), 1.00-0.96 (6H, m). |
| 277 | 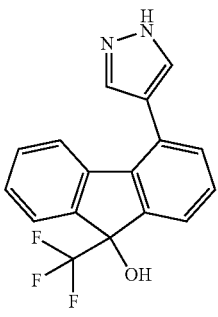 [SMILES: OC1(C(F)(F)F)c2ccccc2-c2c(-c3cn[nH]c3)cccc21] | ¹H-NMR (DMSO-D₆) δ: 13.15 (1H, br s), 7.99 (1H, br s), 7.70-7.58 (3H, m), 7.41-7.27 (4H, m), 7.25-7.20 (2H, m). |

TABLE 1-40-continued

| compound No. | structural formula | NMR |
| --- | --- | --- |
| 278 | (fluorene with C(OH)(F)(CF2... ) and 2-O-pentyl chain ending in CH3) | ¹H-NMR (CDCl₃) δ: 7.68-7.64 (1H, m), 7.57-7.53 (2H, m), 7.46-7.40 (1H, m), 7.30-7.23 (2H, m), 7.00-6.97 (1H, m), 4.04-3.99 (2H, m), 2.69 (1H, br s), 1.86-1.78 (2H, m), 1.52-1.35 (4H, m), 0.98-0.92 (3H, m). |
| 279 | (fluorene with C(OH)(CF3) and 2-O-CH2-C(CH3)3) | ¹H-NMR (CDCl₃) δ: 7.68-7.64 (1H, m), 7.58-7.53 (2H, m), 7.46-7.41 (1H, m), 7.30-7.24 (2H, m), 7.01-6.98 (1H, m), 3.66 (2H, s), 2.70 (1H, s), 1.07 (9H, s). |

TABLE 1-41

| compound No. | structural formula | NMR |
| --- | --- | --- |
| 280 | (fluorene with C(OH)(CF3) and 2-O-(CH2)3-C(=O)NH2) | ¹H-NMR (DMSO-D₆) δ: 7.77-7.72 (2H, m), 7.61-7.57 (1H, m), 7.48-7.43 (1H, m), 7.33 (1H, br s), 7.32-7.27 (1H, m), 7.25-7.22 (1H, m), 7.16-7.14 (1H, m), 7.08-7.04 (1H, m), 6.78 (1H, br s), 4.03 (2H, t, J = 6.3 Hz), 2.25 (2H, t, J = 7.2 Hz), 1.99-1.91 (2H, m). |
| 281 | (fluorene with C(OH)(CF3) and 2-O-(CH2)3-C(=O)NHCH3) | ¹H-NMR (DMSO-D₆) δ: 7.79 (1H, br s), 7.77-7.72 (2H, m), 7.61-7.57 (1H, m), 7.48-7.43 (1H, m), 7.32-7.27 (1H, m), 7.25-7.22 (1H, m), 7.16-7.13 (1H, m), 7.08-7.04 (1H, m), 4.05-3.99 (2H, m), 2.60-2.56 (3H, m), 2.28-2.23 (2H, m), 2.01-1.92 (2H, m). |
| 282 | (fluorene with C(OH)(CF3) and 2-O-(CH2)3-C(=O)N(CH3)2) | ¹H-NMR (DMSO-D₆) δ: 7.77-7.72 (2H, m), 7.61-7.57 (1H, m), 7.48-7.43 (1H, m), 7.32-7.27 (1H, m), 7.24-7.22 (1H, m), 7.17-7.14 (1H, m), 7.09-7.05 (1H, m), 4.06 (2H, t, J = 6.4 Hz), 2.97 (3H, s), 2.83 (3H, s), 2.50-2.45 (2H, m), 2.00-1.92 (2H, m). |
| 283 | (fluorene with C(OH)(CF3) and 2-O-(CH2)4-C(=O)-O-CH2CH3) | ¹H-NMR (CDCl₃) δ: 7.67-7.64 (1H, m), 7.58-7.52 (2H, m), 7.45-7.41 (1H, m), 7.45 (1H, s), 7.30-7.25 (1H, m), 7.25-7.23 (1H, m), 6.97 (1H, dd, J = 8.4, 2.4 Hz), 4.13 (2H, q, J = 7.1 Hz), 4.07-4.01 (2H, m), 2.43-2.37 (2H, m), 1.92-1.78 (4H, m), 1.26 (3H, t, J = 7.2 Hz). |

TABLE 1-41-continued

| compound No. | structural formula | NMR |
|---|---|---|
| 284 | | ¹H-NMR (DMSO-D₆) δ: 7.77-7.72 (2H, m), 7.61-7.57 (1H, m), 7.48-7.43 (1H, m), 7.32-7.27 (1H, m), 7.24-7.22 (1H, m), 7.18-7.14 (1H, m), 7.08-7.05 (1H, m), 4.60-4.56 (1H, m), 4.13-4.07 (2H, m), 3.61-3.55 (2H, m), 1.94-1.85 (2H, m). |
| 285 | | ¹H-NMR (DMSO-D₆) δ: 8.72 (1H, dd, J = 4.9, 1.5 Hz), 8.64 (1H, d, J = 1.5 Hz), 7.92-7.86 (1H, m), 7.61-7.55 (2H, m), 7.30-7.27 (1H, m), 7.22 (1H, s), 7.21-7.14 (2H, m), 6.86 (1H, d, J = 2.4 Hz), 6.55 (1H, d, J = 6.8 Hz), 3.75-3.68 (4H, m), 3.29-3.24 (4H, m), 1.23 (9H, s). |
| 286 | | ¹H-NMR (DMSO-D₆) δ: 8.04 (1H, s), 7.68-7.63 (1H, m), 7.66 (1H, d, J = 0.7 Hz), 7.60-7.57 (1H, m), 7.41 (1H, s), 7.40-7.34 (4H, m), 3.96 (3H, s). |

TABLE 1-42

| compound No. | structural formula | NMR |
|---|---|---|
| 287 | | ¹H-NMR (DMSO-D₆) δ: 13.07 (1H, br s), 7.78-7.73 (2H, m), 7.61-7.56 (1H, m), 7.49-7.43 (1H, m), 7.33-7.28 (1H, m), 7.27-7.24 (1H, m), 7.15-7.13 (1H, m), 7.06-7.02 (1H, m), 4.75 (2H, s). |
| 288 | | ¹H-NMR (DMSO-D₆) δ: 7.79-7.74 (2H, m), 7.63 (1H, br s), 7.62-7.58 (1H, m), 7.49-7.44 (1H, m), 7.43 (1H, br s), 7.34-7.29 (1H, m), 7.27-7.22 (2H, m), 7.10-7.06 (1H, m), 4.49 (2H, s). |

TABLE 1-42-continued

| compound No. | structural formula | NMR |
|---|---|---|
| 289 | | $^1$H-NMR (DMSO-D$_6$) δ: 8.17-8.11 (1H, m), 7.80-7.74 (2H, m), 7.62-7.58 (1H, m), 7.49-7.45 (1H, m), 7.34-7.28 (1H, m), 7.27-7.24 (2H, m), 7.11-7.07 (1H, m), 4.53 (2H, s), 2.70-2.65 (3H, m). |
| 290 | | $^1$H-NMR (DMSO-D$_6$) δ: 7.77-7.72 (2H, m), 7.61-7.57 (1H, m), 7.49-7.44 (1H, m), 7.33-7.28 (1H, m), 7.26-7.23 (1H, m), 7.17-7.14 (1H, m), 7.06-7.01 (1H, m), 4.88 (2H, s), 3.02 (3H, s), 2.86 (3H, s). |
| 291 | | $^1$H-NMR (DMSO-D$_6$) δ: 12.40 (1H, br s), 7.80-7.71 (2H, m), 7.62-7.56 (1H, m), 7.49-7.42 (1H, m), 7.34-7.21 (2H, m), 7.15 (1H, s), 7.11-7.04 (1H, m), 4.28-4.18 (2H, m), 2.77-2.69 (2H, m). |
| 292 | | $^1$H-NMR (DMSO-D$_6$) δ: 7.78-7.72 (2H, m), 7.61-7.57 (1H, m), 7.48-7.43 (1H, m), 7.32-7.27 (1H, m), 7.23 (1H, s), 7.18-7.16 (1H, m), 7.07 (1H, dd, J = 8.4, 2.4 Hz), 4.89 (1H, t, J = 5.5 Hz), 4.07-4.03 (2H, m), 3.77-3.72 (2H, m). |
| 293 | | $^1$H-NMR (DMSO-D$_6$) δ: 7.60-7.56 (2H, m), 7.54-7.50 (1H, m), 7.40-7.36 (1H, m), 7.20-7.15 (1H, m), 7.08-7.05 (1H, m), 6.83-6.80 (1H, m), 6.65-6.61 (1H, m), 3.98-3.88 (1H, m), 3.46-3.39 (1H, m), 3.22-3.13 (1H, m), 2.11-1.94 (3H, m), 1.70 (1H, d, J = 42.9 Hz), 1.15 (3H, t, J = 6.8 Hz). |

TABLE 1-43

| compound No. | structural formula | NMR |
|---|---|---|
| 294 | 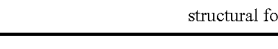 | $^1$H-NMR (CDCl$_3$) δ: 7.67-7.63 (1H, m), 7.57-7.52 (2H, m), 7.46-7.41 (1H, m), 7.30-7.23 (2H, m), 7.00-6.96 (1H, m), 4.01 (2H, t, J = 6.5 Hz), 2.70-2.70 (1H, m), 1.84-1.76 (2H, m), 1.53-1.44 (2H, m), 1.39-1.32 (4H, m), 0.95-0.89 (3H, m). |

TABLE 1-43-continued

| compound No. | structural formula | NMR |
|---|---|---|
| 295 | | $^1$H-NMR (DMSO-D$_6$) δ: 12.05 (1H, br s), 7.77-7.72 (2H, m), 7.60-7.57 (1H, m), 7.48-7.43 (1H, m), 7.32-7.27 (1H, m), 7.22 (1H, s), 7.16-7.14 (1H, m), 7.08-7.05 (1H, m), 4.04 (2H, t, J = 5.9 Hz), 2.31 (2H, t, J = 7.2 Hz), 1.80-1.63 (4H, m). |
| 296 | | $^1$H-NMR (CDCl$_3$) δ: 7.67-7.64 (1H, m), 7.58-7.53 (2H, m), 7.46-7.41 (1H, m), 7.30-7.23 (2H, m), 7.00-6.96 (1H, m), 4.04 (2H, t, J = 6.4 Hz), 3.70 (2H, t, J = 5.8 Hz), 2.79 (1H, s), 1.89-1.81 (2H, m), 1.71-1.63 (2H, m), 1.62-1.53 (2H, m), 1.32-1.20 (1H, m). |
| 297 | | $^1$H-NMR (DMSO-D$_6$) δ: 7.94-7.88 (2H, m), 7.68-7.61 (2H, m), 7.58-7.51 (2H, m), 7.45-7.40 (1H, m), 7.35 (1H, br s), 4.81 (1H, t, J = 5.4 Hz), 3.68-3.45 (4H, m), 3.00 (3H, br s). |
| 298 | | $^1$H-NMR (CDCl$_3$) δ: 7.67-7.64 (1H, m), 7.57-7.53 (2H, m), 7.46-7.41 (1H, m), 7.30-7.23 (2H, m), 6.98 (1H, dd, J = 8.4, 2.4 Hz), 4.03 (2H, t, J = 6.4 Hz), 3.67 (2H, t, J = 6.4 Hz), 2.81 (1H, s), 1.87-1.79 (2H, m), 1.66-1.58 (2H, m), 1.52-1.41 (4H, m), 1.29-1.20 (1H, m). |
| 299 | | $^1$H-NMR (DMSO-D$_6$) δ: 7.76-7.72 (2H, m), 7.60-7.57 (1H, m), 7.48-7.43 (1H, m), 7.32-7.27 (1H, m), 7.21 (1H, s), 7.16-7.14 (1H, m), 7.06 (1H, dd, J = 8.4, 2.4 Hz), 4.04 (2H, t, J = 6.3 Hz), 2.96 (3H, s), 2.81 (3H, s), 2.37 (2H, t, J = 7.3 Hz), 1.80-1.72 (2H, m), 1.70-1.62 (2H, m). |
| 300 | | $^1$H-NMR (DMSO-D$_6$) δ: 9.38 (1H, s), 8.96 (2H, br s), 7.81-7.77 (1H, m), 7.71-7.67 (1H, m), 7.56-7.52 (1H, m), 7.45 (1H, dd, J = 7.7, 1.1 Hz), 7.40-7.35 (1H, m), 7.37 (1H, s), 7.31-7.26 (1H, m), 6.71 (1H, d, J = 7.7 Hz). |

TABLE 1-44

| compound No. | structural formula | NMR |
|---|---|---|
| 301 | | ¹H-NMR (DMSO-D$_6$) δ: 7.78-7.72 (2H, m), 7.61-7.57 (1H, m), 7.50-7.43 (2H, m), 7.33-7.27 (1H, m), 7.25-7.23 (1H, m), 7.16-7.13 (1H, m), 7.08-7.04 (1H, m), 6.95 (1H, br s), 4.25-4.20 (2H, m), 2.59-2.53 (2H, m). |
| 302 | | ¹H-NMR (DMSO-D$_6$) δ: 7.98-7.91 (1H, m), 7.77-7.72 (2H, m), 7.61-7.57 (1H, m), 7.49-7.43 (1H, m), 7.33-7.27 (1H, m), 7.25-7.23 (1H, m), 7.15-7.12 (1H, m), 7.08-7.04 (1H, m), 4.24 (2H, t, J = 5.3 Hz), 2.63-2.60 (3H, m), 2.59-2.54 (2H, m). |
| 303 | | ¹H-NMR (DMSO-D$_6$) δ: 7.77-7.72 (2H, m), 7.60-7.57 (1H, m), 7.48-7.43 (1H, m), 7.32-7.27 (1H, m), 7.24 (1H, s), 7.16-7.14 (1H, m), 7.08-7.04 (1H, m), 4.25 (2H, t, J = 6.3 Hz), 3.01 (3H, s), 2.85 (3H, s), 2.82 (2H, t, J = 6.3 Hz). |
| 304 | | ¹H-NMR (CDCl$_3$) δ: 8.03-7.87 (1H, m), 7.84-7.64 (4H, m), 7.54-7.48 (1H, m), 7.45-7.39 (1H, m), 5.01-4.86 (1H, m), 4.59-4.09 (1H, m), 3.88-3.47 (4H, m), 2.77-2.61 (1H, m), 2.44-2.21 (1H, m). |
| 305 | | ¹H-NMR (DMSO-D$_6$) δ: 7.79-7.71 (3H, m), 7.61-7.57 (1H, m), 7.49-7.43 (1H, m), 7.33-7.27 (1H, m), 7.24-7.22 (1H, m), 7.17-7.14 (1H, m), 7.09-7.04 (1H, m), 4.06-4.00 (2H, m), 2.59-2.55 (3H, m), 2.16-2.11 (2H, m), 1.76-1.62 (4H, m). |
| 306 | | ¹H-NMR (DMSO-D$_6$) δ: 7.77-7.72 (2H, m), 7.61-7.57 (1H, m), 7.49-7.43 (1H, m), 7.33-7.26 (2H, m), 7.24-7.22 (1H, m), 7.17-7.14 (1H, m), 7.09-7.04 (1H, m), 6.73 (1H, br s), 4.06-4.01 (2H, m), 2.16-2.10 (2H, m), 1.78-1.63 (4H, m). |

TABLE 1-44-continued

| compound No. | structural formula | NMR |
|---|---|---|
| 307 | 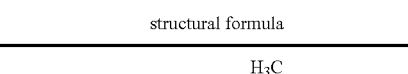 | $^1$H-NMR (DMSO-D$_6$) δ: 7.94-7.90 (2H, m), 7.68-7.64 (1H, m), 7.60-7.47 (3H, m), 7.45-7.40 (1H, m), 7.36 (1H, s), 3.50-3.35 (1H, m), 3.26-3.09 (1H, m), 3.01-2.88 (3H, m), 1.71-1.47 (2H, m), 1.00-0.59 (3H, m). |

TABLE 1-45

| compound No. | structural formula | NMR |
|---|---|---|
| 308 | | $^1$H-NMR (DMSO-D$_6$) δ: 7.94-7.90 (2H, m), 7.68-7.64 (1H, m), 7.60-7.49 (3H, m), 7.45-7.40 (1H, m), 7.36 (1H, s), 3.53-3.11 (2H, m), 3.01-2.89 (3H, m), 1.65-0.68 (7H, m). |
| 309 | | $^1$H-NMR (DMSO-D$_6$) δ: 7.78 (1H, dd, J = 4.9, 3.1 Hz), 7.70-7.64 (2H, m), 7.65 (1H, dd, J = 4.2, 2.1 Hz), 7.43 (1H, t, J = 7.5 Hz), 7.37-7.21 (4H, m), 7.26 (1H, s), 6.89 (1H, d, J = 7.3 Hz). |
| 310 | | $^1$H-NMR (DMSO-D$_6$) δ: 8.62-8.57 (1H, m), 8.17-8.14 (1H, m), 8.06-8.01 (1H, m), 7.97-7.92 (2H, m), 7.70-7.66 (1H, m), 7.58-7.52 (1H, m), 7.48-7.43 (1H, m), 7.37-7.34 (1H, m), 4.78-4.72 (1H, m), 3.58-3.49 (2H, m), 3.43-3.27 (2H, m). |
| 311 | | $^1$H-NMR (DMSO-D$_6$) δ: 8.63-8.57 (1H, m), 8.16-8.11 (1H, m), 8.04-7.99 (1H, m), 7.97-7.91 (2H, m), 7.70-7.65 (1H, m), 7.58-7.52 (1H, m), 7.48-7.42 (1H, m), 7.37-7.33 (1H, m), 4.51-4.47 (1H, m), 3.52-3.45 (2H, m), 3.39-3.27 (2H, m), 1.75-1.67 (2H, m). |
| 312 | | $^1$H-NMR (DMSO-D$_6$) δ: 8.62 (1H, t, J = 5.1 Hz), 8.16-8.13 (1H, m), 8.04-8.00 (1H, m), 7.96-7.91 (2H, m), 7.70-7.65 (1H, m), 7.57-7.53 (1H, m), 7.47-7.42 (1H, m), 7.37-7.35 (1H, m), 4.44-4.40 (1H, m), 3.46-3.40 (2H, m), 3.35-3.24 (2H, m), 1.62-1.53 (2H, m), 1.52-1.44 (2H, m). |

TABLE 1-45-continued
| compound No. | structural formula | NMR |
|---|---|---|
| 313 | 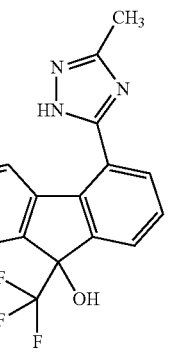 | ¹H-NMR (CD₃OD) δ: 7.81 (1H, d, J = 7.1 Hz), 7.69 (1H, d, J = 7.3 Hz), 7.57 (1H, d, J = 7.5 Hz), 7.49-7.43 (1H, m), 7.37-7.27 (3H, m), 2.56 (3H, s). |
| 314 | 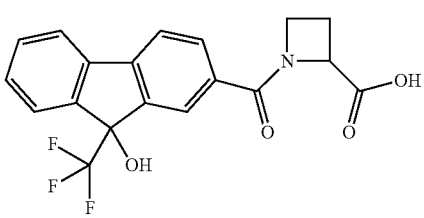 [SMILES: O=C(O)C1CCN1C(=O)c1ccc2c(c1)C(O)(C(F)(F)F)c1ccccc1-2] | ¹H-NMR (DMSO-D₆) δ: 12.86 (1H, br s), 7.99-7.76 (4H, m), 7.67 (1H, d, J = 7.1 Hz), 7.58-7.52 (1H, m), 7.48-7.35 (2H, m), 5.20-5.04 (0.3H, m), 4.81-4.72 (0.7H, m), 4.47-3.91 (2H, m), 2.81-2.57 (1H, m), 2.29-2.05 (1H, m). |
TABLE 1-46
| compound No. | structural formula | NMR |
|---|---|---|
| 315 | 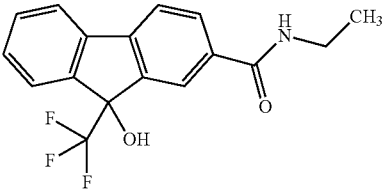 [SMILES: CCNC(=O)c1ccc2c(c1)C(O)(C(F)(F)F)c1ccccc1-2] | ¹H-NMR (DMSO-D₆) δ: 8.62 (1H, t, J = 5.6 Hz), 8.15-8.13 (1H, m), 8.01 (1H, dd, J = 7.9, 1.8 Hz), 7.96-7.91 (2H, m), 7.69-7.66 (1H, m), 7.57-7.52 (1H, m), 7.46-7.42 (1H, m), 7.34 (1H, s), 3.36-3.27 (2H, m), 1.15 (3H, t, J = 7.2 Hz). |
| 316 | 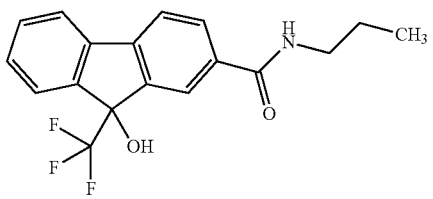 [SMILES: CCCNC(=O)c1ccc2c(c1)C(O)(C(F)(F)F)c1ccccc1-2] | ¹H-NMR (DMSO-D₆) δ: 8.60 (1H, t, J = 5.5 Hz), 8.15-8.13 (1H, m), 8.02 (1H, dd, J = 7.9, 1.5 Hz), 7.96-7.91 (2H, m), 7.69-7.66 (1H, m), 7.57-7.52 (1H, m), 7.46-7.42 (1H, m), 7.34 (1H, s), 3.28-3.21 (2H, m), 1.61-1.51 (2H, m), 0.91 (3H, t, J = 7.5 Hz). |
| 317 | 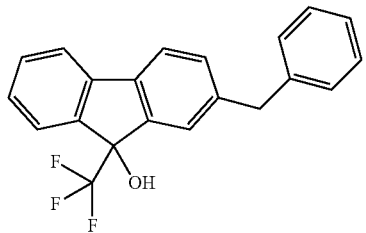 [SMILES: OC1(C(F)(F)F)c2ccccc2-c2ccc(Cc3ccccc3)cc21] | ¹H-NMR (DMSO-D₆) δ: 7.80-7.78 (1H, m), 7.76 (1H, d, J = 7.7 Hz), 7.62-7.59 (1H, m), 7.52-7.45 (2H, m), 7.40-7.26 (6H, m), 7.23-7.17 (1H, m), 7.18 (1H, s), 4.03 (2H, s). |

TABLE 1-46-continued

| compound No. | structural formula | NMR |
|---|---|---|
| 318 | 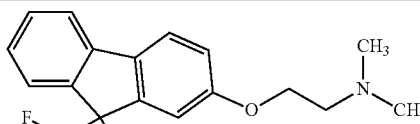 | $^1$H-NMR (DMSO-D$_6$) δ: 11.99 (1H, br s), 7.76-7.72 (2H, m), 7.60-7.56 (1H, m), 7.47-7.43 (1H, m), 7.31-7.27 (1H, m), 7.21 (1H, s), 7.15-7.13 (1H, m), 7.06 (1H, dd, J = 8.4, 2.4 Hz), 4.02 (2H, t, J = 6.6 Hz), 2.24 (2H, t, J = 7.3 Hz), 1.78-1.70 (2H, m), 1.62-1.53 (2H, m), 1.49-1.42 (2H, m). |
| 319 | | $^1$H-NMR (DMSO-D$_6$) δ: 7.94-7.90 (2H, m), 7.68-7.64 (1H, m), 7.60-7.48 (3H, m), 7.45-7.41 (1H, m), 7.37 (1H, s), 4.46-4.34 (1H, m), 3.53-3.14 (4H, m), 3.01-2.86 (3H, m), 1.69-1.13 (4H, m). |
| 320 | | $^1$H-NMR (DMSO-D$_6$) δ: 8.13 (3H, br s), 7.80 (1H, d, J = 8.3 Hz), 7.77 (1H, d, J = 7.4 Hz), 7.62-7.59 (1H, m), 7.50-7.45 (1H, m), 7.34-7.30 (1H, m), 7.24-7.22 (1H, m), 7.13 (1H, dd, J = 8.5, 2.4 Hz), 4.24 (2H, t, J = 5.1 Hz), 3.57 (1H, s), 3.25 (2H, br s). |
| 321 | | $^1$H-NMR (DMSO-D$_6$) δ: 8.91 (2H, br s), 7.81 (1H, d, J = 8.3 Hz), 7.79-7.76 (1H, m), 7.63-7.59 (1H, m), 7.50-7.45 (1H, m), 7.34-7.30 (1H, m), 7.24-7.23 (1H, m), 7.14 (1H, dd, J = 8.3, 2.3 Hz), 4.31 (2H, t, J = 5.1 Hz), 3.39-3.34 (2H, m), 2.65 (3H, br s). |

TABLE 1-47

| compound No. | structural formula | NMR |
|---|---|---|
| 322 | | $^1$H-NMR (DMSO-D$_6$) δ: 7.76-7.73 (2H, m), 7.61-7.56 (1H, m), 7.48-7.43 (1H, m), 7.32-7.27 (1H, m), 7.21 (1H, s), 7.17-7.15 (1H, m), 7.08 (1H, dd, J = 8.4, 2.4 Hz), 4.11 (2H, t, J = 5.7 Hz), 2.64 (2H, t, J = 5.7 Hz), 2.23 (6H, s). |
| 323 | | $^1$H-NMR (CDCl$_3$) δ: 7.68-7.64 (1H, m), 7.58-7.54 (2H, m), 7.47-7.42 (1H, m), 7.31-7.23 (2H, m), 6.98 (1H, dd, J = 8.3, 2.6 Hz), 5.00 (1H, br s), 4.08 (2H, t, J = 5.1 Hz), 3.59-3.52 (2H, m), 2.87 (1H, br s), 1.46 (9H, s). |

TABLE 1-47-continued

| compound No. | structural formula | NMR |
|---|---|---|
| 324 | (structure) | $^1$H-NMR (CDCl$_3$) δ: 7.68-7.65 (1H, m), 7.58-7.54 (2H, m), 7.46-7.42 (1H, m), 7.31-7.21 (2H, m), 6.98 (1H, dd, J = 8.3, 2.3 Hz), 4.15 (2H, br s), 3.65-3.59 (2H, m), 2.99 (3H, br s), 2.96-2.90 (1H, m), 1.46 (9H, s). |
| 325 | (structure) | $^1$H-NMR (CDCl$_3$) δ: 7.68-7.65 (1H, m), 7.58-7.55 (2H, m), 7.47-7.42 (1H, m), 7.32-7.27 (1H, m), 7.27-7.24 (1H, m), 6.98 (1H, dd, J = 8.3, 2.3 Hz), 5.94 (1H, br s), 4.09 (2H, t, J = 5.0 Hz), 3.70-3.65 (2H, m), 3.03 (1H, br s), 2.01 (3H, s). |
| 326 | (structure) | $^1$H-NMR (CDCl$_3$) δ: 7.69-7.65 (1H, m), 7.58-7.53 (2H, m), 7.47-7.41 (1H, m), 7.32-7.21 (2H, m), 6.97 (1H, dd, J = 8.3, 2.6 Hz), 4.19-4.15 (2H, m), 3.80-3.68 (2H, m), 3.26 (0.7H, s), 3.22 (0.3H, s), 3.17 (2.1H, s), 3.00 (0.9H, s), 2.18 (0.9H, s), 2.08 (2.1H, s). |
| 327 | (structure) | $^1$H-NMR (DMSO-D$_6$) δ: 7.92 (2H, d, J = 7.5 Hz), 7.68-7.65 (1H, m), 7.62-7.49 (3H, m), 7.45-7.41 (1H, m), 7.38 (1H, s), 4.55-4.38 (1H, m), 3.57-3.21 (4H, m), 3.01-2.91 (3H, m), 1.81-1.63 (2H, m). |
| 328 | (structure) | $^1$H-NMR (DMSO-D$_6$) δ: 8.32 (1H, d, J = 7.5 Hz), 7.83 (1H, s), 7.79 (1H, s), 7.77-7.73 (1H, m), 7.66-7.61 (1H, m), 7.59-7.52 (2H, m), 4.67 (1H, t, J = 5.4 Hz), 4.56-4.45 (1H, m), 4.42-4.36 (1H, m), 4.33-4.15 (2H, m), 3.94-3.86 (1H, m), 3.54-3.48 (2H, m), 3.46-3.40 (2H, m). |

TABLE 1-48

| compound No. | structural formula | NMR |
|---|---|---|
| 329 | (structure) | $^1$H-NMR (DMSO-D$_6$) δ: 8.32 (1H, d, J = 7.5 Hz), 7.83 (1H, s), 7.79-7.73 (2H, m), 7.66-7.53 (3H, m), 4.58-4.41 (2H, m), 4.32-4.23 (1H, m), 4.18-4.10 (1H, m), 3.83-3.74 (1H, m), 2.86 (3H, s), 2.86 (3H, s). |

TABLE 1-48-continued

| compound No. | structural formula | NMR |
|---|---|---|
| 330 | | ¹H-NMR (DMSO-D₆) δ: 8.32 (1H, d, J = 7.7 Hz), 7.83 (1H, s), 7.79-7.73 (2H, m), 7.66-7.61 (1H, m), 7.59-7.52 (1H, m), 7.58 (1H, s), 4.83 (1H, t, J = 5.3 Hz), 4.41-4.32 (1H, m), 4.12-4.03 (2H, m), 3.85-3.78 (1H, m), 3.56 (2H, t, J = 5.7 Hz), 2.80-2.69 (1H, m). |
| 331 | | ¹H-NMR (DMSO-D₆) δ: 7.76-7.72 (2H, m), 7.60-7.56 (1H, m), 7.48-7.42 (1H, m), 7.32-7.26 (1H, m), 7.22 (1H, s), 7.17-7.14 (1H, m), 7.06 (1H, dd, J = 8.5, 2.4 Hz), 4.09 (2H, t, J = 6.4 Hz), 2.71 (2H, t, J = 6.8 Hz), 1.85-1.75 (2H, m). |
| 332 | | ¹H-NMR (DMSO-D₆) δ: 8.74 (1H, br s), 7.79-7.74 (2H, m), 7.62-7.58 (1H, m), 7.49-7.44 (1H, m), 7.33-7.28 (1H, m), 7.25 (1H, s), 7.19-7.17 (1H, m), 7.08 (1H, dd, J = 8.3, 2.6 Hz), 4.13 (2H, t, J = 6.0 Hz), 3.08 (2H, br s), 2.58 (3H, br s), 2.14-2.06 (2H, m). |
| 333 | | ¹H-NMR (CDCl₃) δ: 7.71-7.67 (1H, m), 7.55 (2H, d, J = 8.3 Hz), 7.44-7.38 (1H, m), 7.30-7.23 (2H, m), 6.95 (1H, dd, J = 8.3, 2.3 Hz), 3.87-3.80 (2H, m), 2.18-2.11 (2H, m), 1.88 (6H, s), 1.81-1.70 (2H, m). |
| 334 | | ¹H-NMR (CDCl₃) δ: 7.69-7.64 (1H, m), 7.58-7.52 (2H, m), 7.47-7.40 (1H, m), 7.34-7.23 (2H, m), 7.00-6.95 (1H, m), 4.07-4.05 (2H, m), 3.66-3.43 (2H, m), 3.03 (1.7H, s), 2.94 (1.3H, s), 2.10-2.00 (2H, m), 2.08 (1.3H, s), 2.05 (1.8H, s). |
| 335 | | ¹H-NMR (DMSO-D₆) δ: 9.40 (1H, s), 8.99 (2H, br s), 7.78-7.75 (1H, m), 7.72-7.68 (1H, m), 7.63 (1H, d, J = 2.0 Hz), 7.58 (1H, s), 7.43-7.38 (1H, m), 7.34-7.29 (1H, m), 6.68 (1H, d, J = 7.5 Hz). |

TABLE 1-49

| compound No. | structural formula | NMR |
|---|---|---|
| 336 | (fluorene with CH2NH2·HCl at 4-position, C(CF3)(OH) at 9-position) | ¹H-NMR (DMSO-D₆) δ: 8.59 (3H, br s), 7.81 (1H, d, J = 7.9 Hz), 7.75-7.67 (2H, m), 7.60-7.54 (2H, m), 7.50-7.44 (2H, m), 7.34 (1H, s), 4.53 (1H, d, J = 15.0 Hz), 4.46 (1H, d, J = 15.0 Hz). |
| 337 | (fluorene-2-carbonyl-azetidin-3-yl-carbonyl-(3-hydroxypyrrolidine), 9-C(CF3)(OH)) | ¹H-NMR (DMSO-D₆) δ: 7.94 (2H, d, J = 7.7 Hz), 7.88-7.86 (1H, m), 7.80-7.76 (1H, m), 7.69-7.66 (1H, m), 7.57-7.53 (1H, m), 7.47-7.43 (1H, m), 7.41 (1H, s), 5.02-4.89 (1H, m), 4.55-4.06 (5H, m), 3.75-3.61 (1H, m), 3.47-3.12 (4H, m), 2.00-1.70 (2H, m). |
| 338 | (4-methyl fluorene-2-carboxamide N-(4-hydroxybutyl), 9-C(CF3)(OH)) | ¹H-NMR (DMSO-D₆) δ: 8.56 (1H, t, J = 5.6 Hz), 8.01-7.98 (1H, m), 7.91 (1H, d, J = 7.7 Hz), 7.84-7.82 (1H, m), 7.73-7.69 (1H, m), 7.59-7.54 (1H, m), 7.48-7.43 (1H, m), 7.27 (1H, s), 4.40 (1H, t, J = 5.1 Hz), 3.46-3.40 (2H, m), 3.30-3.25 (2H, m), 2.68 (3H, s), 1.61-1.53 (2H, m), 1.51-1.43 (2H, m). |
| 339 | (4-chloro fluorene-2-carbonyl-(3-hydroxyazetidine), 9-C(CF3)(OH)) | ¹H-NMR (DMSO-D₆) δ: 8.34-8.30 (1H, m), 7.83-7.80 (1H, m), 7.77-7.73 (2H, m), 7.65-7.61 (1H, m), 7.59-7.53 (2H, m), 5.77 (1H, d, J = 6.2 Hz), 4.56-4.42 (2H, m), 4.34-4.24 (1H, m), 4.15-4.02 (1H, m), 3.87-3.77 (1H, m). |
| 340 | (fluorene-2-O-(CH2)3-NHC(O)CH3, 9-C(CF3)(OH)) | ¹H-NMR (CDCl₃) δ: 7.69-7.64 (1H, m), 7.58-7.54 (2H, m), 7.47-7.41 (1H, m), 7.32-7.24 (2H, m), 6.98 (1H, dd, J = 8.3, 2.3 Hz), 5.76 (1H, br s), 4.10 (2H, t, J = 5.8 Hz), 3.51-3.42 (2H, m), 3.11 (1H, br s), 2.07-1.96 (2H, m), 1.98 (3H, s). |
| 341 | (4-(pyridin-3-yl) fluorene-2-(4-phenyl)-C(O)O-C(CH3)2-CH3, 9-C(CF3)(OH)) | ¹H-NMR (DMSO-D₆) δ: 8.78 (1H, dd, J = 4.7, 1.7 Hz), 8.76-8.74 (1H, m), 8.06-7.99 (4H, m), 7.95-7.91 (2H, m), 7.75 (1H, d, J = 1.8 Hz), 7.73-7.69 (1H, m), 7.63 (1H, dd, J = 7.6, 5.2 Hz), 7.49 (1H, s), 7.41-7.36 (1H, m), 7.31-7.26 (1H, m), 6.72 (1H, d, J = 7.7 Hz), 1.58 (9H, s). |

TABLE 1-49-continued
| compound No. | structural formula | NMR |
|---|---|---|
| 342 | 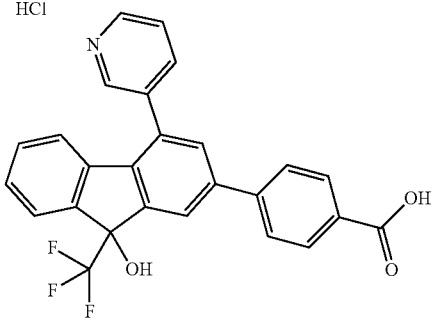 [SMILES: Cl ; O=C(O)c1ccc(-c2cc(-c3cccnc3)c3c(c2)C(O)(C(F)(F)F)c2ccccc2-3)cc1] | $^1$H-NMR (DMSO-D$_6$) δ: 9.00-8.96 (1H, m), 8.91 (1H, dd, J = 5.2, 1.4 Hz), 8.37-8.32 (1H, m), 8.11-8.05 (3H, m), 7.97-7.92 (2H, m), 7.91-7.86 (1H, m), 7.84-7.81 (1H, m), 7.74-7.70 (1H, m), 7.52 (1H, br s), 7.43-7.38 (1H, m), 7.32-7.27 (1H, m), 6.79 (1H, d, J = 7.5 Hz). |
TABLE 1-50
| compound No. | structural formula | NMR |
|---|---|---|
| 343 | 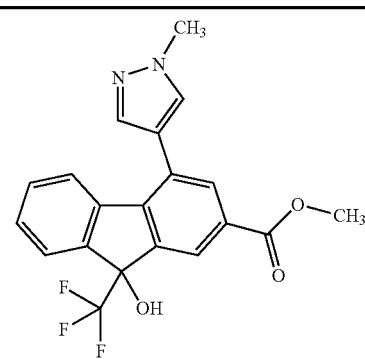 | $^1$H-NMR (DMSO-D$_6$) δ: 8.15-8.13 (1H, m), 8.08-8.05 (1H, m), 7.85 (1H, d, J = 1.5 Hz), 7.73-7.68 (1H, m), 7.67 (1H, d, J = 0.9 Hz), 7.49-7.35 (4H, m), 3.97 (3H, s), 3.90 (3H, s). |
| 344 | 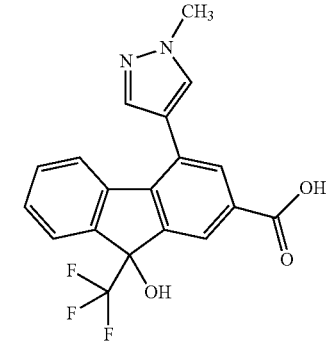 [SMILES: Cn1cc(-c2cc(C(=O)O)cc3c2-c2ccccc2C3(O)C(F)(F)F)cn1] | $^1$H-NMR (DMSO-D$_6$) δ: 13.24 (1H, br s), 8.14-8.12 (1H, m), 8.06-8.05 (1H, m), 7.83 (1H, d, J = 1.6 Hz), 7.72-7.68 (1H, m), 7.66 (1H, d, J = 0.7 Hz), 7.47-7.36 (4H, m), 3.97 (3H, s). |
| 345 | 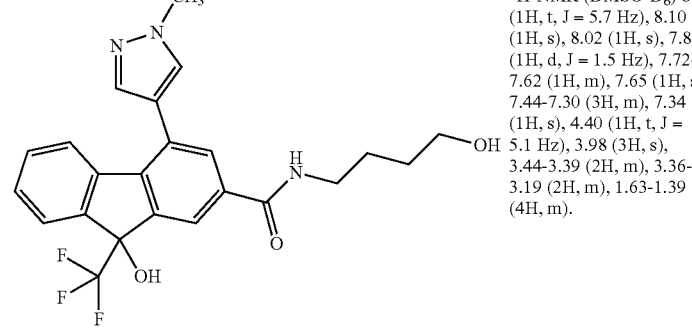 | $^1$H-NMR (DMSO-D$_6$) δ: 8.62 (1H, t, J = 5.7 Hz), 8.10 (1H, s), 8.02 (1H, s), 7.82 (1H, d, J = 1.5 Hz), 7.72-7.62 (1H, m), 7.65 (1H, s), 7.44-7.30 (3H, m), 7.34 (1H, s), 4.40 (1H, t, J = 5.1 Hz), 3.98 (3H, s), 3.44-3.39 (2H, m), 3.36-3.19 (2H, m), 1.63-1.39 (4H, m). |

TABLE 1-50-continued

| compound No. | structural formula | NMR |
|---|---|---|
| 346 | | $^1$H-NMR (DMSO-D$_6$) δ: 8.04-8.00 (1H, m), 7.69-7.63 (2H, m), 7.62-7.58 (1H, m), 7.43-7.30 (5H, m), 4.82 (1H, t, J = 5.3 Hz), 3.96 (3H, s), 3.68-3.59 (1H, m), 3.56-3.48 (2H, m), 3.40-3.33 (1H, m), 3.01 (3H, s). |
| 347 | | $^1$H-NMR (CDCl$_3$) δ: 7.72-7.67 (2H, m), 7.52 (1H, s), 7.49 (1H, s), 7.36-7.21 (5H, m), 4.26 (2H, q, J = 7.3 Hz), 3.15 (1H, br s), 1.57 (3H, t, J = 7.3 Hz). |
| 348 | | $^1$H-NMR (DMSO-D$_6$) δ: 7.79-7.73 (2H, m), 7.61-7.57 (1H, m), 7.49-7.43 (1H, m), 7.33-7.23 (2H, m), 7.17-7.15 (1H, m), 7.11-7.06 (1H, m), 4.54-4.45 (1H, m), 4.23-4.07 (4H, m), 3.73-3.62 (2H, m), 3.00 (1.6H, s), 2.94 (1.4H, s). |
| 349 | | $^1$H-NMR (DMSO-D$_6$) δ: 8.32 (1H, d, J = 7.5 Hz), 7.84-7.82 (1H, m), 7.78 (1H, d, J = 1.3 Hz), 7.77-7.73 (1H, m), 7.65-7.61 (1H, m), 7.58-7.53 (1H, m), 7.57 (1H, s), 7.35 (1H, br s), 7.26 (1H, br s), 4.56-4.48 (1H, m), 4.45-4.39 (1H, m), 4.32-4.23 (2H, m), 4.01-3.93 (1H, m), 3.84 (2H, s). |

TABLE 1-51

| compound No. | structural formula | NMR |
|---|---|---|
| 350 | | $^1$H-NMR (DMSO-D$_6$) δ: 7.91 (1H, d, J = 7.7 Hz), 7.73-7.69 (2H, m), 7.59-7.54 (2H, m), 7.48-7.44 (1H, m), 7.33 (1H, s), 5.76 (1H, d, J = 6.3 Hz), 4.55-4.43 (2H, m), 4.31-4.23 (1H, m), 4.13-4.00 (1H, m), 3.87-3.75 (1H, m), 2.68 (3H, s). |

TABLE 1-51-continued

| compound No. | structural formula | NMR |
|---|---|---|
| 351 | | $^1$H-NMR (DMSO-D$_6$) δ: 7.91 (1H, d, J = 7.7 Hz), 7.73-7.69 (2H, m), 7.59-7.54 (2H, m), 7.48-7.43 (1H, m), 7.33 (1H, s), 4.83 (1H, t, J = 5.4 Hz), 4.38-4.31 (1H, m), 4.09-4.03 (2H, m), 3.82-3.78 (1H, m), 3.56 (2H, t, J = 5.7 Hz), 2.78-2.70 (1H, m), 2.68 (3H, s). |
| 352 | | $^1$H-NMR (DMSO-D$_6$) δ: 7.93-7.90 (1H, m), 7.74-7.69 (2H, m), 7.60-7.54 (2H, m), 7.48-7.44 (1H, m), 7.35 (1H, br s), 7.33 (1H, s), 7.26 (1H, br s), 4.54-4.45 (1H, m), 4.44-4.38 (1H, m), 4.31-4.21 (2H, m), 3.99-3.92 (1H, m), 3.83 (2H, s), 2.69 (3H, s). |
| 353 | | $^1$H-NMR (DMSO-D$_6$) δ: 7.84-7.79 (2H, m), 7.64-7.61 (1H, m), 7.56-7.54 (1H, m), 7.52-7.48 (1H, m), 7.42-7.35 (2H, m), 7.23 (1H, s), 3.79 (2H, s), 3.64 (3H, s). |
| 354 | | $^1$H-NMR (DMSO-D$_6$) δ: 8.03 (1H, s), 7.69-7.65 (1H, m), 7.65 (1H, d, J = 0.7 Hz), 7.60-7.59 (1H, m), 7.42-7.35 (4H, m), 7.30 (1H, d, J = 1.4 Hz), 3.96 (3H, s), 2.99 (6H, s). |
| 355 | | $^1$H-NMR (DMSO-D$_6$) δ: 8.04 (1H, s), 7.83-7.81 (1H, m), 7.70-7.76 (1H, m), 7.66 (1H, d, J = 0.7 Hz), 7.49 (1H, d, J = 1.6 Hz), 7.43-7.36 (4H, m), 4.38-4.32 (2H, m), 4.10-4.04 (2H, m), 3.97 (3H, s), 2.32-2.23 (2H, m). |

TABLE 1-51-continued

| compound No. | structural formula | NMR |
|---|---|---|
| 356 | | ¹H-NMR (DMSO-D₆) δ: 8.03 (1H, s), 7.72-7.70 (1H, m), 7.69-7.65 (1H, m), 7.66 (1H, d, J = 0.9 Hz), 7.43-7.34 (5H, m), 3.96 (3H, s), 3.51-3.42 (4H, m), 1.91-1.81 (4H, m). |

TABLE 1-52

| compound No. | structural formula | NMR |
|---|---|---|
| 357 | | ¹H-NMR (DMSO-D₆) δ: 7.78-7.74 (2H, m), 7.61-7.58 (1H, m), 7.49-7.44 (1H, m), 7.33-7.29 (1H, m), 7.27 (1H, s), 7.16-7.14 (1H, m), 7.07 (1H, dd, J = 8.3, 2.6 Hz), 4.88 (2H, s), 3.72 (3H, s). |
| 358 | | ¹H-NMR (DMSO-D₆) δ: 7.97 (1H, s), 7.64-7.57 (2H, m), 7.60 (1H, s), 7.41 (1H, br s), 7.30-7.25 (3H, m), 7.24 (1H, s), 7.23-7.20 (1H, m), 6.84 (1H, d, J = 2.6 Hz), 4.50 (2H, s), 3.96 (3H, s). |
| 359 | | ¹H-NMR (CDCl₃) δ: 7.69-7.64 (1H, m), 7.58-7.54 (2H, m), 7.47-7.41 (1H, m), 7.32-7.23 (2H, m), 6.97 (1H, dd, J = 8.5, 2.4 Hz), 4.17 (2H, t, J = 5.3 Hz), 3.71-3.67 (2H, m), 3.59 (2H, t, J = 7.2 Hz), 3.11 (1H, br s), 2.38 (2H, t, J = 8.3 Hz), 2.09-1.98 (2H, m). |
| 360 | | ¹H-NMR (DMSO-D₆) δ: 7.74 (2H, d, J = 8.3 Hz), 7.60-7.57 (1H, m), 7.48-7.44 (1H, m), 7.32-7.28 (1H, m), 7.25 (1H, s), 7.17-7.14 (1H, m), 7.03 (1H, dd, J = 8.3, 2.3 Hz), 4.79 (2H, s), 3.52-3.46 (2H, m), 3.36-3.31 (2H, m), 1.95-1.87 (2H, m), 1.82-1.74 (2H, m). |

TABLE 1-52-continued

| compound No. | structural formula | NMR |
|---|---|---|
| 361 | | $^1$H-NMR (DMSO-D$_6$) δ: 7.76-7.73 (2H, m), 7.60-7.57 (1H, m), 7.48-7.44 (1H, m), 7.32-7.28 (1H, m), 7.24 (1H, s), 7.16-7.14 (1H, m), 7.03 (1H, dd, J = 8.3, 2.6 Hz), 4.87 (2H, s), 3.46-3.40 (4H, m), 1.63-1.52 (4H, m), 1.47-1.42 (2H, m). |
| 362 | | $^1$H-NMR (DMSO-D$_6$) δ: 7.77-7.73 (2H, m), 7.61-7.58 (1H, m), 7.48-7.44 (1H, m), 7.32-7.28 (1H, m), 7.25 (1H, s), 7.18-7.16 (1H, m), 7.05 (1H, dd, J = 8.5, 2.4 Hz), 4.91 (2H, s), 3.64-3.55 (4H, m), 3.52-3.44 (4H, m). |
| 363 | | $^1$H-NMR (DMSO-D$_6$) δ: 9.38 (1H, s), 8.96 (2H, br s), 7.67-7.62 (2H, m), 7.43 (1H, br s), 7.40-7.37 (1H, m), 7.39 (1H, s), 7.31-7.22 (2H, m), 7.05 (1H, d, J = 2.4 Hz), 6.64 (1H, d, J = 7.1 Hz), 4.56 (2H, s). |

TABLE 1-53

| compound No. | structural formula | NMR |
|---|---|---|
| 364 | | $^1$H-NMR (DMSO-D$_6$) δ: 9.41 (1H, s), 9.01 (2H, br s), 8.31-8.28 (1H, m), 8.01 (1H, d, J = 1.4 Hz), 7.77-7.73 (1H, m), 7.63 (1H, s), 7.49-7.44 (1H, m), 7.38-7.33 (1H, m), 6.75 (1H, d, J = 7.9 Hz), 3.92 (3H, s). |
| 365 | | $^1$H-NMR (DMSO-D$_6$) δ: 8.13 (1H, t, J = 5.6 Hz), 7.79-7.74 (2H, m), 7.62-7.58 (1H, m), 7.49-7.44 (1H, m), 7.33-7.29 (1H, m), 7.27-7.23 (1H, m), 7.26 (1H, s), 7.09 (1H, dd, J = 8.3, 2.6 Hz), 4.73 (1H, t, J = 5.6 Hz), 4.54 (2H, s), 3.47-3.42 (2H, m), 3.25-3.20 (2H, m). |

TABLE 1-53-continued
| compound No. | structural formula | NMR |
|---|---|---|
| 366 | 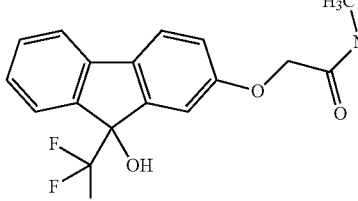 | ¹H-NMR (DMSO-D₆) δ: 7.76-7.71 (2H, m), 7.60-7.57 (1H, m), 7.48-7.43 (1H, m), 7.32-7.27 (1H, m), 7.24 (1H, s), 7.16-7.14 (1H, m), 7.04-7.00 (1H, m), 5.00 (0.6H, t, J = 5.1 Hz), 4.96 (1.2H, s), 4.88 (0.8H, s), 4.69 (0.4H, t, J = 5.6 Hz), 3.61-3.57 (1.2H, m), 3.51-3.47 (0.8H, m), 3.42-3.33 (2H, m), 3.06 (1.2H, s), 2.86 (1.8H, s). |
| 367 | 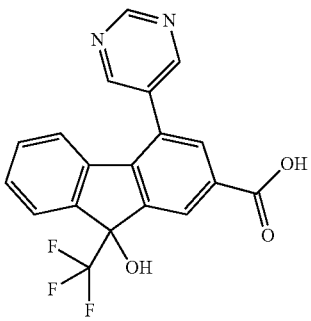 [SMILES: O=C(O)c1cc(-c2cncnc2)c2c(c1)C(O)(C(F)(F)F)c1ccccc1-2] | ¹H-NMR (DMSO-D₆) δ: 13.42 (1H, br s), 9.41 (1H, s), 9.01 (2H, br s), 8.30-8.28 (1H, m), 7.97 (1H, d, J = 1.4 Hz), 7.76-7.72 (1H, m), 7.58 (1H, s), 7.48-7.43 (1H, m), 7.37-7.32 (1H, m), 6.74 (1H, d, J = 7.7 Hz). |
| 368 | 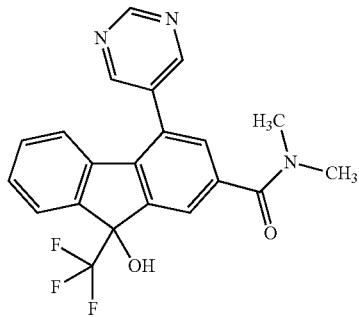 [SMILES: CN(C)C(=O)c1cc(-c2cncnc2)c2c(c1)C(O)(C(F)(F)F)c1ccccc1-2] | ¹H-NMR (DMSO-D₆) δ: 9.39 (1H, s), 9.00 (2H, br s), 7.78-7.76 (1H, m), 7.74-7.69 (1H, m), 7.52-7.51 (2H, m), 7.44-7.39 (1H, m), 7.35-7.30 (1H, m), 6.74 (1H, d, J = 7.7 Hz), 3.02 (6H, s). |
| 369 | 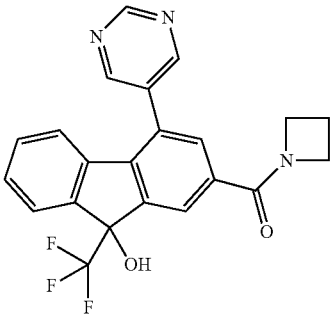 [SMILES: O=C(c1cc(-c2cncnc2)c2c(c1)C(O)(C(F)(F)F)c1ccccc1-2)N1CCC1] | ¹H-NMR (DMSO-D₆) δ: 9.40 (1H, s), 8.99 (2H, br s), 7.99-7.97 (1H, m), 7.74-7.70 (1H, m), 7.66 (1H, d, J = 1.6 Hz), 7.54 (1H, s), 7.45-7.40 (1H, m), 7.35-7.31 (1H, m), 6.75 (1H, d, J = 7.7 Hz), 4.42-4.34 (2H, m), 4.13-4.05 (2H, m), 2.33-2.24 (2H, m). |
| 370 | 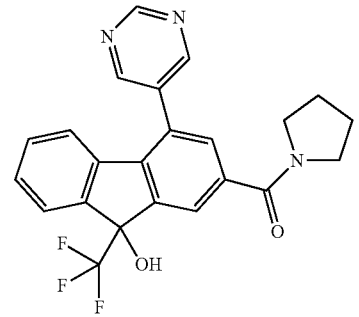 [SMILES: O=C(c1cc(-c2cncnc2)c2c(c1)C(O)(C(F)(F)F)c1ccccc1-2)N1CCCC1] | ¹H-NMR (DMSO-D₆) δ: 9.39 (1H, s), 9.00 (2H, br s), 7.89-7.86 (1H, m), 7.74-7.70 (1H, m), 7.62 (1H, d, J = 1.6 Hz), 7.51 (1H, s), 7.44-7.39 (1H, m), 7.35-7.30 (1H, m), 6.75 (1H, d, J = 7.7 Hz), 3.56-3.44 (4H, m), 1.93-1.81 (4H, m). |

TABLE 1-54

| compound No. | structural formula | NMR |
|---|---|---|
| 371 | | ¹H-NMR (DMSO-D₆) δ: 9.41 (1H, s), 9.02 (2H, br s), 8.67 (1H, t, J = 5.7 Hz), 8.29-8.25 (1H, m), 7.95 (1H, d, J = 1.6 Hz), 7.75-7.71 (1H, m), 7.51 (1H, s), 7.45-7.40 (1H, m), 7.36-7.31 (1H, m), 6.79 (1H, d, J = 7.7 Hz), 4.41 (1H, t, J = 5.1 Hz), 3.45-3.39 (2H, m), 3.37-3.25 (2H, m), 1.61-1.52 (2H, m), 1.51-1.42 (2H, m). |
| 372 | | ¹H-NMR (DMSO-D₆) δ: 9.39 (1H, s), 8.99 (2H, br s), 7.79-7.76 (1H, m), 7.73-7.69 (1H, m), 7.54-7.48 (2H, m), 7.43-7.38 (1H, m), 7.34-7.29 (1H, m), 6.75 (1H, d, J = 7.7 Hz), 4.88-4.79 (1H, m), 3.67-3.60 (1H, m), 3.57-3.50 (2H, m), 3.41-3.36 (1H, m), 3.06-2.99 (3H, m). |
| 373 | | ¹H-NMR (DMSO-D₆) δ: 8.04 (1H, s), 7.82-7.79 (1H, m), 7.70-7.65 (1H, m), 7.66 (1H, s), 7.48 (1H, d, J = 1.5 Hz), 7.43-7.36 (4H, m), 5.76 (1H, d, J = 5.7 Hz), 4.54-4.47 (2H, m), 4.31-4.24 (1H, m), 4.09-4.03 (1H, m), 3.97 (3H, s), 3.84-3.78 (1H, m). |
| 374 | | ¹H-NMR (DMSO-D₆) δ: 8.03 (1H, s), 7.84-7.81 (1H, m), 7.71-7.66 (1H, m), 7.65 (1H, d, J = 0.7 Hz), 7.52-7.48 (1H, m), 7.42-7.36 (4H, m), 4.83 (1H, t, J = 5.4 Hz), 4.39-4.32 (1H, m), 4.12-4.02 (2H, m), 3.97 (3H, s), 3.84-3.77 (1H, m), 3.55 (2H, t, J = 5.5 Hz), 2.79-2.69 (1H, m). |

TABLE 1-54-continued

| compound No. | structural formula | NMR |
|---|---|---|
| 375 | | $^1$H-NMR (DMSO-D$_6$) δ: 8.04 (1H, s), 7.84-7.81 (1H, m), 7.70-7.66 (2H, m), 7.51-7.48 (1H, m), 7.44-7.35 (4H, m), 4.66 (1H, t, J = 5.4 Hz), 4.55-4.46 (1H, m), 4.41-4.35 (1H, m), 4.32-4.24 (1H, m), 4.19-4.13 (1H, m), 3.97 (3H, s), 3.92-3.86 (1H, m), 3.53-3.48 (2H, m), 3.44-3.39 (2H, m). |
| 376 | | $^1$H-NMR (DMSO-D$_6$) δ: 8.04 (1H, s), 7.72-7.65 (3H, m), 7.44-7.34 (5H, m), 5.04-4.95 (1H, m), 4.37-4.23 (1H, m), 3.96 (3H, s), 3.68-3.24 (4H, m), 2.03-1.88 (1H, m), 1.87-1.77 (1H, m). |

TABLE 1-55

| compound No. | structural formula | NMR |
|---|---|---|
| 377 | | $^1$H-NMR (DMSO-D$_6$) δ: 8.25 (1H, s), 7.93 (1H, d, J = 0.7 Hz), 7.85-7.81 (2H, m), 7.79-7.77 (1H, m), 7.71 (1H, dd, J = 7.9, 1.5 Hz), 7.65-7.61 (1H, m), 7.52-7.47 (1H, m), 7.39-7.34 (1H, m), 7.25 (1H, s), 3.88 (3H, s). |
| 378 | | $^1$H-NMR (DMSO-D$_6$) δ: 8.36 (1H, d, J = 2.6 Hz), 7.79 (1H, d, J = 7.5 Hz), 7.71-7.66 (1H, m), 7.59-7.53 (2H, m), 7.49 (1H, s), 7.48-7.43 (1H, m), 3.91 (3H, s). |
| 379 | | $^1$H-NMR (DMSO-D$_6$) δ: 7.79-7.73 (2H, m), 7.61-7.56 (1H, m), 7.49-7.43 (1H, m), 7.33-7.27 (1H, m), 7.24 (0.4H, s), 7.23 (0.6H, s), 7.18-7.14 (1H, m), 7.11-7.06 (1H, m), 4.85 (0.6H, t, J = 5.5 Hz), 4.68 (0.4H, t, J = 5.3 Hz), 4.20 (0.8H, t, J = 5.5 Hz), 4.12 (1.2H, t, J = 6.0 Hz), 3.79-3.73 (0.8H, m), 3.69-3.63 (1.2H, m), 3.61-3.54 (1.2H, m), 3.51-3.38 (2.8H, m), 2.10 (1.2H, s), 2.05 (1.8H, s). |

TABLE 1-55-continued

| compound No. | structural formula | NMR |
|---|---|---|
| 380 | (fluorene with CF(OH)F at 9-position, 2-O-CH(CH3)-CH2-N(CH3)-C(=O)-CH3) | ¹H-NMR (DMSO-D₆) δ: 7.77-7.72 (2H, m), 7.60-7.56 (1H, m), 7.49-7.43 (1H, m), 7.32-7.21 (2H, m), 7.17-7.13 (1H, m), 7.11-7.04 (1H, m), 4.82-4.65 (1H, m), 3.71-3.62 (0.4H, m), 3.52-3.39 (1.6H, m), 3.03 (1.8H, s), 2.85 (0.6H, s), 2.84 (0.6H, s), 2.10 (1.2H, s), 1.96 (0.9H, s), 1.95 (0.9H, s), 1.29-1.21 (3H, m). |
| 381 | (fluorene with CF(OH)F at 9-position, 2-O-CH2-CH(CH3)-N(CH3)-C(=O)-CH3) | ¹H-NMR (DMSO-D₆) δ: 7.79-7.73 (2H, m), 7.61-7.56 (1H, m), 7.49-7.43 (1H, m), 7.33-7.27 (1H, m), 7.25-7.22 (1H, m), 7.18-7.14 (1H, m), 7.11-7.05 (1H, m), 4.92-4.79 (0.5H, m), 4.37-4.25 (0.5H, m), 4.15-3.96 (2H, m), 2.88 (1.5H, s), 2.70 (1.5H, s), 2.05 (1.5H, s), 2.00 (1.5H, s), 1.25-1.13 (3H, m). |
| 382 | (fluorene with CF(OH)F at 9-position, 2-O-CH2-C(=O)-N(pyrrolidine-CH2OH)) | ¹H-NMR (DMSO-D₆) δ: 7.76-7.72 (2H, m), 7.60-7.57 (1H, m), 7.48-7.43 (1H, m), 7.32-7.28 (1H, m), 7.24 (1H, s), 7.16-7.12 (1H, m), 7.05-7.01 (1H, m), 5.14-5.10 (0.3H, m), 4.93 (0.6H, s), 4.80-4.77 (1.4H, m), 4.73 (0.7H, t, J = 5.6 Hz), 4.12-4.04 (0.3H, m), 4.01-3.94 (0.7H, m), 3.55-3.26 (4H, m), 2.01-1.76 (4H, m). |

TABLE 1-56

| compound No. | structural formula | NMR |
|---|---|---|
| 383 | (fluorene with CF(OH)F at 9-position, 2-O-CH2-C(=O)-N(pyrrolidine-CH2OH)) | ¹H-NMR (DMSO-D₆) δ: 7.76-7.72 (2H, m), 7.61-7.57 (1H, m), 7.48-7.43 (1H, m), 7.32-7.28 (1H, m), 7.24 (1H, s), 7.16-7.13 (1H, m), 7.05-7.01 (1H, m), 5.14-5.10 (0.3H, m), 4.95-4.91 (0.6H, m), 4.81-4.77 (1.4H, m), 4.75-4.71 (0.7H, m), 4.12-4.04 (0.3H, m), 4.00-3.94 (0.7H, m), 3.55-3.26 (4H, m), 2.00-1.76 (4H, m). |
| 384 | (4-Cl-fluorene with CF(OH)F at 9-position, 2-O-(CH2)3-COOH) | ¹H-NMR (DMSO-D₆) δ: 12.03 (1H, br s), 8.14 (1H, d, J = 7.7 Hz), 7.68-7.64 (1H, m), 7.56-7.51 (1H, m), 7.42-7.38 (2H, m), 7.17-7.14 (2H, m), 4.08 (2H, t, J = 6.3 Hz), 2.30 (2H, t, J = 7.2 Hz), 1.80-1.72 (2H, m), 1.71-1.64 (2H, m). |

TABLE 1-56-continued

| compound No. | structural formula | NMR |
|---|---|---|
| 385 | | $^1$H-NMR (DMSO-D$_6$) δ: 8.15 (1H, d, J = 7.5 Hz), 7.69-7.64 (2H, m), 7.57-7.52 (1H, m), 7.48-7.39 (3H, m), 7.27-7.25 (1H, m), 7.15 (1H, d, J = 2.4 Hz), 4.55 (2H, s). |
| 386 | | $^1$H-NMR (DMSO-D$_6$) δ: 7.97 (1H, s), 7.67-7.59 (2H, m), 7.61 (1H, s), 7.41-7.26 (5H, m), 7.21 (1H, s), 4.03 (2H, d, J = 7.3 Hz), 2.27-2.16 (1H, m), 0.93 (3H, d, J = 2.0 Hz), 0.92 (3H, d, J = 2.0 Hz). |
| 387 | | $^1$H-NMR (CDCl$_3$) δ: 8.20 (1H, d, J = 7.9 Hz), 7.70-7.65 (1H, m), 7.50-7.46 (1H, m), 7.36-7.31 (1H, m), 7.20-7.17 (1H, m), 6.95 (1H, d, J = 2.2 Hz), 4.02 (2H, t, J = 6.4 Hz), 3.68 (2H, t, J = 6.3 Hz), 2.88 (1H, br s), 1.88-1.80 (2H, m), 1.69-1.51 (4H, m). |
| 388 | | $^1$H-NMR (CDCl$_3$) δ: 8.22-8.17 (1H, m), 7.71-7.66 (1H, m), 7.51-7.45 (1H, m), 7.37-7.30 (1H, m), 7.20-7.16 (1H, m), 6.95-6.92 (1H, m), 4.16-4.09 (2H, m), 3.90 (0.7H, br s), 3.77 (0.3H, br s), 3.73-3.61 (2H, m), 3.13 (2.2H, s), 2.96 (0.8H, s), 2.14 (0.8H, s), 2.03 (2.2H, s). |
| 389 | | $^1$H-NMR (DMSO-D$_6$) δ: 7.75 (2H, d, J = 8.3 Hz), 7.61-7.57 (1H, m), 7.48-7.43 (1H, m), 7.32-7.28 (1H, m), 7.25 (1H, s), 7.18-7.15 (1H, m), 7.04 (1H, dd, J = 8.5, 2.4 Hz), 5.07 (0.5H, d, J = 3.7 Hz), 4.96 (0.5H, d, J = 3.2 Hz), 4.81 (1.0H, s), 4.76 (1.0H, s), 4.36 (0.5H, d, J = 20.4 Hz), 4.27 (0.5H, d, J = 18.3 Hz), 3.65-3.53 (1.5H, m), 3.49-3.27 (2.5H, m), 2.01-1.92 (0.5H, m), 1.91-1.81 (1.0H, m), 1.79-1.71 (0.5H, m). |

TABLE 1-57

| compound No. | structural formula | NMR |
|---|---|---|
| 390 | | ¹H-NMR (DMSO-D₆) δ: 7.74 (2H, d, J = 8.1 Hz), 7.60-7.56 (1H, m), 7.47-7.43 (1H, m), 7.32-7.27 (1H, m), 7.25 (1H, s), 7.17-7.14 (1H, m), 7.03 (1H, dd, J = 8.5, 2.4 Hz), 5.06 (0.5H, d, J = 3.7 Hz), 4.96 (0.5H, d, J = 3.2 Hz), 4.80 (1.0H, s), 4.75 (1.0H, s), 4.38-4.33 (0.5H, m), 4.28-4.24 (0.5H, m), 3.64-3.52 (1.5H, m), 3.48-3.23 (2.5H, m), 1.99-1.91 (0.5H, m), 1.90-1.80 (1.0H, m), 1.78-1.69 (0.5H, m). |
| 391 | | ¹H-NMR (DMSO-D₆) δ: 7.78-7.74 (2H, m), 7.61-7.58 (1H, m), 7.49-7.44 (1H, m), 7.33-7.28 (1H, m), 7.26 (1H, s), 7.16-7.14 (1H, m), 7.04 (1H, dd, J = 8.3, 2.6 Hz), 4.64 (2H, s), 4.26 (2H, t, J = 8.5 Hz), 3.92 (2H, t, J = 7.8 Hz), 2.30-2.20 (2H, m). |
| 392 | | ¹H-NMR (DMSO-D₆) δ: 8.02 (1H, s), 7.73-7.63 (2H, m), 7.65 (1H, s), 7.43-7.32 (5H, m), 4.82-4.76 (1H, m), 4.21-4.12 (1H, m), 3.96 (3H, s), 3.61-3.55 (2H, m), 3.51-3.44 (1H, m), 3.41-3.34 (1H, m), 2.02-1.83 (3H, m), 1.77-1.64 (1H, m). |
| 393 | | ¹H-NMR (DMSO-D₆) δ: 8.03 (1H, s), 7.73-7.63 (2H, m), 7.65 (1H, s), 7.43-7.32 (5H, m), 4.82-4.75 (1H, m), 4.21-4.12 (1H, m), 3.96 (3H, s), 3.61-3.54 (2H, m), 3.51-3.44 (1H, m), 3.43-3.34 (1H, m), 2.01-1.82 (3H, m), 1.78-1.66 (1H, m). |

TABLE 1-57-continued

| compound No. | structural formula | NMR |
|---|---|---|
| 394 | | ¹H-NMR (DMSO-D₆) δ: 8.03 (1H, s), 7.72-7.64 (3H, m), 7.42-7.34 (5H, m), 4.73-4.62 (1H, m), 3.96 (3H, s), 3.63-3.24 (6H, m), 2.39-2.26 (1H, m), 2.00-1.86 (1H, m), 1.71-1.60 (1H, m). |
| 395 | | ¹H-NMR (CDCl₃) δ: 7.68-7.64 (1H, m), 7.57-7.51 (2H, m), 7.46-7.40 (1H, m), 7.30-7.23 (2H, m), 6.97 (1H, dd, J = 8.3, 2.3 Hz), 4.04 (2H, t, J = 6.2 Hz), 3.52-3.38 (5H, m), 2.36-2.29 (2H, m), 2.06-1.95 (4H, m). |

TABLE 1-58

| compound No. | structural formula | NMR |
|---|---|---|
| 396 | | ¹H-NMR (DMSO-D₆) δ: 7.77-7.73 (2H, m), 7.61-7.58 (1H, m), 7.49-7.44 (1H, m), 7.33-7.28 (1H, m), 7.25 (1H, s), 7.17-7.14 (1H, m), 7.03 (1H, dd, J = 8.3, 2.6 Hz), 4.91 (1H, d, J = 13.9 Hz), 4.86 (1H, d, J = 15.5 Hz), 4.78 (1H, d, J = 3.7 Hz), 3.92-3.84 (1H, m), 3.76-3.65 (2H, m), 3.25-3.15 (1H, m), 3.12-3.01 (1H, m), 1.83-1.66 (2H, m), 1.47-1.35 (1H, m), 1.32-1.21 (1H, m). |
| 397 | | ¹H-NMR (DMSO-D₆) δ: 7.77-7.73 (2H, m), 7.61-7.57 (1H, m), 7.48-7.44 (1H, m), 7.32-7.28 (1H, m), 7.25 (1H, s), 7.16-7.13 (1H, m), 7.04 (1H, dd, J = 8.3, 2.3 Hz), 4.95-4.81 (2H, m), 4.52 (1H, t, J = 5.1 Hz), 4.38-4.29 (1H, m), 3.92-3.83 (1H, m), 3.26 (2H, t, J = 5.6 Hz), 3.07-2.97 (1H, m), 2.63-2.54 (1H, m), 1.76-1.58 (3H, m), 1.21-1.07 (1H, m), 1.03-0.90 (1H, m). |
| 398 | | ¹H-NMR (CDCl₃) δ: 8.15 (1H, d, J = 2.2 Hz), 7.81 (1H, d, J = 7.5 Hz), 7.72 (1H, d, J = 7.5 Hz), 7.53-7.47 (2H, m), 7.43-7.38 (1H, m), 4.18-4.03 (2H, m), 3.76-3.67 (3H, m), 3.15 (2.3H, s), 2.98 (0.7H, s), 2.16 (0.7H, s), 2.06 (2.3H, s). |

TABLE 1-58-continued

| compound No. | structural formula | NMR |
|---|---|---|
| 399 | | ¹H-NMR (CDCl₃) δ: 8.16-8.12 (1H, m), 7.86-7.81 (1H, m), 7.74-7.69 (1H, m), 7.56-7.48 (1H, m), 7.48-7.38 (2H, m), 4.27-4.12 (4H, m), 3.89-3.49 (4H, m), 3.09 (0.7H, s), 3.04 (2.3H, s). |
| 400 | | ¹H-NMR (DMSO-D₆) δ: 7.76-7.71 (2H, m), 7.61-7.57 (1H, m), 7.48-7.44 (1H, m), 7.30 (1H, d, J = 18.6 Hz), 7.24 (1H, s), 7.16-7.13 (1H, m), 7.01 (1H, dd, J = 8.5, 2.4 Hz), 5.02 (1H, t, J = 5.1 Hz), 4.97 (2H, s), 4.71 (1H, t, J = 5.4 Hz), 3.63-3.57 (2H, m), 3.53-3.32 (6H, m). |
| 401 | | ¹H-NMR (CDCl₃) δ: 7.69-7.65 (1H, m), 7.58-7.52 (2H, m), 7.45-7.40 (1H, m), 7.30-7.25 (2H, m), 6.97 (1H, dd, J = 8.4, 2.4 Hz), 4.05 (2H, t, J = 6.2 Hz), 3.74 (1H, s), 3.62-3.54 (1H, m), 3.47-3.39 (1H, m), 3.34-3.27 (2H, m), 2.33-2.28 (2H, m), 2.06-1.99 (2H, m), 1.82-1.71 (4H, m). |
| 402 | | ¹H-NMR (DMSO-D₆) δ: 12.39 (1H, br s), 7.83 (1H, d, J = 7.7 Hz), 7.79 (1H, d, J = 7.9 Hz), 7.65-7.61 (1H, m), 7.56-7.53 (1H, m), 7.52-7.47 (1H, m), 7.41-7.35 (2H, m), 7.24 (1H, s), 3.67 (2H, s). |

TABLE 1-59

| compound No. | structural formula | NMR |
|---|---|---|
| 403 | | ¹H-NMR (DMSO-D₆) δ: 7.81 (1H, d, J = 7.5 Hz), 7.77 (1H, d, J = 7.7 Hz), 7.64-7.60 (1H, m), 7.58-7.52 (2H, m), 7.51-7.46 (1H, m), 7.41-7.34 (2H, m), 7.22 (1H, s), 6.92 (1H, br s), 3.47 (1H, d, J = 14.1 Hz), 3.43 (1H, d, J = 14.3 Hz). |
| 404 | | ¹H-NMR (CDCl₃) δ: 8.39-8.36 (1H, m), 7.69-7.65 (1H, m), 7.52-7.47 (1H, m), 7.37-7.32 (1H, m), 7.26 (2H, s), 7.23-7.21 (1H, m), 7.14 (1H, d, J = 2.4 Hz), 4.09 (2H, t, J = 6.1 Hz), 2.61 (2H, t, J = 7.2 Hz), 2.20-2.12 (2H, m). |

TABLE 1-59-continued

| compound No. | structural formula | NMR |
|---|---|---|
| 405 | | ¹H-NMR (DMSO-D₆) δ: 7.80 (1H, d, J = 7.5 Hz), 7.74 (1H, d, J = 7.7 Hz), 7.64-7.59 (1H, m), 7.51-7.45 (2H, m), 7.38-7.32 (2H, m), 7.18 (1H, s), 4.68 (1H, t, J = 5.1 Hz), 3.64 (2H, dt, J = 6.8, 5.1 Hz), 2.80 (2H, t, J = 6.8 Hz). |
| 406 | | ¹H-NMR (CDCl₃) δ: 9.20 (1H, s), 8.98-7.98 (2H, m), 7.72-7.69 (1H, m), 7.42-7.39 (1H, m), 7.25-7.21 (1H, m), 7.11-7.07 (1H, m), 6.69 (1H, d, J = 2.3 Hz), 6.46 (1H, d, J = 7.9 Hz), 4.48 (1H, s), 4.10-4.04 (2H, m), 3.70 (2H, t, J = 6.1 Hz), 1.90-1.83 (2H, m), 1.71-1.54 (4H, m), 1.41 (1H, br s). |
| 407 | | ¹H-NMR (CDCl₃) δ: 7.68-7.63 (1H, m), 7.54 (1H, d, J = 0.7 Hz), 7.49 (1H, s), 7.25-7.21 (4H, m), 6.78 (1H, d, J = 2.3 Hz), 4.04 (2H, t, J = 6.4 Hz), 4.00 (3H, s), 3.69 (2H, t, J = 6.3 Hz), 3.24 (1H, br s), 1.89-1.81 (2H, m), 1.70-1.52 (4H, m), 1.34 (1H, br s). |
| 408 | | ¹H-NMR (DMSO-D₆) δ: 8.15 (1H, d, J = 7.7 Hz), 7.69-7.65 (1H, m), 7.57-7.52 (1H, m), 7.44 (1H, s), 7.43-7.39 (1H, m), 7.21 (1H, d, J = 2.2 Hz), 7.20-7.18 (1H, m), 4.24 (2H, t, J = 5.4 Hz), 3.50 (2H, t, J = 5.4 Hz), 2.95 (3H, s), 2.89 (3H, s). |
| 409 | | ¹H-NMR (DMSO-D₆) δ: 8.15 (1H, d, J = 7.7 Hz), 7.68-7.64 (1H, m), 7.56-7.52 (1H, m), 7.46-7.38 (2H, m), 7.20-7.16 (2H, m), 4.53 (0.4H, t, J = 5.4 Hz), 4.48 (0.6H, t, J = 5.5 Hz), 4.26-4.17 (3H, m), 4.09 (1H, d, J = 5.5 Hz), 3.70 (1.1H, t, J = 5.7 Hz), 3.64 (0.9H, t, J = 5.1 Hz), 2.99 (1.6H, s), 2.93 (1.4H, s). |

TABLE 1-59-continued
| compound No. | structural formula | NMR |
|---|---|---|
| 410 |  | $^1$H-NMR (DMSO-D$_6$) δ: 8.14 (1H, d, J = 7.7 Hz), 7.68-7.63 (1H, m), 7.56-7.51 (1H, m), 7.46-7.38 (2H, m), 7.33 (1H, br s), 7.16 (2H, s), 6.79 (1H, br s), 4.07 (2H, t, J = 6.4 Hz), 2.24 (2H, t, J = 7.4 Hz), 1.98-1.90 (2H, m). |
TABLE 1-60
| compound No. | structural formula | NMR |
|---|---|---|
| 411 | 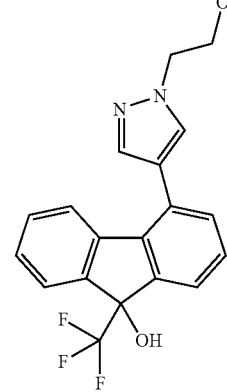 | $^1$H-NMR (CDCl$_3$) δ: 7.73-7.67 (2H, m), 7.59 (1H, s), 7.57 (1H, s), 7.37-7.23 (5H, m), 4.36-4.32 (2H, m), 4.13-4.06 (2H, m), 3.07 (1H, br s), 2.96 (1H, br s). |
| 412 | 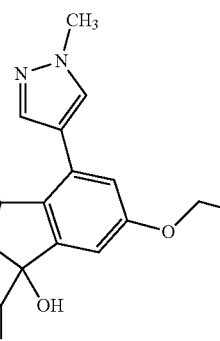 | $^1$H-NMR (CDCl$_3$) δ: 7.68-7.63 (1H, m), 7.59 (1H, s), 7.50 (1H, s), 7.28-7.21 (4H, m), 6.77 (1H, d, J = 2.6 Hz), 4.16 (2H, t, J = 5.2 Hz), 4.02 (3H, s), 3.71-3.66 (2H, m), 3.62-3.56 (2H, m), 3.15 (1H, br s), 2.40-2.35 (2H, m), 2.08-1.99 (2H, m). |
| 413 | 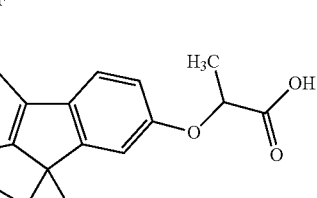 | $^1$H-NMR (DMSO-D$_6$) δ: 7.78-7.72 (2H, m), 7.65-7.56 (2H, m), 7.48-7.43 (1H, m), 7.32-7.27 (2H, m), 7.24 (1H, d, J = 4.6 Hz), 7.20-7.16 (1H, m), 7.05-7.01 (1H, m), 4.71-4.64 (1H, m), 1.49-1.44 (3H, m). |

TABLE 1-60-continued

| compound No. | structural formula | NMR |
|---|---|---|
| 414 | | ¹H-NMR (CDCl₃) δ: 7.93-7.91 (1H, m), 7.83-7.79 (1H, m), 7.61 (1H, d, J = 0.7 Hz), 7.53 (1H, d, J = 1.6 Hz), 7.74-7.45 (1H, m), 7.40-7.33 (2H, m), 7.29-7.25 (1H, m), 6.20 (1H, br s), 4.10-3.97 (2H, m), 4.04 (3H, s), 3.25-3.18 (2H, m). |
| 415 | | ¹H-NMR (CDCl₃) δ: 7.71-7.69 (1H, m), 7.65-7.57 (3H, m), 7.55-7.45 (1H, m), 7.39-7.33 (2H, m), 5.84 (1H, br s), 4.50-4.39 (2H, m), 3.36 (1H, br s), 2.01 (3H, s). |
| 416 | | ¹H-NMR (CDCl₃) δ: 7.69-7.65 (1H, m), 7.58-7.53 (2H, m), 7.46-7.41 (1H, m), 7.31-7.24 (2H, m), 6.97 (1H, dd, J = 8.4, 2.4 Hz), 4.20 (2H, t, J = 5.4 Hz), 3.77-3.65 (2H, m), 3.55-3.44 (3H, m), 2.33 (2H, t, J = 6.3 Hz), 1.84-1.71 (4H, m). |
| 417 | | ¹H-NMR (CDCl₃) δ: 7.76-7.72 (1H, m), 7.65-7.60 (2H, m), 7.53 (1H, d, J = 7.7 Hz), 7.48-7.43 (1H, m), 7.37-7.33 (1H, m), 7.23-7.20 (1H, m), 3.57 (1H, d, J = 13.2 Hz), 3.45 (1H, d, J = 13.2 Hz), 2.09 (3H, s). |

TABLE 1-61

| compound No. | structural formula | NMR |
|---|---|---|
| 418 | | ¹H-NMR (DMSO-D₆) δ: 7.87-7.79 (2H, m), 7.65-7.61 (1H, m), 7.53-7.46 (2H, m), 7.40-7.33 (2H, m), 7.30 (0.4H, s), 7.24 (0.6H, s), 4.65 (0.8H, s), 4.59 (0.6H, d, J = 15.2 Hz), 4.53 (0.6H, d, J = 15.0 Hz), 2.94 (1.8H, s), 2.82 (1.2H, s), 2.09 (1.8H, s), 2.06 (1.2H, s). |

TABLE 1-61-continued

| compound No. | structural formula | NMR |
|---|---|---|
| 419 | | ¹H-NMR (CDCl₃) δ: 7.69-7.65 (1H, m), 7.58-7.54 (2H, m), 7.47-7.42 (1H, m), 7.32-7.27 (1H, m), 7.25-7.22 (1H, m), 6.99-6.95 (1H, m), 5.99 (1H, br s), 4.11-4.04 (2H, m), 3.90-3.84 (1H, m), 3.69 (1H, s), 2.48-2.29 (3H, m), 1.98-1.87 (1H, m). |
| 420 | | ¹H-NMR (CDCl₃) δ: 7.69-7.65 (1H, m), 7.59-7.55 (2H, m), 7.47-7.43 (1H, m), 7.32-7.28 (1H, m), 7.25-7.23 (1H, m), 7.00-6.96 (1H, m), 4.17-4.13 (1H, m), 4.07-4.02 (1H, m), 3.94-3.88 (1H, m), 3.17-3.07 (1H, m), 2.92 (2H, s), 2.90 (1H, s), 2.60-2.48 (1H, m), 2.43-2.33 (1H, m), 2.31-2.20 (1H, m), 2.03-1.94 (1H, m). |
| 421 | | ¹H-NMR (CDCl₃) δ: 7.69-7.65 (1H, m), 7.59-7.55 (2H, m), 7.47-7.43 (1H, m), 7.32-7.28 (1H, m), 7.24-7.22 (1H, m), 6.99-6.95 (1H, m), 4.18-4.13 (1H, m), 4.07-4.03 (1H, m), 4.01-3.95 (1H, m), 3.73 (1H, br s), 3.61-3.52 (2H, m), 3.51-3.42 (2H, m), 3.31-3.25 (1H, m), 2.66-2.56 (1H, m), 2.48-2.39 (1H, m), 2.33-2.23 (1H, m), 2.07-1.98 (1H, m), 1.75-1.52 (2H, m). |
| 422 | | ¹H-NMR (DMSO-D₆) δ: 9.38 (0.5H, s), 9.37 (0.5H, s), 8.96 (2H, br s), 7.66-7.62 (1H, m), 7.39 (1H, d, J = 6.5 Hz), 7.32-7.22 (3H, m), 7.07 (1H, dd, J = 4.6, 2.3 Hz), 6.65-6.61 (1H, m), 4.26 (1.0H, t, J = 5.2 Hz), 4.18 (1.0H, t, J = 5.8 Hz), 3.73 (1.0H, t, J = 5.2 Hz), 3.66 (1.0H, t, J = 5.9 Hz), 3.08 (1.5H, s), 2.88 (1.5H, s), 2.09 (1.5H, s), 2.00 (1.5H, s). |
| 423 | | ¹H-NMR (CDCl₃) δ: 7.69-7.64 (1H, m), 7.55-7.53 (1H, m), 7.50-7.48 (1H, m), 7.25-7.20 (4H, m), 6.75 (1H, d, J = 2.6 Hz), 4.18-4.13 (2H, m), 4.00 (2.1H, s), 3.99 (0.9H, s), 3.79-3.62 (3H, m), 3.16 (2.1H, s), 2.98 0.9H, s), 2.16 (0.9H, s), 2.07 (2.1H, s). |

TABLE 1-62
| compound No. | structural formula | NMR |
|---|---|---|
| 424 | 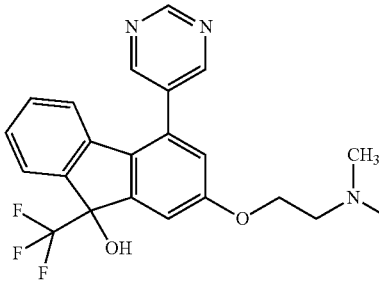 | ¹H-NMR (DMSO-D₆) δ: 9.38 0.4H, s), 9.37 (0.5H, s), 8.96 (2H, br s), 7.66-7.62 (1H, m), 7.39 (1H, d, J = 7.2 Hz), 7.32-7.22 (3H, m), 7.07 (1H, d, J = 2.3 Hz), 6.63 (1H, dd, J = 7.1, 3.4 Hz), 4.53 (0.4H, t, J = 5.6 Hz), 4.48 (0.5H, t, J = 5.4 Hz), 4.28-4.19 (3H, m), 4.08 (1H, d, J = 5.8 Hz), 3.72 (1.1H, t, J = 5.8 Hz), 3.66 (0.9H, t, J = 5.2 Hz), 2.99 (1.7H, s), 2.94 (1.4H, s). |
| 425 | 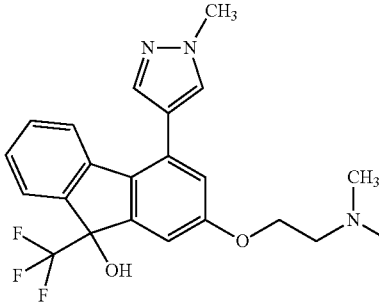 | ¹H-NMR (DMSO-D₆) δ: 7.98 (1H, s), 7.64-7.58 (1H, m), 7.62 (1H, s), 7.31-7.22 (4H, m), 7.16-7.13 (1H, m), 6.84 (1H, d, J = 2.3 Hz), 4.52 (0.4H, t, J = 5.6 Hz), 4.48 (0.6H, t, J = 5.4 Hz), 4.23-4.14 (3.0H, m), 4.09 (1.0H, d, J = 5.3 Hz), 3.95 (3H, s), 3.70 (1.1H, t, J = 5.7 Hz), 3.64 (0.9H, t, J = 5.2 Hz), 2.99 (1.6H, s), 2.93 (1.4H, s). |
| 426 | 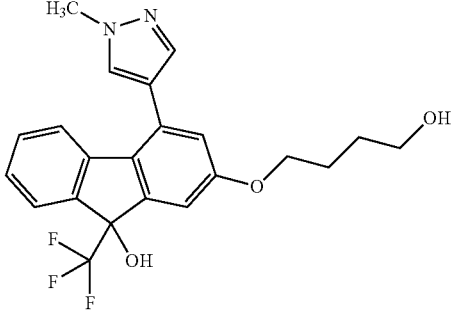 [SMILES: Cn1cc(-c2cc(OCCCCO)cc3c2-c2ccccc2C3(O)C(F)(F)F)cn1] | ¹H-NMR (DMSO-D₆) δ: 7.98 (1H, s), 7.66-7.53 (3H, m), 7.31-7.21 (2H, m), 7.22 (1H, s), 7.14-7.12 (1H, m), 6.81 (1H, d, J = 2.4 Hz), 4.46 (1H, t, J = 5.2 Hz), 4.05 (2H, t, J = 6.5 Hz), 3.95 (3H, s), 3.49-3.43 (2H, m), 1.81-1.74 (2H, m), 1.62-1.54 (2H, m). |
| 427 | 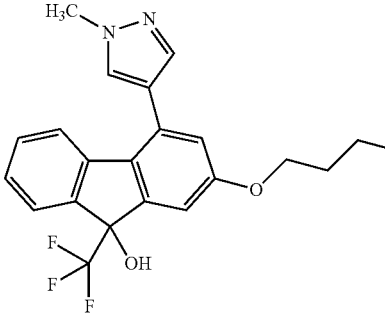 | ¹H-NMR (DMSO-D₆) δ: 7.97 (1H, s), 7.62-7.57 (1H, m), 7.61 (1H, s), 7.29-7.23 (3H, m), 7.22 (1H, s), 7.15-7.12 (1H, m), 6.82 (1H, d, J = 2.4 Hz), 4.07 (2H, t, J = 6.5 Hz), 3.95 (3H, s), 2.97 (3H, s), 2.83 (3H, s), 2.47 (2H, t, J = 7.3 Hz), 1.99-1.92 (2H, m). |

TABLE 1-62-continued
| compound No. | structural formula | NMR |
|---|---|---|
| 428 | 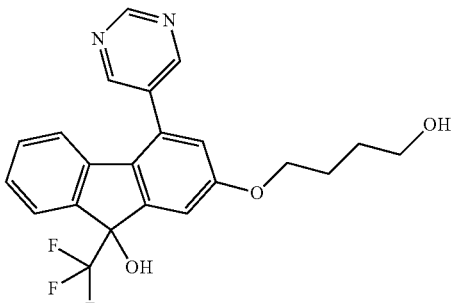 | ¹H-NMR (DMSO-D₆) δ: 9.37 (1H, s), 8.96 (2H, br s), 7.65-7.61 (1H, m), 7.38-7.35 (1H, m), 7.30-7.21 (3H, m), 7.03 (1H, d, J = 2.4 Hz), 6.61 (1H, d, J = 6.8 Hz), 4.46 (1H, t, J = 5.2 Hz), 4.10 (2H, t, J = 6.5 Hz), 3.47 (2H, dt, J = 6.5, 5.2 Hz), 1.82-1.75 (2H, m), 1.63-1.54 (2H, m). |
| 429 | | ¹H-NMR (DMSO-D₆) δ: 9.37 (1H, s), 8.96 (2H, br s), 7.65-7.62 (1H, m), 7.38 (1H, s), 7.31-7.22 (3H, m), 7.04 (1H, d, J = 2.3 Hz), 6.61 (1H, dd, J = 6.7, 0.9 Hz), 4.11 (2H, t, J = 6.5 Hz), 2.97 (3H, s), 2.82 (3H, s), 2.47 (2H, t, J = 7.0 Hz), 2.01-1.94 (2H, m). |
TABLE 1-63
| compound No. | structural formula | NMR |
|---|---|---|
| 430 | 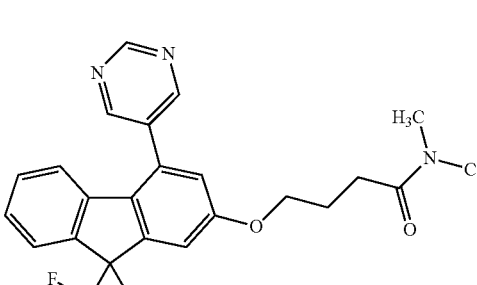 | ¹H-NMR (DMSO-D₆) δ: 8.36 (1H, d, J = 2.8 Hz), 7.81-7.78 (1H, m), 7.70-7.67 (1H, m), 7.60-7.54 (2H, m), 7.50 (1H, s), 7.48-7.44 (1H, m), 4.25 (2H, t, J = 5.4 Hz), 3.59 (2H, t, J = 5.4 Hz), 3.48 (2H, t, J = 7.1 Hz), 2.22 (2H, t, J = 8.1 Hz), 1.97-1.88 (2H, m). |
| 431 | | ¹H-NMR (CDCl₃) δ: 7.68-7.65 (1H, m), 7.59-7.54 (2H, m), 7.47-7.42 (1H, m), 7.32-7.27 (1H, m), 7.25-7.23 (1H, m), 7.00-6.96 (1H, m), 4.57-4.52 (2H, m), 4.24-4.05 (3H, m), 3.84-3.77 (1H, m), 3.70-3.65 (2H, m), 3.42-3.32 (1H, m), 3.31 (1.5H, s), 3.29 (1.5H, s), 3.04 (0.5H, s), 3.00 (0.5H, s), 2.64-2.53 (1H, m), 2.46-2.36 (1H, m), 2.32-2.21 (1H, m), 2.08-1.98 (1H, m). |

TABLE 1-63-continued

| compound No. | structural formula | NMR |
|---|---|---|
| 432 | | ¹H-NMR (CDCl₃) δ: 7.69-7.65 (1H, m), 7.59-7.55 (2H, m), 7.47-7.43 (1H, m), 7.32-7.28 (1H, m), 7.25-7.22 (1H, m), 6.98 (1H, dd, J = 8.2, 2.4 Hz), 4.21-4.13 (1H, m), 4.10-4.03 (2H, m), 3.84-3.67 (2H, m), 3.66-3.57 (1H, m), 3.49-3.42 (1H, m), 3.28 (1H, d, J = 23.9 Hz), 3.23-3.15 (1H, m), 2.65-2.54 (1H, m), 2.47-2.38 (1H, m), 2.37-2.26 (1H, m), 2.08-1.98 (1H, m). |
| 433 | | ¹H-NMR (DMSO-D₆) δ: 13.07 (1H, br s), 7.97 (1H, s), 7.62-7.58 (1H, m), 7.60 (1H, s), 7.30-7.23 (4H, m), 7.14-7.11 (1H, m), 6.80 (1H, d, J = 2.4 Hz), 4.77 (2H, s), 3.96 (3H, s). |
| 434 | | ¹H-NMR (DMSO-D₆) δ: 8.37 (1H, d, J = 2.8 Hz), 7.80 (1H, d, J = 7.4 Hz), 7.72-7.67 (2H, m), 7.61-7.59 (1H, m), 7.59-7.54 (1H, m), 7.52 (1H, s), 7.49-7.44 (2H, m), 4.62 (2H, s). |
| 435 | | ¹H-NMR (CDCl₃) δ: 7.69-7.65 (1H, m), 7.59 (0.2H, s), 7.56 (0.8H, s), 7.51 (0.2H, s), 7.50 (0.8H, s), 7.28-7.22 (4H, m), 6.77 (0.8H, d, J = 2.6 Hz), 6.76 (0.2H, d, J = 2.6 Hz), 5.95 (1H, br s), 4.12-4.08 (2H, m), 4.02 (0.6H, s), 4.02 (2.4H, s), 3.70-3.65 (2H, m), 2.02 (0.6H, s), 2.02 (2.4H, s). |

TABLE 1-64
| compound No. | structural formula | NMR |
|---|---|---|
| 436 | 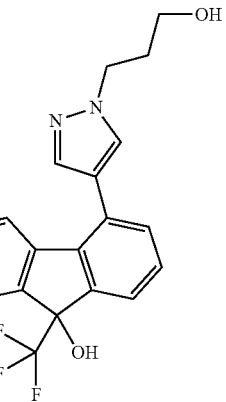 | ¹H-NMR (CDCl₃) δ: 7.73-7.68 (2H, m), 7.52 (1H, s), 7.50 (1H, s), 7.36-7.22 (5H, m), 4.37 (2H, t, J = 6.4 Hz), 3.71 (2H, t, J = 5.7 Hz), 3.34 (1H, br s), 2.59 (1H, br s), 2.16-2.10 (2H, m). |
| 437 | 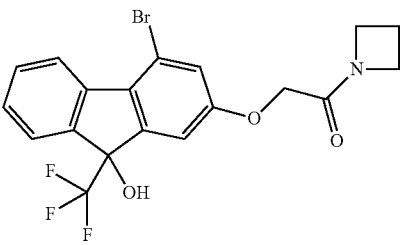 [SMILES: O=C(COc1cc(Br)c2c(c1)C(O)(C(F)(F)F)c1ccccc1-2)N1CCC1] | ¹H-NMR (DMSO-D₆) δ: 8.32 (1H, d, J = 7.9 Hz), 7.68-7.64 (1H, m), 7.58-7.53 (1H, m), 7.45-7.40 (1H, m), 7.44 (1H, s), 7.28 (1H, d, J = 2.4 Hz), 7.22-7.20 (1H, m), 4.71 (2H, s), 4.28-4.22 (2H, m), 3.95-3.89 (2H, m), 2.30-2.22 (2H, m). |
| 438 | 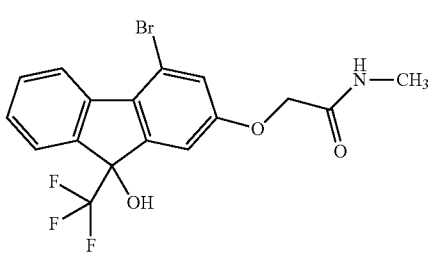 [SMILES: CNC(=O)COc1cc(Br)c2c(c1)C(O)(C(F)(F)F)c1ccccc1-2] | ¹H-NMR (DMSO-D₆) δ: 8.33 (1H, d, J = 7.7 Hz), 8.19-8.14 (1H, m), 7.69-7.65 (1H, m), 7.59-7.54 (1H, m), 7.45-7.40 (1H, m), 7.44 (1H, s), 7.33-7.30 (2H, m), 4.58 (2H, s), 2.67 (3H, d, J = 4.6 Hz). |
| 439 | 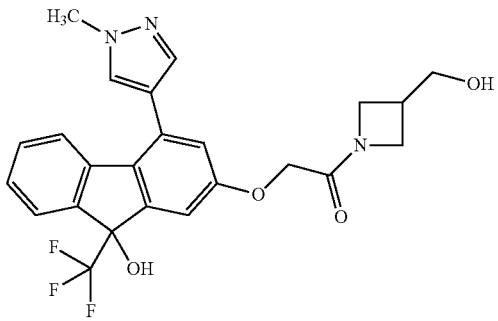 [SMILES: Cn1cc(-c2cc(OCC(=O)N3CC(CO)C3)cc3c2-c2ccccc2C3(O)C(F)(F)F)cn1] | ¹H-NMR (DMSO-D₆) δ: 7.97 (1H, s), 7.62-7.58 (1H, m), 7.60 (1H, d, J = 0.4 Hz), 7.31-7.24 (4H, m), 7.15-7.12 (1H, m), 6.81 (1H, d, J = 2.4 Hz), 4.83-4.78 (1H, m), 4.65 (2H, s), 4.29-4.20 (1H, m), 4.01-3.87 (2H, m), 3.96 (3H, s), 3.67-3.61 (1H, m), 3.55-3.50 (2H, m), 2.74-2.65 (1H, m). |
| 440 | 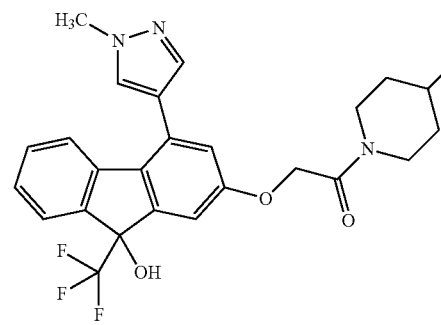 | ¹H-NMR (DMSO-D₆) δ: 7.95 (1H, s), 7.61-7.58 (1H, m), 7.59 (1H, d, J = 0.7 Hz), 7.31-7.22 (3H, m), 7.23 (1H, s), 7.14-7.12 (1H, m), 6.81 (1H, d, J = 2.4 Hz), 4.96-4.81 (2H, m), 4.53-4.49 (1H, m), 4.37-4.30 (1H, m), 3.96 (3H, s), 3.91-3.83 (1H, m), 3.27-3.22 (2H, m), 3.06-2.96 (1H, m), 2.63-2.53 (1H, m), 1.76-1.57 (3H, m), 1.20-1.06 (1H, m), 1.01-0.88 (1H, m). |

TABLE 1-64-continued

| compound No. | structural formula | NMR |
|---|---|---|
| 441 | | ¹H-NMR (DMSO-D₆) δ: 7.97 (1H, s), 7.62-7.58 (1H, m), 7.60 (1H, d, J = 0.7 Hz), 7.32-7.24 (3H, m), 7.25 (1H, s), 7.15-7.13 (1H, m), 6.81 (1H, d, J = 2.4 Hz), 4.65 (2H, s), 4.25 (2H, t, J = 8.0 Hz), 3.96 (3H, s), 3.91 (2H, t, J = 7.8 Hz), 2.28-2.20 (2H, m). |
| 442 | | ¹H-NMR (DMSO-D₆) δ: 8.16-8.11 (1H, m), 7.97 (1H, s), 7.63-7.59 (1H, m), 7.61 (1H, d, J = 0.4 Hz), 7.31-7.24 (3H, m), 7.25 (1H, s), 7.24-7.22 (1H, m), 6.85 (1H, d, J = 2.6 Hz), 4.54 (2H, s), 3.96 (3H, s), 2.67 (3H, d, J = 4.6 Hz). |

TABLE 1-65

| compound No. | structural formula | NMR |
|---|---|---|
| 443 | | ¹H-NMR (DMSO-D₆) δ: 7.79-7.73 (2H, m), 7.61-7.57 (1H, m), 7.48-7.44 (1H, m), 7.32-7.28 (1H, m), 7.26 (1H, br s), 7.18-7.15 (1H, m), 7.11-7.06 (1H, m), 4.19 (1H, t, J = 5.1 Hz), 4.11 (1H, t, J = 5.8 Hz), 3.74 (1H, t, J = 5.4 Hz), 3.66-3.61 (2H, m), 3.54-3.49 (1H, m), 2.60 (1H, t, J = 7.2 Hz), 2.50-2.45 (1H, m), 2.08 (1.5H, s), 2.06 (1.5H, s). |
| 444 | | ¹H-NMR (DMSO-D₆) δ: 7.78-7.73 (2H, m), 7.61-7.57 (1H, m), 7.48-7.43 (1H, m), 7.32-7.28 (1H, m), 7.18-7.16 (1H, m), 7.08 (1H, dd, J = 8.3, 2.3 Hz), 4.16 (2H, t, J = 5.7 Hz), 3.32 (2H, s), 3.01 (2H, t, J = 5.7 Hz), 2.46 (3H, s). |

TABLE 1-65-continued
| compound No. | structural formula | NMR |
|---|---|---|
| 445 | | ¹H-NMR (CDCl₃) δ: 7.69-7.65 (1H, m), 7.59-7.54 (2H, m), 7.47-7.42 (1H, m), 7.32-7.27 (1H, m), 7.24-7.22 (1H, m), 6.99-6.94 (1H, m), 6.00 (1H, br s), 4.11-4.03 (2H, m), 3.89-3.84 (1H, m), 3.39 (0.5H, br s), 3.35 (0.5H, br s), 2.46-2.28 (3H, m), 1.98-1.85 (1H, m). |
| 446 | | ¹H-NMR (CDCl₃) δ: 7.69-7.65 (1H, m), 7.58-7.54 (2H, m), 7.47-7.42 (1H, m), 7.32-7.27 (1H, m), 7.24-7.22 (1H, m), 6.99-6.94 (1H, m), 6.00 (1H, br s), 4.10-4.03 (2H, m), 3.89-3.83 (1H, m), 3.40-3.34 (1H, m), 2.47-2.28 (3H, m), 1.97-1.85 (1H, m). |
| 447 | | ¹H-NMR (CDCl₃) δ: 7.69-7.65 (1H, m), 7.59-7.55 (2H, m), 7.47-7.43 (1H, m), 7.32-7.27 (1H, m), 7.25-7.23 (1H, m), 7.00-6.96 (1H, m), 4.17-4.12 (1H, m), 4.07-4.01 (1H, m), 3.94-3.87 (1H, m), 3.16 (0.5H, s), 3.12 (0.5H, s), 2.91 (1.5H, s), 2.90 (1.5H, s), 2.59-2.48 (1H, m), 2.42-2.33 (1H, m), 2.31-2.20 (1H, m), 2.03-1.93 (1H, m). |
| 448 | | ¹H-NMR (CDCl₃) δ: 7.69-7.65 (1H, m), 7.59-7.55 (2H, m), 7.47-7.43 (1H, m), 7.32-7.28 (1H, m), 7.25-7.23 (1H, m), 7.00-6.96 (1H, m), 4.18-4.13 (1H, m), 4.07-4.02 (1H, m), 3.94-3.88 (1H, m), 3.06 (0.5H, s), 3.04 (0.5H, s), 2.92 (1.5H, s), 2.91 (1.5H, s), 2.60-2.49 (1H, m), 2.43-2.33 (1H, m), 2.31-2.21 (1H, m), 2.03-1.94 (1H, m). |
TABLE 1-66
| compound No. | structural formula | NMR |
|---|---|---|
| 449 | 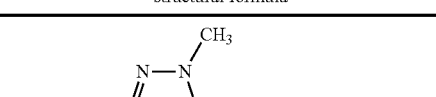 | ¹H-NMR (DMSO-D₆) δ: 12.16 (1H, br s), 7.98 (1H, s), 7.61-7.58 (1H, m), 7.61 (1H, s), 7.31-7.22 (3H, m), 7.22 (1H, s), 7.15-7.12 (1H, m), 6.82 (1H, d, J = 2.6 Hz), 4.06 (2H, t, J = 6.4 Hz), 3.95 (3H, s), 2.40 (2H, t, J = 7.2 Hz), 2.00-1.92 (2H, m). |

TABLE 1-66-continued

| compound No. | structural formula | NMR |
|---|---|---|
| 450 | (structure) | $^1$H-NMR (DMSO-D$_6$) δ: 7.78-7.74 (2H, m), 7.60-7.57 (1H, m), 7.48-7.44 (1H, m), 7.32-7.28 (1H, m), 7.25-7.24 (1H, m), 7.16-7.14 (1H, m), 7.10-7.06 (1H, m), 4.86 (1H, t, J = 5.3 Hz), 4.20-4.07 (2H, m), 3.87-3.79 (1H, m), 3.76-3.68 (1H, m), 3.65-3.59 (1H, m), 3.50-3.36 (2H, m), 2.34-2.23 (1H, m), 2.20-2.11 (1H, m), 2.03-1.93 (1H, m), 1.84-1.74 (1H, m). |
| 451 (optically active form) | (structure) enantiomer of compound No. 452 | $^1$H-NMR (CDCl$_3$) δ: 8.39 (1H, d, J = 7.9 Hz), 7.70-7.67 (1H, m), 7.53-7.48 (1H, m), 7.39-7.35 (1H, m), 7.26-7.24 (1H, m), 7.16 (1H, d, J = 2.3 Hz), 4.68 (2H, s), 3.83 (3H, s), 2.77 (1H, s). |
| 452 (optically active form) | (structure) enantiomer of compound No. 451 | $^1$H-NMR (CDCl$_3$) δ: 8.41-8.38 (1H, m), 7.70-7.67 (1H, m), 7.53-7.49 (1H, m), 7.39-7.35 (1H, m), 7.27-7.25 (1H, m), 7.17 (1H, d, J = 2.3 Hz), 4.69 (2H, s), 3.84 (3H, s), 2.73 (1H, s). |
| 453 | (structure) | $^1$H-NMR (DMSO-D$_6$) δ: 7.98 (1H, s), 7.64-7.58 (1H, m), 7.61 (1H, s), 7.29-7.21 (3H, m), 7.22 (1H, s), 7.16-7.12 (1H, m), 6.82 (1H, d, J = 2.6 Hz), 4.57 (1H, t, J = 5.3 Hz), 4.11 (2H, t, J = 6.6 Hz), 3.95 (3H, s), 3.57 (2H, dt, J = 6.6, 5.3 Hz), 1.93-1.84 (2H, m). |
| 454 | (structure) | $^1$H-NMR (DMSO-D$_6$) δ: 12.41 (1H, br s), 7.99 (1H, s), 7.63-7.57 (1H, m), 7.62 (1H, s), 7.31-7.23 (3H, m), 7.24 (1H, s), 7.15-7.12 (1H, m), 6.82 (1H, d, J = 2.3 Hz), 4.25 (2H, t, J = 6.0 Hz), 3.96 (3H, s), 2.73 (2H, t, J = 6.0 Hz). |

TABLE 1-66-continued
| compound No. | structural formula | NMR |
|---|---|---|
| 455 | 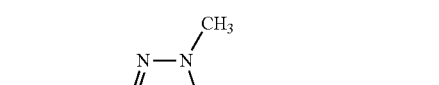 | ¹H-NMR (DMSO-D$_6$) δ: 7.98 (1H, s), 7.63-7.56 (1H, m), 7.61 (1H, s), 7.29-7.22 (3H, m), 7.24 (1H, s), 7.14-7.11 (1H, m), 6.80 (1H, d, J = 2.6 Hz), 4.26 (2H, t, J = 6.4 Hz), 3.95 (3H, s), 3.01 (3H, s), 2.86-2.79 (2H, m), 2.85 (3H, s). |
TABLE 1-67
| compound No. | structural formula | NMR |
|---|---|---|
| 456 | 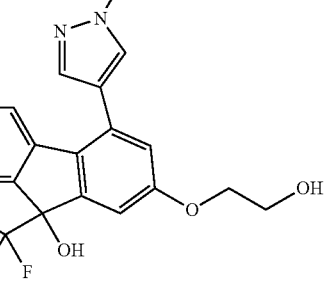 | ¹H-NMR (DMSO-D$_6$) δ: 7.98 (1H, s), 7.62-7.58 (1H, m), 7.61 (1H, d, J = 0.7 Hz), 7.31-7.22 (4H, m), 7.16-7.14 (1H, m), 6.82 (1H, d, J = 2.6 Hz), 4.90 (1H, t, J = 5.6 Hz), 4.06 (2H, t, J = 4.9 Hz), 3.95 (3H, s), 3.73 (2H, dt, J = 5.6, 4.9 Hz). |
| 457 | 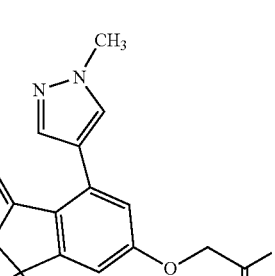 | ¹H-NMR (DMSO-D$_6$) δ: 7.95-7.94 (1H, m), 7.61-7.57 (1H, m), 7.59 (1H, d, J = 0.7 Hz), 7.30-7.21 (3H, m), 7.22 (1H, s), 7.14-7.12 (1H, m), 6.81 (1H, d, J = 2.4 Hz), 4.89 (2H, br s), 3.95 (3H, s), 3.00 (3H, s), 2.85 (3H, s). |
| 458 | 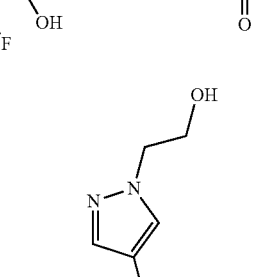 | ¹H-NMR (DMSO-D$_6$) δ: 7.97 (1H, d, J = 0.7 Hz), 7.64 (1H, d, J = 0.7 Hz), 7.61-7.57 (1H, m), 7.33-7.22 (3H, m), 7.23 (1H, s), 7.15-7.13 (1H, m), 6.84 (1H, d, J = 2.3 Hz), 4.97 (1H, t, J = 5.3 Hz), 4.25 (2H, t, J = 5.6 Hz), 3.85-3.80 (2H, m), 3.84 (3H, s). |

TABLE 1-67-continued

| compound No. | structural formula | NMR |
|---|---|---|
| 459 | | $^1$H-NMR (DMSO-D$_6$) δ: 7.79-7.74 (2H, m), 7.61-7.57 (1H, m), 7.49-7.44 (1H, m), 7.33-7.28 (1H, m), 7.25 (1H, s), 7.19-7.16 (1H, m), 7.10 (1H, dd, J = 8.4, 2.4 Hz), 4.30-4.24 (2H, m), 4.19 (2H, t, J = 5.3 Hz), 3.70-3.65 (2H, m), 3.57 (2H, t, J = 5.3 Hz). |
| 460 | | $^1$H-NMR (CDCl$_3$) δ: 7.71-7.68 (1H, m), 7.67-7.65 (1H, m), 7.62 (1H, d, J = 0.7 Hz), 7.60 (1H, s), 7.35-7.26 (4H, m), 4.37-4.34 (2H, m), 4.13-4.08 (2H, m), 3.03 (1H, s), 2.89 (1H, t, J = 5.9 Hz). |
| 461 | | $^1$H-NMR (CDCl$_3$) δ: 7.78-7.74 (2H, m), 7.47-7.44 (1H, m), 7.41-7.33 (4H, m), 7.29-7.24 (1H, m), 4.96 (1H, br s), 4.38-4.24 (4H, m), 4.18-4.10 (2H, m), 4.08-4.03 (2H, m), 3.47 (1H, br s), 2.37-2.28 (2H, m). |
| 462 | | $^1$H-NMR (DMSO-D$_6$) δ: 12.85 (1H, br s), 7.76-7.72 (2H, m), 7.60-7.57 (1H, m), 7.48-7.43 (1H, m), 7.32-7.28 (1H, m), 7.23 (1H, br s), 7.18-7.15 (1H, m), 7.03-6.99 (1H, m), 4.96 (1.2H, s), 4.80 (0.8H, s), 4.19 (0.8H, s), 4.02 (1.2H, s), 3.07 (1.8H, s), 2.86 (1.2H, s). |

TABLE 1-68
| compound No. | structural formula | NMR |
|---|---|---|
| 463 | 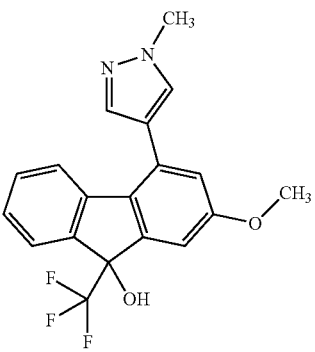 [SMILES: COc1cc(-c2cnn(C)c2)c2c(c1)C(O)(C(F)(F)F)c1ccccc1-2] | ¹H-NMR (CDCl₃) δ: 7.68-7.63 (1H, m), 7.51-7.46 (1H, m), 7.47 (1H, s), 7.29-7.19 (4H, m), 6.77 (1H, d, J = 2.4 Hz), 3.99 (3H, s), 3.87 (3H, s), 3.24 (1H, br s). |
| 464 | 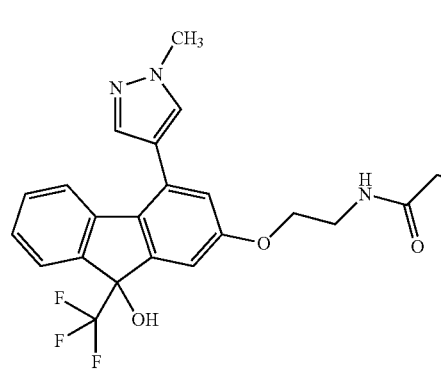 | ¹H-NMR (DMSO-D₆) δ: 7.99 (1H, s), 7.72 (1H, br s), 7.63-7.59 (1H, m), 7.62 (1H, s), 7.31-7.23 (3H, m), 7.28 (1H, s), 7.17-7.13 (1H, m), 6.83 (1H, d, J = 2.4 Hz), 4.23-4.08 (2H, m), 3.96 (3H, s), 3.78-3.67 (1H, m), 3.55-3.45 (1H, m), 2.53-2.42 (3H, m), 2.20-2.08 (1H, m). |
| 465 | 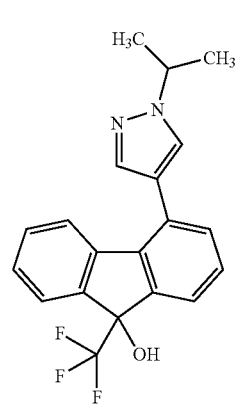 [SMILES: CC(C)n1cc(-c2cccc3c2-c2ccccc2C3(O)C(F)(F)F)cn1] | ¹H-NMR (CDCl₃) δ: 7.73-7.68 (2H, m), 7.51-7.50 (1H, m), 7.36-7.14 (6H, m), 4.57-4.50 (1H, m), 3.70 (1H, br s), 1.55 (3H, s), 1.54 (3H, s). |
| 466 | 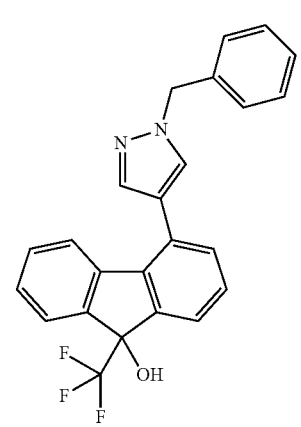 [SMILES: OC1(C(F)(F)F)c2ccccc2-c2c(-c3cnn(Cc4ccccc4)c3)cccc21] | ¹H-NMR (CDCl₃) δ: 7.70-7.65 (2H, m), 7.57 (1H, s), 7.50 (1H, s), 7.42-7.25 (8H, m), 7.22-7.14 (2H, m), 5.39 (2H, s), 2.99 (1H, br s). |

TABLE 1-68-continued

| compound No. | structural formula | NMR |
|---|---|---|
| 467 (optically active form) | | ¹H-NMR (DMSO-D₆) δ: 7.97 (1H, s), 7.64-7.59 (2H, m), 7.60 (1H, s), 7.41 (1H, br s), 7.30-7.25 (3H, m), 7.24 (1H, s), 7.23-7.20 (1H, m), 6.84 (1H, d, J = 2.4 Hz), 4.50 (2H, s), 3.96 (3H, s). |
| 468 | | ¹H-NMR (DMSO-D₆) δ: 7.78-7.75 (2H, m), 7.61-7.57 (1H, m), 7.49-7.44 (1H, m), 7.33-7.28 (1H, m), 7.25 (1H, s), 7.19-7.16 (1H, m), 7.09 (1H, dd, J = 8.4, 2.4 Hz), 4.19 (2H, t, J = 5.4 Hz), 3.39-3.30 (4H, m), 3.23-3.18 (2H, m), 2.29-2.21 (2H, m). |
| 469 | | ¹H-NMR (DMSO-D₆) δ: 7.79-7.73 (2H, m), 7.61-7.57 (1H, m), 7.48-7.43 (1H, m), 7.32-7.27 (1H, m), 7.24 (1H, s), 7.18-7.15 (1H, m), 7.09 (1H, dd, J = 8.4, 2.4 Hz), 6.38 (1H, s), 4.15-4.09 (2H, m), 3.50-3.41 (4H, m), 3.26-3.20 (2H, m). |

TABLE 1-69

| compound No. | structural formula | NMR |
|---|---|---|
| 470 | | ¹H-NMR (DMSO-D₆) δ: 7.78-7.73 (2H, m), 7.61-7.57 (1H, m), 7.49-7.43 (1H, m), 7.33-7.27 (1H, m), 7.25 (1H, s), 7.19-7.17 (1H, m), 7.10 (1H, dd, J = 8.3, 2.3 Hz), 4.21-4.14 (4H, m), 3.66-3.56 (2H, m), 3.45 (2H, t, J = 6.2 Hz), 1.97-1.90 (2H, m). |
| 471 | | ¹H-NMR (CDCl₃) δ: 7.76-7.63 (1H, m), 7.59 (1H, s), 7.50 (1H, s), 7.28-7.21 (4H, m), 6.77 (1H, d, J = 2.3 Hz), 4.19 (2H, t, J = 5.4 Hz), 4.01 (3H, s), 3.81-3.68 (2H, m), 3.26 (3H, br s), 3.14 (1H, s), 1.28 (9H, s). |

TABLE 1-69-continued
| compound No. | structural formula | NMR |
|---|---|---|
| 472 | 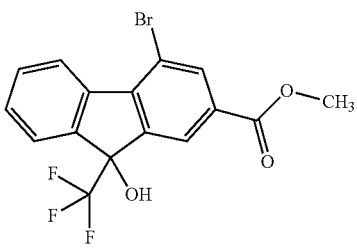 [SMILES: COC(=O)c1cc(Br)c2c(c1)C(O)(C(F)(F)F)c1ccccc1-2] | $^1$H-NMR (DMSO-D$_6$) δ: 8.54 (1H, d, J = 7.9 Hz), 8.24 (1H, d, J = 1.5 Hz), 8.18-8.16 (1H, m), 7.79-7.76 (1H, m), 7.70-7.65 (1H, m), 7.64 (1H, s), 7.62-7.58 (1H, m), 3.92 (3H, s). |
| 473 (optically active form) | 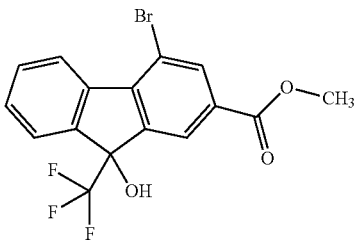 [SMILES: COC(=O)c1cc(Br)c2c(c1)C(O)(C(F)(F)F)c1ccccc1-2] | $^1$H-NMR (CDCl$_3$) δ: 8.58 (1H, d, J = 7.7 Hz), 8.34 (1H, d, J = 1.3 Hz), 8.30-8.29 (1H, m), 7.78-7.75 (1H, m), 7.60-7.56 (1H, m), 7.52-7.48 (1H, m), 3.95 (3H, s), 2.84 (1H, s). |
| 474 (optically active form) | 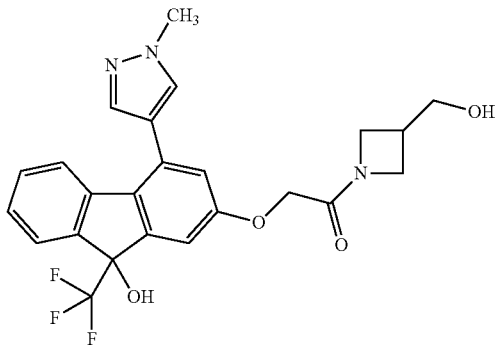 [SMILES: Cn1cc(-c2cc(OCC(=O)N3CC(CO)C3)cc3c2-c2ccccc2C3(O)C(F)(F)F)cn1] | $^1$H-NMR (DMSO-D$_6$) δ: 7.97 (1H, s), 7.62-7.58 (1H, m), 7.61 (1H, s), 7.32-7.24 (3H, m), 7.25 (1H, s), 7.15-7.13 (1H, m), 6.81 (1H, d, J = 2.4 Hz), 4.82-4.79 (1H, m), 4.65 (2H, s), 4.28-4.22 (1H, m), 4.01-3.87 (2H, m), 3.96 (3H, s), 3.64 (1H, dd, J = 9.5, 5.3 Hz), 3.54-3.49 (2H, m), 2.74-2.66 (1H, m). |
| 475 (optically active form) | 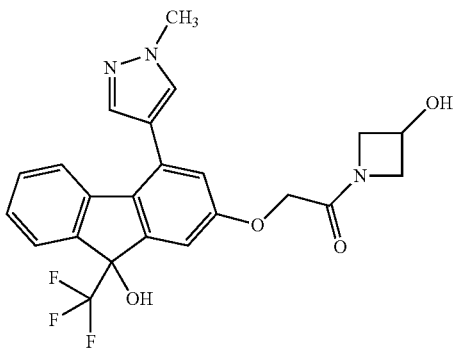 [SMILES: Cn1cc(-c2cc(OCC(=O)N3CC(O)C3)cc3c2-c2ccccc2C3(O)C(F)(F)F)cn1] | $^1$H-NMR (DMSO-D$_6$) δ: 7.97 (1H, s), 7.62-7.58 (1H, m), 7.61 (1H, s), 7.30-7.24 (3H, m), 7.25 (1H, s), 7.15-7.13 (1H, m), 6.81 (1H, d, J = 2.4 Hz), 5.76 (1H, d, J = 6.0 Hz), 4.69 (1H, d, J = 14.8 Hz), 4.65 (1H, d, J = 14.8 Hz), 4.54-4.39 (2H, m), 4.15-4.08 (1H, m), 4.00-3.94 (1H, m), 3.96 (3H, s), 3.67-3.62 (1H, m). |

TABLE 1-69-continued

| compound No. | structural formula | NMR |
|---|---|---|
| 476 | 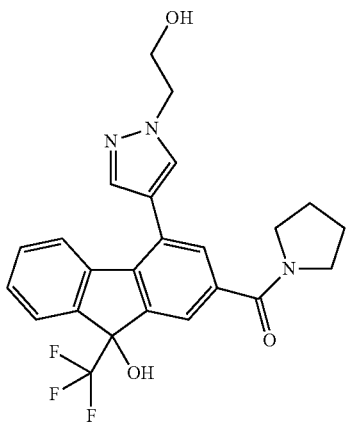 [SMILES: O=C(c1cc(-c2cnn(CCO)c2)c2c(c1)C(O)(C(F)(F)F)c1ccccc1-2)N1CCCC1] | $^1$H-NMR (CDCl$_3$) δ: 7.80-7.76 (1H, m), 7.72-7.70 (1H, m), 7.38-7.32 (3H, m), 7.27-7.22 (1H, m), 7.13 (1H, d, J = 1.6 Hz), 7.06 (1H, s), 5.42 (1H, br s), 4.22-4.18 (2H, m), 4.02-3.98 (2H, m), 3.96 (1H, br s), 3.64-3.58 (2H, m), 3.47-3.40 (2H, m), 2.02-1.85 (4H, m). |

TABLE 1-70

| compound No. | structural formula | NMR |
|---|---|---|
| 477 (optically active form) | 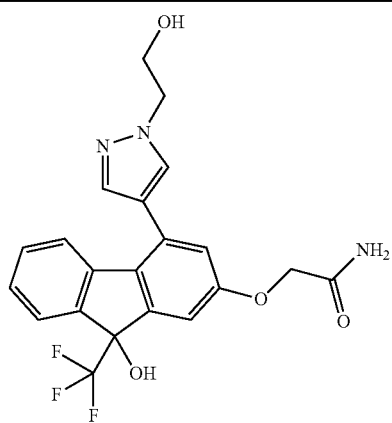 | $^1$H-NMR (DMSO-D$_6$) δ: 7.97 (1H, s), 7.63 (1H, s), 7.62-7.59 (2H, m), 7.41 (1H, br s), 7.34-7.30 (1H, m), 7.29-7.23 (3H, m), 7.22-7.20 (1H, m), 6.86 (1H, d, J = 2.2 Hz), 4.98 (1H, t, J = 5.2 Hz), 4.51 (2H, s), 4.26 (2H, t, J = 5.6 Hz), 3.83 (2H, dt, J = 5.6, 5.2 Hz). |
| 478 | 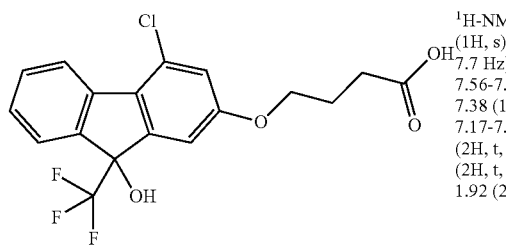 | $^1$H-NMR (DMSO-D$_6$) δ: 12.17 (1H, s), 8.14 (1H, d, J = 7.7 Hz), 7.67-7.64 (1H, m), 7.56-7.51 (1H, m), 7.43-7.38 (1H, m), 7.42 (1H, s), 7.17-7.15 (2H, m), 4.09 (2H, t, J = 6.4 Hz), 2.41 (2H, t, J = 7.3 Hz), 2.01-1.92 (2H, m). |
| 479 (optically active form) | 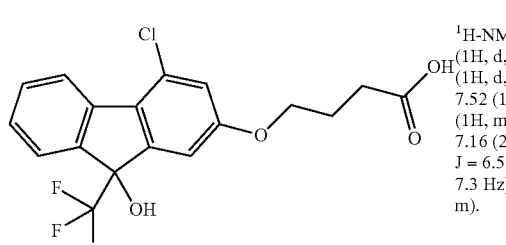 | $^1$H-NMR (DMSO-D$_6$) δ: 8.14 (1H, d, J = 7.7 Hz), 7.66 (1H, d, J = 7.7 Hz), 7.56-7.52 (1H, m), 7.43-7.38 (1H, m), 7.42 (1H, br s), 7.16 (2H, s), 4.09 (2H, t, J = 6.5 Hz), 2.39 (2H, t, J = 7.3 Hz), 1.99-1.93 (2H, m). |

TABLE 1-70-continued
| compound No. | structural formula | NMR |
|---|---|---|
| 480 | 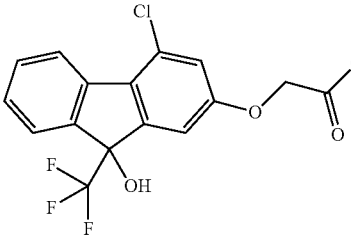 | ¹H-NMR (CDCl₃) δ: 8.23-8.20 (1H, m), 7.70-7.67 (1H, m), 7.51-7.47 (1H, m), 7.38-7.33 (1H, m), 7.21-7.19 (1H, m), 6.97 (1H, d, J = 2.2 Hz), 4.68 (2H, s), 3.83 (3H, s), 2.78 (1H, s). |
| 481 (optically active form) | 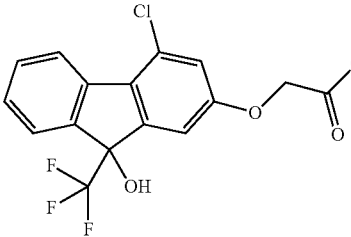 | ¹H-NMR (CDCl₃) δ: 8.23-8.20 (1H, m), 7.70-7.67 (1H, m), 7.52-7.47 (1H, m), 7.38-7.33 (1H, m), 7.21-7.20 (1H, m), 6.97 (1H, d, J = 2.2 Hz), 4.69 (2H, s), 3.84 (3H, s), 2.75 (1H, s). |
| 482 | 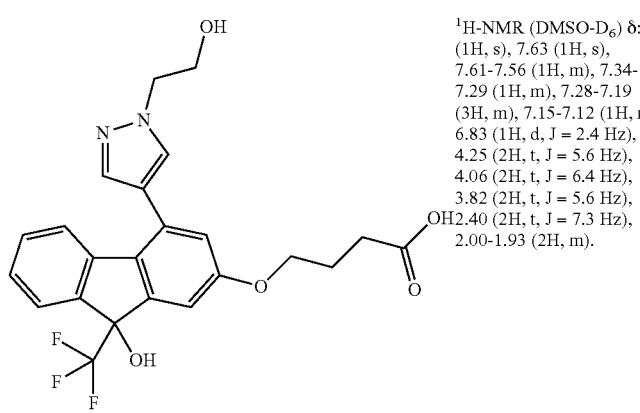 | ¹H-NMR (DMSO-D₆) δ: 7.97 (1H, s), 7.63 (1H, s), 7.61-7.56 (1H, m), 7.34-7.29 (1H, m), 7.28-7.19 (3H, m), 7.15-7.12 (1H, m), 6.83 (1H, d, J = 2.4 Hz), 4.25 (2H, t, J = 5.6 Hz), 4.06 (2H, t, J = 6.4 Hz), 3.82 (2H, t, J = 5.6 Hz), 2.40 (2H, t, J = 7.3 Hz), 2.00-1.93 (2H, m). |
| 483 | 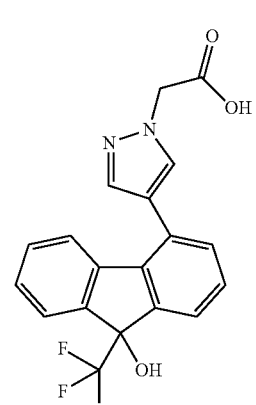 | ¹H-NMR (DMSO-D₆) δ: 13.20 (1H, br s), 8.00 (1H, d, J = 0.7 Hz), 7.66-7.61 (2H, m), 7.63 (1H, d, J = 0.7 Hz), 7.42-7.37 (2H, m), 7.36-7.21 (4H, m), 5.07 (2H, s). |

TABLE 1-71

| compound No. | structural formula | NMR |
|---|---|---|
| 484 | | ¹H-NMR (DMSO-D₆) δ: 7.98 (1H, s), 7.64 (1H, s), 7.61-7.58 (1H, m), 7.35-7.32 (1H, m), 7.28-7.23 (2H, m), 7.24 (1H, s), 7.14-7.12 (1H, m), 6.85 (1H, d, J = 2.3 Hz), 4.98 (1H, t, J = 5.2 Hz), 4.25 (2H, t, J = 5.7 Hz), 4.16 (2H, t, J = 5.2 Hz), 3.85-3.79 (2H, m), 3.57 (2H, t, J = 5.4 Hz), 3.47 (2H, t, J = 7.3 Hz), 2.22 (2H, t, J = 8.1 Hz), 1.96-1.88 (2H, m). |
| 485 | | ¹H-NMR (DMSO-D₆) δ: 12.44 (1H, br s), 7.98 (1H, s), 7.66-7.60 (2H, m), 7.61 (1H, s), 7.41-7.26 (5H, m), 7.21 (1H, s), 4.43 (2H, t, J = 6.6 Hz), 2.90 (2H, t, J = 6.5 Hz). |
| 486 | | ¹H-NMR (CDCl₃) δ: 7.72-7.67 (2H, m), 7.61 (1H, s), 7.59 (1H, s), 7.36-7.22 (5H, m), 5.76 (1H, br s), 5.33 (1H, br s), 4.55 (2H, t, J = 6.3 Hz), 2.95 (1H, br s), 2.91 (2H, t, J = 6.1 Hz). |

TABLE 1-71-continued
| compound No. | structural formula | NMR |
|---|---|---|
| 487 | 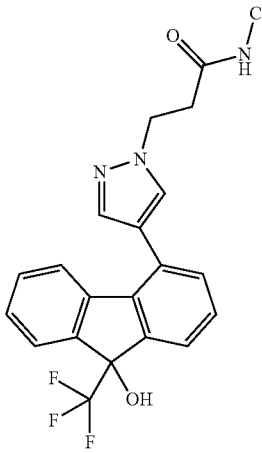 | ¹H-NMR (CDCl₃) δ: 7.72-7.67 (2H, m), 7.54 (1H, s), 7.52 (1H, s), 7.35-7.21 (5H, m), 5.69 (1H, br s), 4.51 (2H, t, J = 6.3 Hz), 3.26 (1H, br s), 2.82 (2H, t, J = 6.3 Hz), 2.77 (3H, d, J = 4.6 Hz). |
| 488 | 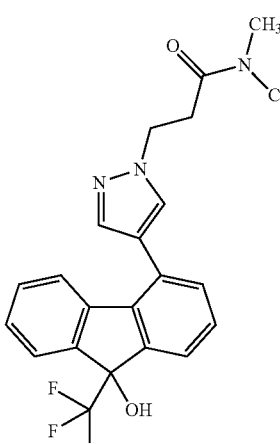 | ¹H-NMR (CDCl₃) δ: 7.72-7.66 (2H, m), 7.59 (1H, s), 7.55 (1H, s), 7.34-7.23 (5H, m), 4.53 (2H, t, J = 6.5 Hz), 3.22 (1H, br s), 3.01 (3H, s), 3.00-2.96 (2H, m), 2.95 (3H, s). |
| 489 | 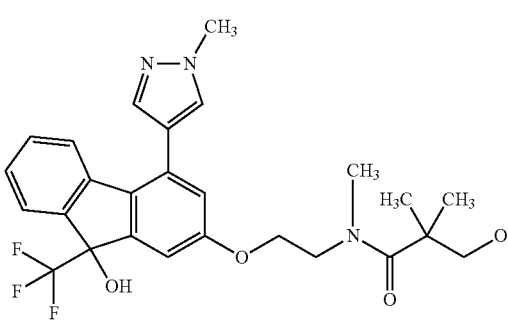 | ¹H-NMR (CDCl₃) δ: 7.68-7.64 (1H, m), 7.58 (1H, s), 7.50 (1H, s), 7.25-7.20 (4H, m), 6.77 (1H, d, J = 1.6 Hz), 4.29-4.17 (2H, m), 4.01 (3H, s), 3.80-3.72 (2H, m), 3.68 (1H, t, J = 7.2 Hz), 3.53-3.40 (2H, m), 3.42 (1H, br s), 3.24 (3H, br s), 1.27 (3H, s), 1.24 (3H, s). |
| 490 | 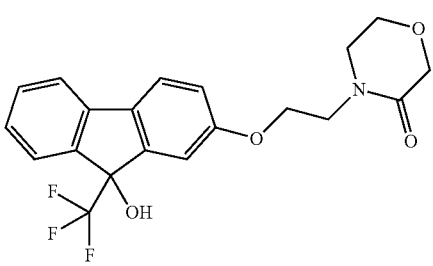 [SMILES: O=C1COCCN1CCOc1ccc2c(c1)C(O)(C(F)(F)F)c1ccccc1-2] | ¹H-NMR (DMSO-D₆) δ: 7.79-7.74 (2H, m), 7.61-7.57 (1H, m), 7.49-7.44 (1H, m), 7.33-7.28 (1H, m), 7.24 (1H, s), 7.19-7.16 (1H, m), 7.10 (1H, dd, J = 8.4, 2.4 Hz), 4.20 (2H, t, J = 5.6 Hz), 4.05 (2H, s), 3.82 (2H, t, J = 5.1 Hz), 3.74-3.69 (2H, m), 3.54-3.50 (2H, m). |

TABLE 1-72
| compound No. | structural formula | NMR |
|---|---|---|
| 491 | 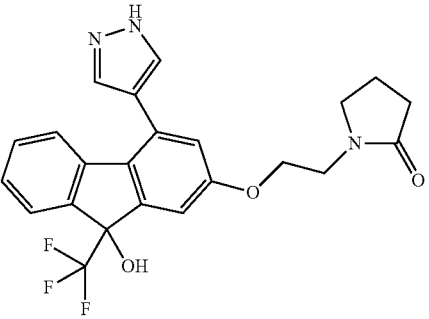 [SMILES: O=C1CCCN1CCOc1cc(-c2cn[nH]c2)c2c(c1)C(O)(C(F)(F)F)c1ccccc1-2] | ¹H-NMR (DMSO-D₆) δ: 13.15 (1H, br s), 8.01 (1H, br s), 7.67 (1H, br s), 7.61-7.58 (1H, m), 7.28-7.24 (2H, m), 7.22 (1H, s), 7.20-7.17 (1H, m), 7.15-7.13 (1H, m), 6.86 (1H, d, J = 2.4 Hz), 4.16 (2H, t, J = 5.4 Hz), 3.57 (2H, t, J = 5.5 Hz), 3.47 (2H, t, J = 7.2 Hz), 2.22 (2H, t, J = 8.0 Hz), 1.96-1.88 (2H, m). |
| 492 | 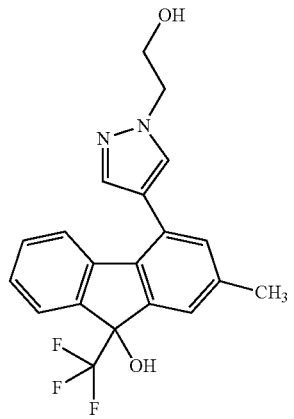 [SMILES: Cc1cc(-c2cnn(CCO)c2)c2c(c1)C(O)(C(F)(F)F)c1ccccc1-2] | ¹H-NMR (DMSO-D₆) δ: 7.93 (1H, s), 7.64-7.58 (1H, m), 7.60 (1H, s), 7.44-7.41 (1H, m), 7.36-7.25 (3H, m), 7.14 (1H, s), 7.12 (1H, d, J = 7.0 Hz), 4.95 (1H, t, J = 5.1 Hz), 4.25 (2H, t, J = 5.7 Hz), 3.83 (2H, dt, J = 5.7, 5.1 Hz), 2.39 (3H, s). |
| 493 | 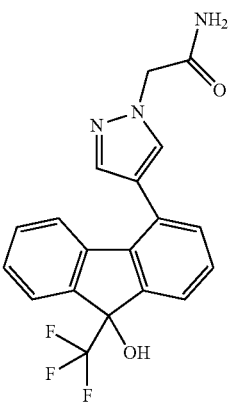 [SMILES: NC(=O)Cn1cc(-c2cccc3c2-c2ccccc2C3(O)C(F)(F)F)cn1] | ¹H-NMR (CDCl₃) δ: 7.77 (1H, s), 7.73-7.69 (2H, m), 7.64 (1H, s), 7.38-7.25 (5H, m), 6.42 (1H, br s), 5.52 (1H, br s), 4.92 (2H, s), 2.79 (1H, br s). |
| 494 | 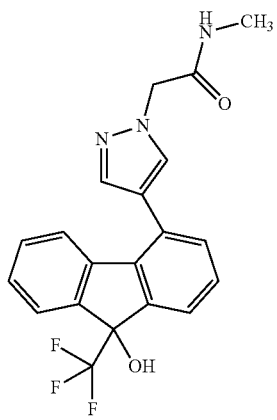 [SMILES: CNC(=O)Cn1cc(-c2cccc3c2-c2ccccc2C3(O)C(F)(F)F)cn1] | ¹H-NMR (CDCl₃) δ: 7.76 (1H, s), 7.73-7.70 (2H, m), 7.61 (1H, s), 7.39-7.25 (5H, m), 6.42 (1H, br s), 4.90 (2H, s), 2.89 (3H, d, J = 4.9 Hz), 2.84 (1H, br s). |

TABLE 1-72-continued
| compound No. | structural formula | NMR |
|---|---|---|
| 495 | 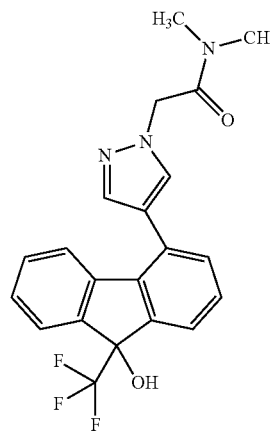 | ¹H-NMR (CDCl₃) δ: 7.70-7.66 (2H, m), 7.63 (1H, s), 7.61 (1H, s), 7.45-7.42 (1H, m), 7.35-7.27 (4H, m), 5.09 (1H, d, J = 16.0 Hz), 5.03 (1H, d, J = 16.0 Hz), 3.14 (3H, s), 3.03 (3H, s), 2.99 (1H, br s). |
| 496 | 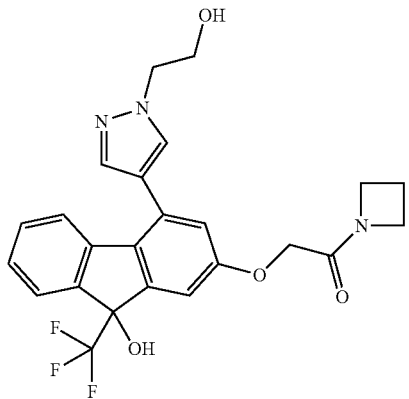 [SMILES: O=C(COc1cc(-c2cnn(CCO)c2)c2c(c1)C(O)(C(F)(F)F)c1ccccc1-2)N1CCC1] | ¹H-NMR (DMSO-D₆) δ: 7.96 (1H, s), 7.62 (1H, s), 7.61-7.57 (1H, m), 7.33-7.29 (1H, m), 7.28-7.23 (3H, m), 7.15-7.12 (1H, m), 6.82 (1H, d, J = 2.4 Hz), 4.97 (1H, t, J = 5.2 Hz), 4.66 (2H, s), 4.25 (4H, t, J = 5.7 Hz), 3.91 (2H, t, J = 7.7 Hz), 3.82 (2H, dt, J = 5.7, 5.2 Hz), 2.28-2.21 (2H, m). |
| 497 | 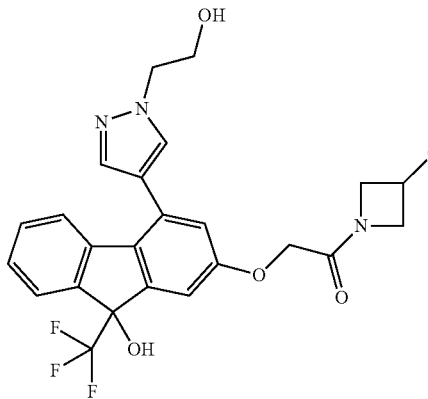 | ¹H-NMR (DMSO-D₆) δ: 7.97 (1H, s), 7.63 (1H, s), 7.61-7.58 (1H, m), 7.33-7.29 (1H, m), 7.28-7.24 (3H, m), 7.15-7.12 (1H, m), 6.82 (1H, d, J = 2.6 Hz), 5.77 (1H, d, J = 5.5 Hz), 4.98 (1H, t, J = 5.2 Hz), 4.72-4.64 (2H, m), 4.52-4.40 (2H, m), 4.25 (2H, t, J = 5.5 Hz), 4.14-4.08 (1H, m), 4.00-3.94 (1H, m), 3.82 (2H, dt, J = 5.5, 5.2 Hz), 3.67-3.61 (1H, m). |

TABLE 1-73

| compound No. | structural formula | NMR |
|---|---|---|
| 498 | | $^1$H-NMR (DMSO-D$_6$) δ: 7.83 (2H, br s), 7.61-7.57 (1H, m), 7.29-7.12 (5H, m), 6.84 (1H, d, J = 2.4 Hz), 4.06 (2H, t, J = 6.4 Hz), 2.40 (2H, t, J = 7.3 Hz), 2.00-1.92 (2H, m). |
| 499 | | $^1$H-NMR (CDCl$_3$) δ: 7.69-7.64 (1H, m), 7.52 (1H, s), 7.47 (1H, s), 7.25-7.20 (4H, m), 6.78-6.76 (1H, m), 4.25-4.11 (2H, m), 4.06-3.89 (2H, m), 3.98 (3H, s), 3.68-3.52 (2H, m), 3.10 (3H, s), 2.11 (3H, s). |
| 500 | | $^1$H-NMR (CDCl$_3$) δ: 7.70-7.65 (1H, m), 7.52 (1H, s), 7.48 (1H, s), 7.25-7.21 (4H, m), 6.79-6.76 (1H, m), 4.27 (1H, dd, J = 20.9, 4.2 Hz), 4.21-4.12 (1H, m), 4.06-3.89 (2H, m), 3.99 (3H, s), 3.69-3.53 (2H, m), 3.11 (3H, s), 2.12 (3H, s). |
| 501 | | $^1$H-NMR (CDCl$_3$) δ: 7.68-7.64 (1H, m), 7.56 (1H, s), 7.50 (1H, s), 7.25-7.22 (4H, m), 6.78-6.75 (1H, m), 4.43 (1H, br s), 4.26-4.21 (2H, m), 4.02-3.99 (3H, m), 3.87-3.77 (2H, m), 3.37-3.21 (3H, m), 1.58-1.56 (6H, m). |
| 502 | | $^1$H-NMR (DMSO-D$_6$) δ: 8.09 (1H, br s), 7.87-7.84 (1H, m), 7.72 (1H, br s), 7.63-7.59 (1H, m), 7.46-7.40 (1H, m), 7.35-7.29 (2H, m), 7.23-7.21 (1H, m), 7.06-7.04 (1H, m), 4.22-4.16 (2H, m), 3.61-3.56 (2H, m), 3.51-3.45 (2H, m), 2.27-2.20 (2H, m), 1.98-1.89 (2H, m). |

TABLE 1-73-continued
| compound No. | structural formula | NMR |
|---|---|---|
| 503 | 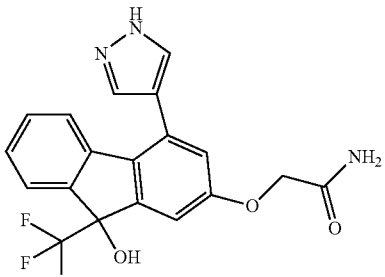 | ¹H-NMR (DMSO-D$_6$) δ: 7.82 (2H, br s), 7.63 (1H, br s), 7.61-7.58 (1H, m), 7.41 (1H, br s), 7.28-7.16 (5H, m), 6.86 (1H, d, J = 2.4 Hz), 4.51 (2H, s). |
| 504 (optically active form) | 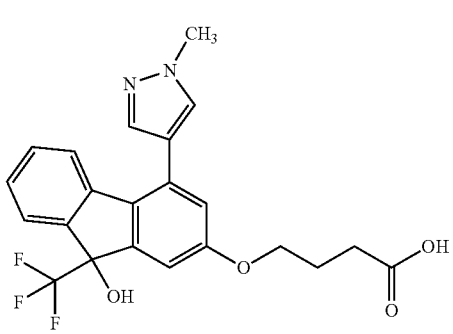 [SMILES: Cn1cc(-c2cc(OCCCC(=O)O)cc3c2-c2ccccc2C3(O)C(F)(F)F)cn1] | ¹H-NMR (DMSO-D$_6$) δ: 12.26 (1H, br s), 7.99-7.96 (1H, m), 7.62-7.57 (2H, m), 7.29-7.20 (4H, m), 7.15-7.12 (1H, m), 6.83-6.80 (1H, m), 4.05 (2H, t, J = 6.1 Hz), 3.95 (3H, s), 2.39 (2H, t, J = 7.0 Hz), 2.00-1.92 (2H, m). |
TABLE 1-74
| compound No. | structural formula | NMR |
|---|---|---|
| 505 | 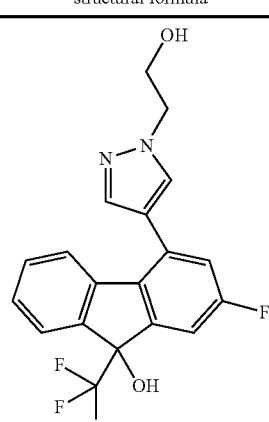 | ¹H-NMR (DMSO-D$_6$) δ: 8.02 (1H, d, J = 1.2 Hz), 7.67 (1H, d, J = 1.2 Hz), 7.65-7.61 (1H, m), 7.41-7.36 (3H, m), 7.35-7.27 (2H, m), 7.18-7.14 (1H, m), 4.99-4.95 (1H, m), 4.24 (2H, t, J = 4.9 Hz), 3.84-3.78 (2H, m). |
| 506 | 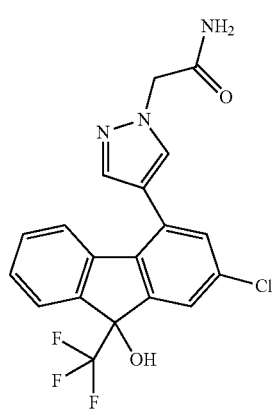 [SMILES: NC(=O)Cn1cc(-c2cc(Cl)cc3c2-c2ccccc2C3(O)C(F)(F)F)cn1] | ¹H-NMR (CDCl$_3$) δ: 7.76-7.73 (1H, m), 7.72-7.67 (2H, m), 7.66-7.63 (1H, m), 7.36-7.22 (4H, m), 6.38 (1H, s), 5.57 (1H, s), 4.93-4.88 (2H, m), 2.98 (1H, br s). |

TABLE 1-74-continued
| compound No. | structural formula | NMR |
|---|---|---|
| 507 | 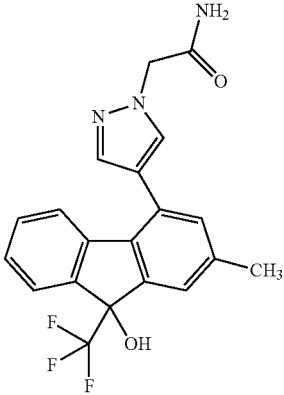 [SMILES: Cc1cc(-c2cnn(CC(N)=O)c2)c2c(c1)C(O)(C(F)(F)F)c1ccccc1-2] | ¹H-NMR (CDCl₃) δ: 7.74-7.73 (1H, m), 7.71-7.67 (1H, m), 7.61-7.61 (1H, m), 7.54-7.51 (1H, m), 7.32-7.19 (3H, m), 7.11-7.09 (1H, m), 6.41 (1H, br s), 5.58 (1H, br s), 4.90-4.88 (2H, m), 2.97 (1H, br s), 2.45-2.42 (3H, m). |
| 508 | 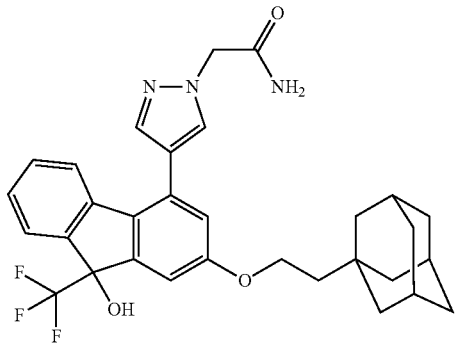 [SMILES: NC(=O)Cn1cc(-c2cc(OCCC34CC5CC(CC(C5)C3)C4)cc3c2-c2ccccc2C3(O)C(F)(F)F)cn1] | ¹H-NMR (DMSO-D₆) δ: 7.97 (1H, d, J = 0.7 Hz), 7.64 (1H, d, J = 0.9 Hz), 7.60-7.55 (1H, m), 7.57 (1H, br s), 7.42-7.37 (1H, m), 7.32 (1H, br s), 7.27-7.22 (2H, m), 7.21 (1H, s), 7.14-7.11 (1H, m), 6.84 (1H, d, J = 2.4 Hz), 4.87 (2H, s), 4.10 (2H, t, J = 6.8 Hz), 1.97-1.91 (3H, m), 1.72-1.53 (14H, m). |
| 509 | 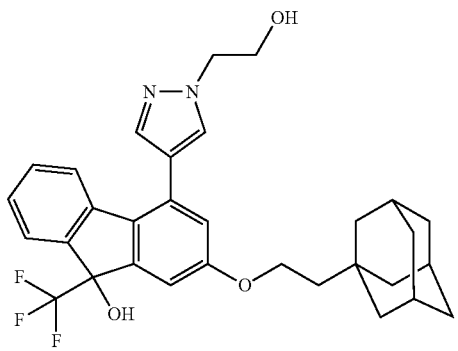 [SMILES: OCCn1cc(-c2cc(OCCC34CC5CC(CC(C5)C3)C4)cc3c2-c2ccccc2C3(O)C(F)(F)F)cn1] | ¹H-NMR (DMSO-D₆) δ: 7.97 (1H, d, J = 0.4 Hz), 7.64 (1H, d, J = 0.7 Hz), 7.60-7.57 (1H, m), 7.32-7.22 (3H, m), 7.20 (1H, s), 7.13-7.11 (1H, m), 6.83 (1H, d, J = 2.4 Hz), 4.97 (1H, t, J = 5.2 Hz), 4.25 (2H, t, J = 5.6 Hz), 4.10 (2H, t, J = 6.8 Hz), 3.84-3.80 (2H, m), 1.97-1.91 (3H, m), 1.71-1.52 (14H, m). |
| 510 | 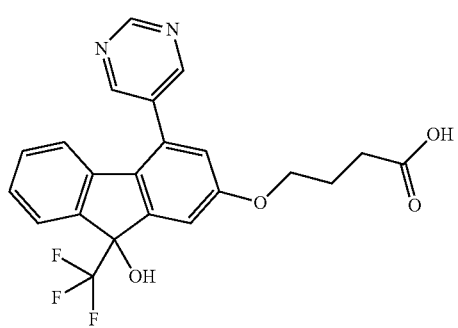 [SMILES: O=C(O)CCCOc1cc(-c2cncnc2)c2c(c1)C(O)(C(F)(F)F)c1ccccc1-2] | ¹H-NMR (DMSO-D₆) δ: 9-37 (1H, s), 8.95 (2H, br s), 7.65-7.62 (1H, m), 7.37 (1H, br s), 7.31-7.21 (3H, m), 7.04-7.04 (1H, m), 6.61 (1H, dd, J = 6.7, 1.0 Hz), 4.11 (2H, t, J = 6.5 Hz), 2.40 (2H, t, J = 7.3 Hz), 2.01-1.95 (2H, m). |

TABLE 1-74-continued
| compound No. | structural formula | NMR |
|---|---|---|
| 511 | 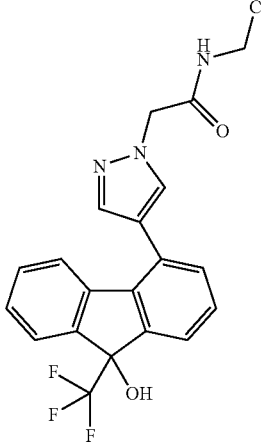 | $^1$H-NMR (DMSO-D$_6$) δ: 8.20-8.16 (1H, m), 7.96 (1H, d, J = 0.7 Hz), 7.66-7.60 (2H, m), 7.62 (1H, d, J = 0.9 Hz), 7.46-7.43 (1H, m), 7.42-7.27 (4H, m), 7.22 (1H, s), 4.87 (2H, s), 3.20-3.13 (2H, m), 1.08 (3H, t, J = 7.2 Hz). |
TABLE 1-75
| compound No. | structural formula | NMR |
|---|---|---|
| 512 | 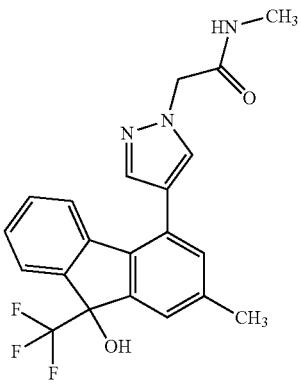 [SMILES: CNC(=O)Cn1cc(-c2cc(Cl)cc3c2-c2ccccc2C3(O)C(F)(F)F)cn1] | $^1$H-NMR (DMSO-D$_6$) δ: 8.13-8.08 (1H, m), 7.95 (1H, d, J = 2.6 Hz), 7.64-7.59 (1H, m), 7.61 (1H, d, J = 2.6 Hz), 7.45-7.40 (2H, m), 7.34-7.25 (2H, m), 7.19-7.12 (2H, m), 4.90-4.86 (2H, m), 2.70-2.67 (3H, m), 2.41-2.37 (3H, m). |
| 513 | 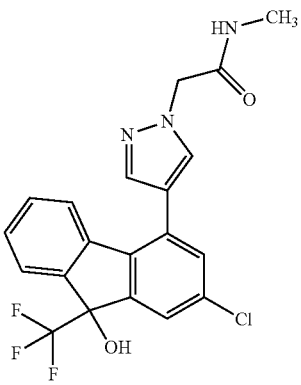 | $^1$H-NMR (DMSO-D$_6$) δ: 8.13-8.07 (1H, m), 8.06 (1H, d, J = 2.6 Hz), 7.70 (1H, d, J = 2.6 Hz), 7.68-7.64 (1H, m), 7.61-7.58 (1H, m), 7.51-7.47 (1H, m), 7.45-7.43 (1H, m), 7.42-7.31 (3H, m), 4.91-4.87 (2H, m), 2.70-2.66 (3H, m). |

TABLE 1-75-continued

| compound No. | structural formula | NMR |
|---|---|---|
| 514 | | $^1$H-NMR (DMSO-D$_6$) δ: 8.12-8.08 (1H, m), 7.95 (1H, d, J = 0.7 Hz), 7.66-7.60 (2H, m), 7.61 (1H, d, J = 0.7 Hz), 7.46-7.26 (5H, m), 7.22 (1H, s), 4.85 (2H, s), 3.93-3.85 (1H, m), 1.11 (6H, d, J = 6.6 Hz). |
| 515 | | $^1$H-NMR (DMSO-D$_6$) δ: 8.13-8.08 (1H, m), 8.04 (1H, d, J = 0.9 Hz), 7.68 (1H, d, J = 0.9 Hz), 7.67-7.63 (1H, m), 7.49-7.45 (1H, m), 7.43-7.39 (2H, m), 7.37-7.29 (2H, m), 7.18 (1H, dd, J = 9.9, 2.4 Hz), 4.89 (2H, s), 2.68 (3H, d, J= 4.4 Hz). |
| 516 | | $^1$H-NMR (DMSO-D$_6$) δ: 13.18 (1H, br s), 8.40 (1H, s), 8.23 (1H, d, J = 7.9 Hz), 8.10 (1H, s), 7.84 (1H, d, J = 1.4 Hz), 7.80-7.78 (1H, m), 7.72-7.69 (1H, m), 7.61-7.56 (1H, m), 7.49-7.45 (2H, m), 5.00 (2H, s). |
| 517 | | $^1$H-NMR (DMSO-D$_6$) δ: 12.42 (1H, s), 8.41 (1H, s), 8.22 (1H, d, J = 7.9 Hz), 8.06 (1H, d, J = 0.7 Hz), 7.82 (1H, d, J = 1.6 Hz), 7.80-7.78 (1H, m), 7.72-7.69 (1H, m), 7.60-7.55 (1H, m), 7.49-7.44 (1H, m), 7.45 (1H, s), 4.35 (2H, t, J = 6.7 Hz), 2.86 (2H, t, J = 6.8 Hz). |

TABLE 1-75-continued

| compound No. | structural formula | NMR |
|---|---|---|
| 518 | 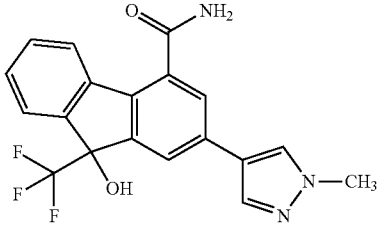 [SMILES: Cn1cc(-c2cc(C(N)=O)c3c(c2)C(O)(C(F)(F)F)c2ccccc2-3)cn1] | $^1$H-NMR (DMSO-D$_6$) δ: 8.32 (1H, s), 8.15 (1H, br s), 7.98 (1H, d, J = 0.8 Hz), 7.91 (1H, d, J = 7.5 Hz), 7.84-7.81 (1H, m), 7.75 (1H, br s), 7.69 (1H, d, J = 1.9 Hz), 7.67-7.63 (1H, m), 7.49-7.43 (1H, m), 7.40-7.34 (1H, m), 7.31 (1H, s), 3.89 (3H, s). |

TABLE 1-76

| compound No. | structural formula | NMR |
|---|---|---|
| 519 | 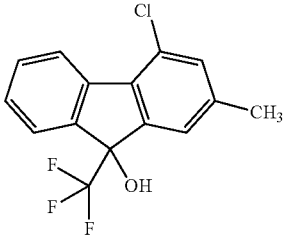 [SMILES: Cc1cc(Cl)c2c(c1)C(O)(C(F)(F)F)c1ccccc1-2] | $^1$H-NMR (CDCl$_3$) δ: 8.27 (1H, d, J = 7.9 Hz), 7.72-7.68 (1H, m), 7.53-7.47 (1H, m), 7.44-7.42 (1H, m), 7.40-7.35 (1H, m), 7.26-7.25 (1H, m), 2.76 (1H, s), 2.41 (3H, s). |
| 520 (optically active form) | 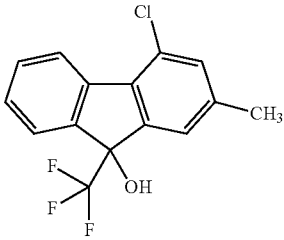 [SMILES: Cc1cc(Cl)c2c(c1)C(O)(C(F)(F)F)c1ccccc1-2] | $^1$H-NMR (CDCl$_3$) δ: 8.28 (1H, d, J = 7.7 Hz), 7.72-7.68 (1H, m), 7.53-7.48 (1H, m), 7.44-7.42 (1H, m), 7.41-7.36 (1H, m), 7.27-7.25 (1H, m), 2.69 (1H, s), 2.41 (3H, s). |
| 521 | 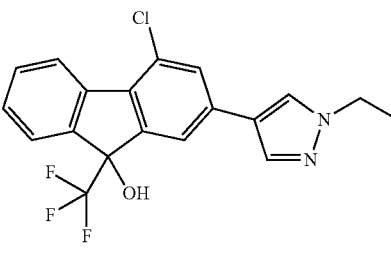 | $^1$H-NMR (DMSO-D$_6$) δ: 8.34 (1H, s), 8.22 (1H, d, J = 7.7 Hz), 8.05 (1H, d, J = 0.7 Hz), 7.81 (1H, d, J = 1.5 Hz), 7.79-7.76 (1H, m), 7.72-7.68 (1H, m), 7.60-7.55 (1H, m), 7.49-7.43 (1H, m), 7.44 (1H, s), 7.42 (1H, br s), 6.91 (1H, br s), 4.33 (2H, t, J = 6.8 Hz), 2.67 (2H, t, J = 6.9 Hz). |
| 522 | 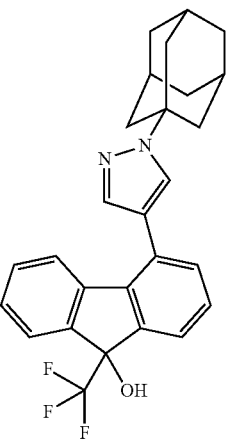 [SMILES: OC1(C(F)(F)F)c2ccccc2-c2c(-c3cnn(C45CC6CC(CC(C6)C4)C5)c3)cccc21] | $^1$H-NMR (CDCl$_3$) δ: 7.71-7.66 (2H, m), 7.64 (1H, d, J = 0.7 Hz), 7.51 (1H, d, J = 0.7 Hz), 7.36-7.22 (5H, m), 3.06 (1H, br s), 2.30-2.25 (3H, m), 2.24-2.22 (6H, m), 1.82-1.78 (6H, m). |

TABLE 1-76-continued

| compound No. | structural formula | NMR |
|---|---|---|
| 523 | | $^1$H-NMR (CDCl$_3$) δ: 7.72-7.66 (2H, m), 7.64 (1H, d, J = 0.7 Hz), 7.53-7.50 (1H, m), 7.36-7.22 (5H, m), 3.06-3.00 (1H, br m), 1.67 (9H, s). |
| 524 | | $^1$H-NMR (CDCl$_3$) δ: 7.72-7.67 (2H, m), 7.51-7.49 (1H, m), 7.47 (1H, s), 7.36-7.19 (5H, m), 3.99 (2H, s), 3.10 (1H, s), 1.04 (9H, br s). |
| 525 | | $^1$H-NMR (CDCl$_3$) δ: 8.30-8.26 (1H, m), 7.74-7.70 (1H, m), 7.56-7.50 (1H, m), 7.44-7.35 (2H, m), 7.23-7.18 (1H, m), 2.83-2.81 (1H, m). |

TABLE 1-77

| compound No. | structural formula | NMR |
|---|---|---|
| 526 (optically active form) | (+) | $^1$H-NMR (CDCl$_3$) δ: 8.27 (1H, d, J = 7.7 Hz), 7.73-7.70 (1H, m), 7.55-7.50 (1H, m), 7.43-7.35 (2H, m), 7.20 (1H, dd, J = 8.6, 2.2 Hz), 2.76 (1H, s). |

TABLE 1-77-continued

| compound No. | structural formula | NMR |
|---|---|---|
| 527 | | ¹H-NMR (CDCl₃) δ: 7.74-7.69 (2H, m), 7.51 (1H, s), 7.46 (1H, s), 7.36-7.28 (2H, m), 7.24-7.21 (3H, m), 6.11 (1H, br s), 4.30 (2H, dd, J = 6.2, 4.9 Hz), 3.77-3.72 (2H, m), 3.54 (1H, br s), 1.98 (3H, s). |
| 528 | | ¹H-NMR (DMSO-D₆) δ: 8.42 (1H, d, J = 0.7 Hz), 8.14 (1H, br s), 7.98 (1H, d, J = 0.7 Hz), 7.93-7.90 (1H, m), 7.87-7.85 (1H, m), 7.75 (1H, br s), 7.72 (1H, d, J = 1.6 Hz), 7.67-7.63 (1H, m), 7.49-7.44 (1H, m), 7.40-7.35 (1H, m), 7.31 (1H, s), 4.58-4.48 (1H, m), 1.47 (3H, s), 1.46 (3H, s). |
| 529 (optically active form) | | ¹H-NMR (DMSO-D₆) δ: 7.94 (1H, d, J = 0.9 Hz), 7.63-7.58 (1H, m), 7.60 (1H, d, J = 0.7 Hz), 7.44-7.41 (1H, m), 7.36-7.33 (1H, m), 7.32-7.25 (2H, m), 7.16 (1H, s), 7.12 (1H, dd, J = 1.7, 0.8 Hz), 4.97 (1H, t, J = 5.3 Hz), 4.25 (2H, t, J = 5.6 Hz), 3.82 (2H, dt, J = 5.3, 5.6 Hz), 2.38 (3H, s). |
| 530 | | ¹H-NMR (DMSO-D₆) δ: 8.38 (1H, s), 8.15 (1H, br s), 7.98 (1H, s), 7.91 (1H, d, J = 7.7 Hz), 7.85-7.83 (1H, m), 7.75 (1H, br s), 7.70 (1H, d, J = 1.6 Hz), 7.66-7.64 (1H, m), 7.49-7.44 (1H, m), 7.40-7.35 (1H, m), 7.31 (1H, s), 4.17 (2H, q, J = 7.3 Hz), 1.42 (3H, t, J = 7.2 Hz). |

TABLE 1-77-continued
| compound No. | structural formula | NMR |
|---|---|---|
| 531 (optically active form) | 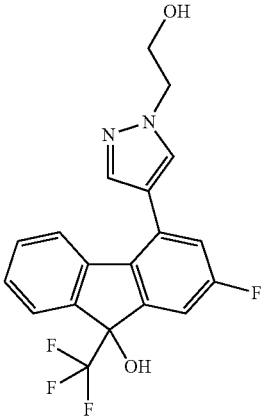 [SMILES: OCCn1cc(-c2cc(F)cc3c2-c2ccccc2C3(O)C(F)(F)F)cn1] | ¹H-NMR (DMSO-D₆) δ: 8.03 (1H, d, J = 0.7 Hz), 7.68 (1H, d, J = 0.7 Hz), 7.66-7.63 (1H, m), 7.42-7.38 (3H, m), 7.36-7.29 (2H, m), 7.18 (1H, dd, J = 10.0, 2.6 Hz), 4.99 (1H, t, J = 5.3 Hz), 4.26 (2H, t, J = 5.6 Hz), 3.82 (2H, dt, J = 5.6, 5.3 Hz). |
| 532 (optically active form) | 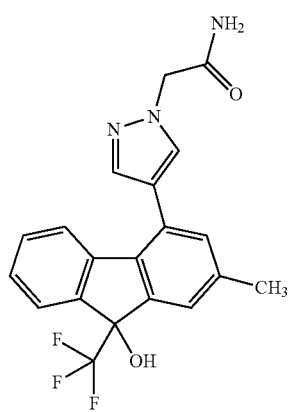 [SMILES: Cc1cc(-c2cnn(CC(N)=O)c2)c2c(c1)C(O)(C(F)(F)F)c1ccccc1-2] | ¹H-NMR (DMSO-D₆) δ: 7.94 (1H, d, J = 0.7 Hz), 7.64-7.59 (1H, m), 7.60 (1H, d, J = 0.7 Hz), 7.57 (1H, br s), 7.46-7.43 (2H, m), 7.32-7.24 (2H, m), 7.32 (1H, br s), 7.17 (1H, s), 7.14 (1H, dd, J = 1.5, 0.9 Hz), 4.88 (2H, s), 2.40 (3H, s). |
TABLE 1-78
| compound No. | structural formula | NMR |
|---|---|---|
| 533 (optically active form) | 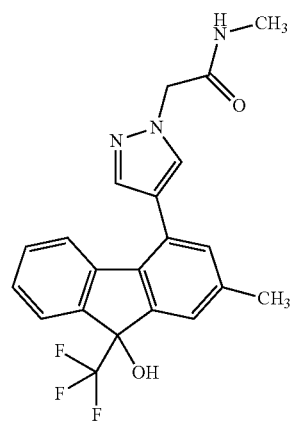 [SMILES: CNC(=O)Cn1cc(-c2cc(C)cc3c2-c2ccccc2C3(O)C(F)(F)F)cn1] | ¹H-NMR (DMSO-D₆) δ: 8.12-8.06 (1H, m), 7.95 (1H, d, J = 0.7 Hz), 7.64-7.59 (1H, m), 7.61 (1H, d, J = 0.7 Hz), 7.45-7.39 (2H, m), 7.33-7.25 (2H, m), 7.17 (1H, s), 7.13 (1H, d, J = 0.7 Hz), 4.88 (2H, s), 2.68 (3H, d, J = 4.6 Hz), 2.39 (3H, s). |

TABLE 1-78-continued

| compound No. | structural formula | NMR |
|---|---|---|
| 534 (optically active form) | | ¹H-NMR (CDCl₃) δ: 7.74 (1H, s), 7.72-7.68 (1H, m), 7.62 (1H, s), 7.46-7.40 (1H, m), 7.34-7.19 (3H, m), 7.01 (1H, dd, J = 9.4, 2.6 Hz), 6.40 (1H, s), 4.88 (2H, s), 3.06 (1H, s), 2.88 (3H, br s). |
| 535 | | ¹H-NMR (CDCl₃) δ: 7.75-7.69 (2H, m), 7.62 (0.2H, s), 7.56 (0.8H, s), 7.45 (0.2H, s), 7.41 (0.8H, s), 7.36-7.20 (5H, m), 4.39-4.32 (2H, m), 3.87-3.79 (2H, m), 2.96 (0.8H, s), 2.82 (2.2H, s), 2.04 (2.2H, s), 1.83 (0.8H, s). |
| 536 | | ¹H-NMR (DMSO-D₆) δ: 8.33-8.31 (1H, m), 8.16 (1H, br s), 8.01-7.99 (1H, m), 7.94-7.90 (1H, m), 7.86-7.83 (1H, m), 7.76 (1H, br s), 7.72-7.69 (1H, m), 7.68-7.63 (1H, m), 7.50-7.44 (1H, m), 7.41-7.35 (1H, m), 7.33 (1H, br s), 4.95 (1H, br s), 4.21-4.16 (2H, m), 3.82-3.76 (2H, m). |
| 537 (optically active form) | | ¹H-NMR (CDCl₃) δ: 7.70-7.67 (1H, m), 7.54 (1H, s), 7.53 (1H, s), 7.42-7.38 (1H, m), 7.30-7.19 (3H, m), 6.98 (1H, dd, J = 9.4, 2.5 Hz), 4.30 (2H, t, J = 6.7 Hz), 2.42 (2H, t, J = 7.1 Hz), 2.27-2.20 (2H, m). |

TABLE 1-78-continued

| compound No. | structural formula | NMR |
|---|---|---|
| 538 (optically active form) | (structure) (+) | ¹H-NMR (CDCl₃) δ: 7.69-7.63 (1H, m), 7.58-7.54 (2H, m), 7.52-7.49 (1H, m), 7.25-7.14 (3H, m), 7.07-7.05 (1H, m), 4.48 (2H, t, J = 6.2 Hz), 3.00 (2H, t, J = 6.2 Hz), 2.41 (3H, s). |
| 539 (optically active form) | (structure) (+) | ¹H-NMR (CDCl₃) δ: 7.70-7.65 (1H, m), 7.55 (1H, s), 7.52-7.49 (2H, m), 7.29-7.20 (3H, m), 7.09-7.07 (1H, m), 4.31 (2H, t, J = 6.6 Hz), 2.45-2.39 (2H, m), 2.42 (3H, s), 2.28-2.20 (2H, m). |

TABLE 1-79

| compound No. | structural formula | NMR |
|---|---|---|
| 540 (optically active form) | (structure) | ¹H-NMR (DMSO-D₆) δ: 7.98 (1H, s), 7.62 (1H, d, J = 0.7 Hz), 7.61-7.58 (1H, m), 7.29-7.23 (3H, m), 7.21 (1H, s), 7.14-7.11 (1H, m), 6.83 (1H, d, J = 2.4 Hz), 4.35 (1H, s), 4.09 (2H, t, J = 7.2 Hz), 3.96 (3H, s), 2.13-2.07 (2H, m), 1.61 (2H, t, J = 6.8 Hz), 1.57-1.43 (12H, m). |

TABLE 1-79-continued

| compound No. | structural formula | NMR |
|---|---|---|
| 541 (optically active form) | | ¹H-NMR (DMSO-D₆) δ: 7.97 (1H, d, J = 0.9 Hz), 7.64 (1H, d, J = 0.9 Hz), 7.60-7.56 (2H, m), 7.41-7.38 (1H, m), 7.32 (1H, br s), 7.26-7.22 (2H, m), 7.21 (1H, s), 7.13-7.12 (1H, m), 6.84 (1H, d, J = 2.4 Hz), 4.87 (2H, s), 4.09 (2H, t, J = 6.9 Hz), 3.57 (1H, s), 2.12-2.07 (2H, m), 1.61 (2H, t, J = 7.2 Hz), 1.56-1.42 (12H, m). |
| 542 (optically active form) | | ¹H-NMR (DMSO-D₆) δ: 7.97 (1H, d, J = 0.7 Hz), 7.64 (1H, d, J = 0.7 Hz), 7.61-7.56 (1H, m), 7.33-7.28 (1H, m), 7.28-7.22 (2H, m), 7.21 (1H, s), 7.13-7.11 (1H, m), 6.83 (1H, d, J = 2.6 Hz), 4.97 (1H, t, J = 5.3 Hz), 4.36 (1H, s), 4.25 (2H, t, J = 5.7 Hz), 4.09 (2H, t, J = 7.1 Hz), 3.82 (2H, dt, J = 5.3, 5.7 Hz), 2.12-2.07 (2H, m), 1.60 (2H, t, J = 7.0 Hz), 1.56-1.42 (13H, m). |
| 543 (optically active form) | | ¹H-NMR (DMSO-D₆) δ: 8.06 (1H, d, J = 0.7 Hz), 7.68 (1H, d, J = 0.9 Hz), 7.66-7.62 (1H, m), 7.43-7.38 (1H, m), 7.36-7.28 (4H, m), 7.17 (1H, dd, J = 10.0, 2.6 Hz), 4.43 (2H, t, J = 6.6 Hz), 2.91 (2H, t, J = 6.6 Hz). |
| 544 (optically active form) | | ¹H-NMR (CDCl₃) δ: 7.70-7.67 (1H, m), 7.62 (1H, d, J = 0.7 Hz), 7.57 (1H, d, J = 0.7 Hz), 7.42-7.38 (1H, m), 7.31-7.20 (3H, m), 7.00 (1H, dd, J = 9.5, 2.4 Hz), 4.17 (2H, s), 3.47 (1H, br s), 2.98 (1H, br s), 1.74-1.25 (10H, m). |

TABLE 1-79-continued
| compound No. | structural formula | NMR |
|---|---|---|
| 545 (optically active form) | 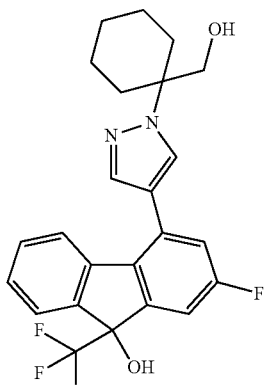 | $^1$H-NMR (DMSO-D$_6$) δ: 8.05 (1H, d, J = 0.7 Hz), 7.67-7.63 (2H, m), 7.42-7.38 (2H, m), 7.35-7.30 (3H, m), 7.21-7.16 (1H, m), 4.47-4.43 (1H, m), 4.17-4.09 (1H, m), 3.20-3.13 (1H, m), 3.09-3.02 (1H, m), 2.04-1.71 (6H, m), 1.45-1.22 (3H, m). |
TABLE 1-80
| compound No. | structural formula | NMR |
|---|---|---|
| 546 (optically active form) | 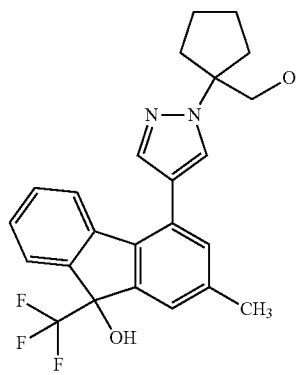 | $^1$H-NMR (DMSO-D$_6$) δ: 7.99 (1H, d, J = 0.7 Hz), 7.64-7.58 (1H, m), 7.60 (1H, s), 7.43-7.40 (1H, m), 7.32-7.23 (3H, m), 7.16 (1H, d, J = 2.2 Hz), 7.14-7.13 (1H, m), 4.70-4.65 (1H, m), 4.57-4.50 (1H, m), 3.51-3.37 (2H, m), 2.48-2.39 (1H, m), 2.38 (3H, s), 2.21-2.03 (2H, m), 1.99-1.89 (1H, m), 1.88-1.78 (1H, m), 1.74-1.63 (1H, m), 1.57-1.47 (1H, m). |
| 547 | 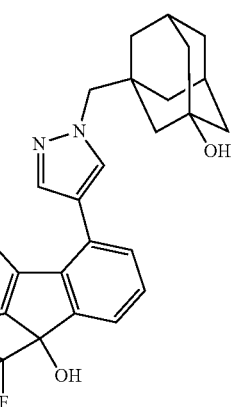 | $^1$H-NMR (DMSO-D$_6$) δ: 7.87 (1H, d, J = 0.7 Hz), 7.67-7.60 (2H, m), 7.59 (1H, d, J = 0.7 Hz), 7.41-7.22 (6H, m), 4.47 (1H, s), 3.96 (2H, s), 2.16-2.12 (2H, m), 1.60-1.41 (12H, m). |

TABLE 1-80-continued

| compound No. | structural formula | NMR |
|---|---|---|
| 548 (optically active form) | | ¹H-NMR (DMSO-D₆) δ: 8.09 (1H, s), 7.67 (1H, s), 7.66-7.62 (1H, m), 7.41-7.37 (2H, m), 7.36-7.27 (3H, m), 7.20 (1H, dd, J = 10.0, 2.5 Hz), 4.71-4.66 (1H, m), 4.58-4.51 (1H, m), 3.51-3.38 (2H, m), 2.48-2.37 (1H, m), 2.21-2.04 (2H, m), 1.99-1.89 (1H, m), 1.88-1.78 (1H, m), 1.74-1.63 (1H, m), 1.57-1.47 (1H, m). |
| 549 (optically active form) | | ¹H-NMR (DMSO-D₆) δ: 12.43 (1H, br s), 8.12 (1H, s), 7.69 (1H, d, J = 0.9 Hz), 7.66-7.62 (1H, m), 7.42-7.38 (2H, m), 7.36-7.31 (2H, m), 7.27-7.24 (1H, m), 7.19 (1H, dd, J = 9.9, 2.6 Hz), 5.00-4.94 (1H, m), 3.28-3.19 (1H, m), 2.27-2.05 (3H, m), 1.94-1.74 (3H, m). |
| 550 (optically active form) | | ¹H-NMR (DMSO-D₆) δ: 13.17 (1H, br s), 7.97 (1H, d, J = 0.7 Hz), 7.63-7.60 (1H, m), 7.61 (1H, d, J = 0.7 Hz), 7.45-7.43 (1H, m), 7.38-7.34 (1H, m), 7.32-7.27 (1H, m), 7.26-7.22 (1H, m), 7.17 (1H, s), 7.14-7.12 (1H, m), 5.06 (2H, s), 2.39 (3H, s). |
| 551 (optically active form) | | ¹H-NMR (DMSO-D₆) δ: 13.22 (1H, br s), 8.07 (1H, d, J = 0.7 Hz), 7.69 (1H, d, J = 0.7 Hz), 7.66-7.62 (1H, m), 7.43-7.38 (3H, m), 7.36-7.31 (1H, m), 7.30-7.25 (1H, m), 7.18 (1H, dd, J = 9.9, 2.4 Hz), 5.07 (2H, s). |

TABLE 1-81

| compound No. | structural formula | NMR |
|---|---|---|
| 552 (optically active form) | (structure) | ¹H-NMR (CDCl₃) δ: 7.70-7.66 (1H, m), 7.43 (1H, s), 7.30 (1H, d, J = 0.7 Hz), 7.25-7.14 (3H, m), 7.12-7.09 (1H, m), 6.70 (1H, d, J = 2.6 Hz), 4.05-3.93 (2H, m), 3.90 (3H, s), 2.37 (2H, t, J = 6.6 Hz), 1.88-1.73 (4H, m). |
| 553 (optically active form) | (structure) | ¹H-NMR (DMSO-D₆) δ: 12.17 (1H, br s), 8.05 (1H, d, J = 0.7 Hz), 7.62 (1H, d, J = 0.7 Hz), 7.61-7.58 (1H, m), 7.31-7.19 (4H, m), 7.16-7.13 (1H, m), 6.85 (1H, d, J = 2.3 Hz), 4.64-4.57 (1H, m), 4.07 (2H, t, J = 6.4 Hz), 2.41 (2H, t, J = 7.3 Hz), 2.01-1.94 (2H, m), 1.52 (3H, d, J = 6.5 Hz), 1.51 (3H, d, J = 6.5 Hz). |
| 554 (optically active form) | (structure) | ¹H-NMR (DMSO-D₆) δ: 12.16 (1H, br s), 8.02 (1H, d, J = 0.7 Hz), 7.61 (1H, d, J = 0.7 Hz), 7.61-7.58 (1H, m), 7.30-7.20 (4H, m), 7.13 (1H, d, J = 1.9 Hz), 6.83 (1H, d, J = 2.6 Hz), 4.24 (2H, q, J = 7.3 Hz), 4.06 (2H, t, J = 6.4 Hz), 2.40 (2H, t, J = 7.3 Hz), 2.00-1.93 (2H, m), 1.46 (3H, t, J = 7.3 Hz). |
| 555 | (structure) | ¹H-NMR (DMSO-D₆) δ: 7.88 (1H, d, J = 7.9 Hz), 7.86 (1H, d, J = 7.7 Hz), 7.66-7.62 (1H, m), 7.53-7.47 (2H, m), 7.41-7.35 (2H, m), 7.28 (1H, s), 3.72 (3H, s), 2.26 (3H, s), 2.17 (3H, s). |
| 556 | (structure) | ¹H-NMR (DMSO-D₆) δ: 7.87-7.84 (1H, m), 7.83-7.82 (1H, m), 7.79-7.77 (1H, m), 7.72-7.67 (1H, m), 7.58-7.53 (1H, m), 7.48-7.43 (1H, m), 7.35 (1H, s), 5.56 (1H, t, J = 5.5 Hz), 4.95-4.85 (2H, m), 4.39-4.24 (2H, m), 4.16-3.99 (2H, m), 2.34-2.25 (2H, m). |

TABLE 1-81-continued

| compound No. | structural formula | NMR |
|---|---|---|
| 557 | 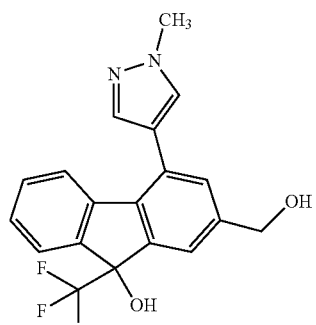 | ¹H-NMR (DMSO-D$_6$) δ: 7.95 (1H, s), 7.66-7.56 (3H, m), 7.35-7.28 (3H, m), 7.22-7.18 (2H, m), 5.35 (1H, t, J = 5.7 Hz), 4.57 (2H, d, J = 5.7 Hz), 3.96 (3H, s). |
| 558 | 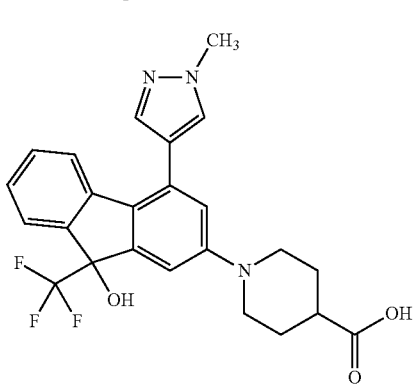 [SMILES: Cn1cc(-c2cc(N3CCC(C(=O)O)CC3)cc3c2-c2ccccc2C3(O)C(F)(F)F)cn1] | ¹H-NMR (DMSO-D$_6$) δ: 12.25 (1H, br s), 7.94 (1H, d, J = 0.5 Hz), 7.58 (1H, d, J = 0.7 Hz), 7.57-7.54 (1H, m), 7.27-7.15 (4H, m), 7.11 (1H, s), 6.77 (1H, d, J = 2.3 Hz), 3.94 (3H, s), 3.77-3.69 (2H, m), 2.90-2.81 (2H, m), 2.48-2.40 (1H, m), 1.96-1.88 (2H, m), 1.70-1.59 (2H, m). |

TABLE 1-82

| compound No. | structural formula | NMR |
|---|---|---|
| 559 | 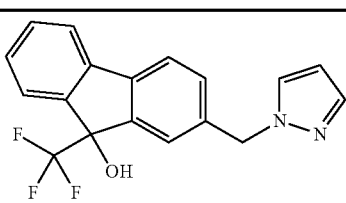 | ¹H-NMR (DMSO-D$_6$) δ: 7.72-7.67 (1H, m), 7.63 (1H, d, J = 7.2 Hz), 7.57 (1H, d, J = 7.9 Hz), 7.50-7.33 (5H, m), 7.23-7.19 (1H, m), 6.29-6.28 (1H, m), 5.30 (2H, s), 3.62 (1H, br s). |
| 560 | 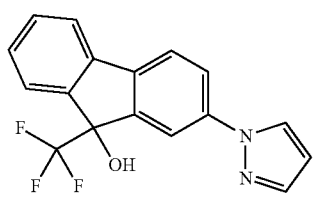 [SMILES: OC1(C(F)(F)F)c2ccccc2-c2ccc(-n3cccn3)cc21] | ¹H-NMR (CDCl$_3$) δ: 7.90-7.86 (2H, m), 7.77-7.72 (2H, m), 7.65 (1H, d, J = 8.3 Hz), 7.62-7.59 (1H, m), 7.54 (1H, d, J = 1.5 Hz), 7.51-7.45 (1H, m), 7.41-7.35 (1H, m), 6.40 (1H, dd, J = 2.4, 1.7 Hz), 3.86 (1H, s). |
| 561 (optically active form) | 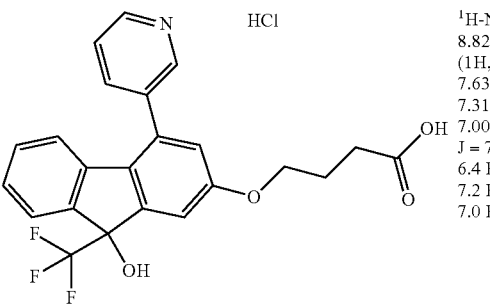 | ¹H-NMR (DMSO-D$_6$) δ: 8.90-8.82 (2H, m), 8.29-8.16 (1H, m), 7.90-7.75 (1H, m), 7.63 (1H, d, J = 6.4 Hz), 7.31-7.13 (5H, m), 7.01-7.00 (1H, m), 6.62 (1H, d, J = 7.9 Hz), 4.10 (2H, t, J = 6.4 Hz), 2.41 (2H, t, J = 7.2 Hz), 1.98 (2H, t, J = 7.0 Hz). |

TABLE 1-82-continued

| compound No. | structural formula | NMR |
|---|---|---|
| 562 | | $^1$H-NMR (DMSO-D$_6$) δ: 8.91 (1H, d, J = 2.1 Hz), 8.40 (1H, s), 8.14 (1H, d, J = 1.4 Hz), 8.07 (1H, s), 7.89-7.86 (1H, m), 7.74-7.71 (1H, m), 7.62-7.58 (1H, m), 7.54-7.49 (1H, m), 7.50 (1H, s), 3.90 (3H, s). |
| 563 | | $^1$H-NMR (DMSO-D$_6$) δ: 8.92 (1H, d, J = 1.8 Hz), 8.41 (1H, s), 8.16-8.14 (1H, m), 8.09 (1H, s), 7.89-7.86 (1H, m), 7.74-7.71 (1H, m), 7.62-7.58 (1H, m), 7.54-7.48 (1H, m), 7.50 (1H, s), 4.95 (1H, t, J = 5.3 Hz), 4.19 (2H, t, J = 5.5 Hz), 3.79 (2H, dt, J = 5.5, 5.3 Hz). |
| 564 | | $^1$H-NMR (DMSO-D$_6$) δ: 9.90 (1H, s), 7.92 (1H, s), 7.58-7.53 (1H, m), 7.56 (1H, d, J = 0.7 Hz), 7.27-7.17 (3H, m), 7.13 (1H, s), 7.05-7.01 (1H, m), 6.64 (1H, d, J = 2.2 Hz), 3.94 (3H, s). |
| 565 (optically active form) | | $^1$H-NMR (DMSO-D$_6$) δ: 7.98 (1H, d, J = 0.7 Hz), 7.67 (1H, d, J = 0.7 Hz), 7.66-7.62 (1H, m), 7.44-7.29 (5H, m), 7.17 (1H, dd, J = 9.9, 2.6 Hz), 5.06 (1H, d, J = 5.3 Hz), 4.79 (1H, t, J = 5.6 Hz), 4.33 (1H, dd, J = 13.8, 4.1 Hz), 4.11 (1H, dd, J = 13.7, 7.7 Hz), 3.95-3.87 (1H, m), 3.46-3.35 (2H, m). |

TABLE 1-83

| compound No. | structural formula | NMR |
|---|---|---|
| 566 (optically active form) | | $^1$H-NMR (DMSO-D$_6$) δ: 7.99 (1H, s), 7.68 (1H, s), 7.66-7.62 (1H, m), 7.45-7.29 (5H, m), 7.16 (1H, dd, J = 9.9, 2.4 Hz), 5.07 (1H, d, J = 5.5 Hz), 4.79 (1H, t, J = 5.5 Hz), 4.34 (1H, dd, J = 13.7, 4.0 Hz), 4.10 (1H, dt, J = 13.7, 7.9 Hz), 3.95-3.86 (1H, m), 3.47-3.35 (2H, m). |

TABLE 1-83-continued

| compound No. | structural formula | NMR |
|---|---|---|
| 567 | | ¹H-NMR (DMSO-D₆) δ: 7.63 (2H, d, J = 7.0 Hz), 7.42 (1H, t, J = 7.5 Hz), 7.36-7.28 (2H, m), 7.26-7.18 (2H, m), 6.90-6.85 (1H, m), 3.79 (1.3H, s), 3.78 (1.7H, s), 2.07 (1.3H, s), 1.97 (1.7H, s), 1.95 (1.7H, s), 1.86 (1.3H, s). |
| 568 | | ¹H-NMR (DMSO-D₆) δ: 8.91 (1H, d, J = 2.0 Hz), 8.44 (1H, s), 8.16-8.13 (1H, m), 8.09 (1H, s), 7.89-7.86 (1H, m), 7.74-7.70 (1H, m), 7.62-7.57 (1H, m), 7.54-7.49 (2H, m), 4.36 (2H, t, J = 6.7 Hz), 2.84 (2H, t, J = 6.6 Hz). |
| 569 | | ¹H-NMR (DMSO-D₆) δ: 7.95 (1H, s), 7.59 (1H, d, J = 0.7 Hz), 7.58-7.55 (1H, m), 7.28-7.19 (3H, m), 7.19-7.16 (1H, m), 7.13 (1H, s), 6.78 (1H, d, J = 2.3 Hz), 3.95 (3H, s), 3.78-3.73 (4H, m), 3.21-3.17 (4H, m). |
| 570 | | ¹H-NMR (DMSO-D₆) δ: 8.26 (1H, s), 7.91 (1H, s), 7.82-7.78 (1H, m), 7.75-7.73 (1H, m), 7.72-7.70 (1H, m), 7.68-7.63 (1H, m), 7.54-7.48 (1H, m), 7.40-7.34 (1H, m), 7.22 (1H, s), 5.47 (1H, t, J = 5.3 Hz), 4.87 (2H, d, J = 5.3 Hz), 3.89 (3H, s). |
| 571 | | ¹H-NMR (DMSO-D₆) δ: 7.98 (1H, d, J = 3.1 Hz), 7.62-7.57 (2H, m), 7.33-7.18 (4H, m), 7.17-7.13 (1H, m), 6.84-6.80 (1H, m), 5.00-4.97 (1H, m), 4.72-4.67 (1H, m), 4.11-4.05 (1H, m), 3.98-3.89 (4H, m), 3.86-3.77 (1H, m), 3.49-3.42 (2H, m). |

TABLE 1-83-continued

| compound No. | structural formula | NMR |
|---|---|---|
| 572 | | ¹H-NMR (DMSO-D₆) δ: 7.85 (1H, d, J = 7.7 Hz), 7.72 (1H, d, J = 1.5 Hz), 7.71-7.66 (2H, m), 7.58-7.53 (1H, m), 7.47-7.42 (1H, m), 7.33 (1H, s), 5.54 (1H, t, J = 5.5 Hz), 4.95-4.85 (2H, m), 3.50 (2H, t, J = 6.6 Hz), 3.47-3.38 (2H, m), 1.94-1.80 (4H, m). |

TABLE 1-84

| compound No. | structural formula | NMR |
|---|---|---|
| 573 (optically active form) | | ¹H-NMR (DMSO-D₆) δ: 7.97 (1H, s), 7.61 (1H, d, J = 0.7 Hz), 7.60-7.57 (1H, m), 7.29-7.22 (4H, m), 7.12 (1H, d, J = 1.9 Hz), 6.80 (1H, d, J = 2.3 Hz), 4.12 (2H, t, J = 6.1 Hz), 3.95 (3H, s), 3.07 (2H, t, J = 7.5 Hz), 2.22-2.15 (2H, m). |
| 574 (optically active form) | | ¹H-NMR (CDCl₃) δ: 7.77 (1H, d, J = 0.7 Hz), 7.76 (1H, d, J = 0.7 Hz), 7.70-7.66 (1H, m), 7.54-7.51 (1H, m), 7.29-7.18 (4H, m), 7.13 (1H, dd, J = 1.5, 0.8 Hz), 2.44 (3H, s), 1.97 (6H, s). |
| 575 (optically active form) | | ¹H-NMR (DMSO-D₆) δ: 12.53 (1H, br s), 7.85 (1H, d, J = 0.7 Hz), 7.64-7.60 (1H, m), 7.59 (1H, d, J = 0.9 Hz), 7.45-7.42 (1H, m), 7.32-7.20 (3H, m), 7.17 (1H, s), 7.10 (1H, dd, J = 1.7, 0.8 Hz), 4.35 (2H, s), 2.38 (3H, s), 1.17 (6H, s). |

TABLE 1-84-continued
| compound No. | structural formula | NMR |
|---|---|---|
| 576 (optically active form) | 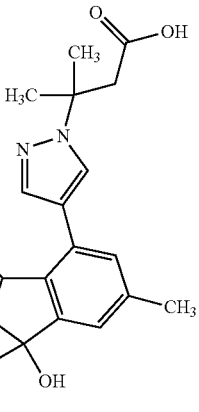 | ¹H-NMR (DMSO-D$_6$) δ: 12.16 (1H, br s), 8.04 (1H, d, J = 0.7 Hz), 7.63-7.57 (1H, m), 7.58 (1H, d, J = 0.7 Hz), 7.43-7.40 (1H, m), 7.32-7.26 (3H, m), 7.15 (1H, s), 7.13 (1H, d, J = 0.9 Hz), 2.94 (2H, s), 2.38 (3H, s), 1.70 (3H, s), 1.69 (3H, s). |
| 577 (optically active form) | 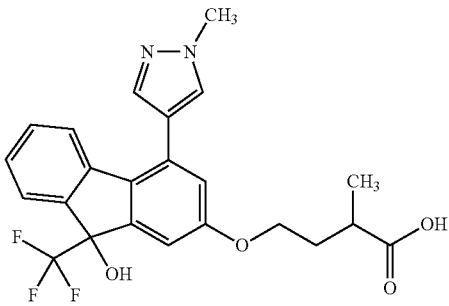 [SMILES: CC(CCOc1cc(-c2cnn(C)c2)c2c(c1)C(O)(C(F)(F)F)c1ccccc1-2)C(=O)O] | ¹H-NMR (DMSO-D$_6$) δ: 12.21 (1H, br s), 7.98 (1H, s), 7.62-7.57 (1H, m), 7.61 (1H, d, J = 0.7 Hz), 7.29-7.21 (4H, m), 7.14-7.12 (1H, m), 6.82 (1H, d, J = 2.6 Hz), 4.07 (2H, t, J = 6.4 Hz), 3.95 (3H, s), 2.60-2.54 (1H, m), 2.11-2.01 (1H, m), 1.85-1.75 (1H, m), 1.15 (3H, d, J = 6.7 Hz). |
| 578 | 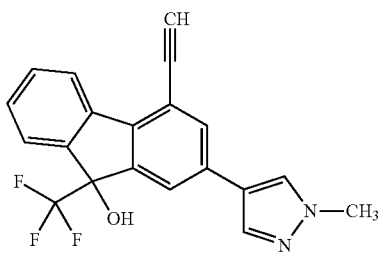 [SMILES: C#Cc1cc(-c2cnn(C)c2)cc2c1-c1ccccc1C2(O)C(F)(F)F] | ¹H-NMR (CDCl$_3$) δ: 8.42 (1H, d, J = 7.5 Hz), 7.78-7.77 (1H, m), 7.76-7.70 (2H, m), 7.69-7.68 (1H, m), 7.67 (1H, d, J = 1.5 Hz), 7.54-7.48 (1H, m), 7.42-7.36 (1H, m), 3.94 (3H, s), 3.53 (1H, s), 3.09 (1H, br s). |
| 579 | 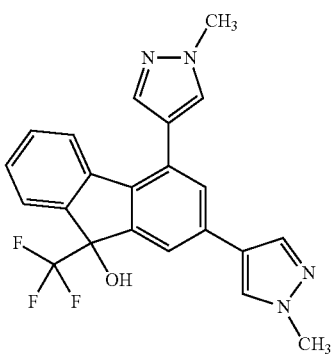 [SMILES: Cn1cc(-c2cc(-c3cnn(C)c3)c3c(c2)C(O)(C(F)(F)F)c2ccccc2-3)cn1] | ¹H-NMR (DMSO-D$_6$) δ: 8.29 (1H, s), 8.00 (1H, s), 7.94 (1H, d, J = 0.7 Hz), 7.77-7.74 (1H, m), 7.67-7.61 (2H, m), 7.50 (1H, d, J = 1.8 Hz), 7.34-7.30 (3H, m), 7.25 (1H, s), 3.97 (3H, s), 3.87 (3H, s). |

TABLE 1-85

| compound No. | structural formula | NMR |
|---|---|---|
| 580 | | ¹H-NMR (DMSO-D₆) δ: 8.30 (1H, d, J = 0.7 Hz), 8.01 (1H, d, J = 0.7 Hz), 7.97 (1H, d, J = 0.7 Hz), 7.78-7.75 (1H, m), 7.67 (1H, d, J = 0.7 Hz), 7.66-7.62 (1H, m), 7.53 (1H, d, J = 1.6 Hz), 7.39-7.27 (3H, m), 7.26 (1H, s), 5.00 (1H, t, J = 5.2 Hz), 4.95 (1H, t, J = 5.3 Hz), 4.28 (2H, t, J = 5.7 Hz), 4.18 (2H, t, J = 5.7 Hz), 3.85 (2H, dt, J = 5.2, 5.7 Hz), 3.79 (2H, dt, J = 5.2, 5.7 Hz). |
| 581 (optically active form) | | ¹H-NMR (DMSO-D₆) δ: 7.99 (1H, s), 7.63 (1H, d, J = 0.7 Hz), 7.61-7.57 (1H, m), 7.30-7.20 (4H, m), 7.13-7.11 (1H, m), 6.80 (1H, d, J = 2.6 Hz), 4.42 (2H, t, J = 6.6 Hz), 4.10 (2H, q, J = 7.0 Hz), 2.90 (2H, t, J = 6.7 Hz). |
| 582 (optically active form) | | ¹H-NMR (DMSO-D₆) δ: 12.20 (1H, br s), 8.01 (1H, s), 7.63 (1H, d, J = 0.7 Hz), 7.62-7.56 (1H, m), 7.28-7.19 (4H, m), 7.14-7.11 (1H, m), 6.83 (1H, d, J = 2.3 Hz), 4.23 (2H, t, J = 6.8 Hz), 4.11 (2H, q, J = 7.0 Hz), 2.27 (2H, t, J = 7.3 Hz), 2.12-2.05 (2H, m), 1.35 (3H, t, J = 7.0 Hz). |
| 583 | | ¹H-NMR (DMSO-D₆) δ: 7.69-7.66 (1H, m), 7.63-7.60 (1H, m), 7.49-7.45 (1H, m), 7.33-7.29 (1H, m), 7.20 (1H, s), 7.14 (1H, d, J = 2.6 Hz), 7.09-7.07 (1H, m), 5.47 (1H, t, J = 5.4 Hz), 4.88-4.78 (2H, m), 4.15 (2H, t, J = 5.6 Hz), 3.58 (2H, t, J = 5.4 Hz), 3.48 (2H, t, J = 7.2 Hz), 2.23 (2H, t, J = 8.1 Hz), 1.98-1.88 (2H, m). |
| 854 | | ¹H-NMR (DMSO-D₆) δ: 8.24 (1H, d, J = 0.9 Hz), 7.94 (1H, d, J = 0.7 Hz), 7.81 (1H, d, J = 7.7 Hz), 7.69-7.64 (2H, m), 7.57-7.55 (1H, m), 7.54-7.49 (1H, m), 7.39-7.35 (1H, m), 7.19 (1H, s), 4.94 (1H, t, J = 5.3 Hz), 4.18 (2H, t, J = 5.6 Hz), 3.78 (2H, dt, J = 5.6, 5.3 Hz), 2.65 (3H, s). |

TABLE 1-85-continued

| compound No. | structural formula | NMR |
|---|---|---|
| 855 | 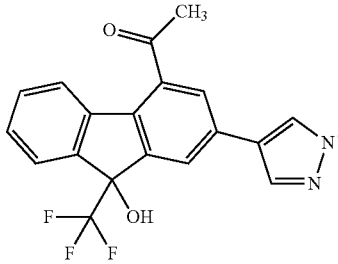 | $^1$H-NMR (DMSO-D$_6$) δ: 8.39 (1H, d, J = 0.7 Hz), 8.08 (1H, d, J = 0.7 Hz), 8.05 (1H, d, J = 1.6 Hz), 7.95-7.93 (1H, m), 7.78-7.75 (1H, m), 7.68-7.65 (1H, m), 7.47-7.43 (1H, m), 7.42-7.38 (1H, m), 7.35 (1H, s), 4.96 (1H, t, J = 5.4 Hz), 4.19 (2H, t, J = 5.6 Hz), 3.79 (2H, dt, J = 5.6, 5.4 Hz), 2.77 (3H, s). |

TABLE 1-86

| compound No. | structural formula | NMR |
|---|---|---|
| 586 | 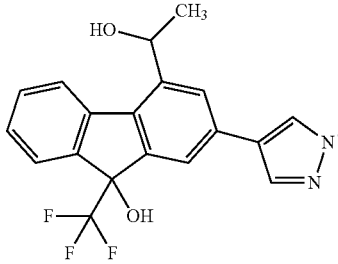 | $^1$H-NMR (DMSO-D$_6$) δ: 8.25-8.23 (1H, m), 7.91-7.78 (3H, m), 7.71-7.65 (2H, m), 7.54-7.49 (1H, m), 7.39-7.34 (1H, m), 7.21 (1H, s), 5.51-5.47 (1H, m), 5.46-5.35 (1H, m), 4.94 (1H, t, J = 5.3 Hz), 4.19 (2H, t, J = 5.7 Hz), 3.81-3.75 (2H, m), 1.50-1.43 (3H, m). |
| 587 | 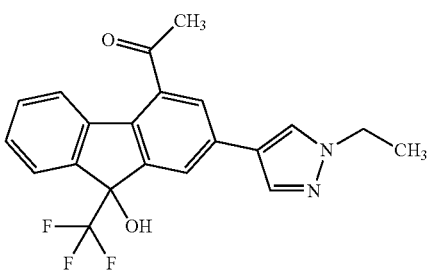 [SMILES: CCn1cc(-c2cc(C(C)=O)c3c(c2)C(O)(C(F)(F)F)c2ccccc2-3)cn1] | $^1$H-NMR (DMSO-D$_6$) δ: 8.44 (1H, s), 8.07 (1H, d, J = 0.5 Hz), 8.05 (1H, d, J = 1.6 Hz), 7.95-7.93 (1H, m), 7.78-7.75 (1H, m), 7.68-7.65 (1H, m), 7.47-7.43 (1H, m), 7.42-7.38 (1H, m), 7.34 (1H, s), 4.18 (2H, q, J = 7.3 Hz), 2.77 (3H, s), 1.43 (3H, t, J = 7.3 Hz). |
| 588 (optically active form) | 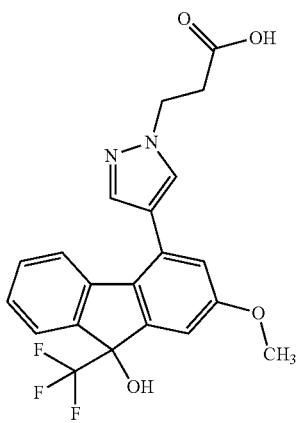 [SMILES: COc1cc(-c2cnn(CCC(=O)O)c2)c2c(c1)C(O)(C(F)(F)F)c1ccccc1-2] | $^1$H-NMR (DMSO-D$_6$) δ: 12.45 (1H, br s), 8.00 (1H, s), 7.64 (1H, d, J = 0.7 Hz), 7.62-7.58 (1H, m), 7.31-7.20 (4H, m), 7.16-7.14 (1H, m), 6.84 (1H, d, J = 2.6 Hz), 4.43 (2H, t, J = 6.7 Hz), 3.84 (3H, s), 2.91 (2H, t, J = 6.7 Hz). |

TABLE 1-86-continued

| compound No. | structural formula | NMR |
|---|---|---|
| 589 (optically active form) | | $^1$H-NMR (DMSO-D$_6$) δ: 12.22 (1H, br s), 8.02 (1H, s), 7.64 (1H, s), 7.62-7.57 (1H, m), 7.30-7.18 (4H, m), 7.16-7.13 (1H, m), 6.86 (1H, d, J = 2.1 Hz), 4.24 (2H, t, J = 6.8 Hz), 3.84 (3H, s), 2.28 (2H, t, J = 7.3 Hz), 2.13-2.06 (2H, m). |
| 590 | | $^1$H-NMR (DMSO-D$_6$) δ: 8.26 (1H, d, J = 0.7 Hz), 7.95 (1H, d, J = 0.9 Hz), 7.82-7.81 (1H, m), 7.79 (1H, d, J = 7.9 Hz), 7.73 (1H, dd, J = 8.0, 1.7 Hz), 7.58-7.52 (2H, m), 7.37-7.33 (1H, m), 7.22 (1H, s), 5.44 (1H, t, J = 5.4 Hz), 4.94 (1H, t, J = 5.4 Hz), 4.91-4.81 (2H, m), 4.18 (2H, t, J = 5.6 Hz), 3.78 (2H, dt, J = 5.6, 5.4 Hz). |
| 591 | | $^1$H-NMR (DMSO-D$_6$) δ: 8.75 (1H, d, J = 7.9 Hz), 8.28 (1H, s), 7.92 (1H, d, J = 0.9 Hz), 7.71-7.69 (1H, m), 7.65 (1H, d, J = 1.5 Hz), 7.64-7.61 (1H, m), 7.48-7.43 (1H, m), 7.35-7.30 (1H, m), 7.14 (1H, s), 5.40 (1H, s), 3.89 (3H, s), 1.73 (3H, s), 1.63 (3H, s). |
| 592 | | $^1$H-NMR (DMSO-D$_6$) δ: 8.75 (1H, d, J = 7.9 Hz), 8.27 (1H, d, J = 0.7 Hz), 7.94 (1H, d, J = 0.7 Hz), 7.72-7.70 (1H, m), 7.65 (1H, d, J = 1.6 Hz), 7.65-7.61 (1H, m), 7.48-7.43 (1H, m), 7.35-7.30 (1H, m), 7.14 (1H, s), 5.41 (1H, s), 4.94 (1H, t, J = 5.3 Hz), 4.18 (2H, t, J = 5.6 Hz), 3.79 (2H, q, J = 5.6 Hz), 1.73 (3H, s), 1.64 (3H, s). |

TABLE 1-87

| compound No. | structural formula | NMR |
|---|---|---|
| 593 | 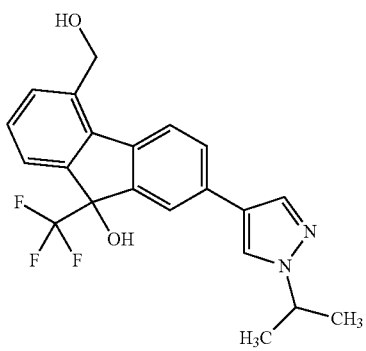 [SMILES: CC(C)n1cc(-c2ccc3c(c2)C(O)(C(F)(F)F)c2cccc(CO)c2-3)cn1] | $^1$H-NMR (DMSO-D$_6$) δ: 8.35 (1H, s), 7.94 (1H, s), 7.85-7.82 (1H, m), 7.78 (1H, d, J = 8.1 Hz), 7.73 (1H, dd, J = 8.1, 1.6 Hz), 7.58-7.51 (2H, m), 7.37-7.33 (1H, m), 7.21 (1H, s), 5.44 (1H, t, J = 5.3 Hz), 4.90-4.81 (2H, m), 4.57-4.50 (1H, m), 1.47 (3H, s), 1.46 (3H, s). |
| 594 | 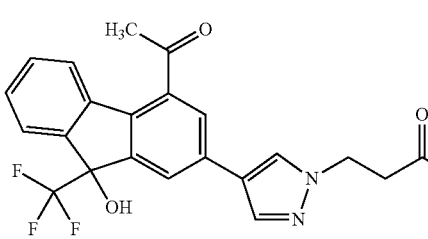 | $^1$H-NMR (DMSO-D$_6$) δ: 12.42 (1H, br s), 8.42 (1H, d, J = 0.7 Hz), 8.08 (1H, d, J = 0.9 Hz), 8.04 (1H, d, J = 1.5 Hz), 7.94-7.92 (1H, m), 7.78-7.75 (1H, m), 7.68-7.65 (1H, m), 7.47-7.43 (1H, m), 7.42-7.38 (1H, m), 7.35 (1H, s), 4.36 (2H, t, J = 6.7 Hz), 3.39 (3H, t, J = 6.9 Hz), 2.87 (2H, t, J = 6.7 Hz), 2.77 (3H, s). |
| 595 (optically active form) | 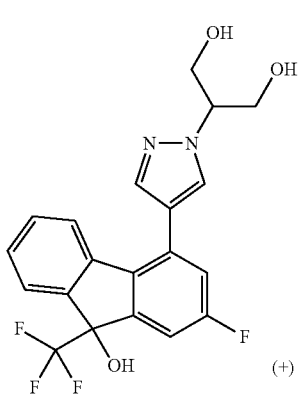 [SMILES: OCC(CO)n1cc(-c2cc(F)cc3c2-c2ccccc2C3(O)C(F)(F)F)cn1] (+) | $^1$H-NMR (DMSO-D$_6$) δ: 8.02 (1H, d, J = 0.5 Hz), 7.68 (1H, d, J = 0.5 Hz), 7.65-7.61 (1H, m), 7.44-7.37 (2H, m), 7.40 (1H, s), 7.36-7.25 (2H, m), 7.18 (1H, dd, J = 10.0, 2.6 Hz), 4.97 (2H, t, J = 5.3 Hz), 4.39-4.32 (1H, m), 3.86-3.76 (4H, m). |
| 596 | 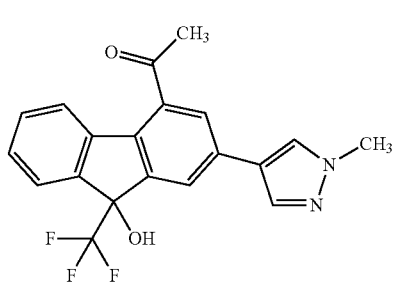 [SMILES: CC(=O)c1cc(-c2cnn(C)c2)cc2c1-c1ccccc1C2(O)C(F)(F)F] | $^1$H-NMR (DMSO-D$_6$) δ: 8.38 (1H, s), 8.06 (1H, d, J = 0.5 Hz), 8.04 (1H, d, J = 1.6 Hz), 7.94-7.91 (1H, m), 7.76 (1H, d, J = 7.4 Hz), 7.68-7.64 (1H, m), 7.48-7.43 (1H, m), 7.42-7.38 (1H, m), 7.35 (1H, s), 3.90 (3H, s), 2.11 (3H, s). |
| 597 | 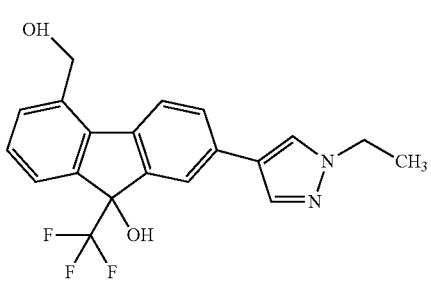 [SMILES: CCn1cc(-c2ccc3c(c2)C(O)(C(F)(F)F)c2cccc(CO)c2-3)cn1] | $^1$H-NMR (DMSO-D$_6$) δ: 8.32 (1H, d, J = 0.5 Hz), 7.94 (1H, d, J = 0.7 Hz), 7.82 (1H, br s), 7.79 (1H, d, J = 8.1 Hz), 7.72 (1H, dd, J = 8.1, 1.6 Hz), 7.58-7.52 (2H, m), 7.37-7.33 (1H, m), 7.22 (1H, s), 5.44 (1H, t, J = 5.4 Hz), 4.90-4.81 (2H, m), 4.17 (2H, q, J = 7.3 Hz), 1.42 (3H, t, J = 7.3 Hz). |

TABLE 1-87-continued

| compound No. | structural formula | NMR |
|---|---|---|
| 598 | | $^1$H-NMR (DMSO-D$_6$) δ: 8.26 (1H, d, J = 4.4 Hz), 7.90-7.79 (3H, m), 7.69-7.65 (2H, m), 7.54-7.49 (1H, m), 7.39-7.34 (1H, m), 7.21 (1H, s), 5.48 (1H, br s), 5.44 (0.5H, q, J = 6.3 Hz), 5.38 (0.5H, q, J = 6.4 Hz), 3.89 (3H, s), 1.48 (1.6H, d, J = 6.3 Hz), 1.45 (1.4H, d, J = 6.3 Hz). |
| 599 | | $^1$H-NMR (CDCl$_3$) δ: 7.82-7.80 (1H, m), 7.71-7.66 (1H, m), 7.43-7.35 (2H, m), 7.35-7.29 (1H, m), 7.11 (1H, d, J = 2.3 Hz), 4.16 (2H, t, J = 5.3 Hz), 3.70 (1H, br s), 3.64 (2H, t, J = 5.2 Hz), 3.57 (2H, t, J = 7.0 Hz), 2.68 (3H, s), 2.34 (2H, t, J = 8.0 Hz), 2.08-1.98 (2H, m). |

TABLE 1-88

| compound No. | structural formula | NMR |
|---|---|---|
| 600 | | $^1$H-NMR (DMSO-D$_6$) δ: 8.29 (1H, s), 7.96 (1H, s), 7.82-7.77 (2H, m), 7.72 (1H, dd, J = 8.0, 1.7 Hz), 7.58-7.52 (2H, m), 7.37-7.33 (1H, m), 4.88 (1H, d, J = 13.7 Hz), 4.84 (1H, d, J = 13.7 Hz), 4.36 (2H, t, J = 6.7 Hz), 2.86 (2H, t, J = 6.7 Hz). |
| 601 | | $^1$H-NMR (DMSO-D$_6$) δ: 8.23 (1H, d, J = 0.5 Hz), 7.95 (1H, d, J = 0.7 Hz), 7.80-7.77 (2H, m), 7.71 (1H, dd, J = 8.0, 1.7 Hz), 7.57-7.52 (2H, m), 7.42 (1H, br s), 7.37-7.33 (1H, m), 7.23 (1H, s), 6.92 (1H, br s), 5.44 (1H, t, J = 5.4 H), 4.90-4.81 (2H, m), 4.34 (2H, t, J = 6.8 Hz), 2.67 (2H, t, J = 7.0 Hz). |
| 602 | | $^1$H-NMR (DMSO-D$_6$) δ: 8.39 (1H, s), 7.95 (1H, s), 7.88-7.86 (1H, m), 7.79-7.74 (2H, m), 7.58-7.52 (2H, m), 7.37-7.33 (1H, m), 7.20 (1H, s), 5.44 (1H, t, J = 5.4 Hz), 4.90-4.81 (2H, m), 1.58 (9H, s). |

TABLE 1-88-continued

| compound No. | structural formula | NMR |
|---|---|---|
| 603 | | ¹H-NMR (DMSO-D₆) δ: 8.39-8.36 (1H, m), 8.34 (1H, d, J = 0.4 Hz), 7.99 (1H, d, J = 0.9 Hz), 7.81-7.79 (1H, m), 7.75 (1H, d, J = 1.5 Hz), 7.69-7.66 (1H, m), 7.56-7.52 (1H, m), 7.45-7.41 (1H, m), 7.35 (1H, s), 5.56 (1H, t, J = 6.0 Hz), 4.50 (2H, d, J = 6.0 Hz), 3.87 (3H, s). |
| 604 (optically active form) | | ¹H-NMR (DMSO-D₆) δ: 9.37 (1H, s), 8.96 (2H, br s), 7.63 (1H, d, J = 7.3 Hz), 7.38 (1H, br s), 7.31-7.21 (3H, m ), 7.04 (1H, d, J = 2.4 Hz), 6.63-6.59 (1H, m), 4.11 (2H, t, J = 6.5 Hz), 2.41 (2H, t, J = 7.3 Hz), 2.01-1.94 (2H, m). |
| 605 (optically active form) | | ¹H-NMR (DMSO-D₆) δ: 7.93 (1H, d, J = 0.7 Hz), 7.63-7.59 (1H, m), 7.61 (1H, d, J = 0.7 Hz), 7.42 (1H, s), 7.37 (1H, dd, J = 6.7, 0.9 Hz), 7.32-7.22 (2H, m), 7.16 (1H, s), 7.14 (1H, dd, J = 1.6, 0.7 Hz), 4.96 (2H, td, J = 5.3, 1.2 Hz), 4.38-4.32 (1H, m), 3.86-3.76 (4H, m), 2.39 (3H, s). |
| 606 (optically active form) | | ¹H-NMR (DMSO-D₆) δ: 12.07 (1H, br s), 7.99 (1H, d, J = 0.7 Hz), 7.64-7.60 (1H, m), 7.59 (1H, d, J = 0.7 Hz), 7.42 (1H, s), 7.32-7.21 (3H, m), 7.17 (1H, s), 7.12 (1H, dd, J = 1.5, 0.8 Hz), 4.21 (2H, t, J = 6.7 Hz), 2.38 (3H, s), 2.28 (2H, t, J = 7.4 Hz), 1.91-1.84 (2H, m), 1.55-1.48 (2H, m). |

TABLE 1-89
| compound No. | structural formula | NMR |
|---|---|---|
| 607 (optically active form) | 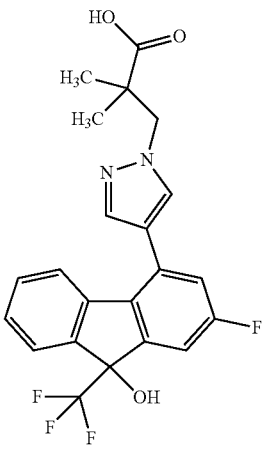 [SMILES: CC(C)(Cn1cc(-c2cc(F)cc3c2-c2ccccc2C3(O)C(F)(F)F)cn1)C(=O)O] | $^1$H-NMR (DMSO-D$_6$) δ: 12.53 (1H, br s), 7.94 (1H, d, J = 0.7 Hz), 7.67 (1H, d, J = 0.7 Hz), 7.65 (1H, d, J = 7.0 Hz), 7.43-7.39 (2H, m), 7.37-7.24 (3H, m), 7.17 (1H, dd, J = 10.0, 2.6 Hz), 4.36 (2H, s), 1.18 (6H, s). |
| 608 | 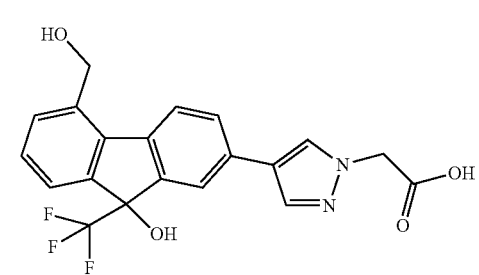 [SMILES: O=C(O)Cn1cc(-c2ccc3c(c2)C(O)(C(F)(F)F)c2cccc(CO)c2-3)cn1] | $^1$H-NMR (DMSO-D$_6$) δ: 13.15 (1H, br s), 8.29 (1H, s), 7.99 (1H, d, J = 0.5 Hz), 7.83-7.79 (2H, m), 7.74 (1H, dd, J = 8.1, 1.6 Hz), 7.58-7.52 (2H, m), 7.38-7.33 (1H, m), 7.24 (1H, s), 5.45 (1H, t, J = 5.3 Hz), 5.00 (2H, s), 4.91-4.82 (2H, m). |
| 609 | 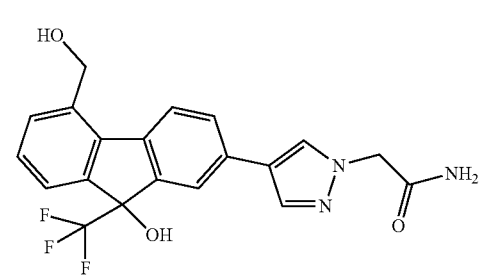 [SMILES: NC(=O)Cn1cc(-c2ccc3c(c2)C(O)(C(F)(F)F)c2cccc(CO)c2-3)cn1] | $^1$H-NMR (DMSO-D$_6$) δ: 8.27-8.25 (1H, m), 7.98-7.96 (1H, m), 7.84-7.79 (2H, m), 7.76-7.72 (1H, m), 7.58-7.51 (3H, m), 7.38-7.33 (1H, m), 7.31 (1H, br s), 7.24 (1H, d, J = 1.9 Hz), 5.47-5.43 (1H, m), 4.87-4.86 (2H, m), 4.80 (2H, d, J = 1.6 Hz). |
| 610 (optically active form) | 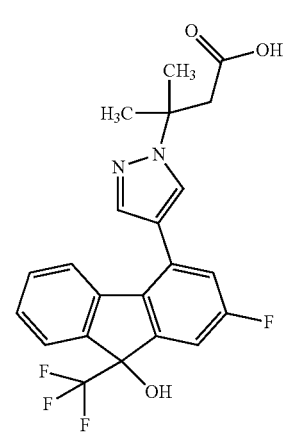 [SMILES: CC(C)(CC(=O)O)n1cc(-c2cc(F)cc3c2-c2ccccc2C3(O)C(F)(F)F)cn1] | $^1$H-NMR (DMSO-D$_6$) δ: 12.19 (1H, br s), 8.14 (1H, d, J = 0.7 Hz), 7.66 (1H, s), 7.65-7.61 (1H, m), 7.41-7.37 (2H, m), 7.37-7.29 (3H, m), 7.18 (1H, dd, J = 10.0, 2.6 Hz), 2.94 (2H, s), 1.70 (3H, s), 1.69 (3H, s). |

TABLE 1-89-continued

| compound No. | structural formula | NMR |
|---|---|---|
| 611 | | ¹H-NMR (DMSO-D₆) δ: 7.67 (1H, d, J = 7.7 Hz), 7.61 (1H, d, J = 7.4 Hz), 7.49-7.44 (1H, m), 7.32-7.28 (1H, m), 7.19 (1H, s), 7.13 (1H, d, J = 2.3 Hz), 7.07-7.05 (1H, m), 5.46 (1H, t, J = 5.4 Hz), 4.87-4.78 (2H, m), 4.47 (1H, t, J = 5.2 Hz), 4.05 (2H, t, J = 6.5 Hz), 3.47 (2H, dd, J = 11.6, 6.5 Hz), 1.82-1.75 (2H, m), 1.63-1.55 (2H, m). |
| 612 | | ¹H-NMR (DMSO-D₆) δ: 8.09 (1H, br s), 7.86 (1H, d, J = 7.6 Hz), 7.72 (1H, br s), 7.61 (1H, d, J = 7.4 Hz), 7.46-7.41 (1H, m), 7.35-7.29 (1H, m), 7.30 (1H, s), 7.25-7.23 (1H, m), 7.07 (1H, d, J = 2.5 Hz), 4.23 (2H, t, J = 5.7 Hz), 4.20-4.16 (2H, m), 3.67-3.59 (2H, m), 3.46 (2H, t, J = 6.4 Hz), 1.98-1.92 (2H, m). |
| 613 | | ¹H-NMR (DMSO-D₆) δ: 12.16 (1H, br s), 8.64 (1H, s), 7.64 (1H, d, J = 7.4 Hz), 7.59 (1H, s), 7.40-7.31 (3H, m), 7.30-7.28 (1H, m), 7.13 (1H, d, J = 2.6 Hz), 7.06 (1H, d, J = 7.0 Hz), 4.11 (2H, t, J = 6.5 Hz), 2.42 (2H, t, J = 7.3 Hz), 2.01-1.94 (2H, m). |

TABLE 1-90

| compound No. | structural formula | NMR |
|---|---|---|
| 614 (optically active form) | | ¹H-NMR (CDCl₃) δ: 7.71 (2H, s), 7.68-7.64 (1H, m), 7.25-7.22 (3H, m), 7.11-7.08 (1H, m), 6.80-6.79 (1H, m), 3.88 (3H, s), 3.15 (2H, s), 2.79 (1H, s), 1.78 (3H, s), 1.77 (3H, s). |
| 615 | | ¹H-NMR (DMSO-D₆) δ: 8.25 (1H, s), 7.93 (1H, s), 7.80 (1H, d, J = 7.7 Hz), 7.76-7.74 (1H, m), 7.73-7.71 (1H, m), 7.67-7.64 (1H, m), 7.53-7.49 (1H, m), 7.39-7.34 (1H, m), 7.23 (1H, s), 5.47 (1H, t, J = 5.3 Hz), 4.95 (1H, t, J = 5.3 Hz), 4.91-4.83 (2H, m), 4.19 (2H, t, J = 5.6 Hz), 3.78 (2H, q, J = 5.5 Hz). |

TABLE 1-90-continued

| compound No. | structural formula | NMR |
|---|---|---|
| 616 | | ¹H-NMR (CDCl₃) δ: 8.28-8.25 (1H, m), 7.88 (1H, d, J = 2.0 Hz), 7.84-7.82 (1H, m), 7.73-7.69 (1H, m), 7.51-7.46 (1H, m), 7.44-7.40 (1H, m), 4.01 (3H, s), 2.83 (1H, br s). |
| 617 (optically active form) | | ¹H-NMR (CDCl₃) δ: 8.30-8.27 (1H, m), 7.89 (1H, d, J = 2.0 Hz), 7.84-7.82 (1H, m), 7.73-7.70 (1H, m), 7.52-7.47 (1H, m), 7.44-7.40 (1H, m), 4.02 (3H, s), 2.77 (1H, br s). |
| 618 | | ¹H-NMR (DMSO-D₆) δ: 8.31 (1H, d, J = 0.7 Hz), 7.92 (1H, d, J = 0.7 Hz), 7.80 (1H, d, J = 7.7 Hz), 7.75 (1H, d, J = 1.4 Hz), 7.73-7.71 (1H, m), 7.67-7.64 (1H, m), 7.53-7.48 (1H, m), 7.39-7.34 (1H, m), 7.22 (1H, s), 5.47 (1H, t, J = 5.4 Hz), 4.91-4.82 (2H, m), 4.18 (2H, q, J = 7.3 Hz), 1.42 (3H, t, J = 7.3 Hz). |
| 619 (optically active form) | | ¹H-NMR (DMSO-D₆) δ: 12.55 (1H, br s), 7.89 (1H, d, J = 0.7 Hz), 7.63 (1H, d, J = 0.7 Hz), 7.62-7.59 (1H, m), 7.28-7.24 (3H, m), 7.21-7.15 (2H, m), 6.83 (1H, d, J = 2.3 Hz), 4.36 (2H, s), 3.84 (3H, s), 1.19 (6H, s). |

TABLE 1-90-continued

| compound No. | structural formula | NMR |
|---|---|---|
| 620 | 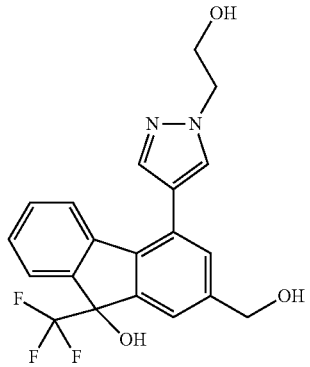 [SMILES: OCCn1cc(-c2cc(CO)cc3c2-c2ccccc2C3(O)C(F)(F)F)cn1] | $^1$H-NMR (DMSO-D$_6$) δ: 7.94 (1H, d, J = 0.7 Hz), 7.64-7.58 (2H, m), 7.60 (1H, d, J = 0.7 Hz), 7.38-7.26 (3H, m), 7.24-7.21 (1H, m), 7.19 (1H, br s), 5.35 (1H, t, J = 5.6 Hz), 4.97 (1H, t, J = 5.2 Hz), 4.57 (2H, d, J = 5.3 Hz), 4.26 (2H, t, J = 5.6 Hz), 3.82 (2H, dt, J = 5.6, 5.6 Hz). |

TABLE 1-91

| compound No. | structural formula | NMR |
|---|---|---|
| 621 | 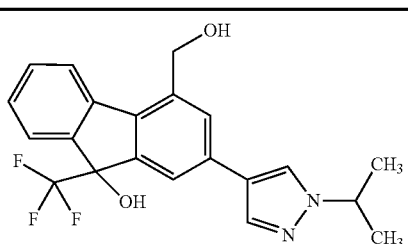 | $^1$H-NMR (DMSO-D$_6$) δ: 8.34 (1H, s), 7.91 (1H, s), 7.80 (1H, d, J = 7.7 Hz), 7.76-7.75 (1H, m), 7.75-7.73 (1H, m), 7.68-7.64 (1H, m), 7.53-7.48 (1H, m), 7.39-7.34 (1H, m), 7.21 (1H, s), 5.46 (1H, t, J = 5.4 Hz), 4.91-4.82 (2H, m), 4.59-4.49 (1H, m), 1.48 (3H, s), 1.46 (3H, s). |
| 622 | 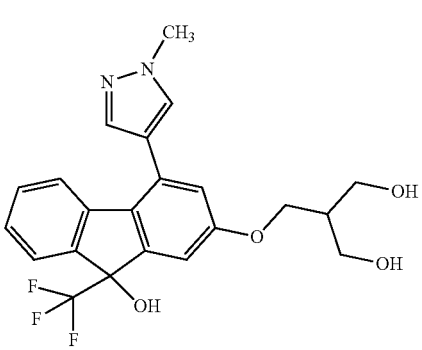 [SMILES: Cn1cc(-c2cc(OCC(CO)CO)cc3c2-c2ccccc2C3(O)C(F)(F)F)cn1] | $^1$H-NMR (DMSO-D$_6$) δ: 7.98 (1H, s), 7.62-7.57 (1H, m), 7.61 (1H, d, J = 0.7 Hz), 7.31-7.22 (4H, m), 7.17-7.13 (1H, m), 6.82 (1H, d, J = 2.6 Hz), 4.56 (2H, t, J = 5.2 Hz), 4.04 (2H, d, J = 6.0 Hz), 3.95 (3H, s), 3.58-3.48 (4H, m), 2.04-1.95 (1H, m). |
| 623 | 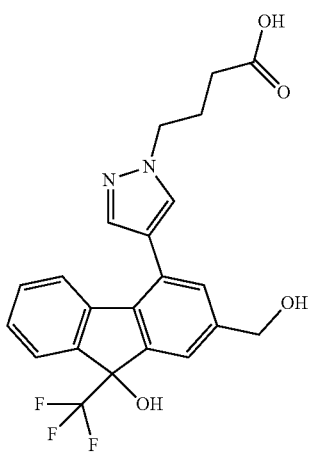 [SMILES: O=C(O)CCCn1cc(-c2cc(CO)cc3c2-c2ccccc2C3(O)C(F)(F)F)cn1] | $^1$H-NMR (DMSO-D$_6$) δ: 12.20 (1H, br s), 7.98 (1H, d, J = 0.5 Hz), 7.65-7.58 (2H, m), 7.61 (1H, d, J = 0.7 Hz), 7.34-7.20 (5H, m), 5.35 (1H, t, J = 5.7 Hz), 4.57 (2H, d, J = 5.3 Hz), 4.24 (2H, t, J = 6.8 Hz), 2.27 (2H, t, J = 7.4 Hz), 2.12-2.05 (2H, m). |

TABLE 1-91-continued

| compound No. | structural formula | NMR |
| --- | --- | --- |
| 624 (optically active form) | | ¹H-NMR (DMSO-D$_6$) δ: 7.97 (1H, d, J = 0.7 Hz), 7.63 (1H, d, J = 0.7 Hz), 7.61-7.56 (1H, m), 7.34-7.29 (1H, m), 7.28-7.23 (2H, m), 7.21 (1H, s), 7.14-7.11 (1H, m), 6.82 (1H, d, J = 2.3 Hz), 4.97 (1H, t, J = 5.2 Hz), 4.46 (1H, t, J = 5.2 Hz), 4.25 (2H, t, J = 5.7 Hz), 4.05 (2H, t, J = 6.5 Hz), 3.85-3.79 (2H, m), 3.49-3.43 (2H, m), 1.81-1.74 (2H, m), 1.61-1.54 (2H, m). |
| 625 | | ¹H-NMR (DMSO-D$_6$) δ: 7.89 (1H, d, J = 7.7 Hz), 7.74-7.70 (1H, m), 7.66-7.58 (3H, m), 7.52 (1H, s), 7.52-7.47 (1H, m), 4.54 (1H, d, J = 18.8 Hz), 4.49 (1H, d, J = 18.8 Hz). |
| 626 | | ¹H-NMR (DMSO-D$_6$) δ: 8.10 (1H, br s), 7.85 (1H, d, J = 7.7 Hz), 7.72 (1H, br s), 7.63-7.59 (1H, m), 7.45-7.40 (1H, m), 7.34-7.29 (1H, m), 7.30 (1H, s), 7.23-7.21 (1H, m), 7.04 (1H, d, J = 2.6 Hz), 3.86 (3H, s). |

TABLE 1-92

| compound No. | structural formula | NMR |
| --- | --- | --- |
| 627 | | ¹H-NMR (DMSO-D$_6$) δ: 7.67 (1H, d, J = 7.9 Hz), 7.63-7.60 (1H, m), 7.49-7.44 (1H, m), 7.33-7.28 (1H, m), 7.20 (1H, s), 7.14 (1H, d, J = 2.3 Hz), 7.09-7.07 (1H, m), 5.48 (1H, t, J = 5.4 Hz), 4.88-4.78 (2H, m), 3.83 (3H, s). |
| 628 | | ¹H-NMR (DMSO-D$_6$) δ: 7.96 (1H, s), 7.61-7.57 (1H, m), 7.59 (1H, d, J = 0.7 Hz), 7.30-7.18 (5H, m), 6.87 (1H, d, J = 2.4 Hz), 4.87-4.82 (2H, m), 4.35-4.29 (1H, m), 3.95 (3H, s), 3.66-3.54 (4H, m). |

TABLE 1-92-continued

| compound No. | structural formula | NMR |
|---|---|---|
| 629 (optically active form) | 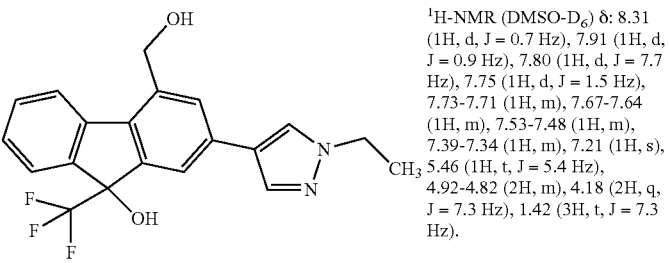 | $^1$H-NMR (DMSO-D$_6$) δ: 8.31 (1H, d, J = 0.7 Hz), 7.91 (1H, d, J = 0.9 Hz), 7.80 (1H, d, J = 7.7 Hz), 7.75 (1H, d, J = 1.5 Hz), 7.73-7.71 (1H, m), 7.67-7.64 (1H, m), 7.53-7.48 (1H, m), 7.39-7.34 (1H, m), 7.21 (1H, s), 5.46 (1H, t, J = 5.4 Hz), 4.92-4.82 (2H, m), 4.18 (2H, q, J = 7.3 Hz), 1.42 (3H, t, J = 7.3 Hz). |
| 630 (optically active form) | 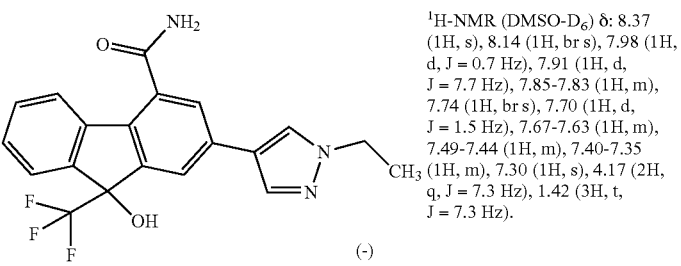 (-) | $^1$H-NMR (DMSO-D$_6$) δ: 8.37 (1H, s), 8.14 (1H, br s), 7.98 (1H, d, J = 0.7 Hz), 7.91 (1H, d, J = 7.7 Hz), 7.85-7.83 (1H, m), 7.74 (1H, br s), 7.70 (1H, d, J = 1.5 Hz), 7.67-7.63 (1H, m), 7.49-7.44 (1H, m), 7.40-7.35 (1H, m), 7.30 (1H, s), 4.17 (2H, q, J = 7.3 Hz), 1.42 (3H, t, J = 7.3 Hz). |
| 631 | 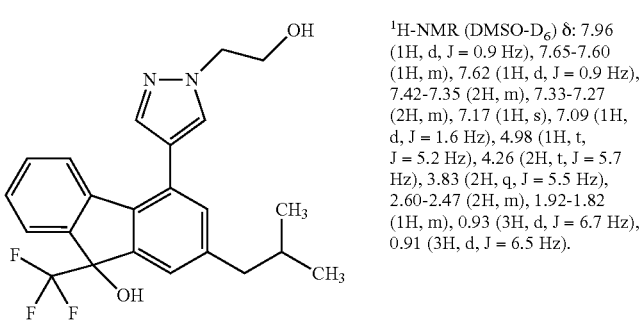 | $^1$H-NMR (DMSO-D$_6$) δ: 7.96 (1H, d, J = 0.9 Hz), 7.65-7.60 (1H, m), 7.62 (1H, d, J = 0.9 Hz), 7.42-7.35 (2H, m), 7.33-7.27 (2H, m), 7.17 (1H, s), 7.09 (1H, d, J = 1.6 Hz), 4.98 (1H, t, J = 5.2 Hz), 4.26 (2H, t, J = 5.7 Hz), 3.83 (2H, q, J = 5.5 Hz), 2.60-2.47 (2H, m), 1.92-1.82 (1H, m), 0.93 (3H, d, J = 6.7 Hz), 0.91 (3H, d, J = 6.5 Hz). |
| 632 | 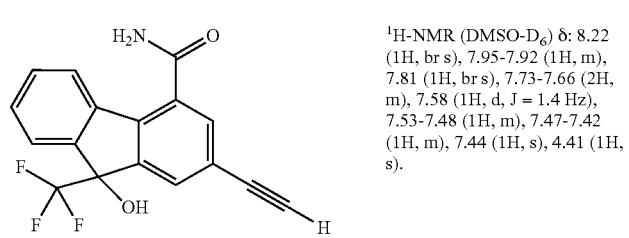 | $^1$H-NMR (DMSO-D$_6$) δ: 8.22 (1H, br s), 7.95-7.92 (1H, m), 7.81 (1H, br s), 7.73-7.66 (2H, m), 7.58 (1H, d, J = 1.4 Hz), 7.53-7.48 (1H, m), 7.47-7.42 (1H, m), 7.44 (1H, s), 4.41 (1H, s). |
| 633 | 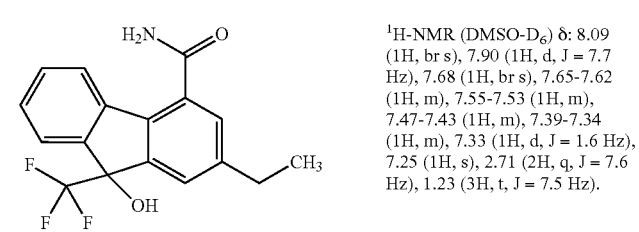 | $^1$H-NMR (DMSO-D$_6$) δ: 8.09 (1H, br s), 7.90 (1H, d, J = 7.7 Hz), 7.68 (1H, br s), 7.65-7.62 (1H, m), 7.55-7.53 (1H, m), 7.47-7.43 (1H, m), 7.39-7.34 (1H, m), 7.33 (1H, d, J = 1.6 Hz), 7.25 (1H, s), 2.71 (2H, q, J = 7.6 Hz), 1.23 (3H, t, J = 7.5 Hz). |

TABLE 1-93

| compound No. | structural formula | NMR |
|---|---|---|
| 634 | (structure) | ¹H-NMR (DMSO-D₆) δ: 8.06 (1H, br s), 7.91 (1H, d, J = 7.7 Hz), 7.67 (1H, br s), 7.65-7.61 (1H, m), 7.55-7.52 (1H, m), 7.47-7.42 (1H, m), 7.38-7.32 (2H, m), 7.23 (1H, s), 2.71-2.63 (2H, m), 0.95 (9H, t, J = 7.9 Hz), 0.92-0.86 (2H, m), 0.56 (6H, q, J = 7.9 Hz). |
| 635 | (structure) | ¹H-NMR (DMSO-D₆) δ: 7.78 (1H, d, J = 7.7 Hz), 7.70-7.66 (1H, m), 7.64-7.61 (1H, m), 7.57-7.52 (2H, m), 7.46-7.40 (1H, m), 7.41 (1H, s), 5.62 (1H, t, J = 5.6 Hz), 4.93-4.82 (2H, m). |
| 636 | (structure) | ¹H-NMR (DMSO-D₆) δ: 8.24 (1H, br s), 7.92-7.89 (1H, m), 7.86 (1H, br s), 7.69-7.64 (2H, m), 7.56 (1H, d, J = 2.1 Hz), 7.53-7.47 (1H, m), 7.49 (1H, s), 7.46-7.41 (1H, m). |
| 637 | (structure) | ¹H-NMR (DMSO-D₆) δ: 8.22 (1H, s), 7.89 (1H, d, J = 0.8 Hz), 7.84 (1H, d, J = 7.7 Hz), 7.69-7.68 (1H, m), 7.67-7.63 (1H, m), 7.58 (1H, d, J = 1.6 Hz), 7.55 (1H, br s), 7.51-7.46 (1H, m), 7.38-7.34 (1H, m), 7.22 (1H, s), 7.09 (1H, br s), 3.89 (3H, s), 3.89 (1H, d, J = 15.7 Hz), 3.81 (1H, d, J = 15.7 Hz). |
| 638 | (structure) | ¹H-NMR (DMSO-D₆) δ: 8.38 (1H, s), 7.93 (1H, s), 7.81 (1H, d, J = 7.7 Hz), 7.78 (2H, s), 7.66 (1H, d, J = 7.4 Hz), 7.53-7.48 (1H, m), 7.39-7.34 (1H, m), 7.20 (1H, s), 5.45 (1H, t, J = 5.4 Hz), 4.92-4.82 (2H, m), 1.58 (9H, s). |
| 639 | (structure) | ¹H-NMR (DMSO-D₆) δ: 8.46 (1H, s), 8.13 (1H, br s), 7.99 (1H, s), 7.91 (1H, d, J = 7.7 Hz), 7.89 (1H, br s), 7.78-7.73 (2H, m), 7.67-7.63 (1H, m), 7.49-7.44 (1H, m), 7.40-7.34 (1H, m), 7.30 (1H, s), 1.57 (9H, s). |

TABLE 1-93-continued

| compound No. | structural formula | NMR |
|---|---|---|
| 640 | (fluorene with CF3, OH, CONH2, and OCH2CH2OH substituents) | ¹H-NMR (DMSO-D₆) δ: 8.09 (1H, br s), 7.85 (1H, d, J = 7.7 Hz), 7.71 (1H, br s), 7.63-7.59 (1H, m), 7.45-7.40 (1H, m), 7.34-7.28 (1H, m), 7.30 (1H, s), 7.24-7.21 (1H, m), 7.04 (1H, d, J = 2.3 Hz), 4.93 (1H, t, J = 5.6 Hz), 4.09 (2H, t, J = 4.9 Hz), 3.75 (2H, q, J = 5.0 Hz). |

TABLE 1-94

| compound No. | structural formula | NMR |
|---|---|---|
| 641 | (fluorene with CF3, OH, CH2OH, and C≡CH substituents) | ¹H-NMR (DMSO-D₆) δ: 7.84-7.81 (1H, m), 7.71-7.65 (2H, m), 7.60-7.58 (1H, m), 7.57-7.52 (1H, m), 7.46-7.41 (1H, m), 7.33 (1H, s), 5.53 (1H, t, J = 5.5 Hz), 4.91-4.81 (2H, m), 4.31 (1H, s). |
| 642 | (fluorene with CF3, OH, CH2OH, and CH2CH3 substituents) | ¹H-NMR (DMSO-D₆) δ: 7.79-7.75 (1H, m), 7.66-7.62 (1H, m), 7.52-7.46 (1H, m), 7.42-7.38 (2H, m), 7.37-7.33 (1H, m), 7.13 (1H, s), 5.40 (1H, t, J = 5.4 Hz), 4.88-4.78 (2H, m), 2.69 (2H, q, J = 7.6 Hz), 1.23 (3H, t, J = 7.5 Hz). |
| 643 | (fluorene with CF3, OH, CH2CH2OH, and N-methylpyrazole substituents) | ¹H-NMR (DMSO-D₆) δ: 8.24 (1H, s), 7.91 (1H, d, J = 0.7 Hz), 7.83 (1H, d, J = 7.7 Hz), 7.68-7.64 (2H, m), 7.56-7.50 (2H, m), 7.40-7.35 (1H, m), 7.19 (1H, s), 4.91 (1H, t, J = 5.3 Hz), 3.88 (3H, s), 3.74-3.67 (2H, m), 3.24-3.09 (2H, m). |
| 644 | (fluorene with CF3, OH, CH2OH, and azetidinyl-hydroxy carbonyl substituents) | ¹H-NMR (DMSO-D₆) δ: 7.86 (1H, d, J = 7.7 Hz), 7.83-7.81 (1H, m), 7.79-7.77 (1H, m), 7.70 (1H, d, J = 7.5 Hz), 7.58-7.54 (1H, m), 7.48-7.43 (1H, m), 7.35 (1H, s), 5.76 (1H, d, J = 6.2 Hz), 5.56 (1H, t, J = 5.5 Hz), 4.96-4.86 (2H, m), 4.56-4.43 (2H, m), 4.34-4.24 (1H, m), 4.11-4.00 (1H, m), 3.88-3.76 (1H, m). |
| 645 | (fluorene with CF3, OH, CONH2, and pyrazole-isobutyl substituents) | ¹H-NMR (DMSO-D₆) δ: 8.36 (1H, d, J = 0.7 Hz), 8.15 (1H, br s), 8.00 (1H, d, J = 0.7 Hz), 7.91 (1H, d, J = 7.7 Hz), 7.86-7.83 (1H, m), 7.75 (1H, br s), 7.70 (1H, d, J = 1.6 Hz), 7.67-7.63 (1H, m), 7.49-7.44 (1H, m), 7.40-7.35 (1H, m), 7.31 (1H, s), 3.95 (2H, d, J = 7.2 Hz), 2.20-2.13 (1H, m), 0.88 (3H, d, J = 1.2 Hz), 0.86 (3H, d, J = 1.4 Hz). |

TABLE 1-94-continued

| compound No. | structural formula | NMR |
|---|---|---|
| 646 | | ¹H-NMR (DMSO-D₆) δ: 8.32 (1H, s), 8.15 (1H, br s), 8.00 (1H, s), 7.91 (1H, d, J = 7.7 Hz), 7.86-7.84 (1H, m), 7.75 (1H, br s), 7.71 (1H, d, J = 1.6 Hz), 7.67-7.63 (1H, m), 7.49-7.44 (1H, m), 7.40-7.35 (1H, m), 7.31 (1H, s), 3.95 (2H, s), 0.94 (9H, s). |
| 647 (optically active form) | | ¹H-NMR (CDCl₃) δ: 8.41-8.37 (1H, m), 8.24-8.22 (1H, m), 8.11 (1H, d, J = 1.5 Hz), 7.79-7.75 (1H, m), 7.59-7.54 (1H, m), 7.51-7.46 (1H, m), 3.92 (3H, s), 3.06 (1H, br s). |

TABLE 1-95

| compound No. | structural formula | NMR |
|---|---|---|
| 648 | | ¹H-NMR (DMSO-D₆) δ: 7.94 (1H, s), 7.63-7.59 (1H, m), 7.61 (1H, d, J = 0.7 Hz), 7.40-7.37 (2H, m), 7.32-7.22 (2H, m), 7.15 (1H, s), 7.10 (1H, d, J = 1.5 Hz), 4.96-4.92 (2H, m), 4.38-4.32 (1H, m), 3.85-3.78 (4H, m), 2.58-2.48 (2H, m), 1.92-1.82 (1H, m), 0.92 (3H, d, J = 6.8 Hz), 0.90 (3H, d, J = 6.6 Hz). |
| 649 | | ¹H-NMR (DMSO-D₆) δ: 8.28 (1H, d, J = 0.7 Hz), 7.93 (1H, d, J = 0.7 Hz), 7.80 (1H, d, J = 7.9 Hz), 7.76-7.74 (1H, m), 7.73-7.71 (1H, m), 7.66 (1H, d, J = 7.3 Hz), 7.53-7.48 (1H, m), 7.39-7.35 (1H, m), 4.89 (1H, d, J = 13.5 Hz), 4.85 (1H, d, J = 13.7 Hz), 3.96 (2H, d, J = 7.1 Hz), 2.21-2.13 (1H, m), 0.88 (3H, d, J = 1.1 Hz), 0.86 (3H, d, J = 1.1 Hz). |
| 650 | | ¹H-NMR (DMSO-D₆) δ: 8.24 (1H, d, J = 0.7 Hz), 7.93 (1H, d, J = 0.7 Hz), 7.80 (1H, d, J = 7.7 Hz), 7.76 (1H, d, J = 1.8 Hz), 7.73 (1H, s), 7.66 (1H, d, J = 7.5 Hz), 7.53-7.49 (1H, m), 7.39-7.34 (1H, m), 4.89 (1H, d, J = 13.7 Hz), 4.85 (1H, d, J = 14.1 Hz), 3.95 (3H, s), 0.94 (8H, s). |

TABLE 1-95-continued
| compound No. | structural formula | NMR |
|---|---|---|
| 651 | 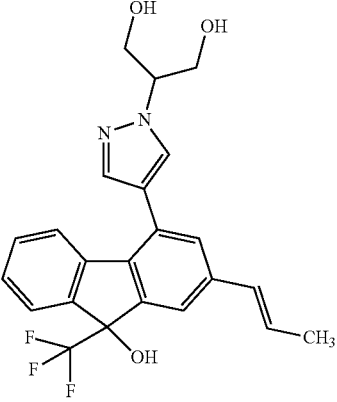 [SMILES: C/C=C/c1cc(-c2cnn(C(CO)CO)c2)c2c(c1)C(O)(C(F)(F)F)c1ccccc1-2] | $^1$H-NMR (DMSO-D$_6$) δ: 7.96 (1H, s), 7.64-7.59 (2H, m), 7.63 (1H, s), 7.39-7.35 (1H, m), 7.33-7.23 (3H, m), 7.21 (1H, s), 6.55-6.48 (1H, m), 6.40 (1H, dq, J = 17.2, 5.3 Hz), 4.98-4.93 (2H, m), 4.38-4.32 (1H, m), 3.86-3.77 (4H, m), 1.88 (3H, dd, J = 6.5, 1.2 Hz). |
| 652 | 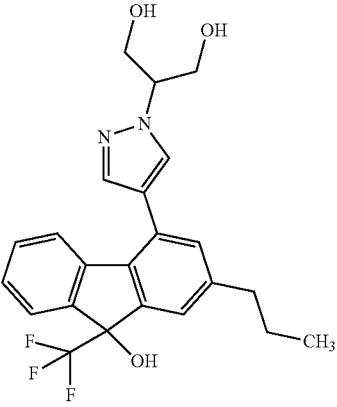 [SMILES: CCCc1cc(-c2cnn(C(CO)CO)c2)c2c(c1)C(O)(C(F)(F)F)c1ccccc1-2] | $^1$H-NMR (DMSO-D$_6$) δ: 7.93 (1H, d, J = 0.7 Hz), 7.63-7.59 (2H, m), 7.61 (1H, d, J = 0.7 Hz), 7.44-7.41 (1H, m), 7.39-7.36 (1H, m), 7.32-7.22 (2H, m), 7.15 (1H, s), 7.13 (1H, d, J = 1.5 Hz), 4.96-4.93 (2H, m), 4.38-4.32 (1H, m), 3.86-3.78 (4H, m), 2.69-2.60 (2H, m), 1.70-1.57 (2H, m), 0.93 (3H, t, J = 7.4 Hz). |
| 653 | 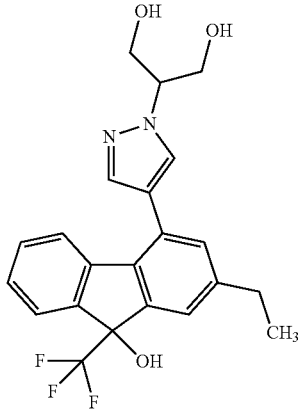 [SMILES: CCc1cc(-c2cnn(C(CO)CO)c2)c2c(c1)C(O)(C(F)(F)F)c1ccccc1-2] | $^1$H-NMR (DMSO-D$_6$) δ: 7.94 (1H, s), 7.64-7.59 (1H, m), 7.61 (1H, s), 7.47-7.44 (1H, m), 7.39-7.35 (1H, m), 7.32-7.22 (2H, m), 7.17 (1H, s), 7.15 (1H, d, J = 1.2 Hz), 4.98-4.93 (2H, m), 4.38-4.32 (1H, m), 3.86-3.78 (4H, m), 2.69 (2H, q, J = 7.5 Hz), 1.23 (3H, t, J = 7.7 Hz). |

TABLE 1-96

| compound No. | structural formula | NMR |
|---|---|---|
| 654 | 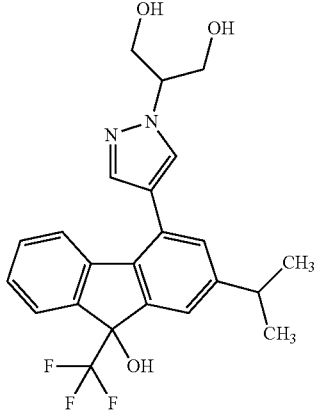 [SMILES: CC(C)c1cc(-c2cnn(C(CO)CO)c2)c2c(c1)C(O)(C(F)(F)F)c1ccccc1-2] | $^1$H-NMR (DMSO-D$_6$) δ: 7.93 (1H, d, J = 0.7 Hz), 7.61 (1H, d, J = 0.7 Hz), 7.60-7.58 (1H, m), 7.49-7.46 (1H, m), 7.38-7.33 (1H, m), 7.31-7.21 (2H, m), 7.16 (2H, br s), 4.98-4.93 (2H, m), 4.37-4.31 (1H, m), 3.85-3.76 (4H, m), 3.02-2.94 (1H, m), 1.26 (3H, d, J = 7.2 Hz), 1.25 (3H, d, J = 7.2 Hz). |
| 655 | 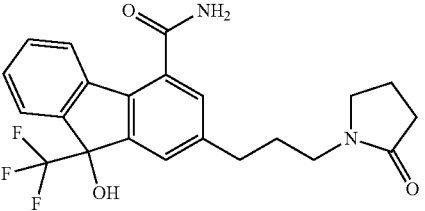 [SMILES: NC(=O)c1cc(CCCN2CCCC2=O)cc2c1-c1ccccc1C2(O)C(F)(F)F] | $^1$H-NMR (DMSO-D$_6$) δ: 8.06 (1H, br s), 7.92 (1H, d, J = 7.7 Hz), 7.69 (1H, br s), 7.63 (1H, d, J = 7.2 Hz), 7.55 (1H, br s), 7.47-7.42 (1H, m), 7.38-7.34 (1H, m), 7.34 (1H, d, J = 1.6 Hz), 7.25 (1H, s), 3.34 (2H, t, J = 6.8 Hz), 3.28-3.20 (2H, m), 2.68-2.60 (2H, m), 2.23-2.17 (2H, m), 1.94-1.85 (2H, m), 1.85-1.75 (2H, m). |
| 656 | 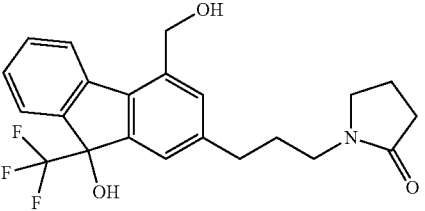 [SMILES: O=C1CCCN1CCCc1cc(CO)c2c(c1)C(O)(C(F)(F)F)c1ccccc1-2] | $^1$H-NMR (DMSO-D$_6$) δ: 7.77 (1H, d, J = 7.7 Hz), 7.64 (1H, d, J = 7.4 Hz), 7.52-7.47 (1H, m), 7.41 (1H, br s), 7.40 (1H, br s), 7.38-7.33 (1H, m), 7.15 (1H, s), 5.41 (1H, t, J = 5.3 Hz), 4.87-4.78 (2H, m), 3.34 (2H, t, J = 6.7 Hz), 3.24 (2H, t, J = 7.2 Hz), 2.65-2.61 (2H, m), 2.23-2.18 (2H, m), 1.94-1.86 (2H, m), 1.83-1.74 (2H, m). |
| 657 (optically active form) | 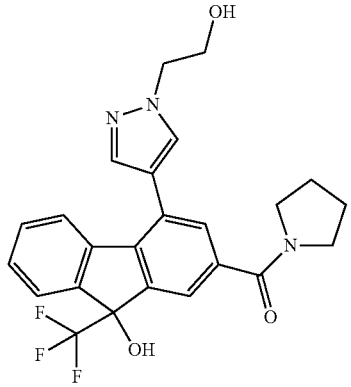 [SMILES: O=C(c1cc(-c2cnn(CCO)c2)c2c(c1)C(O)(C(F)(F)F)c1ccccc1-2)N1CCCC1] | $^1$H-NMR (DMSO-D$_6$) δ: 8.02 (1H, d, J = 0.7 Hz), 7.71-7.65 (2H, m), 7.67 (1H, d, J = 0.7 Hz), 7.48-7.31 (4H, m), 7.34 (1H, s), 4.97 (1H, t, J = 5.3 Hz), 4.26 (2H, t, J = 5.6 Hz), 3.83 (2H, dt, J = 5.3, 5.6 Hz), 3.52-3.42 (4H, m), 1.93-1.80 (4H, m). |

TABLE 1-96-continued

| compound No. | structural formula | NMR |
|---|---|---|
| 658 | | ¹H-NMR (DMSO-D₆) δ: 9.24 (1H, s), 9.23 (2H, br s), 8.23 (1H, br s), 8.09 (1H, br s), 8.03 (1H, d, J = 7.7 Hz), 7.97 (1H, d, J = 1.9 Hz), 7.86 (1H, br s), 7.71 (1H, d, J = 7.4 Hz), 7.55-7.50 (1H, m), 7.48-7.43 (1H, m), 7.45 (1H, s). |
| 659 (optically active form) | | ¹H-NMR (DMSO-D₆) δ: 8.31 (1H, s), 8.14 (1H, br s), 7.99 (1H, d, J = 0.5 Hz), 7.91 (1H, d, J = 7.4 Hz), 7.84 (1H, br s), 7.74 (1H, br s), 7.71 (1H, d, J = 1.6 Hz), 7.64 (1H, d, J = 7.4 Hz), 7.48-7.43 (1H, m), 7.40-7.34 (1H, m), 7.31 (1H, s), 3.94 (2H, s), 0.93 (9H, s). |

TABLE 1-97

| compound No. | structural formula | NMR |
|---|---|---|
| 660 (optically active form) | | ¹H-NMR (DMSO-D₆) δ: 8.25 (1H, d, J = 0.7 Hz), 7.93 (1H, d, J = 0.7 Hz), 7.80 (1H, d, J = 7.9 Hz), 7.76 (1H, d, J = 1.6 Hz), 7.74-7.72 (1H, m), 7.66 (1H, d, J = 7.4 Hz), 7.54-7.48 (1H, m), 7.40-7.34 (1H, m), 7.22 (1H, s), 5.46 (1H, br s), 4.92-4.83 (2H, m), 3.95 (2H, s), 0.94 (9H, s). |
| 661 | | ¹H-NMR (DMSO-D₆) δ: 8.18 (1H, s), 7.93 (1H, d, J = 0.7 Hz), 7.80 (1H, d, J = 7.7 Hz), 7.75 (1H, d, J = 1.4 Hz), 7.73-7.71 (1H, m), 7.66 (1H, d, J = 7.7 Hz), 7.54-7.48 (1H, m), 7.39-7.34 (1H, m), 7.23 (1H, s), 5.47 (1H, t, J = 5.4 Hz), 4.92-4.83 (2H, m), 4.76 (1H, s), 4.06 (2H, s), 1.10 (3H, s), 1.10 (3H, s). |
| 662 | | ¹H-NMR (DMSO-D₆) δ: 8.33 (1H, s), 8.13 (1H, br s), 7.98 (1H, s), 7.92 (1H, d, J = 7.7 Hz), 7.84 (1H, br s), 7.73 (1H, br s), 7.70 (1H, d, J = 1.8 Hz), 7.65 (1H, d, J = 7.5 Hz), 7.49-7.44 (1H, m), 7.40-7.35 (1H, m), 7.30 (1H, s), 3.98 (2H, d, J = 7.1 Hz), 1.92-1.80 (1H, m), 1.72-1.50 (5H, m), 1.26-1.10 (3H, m), 1.03-0.92 (2H, m). |

TABLE 1-97-continued
| compound No. | structural formula | NMR |
|---|---|---|
| 663 (optically active form) | 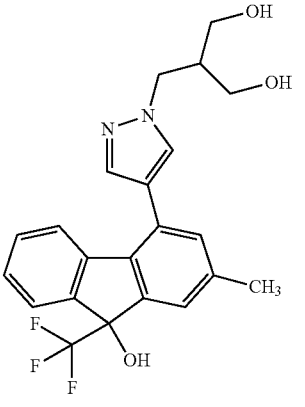 [SMILES: Cc1cc(-c2cnn(CC(CO)CO)c2)c2c(c1)C(O)(C(F)(F)F)c1ccccc1-2] | $^1$H-NMR (DMSO-D$_6$) δ: 7.92 (1H, s), 7.63-7.59 (1H, m), 7.60 (1H, d, J = 0.7 Hz), 7.44-7.41 (1H, m), 7.33-7.25 (3H, m), 7.16 (1H, s), 7.13-7.11 (1H, m), 4.59 (2H, t, J = 4.9 Hz), 4.22 (2H, d, J = 7.1 Hz), 3.48-3.40 (4H, m), 2.39 (3H, s), 2.19-2.13 (1H, m). |
| 664 (optically active form) | 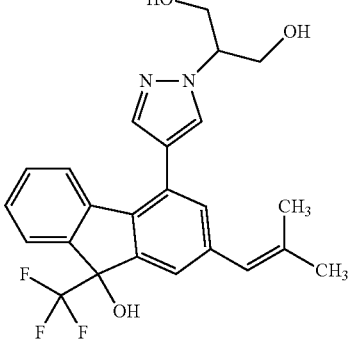 | $^1$H-NMR (CDCl$_3$) δ: 7.72-7.68 (1H, m), 7.66-7.64 (1H, m), 7.59-7.55 (2H, m), 7.31-7.21 (3H, m), 7.15-7.13 (1H, m), 6.32-6.29 (1H, m), 4.37-4.31 (1H, m), 4.21-4.10 (4H, m), 3.23-3.07 (1H, m), 2.90-2.71 (2H, m), 1.95 (3H, d, J = 1.3 Hz), 1.93 (3H, d, J = 1.3 Hz). |
| 665 (optically active form) | 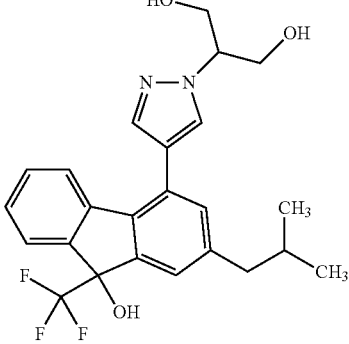 | $^1$H-NMR (DMSO-D$_6$) δ: 7.94 (1H, d, J = 0.7 Hz), 7.63-7.59 (2H, m), 7.61 (1H, d, J = 0.7 Hz), 7.41-7.37 (2H, m), 7.32-7.22 (2H, m), 7.15 (1H, s), 7.10 (1H, d, J = 1.5 Hz), 4.97-4.92 (2H, m), 4.39-4.32 (1H, m), 3.86-3.79 (4H, m), 2.58-2.48 (2H, m), 1.92-1.82 (1H, m), 0.93 (3H, d, J = 6.6 Hz), 0.91 (6H, d, J = 6.6 Hz). |

TABLE 1-98

| compound No. | structural formula | NMR |
|---|---|---|
| 666 | | ¹H-NMR (DMSO-D₆) δ: 7.94 (1H, d, J = 0.7 Hz), 7.63-7.59 (2H, m), 7.61 (1H, d, J = 0.7 Hz), 7.44-7.41 (1H, m), 7.39-7.35 (1H, m), 7.32-7.22 (2H, m), 7.16 (1H, s), 7.14 (1H, d, J = 1.62 Hz), 4.98-4.94 (2H, m), 4.38-4.32 (1H, m), 3.86-3.77 (4H, m), 2.65-2.59 (2H, m), 1.53-1.47 (2H, m), 0.96 (9H, s). |
| 667 (optically active form) | | ¹H-NMR (DMSO-D₆) δ: 8.33 (1H, d, J = 0.7 Hz), 8.13 (1H, br s), 7.98 (1H, d, J = 0.9 Hz), 7.92 (1H, d, J = 7.5 Hz), 7.84 (1H, br s), 7.73 (1H, br s), 7.70 (1H, d, J = 1.8 Hz), 7.65 (1H, d, J = 7.3 Hz), 7.49-7.44 (1H, m), 7.40-7.35 (1H, m), 7.30 (1H, s), 3.98 (2H, d, J = 7.3 Hz), 1.92-1.80 (1H, m), 1.73-1.50 (5H, m), 1.26-1.10 (3H, m), 1.03-0.91 (2H, m). |
| 668 (optically active form) | | ¹H-NMR (DMSO-D₆) δ: 8.27 (1H, s), 7.92 (1H, s), 7.80 (1H, d, J = 7.9 Hz), 7.74 (1H, s), 7.72 (1H, s), 7.66 (1H, d, J = 7.4 Hz), 7.53-7.48 (1H, m), 7.40-7.34 (1H, m), 7.21 (1H, s), 5.46 (1H, t, J = 5.3 Hz), 4.91-4.82 (2H, m), 3.98 (2H, d, J = 7.2 Hz), 1.91-1.79 (1H, m), 1.72-1.50 (5H, m), 1.26-1.11 (3H, m), 1.03-0.92 (2H, m). |
| 669 (optically active form) | | ¹H-NMR (DMSO-D₆) δ: 7.94 (1H, d, J = 0.7 Hz), 7.63-7.59 (1H, m), 7.61 (1H, d, J = 0.7 Hz), 7.45-7.41 (1H, m), 7.39-7.35 (1H, m), 7.32-7.22 (2H, m), 7.16 (1H, s), 7.14 (1H, d, J = 1.6 Hz), 4.98-4.93 (2H, m), 4.38-4.32 (1H, m), 3.86-3.78 (4H, m), 2.65-2.59 (2H, m), 1.54-1.47 (2H, m), 0.96 (9H, s). |

TABLE 1-99

| compound No. | structural formula | NMR |
|---|---|---|
| 670 | | $^1$H-NMR (DMSO-D$_6$) δ: 12.17 (1H, br s), 7.97 (1H, s), 7.65-7.58 (2H, m), 7.43 (1H, s), 7.32-7.22 (3H, m), 7.17 (1H, s), 7.13-7.12 (1H, m), 4.24 (2H, t, J = 6.7 Hz), 2.38 (3H, s), 2.27 (2H, t, J = 7.4 Hz), 2.13-2.04 (2H, m). |
| 671 | | $^1$H-NMR (DMSO-D$_6$) δ: 8.14-8.10 (1H, m), 8.07-8.01 (3H, m), 7.73-7.69 (1H, m), 7.63-7.57 (1H, m), 7.56-7.49 (2H, m). |
| 672 (optically active form) | | $^1$H-NMR (DMSO-D$_6$) δ: 8.03 (1H, d, J = 0.4 Hz), 7.67-7.63 (1H, m), 7.66 (1H, d, J = 0.9 Hz), 7.42-7.38 (1H, m), 7.40 (1H, s), 7.36-7.32 (3H, m), 7.18-7.14 (1H, m), 3.96 (3H, s). |
| 673 (optically active form) | | $^1$H-NMR (DMSO-D$_6$) δ: 8.05 (1H, d, J = 0.7 Hz), 7.68 (1H, d, J = 0.7 Hz), 7.65-7.62 (1H, m), 7.44-7.42 (1H, m), 7.40-7.36 (2H, m), 7.35-7.26 (2H, m), 7.21-7.17 (1H, m), 4.98-4.93 (2H, m), 3.84-3.79 (2H, m), 3.76-3.70 (2H, m), 1.52 (3H, s). |

TABLE 1-99-continued
| compound No. | structural formula | NMR |
|---|---|---|
| 674 (optically active form) | 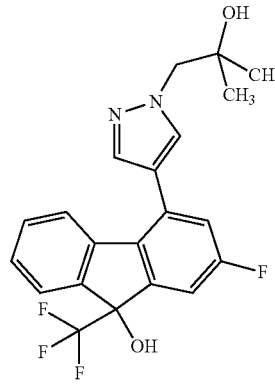 | $^1$H-NMR (DMSO-D$_6$) δ: 7.97 (1H, s), 7.67 (1H, s), 7.66-7.63 (1H, m), 7.44-7.38 (3H, m), 7.36-7.27 (2H, m), 7.21-7.17 (1H, m), 4.79 (1H, s), 4.13 (2H, s), 1.15 (6H, s). |
| 675 (optically active form) | 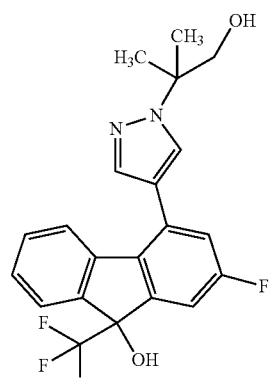 | $^1$H-NMR (DMSO-D$_6$) δ: 8.08 (1H, d, J = 0.5 Hz), 7.68 (1H, s), 7.66-7.62 (1H, m), 7.41-7.36 (3H, m), 7.36-7.28 (2H, m), 7.23-7.18 (1H, m), 5.08 (1H, t, J = 5.6 Hz), 3.66 (2H, d, J = 5.6 Hz), 1.55 (6H, s). |
TABLE 1-100
| compound No. | structural formula | NMR |
|---|---|---|
| 676 (optically active form) | 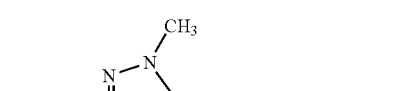 | $^1$H-NMR (CDCl$_3$) δ: 7.70-7.66 (1H, m), 7.54-7.48 (2H, m), 7.32-7.21 (4H, m), 7.11-7.09 (1H, m), 4.00 (3H, s), 2.80-2.74 (2H, m), 1.86-1.80 (2H, m), 1.31 (6H, s). |

TABLE 1-100-continued

| compound No. | structural formula | NMR |
|---|---|---|
| 677 (optically active form) | 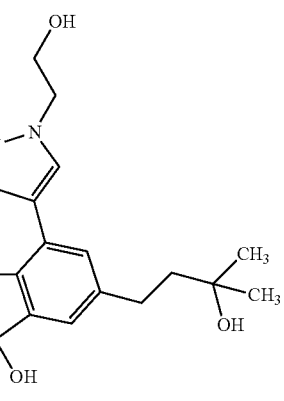 | $^1$H-NMR (CDCl$_3$) δ: 7.71-7.67 (1H, m), 7.59-7.57 (2H, m), 7.54-7.52 (1H, m), 7.30-7.23 (3H, m), 7.13-7.11 (1H, m), 4.37-4.32 (2H, m), 4.13-4.07 (2H, m), 3.05 (1H, s), 3.00-2.95 (1H, m), 2.82-2.74 (2H, m), 1.87-1.80 (2H, m), 1.31 (7H, s). |
| 678 (optically active form) | 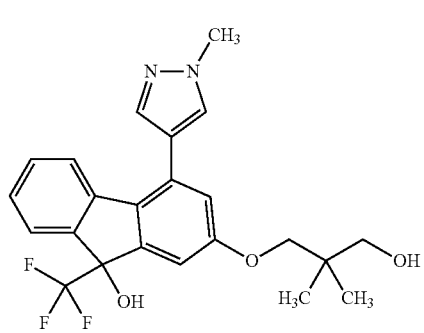 [SMILES: Cn1cc(-c2cc(OCC(C)(C)CO)cc3c2-c2ccccc2C3(O)C(F)(F)F)cn1] | $^1$H-NMR (DMSO-D$_6$) δ: 7.98 (1H, s), 7.63-7.57 (1H, m), 7.61 (1H, s), 7.31-7.20 (3H, m), 7.22 (1H, s), 7.16-7.11 (1H, m), 6.82-6.80 (1H, m), 4.64 (1H, t, J = 5.4 Hz), 3.95 (3H, s), 3.77 (2H, s), 3.29 (2H, d, J = 5.3 Hz), 0.94 (6H, s). |
| 679 (optically active form) | 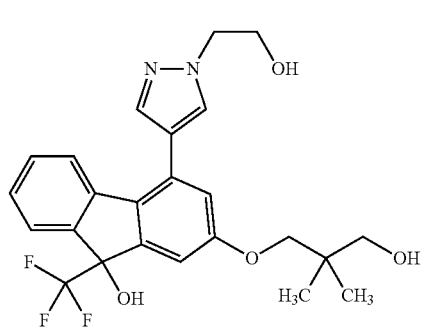 [SMILES: CC(C)(CO)COc1cc(-c2cnn(CCO)c2)c2c(c1)C(O)(C(F)(F)F)c1ccccc1-2] | $^1$H-NMR (DMSO-D$_6$) δ: 7.97 (1H, s), 7.63 (1H, s), 7.61-7.57 (1H, m), 7.33-7.30 (1H, m), 7.27-7.24 (2H, m), 7.22 (1H, s), 7.15-7.13 (1H, m), 6.83-6.81 (1H, m), 4.97 (1H, t, J = 5.3 Hz), 4.65 (1H, t, J = 5.4 Hz), 4.25 (2H, t, J = 5.6 Hz), 3.85-3.80 (2H, m), 3.77 (2H, s), 3.29 (2H, d, J = 5.3 Hz), 0.95 (6H, s). |
| 680 (optically active form) | 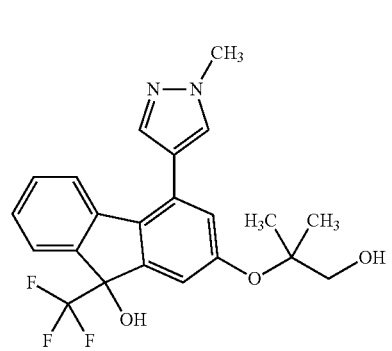 [SMILES: Cn1cc(-c2cc(OC(C)(C)CO)cc3c2-c2ccccc2C3(O)C(F)(F)F)cn1] | $^1$H-NMR (DMSO-D$_6$) δ: 7.98 (1H, s), 7.63-7.59 (2H, m), 7.32-7.26 (3H, m), 7.26-7.24 (1H, m), 7.23 (1H, s), 6.91-6.89 (1H, m), 4.96 (1H, t, J = 5.7 Hz), 3.95 (3H, s), 3.41 (2H, d, J = 5.6 Hz), 1.25 (3H, s), 1.24 (3H, s). |

TABLE 1-100-continued
| compound No. | structural formula | NMR |
|---|---|---|
| 681 (optically active form) | 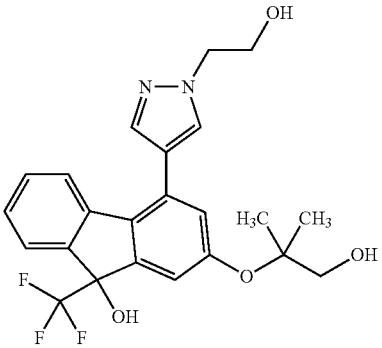 [SMILES: CC(C)(CO)Oc1cc(-c2cnn(CCO)c2)c2c(c1)C(O)(C(F)(F)F)c1ccccc1-2] | $^1$H-NMR (CDCl$_3$) δ: 7.71-7.67 (1H, m), 7.58 (2H, s), 7.34-7.32 (1H, m), 7.30-7.22 (3H, m), 6.90-6.89 (1H, m), 4.36-4.33 (2H, m), 4.13-4.09 (2H, m), 3.65-3.61 (2H, m), 3.14 (1H, s), 3.03-2.98 (1H, m), 2.18-2.13 (1H, m), 1.36 (3H, s), 1.33 (3H, s). |
TABLE 1-101
| compound No. | structural formula | NMR |
|---|---|---|
| 682 (optically active form) | 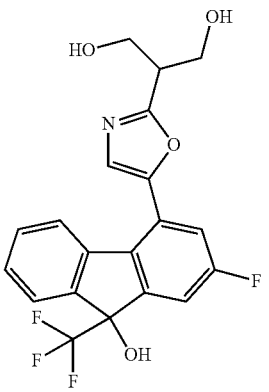 [SMILES: OCC(CO)c1ncc(-c2cc(F)cc3c2-c2ccccc2C3(O)C(F)(F)F)o1] | $^1$H-NMR (DMSO-D$_6$) δ: 7.70-7.65 (1H, m), 7.57-7.53 (1H, m), 7.53-7.48 (3H, m), 7.46-7.38 (3H, m), 4.94-4.89 (2H, m), 3.83-3.74 (4H, m), 3.23-3.19 (1H, m). |
| 683 (optically active form) | 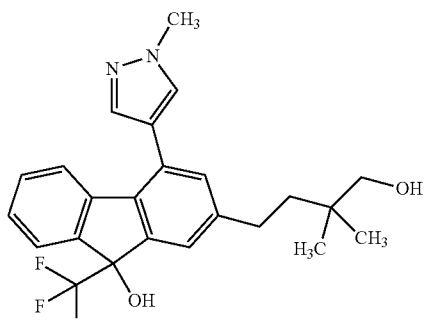 | $^1$H-NMR (DMSO-D$_6$) δ: 7.96-7.94 (1H, m), 7.64-7.59 (1H, m), 7.58 (1H, d, J = 0.9 Hz), 7.45-7.42 (1H, m), 7.32-7.27 (3H, m), 7.16 (1H, s), 7.12-7.09 (1H, m), 4.53 (1H, t, J = 5.4 Hz), 3.95 (3H, s), 3.17 (2H, d, J = 5.5 Hz), 2.63-2.55 (2H, m), 1.53-1.44 (2H, m), 0.88 (6H, s). |

TABLE 1-101-continued
| compound No. | structural formula | NMR |
|---|---|---|
| 684 (optically active form) | 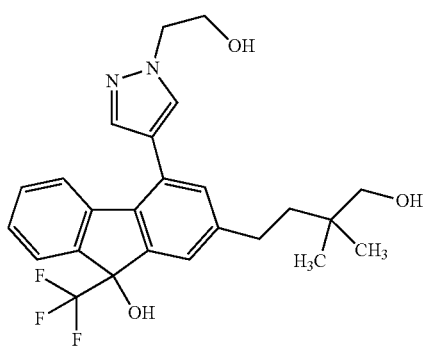 [SMILES: CC(C)(CO)CCc1cc(-c2cnn(CCO)c2)c2c(c1)C(O)(C(F)(F)F)c1ccccc1-2] | $^1$H-NMR (DMSO-D$_6$) δ: 7.94 (1H, d, J = 0.7 Hz), 7.64-7.59 (1H, m), 7.61 (1H, d, J = 0.9 Hz), 7.45-7.42 (1H, m), 7.37-7.24 (3H, m), 7.16 (1H, s), 7.13-7.10 (1H, m), 4.96 (1H, d, J = 5.2 Hz), 4.53 (1H, t, J = 5.4 Hz), 4.25 (2H, t, J = 5.6 Hz), 3.85-3.79 (2H, m), 3.17 (2H, d, J = 5.3 Hz), 2.63-2.56 (2H, m), 1.54-1.45 (2H, m), 0.88 (6H, s). |
| 685 (optically active form) | 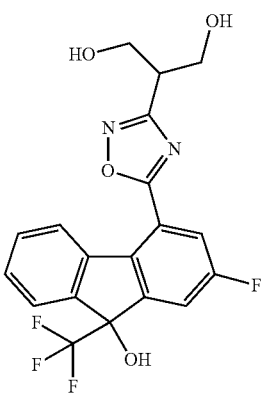 [SMILES: OCC(CO)c1noc(-c2cc(F)cc3c2-c2ccccc2C3(O)C(F)(F)F)n1] | $^1$H-NMR (DMSO-D$_6$) δ: 8.11-8.05 (1H, m), 7.91-7.86 (1H, m), 7.83-7.78 (1H, m), 7.75-7.70 (1H, m), 7.63 (1H, s), 7.51-7.45 (2H, m), 4.91-4.86 (2H, m), 3.89-3.75 (4H, m), 3.31-3.23 (1H, m). |
| 686 (optically active form) | 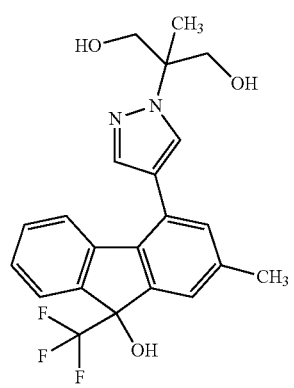 [SMILES: Cc1cc(-c2cnn(C(C)(CO)CO)c2)c2c(c1)C(O)(C(F)(F)F)c1ccccc1-2] | $^1$H-NMR (DMSO-D$_6$) δ: 7.96 (1H, s), 7.64-7.58 (1H, m), 7.61 (1H, s), 7.44-7.35 (2H, m), 7.33-7.22 (2H, m), 7.18-7.13 (2H, m), 4.96 (2H, t, J = 5.4 Hz), 3.85-3.78 (2H, m), 3.77-3.70 (2H, m), 2.39 (3H, s), 1.52 (3H, s). |

TABLE 1-102

| compound No. | structural formula | NMR |
|---|---|---|
| 687 (optically active form) | 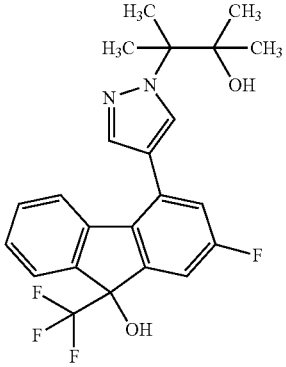 [SMILES: CC(C)(O)C(C)(C)n1cc(-c2cc(F)cc3c2-c2ccccc2C3(O)C(F)(F)F)cn1] | $^1$H-NMR (DMSO-D$_6$) δ: 8.10 (1H, d, J = 0.7 Hz), 7.67 (1H, d, J = 0.7 Hz), 7.66-7.62 (1H, m), 7.47-7.44 (1H, m), 7.40-7.37 (2H, m), 7.36-7.28 (2H, m), 7.22-7.18 (1H, m), 4.78 (1H, s), 1.63 (3H, s), 1.63 (3H, s), 1.08 (3H, s), 1.07 (3H, s). |
| 688 (optically active form) | 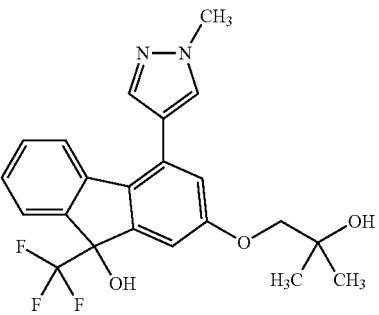 [SMILES: Cn1cc(-c2cc(OCC(C)(C)O)cc3c2-c2ccccc2C3(O)C(F)(F)F)cn1] | $^1$H-NMR (DMSO-D$_6$) δ: 7.98 (1H, s), 7.63-7.57 (1H, m), 7.61 (1H, s), 7.30-7.24 (3H, m), 7.22 (1H, s), 7.17-7.14 (1H, m), 6.84-6.80 (1H, m), 4.66 (1H, br s), 3.95 (3H, s), 3.78 (2H, s), 1.22 (3H, s), 1.22 (3H, s). |
| 689 (optically active form) | 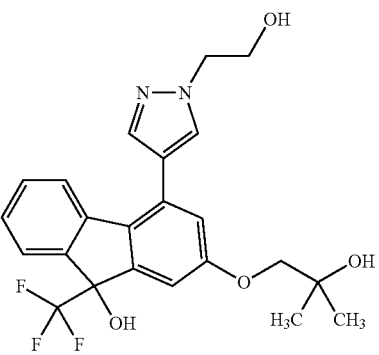 [SMILES: CC(C)(O)COc1cc(-c2cnn(CCO)c2)c2c(c1)C(O)(C(F)(F)F)c1ccccc1-2] | $^1$H-NMR (DMSO-D$_6$) δ: 7.97 (1H, d, J = 0.7 Hz), 7.64 (1H, d, J = 0.7 Hz), 7.61-7.56 (1H, m), 7.34-7.30 (1H, m), 7.29-7.23 (2H, m), 7.21 (1H, s), 7.17-7.13 (1H, m), 6.85-6.82 (1H, m), 4.96 (1H, t, J = 5.3 Hz), 4.65 (1H, s), 4.25 (2H, t, J = 5.6 Hz), 3.84-3.80 (2H, m), 3.79 (2H, s), 1.22 (3H, s), 1.22 (3H, s). |
| 690 (optically active form) | 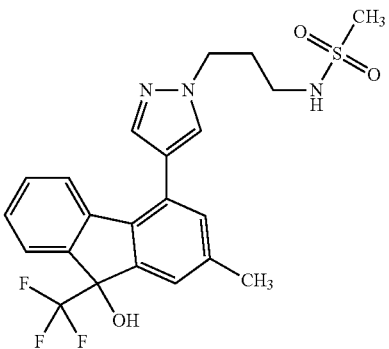 [SMILES: Cc1cc(-c2cnn(CCCNS(C)(=O)=O)c2)c2c(c1)C(O)(C(F)(F)F)c1ccccc1-2] | $^1$H-NMR (DMSO-D$_6$) δ: 7.98 (1H, s), 7.64-7.59 (2H, m), 7.44-7.40 (1H, m), 7.33-7.21 (3H, m), 7.17 (1H, s), 7.15-7.10 (2H, m), 4.27 (2H, t, J = 6.5 Hz), 3.02-2.95 (2H, m), 2.92-2.89 (3H, m), 2.37 (3H, s), 2.10-2.01 (2H, m). |

TABLE 1-102-continued
| compound No. | structural formula | NMR |
|---|---|---|
| 691 (optically active form) | 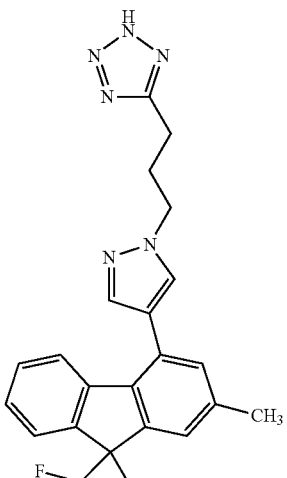 | $^1$H-NMR (DMSO-D$_6$) δ: 16.09 (1H, br s), 8.01 (1H, d, J = 0.7 Hz), 7.65-7.60 (1H, m), 7.63 (1H, d, J = 0.7 Hz), 7.45-7.42 (1H, m), 7.33-7.23 (3H, m), 7.20-7.16 (1H, m), 7.15-7.11 (1H, m), 4.32 (2H, t, J = 6.6 Hz), 2.93 (2H, t, J = 7.7 Hz), 2.39 (3H, s), 2.36-2.27 (2H, m). |
TABLE 1-103
| compound No. | structural formula | NMR |
|---|---|---|
| 692 (optically active form) | 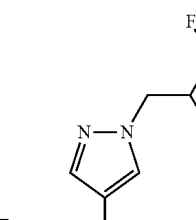 | $^1$H-NMR (DMSO-D$_6$) δ: 8.13-8.10 (1H, m), 7.77-7.73 (1H, m), 7.67-7.63 (1H, m), 7.44-7.40 (2H, m), 7.38-7.28 (3H, m), 7.18-7.14 (1H, m), 6.83-6.78 (1H, m), 4.61-4.48 (2H, m), 4.42-4.31 (1H, m). |
| 693 (optically active form) | 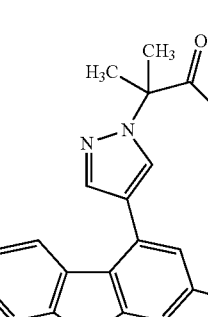 | $^1$H-NMR (DMSO-D$_6$) δ: 8.17 (1H, s), 7.72 (1H, s), 7.66-7.62 (1H, m), 7.46-7.38 (3H, m), 7.36-7.27 (3H, m), 7.25-7.20 (1H, m), 7.02 (1H, br s), 1.80 (3H, s), 1.79 (3H, s). |

TABLE 1-103-continued
| compound No. | structural formula | NMR |
|---|---|---|
| 694 (optically active form) | 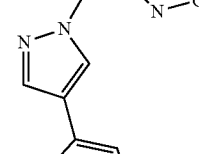 | ¹H-NMR (DMSO-D$_6$) δ: 8.16 (1H, d, J = 0.7 Hz), 7.73 (1H, d, J = 0.4 Hz), 7.66-7.63 (1H, m), 7.52-7.47 (1H, m), 7.43-7.38 (3H, m), 7.36-7.29 (2H, m), 7.24-7.20 (1H, m), 2.63 (3H, d, J = 4.6 Hz), 1.79 (3H, s), 1.79 (3H, s). |
| 695 (optically active form) | 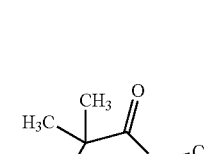 | ¹H-NMR (DMSO-D$_6$) δ: 8.23 (1H, s), 7.80 (1H, s), 7.68-7.63 (1H, m), 7.44-7.40 (2H, m), 7.37-7.31 (3H, m), 7.25-7.21 (1H, m), 3.00-2.20 (6H, m), 1.77 (3H, s), 1.77 (3H, s). |
| 696 (optically active form) | 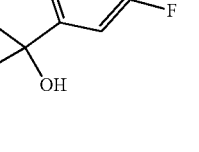 | ¹H-NMR (CDCl$_3$) δ: 7.69-7.65 (1H, m), 7.54 (1H, s), 7.51-7.49 (2H, m), 7.28-7.19 (3H, m), 7.10-7.07 (1H, m), 4.34-4.29 (2H, m), 4.31 (3H, s), 3.20 (1H, s), 2.94 (2H, t, J = 7.2 Hz), 2.46-2.38 (2H, m), 2.42 (3H, s). |

TABLE 1-104
| compound No. | structural formula | NMR |
|---|---|---|
| 697 (optically active form) | 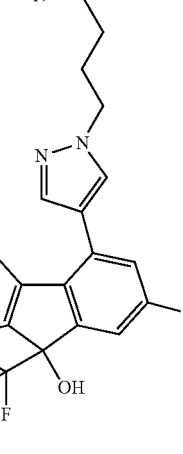 | $^1$H-NMR (CDCl$_3$) δ: 7.69-7.66 (1H, m), 7.63 (1H, s), 7.55 (1H, s), 7.51-7.49 (1H, m), 7.31-7.20 (3H, m), 7.09-7.08 (1H, m), 4.40 (2H, t, J = 6.4 Hz), 4.01 (3H, s), 2.93 (2H, t, J = 7.1 Hz), 2.78 (1H, s), 2.58-2.51 (2H, m), 2.43 (3H, s). |
| 698 (optically active form) | 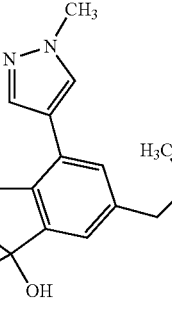 | $^1$H-NMR (CDCl$_3$) δ: 7.72-7.67 (1H, m), 7.56-7.52 (1H, m), 7.48 (1H, s), 7.45 (1H, s), 7.33-7.21 (3H, m), 7.11 (1H, s), 3.99 (3H, s), 3.38 (1H, s), 2.84 (1H, d, J = 13.0 Hz), 2.80 (1H, d, J = 13.2 Hz), 1.43 (1H, br s), 1.28 (3H, s), 1.25 (3H, s). |
| 699 (optically active form) | 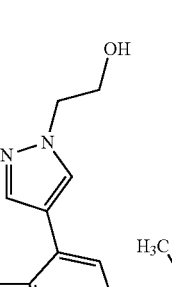 | $^1$H-NMR (CDCl$_3$) δ: 7.71-7.67 (1H, m), 7.56 (1H, s), 7.53 (1H, s), 7.47-7.44 (1H, m), 7.31-7.20 (3H, m), 7.04-7.02 (1H, m), 4.35-4.31 (2H, m), 4.11-4.07 (2H, m), 3.10 (1H, br s), 2.96-2.91 (1H, m), 2.56 (2H, s), 0.95 (9H, s). |

TABLE 1-104-continued

| compound No. | structural formula | NMR |
|---|---|---|
| 700 (optically active form) | | $^1$H-NMR (CDCl$_3$) δ: 7.94-7.92 (1H, m), 7.77-7.72 (1H, m), 7.64 (1H, s), 7.63 (1H, s), 7.59-7.57 (1H, m), 7.44-7.30 (3H, m), 4.40-4.34 (2H, m), 4.15-4.08 (2H, m), 3.19 (1H, br s), 2.83 (1H, t, J = 5.8 Hz). |
| 701 (optically active form) | | $^1$H-NMR (CDCl$_3$) δ: 8.24-8.22 (1H, m), 7.89-7.86 (1H, m), 7.77-7.73 (1H, m), 7.63 (2H, s), 7.41-7.36 (2H, m), 7.32-7.27 (1H, m), 4.38-4.35 (2H, m), 4.14-4.09 (2H, m), 3.23 (1H, br s), 2.94 (1H, t, J = 5.9 Hz), 2.65 (3H, s). |

TABLE 1-105

| compound No. | structural formula | NMR |
|---|---|---|
| 702 (optically active form) | | $^1$H-NMR (DMSO-D$_6$) δ: 7.98 (1H, d, J = 0.7 Hz), 7.65-7.58 (2H, m), 7.62 (1H, d, J = 0.7 Hz), 7.42-7.24 (5H, m), 7.19 (1H, s), 4.98-4.92 (2H, m), 3.84-3.79 (2H, m), 3.77-3.70 (2H, m), 1.52 (3H, s). |

TABLE 1-105-continued
| compound No. | structural formula | NMR |
|---|---|---|
| 703 (optically active form) | 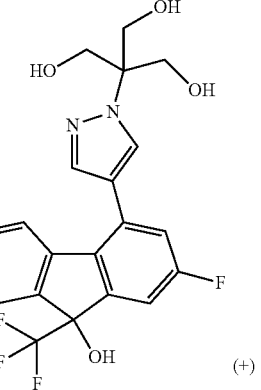 (+) | $^1$H-NMR (DMSO-D$_6$) δ: 8.05 (1H, d, J = 0.7 Hz), 7.70 (1H, d, J = 0.7 Hz), 7.65-7.61 (1H, m), 7.51-7.47 (1H, m), 7.40-7.36 (2H, m), 7.35-7.30 (1H, m), 7.29-7.24 (1H, m), 7.21-7.17 (1H, m), 4.83 (3H, t, J = 5.4 Hz), 3.90 (6H, d, J = 5.6 Hz). |
| 704 (optically active form) | 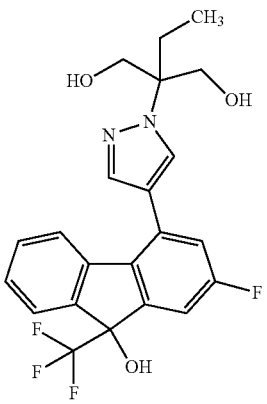 [SMILES: CCC(CO)(CO)n1cc(-c2cc(F)cc3c2-c2ccccc2C3(O)C(F)(F)F)cn1] | $^1$H-NMR (DMSO-D$_6$) δ: 8.04 (1H, d, J = 0.7 Hz), 7.69 (1H, d, J = 0.7 Hz), 7.66-7.62 (1H, m), 7.42-7.37 (2H, m), 7.38 (1H, s), 7.36-7.31 (1H, m), 7.29-7.25 (1H, m), 7.21-7.16 (1H, m), 4.90-4.86 (2H, m), 3.91-3.81 (4H, m), 1.92 (2H, q, J = 7.4 Hz), 0.75 (3H, t, J = 7.5 Hz). |
| 705 (optically active form) | 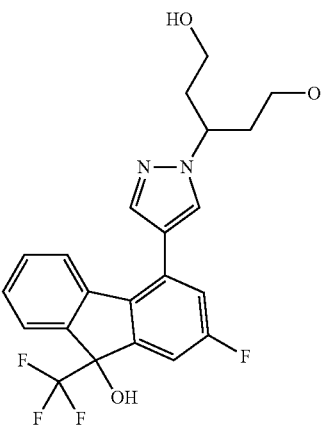 | $^1$H-NMR (DMSO-D$_6$) δ: 8.01 (1H, s), 7.68 (1H, s), 7.66-7.61 (1H, m), 7.45-7.37 (2H, m), 7.36-7.27 (3H, m), 7.20-7.15 (1H, m), 4.66-4.52 (3H, m), 3.42-3.29 (2H, m), 3.27-3.15 (2H, m), 2.13-2.01 (2H, m), 1.99-1.86 (2H, m). |

TABLE 1-105-continued

| compound No. | structural formula | NMR |
|---|---|---|
| 706 (optically active form) | (structure) | $^1$H-NMR (DMSO-D$_6$) δ: 7.98 (1H, d, J = 0.7 Hz), 7.65-7.59 (2H, m), 7.64 (1H, s), 7.49-7.46 (1H, m), 7.41-7.36 (1H, m), 7.35-7.30 (2H, m), 7.28-7.23 (1H, m), 7.19 (1H, s), 4.82 (3H, t, J = 5.4 Hz), 3.92 (6H, t, J = 5.5 Hz). |

TABLE 1-106

| compound No. | structural formula | NMR |
|---|---|---|
| 707 (optically active form) | (structure) (+) | $^1$H-NMR (DMSO-D$_6$) δ: 7.96 (1H, d, J = 0.7 Hz), 7.63-7.59 (1H, m), 7.62 (1H, d, J = 0.7 Hz), 7.46-7.40 (2H, m), 7.31-7.21 (2H, m), 7.14 (2H, s), 4.82 (3H, t, J = 5.6 Hz), 3.91 (6H, d, J = 5.6 Hz), 2.39 (3H, s). |

Among these compounds, compound Nos. 42-44, 56, 57, 72, 73 and 143 are Reference Examples.

Among the above-mentioned optically active compounds, the structural formulas of the compounds having a specified absolute configuration are shown in the following Table 2-1 to 2-11.

TABLE 2-1

| compound No. | structural formula (absolute configuration) |
|---|---|
| 520 | (structure) |

TABLE 2-1-continued

| compound No. | structural formula (absolute configuration) |
|---|---|
| 526 | (structure) |
| 529 | (structure) |
| 531 | (structure) |

TABLE 2-1-continued
| compound No. | structural formula (absolute configuration) |
|---|---|
| 532 | 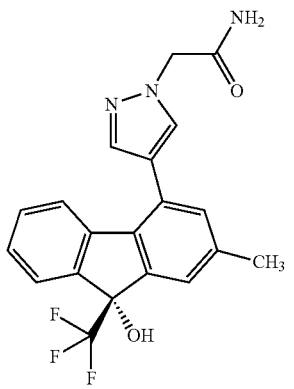 [SMILES: Cc1cc(-c2cnn(CC(N)=O)c2)c2c(c1)[C@@](O)(C(F)(F)F)c1ccccc1-2] |
TABLE 2-2
| compound No. | structural formula (absolute configuration) |
|---|---|
| 533 | 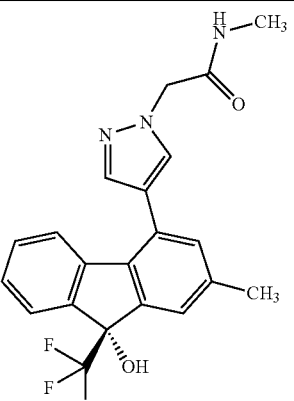 |
| 534 | 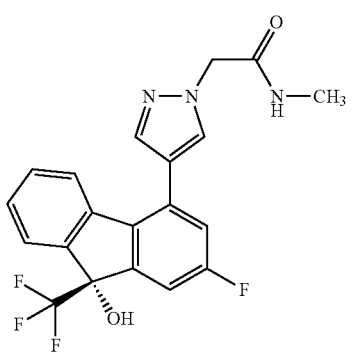 [SMILES: CNC(=O)Cn1cc(-c2cc(F)cc3c2-c2ccccc2[C@]3(O)C(F)(F)F)cn1] |
TABLE 2-2-continued
| compound No. | structural formula (absolute configuration) |
|---|---|
| 537 | 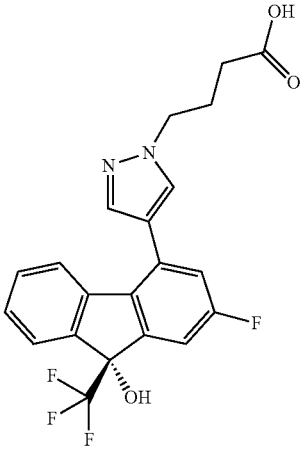 [SMILES: O=C(O)CCCn1cc(-c2cc(F)cc3c2-c2ccccc2[C@]3(O)C(F)(F)F)cn1] |
| 538 | 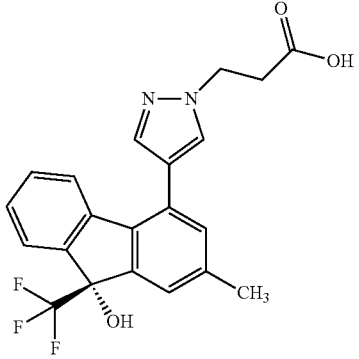 [SMILES: Cc1cc(-c2cnn(CCC(=O)O)c2)c2c(c1)[C@@](O)(C(F)(F)F)c1ccccc1-2] |
| 539 | 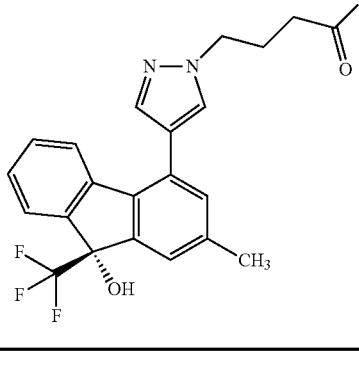 |

TABLE 2-3
| compound No. | structural formula (absolute configuration) |
|---|---|
| 543 | 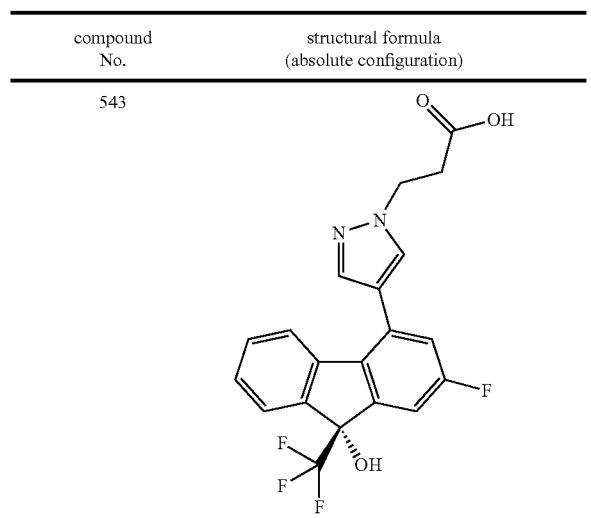 |
| 544 | |
| 545 | |
TABLE 2-3-continued
| compound No. | structural formula (absolute configuration) |
|---|---|
| 546 | 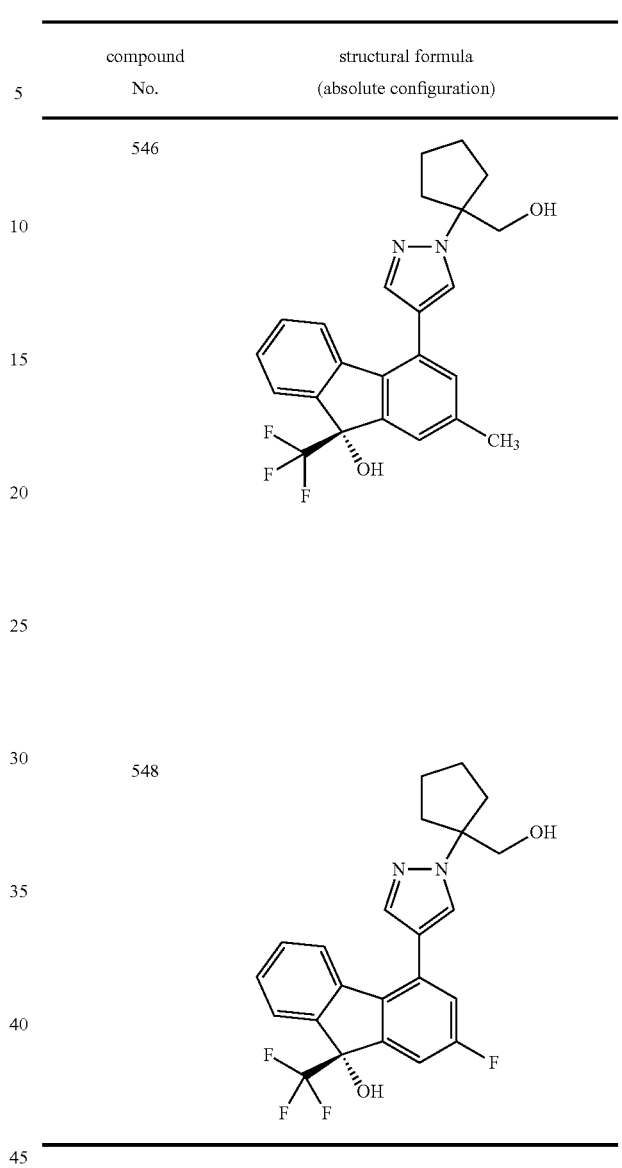 |
| 548 | |
TABLE 2-4
| compound No. | structural formula (absolute configuration) |
|---|---|
| 549 | 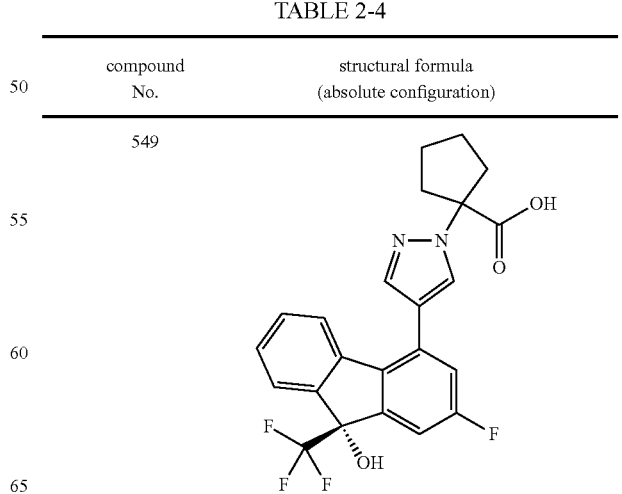 |

TABLE 2-4-continued

| compound No. | structural formula (absolute configuration) |
|---|---|
| 550 | |
| 551 | |
| 565 | |
| 566 | |

TABLE 2-5

| compound No. | structural formula (absolute configuration) |
|---|---|
| 574 | |
| 575 | |
| 576 | |
| 595 | |

TABLE 2-5-continued

| compound No. | structural formula (absolute configuration) |
|---|---|
| 605 | (structure) |

TABLE 2-6

| compound No. | structural formula (absolute configuration) |
|---|---|
| 606 | (structure) |
| 607 | (structure) |

TABLE 2-6-continued

| compound No. | structural formula (absolute configuration) |
|---|---|
| 610 | (structure) |
| 663 | (structure) |

TABLE 2-7

| compound No. | structural formula (absolute configuration) |
|---|---|
| 670 | (structure) |

TABLE 2-7-continued

| compound No. | structural formula (absolute configuration) |
|---|---|
| 672 | |
| 673 | |
| 674 | |
| 675 | |

TABLE 2-8

| compound No. | structural formula (absolute configuration) |
|---|---|
| 682 | |
| 685 | |
| 686 | |
| 687 | |

TABLE 2-8-continued
| compound No. | structural formula (absolute configuration) |
|---|---|
| 690 | 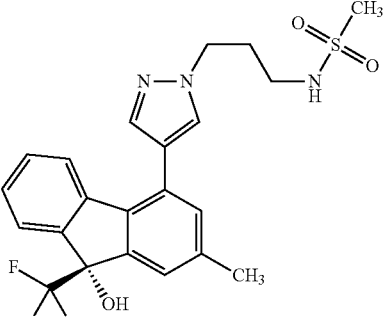 |
TABLE 2-9
| compound No. | structural formula (absolute configuration) |
|---|---|
| 691 | 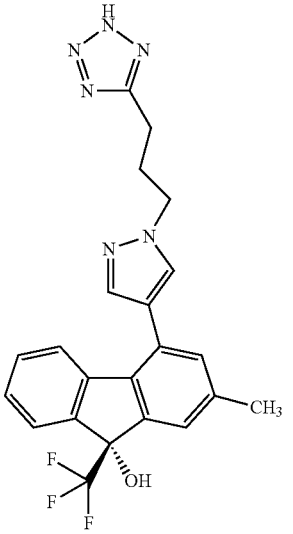 [SMILES: Cc1cc(-c2cnn(CCCc3nn[nH]n3)c2)c2c(c1)[C@@](O)(C(F)(F)F)c1ccccc1-2] |
| 692 | 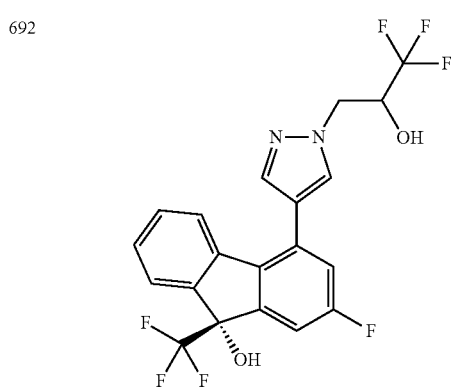 |
TABLE 2-9-continued
| compound No. | structural formula (absolute configuration) |
|---|---|
| 693 | 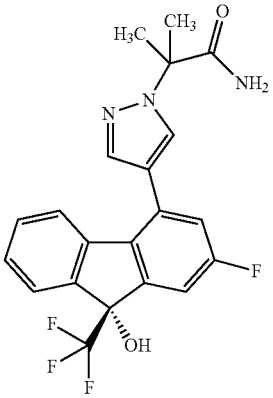 [SMILES: CC(C)(C(N)=O)n1cc(-c2cc(F)cc3c2-c2ccccc2[C@]3(O)C(F)(F)F)cn1] |
| 694 | 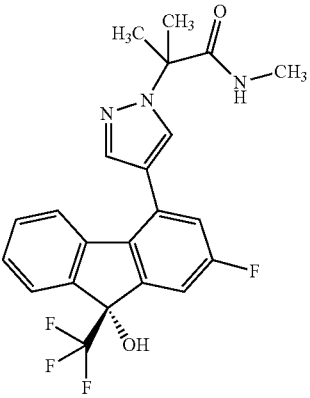 [SMILES: CNC(=O)C(C)(C)n1cc(-c2cc(F)cc3c2-c2ccccc2[C@]3(O)C(F)(F)F)cn1] |
TABLE 2-10
| compound No. | structural formula (absolute configuration) |
|---|---|
| 695 | 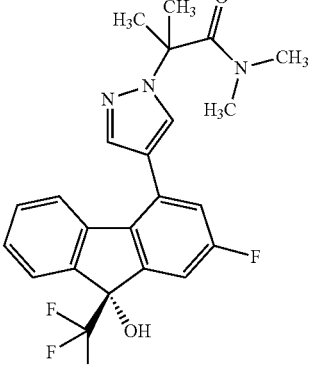 |

463
TABLE 2-10-continued
| compound No. | structural formula (absolute configuration) |
|---|---|
| 696 | 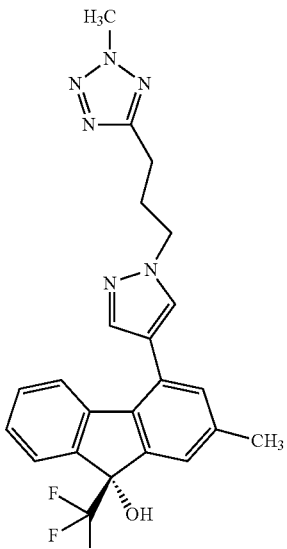 |
| 697 | 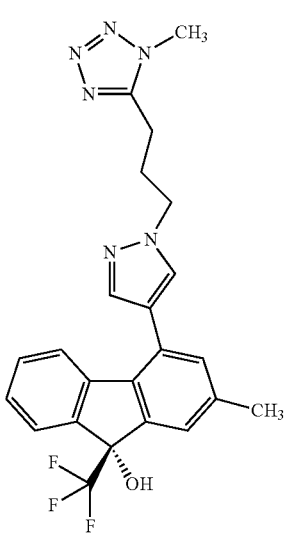 [SMILES: Cc1cc(-c2cnn(CCCc3nnnn3C)c2)c2c(c1)[C@@](O)(C(F)(F)F)c1ccccc1-2] |
| 702 | 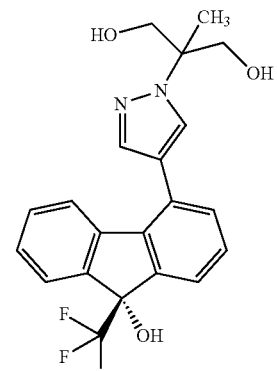 |
464
TABLE 2-11
| compound No. | structural formula (absolute configuration) |
|---|---|
| 703 | 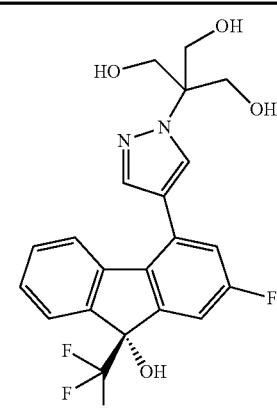 |
| 704 | 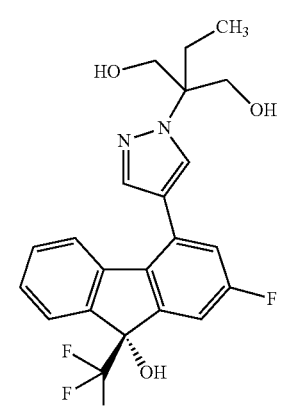 |
| 705 | 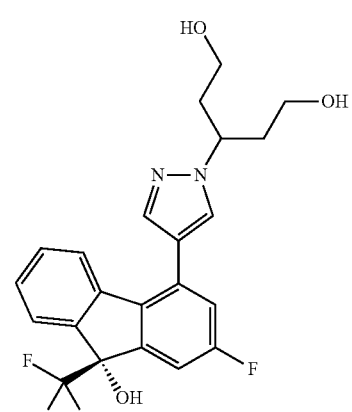 |

TABLE 2-11-continued

| compound No. | structural formula (absolute configuration) |
|---|---|
| 706 | [structure: fluorene with CF2F group and OH, connected to pyrazole bearing C(CH2OH)2(NH?) with HO-CH2, OH, OH groups] |
| 707 | [structure: similar fluorene-pyrazole scaffold with additional CH3 substituent on the fluorene ring] |

The Formulation Examples of the present invention include the following preparations, which are not to be construed as limitative.

| Formulation Example 1 (production of capsule) | |
|---|---|
| 1) compound of Example 1 | 30 mg |
| 2) microcrystalline cellulose | 10 mg |
| 3) lactose | 19 mg |
| 4) magnesium stearate | 1 mg |

1), 2), 3) and 4) are mixed and filled in a gelatin capsule.

| Formulation Example 2 (production of tablet) | |
|---|---|
| 1) compound of Example 1 | 10 g |
| 2) lactose | 50 g |
| 3) cornstarch | 15 g |
| 4) carmellose calcium | 44 g |
| 5) magnesium stearate | 1 g |

The total amount of 1), 2) and 3), and 30 g of 4) are kneaded with water, dried in vacuo and sieved. The sieved powder is mixed with 14 g of 4) and 1 g of 5) and the mixture is tableted by a tableting machine, whereby 1000 tablets containing 10 mg of the compound of Example 1 per tablet are obtained.

Experimental Example 1

Inhibitory Action of PDHK Activity in vitro

The inhibitory action of PDHK activity was indirectly evaluated by performing a kinase reaction in the presence of a test compound and measuring the residual PDH activity.

In the case of human PDHK2 (hPDHK2, Genbank Accession No. NM_002611), modified hPDHK2 cDNA wherein FLAG-Tag sequence is added to the N terminal by a polymerase linkage reaction was prepared based on hPDHK2 cDNA clone (pReceiver-M01/PDK2-GeneCopoeia), and cloned into a vector (pET17b-Novagen). The recombinant construct was transformed into *Escherichia coli* (DH5α-TOYOBO). The recombinant clones were identified, plasmid DNA was isolated and subjected to the DNA sequence analysis. One clone which had the expected nucleic acid sequence was selected for expression work.

For expression of hPDHK2 activity, *Escherichia coli* strain BL21(DE3) cells (Novagen) were transformed with the pET17b vector containing modified hPDHK2 cDNA. *Escherichia coli* were grown to an optical density 0.6 (600 nmol/L) at 30° C. Protein expression was induced by the addition of 500 μmol/L isopropyl-β-thiogalactopyranoside. *Escherichia coli* were cultured at 30° C. for 5 hr and harvested by centrifugation. Resuspension of the *Escherichia coli* paste was disrupted by a microfluidizer. FLAG-Tagged protein was separated using FLAG affinity gel (Sigma). The gel was washed with 20 mmol/L N-(2-hydroxyethyl)piperazine-N'-2-ethanesulfonic acid-sodium hydroxide (HEPES-NaOH), 500 mmol/L sodium chloride, 1% ethylene glycol, and 0.1% Pluronic F-68 (pH 8.0), and the binding protein was eluted with 20 mmol/L HEPES-NaOH, 100 μg/mL FLAG peptide, 500 mmol/L sodium chloride, 1% ethylene glycol, and 0.1% Pluronic F-68 (pH 8.0). The eluted fractions containing FLAG-Tagged protein were pooled, dialyzed against 20 mmol/L HEPES-NaOH, 150 mmol/L sodium chloride, 0.5 mmol/L ethylenediaminetetraacetic acid (EDTA), 1% ethylene glycol, and 0.1% Pluronic F-68 (pH 8.0), and preserved at −80° C. During the assay, the hPDHK2 enzyme concentration was set to the minimal concentration at which PDH is inhibited the most.

0.05 U/mL PDH (porcine heart PDH complex, Sigma P7032) and 1.6 μg/mL hPDHK2 were mixed in a buffer (50 mmol/L 3-morpholinopropanesulfonic acid (pH 7.0), 20 mmol/L dipotassium hydrogen phosphate, 60 mmol/L potassium chloride, 2 mmol/L magnesium chloride, 0.4 mmol/L EDTA, and 0.2% Pluronic F-68, 2 mmol/L dithiothreitol), the mixture was incubated at 4° C. overnight to give PDH/hPDHK2 complex. The test compound was diluted with dimethyl sulfoxide (DMSO). PDH/hPDHK2 complex (20 μL), test compound (1.5 μL) and 3.53 μmol/L ATP (diluted with buffer, 8.5 μL) were added to a half area 96 well UV-transparent microplate (Corning 3679), and PDHK reaction was performed at room temperature for 45 min. Instead of the test compound, DMSO (1.5 μL) was added to a control well. DMSO (1.5 μL) was added instead of the test compound to a blank well for the measurement of the maximum rate of PDH reaction, and hPDHK2 was not added. Than, 10 μL of substrates (5 mmol/L sodium pyruvate, 5 mmol/L Coenzyme A, 12 mmol/L NAD, and 5 mmol/L thiamine pyrophosphate, diluted with buffer) was added. The mixture was incubated at room temperature for 90 min, and the residual PDH activity was measured. The absorbance at 340 nm before and after PDH reaction was measured on a microplate reader to detect NADH produced by the PDH reaction. The PDHK inhibitory rate (%) of the test compound was calculated from the formula [{(PDH activity of test compound—PDH activity of control)/PDH activity of blank—PDH activity of control)}× 100]. The $IC_{50}$ value was calculated from the concentrations of the test compound at two points enclosing 50% inhibition of the PDHK activity.

The obtained results are shown in the following Table 3-1-Table 3-29. In the Tables, the inhibitory activity of the compound is shown as follows. +++: $IC_{50}$ (µmol/L) of less than 0.1 µmol/L, ++: not less than 0.1 µmol/L and less than 1 µmol/L, +: not less than 1 mol/L. The compounds for which the measurement was not conducted is shown as ND.

TABLE 3-1

| compound No. | PDHK inhibitory activity | $IC_{50}$ (µmol/L) |
|---|---|---|
| 1 | + | 2.208 |
| 2 | + | 2.286 |
| 3 | + | 1.567 |
| 4 | + | 2.292 |
| 5 | + | 1.169 |
| 6 | + | 2.294 |
| 7 | + | 1.435 |
| 8 | + | 45.643 |
| 9 | + | 20.040 |
| 10 | + | 30.793 |
| 11 | + | 6.792 |
| 12 | + | 5.495 |
| 13 | + | 15.876 |
| 14 | + | 56.574 |
| 15 | + | 16.312 |
| 16 | + | 19.303 |
| 17 | + | 13.871 |
| 18 | ++ | 0.457 |
| 19 | + | >100 |
| 20 | + | 3.497 |
| 21 | ++ | 0.302 |
| 22 | + | 16.691 |
| 23 | ++ | 0.571 |
| 24 | + | >100 |
| 25 | + | 30.863 |

TABLE 3-2

| compound No. | PDHK inhibitory activity | $IC_{50}$ (µmol/L) |
|---|---|---|
| 26 | + | 17.596 |
| 27 | ++ | 0.848 |
| 28 | + | 2.815 |
| 29 | + | 5.739 |
| 30 | + | 8.609 |
| 31 | + | 1.353 |
| 32 | + | >100 |
| 33 | + | 1.814 |
| 34 | + | 33.181 |
| 35 | + | >100 |
| 36 | ++ | 0.626 |
| 37 | + | 3.959 |
| 38 | + | 12.022 |
| 39 | + | 4.522 |
| 40 | + | 2.469 |
| 41 | + | 68.593 |
| 42 | + | 5.564 |
| 43 | + | 3.920 |
| 44 | + | >100 |
| 45 | ++ | 0.247 |
| 46 | + | 6.486 |
| 47 | + | 4.909 |
| 48 | ++ | 0.639 |
| 49 | + | 1.787 |
| 50 | ++ | 0.100 |

TABLE 3-3

| compound No. | PDHK inhibitory activity | $IC_{50}$ (µmol/L) |
|---|---|---|
| 51 | + | 2.590 |
| 52 | + | 4.010 |
| 53 | ++ | 0.567 |
| 54 | + | 21.913 |
| 55 | + | 19.786 |
| 56 | + | >100 |
| 57 | + | 5.621 |
| 58 | ++ | 0.195 |
| 59 | ++ | 0.772 |
| 60 | + | 2.037 |
| 61 | ++ | 0.294 |
| 62 | + | 15.728 |
| 63 | + | 8.484 |
| 64 | + | 17.963 |
| 65 | + | >100 |
| 66 | + | 66.305 |
| 67 | + | 4.199 |
| 68 | ++ | 0.624 |
| 69 | + | 16.015 |
| 70 | + | 2.213 |
| 71 | + | 10.220 |
| 72 | + | 4.424 |
| 73 | + | 4.814 |
| 74 | + | 3.317 |
| 75 | + | 6.783 |

TABLE 3-4

| compound No. | PDHK inhibitory activity | $IC_{50}$ (µmol/L) |
|---|---|---|
| 76 | + | 1.754 |
| 77 | + | 2.497 |
| 78 | + | 1.358 |
| 79 | ++ | 0.696 |
| 80 | + | 8.245 |
| 81 | + | 2.762 |
| 82 | + | 67.348 |
| 83 | + | 1.141 |
| 84 | + | 42.066 |
| 85 | + | 23.099 |
| 86 | ++ | 0.378 |
| 87 | ++ | 0.669 |
| 88 | + | 2.526 |
| 89 | + | 2.147 |
| 90 | ++ | 0.474 |
| 91 | +++ | 0.072 |
| 92 | ++ | 0.405 |
| 93 | + | 29.507 |
| 94 | +++ | 0.049 |
| 95 | + | 7.831 |
| 96 | + | 6.568 |
| 97 | ++ | 0.849 |
| 98 | + | 2.423 |
| 99 | ++ | 0.718 |
| 100 | + | 6.148 |

TABLE 3-5

| compound No. | PDHK inhibitory activity | $IC_{50}$ µmol/L) |
|---|---|---|
| 101 | + | 10.296 |
| 102 | ++ | 0.323 |
| 103 | ++ | 0.151 |
| 104 | ++ | 0.279 |
| 105 | ++ | 0.259 |
| 106 | ++ | 0.461 |
| 107 | + | 2.613 |

TABLE 3-5-continued

| compound No. | PDHK inhibitory activity | IC$_{50}$ (μmol/L) |
|---|---|---|
| 108 | ++ | 0.462 |
| 109 | + | 1.317 |
| 110 | + | 2.488 |
| 111 | + | >10 |
| 112 | + | 1.230 |
| 113 | + | 1.113 |
| 114 | +++ | 0.051 |
| 115 | ++ | 0.417 |
| 116 | ++ | 0.601 |
| 117 | ++ | 0.909 |
| 118 | ++ | 0.839 |
| 119 | + | 1.005 |
| 120 | ++ | 0.174 |
| 121 | + | 3.676 |
| 122 | +++ | 0.049 |
| 123 | ++ | 0.877 |
| 124 | ++ | 0.736 |
| 125 | ++ | 0.227 |

TABLE 3-6

| compound No. | PDHK inhibitory activity | IC$_{50}$ (μmol/L) |
|---|---|---|
| 126 | + | >10 |
| 127 | + | >10 |
| 128 | + | 2.395 |
| 129 | ++ | 0.864 |
| 130 | + | >10 |
| 131 | + | >10 |
| 132 | ++ | 0.694 |
| 133 | + | 2.498 |
| 134 | + | >10 |
| 135 | + | >1 |
| 136 | +++ | 0.025 |
| 137 | + | 1.007 |
| 138 | + | >10 |
| 139 | + | >10 |
| 140 | + | 2.402 |
| 141 | +++ | 0.077 |
| 142 | ++ | 0.543 |
| 143 | + | >10 |
| 144 | + | 1.122 |
| 145 | + | 1.382 |
| 146 | ++ | 0.213 |
| 147 | + | 1.729 |
| 148 | + | 8.450 |
| 149 | + | 1.220 |
| 150 | + | 6.838 |

TABLE 3-7

| compound No. | PDHK inhibitory activity | IC$_{50}$ (μmol/L) |
|---|---|---|
| 151 | + | 5.213 |
| 152 | +++ | 0.054 |
| 153 | +++ | 0.036 |
| 154 | ++ | 0.309 |
| 155 | ++ | 0.805 |
| 156 | ++ | 0.464 |
| 157 | ++ | 0.358 |
| 158 | ++ | 0.221 |
| 159 | ++ | 0.318 |
| 160 | + | 2.538 |
| 161 | + | 2.113 |
| 162 | + | 2.886 |
| 163 | ++ | 0.232 |
| 164 | + | 2.747 |

TABLE 3-7-continued

| compound No. | PDHK inhibitory activity | IC$_{50}$ (μmol/L) |
|---|---|---|
| 165 | ++ | 0.957 |
| 166 | + | 5.899 |
| 167 | + | 1.947 |
| 168 | + | >10 |
| 169 | + | 7.362 |
| 170 | + | 6.735 |
| 171 | ++ | 0.951 |
| 172 | ++ | 0.779 |
| 173 | + | >10 |
| 174 | +++ | 0.066 |
| 175 | ++ | 0.517 |

TABLE 3-8

| compound No. | PDHK inhibitory activity | IC$_{50}$ (μmol/L) |
|---|---|---|
| 176 | + | 8.013 |
| 177 | + | 9.189 |
| 178 | + | >10 |
| 179 | + | 1.340 |
| 180 | + | >10 |
| 181 | + | 1.514 |
| 182 | + | >10 |
| 183 | + | >10 |
| 184 | + | >10 |
| 185 | +++ | 0.053 |
| 186 | + | 5.906 |
| 187 | + | 2.478 |
| 188 | ++ | 0.383 |
| 189 | + | 6.000 |
| 190 | + | >10 |
| 191 | ++ | 0.216 |
| 192 | ++ | 0.182 |
| 193 | ++ | 0.560 |
| 194 | ++ | 0.368 |
| 195 | + | 5.485 |
| 196 | ++ | 0.475 |
| 197 | ++ | 0.298 |
| 198 | ++ | 0.126 |
| 199 | ++ | 0.182 |
| 200 | ++ | 0.236 |

TABLE 3-9

| compound No. | PDHK inhibitory activity | IC$_{50}$ (μmol/L) |
|---|---|---|
| 201 | ++ | 0.162 |
| 202 | ++ | 0.247 |
| 203 | ++ | 0.423 |
| 204 | + | >10 |
| 205 | ++ | 0.707 |
| 206 | + | 2.240 |
| 207 | ++ | 0.998 |
| 208 | ++ | 0.677 |
| 209 | ++ | 0.281 |
| 210 | + | 1.327 |
| 211 | + | 1.012 |
| 212 | ++ | 0.685 |
| 213 | ++ | 0.173 |
| 214 | ++ | 0.345 |
| 215 | + | 4.599 |
| 216 | + | 2.565 |
| 217 | + | 5.329 |
| 218 | + | 1.837 |
| 219 | + | >10 |
| 220 | ++ | 0.488 |
| 221 | + | >10 |

TABLE 3-9-continued

| compound No. | PDHK inhibitory activity | IC$_{50}$ (μmol/L) |
|---|---|---|
| 222 | + | 5.391 |
| 223 | + | 2.327 |
| 224 | ++ | 0.214 |
| 225 | ++ | 0.619 |

TABLE 3-10

| compound No. | PDHK inhibitory activity | IC$_{50}$ (μmol/L) |
|---|---|---|
| 226 | + | 1.142 |
| 227 | + | 1.048 |
| 228 | + | 2.192 |
| 229 | ++ | 0.552 |
| 230 | + | 3.712 |
| 231 | + | 3.607 |
| 232 | + | 1.988 |
| 233 | ++ | 0.142 |
| 234 | +++ | 0.058 |
| 235 | ++ | 0.803 |
| 236 | ++ | 0.355 |
| 237 | + | 1.999 |
| 238 | ++ | 0.252 |
| 239 | ++ | 0.178 |
| 240 | ++ | 0.149 |
| 241 | +++ | 0.098 |
| 242 | +++ | 0.086 |
| 243 | +++ | 0.075 |
| 244 | + | 2.929 |
| 245 | ++ | 0.190 |
| 246 | ++ | 0.809 |
| 247 | ++ | 0.547 |
| 248 | + | 1.019 |
| 249 | ++ | 0.719 |
| 250 | + | 1.609 |

TABLE 3-11

| compound No. | PDHK inhibitory activity | IC$_{50}$ (μmol/L) |
|---|---|---|
| 251 | + | >10 |
| 252 | + | 1.273 |
| 253 | + | 1.947 |
| 254 | + | 1.131 |
| 255 | + | 1.078 |
| 256 | + | 1.003 |
| 257 | ++ | 0.567 |
| 258 | + | 2.625 |
| 259 | + | 1.386 |
| 260 | + | 2.813 |
| 261 | + | 1.404 |
| 262 | + | 1.365 |
| 263 | ++ | 0.133 |
| 264 | + | 1.169 |
| 265 | + | 1.258 |
| 266 | + | 1.556 |
| 267 | + | 1.197 |
| 268 | + | >10 |
| 269 | + | 1.338 |
| 270 | ++ | 0.533 |
| 271 | +++ | 0.056 |
| 272 | ++ | 0.342 |
| 273 | ++ | 0.396 |
| 274 | + | 7.487 |
| 275 | ++ | 0.278 |

TABLE 3-12

| compound No. | PDHK inhibitory activity | IC$_{50}$ (μmol/L) |
|---|---|---|
| 276 | + | 1.013 |
| 277 | ++ | 0.125 |
| 278 | ++ | 0.862 |
| 279 | + | 1.849 |
| 280 | + | 1.514 |
| 281 | + | 1.000 |
| 282 | ++ | 0.226 |
| 283 | ++ | 0.571 |
| 284 | + | 1.168 |
| 285 | +++ | 0.020 |
| 286 | +++ | 0.017 |
| 287 | + | >10 |
| 288 | ++ | 0.635 |
| 289 | ++ | 0.641 |
| 290 | ++ | 0.793 |
| 291 | + | 5.826 |
| 292 | + | 2.571 |
| 293 | + | 4.947 |
| 294 | ++ | 0.710 |
| 295 | ++ | 0.861 |
| 296 | ++ | 0.180 |
| 297 | + | 3.034 |
| 298 | ++ | 0.177 |
| 299 | ++ | 0.235 |
| 300 | ++ | 0.114 |

TABLE 3-13

| compound No. | PDHK inhibitory activity | IC$_{50}$ (μmol/L) |
|---|---|---|
| 301 | + | 1.586 |
| 302 | + | 1.167 |
| 303 | ++ | 0.755 |
| 304 | ++ | 0.723 |
| 305 | ++ | 0.562 |
| 306 | ++ | 0.453 |
| 307 | + | 3.198 |
| 308 | + | 2.666 |
| 309 | + | >10 |
| 310 | + | >10 |
| 311 | + | 7.151 |
| 312 | + | 1.824 |
| 313 | + | >10 |
| 314 | + | >10 |
| 315 | + | 6.371 |
| 316 | + | 4.480 |
| 317 | + | 2.313 |
| 318 | ++ | 0.553 |
| 319 | + | 3.086 |
| 320 | + | 8.765 |
| 321 | + | 5.385 |
| 322 | + | 2.503 |
| 323 | ++ | 0.362 |
| 324 | ++ | 0.203 |
| 325 | + | 1.080 |

TABLE 3-14

| compound No. | PDHK inhibitory activity | IC$_{50}$ (μmol/L) |
|---|---|---|
| 326 | ++ | 0.303 |
| 327 | + | 2.941 |
| 328 | +++ | 0.078 |
| 329 | +++ | 0.066 |
| 330 | ++ | 0.125 |
| 331 | + | 1.415 |
| 332 | ++ | 0.912 |

TABLE 3-14-continued

| compound No. | PDHK inhibitory activity | IC$_{50}$ (μmol/L) |
|---|---|---|
| 333 | ++ | 0.924 |
| 334 | ++ | 0.674 |
| 335 | +++ | 0.080 |
| 336 | + | >10 |
| 337 | ++ | 0.499 |
| 338 | + | >1 |
| 339 | ++ | 0.177 |
| 340 | + | 1.594 |
| 341 | +++ | 0.079 |
| 342 | +++ | 0.047 |
| 343 | +++ | 0.053 |
| 344 | + | >1 |
| 345 | ++ | 0.121 |
| 346 | ++ | 0.200 |
| 347 | +++ | 0.088 |
| 348 | ++ | 0.634 |
| 349 | ++ | 0.126 |
| 350 | ++ | 0.152 |

TABLE 3-15

| compound No. | PDHK inhibitory activity | IC$_{50}$ (μmol/L) |
|---|---|---|
| 351 | ++ | 0.168 |
| 352 | ++ | 0.109 |
| 353 | + | 7.398 |
| 354 | +++ | 0.071 |
| 355 | +++ | 0.040 |
| 356 | +++ | 0.053 |
| 357 | + | 1.939 |
| 358 | +++ | 0.034 |
| 359 | ++ | 0.187 |
| 360 | ++ | 0.548 |
| 361 | ++ | 0.436 |
| 362 | + | 1.077 |
| 363 | +++ | 0.047 |
| 364 | ++ | 0.178 |
| 365 | + | 1.327 |
| 366 | + | 2.170 |
| 367 | + | >1 |
| 368 | ++ | 0.180 |
| 369 | +++ | 0.081 |
| 370 | ++ | 0.114 |
| 371 | ++ | 0.617 |
| 372 | ++ | 0.564 |
| 373 | +++ | 0.049 |
| 374 | +++ | 0.049 |
| 375 | +++ | 0.050 |

TABLE 3-16

| compound No. | PDHK inhibitory activity | IC$_{50}$ (μmol/L) |
|---|---|---|
| 376 | +++ | 0.085 |
| 377 | ++ | 0.189 |
| 378 | ++ | 0.703 |
| 379 | ++ | 0.351 |
| 380 | + | 1.490 |
| 381 | ++ | 0.495 |
| 382 | ++ | 0.863 |
| 383 | + | 1.225 |
| 384 | ++ | 0.219 |
| 385 | ++ | 0.234 |
| 386 | +++ | 0.089 |
| 387 | +++ | 0.063 |
| 388 | +++ | 0.063 |
| 389 | ++ | 0.822 |

TABLE 3-16-continued

| compound No. | PDHK inhibitory activity | IC$_{50}$ (μmol/L) |
|---|---|---|
| 390 | ++ | 0.954 |
| 391 | ++ | 0.485 |
| 392 | ++ | 0.200 |
| 393 | ++ | 0.176 |
| 394 | +++ | 0.058 |
| 395 | ++ | 0.699 |
| 396 | ++ | 0.627 |
| 397 | ++ | 0.424 |
| 398 | ++ | 0.119 |
| 399 | ++ | 0.149 |
| 400 | + | 7.077 |

TABLE 3-17

| compound No. | PDHK inhibitory activity | IC$_{50}$ (μmol/L) |
|---|---|---|
| 401 | ++ | 0.554 |
| 402 | + | >10 |
| 403 | + | >10 |
| 404 | ++ | 0.195 |
| 405 | + | 6.377 |
| 406 | +++ | 0.025 |
| 407 | +++ | 0.031 |
| 408 | +++ | 0.065 |
| 409 | +++ | 0.067 |
| 410 | ++ | 0.154 |
| 411 | +++ | 0.066 |
| 412 | +++ | 0.022 |
| 413 | + | 1.230 |
| 414 | +++ | 0.032 |
| 415 | + | 9.190 |
| 416 | ++ | 0.104 |
| 417 | + | >1 |
| 418 | + | 6.065 |
| 419 | ++ | 0.504 |
| 420 | ++ | 0.225 |
| 421 | ++ | 0.233 |
| 422 | +++ | 0.023 |
| 423 | +++ | 0.021 |
| 424 | +++ | 0.023 |
| 425 | +++ | 0.021 |

TABLE 3-18

| compound No. | PDHK inhibitory activity | IC$_{50}$ (μmol/L) |
|---|---|---|
| 426 | +++ | 0.024 |
| 427 | +++ | 0.020 |
| 428 | +++ | 0.025 |
| 429 | +++ | 0.019 |
| 430 | +++ | 0.064 |
| 431 | ++ | 0.250 |
| 432 | ++ | 0.247 |
| 433 | ++ | 0.388 |
| 434 | ++ | 0.561 |
| 435 | +++ | 0.039 |
| 436 | +++ | 0.065 |
| 437 | +++ | 0.060 |
| 438 | ++ | 0.112 |
| 439 | +++ | 0.034 |
| 440 | +++ | 0.032 |
| 441 | +++ | 0.036 |
| 442 | +++ | 0.040 |
| 443 | + | 1.152 |
| 444 | + | 3.934 |
| 445 | ++ | 0.605 |
| 446 | ++ | 0.565 |

TABLE 3-18-continued

| compound No. | PDHK inhibitory activity | IC$_{50}$ (μmol/L) |
|---|---|---|
| 447 | ++ | 0.202 |
| 448 | ++ | 0.381 |
| 449 | +++ | 0.047 |
| 450 | ++ | 0.442 |

TABLE 3-19

| compound No. | PDHK inhibitory activity | IC$_{50}$ (μmol/L) |
|---|---|---|
| 451 | ++ | 0.102 |
| 452 | + | 2.719 |
| 453 | +++ | 0.028 |
| 454 | +++ | 0.064 |
| 455 | +++ | 0.026 |
| 456 | +++ | 0.045 |
| 457 | +++ | 0.030 |
| 458 | +++ | 0.039 |
| 459 | ++ | 0.185 |
| 460 | +++ | 0.030 |
| 461 | +++ | 0.030 |
| 462 | + | 5.979 |
| 463 | +++ | 0.047 |
| 464 | +++ | 0.042 |
| 465 | +++ | 0.061 |
| 466 | +++ | 0.055 |
| 467 | +++ | 0.018 |
| 468 | ++ | 0.327 |
| 469 | ++ | 0.193 |
| 470 | ++ | 0.168 |
| 471 | +++ | 0.026 |
| 472 | ++ | 0.184 |
| 473 | +++ | 0.090 |
| 474 | +++ | 0.019 |
| 475 | +++ | 0.020 |

TABLE 3-20

| compound No. | PDHK inhibitory activity | IC$_{50}$ (μmol/L) |
|---|---|---|
| 476 | +++ | 0.053 |
| 477 | +++ | 0.018 |
| 478 | ++ | 0.433 |
| 479 | + | >10 |
| 480 | ++ | 0.553 |
| 481 | ++ | 0.251 |
| 482 | +++ | 0.040 |
| 483 | ++ | 0.542 |
| 484 | +++ | 0.024 |
| 485 | ++ | 0.117 |
| 486 | +++ | 0.055 |
| 487 | +++ | 0.064 |
| 488 | +++ | 0.052 |
| 489 | +++ | 0.022 |
| 490 | ++ | 0.223 |
| 491 | +++ | 0.020 |
| 492 | +++ | 0.040 |
| 493 | +++ | 0.039 |
| 494 | +++ | 0.044 |
| 495 | ++ | 0.119 |
| 496 | +++ | 0.023 |
| 497 | +++ | 0.031 |
| 498 | +++ | 0.047 |
| 499 | +++ | 0.039 |
| 500 | +++ | 0.031 |

TABLE 3-21

| compound No. | PDHK inhibitory activity | IC$_{50}$ (μmol/L) |
|---|---|---|
| 501 | +++ | 0.032 |
| 502 | +++ | 0.048 |
| 503 | +++ | 0.045 |
| 504 | +++ | 0.019 |
| 505 | +++ | 0.046 |
| 506 | +++ | 0.030 |
| 507 | +++ | 0.026 |
| 508 | +++ | 0.048 |
| 509 | +++ | 0.051 |
| 510 | +++ | 0.062 |
| 511 | +++ | 0.056 |
| 512 | +++ | 0.038 |
| 513 | +++ | 0.032 |
| 514 | +++ | 0.058 |
| 515 | +++ | 0.038 |
| 516 | ++ | 0.110 |
| 517 | +++ | 0.057 |
| 518 | +++ | 0.054 |
| 519 | ++ | 0.418 |
| 520 | + | 3.330 |
| 521 | +++ | 0.036 |
| 522 | +++ | 0.061 |
| 523 | +++ | 0.048 |
| 524 | +++ | 0.087 |
| 525 | ++ | 0.677 |

TABLE 3-22

| compound No. | PDHK inhibitory activity | IC$_{50}$ (μmol/L) |
|---|---|---|
| 526 | ++ | 0.397 |
| 527 | +++ | 0.079 |
| 528 | +++ | 0.049 |
| 529 | +++ | 0.017 |
| 530 | +++ | 0.043 |
| 531 | +++ | 0.020 |
| 532 | +++ | 0.016 |
| 533 | +++ | 0.015 |
| 534 | +++ | 0.016 |
| 535 | ++ | 0.197 |
| 536 | +++ | 0.054 |
| 537 | +++ | 0.035 |
| 538 | +++ | 0.026 |
| 539 | +++ | 0.027 |
| 540 | +++ | 0.016 |
| 541 | +++ | 0.015 |
| 542 | +++ | 0.015 |
| 543 | +++ | 0.036 |
| 544 | +++ | 0.022 |
| 545 | +++ | 0.017 |
| 546 | +++ | 0.015 |
| 547 | +++ | 0.062 |
| 548 | +++ | 0.016 |
| 549 | +++ | 0.027 |
| 550 | +++ | 0.069 |

TABLE 3-23

| compound No. | PDHK inhibitory activity | IC$_{50}$ (μmol/L) |
|---|---|---|
| 551 | ++ | 0.109 |
| 552 | +++ | 0.017 |
| 553 | +++ | 0.018 |
| 554 | +++ | 0.020 |
| 555 | + | >1 |
| 556 | +++ | 0.053 |
| 557 | +++ | 0.077 |

TABLE 3-23-continued

| compound No. | PDHK inhibitory activity | IC$_{50}$ (μmol/L) |
|---|---|---|
| 558 | +++ | 0.081 |
| 559 | + | >1 |
| 560 | ++ | 0.970 |
| 561 | +++ | 0.050 |
| 562 | +++ | 0.059 |
| 563 | +++ | 0.063 |
| 564 | ++ | 0.105 |
| 565 | +++ | 0.018 |
| 566 | +++ | 0.021 |
| 567 | + | >1 |
| 568 | +++ | 0.083 |
| 569 | +++ | 0.044 |
| 570 | ++ | 0.110 |
| 571 | +++ | 0.050 |
| 572 | ++ | 0.109 |
| 573 | +++ | 0.018 |
| 574 | +++ | 0.052 |
| 575 | +++ | 0.036 |

TABLE 3-24

| compound No. | PDHK inhibitory activity | IC$_{50}$ (μmol/L) |
|---|---|---|
| 576 | +++ | 0.030 |
| 577 | +++ | 0.023 |
| 578 | +++ | 0.078 |
| 579 | +++ | 0.019 |
| 580 | +++ | 0.021 |
| 581 | +++ | 0.019 |
| 582 | +++ | 0.021 |
| 583 | +++ | 0.064 |
| 584 | +++ | 0.077 |
| 585 | +++ | 0.026 |
| 586 | ++ | 0.513 |
| 587 | +++ | 0.021 |
| 588 | +++ | 0.029 |
| 589 | +++ | 0.025 |
| 590 | + | 5.922 |
| 591 | + | >1 |
| 592 | + | >1 |
| 593 | + | >1 |
| 594 | +++ | 0.048 |
| 595 | +++ | 0.022 |
| 596 | +++ | 0.041 |
| 597 | + | >1 |
| 598 | ++ | 0.653 |
| 599 | +++ | 0.033 |
| 600 | + | >1 |

TABLE 3-25

| compound No. | PDHK inhibitory activity | IC$_{50}$ (μmol/L) |
|---|---|---|
| 601 | + | >1 |
| 602 | + | >1 |
| 603 | ++ | 0.228 |
| 604 | +++ | 0.035 |
| 605 | +++ | 0.019 |
| 606 | +++ | 0.028 |
| 607 | +++ | 0.045 |
| 608 | + | >1 |
| 609 | + | >1 |
| 610 | +++ | 0.041 |
| 611 | ++ | 0.329 |
| 612 | +++ | 0.047 |
| 613 | +++ | 0.076 |
| 614 | +++ | 0.037 |

TABLE 3-25-continued

| compound No. | PDHK inhibitory activity | IC$_{50}$ (μmol/L) |
|---|---|---|
| 615 | ++ | 0.105 |
| 616 | ++ | 0.192 |
| 617 | +++ | 0.084 |
| 618 | +++ | 0.056 |
| 619 | +++ | 0.033 |
| 620 | +++ | 0.065 |
| 621 | +++ | 0.065 |
| 622 | +++ | 0.033 |
| 623 | ++ | 0.133 |
| 624 | +++ | 0.014 |
| 625 | + | >1 |

TABLE 3-26

| compound No. | PDHK inhibitory activity | IC$_{50}$ (μmol/L) |
|---|---|---|
| 626 | ++ | 0.674 |
| 627 | + | >1 |
| 628 | +++ | 0.058 |
| 629 | +++ | 0.045 |
| 630 | +++ | 0.020 |
| 631 | +++ | 0.062 |
| 632 | ++ | 0.195 |
| 633 | ++ | 0.560 |
| 634 | ++ | 0.100 |
| 635 | ++ | 0.515 |
| 636 | ++ | 0.239 |
| 637 | + | >1 |
| 638 | ++ | 0.127 |
| 639 | +++ | 0.063 |
| 640 | ++ | 0.732 |
| 641 | ++ | 0.510 |
| 642 | + | >1 |
| 643 | ++ | 0.184 |
| 644 | ++ | 0.130 |
| 645 | +++ | 0.037 |
| 646 | +++ | 0.040 |
| 647 | ++ | 0.169 |
| 648 | +++ | 0.044 |
| 649 | +++ | 0.037 |
| 650 | +++ | 0.036 |

TABLE 3-27

| compound No. | PDHK inhibitory activity | IC$_{50}$ (μmol/L) |
|---|---|---|
| 651 | +++ | 0.025 |
| 652 | +++ | 0.036 |
| 653 | +++ | 0.037 |
| 654 | +++ | 0.055 |
| 655 | +++ | 0.073 |
| 656 | ++ | 0.172 |
| 657 | +++ | 0.020 |
| 658 | +++ | 0.071 |
| 659 | +++ | 0.016 |
| 660 | +++ | 0.017 |
| 661 | +++ | 0.059 |
| 662 | +++ | 0.034 |
| 663 | +++ | 0.018 |
| 664 | +++ | 0.015 |
| 665 | +++ | 0.023 |
| 666 | +++ | 0.027 |
| 667 | +++ | 0.015 |
| 668 | +++ | 0.017 |
| 669 | +++ | 0.017 |
| 670 | ND | ND |
| 671 | + | 1.443 |

TABLE 3-27-continued

| compound No. | PDHK inhibitory activity | |
|---|---|---|
| | | $IC_{50}$ (μmol/L) |
| 672 | ND | ND |
| 673 | +++ | 0.022 |
| 674 | +++ | 0.030 |
| 675 | ND | ND |

TABLE 3-28

| compound No. | PDHK inhibitory activity | |
|---|---|---|
| | | $IC_{50}$ (μmol/L) |
| 676 | ND | ND |
| 677 | ND | ND |
| 678 | ND | ND |
| 679 | ND | ND |
| 680 | ND | ND |
| 681 | ND | ND |
| 682 | +++ | 0.079 |
| 683 | ND | ND |
| 684 | ND | ND |
| 685 | ++ | 0.338 |
| 686 | ND | ND |
| 687 | +++ | 0.051 |
| 688 | ND | ND |
| 689 | ND | ND |
| 690 | ND | ND |
| 691 | +++ | 0.030 |
| 692 | ND | ND |
| 693 | ND | ND |
| 694 | ND | ND |
| 695 | ND | ND |
| 696 | ND | ND |
| 697 | ND | ND |
| 698 | ND | ND |
| 699 | ND | ND |
| 700 | ND | ND |

TABLE 3-29

| compound No. | PDHK inhibitory activity | |
|---|---|---|
| | | $IC_{50}$ (μmol/L) |
| 701 | ND | ND |
| 702 | +++ | 0.030 |
| 703 | +++ | 0.020 |
| 704 | ND | ND |
| 705 | ND | ND |
| 706 | +++ | 0.031 |
| 707 | +++ | 0.019 |

As is clear from the above-mentioned Experimental Example 1, the compound of the present invention has a PDHK activity inhibitory action.

Therefrom it is suggested that the compound of the present invention provides an effect of strong inhibition of PDHK.

Therefore, by inhibition of PDHK, the compound of the present invention effectively activates pyruvate dehydrogenase (PDH), and can provide an agent for the treatment or prophylaxis of diabetes (e.g., type 1 diabetes, type 2 diabetes etc.), insulin resistance syndrome, metabolic syndrome, hyperglycemia, dyslipidemia, atherosclerosis, cardiac failure, cardiomyopathy, myocardial ischemia, hyperlactacidemia, mitochondrial disease, mitochondrial encephalomyopathy or cancer and the like. Moreover, the compound of the present invention can provide an agent for the treatment or prophylaxis of diabetic complications (e.g., neuropathy, retinopathy, nephropathy, cataract etc.), brain ischemia, cerebral apoplexy or pulmonary hypertension.

Industrial Applicability

The present invention is useful for the treatment or prophylaxis and the like of diabetes (e.g., type 1 diabetes, type 2 diabetes etc.), insulin resistance syndrome, metabolic syndrome, hyperglycemia, dyslipidemia, atherosclerosis, cardiac failure, cardiomyopathy, myocardial ischemia, hyperlactacidemia, mitochondrial disease, mitochondrial encephalomyopathy or cancer and the like. In addition, the present invention is useful for the treatment or prophylaxis and the like of diabetic complications (e.g., neuropathy, retinopathy, nephropathy, cataract etc.), brain ischemia, cerebral apoplexy or pulmonary hypertension.

The invention claimed is:

1. A compound of formula [Vd]

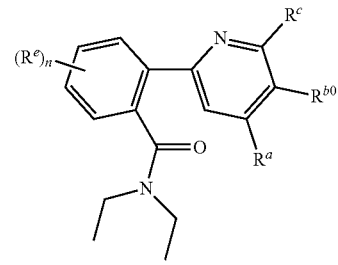

wherein, $R^a$ is (1) a hydrogen atom, or (2) a halogen atom;

$R^{b0}$ is a substituent that can be converted to $R^b$ by a functional group conversion reaction;

$R^b$ is (1) a hydrogen atom, (2) a halogen atom, (3) a $C_{1-6}$ alkyl group optionally substituted by the same or different 1 to 5 substituents selected from the following group A, (4) a $C_{2-6}$ alkenyl group optionally substituted by the same or different 1 to 5 substituents selected from the following group C, (5) a $C_{2-6}$ alkynyl group optionally substituted by the same or different 1 to 5 substituents selected from the following group C, (6) a cyano group, (7) —C(=O)—$R^{b1}$ wherein $R^{b1}$ is a hydrogen atom or a $C_{1-6}$ alkyl group optionally substituted by the same or different 1 to 5 substituents selected from the following group B, (8) —C(=O)—$OR^{b2}$ wherein $R^{b2}$ is a hydrogen atom or a $C_{1-6}$ alkyl group optionally substituted by the same or different 1 to 5 substituents selected from the following group B, (9) —C(=O)—$NR^{b3}R^{b4}$ wherein $R^{b3}$ and $R^{b4}$ are the same or different and each is a hydrogen atom or a $C_{1-6}$ alkyl group optionally substituted by the same or different 1 to 5 substituents selected from the following group B,

(10) —C(=O)—$NR^{b5}$—$OR^{b6}$ wherein $R^{b5}$ and $R^{b6}$ are the same or different and each is a hydrogen atom or a $C_{1-6}$ alkyl group optionally substituted by the same or different 1 to 5 substituents selected from the following group B,

(11) —OR$^{b7}$ wherein R$^{b7}$ is a hydrogen atom or a C$_{1-6}$ alkyl group optionally substituted by the same or different 1 to 5 substituents selected from the following group B,

(12) —NR$^{b8}$R$^{b9}$ wherein R$^{b8}$ and R$^9$ the same or different and each is a hydrogen atom or a C$_{1-6}$ alkyl group optionally substituted by the same or different 1 to 5 substituents selected from the following group B,

(13) —NR$^{b10}$—C(=O)—R$^{b11}$ wherein R$^{b10}$ and R$^{b11}$ are the same or different and each is a hydrogen atom or a C$_{1-6}$ alkyl group optionally substituted by the same or different 1 to 5 substituents selected from the following group B,

(14) —NR$^{b12}$—C(=O)—OR$^{b13}$ wherein R$^{b12}$ is a hydrogen atom or a C$_{1-6}$ alkyl group optionally substituted by the same or different 1 to 5 substituents selected from the following group B, and R$^{b13}$ is a C$_{1-6}$ alkyl group optionally substituted by the same or different 1 to 5 substituents selected from the following group B,

(15) —O—C(=O)—NR$^{b14}$R$^{b15}$ wherein R$^{b14}$ and R$^{b15}$ are the same or different and each is a hydrogen atom or a C$_{1-6}$ alkyl group optionally substituted by the same or different 1 to 5 substituents selected from the following group B, or

(16) a group represented by the following formula:

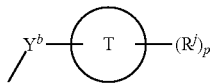

wherein
Y$^b$ is
(i) a single bond,
(ii) a C$_{1-6}$ alkylene,
(iii) a C$_{2-6}$ alkenylene,
(iv) —O—(CH$_2$)$_{n1}$-wherein n1 is an integer of 0, or 1 to 4,
(v) —O—(CH$_2$)$_{n2}$—C(=O)-wherein n2 is an integer of 0, or 1 to 4,
(vi) —C(=O)—, or
(vii) —NR$^{b16}$-wherein R$^{b16}$ is a hydrogen atom or a C$_{1-6}$ alkyl group optionally substituted by the same or different 1 to 5 substituents selected from the following group B;

ring T is
(i) a C$_{6-10}$ aryl group,
(ii) a C$_{3-10}$ cycloalkyl group,
(iii) a C$_{5-10}$ bridged cycloalkyl group,
(iv) a monocyclic aromatic heterocyclic group which contains, besides carbon atom, 1 to 4 hetero atoms selected from a nitrogen atom, an oxygen atom and a sulfur atom, and has 3 to 7 ring-constituting atoms, or
(v) a monocyclic non-aromatic heterocyclic group which contains, besides carbon atom, 1 to 4 hetero atoms selected from a nitrogen atom, an oxygen atom and a sulfur atom, and has 3 to 7 ring-constituting atoms, R$^j$ are the same or different and each is a substituent selected from the following group D, and p is an integer of 0, or 1 to 4;

R$^c$ is
(1) a hydrogen atom,
(2) a halogen atom,
(3) a C$_{1-6}$ alkyl group,
(4) —C(=O)—OR$^{c1}$ wherein R$^{c1}$ is a hydrogen atom or a C$_{1-6}$ alkyl group,
(5) —OR$^{c2}$ wherein R$^{c2}$ is a hydrogen atom or a C$_{1-6}$ alkyl group,
(6) —NR$^{c3}$R$^{c4}$ wherein R$^{c3}$ and R$^{c4}$ are the same or different and each is a hydrogen atom or a C$_{1-6}$ alkyl group, or
(7) —NR$^{c5}$—C(=O)—R$^{c6}$ wherein R$^{c5}$ and R$^{c6}$ are the same or different and each is a hydrogen atom or a C$_{1-6}$ alkyl group;

R$^e$ are the same or different and each is,
(1) a halogen atom, or
(2) a C$_{1-6}$ alkyl group optionally substituted by the same or different 1 to 5 substituents selected from the following group C; and n is an integer of 0, or 1 to 3, Group A is selected from the group consisting of
(a) a halogen atom,
(b) a cyano group,
(c) —C(=O)—R$^{A1}$ wherein R$^{A1}$ is a hydrogen atom or a C$_{1-6}$ alkyl group optionally substituted by the same or different 1 to 5 substituents selected from the following group B,
(d) —C(=O)—OR$^{A2}$ wherein R$^{A2}$ is a hydrogen atom or a C$_{1-6}$ alkyl group optionally substituted by the same or different 1 to 5 substituents selected from the following group B,
(e) —C(=O)—NR$^{A3}$R$^{A4}$ wherein R$^{A3}$ and R$^{A4}$ are the same or different and each is a hydrogen atom or a C$_{1-6}$ alkyl group optionally substituted by the same or different 1 to 5 substituents selected from the following group B,
(f) —C(=O)—NR$^{A5}$OR$^{A6}$ wherein R$^{A5}$ and R$^{A6}$ are the same or different and each is a hydrogen atom or a C$_{1-6}$ alkyl group optionally substituted by the same or different 1 to 5 substituents selected from the following group B,
(g) —OR$^{A7}$ wherein R$^{A7}$ is a hydrogen atom or a C$_{1-6}$ alkyl group optionally substituted by the same or different 1 to 5 substituents selected from the following group B,
(h) —NR$^{A8}$R$^{A9}$ wherein R$^{A8}$ and R$^{A9}$ are the same or different and each is a hydrogen atom or a C$_{1-6}$ alkyl group optionally substituted by the same or different 1 to 5 substituents selected from the following group B,
(i) —NR$^{A10}$—C(=O) —R$^{A11}$ wherein R$^{A10}$ and R$^{A11}$ are the same or different and each is a hydrogen atom or a C$_{1-6}$ alkyl group optionally substituted by the same or different 1 to 5 substituents selected from the following group B,
(j) —NR$^{A12}$—C(=O)—OR$^{A13}$ wherein R$^{A12}$ is a hydrogen atom or a C$_{1-6}$ alkyl group optionally substituted by the same or different 1 to 5 substituents selected from the following group B, and R$^{A13}$ is a C$_{1-6}$ alkyl group optionally substituted by the same or different 1 to 5 substituents selected from the following group B,
(k) —S(=O)$_2$—OR$^{A14}$ wherein R$^{A14}$ is a hydrogen atom or a C$_{1-6}$ alkyl group optionally substituted by the same or different 1 to 5 substituents selected from the following group B,
(l) —S(=O)$_2$—OR$^{A15}$ wherein R$^{A15}$ is a hydrogen atom or a C$_{1-6}$ alkyl group optionally substituted by the same or different 1 to 5 substituents selected from the following group B, and
(m) —Si—(CH$_2$- CH$_3$)$_3$, Group B is selected from the group consisting of
(a) a halogen atom,
(b) a cyano group,
(c) —C(=O)—R$^{B1}$ wherein R$^{B1}$ is a hydrogen atom or a C$_{1-6}$ alkyl group optionally substituted by the same or different 1 to 5 substituents selected from the following group C, (d) —C(=O)—OR$^{B2}$ wherein R$^{B2}$ is a hydrogen atom or a C$_{1-6}$ alkyl group optionally substituted by the same or different 1 to 5 substituents selected from the following group C,
(e) —C(=O)—NR$^{B3}$R$^{B4}$ wherein R$^{B3}$ and R$^{B4}$ are the same or different and each is a hydrogen atom or a C$_{1-6}$ alkyl group optionally substituted by the same or different 1 to 5 substituents selected from the following group C,
(f) —C(=O)—NR$^{B5}$—OR$^{B6}$ wherein R$^{B5}$ and R$^{B6}$ are the same or different and each is a hydrogen atom or a C$_{1-6}$ alkyl group optionally substituted by the same or different 1 to 5 substituents selected from the following group C,
(g) —OR$^{B7}$ wherein R$^{B7}$ is a hydrogen atom or a C$_{1-6}$ alkyl group optionally substituted by the same or different 1 to 5 substituents selected from the following group C,
(h) —NR$^{B8}$R$^{B9}$ wherein R$^{B8}$ and R$^{B9}$ are the same or different and each is a hydrogen atom or a C$_{1-6}$ alkyl group optionally substituted by the same or different 1 to 5 substituents selected from the following group C,
(i) —NR$^{B10}$—C(=O)—R$^{B11}$ wherein R$^{B10}$ and R$^{B11}$ are the same or different and each is a hydrogen atom or a C$_{1-6}$ alkyl group optionally substituted by the same or different 1 to 5 substituents selected from the following group C,
(j) —NR$^{B12}$—S(=O)$_2$—R$^{B13}$ wherein R$^{B12}$ and R$^{B13}$ are the same or different and each is a hydrogen atom or a C$_{1-6}$ alkyl group optionally substituted by the same or different 1 to 5 substituents selected from the following group C,
(k) —NR$^{B14}$—C(=O)—OR$^{B15}$ wherein R$^{B14}$ is a hydrogen atom or a C$_{1-6}$ alkyl group optionally substituted by the same or different 1 to 5 substituents selected from the following group C, and R$^{B15}$ is a C$_{1-6}$ alkyl group optionally substituted by the same or different 1 to 5 substituents selected from the following group C,
(l) —S(=O)$_2$R$^{B16}$ wherein R$^{B16}$ is a hydrogen atom or a C$_{1-6}$ alkyl group optionally substituted by the same or different 1 to 5 substituents selected from the following group C, and
(m) —S(=O)$_2$—OR$^{B17}$ wherein R$^{B17}$ is a hydrogen atom or a C$_{1-6}$ alkyl group optionally substituted by the same or different 1 to 5 substituents selected from the following group C,
Group C is selected from the group consisting of
(a) a halogen atom,
(b) —C(=O)—R$^{C1}$ wherein R$^{C1}$ is a hydrogen atom or a C$_{1-6}$ alkyl group optionally substituted by the same or different 1 to 5 halogen atoms,
(c) —C(=O)—OR$^{C2}$ wherein R$^{C2}$ is a hydrogen atom or a C$_{1-6}$ alkyl group, and
(d) —OR$^{C3}$ wherein R$^{C3}$ is a hydrogen atom or a C$_{1-6}$ alkyl group,
Group D is selected from the group consisting of
(a) a halogen atom,
(b) a C$_{1-6}$ alkyl group optionally substituted by the same or different 1 to 5 substituents selected from the following group E,
(c) a C$_{1-6}$ alkyl group substituted by a C$_{6-10}$ aryl group optionally substituted by the same or different 1 to 5 substituents selected from the following group F,
(d) a C$_{1-6}$ alkyl group substituted by a C$_{3-10}$ cycloalkyl optionally substituted by the same or different 1 to 5 substituents selected from the following group F,
(e) a C$_{1-6}$ alkyl group substituted by a C$_{5-10}$ bridged cycloalkyl optionally substituted by the same or different 1 to 5 substituents selected from the following group F,
(f) a C$_{1-6}$ alkyl group substituted by a monocyclic aromatic heterocyclic group optionally substituted by the same or different 1 to 5 C$_{1-6}$ alkyl groups (the monocyclic aromatic heterocyclic group contains, besides carbon atom, 1 to 4 hetero atoms selected from a nitrogen atom, an oxygen atom and a sulfur atom, and has 3 to 7 ring-constituting atoms),
(g) a C$_{3-10}$ cycloalkyl group optionally substituted by the same or different 1 to 5 substituents selected from the following group F,
(h) a C$_{5-10}$ bridged cycloalkyl group optionally substituted by the same or different 1 to 5 substituents selected from the following group F,
(i) a cyano group,
(j) —C(=O)—R$^{D1}$ wherein R$^{D1}$ is a hydrogen atom, a C$_{1-6}$ alkyl group optionally substituted by the same or different 1 to 5 substituents selected from the following group E, or a monocyclic non-aromatic heterocyclic group optionally substituted by the same or different 1 to 5 substituents selected from the following group F (the monocyclic non-aromatic heterocyclic group contains, besides carbon atom, 1 to 4 hetero atoms selected from a nitrogen atom, an oxygen atom and a sulfur atom, and has 3 to 7 ring-constituting atoms),
(k) —C(=O)—OR$^{D2}$ wherein R$^{D2}$ is a hydrogen atom, or a C$_{1-6}$ alkyl group optionally substituted by the same or different 1 to 5 substituents selected from the following group E,
(l) C(=O)—NR$^{D3}$R$^{D4}$ wherein R$^{D3}$ and R$^{D4}$ are the same or different and each is a hydrogen atom, or a C$_{1-6}$ alkyl group optionally substituted by the same or different 1 to 5 substituents selected from the following group E,
(m) —C(=O)—NR$^{D5}$—OR$^{D6}$ wherein R$^{D5}$ and R$^{D6}$ are the same or different and each is a hydrogen atom, or a C$_{1-6}$ alkyl group optionally substituted by the same or different 1 to 5 substituents selected from the following group E,
(n) —OR$^{D7}$ wherein R$^{D7}$ is a hydrogen atom, or a C$_{1-6}$ alkyl group optionally substituted by the same or different 1 to 5 substituents selected from the following group E,
(o) —NR$^{D8}$R$^{D9}$ wherein R$^{D8}$ and R$^{D9}$ are the same or different and each is a hydrogen atom, or a C$_{1-6}$ alkyl group optionally substituted by the same or different 1 to 5 substituents selected from the following group E,
(p) —NR$^{D10}$—C(=O)—R$^{D11}$ wherein R$^{D10}$ and R$^{D11}$ are the same or different and each is a hydrogen atom, or a C$_{1-6}$ alkyl group optionally substituted by the same or different 1 to 5 substituents selected from the following group E,
(q) —NR$^{D12}$—C(=O)—OR$^{D13}$ wherein R$^{D12}$ is a hydrogen atom, or a C$_{1-6}$ alkyl group optionally substituted by the same or different 1 to 5 substituents selected from the following group E, and R$^{D13}$ is a C$_{1-6}$ alkyl group optionally substituted by the same or different 1 to 5 substituents selected from the following group E,
(r) —S(=O)$_2$—R$^{D14}$ wherein R$^{D14}$ is a hydrogen atom, or a C$_{1-6}$ alkyl group optionally substituted by the same or different 1 to 5 substituents selected from the following group E, and
(s) —S(=O)$_2$—OR$^{D15}$ wherein R$^{D15}$ is a hydrogen atom, or a C$_{1-6}$ alkyl group optionally substituted by the same or different 1 to 5 substituents selected from the following group E, Group E is selected from the group consisting of
(a) a halogen atom,
(b) a cyano group,
(c) —C(=O)—$R^{E1}$ wherein $R^{E1}$ is a hydrogen atom or a $C_{1-6}$ alkyl group optionally substituted by the same or different 1 to 5 substituents selected from the following group F,
(d) —C(=O)—$OR^{E2}$ wherein $R^{E2}$ is a hydrogen atom or a $C_{1-6}$ alkyl group optionally substituted by the same or different 1 to 5 substituents selected from the following group F,
(e) —C(=O)—$NR^{E3}R^{E4}$ wherein $R^{E3}$ and $R^{E4}$ are the same or different and each is a hydrogen atom or a $C_{1-6}$ alkyl group optionally substituted by the same or different 1 to 5 substituents selected from the following group F,
(f) —C(=O)—$NR^{E5}$—$OR^{E6}$ wherein $R^{E5}$ and $R^{E6}$ are the same or different and each is a hydrogen atom or a $C_{1-6}$ alkyl group optionally substituted by the same or different 1 to 5 substituents selected from the following group F,
(g) —$OR^{E7}$ wherein $R^{E7}$ is a hydrogen atom or a $C_{1-6}$ alkyl group optionally substituted by the same or different 1 to 5 substituents selected from the following group F,
(h) —$NR^{E8}R^{E9}$ wherein $R^{E8}$ and $R^{E9}$ are the same or different and each is a hydrogen atom or a $C_{1-6}$ alkyl group optionally substituted by the same or different 1 to 5 substituents selected from the following group F,
(i) —$NR^{E10}$—C(=O)—$R^{E11}$ wherein $R^{E10}$ and $R^{E11}$ are the same or different and each is a hydrogen atom or a $C_{1-6}$ alkyl group optionally substituted by the same or different 1 to 5 substituents selected from the following group F,
(j) —$NR^{E12}$—C(=O)—$OR^{E13}$ wherein $R^{E12}$ is a hydrogen atom or a $C_{1-6}$ alkyl group optionally substituted by the same or different 1 to 5 substituents selected from the following group F, and $R^{E13}$ is a $C_{1-6}$ alkyl group optionally substituted by the same or different 1 to 5 substituents selected from the following group F,
(k) —$S(=O)_2$—$R^{E14}$ wherein $R^{E14}$ is a hydrogen atom or a $C_{1-6}$ alkyl group optionally substituted by the same or different 1 to 5 substituents selected from the following group F,
(l) —$S(=O)_2$—$OR^{E15}$ wherein $R^{E15}$ is a hydrogen atom or a $C_{1-6}$ alkyl group optionally substituted by the same or different 1 to 5 substituents selected from the following group F, and
(m) —$NR^{E16}$—$S(=O)_2$—$R^{E17}$ wherein $R^{E16}$ and $R^{E17}$ are the same or different and each is a hydrogen atom or a $C_{1-6}$ alkyl group,
Group F is selected from the group consisting of
(a) —$(CH_2)_{nF1}$—C(=O)—$OR^{F1}$ wherein $R^{F1}$ is a hydrogen atom or a $C_{1-6}$ alkyl group, and nF1 is an integer of 0, or 1 to 4, and
(b) —$(CH_2)_{nF2}$—$OR^{F2}$ wherein $R^{F2}$ is a hydrogen atom or a $C_{1-6}$ alkyl group, and nF2 is an integer of 0, or 1 to 4.

\* \* \* \* \*